United States Patent
Yoshida et al.

[11] Patent Number: 5,880,147
[45] Date of Patent: Mar. 9, 1999

[54] AMIDE DERIVATIVES HAVING ACAT INHIBITORY ACTIVITY, THEIR PREPARATION AND THEIR THERAPEUTIC AND PROHYLACTIC USE

[75] Inventors: Akira Yoshida; Kozo Oda; Takashi Kasai; Kousei Shimada; Hiroshi Kogen; Ichiro Hayakawa; Sadao Ishihara; Teiichiro Koga; Eiichi Kitazawa; Taro Tokui, all of Tokyo, Japan

[73] Assignee: Sankyo Company, Limited, Tokyo, Japan

[21] Appl. No.: 715,589

[22] Filed: Sep. 18, 1996

[30] Foreign Application Priority Data

Sep. 18, 1995 [JP] Japan .................. 7-238042

[51] Int. Cl.⁶ .............. A61K 31/335; A61K 31/165; C07D 319/16; C07C 233/05

[52] U.S. Cl. .............. 514/452; 514/464; 514/465; 514/469; 514/524; 514/563; 514/617; 514/618; 514/619; 549/377; 549/378; 549/441; 549/467; 549/468; 554/35; 554/36; 554/37; 558/412; 558/411; 558/415; 564/154; 564/155; 564/158

[58] Field of Search .............. 514/676, 452, 514/464, 465, 469, 524, 563, 617, 618, 619; 564/158, 154, 155; 549/377, 378, 441, 467, 468; 554/35, 36, 37; 558/412, 411, 415

[56] References Cited

U.S. PATENT DOCUMENTS

| | | | |
|---|---|---|---|
| 4,536,346 | 8/1985 | Shepherd et al. | 564/163 |
| 5,534,529 | 7/1996 | Yoshida et al. | 514/357 |
| 5,614,550 | 3/1997 | Yoshida et al. | 514/450 |

FOREIGN PATENT DOCUMENTS

| | | |
|---|---|---|
| 0 344 425 | 12/1989 | European Pat. Off. . |
| 0 415 123 | 3/1991 | European Pat. Off. . |
| 0 432 442 | 6/1991 | European Pat. Off. . |
| 0 439 059 | 7/1991 | European Pat. Off. . |
| 0 591 830 | 4/1994 | European Pat. Off. . |
| WO 93/24458 | 12/1993 | WIPO . |
| WO 9603378 | 2/1996 | WIPO . |

OTHER PUBLICATIONS

Chemical Abstracts, O'Brien et al., "Inhibitors of Acyl-CoA:Cholesterol O-Acyl Transferase (ACAT) as Hypocholesterolemic Agents", vol. 121, No. 1, Jul. 4, 1994, Abstract No. 8837r.

*Primary Examiner*—Shailendra Kumar
*Attorney, Agent, or Firm*—Frishauf, Holtz, Goodman, Langer & Chick, P.C.

[57] ABSTRACT

Compounds of formula (I):

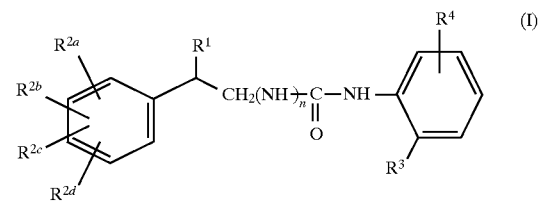

wherein: $R^1$ is alkyl; $R^{2a}$, $R^{2b}$, $R^{2c}$ and $R^{2d}$ are the same or different and each is hydrogen, optionally substituted alkyl, $-(C=O)-B^1$ (wherein $B^1$ is hydrogen or alkyl), nitro, $-NR^cR^d$ (wherein $R^c$ is hydrogen or alkyl and Rd is alkyl), hydroxy, protected hydroxy group, alkoxy, cyano, alkylthio, alkylsulfinyl, alkylsulfonyl or halogen;
$R^3$ is alkyl; $R^4$ is a group of the formula (II)

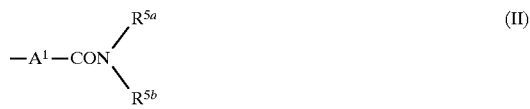

wherein $A^1$ is a single bond, alkylene or alkenylene; $R^{5a}$ and $R^{5b}$ are the same or different and each is hydrogen, alkyl or $-A^4R^5_c$ wherein A is a single bond, alkylene or alkenylene and $R^5_c$ is alkoxy; and n is 0, and pharmaceutically acceptable salts thereof. Such compounds have valuable inhibitory activity against acyl-CoA (cholesterol acyl transferase).

80 Claims, No Drawings

AMIDE DERIVATIVES HAVING ACAT INHIBITORY ACTIVITY, THEIR PREPARATION AND THEIR THERAPEUTIC AND PROHYLACTIC USE

BACKGROUND TO THE INVENTION

The present invention relates to a series of new urea and other amide derivatives which have valuable inhibitory activity against acyl-CoA: cholesterol acyl transferase (hereinafter referred to, as is conventional, as "ACAT"). The compounds are thus useful for the treatment and prophylaxis of arteriosclerosis, including atherosclerosis. The invention also provides methods and compositions using these new compounds for such treatment and prophylaxis as well as processes for their preparation.

Among the causes of ischemic cardiac insufficiency (which may result in angina, myocardial infarction and the like), arteriosclerosis, including atherosclerosis, is thought to be most important. These diseases are of considerable importance in the world today and can be fatal or can severely impair the quality of life of the sufferer. It is believed that the foam cells under the endothelial cell layer of blood vessels accumulate cholesterol esters, and that this is a major cause of arteriosclerosis.

Inhibitors of acyl-CoA: cholesterol acyl transferase inhibit the synthesis of cholesterol esters in the foam cells, diminish the accumulation of cholesterol esters in the foam cells and inhibit the formation and development of atheromatous morbidity due to the accumulation of cholesterol esters.

Additionally, it has been established that there is a correlation between arteriosclerosis and hypercholesterolemia. Cholesterols in food are absorbed as free cholesterol in the intestinal mucosal cell tract. They are then esterified by ACAT, and the resulting cholesterol ester can be passed into the blood. Therefore, an ACAT inhibitor inhibits any rise in the cholesterol concentration in the blood by inhibiting the absorption of food cholesterol into the blood.

For these reasons compounds having ACAT inhibiting activity are useful as therapeutic and/or prophylactic agents against arteriosclerosis.

Phenylpropionic acid amides and phenethylurea derivatives having ACAT inhibiting activity are well-known and are disclosed, for example, in European Patent Publications No. 591 830, 344 425, 415 123, 439 059 and 432 442 and WO 93/24 458. We believe European Patent Publication No. 591 830 to be the closest prior art to the present invention. The compounds of this prior art, however, differ from those of the present invention in the nature of the group hereinafter defined as $R^4$.

We have now surprisingly discovered a series of new urea and other amide derivatives which have more potent inhibitory activity against ACAT and have better oral absorption than do the prior art compounds referred to above.

BRIEF SUMMARY OF INVENTION

The present invention thus provides compounds of formula (I):

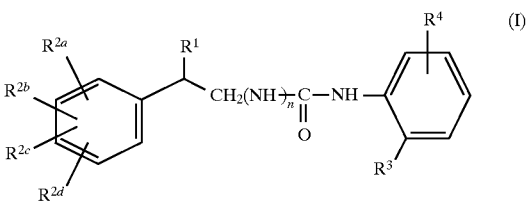

wherein:
$R^1$ represents an alkyl group having from 1 to 12 carbon atoms;
$R^{2a}$, $R^{2b}$, $R^{2c}$ and $R^{2d}$ are the same or different and each represents:
a hydrogen atom;
an alkyl group having from 1 to 12 carbon atoms;
an alkyl group which has from 1 to 4 carbon atoms and which is substituted by from 1 to 5 fluorine atoms;
an alkyl group which has from 1 to 12 carbon atoms and which is substituted by an unprotected or protected hydroxy group;
a group of formula —(C=O)—$B^1$
wherein $B^1$ represents a hydrogen atom, an alkyl group having from 1 to 12 carbon atoms, a group of formula —O—D
wherein D represents a hydrogen atom or a carboxy-protecting group,
a group of formula —NR$^a$R$^b$,
wherein R$^a$ and R$^b$ are the same or different and each represents a hydrogen atom, an alkyl group having from 1 to 12 carbon atoms,
a 1-pyrrolidinyl group which is substituted or unsubstituted, a 1-piperidinyl group which is substituted or unsubstituted or a 4-morpholinyl group which is substituted or unsubstituted;
a nitro group;
a group of formula —NR$^c$R$^d$
wherein R$^c$ represents a hydrogen atom or an alkyl group having from 1 to 4 carbon atoms and R$^d$ represents an alkyl group having from 1 to 4 carbon atoms;
a hydroxy group or a protected hydroxy group;
an alkoxy group having from 1 to 10 carbon atoms;
a group of formula —O—$B^2$—(C=O)—$B^1$
wherein $B^1$ is as defined above and $B^2$ represents an alkylene group having from 1 to 5 carbon atoms;
a group of formula —O—$B^2$—$B^3$
wherein $B^2$ is as defined above and $B^3$ represents an alkoxy group having from 1 to 6 carbon atoms, an alkylthio group having from 1 to 6 carbon atoms, an alkylsulfinyl group having from 1 to 6 carbon atoms, an alkylsulfonyl group having from 1 to 6 carbon atoms or an alkylsulfonylamino group having from 1 to 6 carbon atoms;
a cyano group;
a group of formula —CH=N—O$B^4$
wherein $B^4$ represents a hydrogen atom or an alkyl group having from 1 to 4 carbon atoms;
an alkylthio group having from 1 to 6 carbon atoms;
an alkylsulfinyl group having from 1 to 6 carbon atoms;
an alkylsulfonyl group having from 1 to 6 carbon atoms;
an alkylsulfonylamino group having from 1 to 6 carbon atoms;
a group of formula —SO$_2$NR$^e$R$^f$ wherein $R^e$ represents a hydrogen atom or an alkyl group which has from 1 to 6 carbon atoms and $R^f$ represents an alkyl group which has from 1 to 6 carbon atoms;

or a halogen atom; or $R^{2a}$ and $R^{2b}$ are adjacent to each other and together represent a group of formula $$-O-(CH_2)_m-O-$$

wherein m is an integer of from 1 to 3;

$R^3$ represents an alkyl group having from 1 to 6 carbon atoms;

$R^4$ represents a group of formula (II), (III), (IV), (V), (VI), (VII), (VIII) or (IX):

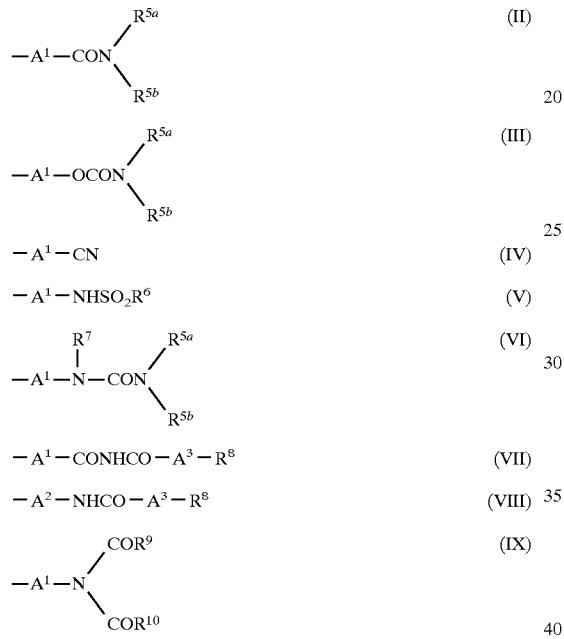

wherein:

$A^1$ represents a single bond, an alkylene group having from 1 to 6 carbon atoms or an alkenylene group having from 2 to 6 carbon atoms;

$A^2$ represents an alkylene group having from 1 to 6 carbon atoms or an alkenylene group having from 2 to 6 carbon atoms;

$A^3$ represents a single bond, an alkylene group having from 1 to 6 carbon atoms or an alkenylene group having from 2 to 6 carbon atoms;

$R^{5a}$ and $R^{5b}$ are the same or different and each represents a hydrogen atom, an alkyl group having from 1 to 4 carbon atoms or a group of formula $-A^4 R^{5c}$ wherein $A^4$ represents a single bond, an alkylene group having from 1 to 6 carbon atoms or an alkenylene group having from 2 to 6 carbon atoms;

$R^{5c}$ represents an alkoxy group having from 1 to 4 carbon atoms, a pyridyl group which is substituted or unsubstituted, a pyrimidinyl group which is substituted or unsubstituted, a pyrazinyl group which is substituted or unsubstituted, a pyrazolyl group which is substituted or unsubstituted, an imidazolyl group which is substituted or unsubstituted, a thiazolyl group which is substituted or unsubstituted or a 1,2,4-triazolyl group which is substituted or unsubstituted;

or $R^{5a}$ and $R^{5b}$ together represent a group of formula $$-(CH_2)_{p1}-(A^5)_{p2}-(CH_2)_{p3}-$$

wherein p1 is an integer of 1 or 2; $p^2$ is 0 or the integer of 1; p3 is an integer of 1 or 2; and $A^5$ represents an oxygen atom, an imino group or an alkylimino group having from 1 to 4 carbon atoms;

$R^6$ represents an alkyl group having from 1 to 4 carbon atoms or a phenyl group which is substituted or unsubstituted;

$R^7$ represents a hydrogen atom or an alkyl group having from 1 to 4 carbon atoms;

$R^8$ represents an alkyl group having from 1 to 12 carbon atoms, an alkyl group having from 1 to 12 carbon atoms substituted by an unprotected or protected carboxy group, an alkyl group having from 1 to 12 carbon atoms substituted by from 1 to 5 fluorine atoms, an alkoxy group having from 1 to 10 carbon atoms, an aralkoxy group in which an alkoxy group having from 1 to 4 carbon atoms is substituted by a carbocyclic aryl group having from 6 to 10 ring carbon atoms, a phenyl group which is substituted or unsubstituted, a pyridyl group which is substituted or unsubstituted, a pyrimidinyl group which is substituted or unsubstituted, a pyrazinyl group which is substituted or unsubstituted, a piperidinyl group which is substituted or unsubstituted, a pyrrolidinyl group which is substituted or unsubstituted, a morpholinyl group which is substituted or unsubstituted, a piperazinyl group which is substituted or unsubstituted, an imidazolyl group which is substituted or unsubstituted, a pyrazolyl group which is substituted or unsubstituted, a thiazolyl group which is substituted or unsubstituted, or a 1,2,4-triazolyl group which is substituted or unsubstituted;

$R^9$ and $R^{10}$ are the same or different and each represents an alkyl group having from 1 to 4 carbon atoms; or $R^9$ and $R^{10}$ together represent a group of formula $$-(CH_2)_{p4}-$$

wherein p4 represents an integer of from 2 to 4 or a ortho-phenylene group; and n represents 0 or 1 and pharmaceutically acceptable salts thereof.

The invention also provides a composition for the treatment and prophylaxis of hypercholesteremia or arteriosclerosis, which comprises an effective amount of a compound of formula (I) or a pharmaceutically acceptable salt thereof in admixture with a pharmaceutically acceptable carrier or diluent.

The invention still further provides a method for the treatment and prophylaxis of hypercholesteremia or arteriosclerosis in a mammal, which may be human, which comprises administering to said mammal an effective amount of a compound of formula (I) or a pharmaceutically acceptable salt thereof.

Processes for preparing these compounds and salts thereof also form part of the present invention and are described in more detail hereafter.

DETAILED DESCRIPTION OF INVENTION

In the compounds of the present invention, where $R^1$ represents an alkyl group, this may be a straight or branched chain alkyl group having from 1 to 12 carbon atoms, and examples include the methyl, ethyl, propyl, isopropyl, butyl, isobutyl, sec-butyl, t-butyl, pentyl, isopentyl, 2-methylbutyl, neopentyl, 1-ethyl-propyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl and dodecyl groups. Of these, we prefer those groups having from 3 to 12 carbon atoms, and more preferably from 3 to 6 carbon atoms. The propyl, isopropyl, butyl, isobutyl, pentyl, isopentyl, hexyl and 4-methyl-pentyl groups are particularly preferred.

We prefer that $R^1$ should represent a propyl, isopropyl, butyl, isobutyl, pentyl, isopentyl, hexyl or 4-methylpentyl group, more preferably a propyl, butyl, pentyl or hexyl group.

Where any of $R^{2a}$, $R^{2b}$, $R^{2c}$ or $R^{2d}$ represents an alkyl group, this may be a straight or branched chain alkyl group having from 1 to 12 carbon atoms, and examples include the alkyl groups exemplified above in relation to $R^1$. In these cases, however, the preferred groups are those having from 1 to 5 carbon atoms, more preferably those having from 1 to 3 carbon atoms. Of these, the methyl group is most preferred.

Where any of $R^{2a}$, $R^{2b}$, $R^{2c}$ or $R^{2d}$ represents an alkyl group substituted by from 1 to 5 fluorine atoms, the alkyl part of this group may be a straight or branched chain alkyl group having from 1 to 4, preferably from 1 to 3, carbon atoms. The number of substituents is no more than 5, but, additionally is, of course limited by the number of substitutable positions on the alkyl group. Thus, the maximum number of substituents on a methyl group is 3, whilst the maximum number on an ethyl or higher group is 5. Examples of such fluoroalkyl groups include the fluoromethyl, difluoromethyl, trifluoromethyl, 2,2,2-trifluoro-ethyl, 1,1,2,2,2-pentafluoroethyl, 3,3,3-trifluoropropyl and 4,4,4-trifluorobutyl groups. Of these, we prefer the fluoromethyl, difluoromethyl and trifluoromethyl groups, of which the trifluoromethyl group is preferred.

Where any of $R^{2a}$, $R^{2b}$, $R^{2c}$ or $R^{2d}$ represents an alkyl group substituted by a hydroxy group or a protected hydroxy group, the alkyl part of this group may be a straight or branched chain alkyl group having from 1 to 12, preferably from 1 to 6, and more preferably from 1 to 4, carbon atoms, which may be any of those alkyl groups exemplified above in relation to $R^1$. There is no particular restriction on the nature of the protecting group employed, especially if the resulting compound is merely intended for use as a synthetic intermediate. If the compound is intended for pharmaceutical use, then, of course, the resulting compound should be pharmaceutically acceptable. Examples of protecting groups for hydroxy groups are described in "Protective Groups in Organic Synthesis", 2nd edition, T. W. Greene and P. G. M. Wut; John Wiley and Sons, Inc., New York (1991), the disclosure of which is incorporated herein by reference. Examples of preferred protecting groups include:

aliphatic acyl groups, preferably:

alkanoyl groups having from 1 to 25 carbon atoms, more preferably from 1 to 20 carbon atoms, still more preferably from 1 to 6 carbon atoms, and most preferably from 1 to 4 carbon atoms, such as the formyl, acetyl, propionyl, butyryl, isobutyryl, pivaloyl, valeryl, isovaleryl, hexanoyl, heptanoyl, octanoyl, lauroyl, myristoyl, tridecanoyl, palmitoyl and stearoyl groups, of which the acetyl group is most preferred;

halogenated alkanoyl groups having from 2 to 6 carbon atoms, especially halogenated acetyl groups, such as the chloroacetyl, dichloroacetyl, trichloroacetyl and trifluoroacetyl groups;

lower alkoxyalkanoyl groups in which the alkoxy part has from 1 to 5, preferably from 1 to 3, carbon atoms and the alkanoyl part has from 2 to 6 carbon atoms and is preferably an acetyl group, such as the methoxyacetyl group; and unsaturated analogs of such groups, especially alkenoyl or alkynoyl groups having from 3 to 6 carbon atoms such as the acryloyl, methacryloyl, propioloyl, crotonoyl, isocrotonoyl and (E)-2-methyl-2-butenoyl groups;

aromatic acyl groups, preferably arylcarbonyl groups, in which the aryl part has from 6 to 14, more preferably from 6 to 10, still more preferably 6 or 10, and most preferably 6, ring carbon atoms and is a carbocyclic group, which is unsubstituted or has from 1 to 5, preferably from 1 to 3 substituents, selected from the group consisting of substituents β, defined and exemplified below, preferably:

unsubstituted groups, such as the benzoyl, α-naphthoyl and β-naphthoyl groups;

halogenated arylcarbonyl groups, such as the 2-bromobenzoyl and 4-chlorobenzoyl groups;

lower alkyl-substituted arylcarbonyl groups, in which the or each alkyl substituent has from 1 to 5, preferably from 1 to 4, carbon atoms, such as the 2,4,6-trimethylbenzoyl and 4-toluoyl groups;

lower alkoxy-substituted arylcarbonyl groups, in which the or each alkoxy substituent preferably has from 1 to 5, more preferably from 1 to 4, carbon atoms, such as the 4-anisoyl group;

nitro-substituted arylcarbonyl groups, such as the 4-nitrobenzoyl and 2-nitrobenzoyl groups;

lower alkoxycarbonyl-substituted arylcarbonyl groups, in which the or each alkoxycarbonyl substituent preferably has from 2 to 6 carbon atoms, such as the 2-(methoxycarbonyl)benzoyl group; and aryl-substituted arylcarbonyl groups, in which the aryl substituent is as defined above, except that, if it is substituted by a further aryl group, that aryl group is not itself substituted by an aryl group, such as the 4-phenylbenzoyl group;

heterocyclic groups having 5 or 6 ring atoms, of which 1 or 2 are hetero-atoms selected from the group consisting of oxygen, sulfur and nitrogen atoms, preferably oxygen or sulfur atoms, which groups may be unsubstituted or may have at least one substituent selected from the group consisting of substituents a, defined and exemplified below, and oxygen atoms; examples include:

the tetrahydropyranyl groups, which may be substituted or unsubstituted, such as the tetrahydropyran-2-yl, 3-bromo-tetrahydropyran-2-yl and 4-methoxytetrahydropyran-4-yl groups;

tetrahydrothiopyranyl groups, which may be substituted or unsubstituted, such as the tetrahydrothiopyran-2-yl and 4-methoxy-tetrahydrothiopyran-4-yl groups;

tetrahydrofuranyl groups, which may be substituted or unsubstituted, such as the tetrahydrofuran-2-yl group; and tetrahydrothienyl groups, which may be substituted or unsubstituted, such as the tetrahydrothien-2-yl group;

tri-substituted silyl groups, in which all three or two or one of the substituents are alkyl groups having from 1 to 5, preferably from 1 to 4, carbon atoms, and none, one or two of the substituents are aryl groups, as defined above, but preferably phenyl or substituted phenyl groups, preferably:

tri(lower alkyl)silyl groups, such as the trimethylsilyl, triethylsilyl, isopropyldimethylsilyl, t-butyldimethylsilyl, methyldiisopropylsilyl, methyldi-t-butylsilyl and triisopropylsilyl groups; and tri(lower alkyl)silyl groups in which one or two of the alkyl groups have been replaced by aryl groups, such as the diphenylmethylsilyl, diphenylbutylsilyl, diphenyl-t-butylsilyl, diphenylisopropylsilyl and phenyldiisopropylsilyl groups;

alkoxyalkyl groups, in which the alkoxy and alkyl parts each have from 1 to 5, preferably from 1 to 4, carbon atoms, especially alkoxymethyl groups, and such groups which have at least one, preferably from 1 to 5, more preferably from 1 to 3, and most preferably 1, substituents, preferably:

alkoxyalkyl groups in which the alkoxy and alkyl parts independently have from 1 to 4 carbon atoms and may be straight or branched chain groups selected from those alkyl groups included in those exemplified in relation to $R^1$ and having from 1 to 4 carbon atoms; examples of such alkoxyalkyl groups include the methoxymethyl, ethoxymethyl, propoxymethyl, isopropoxymethyl, butoxymethyl, isobutoxymethyl, t-butoxymethyl, 2-methoxyethyl, 2-ethoxyethyl, 2-propoxyethyl, 2-isopropoxyethyl, 2-butoxyethyl, 2-isobutoxyethyl, 2-t-butoxyethyl, 3-methoxypropyl, 3-ethoxypropyl, 3-propoxypropyl, 3-isopropoxypropyl, 3-butoxypropyl, 3-isobutoxypropyl, 3-t-butoxypropyl, 4-methoxybutyl, 4-ethoxybutyl, 4-propoxybutyl, 4-isopropoxybutyl, 4-butoxybutyl, 4-isobutoxybutyl and 4-t-butoxybutyl groups, especially lower alkoxymethyl groups, such as the methoxymethyl, 1,1-dimethyl-1-methoxymethyl, ethoxymethyl, propoxymethyl, isopropoxymethyl, butoxymethyl and t-butoxymethyl groups, of which the methoxymethyl group is preferred;

alkoxyalkoxyalkyl groups in which the alkoxy and alkyl parts independently have from 1 to 4 carbon atoms and may be straight or branched chain groups selected from those alkyl groups included in those exemplified in relation to $R^1$ and having from 1 to 4 carbon atoms; examples of such alkoxyalkoxyalkyl groups include alkoxyalkoxymethyl groups, such as the methoxymethoxymethyl, ethoxymethoxymethyl, propoxymethoxymethyl, isopropoxy-methoxymethyl, butoxymethoxymethyl, isobutoxymethoxymethyl, t-butoxymethoxymethyl, 2-methoxyethoxymethyl, 2-ethoxyethoxy-methyl, 2-propoxyethoxymethyl, 2-isopropoxyethoxymethyl, 2-butoxyethoxyrnethyl, .2-isobutoxyethoxymethyl, 2-t-butoxyethoxy-methyl, 3-methoxypropoxymethyl, 3-ethoxypropoxymethyl, 3-propoxypropoxymethyl, 3-isopropoxypropoxymethyl, 3-butoxy-propoxymethyl, 3-isobutoxypropoxymethyl, 3-t-butoxypropoxy-methyl, 4-methoxybutoxymethyl, 4-ethoxybutoxymethyl, 4-propoxy-butoxymethyl, 4-isopropoxybutoxymethyl, 4-butoxybutoxymethyl, 4-isobutoxybutoxy and 4-t-butoxybutoxymethyl groups, especially lower alkoxy-substituted lower alkoxymethyl groups, of which the 2-methoxyethoxymethyl group is preferred;

halogenated lower alkoxymethyl groups, such as the 2,2,2-trichloro-ethoxymethyl and bis(2-chloroethoxy) methyl groups; and lower alkoxy-substituted ethyl groups, such as the 1-ethoxyethyl, 1-methyl-1-methoxyethyl and 1-isopropoxyethyl groups;

other substituted ethyl groups, preferably:

halogenated ethyl groups, such as the 2,2,2-tri-chloroethyl group; and arylselenyl-substituted ethyl groups, in which the aryl part is as defined above, such as the 2-(phenylselenyl)ethyl group;

aralkyl groups, preferably alkyl groups having from 1 to 4, more preferably from 1 to 3 and most preferably 1 or 2, carbon atoms which are substituted with from 1 to 3 aryl groups, as defined and exemplified above, which may be unsubstituted (such as the benzyl, phenethyl, 1-phenylethyl, 3-phenylpropyl, α-naphthylmethyl, β-naphthylmethyl, diphenylmethyl, triphenylmethyl, α-naphthyldiphenylmethyl and 9-anthrylmethyl groups) or substituted on the aryl part with a lower alkyl group, a lower alkoxy group, a nitro group, a halogen atom, a cyano group, or an alkylenedioxy group having from 1 to 3 carbon atoms, preferably a methylenedioxy group, (such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzoyl, 4-bromobenzyl, 4-cyanobenzyl, 4-cyanobenzyldiphenylmethyl, bis(2-nitrophenyl)methyl and piperonyl groups);

alkoxycarbonyl groups, especially such groups having from 2 to 7, more preferably 2 to 5, carbon atoms and which may be unsubstituted (such as the methoxycarbonyl, ethoxycarbonyl, t-butoxycarbonyl and isobutoxycarbonyl groups) or substituted with a halogen atom or a tri-substituted silyl group, e.g. a tri(lower alkylsilyl) group (such as the 2,2,2-trichloroethoxycarbonyl and 2-trimethylsilylethoxycarbonyl groups);

alkenyloxycarbonyl groups in which the alkenyl part has from 2 to 6, preferably from 2 to 4, carbon atoms, such as the vinyloxycarbonyl and allyloxycarbonyl groups;

sulfo groups; and aralkyloxycarbonyl groups, in which the aralkyl part is as defined and exemplified above, and in which the aryl ring, if substituted, preferably has one or two lower alkoxy or nitro substituents, such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

Preferred protecting groups are, in general, acyl groups, alkoxyalkyl groups, alkoxyalkoxyalkyl groups, and trialkylsilyl groups. More specifically, preferred protecting groups include:

alkanoyl groups having from 2 to 6 carbon atoms, such as the acetyl, butyryl, isobutyryl, pivaloyl and valeryl groups, especially the acetyl group;

aromatic carboxylic acyl groups, such as the benzyl group or naphthoyl group and corresponding groups substituted as described hereafter in relation to substituted phenyl groups;

aryloxycarbonyl groups, such as the benzyloxycarbonyl group and corresponding groups substituted as described hereafter in relation to substituted phenyl groups, such as the 4-nitrobenzyloxycarbonyl group;

alkoxyalkyl groups in which the alkoxy and alkyl parts independently have from 1 to 4 carbon atoms and may be straight or branched chain groups selected from those alkyl groups included in those exemplified in relation to $R^1$ and having from 1 to 4 carbon atoms; examples of such alkoxyalkyl groups include the methoxymethyl, ethoxymethyl, propoxymethyl, isopropoxymethyl, butoxymethyl, isobutoxymethyl, t-butoxymethyl, 2-methoxyethyl, 2-ethoxyethyl, 2-propoxyethyl, 2-isopropoxyethyl, 2-butoxyethyl, 2-isobutoxyethyl, 2-t-butoxyethyl, 3-methoxypropyl, 3-ethoxypropyl, 3-propoxypropyl, 3-isopropoxypropyl, 3-butoxypropyl, 3-isobutoxypropyl, 3-t-butoxypropyl, 4-methoxybutyl, 4-ethoxybutyl, 4-propoxybutyl, 4-isopropoxybutyl, 4-butoxybutyl, 4-isobutoxybutyl and 4-t-butoxybutyl groups, of which the methoxymethyl group is preferred;

benzyl groups, which may be unsubstituted or may be substituted as defined and exemplified below in relation to substituted phenyl groups, for example the benzyl and p-methoxybenzyl groups;

alkenyloxycarbonyl groups having from 3 to 5 carbon atoms, for example the allyloxycarbonyl, 1-propenyloxycarbonyl, 2-butenyloxycarbonyl and 2-pentenyloxycarbonyl groups, of which the allyloxycarbonyl group is preferred;

alkoxyalkoxyalkyl groups in which the alkoxy and alkyl parts independently have from 1 to 4 carbon atoms and may be straight or branched chain groups selected from those alkyl groups included in those exemplified in relation to $R^1$ and having from 1 to 4 carbon atoms; examples of such alkoxyalkoxyalkyl groups include alkoxyalkoxymethyl groups, such as the methoxymethoxymethyl, ethoxymethoxymethyl, propoxymethoxymethyl, isopropoxymethoxymethyl, butoxymethoxy-methyl, isobutoxymethoxymethyl, t-butoxymethoxymethyl, 2-methoxy-ethoxymethyl, 2-ethoxyethoxymethyl, 2-propoxyethoxymethyl, 2-isopropoxyethoxymethyl, 2-butoxyethoxymethyl, 2-isobutoxyethoxy-methyl, 2-t-butoxyethoxymethyl, 3-methoxypropoxymethyl, 3-ethoxy-propoxymethyl, 3-propoxypropoxymethyl, 3-isopropoxypropoxymethyl, 3-butoxypropoxymethyl, 3-isobutoxypropoxymethyl, 3-t-butoxypropoxymethyl, 4-methoxybutoxymethyl, 4-ethoxybutoxymethyl, 4-propoxy-butoxymethyl, 4-isopropoxybutoxym ethyl, 4-butoxybutoxymethyl, 4-isobutoxybutoxy and 4-t-butoxybutoxymethyl groups, of which the 2-methoxyethoxymethyl group is preferred; and trialkylsilyl groups, in which the alkyl parts independently have from 1 to 4 carbon atoms and may be straight or branched chain groups selected from those alkyl groups included in those exemplified in relation to $R^1$ and having from 1 to 4 carbon atoms, or in which one or two of the alkyl groups may be replaced by phenyl groups; examples of such trialkylsilyl groups include the trimethylsilyl, t-butyldimethylsilyl, t-butyldiphenylsilyl and di-t-butylphenylsilyl groups, of which the t-butyldimethylsilyl group is preferred.

Of the above protecting groups, in the case of the protecting groups for protected hydroxyalkyl groups, we prefer the aliphatic acyl groups having from 2 to 6 carbon atoms, especially the acetyl group, the aralkyloxycarbonyl groups, especially the 4-nitrobenzyloxycarbonyl group, the alkenyloxycarbonyl groups, especially the allyloxycarbonyl group, the alkoxyalkyl groups, especially the methoxymethyl group, the alkoxyalkoxyalkyl groups, especially the 2-methoxyethoxymethyl group, and the trialkylsilyl groups, especially the t-butyldimethylsilyl group.

Specific examples of alkyl groups having from 1 to 12 carbon atoms and substituted by a hydroxy group include the hydroxymethyl, 1-hydroxyethyl, 1-hydroxypropyl, 2-hydroxypropyl, 1-hydroxy-1-methylethyl, 1-hydroxybutyl, 2-hydroxybutyl, 3-hydroxybutyl, 1-hydroxy-2-methylpropyl, 1-hydroxypentyl, 1-hydroxy-3-methylbutyl, 1-hydroxyhexyl, 1-hydroxyheptyl, 1-hydroxynonyl, 1-hydroxydecyl, 1-hydroxyundecyl, and 1-hydroxydodecyl groups, of which we prefer the hydroxymethyl, 1-hydroxyethyl, 1-hydroxypropyl, 1-hydroxy-1-methylethyl, 1-hydroxybutyl, 1-hydroxy-2-methylpropyl, 1-hydroxypentyl and 1-hydroxy-3-methylbutyl groups.

Where any Of $R^{2a}$, $R^{2b}$, $R^{2c}$ or $R^{2d}$ represents a group of formula —(C=O)—$B^1$, and $B^1$ represents an alkyl group having from 1 to 12 carbon atoms, this may be a straight or branched chain alkyl group having from 1 to 12 carbon atoms, and examples include the alkyl groups exemplified above in relation to $R^1$. In these cases, however, the preferred groups are those having from 1 to 6 carbon atoms, more preferably those having from 1 to 5 carbon atoms. Of these, the methyl, ethyl, propyl, isopropyl, butyl, isobutyl and pentyl groups are most preferred.

Where any of $R^{2a}$, $R^{2b}$, $R^{2c}$ or $R^{2d}$ represents a group of formula —(C=O)—$B^1$, $B^1$ represents group of formula —O—D and represents a protecting group for a carboxy group, the carboxy-protecting group may be any of the protecting groups described and exemplified in "Protective Groups in Organic Synthesis", described above. In general, the protecting group is preferably an ester-forming group, and examples of such groups include:

alkyl groups having from 1 to 20 carbon atoms, more preferably from 1 to 6 carbon atoms, such as those exemplified in relation to $R^1$ and higher alkyl groups as are well known in the art, such as the heptyl, octyl, nonyl, decyl, dodecyl, tridecyl, pentadecyl, octadecyl, nonadecyl and icosyl groups, but most preferably the methyl, ethyl and t-butyl groups;

cycloalkyl groups having from 3 to 7 carbon atoms, for example the cyclopropyl, cyclobutyl, cyclopentyl, cyclohexyl and cycloheptyl groups;

aralkyl groups, in which the alkyl part has from 1 to 3 carbon atoms and the aryl part is a carbocyclic aromatic group having from 6 to 14 carbon atoms, which may be substituted or unsubstituted and, if substituted, has at least one of substituents β defined and exemplified above, although the unsubstituted groups are preferred; examples of such aralkyl groups include the benzyl, phenethyl, 1-phenylethyl, 3-phenylpropyl, 2-phenylpropyl, 1-naphthyl-methyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 3-nitrobenzyl, 4-methoxybenzyl and piperonyl groups;

alkenyl groups having from 2 to 6 carbon atoms, such as the the vinyl, allyl, 2-methylallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the vinyl, allyl, 2-methylallyl, 1-propenyl, isopropenyl and butenyl groups are preferred, the allyl and 2-methylallyl groups being most preferred.

halogenated alkyl groups having from 1 to 6, preferably from 1 to 4, carbon atoms, in which the alkyl part is as defined and exemplified in relation to the alkyl groups above, and the halogen atom is chlorine, fluorine, bromine or iodine, such as the 2,2,2-trichloroethyl, 2-haloethyl (e.g. 2-chloro-ethyl, 2-fluoroethyl, 2-bromoethyl or 2-iodoethyl), 2,2-dibromoethyl and 2,2,2-tribromoethyl groups; substituted silylalkyl groups, in which the alkyl part is as defined and exemplified above, and the silyl group has up to 3 substituents selected from alkyl groups having from 1 to 6 carbon atoms and phenyl groups which are unsubstituted or have at least one substituent selected from substituents β defined and exemplified above, for example a 2-trimethylsilylethyl group;

phenyl groups, in which the phenyl group is unsubstituted or substituted, preferably with at least one alkyl group having from 1 to 4 carbon atoms or acylamino group, for example the phenyl, tolyl and benzamidophenyl groups;

phenacyl groups, which may be unsubstituted or have at least one of substituents β defined and exemplified above, for example the phenacyl group itself or the p-bromophenacyl group;

cyclic and acyclic terpenyl groups, for example the geranyl, neryl, linalyl, phytyl, menthyl (especially m- and p- menthyl), thujyl, caryl, pinanyl, bornyl, notcaryl, norpinanyl, norbomyl, menthenyl, camphenyl and norbomenyl groups;

alkoxymethyl groups, in which the alkoxy part has from 1 to 6, preferably from 1 to 4, carbon atoms and may itself be substituted by a single unsubstituted alkoxy group, such as the methoxymethyl, ethoxymethyl, propoxymethyl, isopropoxymethyl, butoxymethyl and methoxyethoxymethyl groups;

aliphatic acyloxyalkyl groups, in which the acyl group is preferably an alkanoyl group and is more preferably an alkanoyl group having from 2 to 6 carbon atoms, and the alkyl part has from 1 to 6, and preferably from 1 to 4, carbon atoms such as the acetoxymethyl, propionyloxymethyl, butyryloxy-methyl, isobutyryloxymethyl, pivaloyloxymethyl, 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryl-oxypropyl, 1-acetoxypropyl, 1-acetoxy-2-methylpropyl, 1-propionyloxy-ethyl, 1-propionyloxypropyl, 2-acetoxypropyl and 1-butyryloxyethyl groups;

cycloalkyl-substituted aliphatic acyloxyalkyl groups, in which the acyl group is preferably an alkanoyl group and is more preferably an alkanoyl group having from 2 to 6 carbon atoms, the cycloalkyl substituent has from 3 to 7 carbon atoms, and the alkyl part has from 1 to 6, preferably from 1 to 4, carbon atoms, such as the (cyclohexylacetoxy)methyl, 1-(cyclohexyl-acetoxy)ethyl, 1-(cyclohexylacetoxy)propyl, 2-methyl-1-(cyclohexyl-acetoxy)propyl, (cyclopentylacetoxy)methyl, 1-(cyclopentylacetoxy)ethyl, 1-(cyclopentyl-acetoxy)propyl and 2-methyl-1-(cyclopentylacetoxy)propyl, groups;

alkoxycarbonyloxyalkyl groups, especially 1-(alkoxycarbonyloxy)ethyl groups, in which the alkoxy part has from 1 to 10, preferably 1 to 6, and more preferably from 1 to 4, carbon atoms, and the alkyl part has from 1 to 6, preferably from 1 to 4, carbon atoms, such as the 1-methoxycarbonyloxyethyl, 1-ethoxycarbonyloxyethyl, 1-propoxycarbonyloxyethyl, 1-isopropoxy-carbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethyl-propoxycarbonyloxy)ethyl and 1-(1,1-dipropylbutoxycarbonyloxy)ethyl groups, and other alkoxycarbonylalkyl groups, in which both the alkoxy and alkyl groups have from 1 to 6, preferably from 1 to 4, carbon atoms, such as the 2-methyl-1-(isopropoxycarbonyloxy)propyl, 2-(isopropoxycarbonyloxy)-propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group has from 3 to 10, preferably from 3 to 7, carbon atoms, is mono- or poly- cyclic and is optionally substituted by at least one (and preferably only one) alkyl group having from 1 to 4 carbon atoms (e.g. selected from those alkyl groups exemplified above) and the alkyl part has from 1 to 6, more preferably from 1 to 4, carbon atoms (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentyl-carbonyloxyethyl, 1-cycloheptyloxycarbonyloxyethyl, 1-cycloheptylcarbonyloxyethyl, 1-methylcyclopentylcarbonyloxymethyl, 1-methylcyclo-pentyloxycarbonyloxymethyl, 2-methyl-1-(1-methylcyclohexylcarbonyloxy)-propyl, 1-(1-methylcyclohexylcarbonyloxy)propyl, 2-(1-methylcyclohexyl-carbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentyl-carbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxyethyl groups;

cycloalkylalkoxycarbonyloxyalkyl groups in which the alkoxy group has a single cycloalkyl substituent, the cycloalkyl substituent having from 3 to 10, preferably from 3 to 7, carbon atoms and mono- or poly- cyclic, for example the cyclopropylmethoxycarbonyloxymethyl, cyclobutyhnethoxycarbonyl-oxymethyl, cyclopentylmethoxycarbonyloxymethyl, cyclohexyhnethoxy-carbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexyhnethoxycarbonyloxy)ethyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthyl-carbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

5-alkyl or 5-phenyl [which may be substituted by at least one of substituents β, defined and exemplified above] (2-oxo-1,3-dioxolen-4-yl)alkyl groups in which each alkyl group (which may be the same or different) has from 1 to 6, preferably from 1 to 4, carbon atoms, for example the (5-methyl-2-oxo-1,3-dioxolen-4-yl) methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and other groups, such as the phthalidyl, indanyl and 2-oxo-4,5,6,7-tetrahydro-1,3-benzodioxolen-4-yl groups.

Of these, we prefer the benzyl, 4-nitrobenzyl, allyl, methyl and ethyl groups.

Alternatively, $B^1$ may represent a group of formula —$NR^aR^b$ (wherein Ra and $R^b$ are the same or different and each represents a hydrogen atom, an alkyl group having from 1 to 12 carbon atoms), i.e. an amino group or a mono- or di-alkylamino group in which the or each alkyl group has from 1 to 12 carbon atoms. The alkyl group may be a straight or branched chain alkyl group having from 1 to 12 carbon atoms, and examples include the alkyl groups exemplified above in relation to $R^1$. In these cases, however, the preferred groups are those having from 1 to 6 carbon atoms, more preferably those having from 1 to 4 carbon atoms. Of these alkylamino groups, the methylamino, dimethylamino, ethylamino, diethylamino, isopropylamino, propylamino, butylamino, pentylamino, hexylamino and nonylamino group are preferred, the dimethylamino, diethylamino, isopropylamino and butylamino groups being most preferred.

Where $B^1$ represents a 1-pyrrolidinyl group which is substituted or unsubstituted, a 1-piperidinyl group which is substituted or unsubstituted or a 4-morpholinyl group which is substituted or unsubstituted, there is no specific restriction on the nature of the substituent, and substituents which may be present on these groups are well known to those skilled in the art. Examples of suitable substituents include the following substituents α:

alkyl groups having from 1 to 4 carbon atoms, which may be straight or branched chain groups, such as the methyl, ethyl, propyl, isopropyl, butyl, isobutyl, sec-butyl and t-butyl groups;

alkoxy groups having from 1 to 4 carbon atoms, which may be straight or branched chain groups, such as the methoxy, ethoxy, propoxy, isopropoxy, butoxy, isobutoxy, sec-butoxy and t-butoxy groups;

phenyl groups;

nitro groups; and amino and mono- and di- alkylamino groups such as those exemplified above having the formula —$NR^aR^b$.

There is no particular restriction on the number of substituents on these heterocyclic groups, and the maximum number is limited only by the number of substitutable positions and possibly, in some cases, by steric constraints. In general, from 1 to 3 substituents are preferred, one substituent being more preferred.

Examples of optionally substituted 1-pyrrolidinyl groups which may be represented by $B^1$ in the above —(C=O)—$B^1$ group include the 1-pyrrolidinyl, 3-methoxy-1-pyrrolidinyl and 3-ethoxy-1-pyrrolidinyl groups.

Examples of optionally substituted 1-piperidinyl groups which may be represented by $B^1$ in the above —(C=O)—$B^1$ group include the 1-piperidinyl, 3-methoxy-1-piperidinyl and 4-methoxy-1-piperidinyl groups.

Examples of optionally substituted 1-morpholinyl groups which may be represented by $B^1$ in the above —(C=O)—$B^1$ group include the 1-morpholinyl, 4-methyl-1-morpholinyl and 4-ethyl-1-morpholinyl groups.

Where any of $R^{2a}$, $R^{2b}$, $R^{2c}$ or $R^{2d}$ represents a group of formula a group of formula —$NR^cR^d$ (wherein $R^c$ represents a hydrogen atom or an alkyl group having from 1 to 4 carbon atoms and $R^d$ represents an alkyl group having from 1 to 4 carbon atoms) these are mono- or di-alkylamino groups, of which the alkyl group or groups may be straight or branched chain alkyl groups having from 1 to 4 carbon atoms. Examples of such alkyl groups include the methyl, ethyl, propyl, isopropyl, butyl, isobutyl, sec-butyl and t-butyl groups. Examples of such mono- or di-alkylamino groups include the methylamino, dimethylamino, ethylamino, diethylamino, propylamino, dipropylamino, isopropylamino, butylamino and isobutylamino groups, of which we prefer the methylamino, dimethylamino, ethylamino and diethylamino groups.

Where any of $R^{2a}$, $R^{2b}$, $R^{2c}$ or $R^{2d}$ represents a protected hydroxy group, there is no particular restriction on the nature of the protecting group employed, especially if the resulting compound is merely intended for use as a synthetic intermediate. If the compound is intended for pharmaceutical use, then, of course, the resulting compound should be pharmaceutically acceptable. Examples of protecting groups for hydroxy groups are described in "Protective Groups in Organic Synthesis", 2nd edition, T. W. Greene and P. G. M. Wut; John Wiley and Sons, Inc., New York (1991), referred to above. Preferred protecting groups are, in general, as described above in relation to the protecting groups which may be employed for protected hydroxyalkyl groups. In this case, the most preferred groups are benzyl groups, especially the benzyl and p-methoxy-benzyl groups, the alkoxyalkyl groups, especially the methoxymethyl group, the alkoxy-alkoxyalkyl groups, especially the 2-methoxyethoxymethyl group, alkenyl groups the allyl group, the trialkylsilyl groups, especially the t-butyldimethylsilyl group, and the alkanoyl groups having from 2 to 6 carbon atoms, especially the acetyl group.

Where any of $R^{2a}$, $R^{2b}$, $R^{2c}$ or $R^{2d}$ represents an alkoxy group having from 1 to 10 carbon atoms, this may be a straight or branched chain alkoxy group having from 1 to 10 carbon atoms, and examples include the methoxy, ethoxy, propoxy, isopropoxy, butoxy, isobutoxy, sec-butoxy, t-butoxy, pentyloxy, isopentyloxy, 2-methylbutoxy, neopentyloxy, 1-ethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethyl-butoxy, 1,3-dimethylbutoxy, 2,3-dimethylbutoxy, 2-ethylbutoxy, heptyloxy, 1-methylhexyloxy, 2-methylhexyloxy, 3-methylhexyloxy, 4-methylhexyloxy, 5-methylhexyloxy, 1-propylbutoxy, 4,4-dimethylpentyloxy, octyloxy, 1-methyl-heptyloxy, 2-methylheptyloxy, 3-methylheptyloxy, 4-methylheptyloxy, 5-methylheptyloxy, 6-methylheptyloxy, 1-propylpentyloxy, 2-ethylhexyloxy, 5,5-dimethylhexyloxy, nonyloxy, 3-methyloctyloxy, 4-methyloctyloxy, 5-methyloctyloxy, 6-methyloctyloxy, 1-propylhexyloxy, 2-ethylheptyloxy, 6,6-dimethylheptyloxy, decyloxy, 1-methylnonyloxy, 3-methylnonyloxy, 8-methylnonyloxy, 3-ethyloctyloxy, 3,7-dimethyloctyloxy and 7,7-dimethyl-octyloxy groups. Of these, we prefer those having from 1 to 5 carbon atoms; and more prefer those having from 1 to 3 carbon atoms.

Where any of $R^{2a}$, $R^{2b}$, $R^{2c}$ or $R^{2d}$ represents a group of formula —O—$B^2$—(C=O)—$B^1$, and $B^2$ represents an alkylene group having from 1 to 5 carbon atoms, this may be, for example, a methylene, ethylene, trimethylene, tetramethylene or pentamethylene group, preferably a methylene, ethylene or trimethylene group. $B^1$ in the above group of formula —O—$B^2$—(C=O)—$B^1$ may be any of the groups defined and exemplified above for $B^1$ in the group of formula —(C=O)—$B^1$ above, preferably any of those defined as preferred.

Where any of $R^{2a}$, $R^{2b}$, $R^{2c}$ or $R^{2d}$ represents a group of formula —O—$B^2$—$B^3$, and $B^2$ represents an alkylene group having from 1 to 5 carbon atoms, this may be any of the groups defined and exemplified above for $B^2$ in the group of formula —O—$B^2$—(C=O)—$B^1$, preferably an ethylene, trimethylene or tetramethylene group.

Where $B^3$ in the above group of formula —O—$B^2$—$B^3$ represents an alkoxy group having from 1 to 6 carbon atoms, this may be a straight or branched chain alkoxy group, and examples include the methoxy, ethoxy, propoxy, isopropoxy, butoxy, pentyloxy and 5-methylpentyloxy groups, of which we prefer the methoxy, ethoxy and propoxy groups.

Where $B^3$ in the above group of formula —O—$B^2$—$B^3$ represents an alkylthio group having from 1 to 6 carbon atoms, this may be a straight or branched chain alkylthio group, and examples include the methylthio, ethylthio, propylthio, isopropylthio, butylthio and pentylthio groups, of which we prefer the methylthio, ethylthio, propylthio and butylthio groups.

Where $B^3$ in the above group of formula —O—$B^2$—$B^3$ represents an alkylsulfinyl group having from 1 to 6 carbon atoms, this may be a straight or branched chain alkylsulfinyl group, and examples include the methylsulfinyl, ethylsulfmyl, propylsulfinyl, isopropylsulfinyl, butylsulfinyl and pentylsulfinyl groups, of which we prefer the methylsulfmyl, ethylsulfinyl, propylsulfinyl and butylsulfinyl groups.

Where $B^3$ in the above group of formula —O—$B^2$—$B^3$ represents an alkylsulfonyl group having from 1 to 6 carbon atoms, this may be a straight or branched chain alkylsulfonyl group, and examples include the methylsulfonyl, ethylsulfonyl, propylsulfonyl, isopropylsulfonyl, butylsulfonyl and pentylsulfonyl groups, of which we prefer the methylsulfonyl, ethylsulfonyl, propylsulfonyl and butylsulfonyl groups.

Where $B^3$ in the above group of formula —O—$B^2$—$B^3$ represents an alkylsulfonylamino group having 1 from 6 carbon atoms, the alkyl part may be a straight or branched chain alkyl group having from 1 to 6, preferably from 1 to 4, carbon atoms, and examples include the methylsulfonylamino, ethylsulfonylamino, propylsulfonylamino, isopropylsulfonylamino, butylsulfonylamino, isobutyl-sulfonylamino, pentylsulfonylamino, 3-methylbutylsulfonylamino, hexylsulfonylamino and 4-methylpentylsulfonylamino groups, of which we prefer the methylsulfonylamino, ethylsulfonylamino, isopropylsulfonylamino, butylsulfonylamino, isobutylsulfonylamino and pentylsulfonylamino groups.

Where any of $R^{2a}$, $R^{2b}$, $R^{2c}$ or $R^{2d}$ represents a group of formula —CH=N—$OB^4$, and $B^4$ represents an alkyl group having from 1 to 4 carbon atoms, this may be a straight or branched chain alkyl group, and examples include the methyl, ethyl, propyl, isopropyl, butyl and isobutyl groups, of which we prefer the methyl, ethyl and propyl groups.

Where any of $R^{2a}$, $R^{2b}$, $R^{2c}$ or $R^{2d}$ represents an alkylthio group having from 1 to 6 carbon atoms, this may be a straight or branched chain alkylthio group having from 1 to 6, preferably from 1 to 4, carbon atoms, and examples include the methylthio, ethylthio, propylthio, isopropylthio, butylthio, isobutylthio, sec-butylthio, t-butylthio, pentylthio, isopentylthio, neopentylthio, t-pentylthio, hexylthio and isohexylthio groups, of which we prefer the methylthio, ethylthio, propylthio, isopropylthio and butylthio groups, more preferably the methylthio and ethylthio groups.

Where any of $R^{2a}$, $R^{2b}$, $R^{2c}$ or $R^{2d}$ represents an alkylsulfinyl group having from 1 to 6 carbon atoms, this may be a straight or branched chain alkylsulfinyl group having from 1 to 6, preferably from 1 to 4, carbon atoms, and examples include the methylsulfinyl, ethylsulfinyl, propylsulfinyl, isopropyl-sulfinyl, butylsulfinyl, isobutylsulfinyl, sec-butylsulfinyl, t-butylsulfmyl, pentylsulfmyl, isopentylsulfmyl, neopentylsulfinyl, t-pentylsulfinyl, hexylsulfinyl and isohexylsulfinyl groups, of which we prefer the methylsulfinyl, ethylsulfmyl, propylsulfinyl, isopropylsulfinyl and butylsulfinyl groups, more preferably the methylsulfinyl and ethylsulfmyl groups.

Where any of $R^{2a}$, $R^{2b}$, $R^{2c}$ or $R^{2d}$ represents an alkylsulfonyl group having from 1 to 6 carbon atoms, this may be a straight or branched chain alkylsulfonyl group having from 1 to 6, preferably from 1 to 4, carbon atoms, and examples include the methylsulfonyl, ethylsulfonyl, propylsulfonyl, isopropyl-sulfonyl, butylsulfonyl, isobutylsulfonyl, sec-butylsulfonyl, t-butylsulfonyl, pentylsulfonyl, isopentylsulfonyl, neopentylsulfonyl, t-pentylsulfonyl, hexylsulfonyl and isohexylsulfonyl groups, of which we prefer the methylsulfonyl, ethylsulfonyl, propylsulfonyl, isopropylsulfonyl, butylsulfonyl, isobutylsulfonyl and pentylsulfonyl groups, more preferably the methylsulfonyl and ethylsulfonyl groups.

Where any of $R^{2a}$, $R^{2b}$, $R^{2c}$ or $R^{2d}$ represents an alkylsulfonylamino group having from 1 to 6 carbon atoms, the allyl part may be a straight or branched chain alkyl group having from 1 to 6, preferably from 1 to 4, carbon atoms, and examples include the methylsulfonylamino, ethylsulfonylamino, propylsulfonylamino, isopropylsulfonylamino, butylsulfonylamino, isobutylsulfonylamino, pentylsulfonylamino, 3-methylbutylsulfonylamino, hexylsulfonylamino and 4-methylpentylsulfonylamino groups, of which we prefer the methylsulfonylamino, ethylsulfonylamino, isopropylsulfonylamino, butylsulfonylamino, isobutylsulfonylamino and pentylsulfonylamino groups.

Where any of $R^{2a}$, $R^{2b}$, $R^{2c}$ or $R^{2d}$ represents a group of formula —$SO_2NR^eR^f$ (wherein $R^e$ represents a hydrogen atom or an alkyl group which has from 1 to 6 carbon atoms and $R^f$ represents an alkyl group which has from 1 to 6 carbon atoms), this is a mono- or di-alkylaminosulfonyl group in which the or each alkyl group has from 1 to 6 carbon atoms. The or each alkyl group may be a straight or branched chain alkyl group having from 1 to 6, preferably from 1 to 4, carbon atoms, and examples include those alkyl groups having from 1 to 6 carbon atoms and included in those given above in relation to $R^1$. Examples of such alkylaminosulfonyl groups include the dimethylaminosulfonyl, diethylaminosulfonyl, propylaminosulfonyl, isopropylaminosulfonyl, butylaminosulfonyl, pentylaminosulfonyl and hexylaminosulfonyl groups, of which we prefer the dimethylaminosulfonyl, diethylaminosulfonyl, isopropylaminosulfonyl and butylaminosulfonyl groups.

Where $R^{2a}$ and $R^{2b}$ are adjacent and together represent a group of formula —O—$(CH_2)_m$—O—, m is an integer of from 1 to 3, and this group this may be a methylenedioxy, ethylenedioxy, trimethylenedioxy or propylenedioxy group; preferably a methylenedioxy or ethylenedioxy group.

Where any of $R^{2a}$, $R^{2b}$, $R^{2c}$ or $R^{2d}$ represents a halogen atom, this may be, for example, a fluorine, chlorine, bromine or iodine atom, preferably a fluorine, chlorine or bromine atom.

The compounds of formula (I) include a substituted phenyl group which may be represented by the following partial structure:

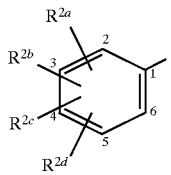

(in which R²a, R2b, R²c and R2d are as defined above).

Examples of preferred substituted phenyl groups which may be represented by the above partial formula include the 3,4-methylenedioxyphenyl, 2,3-methylenedioxyphenyl, 3,4-ethylenedioxyphenyl, 2,3-ethylenedioxyphenyl, 2-methoxyphenyl, 2-ethoxyphenyl, 4-methoxyphenyl, 2,3-dimethoxyphenyl, 2,4-dimethoxyphenyl, 2,5-dimethoxyphenyl, 2,3,4-trimethoxyphenyl, 2,4,5-trimethoxyphenyl, 2-chlorophenyl, 4-chlorophenyl, 2-fluorophenyl, 2-bromophenyl, 2-methylphenyl, 4-methylphenyl, 2-trifluoromethylphenyl, 3-trifluoromethylphenyl, 4-trifluoromethylphenyl, 2-nitrophenyl, 2-hydroxy-3-methoxyphenyl, 2-methoxy-4-hydroxyphenyl, 2-methoxy-4-methylphenyl, 2-methoxy-4-dimethylaminophenyl, 2,3-dimethoxy-5-nitrophenyl, 2,3-dimethoxy-5-dimethylaminophenyl, 2-methoxy-4-diethylaminophenyl, 2-(methoxymethoxy)phenyl, 2-methoxy-4-benzyloxyphenyl, 2-benzyloxy-3-methoxyphenyl, 2-methoxy-4-cyanophenyl, 2,4-dimethoxy-5-cyanophenyl, 2-methoxy-4-methylthiophenyl, 2-methoxy-4-methylsulfinylphenyl, 2-methoxy-4-methylsulfonylphenyl, 2-methoxy-4-ethoxyphenyl, 2-methoxy-4-(1-hydroxy-1-methylethyl)phenyl, 2-methoxy-4-(1-hydroxypropyl)phenyl, 2-methoxy-4-(1-hydroxy-2-methylpropyl)phenyl, 2-methoxy-4-(1-hydroxybutyl)phenyl, 2-methoxy-(1-hydroxy-3-methylbutyl)phenyl, 2-methoxy-4-propionylphenyl, 2-methoxy-4-isobutyrylphenyl, 2-methoxy-4-butyrylphenyl, 2-methoxy-4-isovalerylphenyl, 2-methoxy-4-isopropylsulfonylphenyl, 2-methoxy-4-isobutylsulfonylphenyl, 2,4-dimethoxy-5-butylaminosulfonylphenyl and 2-chloro-4-methoxyphenyl groups. Of these, we prefer the 3,4-methylenedioxyphenyl, 2,3-dimethylenedioxyphenyl, 3,4-ethylenedioxypheny, 2,3-ethylenedioxyphenyl, 2,3-dimethoxyphenyl, 2,4-dimethoxyphenyl, 2,5-dimethoxyphenyl, 2-hydroxy-3-methoxyphenyl, 2-methoxy-4-hydroxyphenyl, 2,3,4-trimethoxyphenyl, 2,4,5-trimethoxyphenyl, 2-methoxy-4-ethoxyphenyl, 2-methoxy-4-(1-hydroxy-1-methylethyl) phenyl, 2-methoxy-4-(1-hydroxypropyl)phenyl, 2-methoxy-4-(1-hydroxy-2-methylpropyl)phenyl, 2-methoxy-4-(1-hydroxybutyl)phenyl, 2-methoxy-(1-hydroxy-3-methylbutyl)phenyl, 2-methoxy-4-propionylphenyl, 2-methoxy-4-isobutyrylphenyl, 2-methoxy-4-butyrylphenyl, 2-methoxy-4-isovalerylphenyl, 2-methoxy-4-isopropylsulfonylphenyl, 2-methoxy-4-isobutylsulfonylphenyl, 2,4-dimethoxy-5-butylaminosulfonylphenyl and 2-chloro-4-methoxyphenyl groups.

Where $R^3$ represents an alkyl group having from 1 to 6 carbon atoms, this may be a straight or branched chain alkyl group having from 1 to 6, preferably from 2 to 4, carbon atoms, and examples include the methyl, ethyl, propyl, isopropyl, butyl, isobutyl, sec-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups. Of these, we prefer those groups having from 2 to 4 carbon atoms; and more prefer those having 3 or 4 carbon atoms, particularly the isopropyl and t-butyl groups.

Where $R^4$ in the compound of formula (I) represents a group of formula (II), (III), (IV), (V), (VI), (VII), (VI) or (IX), and any of $A^1$, $A^2$ and $A^3$ represents an alkylene group having from 1 to 6 carbon atoms, this may be a straight or branched chain group and examples include the methylene, ethylene, 1-methylethylene, propylene, trimethylene, tetramethylene, pentamethylene and hexamethylene groups; preferably those having from 1 to 4 carbon atoms.

Where $R^4$ in the compound of formula (I) represents a group of formula (II), (III), (IV), (V), (VI), (VII), (VIII) or (IX), and any of $A^1$, $A^2$ and $A^3$ represents an alkenylene group having 2 to 6 carbon atoms, this may be a straight or branched chain group and examples include the vinyl, 2-propenylene, 2 -butenylene and 3-butenylene groups, of which we prefer the vinyl and 2-propenylene groups.

Where $R^4$ in the compound of formula (I) represents a group of formula (II), (I) or (VI), and $R^{5a}$ or $R^{5b}$ represents an alkyl group having from 1 to 4 carbon atoms, this may be a straight or branched chain alkyl group having from 1 to 6, preferably from 1 to 4, carbon atoms, and examples include the methyl, ethyl, propyl, isopropyl, butyl, isobutyl, sec-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups. Of these, we prefer the methyl, ethyl, isopropyl, butyl and isobutyl groups, more preferably the methyl and ethyl groups.

Where $R^{5a}$ or $R^{5b}$ represents a group of formula —$A^4R^{5c}$ and $A^4$ represents an alkylene group having from 1 to 6 carbon atoms, this may be a straight or branched chain group and examples include the methylene, ethylene, trimethylene, tetramethylene and pentamethylene groups, of which we prefer the methylene and ethylene groups.

Where $R^{5a}$ or $R^{5b}$ represents a group of formula —$A^4R^{5c}$ and $A^4$ represents an alkenylene group having 2 to 6 carbon atoms, this may be a straight or branched chain group and examples include the vinyl, 2-propenylene and 2-butenylene groups, preferably the vinyl group.

Where $R^{5a}$ or $R^{5b}$ represents a group of formula —$A^4R^{5c}$ and $R^{5c}$ represents an alkoxy group having from 1 to 4 carbon atoms, this may be a straight or branched chain group and examples include the methoxy, ethoxy, propoxy and butoxy groups, of which we prefer the methoxy and ethoxy groups.

Where $R^{5a}$ or $R^{5b}$ represents a group of formula —$A^4R^{5c}$ and $R^{5c}$ represents an optionally substituted pyridyl group or where $R^4$ represents a group of formula (VII) or (VIII) and $R^8$ represents an optionally substituted pyridyl group, this may be a 2-pyridyl, 3-pyridyl or 4-pyridyl group which is unsubstituted or which has one or more (preferably from 1 to 3) substituents. There is no particular restriction on the nature of the substituents, and examples include substituents α, defined and exemplified above, preferably the alkyl and alkoxy groups, and more preferably the methyl and methoxy groups. Specific examples of such unsubstituted and substituted pyridyl groups include the 2-pyridyl, 3-pyridyl, 4-pyridyl, 4-methoxy-2-pyridyl, 3-methyl-2-pyridyl, 4-methoxy-3-pyridyl and 5-methoxypyridyl groups, of which we prefer the 2-pyridyl, 3-pyridyl and 4-pyridyl groups.

Where $R^{5a}$ or $R^{5b}$ represents a group of formula —$A^4R^{5c}$ and $R^{5c}$ represents an optionally substituted pyrimidinyl group or where $R^4$ represents a group of formula (VII) or (VIII) and $R^8$ represents an optionally substituted pyrimidinyl group, this may be a 2-pyrimidinyl, 4-pyrimidinyl or 5-pyrimidinyl group which is unsubstituted or which has one or more (preferably from 1 to 3) substituents. There is no particular restriction on the nature of the substituents, and examples include substituents α, defined and exemplified above, preferably the alkyl and alkoxy groups, and more preferably the methyl and methoxy groups. Specific examples of such unsubstituted and substituted pyrimidinyl groups include the 2-pyrimidinyl, 4-pyrimidinyl, 5-pyrimidinyl, 2-methoxy-4-pyrimidinyl and 2-methoxy-5-pyrimidinyl groups, of which we prefer the 2-pyrimidinyl, 4-pyrimidinyl and 5-pyrimidinyl groups.

Where $R^{5a}$ or $R^{5b}$ represents a group of formula —$A^4R^{5c}$ and $R^{5c}$ represents an optionally substituted pyrazinyl group or where $R^4$ represents a group of formula (VII) or (VIII) and $R^8$ represents an optionally substituted pyrazinyl group, this is a 2-pyrazinyl group which is unsubstituted or which has one or more (preferably from 1 to 3) substituents. There is no particular restriction on the nature of the substituents, and examples include substituents α, defined and exemplified above, preferably the alkyl and alkoxy groups, and more preferably the methyl and methoxy groups. Specific examples of such unsubstituted and substituted pyrazinyl groups include the 2-pyrazinyl and 2-methoxy-5-pyrazinyl groups.

Where $R^{5a}$ or $R^{5b}$ represents a group of formula —$A^4R^{5c}$ and $R^{5c}$ represents an optionally substituted pyrazolyl group or where $R^4$ represents a group of formula (VII) or (VIII) and $R^8$ represents an optionally substituted pyrazolyl group, this may be a 3-pyrazolyl or 2-pyrazolyl group which is unsubstituted or which has one or more (preferably from 1 to 3) substituents. There is no particular restriction on the nature of the substituents, and examples include substituents α, defined and exemplified above, preferably the alkyl and alkoxy groups, and more preferably the methyl and methoxy groups. Specific examples of such unsubstituted and substituted pyrazolyl groups include the 3-pyrazolyl, 2-pyrazolyl, 4-methyl-2-pyrazolyl and 4-methyl-3-pyrazolyl groups, of which we prefer the 3-pyrazolyl and 2-pyrazolyl groups.

Where $R^{5a}$ or $R^{5b}$ represents a group of formula —$A^4R^{5c}$ and $R^{5c}$ represents an optionally substituted imidazolyl group or where $R^4$ represents a group of formula (VII) or (VIII) and $R^8$ represents an optionally substituted imidazolyl group, this may be a 2-imidazolyl, 3-imidazolyl or 4-imidazolyl group which is unsubstituted or which has one or more (preferably from 1 to 3) substituents. There is no particular restriction on the nature of the substituents, and examples include substituents a, defined and exemplified above, preferably the alkyl and alkoxy groups, and more preferably the methyl and methoxy groups. Specific examples of such unsubstituted and substituted imidazolyl groups include the 2-imidazolyl, 3-imidazolyl, 4-imidazolyl, 2-methoxy-3-imidazolyl and 2-methoxy-4-imidazolyl groups, of which we prefer the 2-imidazolyl and 3-imidazolyl groups.

Where $R^{5a}$ or $R^{5b}$ represents a group of formula —$A^4R^{5c}$ and $R^{5c}$ represents an optionally substituted thiazolyl group or where $R^4$ represents a group of formula (V) or (VI) and $R^8$ represents an optionally substituted thiazolyl group, this may be a 2-thiazolyl, 4-thiazolyl or 5-thiazolyl group which is unsubstituted or which has one or more preferably from 1 to 3) substituents. There is no particular restriction on the nature of the substituents, and examples include substituents a, defined and exemplified above, preferably the alkyl and alkoxy groups, and more preferably the methyl and methoxy groups. Specific examples of such unsubstituted and substituted thiazolyl groups include the 2-thiazolyl, 4-thiazolyl, 5-thiazolyl, 2-methyl-4-thiazolyl and 2-methoxy-4-thiazolyl groups, of which we prefer the 2-thiazolyl and 4-thiazolyl groups.

Where $R^{5a}$ or $R^{5b}$ represents a group of formula —$A^4R^{5c}$ and $R^{5c}$ represents an optionally substituted 1,2,4-triazolyl group or where $R^4$ represents a group of formula (VII) or (VIII) and $R^8$ represents an optionally substituted 1,2,4-triazolyl group, this may be a 1,2,4-triazol-1-yl, 1,2,4-triazol-3-yl or 1,2,4-triazol-4-yl group, which is unsubstituted or which has one or more (preferably from 1 to 3) substituents. There is no particular restriction on the nature of the substituents, and examples include substituents α, defined and exemplified above, preferably the alkyl and alkoxy groups, and more preferably the methyl and methoxy groups. A particularly preferred group is the 1,2,4-triazol-1-yl group.

Where $R^{5a}$ and $R^{5b}$ together represent a group of formula

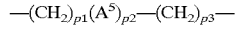

(wherein p1 is an integer of 1 or 2; p2 is 0 or the integer 1; p3 is an integer of 1 or 2; and $A^5$ represents an oxygen atom, an imino group or an alkylimino group having from 1 to 4 carbon atoms), then they, together with the nitrogen atom to which they are attached, form a nitrogen-containing heterocyclic ring. Examples of such nitrogen-containing heterocyclic rings include the 1-pyrrolidinyl, 1-piperidinyl, 1-morpholinyl, 1-piperazinyl, 4-methyl-1-piperazinyl and 4-ethyl-1-piperazinyl groups, of which we prefer the 1-pyrrolidinyl, 1-morpholinyl, 1-piperazinyl and 4-methyl-1-piperazinyl groups.

Where $R^4$ represents a group of formula (V), and $R^6$ represents an alkyl group having from 1 to 4 carbon atoms, this may be a straight or branched chain group and examples include the methyl, ethyl, propyl, isopropyl and butyl groups, of which we prefer the methyl, ethyl and propyl groups.

Where $R^4$ represents a group of formula (V), and $R^6$ represents an optionally substituted phenyl group, there is no specific restriction on the nature of the substituents, and any substituent commonly used on a phenyl group in compounds of this type may equally be employed here. Examples of suitable substituents include the following substituents β:

alkyl groups having from 1 to 4 carbon atoms, which may be straight or branched chain groups, such as the methyl, ethyl, propyl, isopropyl, butyl, isobutyl, sec-butyl and t-butyl groups;

alkoxy groups having from 1 to 4 carbon atoms, which may be straight or branched chain groups, such as the methoxy, ethoxy, propoxy, isopropoxy, butoxy, isobutoxy, sec-butoxy and t-butoxy groups;

halogen atoms, such as the fluorine, chlorine, bromine or iodine atoms, especially the fluorine atom;

nitro groups; and amino and mono- and di- alkylamino groups such as those exemplified above having the formula —$NR^aR^b$.

Of these, the alkoxy groups and halogen atoms are preferred, especially the methoxy group and fluorine atom. Specific examples of such unsubstituted and substituted phenyl groups include the phenyl, 4-methoxyphenyl, 4-fluorophenyl and 2-fluorophenyl groups, of which we prefer the phenyl group and the 4-methoxyphenyl group.

Where $R^4$ represents a group of formula (VI), and $R^7$ represents an alkyl group having from 1 to 4 carbon atoms, this group may be as defined and exemplified above in relation to $R^6$. The preferred groups are also the same as those preferred for $R^6$.

Where $R^4$ represents a group of formula (VII) or (VIII), and $R^8$ represents an alkyl group having from 1 to 12 carbon atoms, this group may be as defined and exemplified above in relation to $R^1$. The preferred groups are the methyl, ethyl, propyl, isopropyl and butyl groups.

Where $R^4$ represents a group of formula (VII) or (VIII), and $R^8$ represents an alkyl group having from 1 to 12 carbon atoms and substituted by a carboxy group which may be protected, the alkyl part may be any of those exemplified above in relation to $R^1$. There is no specific restriction on the nature of the protecting group, and any protecting group commonly used in compounds of this type may equally be used here. Examples of suitable protecting groups include alkyl groups having from 1 to 12 carbon atoms (such as those exemplified above in relation to $R^1$, preferably the methyl, ethyl and propyl groups), and benzyl and phenyl groups which may be unsubstituted or may be substituted by at least one of substituents β, defined and exemplified above. Specific examples of such optionally protected carboxyalkyl groups include the benzyloxycarbonylmethyl, carboxymethyl, 2-(benzyloxycarbonyl)ethyl, 2-(methoxycarbonyl)ethyl, 2-carboxyethyl, 3-(benzyloxycarbonyl)propyl, 3-ethoxycarbonylpropyl and 3-carboxypropyl groups, of which we prefer the 2-(benzyloxycarbonyl)ethyl and 2-carboxyethyl groups.

Where $R^4$ represents a group of formula (VII) or (VIII), and $R^8$ represents an alkyl group having from 1 to 12 carbon atoms and substituted by from 1 to 5 fluorine atoms, these may be as defined and exemplified above in relation to $R^{2a}$, $R^{2b}$, $R^{2c}$ and $R^{2d}$, and the preferred groups are also those as listed as preferred in relation to $R^{2a}$, $R^{2b}$, $R^{2c}$ and $R^{2d}$.

Where $R^4$ represents a group of formula (VII) or (VIII), and $R^8$ represents an alkoxy group having from 1 to 10 carbon atoms, these may be as defined and exemplified above in relation to $R^{2a}$, $R^{2b}$, $R^{2c}$ and $R^{2d}$. Preferred groups are the methoxy, ethoxy, propoxy and butoxy groups.

Where $R^4$ represents a group of formula (VII) or (VIII), and $R^8$ represents an aralkoxy group in which an alkoxy group having from 1 to 4 carbon atoms is substituted by a carbocyclic aryl group having from 6 to 10 ring carbon atoms, the alkoxy part may be any of those defined and exemplified above in relation to substituents β, and the aryl part is preferably a phenyl or naphthyl group, more preferably a phenyl group. More preferably the aralkoxy group has a total of from 7 to 10 carbon atoms in the alkoxy and aryl parts. Specific examples of such groups include the benzyloxy, 2-phenylethyloxy and 3-phenylethyloxy groups, of which we prefer the benzyloxy group.

Where $R^4$ represents a group of formula (VII) or (VIII), and $R^8$ represents an optionally substituted phenyl group, this group may be as defined and exemplified above in relation to $R^6$. The preferred groups are also the same as those preferred for $R^6$.

Where $R^4$ represents a group of formula (VII) or (VIII), and $R^8$ represents an optionally substituted piperidinyl group, the substituents are preferably selected from substituents α, defined and exemplified above. Specific examples of such groups include the 2-piperidinyl, 3-methoxy-6-piperidinyl and 4-methoxy-6-piperidinyl groups, preferably the 2-piperidinyl group.

Where $R^4$ represents a group of formula (VII) or (VIR), and $R^8$ represents an optionally substituted pyrrolidinyl group, the substituents are preferably selected from substituents α, defined and exemplified above. The pyrrolidinyl group is preferably a 2-pyrrolidinyl, 3-pyrrolidinyl or 5-pyrrolidinyl groups. Specific examples of such groups include the 2-pyrrolidinyl, 3-pyrrolidinyl and 3-methoxy-5-pyrrolidinyl groups, preferably the 2-pyrrolidinyl group.

Where $R^4$ represents a group of formula (VII) or (VIII), and $R^8$ represents an optionally substituted. morpholinyl group, the substituents are preferably selected from substituents α, defined and exemplified above. The morpholinyl group is preferably a 2-morpholinyl or 3-morpholinyl group. Specific examples of such groups include the 2-morpholinyl, 3-morpholinyl, 4-methyl-2-morpholinyl and 4-methyl-3-morpholinyl groups, preferably the 3-morpholinyl group.

Where $R^4$ represents a group of formula (VII) or (VIII), and $R^8$ represents an optionally substituted piperazinyl group, the substituents are preferably selected from substituents α, defined and exemplified above. The piperazinyl group is preferably a 2-piperazinyl group. Specific examples of such groups include the 4-methyl-2-piperazinyl and 2-piperazinyl groups.

Where $R^4$ represents a group of formula (IX), and $R^9$ or $R^{10}$ represents an an alkyl group having from 1 to 4 carbon atoms, this group may be as defined and exemplified above in relation to $R^6$. The preferred groups are also the same as those preferred for $R^6$.

Where $R^4$ represents a group of formula (IX), and $R^9$ or $R^{10}$ together represent a group of formula $-(CH_2)_{p4}-$ (wherein p4 is an integer of from 2 to 4), this is preferably an ethylene, trimethylene or propylene group, preferably an ethylene group.

In the compounds of formula (I) $R^4$ is preferably located on the benzene ring at the meta-position with respect to $R^3$ and at the ortho-position with respect to the amino group (that is, at the 6-position) or at the para-position with respect to $R^3$ and at the meta-position with respect to the amino group (that is, at the 5-position).

Particularly preferred groups represented by $R^4$ in the compounds of the present invention include the 5-carbamoyl, 6-carbamoyl, 5-N-methylcarbamoyl, 6-N-methylcarbamoyl, 5-carbamoylmethyl, 5-(N-methylcarbamoyl)methyl, 5-(2-carbamoyl)ethyl, 5-[2-(N-methylcarbamoyl)ethyl], 5-(4-morpholinyl)-carbonyl, 5-carbamoyloxymethyl, 5-(N-methylcarbamoyl)oxymethyl, 5-cyano, 5-cyanomethyl, 6-cyano, 5-methylsulfonylaminomethyl, 5-(N-methylamino)-carbonylaminomethyl, 5-ethylsulfonylaminomethyl, 5-aminocarbonylamino-methyl, 5-(N-ethylamino)carbonylaminomethyl, 5-(N-isopropylamino)carbonyl-aminomethyl, 5-acetylaminocarbonyl, 5-propionylaminocarbonyl, 5-(2-methylpropionyl)aminocarbonyl, 5-(3-pyridyl)carbonylaminocarbonyl, 5-(2-pyridyl)aminocarbonyl, 5-(3-pyridyl)aminocarbonyl, 5-succinimidomethyl and 5-phthalimidomethyl groups. In these groups, the "5-" or "6-" represents the position at which the group represented by $R^4$ is bound to the phenyl ring.

We particularly prefer that n should represent 0.

The compounds of the present invention can exist in the form of various stereoisomers, depending upon the presence of asymmetric carbon atoms. The present invention covers both the individual isomers and mixtures thereof.

The compounds of the present invention can also exist in the form of salts. Where the compound is intended for pharmaceutical use, the resulting salt should be pharmaceutically acceptable, which, as is well known, means that it must not exhibit a lower activity (or unacceptably lower activity) or a higher toxicity (or unacceptably higher toxicity) than does the parent compound. Examples of preferred such salts include: salts with alkali metals, e.g. sodium, potassium or lithium; salts with alkaline earth metal, e.g. calcium or magnesium; salts with other metals, e.g. aluminum, iron, zinc, copper, nickel or cobalt; inorganic salts such as ammonium salts; amine salts, e.g. salts with organic amines such as t-octylamine, dibenzylamine, morpholine, glucosamine, alkyl phenylglycinate, ethylenediamine, methylglucamine, guanidine, diethylamine, triethylamine, dicyclohexylamine, N,N'-dibenzylethylenediamine, chloroprocaine, procaine, diethanolamine, benzylphenethylamine, piperazine, tetramethylammonium or tris(hydroxymethyl)aminomethane; salts with inorganic acids such as the hydrohalic acids (e.g. hydrofluoric acid, hydrochloric acid, hydrobromic acid or hydroiodic acid), or with other inorganic acids (e.g. nitric acid, perchloric acid, sulfuric acid or phosphoric acid); salts with organic acids such as salts with lower alkanesulfonic acids, e.g. methanesulfonic acid, trifluoromethanesulfonic acid or ethanesulfonic acid, salts of arylsulfonic acids, e.g. benzenesulfonic acid or p-toluenesulfonic acid, acetic acid, fumaric acid, succinic acid, citric acid, tartaric acid, oxalic acid or maleic acid; salts of amino acids such as glycine, lysine, arginine, ornithine, glutamic acid or aspartic acid.

The compounds of the invention take up water upon exposure to the atmosphere to absorb water or to produce a hydrate. The present invention covers such hydrates.

Preferred compounds of the present invention are those compounds of formula (I) and salts thereof in which:

(A) $R^1$ represents a propyl, isopropyl, butyl, isobutyl, pentyl, isopentyl, hexyl or heptyl group.

(B) Two adjacent groups among $R^{2a}$, $R^{2b}$, $R^{2c}$ and $R^{2d}$ together represent a methylenedioxy or ethylenedioxy group and the remaining two groups each represents a hydrogen atom.

(C) Two or three groups among $R^{2a}$, $R^{2b}$, $R^{2c}$ and $R^{2d}$ each represents a methoxy group and the remaining two or one groups each represents a hydrogen atom.

(D) One of $R^{2a}$, $R^{2b}$, $R^{2c}$ and $R^{2d}$ represents a methoxy group, another one group represents a hydroxy group, and the remaining two groups each represents a hydrogen atom.

(E) One of $R^{2a}$, $R^{2b}$, $R^{2c}$ and $R^{2d}$ represents a methoxy group, another one group represents a ethoxy group and the remaining two groups each represents a hydrogen atom.

(F) One of $R^{2a}$, $R^{2b}$, $R^{2c}$ and $R^{2d}$ represents a methoxy group, another one group represents a 1-hydroxy-1-methylethyl, 1-hydroxypropyl, 1-hydroxy-2-methylpropyl, 1-hydroxybutyl or 1-hydroxy-3-methylbutyl group and the remaining two groups each represents a hydrogen atom.

(G) One of $R^{2a}$, $R^{2b}$, $R^{2c}$ and $R^{2d}$ represents a methoxy group, another one group represents a propionyl, isobutyryl, butyryl or isovaleryl group and the remaining two groups each represents a hydrogen atom.

(H) One of $R^{2a}$, $R^{2b}$, $R^{2c}$ and $R^{2d}$ represents a methoxy group, another one group represents an isopropylsulfonyl, isobutylsulfonyl or butylsulfonyl group and the remaining two groups each represents a hydrogen atom.

(J) $R^3$ represents an isopropyl or t-butyl group.

(K) $R^4$ represents a carbamoyl, methylcarbamoyl, carbamoylmethyl, 2-carbamoylethyl, methylcarbamoylmethyl, 2-(N-methylcarbamoyl)ethyl, carbamoyloxymethyl, cyano, cyanomethyl, methylsulfonylaminomethyl, ethylsulfonylaminomethyl, aminocarbonylaminomethyl, (methylamino)-carbonylaminomethyl, acetylaminocarbonyl, propionylaminocarbonyl, (2-methylpropionyl)aminocarbonyl, 3-(pyridyl) aminocarbonyl or phthalimidomethyl group, preferably a carbamoyl, methylcarbamoyl, carbamoylmethyl, 2-carbamoylethyl, methylcarbamoylmethyl or 2-N-methylcarbamoylethyl group.

(L) n represents 0.

The most preferred compounds are those compounds of formula (I) and salts thereof in which $R^1$ is as defined in (A), $R^{2a}$, $R^{2b}$, $R^{2c}$ and $R^{2d}$ are as defined in any one of (B) to (H), $R^3$ is as defined in (J), $R^4$ is as defined in (K) and n is as defined in (L).

Examples of certain compounds of the present invention are those compounds of formula (I-1):

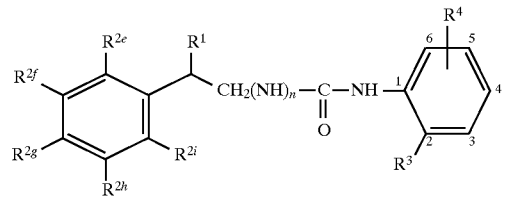

In the above formula, the substituents are as defined in Table 1. In the Table, the following abbreviations are used:

Ac: acetyl
Bu: butyl
iBu: isobutyl
tBu: t-butyl
Dc: decyl
Ddc: dodecyl
Et: ethyl
Hp: heptyl
Hx: hexyl
Imid: imidazolyl
Me: methyl
Morp: morpholinyl
Nn: nonyl
Oc: octyl
1-Para-4-Me: 4-methyl-1-piperazinyl
Ph: phenyl
PhCH$_2$: benzyl
Phth: phthaloyl
Pipe: piperidinyl
Pn: pentyl
iPn: isopentyl
Pr: propyl
iPr: isopropyl
Ppra: piperazinyl
Pyri: pyridyl
Pyrm: pyrimidinyl
Pyro: pyrrolidinyl
Pyrz: pyrazinyl
Pyzo: pyrazolyl
Succ: succinyl
Thia: thiazolyl
Tria: 1,2,4-triazolyl.

TABLE 1

| Cpd No. | R$^1$ | R$^{2e}$ | R$^{2f}$ | R$^{2g}$ | R$^{2h}$ | R$^{2i}$ | R$^3$ | R$^4$ | n |
|---|---|---|---|---|---|---|---|---|---|
| 1 | Pn | —OCH$_2$O— | | H | H | H | tBu | 5-CONH$_2$ | 0 |
| 2 | Pn | —OCH$_2$O— | | H | H | H | tBu | 5-CONHMe | 0 |
| 3 | Pn | —OCH$_2$O— | | H | H | H | tBu | 5-CONMe$_2$ | 0 |
| 4 | Pn | —OCH$_2$O— | | H | H | H | iPr | 6-CONH$_2$ | 0 |
| 5 | Pn | —OCH$_2$O— | | H | H | H | tBu | 5-CH$_2$CONHMe | 0 |
| 6 | Pn | —OCH$_2$O— | | H | H | H | tBu | 5-(CH$_2$)$_2$CONHMe | 0 |
| 7 | Pn | —OCH$_2$O— | | H | H | H | tBu | 5-CONHMe | 1 |
| 8 | Pn | —OCH$_2$O— | | H | H | H | tBu | 5-CH$_2$OCONH$_2$ | 0 |
| 9 | Pn | —OCH$_2$O— | | H | H | H | tBu | 5-CH$_2$OCONHMe | 0 |
| 10 | Pn | —O(CH$_2$)$_2$O— | | H | H | H | tBu | 5-CONH$_2$ | 0 |
| 11 | Pn | —O(CH$_2$)$_2$O— | | H | H | H | tBu | 5-CONHPr | 0 |
| 12 | Pn | —O(CH$_2$)$_2$O— | | H | H | H | tBu | 5-CH=CH—CONH$_2$ | 0 |
| 13 | Pn | —O(CH$_2$)$_2$O— | | H | H | H | tBu | 5-CH=CH—CH$_2$OCONH$_2$ | 0 |
| 14 | Pn | —O(CH$_2$)$_2$O— | | H | H | H | iPr | 6-CONMe$_2$ | 0 |
| 15 | Bu | H | | —O(CH$_2$)$_2$O— | H | H | tBu | 5-(CH$_2$)$_2$CONMe$_2$ | 0 |
| 16 | Hx | H | | —OCH$_2$O— | H | H | tBu | 5-(CH$_2$)$_3$CONHMe | 0 |
| 17 | Bu | H | | —OCH$_2$O— | H | H | tBu | 5-(CH$_2$)$_4$CONMe$_2$ | 0 |
| 18 | Bu | OMe | H | H | H | H | tBu | 5-CONH$_2$ | 0 |
| 19 | Pn | OMe | H | H | H | H | tBu | 5-CH$_2$CONHMe | 0 |
| 20 | Pn | OMe | H | H | H | H | tBu | 5-(CH$_2$)$_2$CONHMe | 0 |
| 21 | Pn | OMe | H | H | H | H | iPr | 6-CONMe$_2$ | 0 |
| 22 | Pn | H | OMe | H | H | H | tBu | 5-CONHMe | 0 |
| 23 | Pn | H | H | OMe | H | H | tBu | 5-CONH$_2$ | 0 |
| 24 | Pn | H | H | OMe | H | H | tBu | 5-CH$_2$OCONHMe | 0 |
| 25 | Bu | OEt | H | H | H | H | tBu | 5-CONH$_2$ | 0 |
| 26 | Pn | OMe | OMe | H | H | H | tBu | 5-CONH$_2$ | 0 |
| 27 | Pn | OMe | OMe | H | H | H | tBu | 5-CONHMe | 0 |
| 28 | Pn | OMe | OMe | H | H | H | tBu | 5-CH$_2$CONHMe | 0 |
| 29 | Pn | OMe | OMe | H | H | H | tBu | 5-CH$_2$OCONHMe | 0 |
| 30 | Pn | OMe | H | OMe | H | H | tBu | 5-CONH$_2$ | 0 |
| 31 | Pn | OMe | H | OMe | H | H | tBu | 5-CONHMe | 0 |
| 32 | Pn | OMe | H | OMe | H | H | tBu | 5-CONMe$_2$ | 0 |
| 33 | Pn | OMe | H | OMe | H | H | tBu | 5-CONHEt | 0 |
| 34 | Pn | OMe | H | OMe | H | H | tBu | 5-CONHPr | 0 |
| 35 | Pn | OMe | H | OMe | H | H | tBu | 5-CONHBu | 0 |
| 36 | Pn | OMe | H | OMe | H | H | iPr | 6-CONH$_2$ | 0 |
| 37 | Pn | OMe | H | OMe | H | H | iPr | 6-CONHMe | 0 |
| 38 | Pn | OMe | H | OMe | H | H | tBu | 5-CH$_2$CONH$_2$ | 0 |
| 39 | Pn | OMe | H | OMe | H | H | tBu | 5-CH$_2$CONHMe | 0 |
| 40 | Pn | OMe | H | OMe | H | H | tBu | 5-CH$_2$CONMe$_2$ | 0 |
| 41 | Pn | OMe | H | OMe | H | H | tBu | 5-(CH$_2$)$_2$CONH$_2$ | 0 |
| 42 | Pn | OMe | H | OMe | H | H | tBu | 5-(CH$_2$)$_2$CONHMe | 0 |
| 43 | Pn | OMe | H | OMe | H | H | tBu | 5-(CH$_2$)$_3$CONHMe | 0 |
| 44 | Pn | OMe | H | OMe | H | H | tBu | 5-(CH$_2$)$_4$CONHMe | 0 |
| 45 | Pn | OMe | H | OMe | H | H | tBu | 5-CH=CH—CONHMe | 0 |
| 46 | Pn | OMe | H | OMe | H | H | tBu | 5-CH$_2$OCONH$_2$ | 0 |
| 47 | Pn | OMe | H | OMe | H | H | tBu | 5-CH$_2$OCONHMe | 0 |
| 48 | Pn | OMe | H | OMe | H | H | tBu | 5-CH$_2$OCONMe$_2$ | 0 |
| 49 | Pn | OMe | H | OMe | H | H | tBu | 5-CH$_2$OCONHPr | 0 |
| 50 | Pn | OMe | H | OMe | H | H | tBu | 5-(CH$_2$)$_2$OCONH$_2$ | 0 |
| 51 | Pn | OMe | H | OMe | H | H | tBu | 5-(CH$_2$)$_2$OCONHMe | 0 |
| 52 | Pn | OMe | H | OMe | H | H | tBu | 5-(CH$_2$)$_3$OCONH$_2$ | 0 |
| 53 | Pn | OMe | H | OMe | H | H | tBu | 5-(CH$_2$)$_3$OCONMe$_2$ | 0 |
| 54 | Pn | OMe | H | OMe | H | H | tBu | 5-CH=CH—CH$_2$OCONH$_2$ | 0 |
| 55 | Pn | OMe | H | OMe | H | H | iPr | 6-CH$_2$OCONH$_2$ | 0 |
| 56 | Pn | OMe | H | OMe | H | H | iPr | 6-CH$_2$OCONHMe | 0 |
| 57 | Bu | OMe | H | OMe | H | H | tBu | 5-CONH$_2$ | 0 |
| 58 | Bu | OMe | H | OMe | H | H | tBu | 5-CONHMe | 0 |
| 59 | Bu | OMe | H | OMe | H | H | tBu | 5-CONMe$_2$ | 0 |
| 60 | Bu | OMe | H | OMe | H | H | tBu | 5-CH$_2$CONHMe | 0 |
| 61 | Bu | OMe | H | OMe | H | H | tBu | 5-(CH$_2$)$_2$CONHMe | 0 |
| 62 | Bu | OMe | H | OMe | H | H | tBu | 5-CH$_2$OCONHMe | 0 |
| 63 | Bu | OMe | H | OMe | H | H | iPr | 6-(CH$_2$)$_3$OCONH$_2$ | 0 |
| 64 | Hx | OMe | H | OMe | H | H | tBu | 5-CONH$_2$ | 0 |
| 65 | Hx | OMe | H | OMe | H | H | tBu | 5-CONHMe | 0 |
| 66 | Hx | OMe | H | OMe | H | H | tBu | 5-CH$_2$CONHMe | 0 |
| 67 | Hx | OMe | H | OMe | H | H | tBu | 5-CH$_2$OCONH$_2$ | 0 |
| 68 | Hp | OMe | H | OMe | H | H | tBu | 5-CONH$_2$ | 0 |
| 69 | Oc | OMe | H | OMe | H | H | tBu | 5-CONH$_2$ | 0 |
| 70 | Pr | OMe | H | OMe | H | H | tBu | 5-CONHEt | 0 |
| 71 | Pn | —O(CH$_2$)$_2$O— | | H | H | H | tBu | 5-CONH$_2$ | 1 |
| 72 | Bu | —O(CH$_2$)$_2$O— | | H | H | H | tBu | 5-CONHMe | 1 |
| 73 | Pn | —O(CH$_2$)$_2$O— | | H | H | H | tBu | 5-CH$_2$OCONH$_2$ | 1 |
| 74 | Hx | H | | —O(CH$_2$)$_2$O— | H | H | tBu | 5-CONH$_2$ | 1 |
| 75 | Pn | H | | —OCH$_2$— | H | H | tBu | 5-CONHPr | 1 |
| 76 | Pn | OMe | H | H | H | H | tBu | 5-CONH$_2$ | 1 |

TABLE 1-continued

| Cpd No. | R¹ | R²ᵉ | R²ᶠ | R²ᵍ | R²ʰ | R²ⁱ | R³ | R⁴ | n |
|---|---|---|---|---|---|---|---|---|---|
| 77 | Pn | H | OMe | H | H | H | tBu | 5-CONHEt | 1 |
| 78 | Pn | H | H | OMe | H | H | tBu | 5-CONHMe | 1 |
| 79 | Pn | OMe | OMe | H | H | H | tBu | 5-CONHMe | 1 |
| 80 | Pn | OMe | OMe | H | H | H | tBu | 5-CH₂OCONH₂ | 1 |
| 81 | Pn | OMe | OMe | H | H | H | tBu | 5-CH₂CONMe₂ | 1 |
| 82 | Pn | OMe | H | OMe | H | H | tBu | 5-CONH₂ | 1 |
| 83 | Pn | OMe | H | OMe | H | H | tBu | 5-CONHMe | 1 |
| 84 | Pn | OMe | H | OMe | H | H | tBu | 5-CONMe₂ | 1 |
| 85 | Bu | OMe | H | OMe | H | H | tBu | 5-CH₂CONHMe | 1 |
| 86 | Bu | OMe | H | OMe | H | H | tBu | 5-(CH₂)₂CONHMe | 1 |
| 87 | Bu | OMe | H | OMe | H | H | tBu | 5-CH₂OCONH₂ | 1 |
| 88 | Bu | OMe | H | OMe | H | H | tBu | 5-CH₂OCONHMe | 1 |
| 89 | Pn | OMe | H | H | OMe | H | tBu | 5-CONH₂ | 0 |
| 90 | Pn | OMe | H | H | OMe | H | tBu | 5-CONHMe | 0 |
| 91 | Pn | OMe | H | H | OMe | H | tBu | 5-CH₂CONHMe | 0 |
| 92 | Pn | OMe | H | H | OMe | H | tBu | 5-CH₂OCONH₂ | 0 |
| 93 | Pn | OMe | OMe | OMe | H | H | tBu | 5-CONH₂ | 0 |
| 94 | Pn | OMe | OMe | OMe | H | H | tBu | 5-CH₂OCONH₂ | 0 |
| 95 | Pn | OMe | OMe | OMe | H | H | tBu | 5-CH₂CONHMe | 0 |
| 96 | Pn | OMe | H | OMe | OMe | H | tBu | 5-CONH₂ | 0 |
| 97 | Pn | OMe | H | OMe | OMe | H | tBu | 5-CONHMe | 0 |
| 98 | Pn | OMe | H | OMe | OMe | H | tBu | 5-CONMe₂ | 0 |
| 99 | Pn | OMe | H | OMe | OMe | H | iPr | 6-CONH₂ | 0 |
| 100 | Pn | OMe | H | OMe | OMe | H | tBu | 5-CH₂CONHMe | 0 |
| 101 | Pn | OMe | H | OMe | OMe | H | tBu | 5-(CH₂)₂CONHMe | 0 |
| 102 | Pn | OMe | H | OMe | OMe | H | tBu | 5-CONHMe | 1 |
| 103 | Pn | OMe | H | OMe | OMe | H | tBu | 5-CH₂OCONH₂ | 0 |
| 104 | Bu | OMe | H | OMe | OMe | H | tBu | 5-CH₂OCONHMe | 0 |
| 105 | Bu | Cl | H | H | H | H | tBu | 5-CONH₂ | 0 |
| 106 | Pn | Cl | H | H | H | H | tBu | 5-CONMe₂ | 0 |
| 107 | Pn | Cl | H | H | H | H | tBu | 5-CONHMe | 0 |
| 108 | Pn | Cl | H | H | H | H | tBu | 5-CH₂CONHMe | 0 |
| 109 | Pn | Cl | H | H | H | H | tBu | 5-CH₂OCONH₂ | 0 |
| 110 | Pn | H | Cl | H | H | H | tBu | 5-CONHMe | 0 |
| 111 | Bu | H | H | Cl | H | H | tBu | 5-CH₂CONHMe | 0 |
| 112 | Pn | F | H | H | H | H | tBu | 5-CONH₂ | 0 |
| 113 | Pn | F | H | H | H | H | tBu | 5-CH₂CONHMe | 0 |
| 114 | Pn | Me | H | H | H | H | tBu | 5-CH=CH—CONHMe | 0 |
| 115 | Bu | H | H | Me | H | H | tBu | 5-CH=CH—CH₂OCONH₂ | 0 |
| 116 | Pn | CF₃ | H | H | H | H | tBu | 5-CONH₂ | 0 |
| 117 | Pn | CF₃ | H | H | H | H | tBu | 5-CONHMe | 0 |
| 118 | Pn | CF₃ | H | H | H | H | tBu | 5-CONHtBu | 0 |
| 119 | Pn | CF₃ | H | H | H | H | tBu | 5-CH₂OCONH₂ | 0 |
| 120 | Pn | H | CF₃ | H | H | H | tBu | 5-CONH₂ | 0 |
| 121 | Pr | H | H | CF₃ | H | H | tBu | 5-CONHEt | 0 |
| 122 | Pn | NO₂ | H | H | H | H | tBu | 5-CONH₂ | 0 |
| 123 | Oc | OH | OMe | H | H | H | tBu | 5-CONH₂ | 0 |
| 124 | Pn | OH | OMe | H | H | H | tBu | 5-CONHMe | 0 |
| 125 | Pn | OH | OMe | H | H | H | tBu | 5-CONMe₂ | 0 |
| 126 | Pn | OH | OMe | H | H | H | tBu | 5-CH₂CONHMe | 0 |
| 127 | Pn | OH | OMe | H | H | H | tBu | 5-CH₂OCONH₂ | 0 |
| 128 | Pn | OMe | H | OH | H | H | tBu | 5-CONH₂ | 0 |
| 129 | Pn | OMe | H | OH | H | H | tBu | 5-CONHMe | 0 |
| 130 | Pn | OMe | H | OH | H | H | tBu | 5-CONMe₂ | 0 |
| 131 | Pn | OMe | H | OH | H | H | tBu | 5-CH₂CONHMe | 0 |
| 132 | Pn | OMe | H | OH | H | H | tBu | 5-(CH₂)₂CONHMe | 0 |
| 133 | Pn | OMe | H | OH | H | H | tBu | 5-CH₂OCONH₂ | 0 |
| 134 | Pn | OMe | H | Me | H | H | tBu | 5-CONHMe | 0 |
| 135 | Pn | OMe | H | NMe₂ | H | H | tBu | 5-CONH₂ | 0 |
| 136 | Pn | OMe | H | NMe₂ | H | H | tBu | 5-CONHMe | 0 |
| 137 | Pn | OMe | H | NMe₂ | H | H | tBu | 5-CH₂CONHMe | 0 |
| 138 | Pn | OMe | H | H | NMe₂ | H | tBu | 5-CONH₂ | 0 |
| 139 | Pn | OCH₂OMe | H | H | H | H | tBu | 5-CONHMe | 0 |
| 140 | Bu | OMe | H | OCH₂Ph | H | H | tBu | 5-CONHMe | 0 |
| 141 | Bu | OCH₂Ph | OMe | H | H | H | tBu | 5-CONH₂ | 0 |
| 142 | Pn | OMe | H | CN | H | H | tBu | 5-CONH₂ | 0 |
| 143 | Pn | OMe | H | CN | H | H | tBu | 5-CH₂CONHMe | 0 |
| 144 | Pn | OMe | H | OMe | CN | H | tBu | 5-CONH₂ | 0 |
| 145 | Pn | OMe | H | OMe | CN | H | tBu | 5-CH₂CONHMe | 0 |
| 146 | Pn | OMe | H | SMe | H | H | tBu | 5-CONH₂ | 0 |
| 147 | Pn | OMe | H | S(O)Me | H | H | tBu | 5-CONH₂ | 0 |
| 148 | Pn | OMe | H | SO₂Me | H | H | tBu | 5-CONH₂ | 0 |
| 149 | Hx | H | H | SO₂Me | H | H | tBu | 5-CH=CH—CONH₂ | 0 |
| 150 | Pn | —OCH₂O— | | H | H | H | Me | 5-CONH₂ | 0 |
| 151 | Pn | —OCH₂O— | | H | H | H | Et | 5-CONH₂ | 0 |
| 152 | Pn | —OCH₂O— | | H | H | H | Pn | 5-CONH₂ | 0 |

TABLE 1-continued

| Cpd No. | R¹ | R²ᵉ | R²ᶠ | R²ᵍ | R²ʰ | R²ⁱ | R³ | R⁴ | n |
|---|---|---|---|---|---|---|---|---|---|
| 153 | Pn | —OCH₂O— | | H | H | H | Hx | 5-CONH₂ | 0 |
| 154 | Dd | —OCH₂O— | | H | H | H | tBu | 5-CONH₂ | 0 |
| 155 | Ddc | —OCH₂O— | | H | H | H | tBu | 5-CONH₂ | 0 |
| 156 | Pn | —OCH₂O— | | H | H | H | Me | 5-CH₂CONHMe | 0 |
| 157 | Pn | —OCH₂O— | | H | H | H | Et | 5-CH₂CONHMe | 0 |
| 158 | Pn | —OCH₂O— | | H | H | H | Pn | 5-CH₂CONHMe | 0 |
| 159 | Pn | —OCH₂O— | | H | H | H | Hx | 5-CH₂CONHMe | 0 |
| 160 | Dd | —OCH₂O— | | H | H | H | tBu | 5-CH₂CONHMe | 0 |
| 161 | Ddc | —OCH₂O— | | H | H | H | tBu | 5-CH₂CONHMe | 0 |
| 162 | Pn | OMe | OMe | H | H | H | Me | 5-CONH₂ | 0 |
| 163 | Pn | OMe | OMe | H | H | H | Et | 5-CONH₂ | 0 |
| 164 | Pn | OMe | OMe | H | H | H | Pn | 5-CONH₂ | 0 |
| 165 | Pn | OMe | OMe | H | H | H | Hx | 5-CONH₂ | 0 |
| 166 | Dd | OMe | OMe | H | H | H | tBu | 5-CONH₂ | 0 |
| 167 | Ddc | OMe | OMe | H | H | H | tBu | 5-CONH₂ | 0 |
| 168 | Pn | OMe | OMe | H | H | H | Me | 5-CH₂CONHMe | 0 |
| 169 | Pn | OMe | OMe | H | H | H | Et | 5-CH₂CONHMe | 0 |
| 170 | Pn | OMe | OMe | H | H | H | Pn | 5-CH₂CONHMe | 0 |
| 171 | Pn | OMe | OMe | H | H | H | Hx | 5-CH₂CONHMe | 0 |
| 172 | Dd | OMe | OMe | H | H | H | tBu | 5-CH₂CONHMe | 0 |
| 173 | Ddc | OMe | OMe | H | H | H | tBu | 5-CH₂CONHMe | 0 |
| 174 | Pn | OMe | H | OMe | H | H | Me | 5-CONH₂ | 0 |
| 175 | Pn | OMe | H | OMe | H | H | Et | 5-CONH₂ | 0 |
| 176 | Pn | OMe | H | OMe | H | H | Pn | 5-CONH₂ | 0 |
| 177 | Pn | OMe | H | OMe | H | H | Hx | 5-CONH₂ | 0 |
| 178 | Dd | OMe | H | OMe | H | H | tBu | 5-CONH₂ | 0 |
| 179 | Ddc | OMe | H | OMe | H | H | tBu | 5-CONH₂ | 0 |
| 180 | Pn | OMe | H | OMe | H | H | Me | 5-CH₂CONHMe | 0 |
| 181 | Pn | OMe | H | OMe | H | H | Et | 5-CH₂CONHMe | 0 |
| 182 | Pn | OMe | H | OMe | H | H | Pn | 5-CH₂CONHMe | 0 |
| 183 | Pn | OMe | H | OMe | H | H | Hx | 5-CH₂CONHMe | 0 |
| 184 | Dd | OMe | H | OMe | H | H | tBu | 5-CH₂CONHMe | 0 |
| 185 | Ddc | OMe | H | OMe | H | H | tBu | 5-CH₂CONHMe | 0 |
| 186 | Pn | OMe | H | OH | H | H | Me | 5-CONH₂ | 0 |
| 187 | Pn | OMe | H | OH | H | H | Et | 5-CONH₂ | 0 |
| 188 | Pn | OMe | H | OH | H | H | Pn | 5-CONH₂ | 0 |
| 189 | Pn | OMe | H | OH | H | H | Hx | 5-CONH₂ | 0 |
| 190 | Dd | OMe | H | OH | H | H | tBu | 5-CONH₂ | 0 |
| 191 | Ddc | OMe | H | OH | H | H | tBu | 5-CONH₂ | 0 |
| 192 | Pn | OMe | H | OH | H | H | Me | 5-CH₂CONHMe | 0 |
| 193 | Pn | OMe | H | OH | H | H | Et | 5-CH₂CONHMe | 0 |
| 194 | Pn | OMe | H | OH | H | H | Pn | 5-CH₂CONHMe | 0 |
| 195 | Pn | OMe | H | OH | H | H | Hx | 5-CH₂CONHMe | 0 |
| 196 | Dd | OMe | H | OH | H | H | tBu | 5-CH₂CONHMe | 0 |
| 197 | Ddc | OMe | H | OH | H | H | tBu | 5-CH₂CONHMe | 0 |
| 198 | Dd | OH | OMe | H | H | H | tBu | 5-CH₂CONHMe | 0 |
| 199 | Ddc | OH | OMe | H | H | H | tBu | 5-CH₂CONHMe | 0 |
| 200 | Dd | OH | OMe | H | H | H | tBu | 5-CONH₂ | 0 |
| 201 | Pn | OMe | H | OMe | Me | H | tBu | 5-CONHMe | 0 |
| 202 | Pn | OMe | H | OMe | Me | H | tBu | 5-CONH₂ | 0 |
| 203 | Pn | OMe | H | Me | H | H | tBu | 5-CONH₂ | 0 |
| 204 | Pn | OMe | H | Me | H | H | tBu | 5-CONHiBu | 0 |
| 205 | Pn | OMe | H | Me | H | H | tBu | 5-CO-(1-Ppra-4-Me) | 0 |
| 206 | Pn | OMe | H | Me | H | H | tBu | 5-CONHOMe | 0 |
| 207 | Pn | OMe | H | CF₃ | H | H | tBu | 5-CONH₂ | 0 |
| 208 | Hx | CF₃ | H | H | H | H | tBu | 5-CONH₂ | 0 |
| 209 | Pn | CF₃ | H | H | H | H | tBu | 5-CONHMe | 0 |
| 210 | iBu | CF₃ | H | H | H | H | tBu | 5-CH₂CONHMe | 0 |
| 211 | Pn | OMe | H | CH₂OAc | H | H | tBu | 5-CONH₂ | 0 |
| 212 | Pr | OMe | H | CH₂OAc | H | H | tBu | 5-CONH₂ | 0 |
| 213 | Pr | OMe | H | CH₂OH | H | H | tBu | 5-CONH₂ | 0 |
| 214 | Pr | OMe | H | CH₂OH | H | H | tBu | 5-CH₂CONH₂ | 0 |
| 215 | Bu | OMe | H | CH₂OH | H | H | tBu | 5-CH₂CONHMe | 0 |
| 216 | Bu | OMe | H | CH₂OH | H | H | tBu | 5-CONH₂ | 0 |
| 217 | iBu | OMe | H | CH₂OAc | H | H | tBu | 5-CONH₂ | 0 |
| 218 | Pn | OMe | H | CH₂OH | H | H | tBu | 5-CONH₂ | 0 |
| 219 | Pn | OMe | H | CH₂OAc | H | H | tBu | 5-CONHMe | 0 |
| 220 | Pn | OMe | H | CH₂OH | H | H | tBu | 5-CONHMe | 0 |
| 221 | Pn | OMe | H | CH(OH)Me | H | H | tBu | 5-CONH₂ | 0 |
| 222 | Pn | OMe | H | C(OH)Me₂ | H | H | tBu | 5-CONH₂ | 0 |
| 223 | iBu | OMe | H | C(OH)Me₂ | H | H | tBu | 5-CONH₂ | 0 |
| 224 | Bu | OMe | H | C(OH)Me₂ | H | H | tBu | 5-CONH₂ | 0 |
| 225 | Pr | OMe | H | C(OH)Me₂ | H | H | tBu | 5-CONH₂ | 0 |
| 226 | iPr | OMe | H | C(OH)Me₂ | H | H | tBu | 5-CONH₂ | 0 |
| 227 | Pn | OMe | H | CHOH(CH₂)₂CH₃ | H | H | tBu | 5-CONH₂ | 0 |
| 228 | Pn | OMe | H | CH(OH)CH₂CH₃ | H | H | tBu | 5-CONH₂ | 0 |

TABLE 1-continued

| Cpd No. | $R^1$ | $R^{2e}$ | $R^{2f}$ | $R^{2g}$ | $R^{2h}$ | $R^{2i}$ | $R^3$ | $R^4$ | n |
|---|---|---|---|---|---|---|---|---|---|
| 229 | Pn | OMe | H | CH(OH)(CH$_2$)$_3$CH$_3$ | H | H | tBu | 5-CONH$_2$ | 0 |
| 230 | iBu | OMe | H | CH(OH)(CH$_2$)$_3$CH$_3$ | H | H | tBu | 5-CONH$_2$ | 0 |
| 231 | Bu | OMe | H | CH(OH)(CH$_2$)$_3$CH$_3$ | H | H | tBu | 5-CONH$_2$ | 0 |
| 232 | Bu | OMe | H | CH(OH)(CH$_2$)$_2$CH$_3$ | H | H | tBu | 5-CONH$_2$ | 0 |
| 233 | iBu | OMe | H | CH(OH)(CH$_2$)$_2$CH$_3$ | H | H | tBu | 5-CONH$_2$ | 0 |
| 234 | Pr | OMe | H | CH(OH)(CH$_2$)$_3$CH$_3$ | H | H | tBu | 5-CONH$_2$ | 0 |
| 235 | iPr | OMe | H | CH(OH)(CH$_2$)$_3$CH$_3$ | H | H | tBu | 5-CONH$_2$ | 0 |
| 236 | Pn | OMe | H | CH(OH)(CH$_2$)$_2$CH$_3$ | H | H | tBu | 5-CH$_2$CONH$_2$ | 0 |
| 237 | Pn | OMe | H | CH(OH)(CH$_2$)$_2$CH$_3$ | H | H | tBu | 5-CH$_2$NHCONH$_2$ | 0 |
| 238 | Pn | OMe | H | CH(OH)(CH$_2$)$_2$CH$_3$ | H | H | tBu | 5-CONHCOCH$_3$ | 0 |
| 239 | Hx | OMe | H | CH(OH)CH$_2$CH$_3$ | H | H | tBu | 5-CONH$_2$ | 0 |
| 240 | Pr | OMe | H | CH(OH)(CH$_2$)$_2$CH$_3$ | H | H | tBu | 5-CH$_2$CONH$_2$ | 0 |
| 241 | Pn | OMe | H | CH(OH)(CH$_2$)$_2$CH$_3$ | H | H | tBu | 5-CH$_2$NHSO$_2$CH$_3$ | 0 |
| 242 | Pn | OMe | H | CH(OH)(CH$_2$)$_2$CH$_3$ | H | H | tBu | 5-CH$_2$NHCONHMe | 0 |
| 243 | iPn | OMe | H | CH(OH)(CH$_2$)$_2$CH$_3$ | H | H | iPr | 5-CN | 0 |
| 244 | Pn | OMe | H | OMe | COOH | H | tBu | 5-CONH$_2$ | 0 |
| 245 | Pn | OMe | H | OMe | COOH | H | tBu | 5-CONHMe | 0 |
| 246 | Pn | OMe | H | OMe | COOMe | H | tBu | 5-CONHMe | 0 |
| 247 | Pn | OMe | H | OMe | CONMe$_2$ | H | tBu | 5-CONH$_2$ | 0 |
| 248 | Pn | OMe | H | OMe | CONH$_2$ | H | tBu | 5-CONH$_2$ | 0 |
| 249 | Pn | OMe | H | OMe | CONHMe | H | tBu | 5-CONH$_2$ | 0 |
| 250 | Pn | OMe | H | OMe | COOMe | H | tBu | 5-CONH$_2$ | 0 |
| 251 | Pn | OMe | H | OMe | CONH$_2$ | H | tBu | 5-CONHMe | 0 |
| 252 | Pn | OMe | H | OMe | CONHMe | H | tBu | 5-CONHMe | 0 |
| 253 | Pn | OMe | H | OMe | CONMe$_2$ | H | tBu | 5-CONHMe | 0 |
| 254 | Pn | OMe | H | OMe | CONHBu | H | tBu | 5-CONHMe | 0 |
| 255 | Pn | OMe | H | OMe | CO-1-Pyro | H | tBu | 5-CONHMe | 0 |
| 256 | Pn | OMe | H | OMe | CO-1-Morp | H | tBu | 5-CONHMe | 0 |
| 257 | Pn | OMe | H | OMe | COC$_2$H$_5$ | H | tBu | 5-CONHMe | 0 |
| 258 | Pn | OMe | H | OMe | CONHPr | H | tBu | 5-CONHMe | 0 |
| 259 | Pn | OMe | H | OMe | COCH$_3$ | H | tBu | 5-CONHMe | 0 |
| 260 | Hx | OMe | H | OMe | CONMe$_2$ | H | tBu | 5-CONHMe | 0 |
| 261 | Hx | OMe | H | OMe | CONMe$_2$ | H | tBu | 5-CH$_2$CONHMe | 0 |
| 262 | Pn | OMe | H | CONH$_2$ | H | H | tBu | 5-CONHMe | 0 |
| 263 | Pn | OMe | H | CONHMe | H | H | tBu | 5-CONHMe | 0 |
| 264 | Pn | OMe | H | CONMe$_2$ | H | H | tBu | 5-CONHMe | 0 |
| 265 | Pn | OMe | H | CONMe$_2$ | H | H | tBu | 5-CONH$_2$ | 0 |
| 266 | Pn | OMe | H | CONHMe | H | H | tBu | 5-CONH$_2$ | 0 |
| 267 | Pn | OMe | H | CONMe$_2$ | H | H | tBu | 5-CH$_2$CONH$_2$ | 0 |
| 268 | Pn | OMe | H | CONEt$_2$ | H | H | tBu | 5-CH$_2$CONMe$_2$ | 0 |
| 269 | Hx | OMe | H | CONMe$_2$ | H | H | tBu | 5-CH$_2$CONH$_2$ | 0 |
| 270 | Pn | OMe | H | CO-1-Pipe | H | H | tBu | 5-CONH$_2$ | 0 |
| 271 | Pn | OMe | H | CO-1-Morp | H | H | tBu | 5-CONH$_2$ | 0 |
| 272 | Pn | OMe | H | CO(CH$_2$)$_2$CH$_3$ | H | H | tBu | 5-CONH$_2$ | 0 |
| 273 | Pn | OMe | H | COCH$_3$ | H | H | tBu | 5-CONH$_2$ | 0 |
| 274 | Pn | OMe | H | COCH$_2$CH$_3$ | H | H | tBu | 5-CONH$_2$ | 0 |
| 275 | Pn | OMe | H | CO(CH$_2$)$_3$CH$_3$ | H | H | tBu | 5-CONH$_2$ | 0 |
| 276 | Hx | OMe | H | CO(CH$_2$)$_2$CH$_3$ | H | H | tBu | 5-CONH$_2$ | 0 |
| 277 | iBu | OMe | H | CO(CH$_2$)$_2$CH$_3$ | H | H | tBu | 5-CONH$_2$ | 0 |
| 278 | iBu | OMe | H | COCH$_2$CH$_3$ | H | H | tBu | 5-CH$_2$CONH$_2$ | 0 |
| 279 | Bu | OMe | H | CO(CH$_2$)$_3$CH$_3$ | H | H | tBu | 5-CONH$_2$ | 0 |
| 280 | Bu | OMe | H | CO(CH$_2$)$_2$CH$_3$ | H | H | tBu | 5-CONH$_2$ | 0 |
| 281 | Bu | OMe | H | COCH$_2$CH$_3$ | H | H | tBu | 5-CH$_2$CONH$_2$ | 0 |
| 282 | iBu | OMe | H | CO(CH$_2$)$_3$CH$_3$ | H | H | tBu | 5-CONH$_2$ | 0 |
| 283 | Pr | OMe | H | CO(CH$_2$)$_3$CH$_3$ | H | H | tBu | 5-CONH$_2$ | 0 |
| 284 | Pr | OMe | H | CO(CH$_2$)$_2$CH$_3$ | H | H | tBu | 5-CH$_2$CONH$_2$ | 0 |
| 285 | iBu | OMe | H | CO(CH$_2$)$_2$CH$_3$ | H | H | tBu | 5-CH$_2$NHCONHMe | 0 |
| 286 | Pn | OMe | H | CO(CH$_2$)$_3$CH$_3$ | H | H | tBu | 5-CH$_2$NHCONHMe | 0 |
| 287 | Pn | OMe | H | CO(CH$_2$)$_2$CH$_3$ | H | H | tBu | 5-CH$_2$NHSO$_2$CH$_3$ | 0 |
| 288 | Pn | OMe | H | CO(CH$_2$)$_2$CH$_3$ | H | H | tBu | 5-CONHCOCH$_3$ | 0 |
| 289 | Pn | OMe | H | CO(CH$_2$)$_2$CH$_3$ | H | H | tBu | 5-CH$_2$OCONH$_2$ | 0 |
| 290 | iPn | OMe | H | CO(CH$_2$)$_2$CH$_3$ | H | H | tBu | 5-CONH$_2$ | 0 |
| 291 | Bu | OMe | H | COCH$_2$CH$_3$ | H | H | tBu | 5-CONH$_2$ | 0 |
| 292 | iBu | OMe | H | COCH$_2$CH$_3$ | H | H | tBu | 5-CONH$_2$ | 0 |
| 293 | iPn | OMe | H | CO(CH$_2$)$_2$CH$_3$ | H | H | tBu | 5-CN | 0 |
| 294 | Pn | OMe | H | COCH$_2$CH$_3$ | H | H | tBu | 5-CONHCOEt | 0 |
| 295 | iBu | OMe | H | COCH$_2$CH$_3$ | H | H | tBu | 5-CONHCOiPr | 0 |
| 296 | Pn | OMe | H | CO(CH$_2$)$_2$CH$_3$ | H | H | tBu | 5-CONH$_2$ | 1 |
| 297 | Pn | OMe | H | COCH$_2$CH$_3$ | H | H | tBu | 5-CONH(CH$_2$)$_2$OMe | 0 |
| 298 | Pn | OMe | H | COCH$_2$CH$_3$ | H | H | tBu | 5-CONH(3-Pyri) | 0 |
| 299 | Pn | OMe | H | CHO | H | H | tBu | 5-CONH$_2$ | 0 |
| 300 | Pn | OMe | H | CHO | H | H | tBu | 5-CONHMe | 0 |
| 301 | Pn | OMe | H | COOH | H | H | tBu | 5-CONHMe | 0 |
| 302 | Pn | OMe | H | COOH | H | H | tBu | 5-CONH$_2$ | 0 |
| 303 | iBu | OMe | H | CHO | H | H | tBu | 5-CONH$_2$ | 0 |
| 304 | Bu | OMe | H | CHO | H | H | tBu | 5-CONH$_2$ | 0 |

TABLE 1-continued

| Cpd No. | R$^1$ | R$^{2e}$ | R$^{2f}$ | R$^{2g}$ | R$^{2h}$ | R$^{2i}$ | R$^3$ | R$^4$ | n |
|---|---|---|---|---|---|---|---|---|---|
| 305 | iPr | OMe | H | CHO | H | H | tBu | 5-CONH$_2$ | 0 |
| 306 | Pr | OMe | H | CHO | H | H | tBu | 5-CONH$_2$ | 0 |
| 307 | Pn | OMe | H | NO$_2$ | H | H | tBu | 5-CONH$_2$ | 0 |
| 308 | Pn | OMe | H | NO$_2$ | H | H | tBu | 5-CH$_2$CONH$_2$ | 0 |
| 309 | Bu | OMe | OMe | H | NMe$_2$ | H | tBu | 5-CONH$_2$ | 0 |
| 310 | Pn | OMe | OMe | H | NMe$_2$ | H | tBu | 5-CH$_2$CONHMe | 0 |
| 311 | iBu | OMe | OMe | H | NMe$_2$ | H | tBu | 5-CONH$_2$ | 0 |
| 312 | Pr | OMe | OMe | H | NMe$_2$ | H | tBu | 5-CONHMe | 0 |
| 313 | Pn | OMe | OMe | H | NHBu | H | tBu | 5-CONH$_2$ | 0 |
| 314 | Pn | OMe | H | OMe | NHBu | H | tBu | 5-CONH$_2$ | 0 |
| 315 | Pn | OMe | H | OMe | NEt$_2$ | H | tBu | 5-CH$_2$CONHMe | 0 |
| 316 | Pn | OCH$_2$Ph | OMe | H | H | H | tBu | 5-CONH$_2$ | 0 |
| 317 | Pn | OCH$_2$Ph | OMe | H | H | H | tBu | 5-CONHMe | 0 |
| 318 | Pn | OMe | H | OCH$_2$Ph | H | H | tBu | 5-CONHMe | 0 |
| 319 | iBu | OMe | H | OH | H | H | tBu | 5-CONHMe | 0 |
| 320 | Pn | OMe | H | OCH$_2$Ph | H | H | tBu | 5-CONH$_2$ | 0 |
| 321 | Bu | OMe | H | OH | H | H | tBu | 5-CONH$_2$ | 0 |
| 322 | Pn | OH | OMe | H | H | H | tBu | 5-CH$_2$CONMe$_2$ | 0 |
| 323 | Pn | OH | OMe | H | H | H | tBu | 5-(CH$_2$)$_2$CONH$_2$ | 0 |
| 324 | iBu | OMe | H | OH | H | H | tBu | 5-CH$_2$CONMe$_2$ | 0 |
| 325 | Pn | OMe | H | H | H | H | tBu | 5-CONMe$_2$ | 0 |
| 326 | Pn | OMe | H | H | H | H | tBu | 5-CONH$_2$ | 0 |
| 327 | Pn | OMe | H | H | H | H | tBu | 5-CO-(1-Ppra-4-Me) | 0 |
| 328 | Pn | OMe | H | H | H | H | tBu | 5-CO-(4-Morp) | 0 |
| 329 | Pn | OMe | H | H | H | H | tBu | 5-CONHCOMe | 0 |
| 330 | iBu | OMe | H | H | H | H | tBu | 5-CH$_2$OCONH$_2$ | 0 |
| 331 | Bu | OMe | H | H | H | H | iPr | 5-CH$_2$NHSO$_2$Et | 0 |
| 332 | Pn | OMe | H | H | H | H | tBu | 5-CH$_2$NHCONHMe | 0 |
| 333 | Pr | OMe | H | H | H | H | tBu | 5-CH$_2$NHCONMe$_2$ | 0 |
| 334 | Pn | OMe | OMe | H | H | H | tBu | 5-(CH$_2$)$_2$CONHMe | 0 |
| 335 | Pn | OMe | OMe | H | H | H | tBu | 5-CO(4-Morp) | 0 |
| 336 | Pn | OMe | OMe | H | H | H | tBu | 5-CH$_2$OCONHMe | 0 |
| 337 | Pn | OMe | OMe | H | H | H | tBu | 5-CH$_2$NHSO$_2$Ph | 0 |
| 338 | iBu | OMe | OMe | H | H | H | tBu | 5-CH$_2$NHCONHMe | 0 |
| 339 | Pn | OMe | OMe | H | H | H | tBu | 5-CONH-(5-Pyrz) | 0 |
| 340 | Pn | OMe | OMe | H | H | H | tBu | 5-(CH$_2$)$_2$CONH(2-Thia) | 0 |
| 341 | Pn | OMe | OMe | H | H | H | tBu | 5-CH$_2$NHCONHMe | 0 |
| 342 | Pn | OMe | OMe | H | H | H | tBu | 5-CH$_2$NHSO$_2$Me | 0 |
| 343 | Pn | OMe | OMe | H | H | H | tBu | 5-CONHCOMe | 0 |
| 344 | Pn | OMe | OMe | H | H | H | tBu | 5-CO(1-Ppra-4-Me) | 0 |
| 345 | Bu | OMe | OMe | H | H | H | tBu | 5-CH$_2$CONH$_2$ | 0 |
| 346 | iBu | OMe | OMe | H | H | H | tBu | 5-CH$_2$CONHMe | 0 |
| 347 | Pn | OMe | OMe | H | H | H | tBu | 5-CH$_2$NHSO$_2$CH$_3$ | 0 |
| 348 | Pn | OMe | OMe | H | H | H | tBu | 5-CH$_2$CH$_2$CONHMe | 0 |
| 349 | Pn | OMe | OMe | H | H | H | tBu | 5-CH$_2$NHCO(3-Pyri) | 0 |
| 350 | Pn | OMe | OMe | H | H | H | tBu | 5-CN | 0 |
| 351 | Pn | OMe | H | OMe | H | H | tBu | 5-CONHOMe | 0 |
| 352 | iBu | OMe | H | OMe | H | H | tBu | 5-CONHOMe | 0 |
| 353 | Pn | OMe | H | OMe | H | H | tBu | 5-CONH(CH$_2$)$_2$OMe | 0 |
| 354 | Hx | OMe | H | OMe | H | H | tBu | 5-CONH(CH$_2$)$_2$OMe | 0 |
| 355 | Pn | OMe | H | OMe | H | H | tBu | 5-CH$_2$NHCONH$_2$ | 0 |
| 356 | Pn | OMe | H | OMe | H | H | tBu | 5-CONHCOMe | 0 |
| 357 | Pn | OMe | H | OMe | H | H | tBu | 5-CH$_2$NHSO$_2$Me | 0 |
| 358 | Pn | OMe | H | OMe | H | H | tBu | 5-CH$_2$NHSO$_2$Et | 0 |
| 359 | Pn | OMe | H | OMe | H | H | tBu | 5-CH$_2$NHSO$_2$Ph | 0 |
| 360 | Pn | OMe | H | OMe | H | H | tBu | 5-CH$_2$NHSO$_2$(4-OMePh) | 0 |
| 361 | Pn | OMe | H | OMe | H | H | tBu | 5-(CH$_2$)$_3$NHCONH$_2$ | 0 |
| 362 | Pn | OMe | H | OMe | H | H | tBu | 5-(CH$_2$)$_2$CONMe$_2$ | 0 |
| 363 | Pn | OMe | H | OMe | H | H | tBu | 5-CH$_2$CN | 0 |
| 364 | Pn | OMe | H | OMe | H | H | tBu | 5-CH$_2$NHCONMe$_2$ | 0 |
| 365 | Pn | OMe | H | OMe | H | H | tBu | 5-CN | 0 |
| 366 | Pn | OMe | H | OMe | H | H | tBu | 5-CH$_2$NMeCONH$_2$ | 0 |
| 367 | Pn | OMe | H | OMe | H | H | tBu | 5-CONHCO(CH$_2$)$_2$COOH | 0 |
| 368 | Pn | OMe | H | OMe | H | H | tBu | 5-CONHCO(CH$_2$)$_2$COONa | 0 |
| 369 | Pn | OMe | H | OMe | H | H | tBu | 5-CONHCO(CH$_2$)$_2$COOCH$_2$Ph | 0 |
| 370 | Pn | OMe | H | OMe | H | H | tBu | 5-CONHCO(CH$_2$)$_3$COONa | 0 |
| 371 | iBu | OMe | H | OMe | H | H | tBu | 5-CONH$_2$ | 0 |
| 372 | iBu | OMe | H | OMe | H | H | tBu | 5-CONHMe | 0 |
| 373 | iBu | OMe | H | OMe | H | H | tBu | 5-CH$_2$CONH$_2$ | 0 |
| 374 | iBu | OMe | H | OMe | H | H | tBu | 5-CH$_2$CONHMe | 0 |
| 375 | iPr | OMe | H | OMe | H | H | tBu | 5-CONH$_2$ | 0 |
| 376 | iPr | OMe | H | OMe | H | H | tBu | 5-CH$_2$CONH$_2$ | 0 |
| 377 | Pn | OMe | H | OMe | Cl | H | tBu | 5-CONH$_2$ | 0 |
| 378 | Pn | OMe | H | OMe | Br | H | tBu | 5-CONH$_2$ | 0 |
| 379 | Bu | OMe | H | OMe | Cl | H | tBu | 5-CONH$_2$ | 0 |
| 380 | Pn | OMe | H | OMe | F | H | tBu | 5-CONH$_2$ | 0 |

TABLE 1-continued

| Cpd No. | R¹ | R²ᵉ | R²ᶠ | R²ᵍ | R²ʰ | R²ⁱ | R³ | R⁴ | n |
|---|---|---|---|---|---|---|---|---|---|
| 381 | Pr | OMe | H | OMe | H | H | tBu | 5-CONH₂ | 0 |
| 382 | Pn | OMe | H | OMe | H | H | tBu | 5-CONHCO(2-Pyri) | 0 |
| 383 | Pn | OMe | H | OMe | H | H | tBu | 5-CONHCOCH₂(3-Pyri) | 0 |
| 384 | Pn | OMe | H | OMe | H | H | tBu | 5-CH₂NHCO(3-Pyri) | 0 |
| 385 | Pn | OMe | H | OMe | H | H | tBu | 5-CONHCOOtBu | 0 |
| 386 | Pn | OMe | H | OMe | H | H | tBu | 5-CONHCOPr | 0 |
| 387 | Pn | OMe | H | OMe | H | H | tBu | 5-CONHCOiPr | 0 |
| 388 | Pn | OMe | H | OMe | H | H | tBu | 5-CONHCO(4-Pyri) | 0 |
| 389 | Pn | OMe | H | OMe | H | H | tBu | 5-CONHCOtBu | 0 |
| 390 | Pn | OMe | H | OMe | H | H | tBu | 5-CONHCO(3-Pyri) | 0 |
| 391 | Pn | OMe | H | OMe | H | H | tBu | 5-CONHCONn | 0 |
| 392 | Pn | OMe | H | OMe | H | H | tBu | 5-CONHCOEt | 0 |
| 393 | Hx | OMe | H | OMe | H | H | tBu | 5-CONHCOMe | 0 |
| 394 | Bu | OMe | H | OMe | H | H | tBu | 5-CONHCOMe | 0 |
| 395 | Bu | OMe | H | OMe | H | H | tBu | 5-CONHCOiPr | 0 |
| 396 | Bu | OMe | H | OMe | H | H | tBu | 5-CONHCOtBu | 0 |
| 397 | Pn | OMe | H | OMe | H | H | tBu | 5-CH₂NHCO(2-Pyri) | 0 |
| 398 | Pn | OMe | H | OMe | H | H | tBu | 5-CONH(CH₂)₃OMe | 0 |
| 399 | Pn | OMe | H | OMe | H | H | tBu | 5-CONHCO(2-Ppra-4-Me) | 0 |
| 400 | Pn | OMe | H | OMe | H | H | tBu | 5-CONHCO(2-Morp) | 0 |
| 401 | Bu | OMe | H | OMe | H | H | tBu | 5-CONHCO(2-Pyrm) | 0 |
| 402 | iPr | OMe | H | OMe | H | H | tBu | 5-CONHCO(2-Pyrz) | 0 |
| 403 | iBu | OMe | H | OMe | H | H | tBu | 5-CONHCOCH₂(3-Pyzo) | 0 |
| 404 | iBu | OMe | H | OMe | H | H | tBu | 5-CONHCOCH₂(2-Imid) | 0 |
| 405 | iBu | OMe | H | OMe | H | H | tBu | 5-CONHCOCH₂(2-Thia) | 0 |
| 406 | iBu | OMe | H | OMe | H | H | tBu | 5-CONHCOCH₂(3-Thia) | 0 |
| 407 | Pn | OMe | H | OMe | H | H | tBu | 5-CONHCOOMe | 0 |
| 408 | Pn | OMe | H | OEt | H | H | tBu | 5-CONH₂ | 0 |
| 409 | Pn | OMe | H | OiPr | H | H | tBu | 5-CONH₂ | 0 |
| 410 | Pn | OMe | H | OiPr | H | H | tBu | 5-CONHMe | 0 |
| 411 | Pn | OMe | H | OEt | H | H | tBu | 5-CONHMe | 0 |
| 412 | Bu | OEt | H | OMe | H | H | tBu | 5-CONH₂ | 0 |
| 413 | iBu | OEt | H | OMe | H | H | tBu | 5-CONH₂ | 0 |
| 414 | Pn | OMe | H | H | H | OMe | tBu | 5-CH₂NPhth | 0 |
| 415 | Pn | OMe | H | H | H | OMe | tBu | 5-CH₂NSucc | 0 |
| 416 | Pn | OMe | H | H | H | OMe | tBu | 5-(CH₂)₂CONHMe | 0 |
| 417 | Pn | OMe | H | H | H | OMe | tBu | 5-CONH₂ | 0 |
| 418 | Pn | OMe | H | H | H | OMe | tBu | 5-CONH(4-Pyri) | 0 |
| 419 | Pn | OMe | H | H | H | OMe | tBu | 5-CONH(2-Pyri) | 0 |
| 420 | Pn | OMe | H | H | H | OMe | tBu | 5-CH₂NHCOCH₃ | 0 |
| 421 | Pn | OMe | H | H | H | OMe | tBu | 5-CH₂NHCOPh | 0 |
| 422 | Pn | OMe | H | H | H | OMe | tBu | 5-CH₂NHCO(3-Pyri) | 0 |
| 423 | Pn | OMe | H | H | H | OMe | tBu | 5-CH₂NHCO(2-Pyri) | 0 |
| 424 | Pn | OMe | H | H | H | OMe | tBu | 5-CH₂NHCOOtBu | 0 |
| 425 | Pn | OMe | H | H | H | OMe | tBu | 5-CH₂NHCONHiPr | 0 |
| 426 | Pn | H | OMe | OMe | OMe | H | tBu | 5-CH₂NSucc | 0 |
| 427 | Pn | H | OMe | OMe | OMe | H | tBu | 5-CH₂NPhth | 0 |
| 428 | Pn | H | OMe | OMe | OMe | H | tBu | 5-CH₂NHCOCH₃ | 0 |
| 429 | Pn | H | OMe | OMe | OMe | H | tBu | 5-CH₂NHCO(3-Pyri) | 0 |
| 430 | Pn | H | OMe | OMe | OMe | H | tBu | 5-CH₂NHCOOtBu | 0 |
| 431 | Pn | H | OMe | OMe | OMe | H | tBu | 5-CH₂NHCONHiPr | 0 |
| 432 | Pn | OMe | H | OMe | H | OMe | tBu | 5-CH₂NSucc | 0 |
| 433 | Pn | OMe | H | OMe | H | OMe | tBu | 5-CH₂NPhth | 0 |
| 434 | Pn | OMe | H | OMe | H | OMe | tBu | 5-CH₂NHCOMe | 0 |
| 435 | Pn | OMe | H | OMe | H | OMe | tBu | 5-CH₂NHCO(3-Pyri) | 0 |
| 436 | Pn | OMe | H | OMe | H | OMe | tBu | 5-CH₂NHCO(2-Pyri) | 0 |
| 437 | Pn | OMe | H | OMe | H | OMe | tBu | 5-CH₂NHCO(4-Pyri) | 0 |
| 438 | Pn | OMe | H | OMe | H | OMe | tBu | 5-CH₂NHCOOtBu | 0 |
| 439 | Pn | OMe | H | OMe | H | OMe | tBu | 5-CH₂NHCONHiPr | 0 |
| 440 | Pn | OMe | H | OMe | OMe | H | tBu | 5-CH₂NSucc | 0 |
| 441 | Pn | OMe | H | OMe | OMe | H | tBu | 5-CH₂NPhth | 0 |
| 442 | Pn | OMe | H | OMe | OMe | H | tBu | 5-CH₂NHCOMe | 0 |
| 443 | Pn | OMe | H | OMe | OMe | H | tBu | 5-CH₂NHCO(3-Pyri) | 0 |
| 444 | Pn | OMe | H | OMe | OMe | H | tBu | 5-CH₂NHCO(2-Pyri) | 0 |
| 445 | Pn | OMe | H | OMe | OMe | H | tBu | 5-CH₂NHCO(4-Pyri) | 0 |
| 446 | Pn | OMe | H | OMe | OMe | H | tBu | 5-CH₂NHCOOtBu | 0 |
| 447 | Pn | OMe | H | OMe | OMe | H | tBu | 5-(CH₂)₂CONMe₂ | 0 |
| 448 | Pn | OMe | H | OMe | OMe | H | tBu | 5-(CH₂)₂CONH₂ | 0 |
| 449 | Pn | OMe | H | OMe | OMe | H | tBu | 5-CH₂NHCONHiPr | 0 |
| 450 | Pn | OMe | H | OMe | OMe | H | tBu | 5-CONH₂ | 0 |
| 451 | Pn | OMe | H | OMe | OMe | H | tBu | 5-CONHMe | 0 |
| 452 | iBu | OMe | H | OMe | OMe | H | tBu | 5-CONH₂ | 0 |
| 453 | Bu | OMe | H | OMe | OMe | H | tBu | 5-CONH₂ | 0 |
| 454 | Pr | OMe | H | OMe | OMe | H | tBu | 5-CONH₂ | 0 |
| 455 | Pn | OMe | H | OMe | OMe | H | tBu | 5-CONHCOCH₃ | 0 |
| 456 | Pn | OMe | H | OMe | OMe | H | tBu | 5-CONHCOEt | 0 |

TABLE 1-continued

| Cpd No. | R¹ | R²ᵉ | R²ᶠ | R²ᵍ | R²ʰ | R²ⁱ | R³ | R⁴ | n |
|---|---|---|---|---|---|---|---|---|---|
| 457 | Pn | OMe | H | OMe | OMe | H | tBu | 5-CONHCOiPr | 0 |
| 458 | Pn | OMe | H | OMe | OMe | H | tBu | 5-CH₂OCONHMe | 0 |
| 459 | Pn | OMe | H | OMe | OMe | H | tBu | 5-CH₂NHSO₂CH₃ | 0 |
| 460 | Pn | OMe | H | OMe | OMe | H | tBu | 5-CH₂NHCONHMe | 0 |
| 461 | Pn | OMe | H | OMe | OMe | H | tBu | 5-CH₂CN | 0 |
| 462 | Pn | OMe | H | OMe | OMe | H | tBu | 5-CONHCOOMe | 0 |
| 463 | iPr | OMe | H | OMe | OMe | H | tBu | 5-CH₂CONHMe | 0 |
| 464 | iPr | OMe | H | OMe | OMe | H | tBu | 5-CH₂CONH₂ | 0 |
| 465 | Pn | OMe | OMe | OMe | H | H | tBu | 5-CONHMe | 0 |
| 466 | Pn | OMe | OMe | OMe | H | H | tBu | 5-CONH(2-Pyrm) | 0 |
| 467 | Pn | OMe | OMe | OMe | H | H | tBu | 5-CONH(2-Pyri) | 0 |
| 468 | Pn | OMe | OMe | OMe | H | H | tBu | 5-CONH(2-Pyrz) | 0 |
| 469 | Pn | OMe | OMe | OMe | H | H | tBu | 5-CONH(4-Pyri) | 0 |
| 470 | Pn | OMe | OMe | OMe | H | H | tBu | 5-(CH₂)₂CONH₂ | 0 |
| 471 | Pn | OMe | OMe | OMe | H | H | tBu | 5-CONH(2-Thia) | 0 |
| 472 | Pn | OMe | OMe | OMe | H | H | tBu | 5-CONH(3-Pyri) | 0 |
| 473 | Pn | OMe | OMe | OMe | H | H | tBu | 5-(CH₂)₂CONH(2-Pyri) | 0 |
| 474 | Pn | OMe | OMe | OMe | H | H | tBu | 5-(CH₂)₂CONHMe | 0 |
| 475 | Pn | OMe | H | OCH₂CONEt₂ | H | H | tBu | 5-CONHMe | 0 |
| 476 | Pn | OMe | H | OCH₂CONEt₂ | H | H | tBu | 5-CONH₂ | 0 |
| 477 | Pn | OMe | H | OCH₂CONHBu | H | H | tBu | 5-CONHMe | 0 |
| 478 | Pn | OMe | H | OCH₂CONHPr | H | H | tBu | 5-CONHMe | 0 |
| 479 | Pn | OMe | H | OCH₂CONHPr | H | H | tBu | 5-CH₂CONHMe | 0 |
| 480 | Pn | OMe | H | OCH₂CONHBu | H | H | tBu | 5-CH₂CONH₂ | 0 |
| 481 | Pn | OMe | H | OCH₂CONHBu | H | H | tBu | 5-CH₂CONHMe | 0 |
| 482 | Pn | OMe | H | OCH₂CONHBu | H | H | tBu | 5-CONMe₂ | 0 |
| 483 | Pn | OMe | H | O(CH₂)₂CONHBu | H | H | tBu | 5-CONH₂ | 0 |
| 484 | Pn | OMe | H | O(CH₂)₄CONHMe | H | H | tBu | 5-CONHMe | 0 |
| 485 | Pn | OMe | H | OCH₂COCH₃ | H | H | tBu | 5-CONH₂ | 0 |
| 486 | Pn | OMe | H | OCH₂COEt | H | H | tBu | 5-CONH₂ | 0 |
| 487 | Pn | OMe | H | OCH₂COPr | H | H | tBu | 5-CONHMe | 0 |
| 488 | Pn | OMe | H | OCH₂COBu | H | H | tBu | 5-CONH₂ | 0 |
| 489 | Pn | OMe | H | OCH₂COOtBu | H | H | tBu | 5-CONH₂ | 0 |
| 490 | Pn | OMe | H | OCH₂COPr | H | H | tBu | 5-CONHCOMe | 0 |
| 491 | Pn | OMe | H | O(CH₂)₃OEt | H | H | tBu | 5-CONHMe | 0 |
| 492 | Pn | OMe | H | O(CH₂)₃OMe | H | H | tBu | 5-CONH₂ | 0 |
| 493 | Pn | OMe | H | O(CH₂)₃OMe | H | H | tBu | 5-CONHMe | 0 |
| 494 | Pn | OMe | H | O(CH₂)₃OEt | H | H | tBu | 5-CONH₂ | 0 |
| 495 | Pn | OMe | H | O(CH₂)₂OMe | H | H | tBu | 5-CONH₂ | 0 |
| 496 | Pn | OMe | H | O(CH₂)₂OMe | Cl | H | tBu | 5-CONH₂ | 0 |
| 497 | Pn | OMe | H | O(CH₂)₂OEt | H | H | tBu | 5-CONH₂ | 0 |
| 498 | Pn | OMe | H | O(CH₂)₂OEt | Cl | H | tBu | 5-CONH₂ | 0 |
| 499 | Bu | OMe | H | O(CH₂)₃OMe | H | H | tBu | 5-CONH₂ | 0 |
| 500 | Bu | OMe | H | O(CH₂)₃OMe | Cl | H | tBu | 5-CONH₂ | 0 |
| 501 | iBu | OMe | H | O(CH₂)₃OMe | H | H | tBu | 5-CH₂CONH₂ | 0 |
| 502 | iPr | OMe | H | O(CH₂)₃OEt | H | H | tBu | 5-CH₂CONHMe | 0 |
| 503 | iBu | OMe | H | O(CH₂)₂OMe | Cl | H | tBu | 5-CONH₂ | 0 |
| 504 | iBu | OMe | H | O(CH₂)₂OEt | Cl | H | tBu | 5-CONH₂ | 0 |
| 505 | iBu | OMe | H | O(CH₂)₂OMe | Cl | H | tBu | 5-CONHCOMe | 0 |
| 506 | Pn | OMe | H | O(CH₂)₃SO₂Me | H | H | tBu | 5-CONH₂ | 0 |
| 507 | Pn | OMe | H | O(CH₂)₃SO₂Me | H | H | tBu | 5-CONHMe | 0 |
| 508 | Pn | OMe | H | O(CH₂)₃SO₂Pr | H | H | tBu | 5-CONH₂ | 0 |
| 509 | Pn | OMe | H | O(CH₂)₃SO₂Pr | Cl | H | tBu | 5-CONH₂ | 0 |
| 510 | Pn | OMe | H | O(CH₂)₃SO₂Pr | H | H | tBu | 5-CH₂CONHMe | 0 |
| 511 | Pn | OMe | H | O(CH₂)₃SO₂Et | H | H | tBu | 5-CONHMe | 0 |
| 512 | Pn | OMe | H | O(CH₂)₃SO₂Et | Cl | H | tBu | 5-CONHMe | 0 |
| 513 | Pn | OMe | H | O(CH₂)₃SEt | H | H | tBu | 5-CONH₂ | 0 |
| 514 | Pn | OMe | H | O(CH₂)₃S(O)Et | H | H | tBu | 5-CONH₂ | 0 |
| 515 | Pn | OMe | H | O(CH₂)₄SMe | H | H | tBu | 5-CONH₂ | 0 |
| 516 | Pn | OMe | H | O(CH₂)₄S(O)Me | H | H | tBu | 5-CONH₂ | 0 |
| 517 | Pn | OMe | H | O(CH₂)₄SO₂Me | H | H | tBu | 5-CONH₂ | 0 |
| 518 | Pn | OMe | H | O(CH₂)₃SO₂Pr | H | H | tBu | 5-CONHCOMe | 0 |
| 519 | Pn | OMe | H | O(CH₂)₃SO₂Pr | H | H | tBu | 5-CONHCOEt | 0 |
| 520 | Pn | OMe | H | O(CH₂)₃SO₂Pr | H | H | tBu | 5-CONHCOiPr | 0 |
| 521 | Bu | OMe | H | O(CH₂)₃SO₂Pr | H | H | tBu | 5-CH₂NHSO₂Ph | 0 |
| 522 | Bu | OMe | H | O(CH₂)₃SO₂Pr | H | H | tBu | 5-CH₂NHSO₂Et | 0 |
| 523 | iBu | OMe | H | O(CH₂)₃SO₂Pr | H | H | tBu | 5-CN | 0 |
| 524 | iBu | OMe | H | O(CH₂)₃SO₂Pr | H | H | tBu | 5-CH₂NHCONHMe | 0 |
| 525 | Pn | OMe | H | O(CH₂)₃NHSO₂Me | H | H | tBu | 5-CONH₂ | 0 |
| 526 | Pn | OMe | H | O(CH₂)₃NHSO₂Me | H | H | tBu | 5-CONHMe | 0 |
| 527 | Pn | OMe | H | O(CH₂)₃NHSO₂Et | H | H | tBu | 5-CH₂CONHMe | 0 |
| 528 | Pn | OMe | H | O(CH₂)₃NHSO₂Pr | H | H | tBu | 5-CH₂CONH₂ | 0 |
| 529 | iBu | OMe | H | O(CH₂)₃NHSO₂Et | Cl | H | tBu | 5-CONHMe | 0 |
| 530 | Bu | OMe | H | O(CH₂)₄NHSO₂Me | H | H | tBu | 5-CONH₂ | 0 |
| 531 | iBu | OMe | H | O(CH₂)₄NHSO₂Pn | H | H | tBu | 5-CN | 0 |
| 532 | iBu | OMe | H | O(CH₂)₃NHSO₂Pn | H | H | tBu | 5-CH₂NHSO₂Me | 0 |

TABLE 1-continued

| Cpd No. | R¹ | R²ᵉ | R²ᶠ | R²ᵍ | R²ʰ | R²ⁱ | R³ | R⁴ | n |
|---|---|---|---|---|---|---|---|---|---|
| 533 | Pn | OMe | H | O(CH₂)₃NHSO₂Pn | H | H | tBu | 5-CH₂NHCONHMe | 0 |
| 534 | Pn | OMe | H | CN | H | H | tBu | 5-CN | 0 |
| 535 | Pn | OMe | H | CN | H | H | tBu | 5-CONH₂ | 0 |
| 536 | Pn | OMe | H | CN | H | H | tBu | 5-CONHMe | 0 |
| 537 | Pn | OMe | H | CN | H | H | tBu | 5-CH₂CONHMe | 0 |
| 538 | iBu | OMe | H | CN | H | H | tBu | 5-CH₂CONH₂ | 0 |
| 539 | Pn | OMe | H | OMe | CN | H | tBu | 5-CONH₂ | 0 |
| 540 | Pn | OMe | H | OMe | CN | H | tBu | 5-CONHMe | 0 |
| 541 | Pn | OMe | H | OMe | CN | H | tBu | 5-CH₂CH₂CONH₂ | 0 |
| 542 | Pn | OMe | H | CH=N—OH | H | H | tBu | 5-CONH₂ | 0 |
| 543 | Pn | OMe | H | CH=N—OH | H | H | tBu | 5-CONHMe | 0 |
| 544 | Pn | OMe | H | OMe | CH=N—OMe | H | tBu | 5-CONH₂ | 0 |
| 545 | Pn | OMe | H | OMe | CH=N—OEt | H | tBu | 5-CONH₂ | 0 |
| 546 | Pn | OMe | H | OMe | CH=N—O-iPr | H | tBu | 5-CONH₂ | 0 |
| 547 | Pn | OMe | H | CH=N—OEt | H | H | tBu | 5-CONH₂ | 0 |
| 548 | Pn | OMe | H | CH=N—O-iPr | H | H | tBu | 5-CONHMe | 0 |
| 549 | iBu | OMe | H | CH=N—OPr | H | H | tBu | 5-CH₂CONHMe | 0 |
| 550 | Pn | OMe | H | SMe | H | H | tBu | 5-CONH₂ | 0 |
| 551 | Pn | OMe | H | S(O)Me | H | H | tBu | 5-CONH₂ | 0 |
| 552 | Pn | OMe | H | SO₂Me | H | H | tBu | 5-CONH₂ | 0 |
| 553 | Pn | OMe | H | SO₂Et | H | H | tBu | 5-CONH₂ | 0 |
| 554 | Pn | OMe | H | SO₂Et | H | H | tBu | 5-CONHMe | 0 |
| 555 | Pn | OMe | H | SO₂Et | H | H | tBu | 5-CH₂CONHMe | 0 |
| 556 | Pn | OMe | H | SO₂Pr | H | H | tBu | 5-CONH₂ | 0 |
| 557 | Pn | OMe | H | SO₂Pr | H | H | tBu | 5-CH₂CONHMe | 0 |
| 558 | Pn | OMe | H | SO₂Bu | H | H | tBu | 5-CONH₂ | 0 |
| 559 | Pn | OMe | H | SO₂Bu | H | H | tBu | 5-CONHMe | 0 |
| 560 | Pn | OMe | H | SO₂Bu | H | H | tBu | 5-CH₂CONH₂ | 0 |
| 561 | Pn | OMe | H | SO₂Bu | H | H | tBu | 5-CH₂CONHMe | 0 |
| 562 | Pn | OMe | H | SO₂Pn | H | H | tBu | 5-CONH₂ | 0 |
| 563 | Pn | OMe | H | SO₂Pn | H | H | tBu | 5-CONHMe | 0 |
| 564 | iBu | OMe | H | SO₂Bu | H | H | tBu | 5-CONH₂ | 0 |
| 565 | iBu | OMe | H | SO₂Bu | H | H | tBu | 5-CONHMe | 0 |
| 566 | iBu | OMe | H | SO₂Bu | H | H | tBu | 5-CH₂CONH₂ | 0 |
| 567 | iBu | OMe | H | SO₂Pn | H | H | tBu | 5-CONH₂ | 0 |
| 568 | iBu | OMe | H | SO₂Pn | H | H | tBu | 5-CH₂CONH₂ | 0 |
| 569 | Bu | OMe | H | SO₂Bu | H | H | tBu | 5-CONH₂ | 0 |
| 570 | Bu | OMe | H | SO₂Bu | H | H | tBu | 5-CH₂CONH₂ | 0 |
| 571 | Bu | OMe | H | SO₂Pn | H | H | tBu | 5-CONH₂ | 0 |
| 572 | Pr | OMe | H | SO₂Pn | H | H | tBu | 5-CONH₂ | 0 |
| 573 | Pr | OMe | H | SO₂Bu | H | H | tBu | 5-CH₂CONH₂ | 0 |
| 574 | Pn | OMe | H | SO₂Bu | H | H | tBu | 5-CONHCOMe | 0 |
| 575 | Bu | OMe | H | SO₂Bu | H | H | tBu | 5-CONHCOEt | 0 |
| 576 | Pr | OMe | H | SO₂Bu | H | H | tBu | 5-CONHCOiPr | 0 |
| 577 | Pn | OMe | H | SO₂Bu | H | H | tBu | 5-CH₂NHCONHiPr | 0 |
| 578 | Pn | OMe | H | SO₂Bu | H | H | tBu | 5-CH₂CN | 0 |
| 579 | Pn | OMe | H | SO₂iPr | H | H | tBu | 5-CONH₂ | 0 |
| 580 | iPn | OMe | H | SO₂iPr | H | H | tBu | 5-CONH₂ | 0 |
| 581 | Pn | OMe | H | SO₂Pr | H | H | tBu | 5-CONH₂ | 1 |
| 582 | Pn | OMe | H | SO₂iBu | H | H | tBu | 5-CONH₂ | 0 |
| 583 | iBu | OMe | H | SO₂iPr | H | H | tBu | 5-CONH₂ | 0 |
| 584 | iBu | OMe | H | SO₂Pr | H | H | tBu | 5-CONH₂ | 0 |
| 585 | Bu | OMe | H | SO₂iPr | H | H | tBu | 5-CONH₂ | 0 |
| 586 | Pn | OMe | H | OMe | SO₂NMe₂ | H | tBu | 5-CONH₂ | 0 |
| 587 | Pn | OMe | H | OMe | SO₂NMe₂ | H | tBu | 5-CONHMe | 0 |
| 588 | Pn | OMe | H | OMe | SO₂NEt₂ | H | tBu | 5-CONH₂ | 0 |
| 589 | Pn | OMe | H | OMe | SO₂NHBu | H | tBu | 5-CONH₂ | 0 |
| 590 | iBu | OMe | H | OMe | SO₂NHPn | H | tBu | 5-CH₂CONH₂ | 0 |
| 591 | Bu | OMe | H | OMe | SO₂NHPr | H | tBu | 5-CH₂CONHMe | 0 |
| 592 | Pn | OMe | H | SO₂NHBu | H | H | tBu | 5-CONHMe | 0 |
| 593 | Pn | OMe | H | SO₂NHPn | H | H | tBu | 5-CH₂CONH₂ | 0 |
| 594 | Pn | OMe | H | SO₂NEt₂ | H | H | tBu | 5-CH₂CONHMe | 0 |
| 595 | Pn | OMe | H | SO₂NEt₂ | H | H | tBu | 5-CONH₂ | 0 |
| 596 | Pn | OMe | H | SO₂NHBu | H | H | tBu | 5-CONH₂ | 0 |
| 597 | Bu | OMe | H | SO₂NHBu | H | H | tBu | 5-CONHCOMe | 0 |
| 598 | Pn | Cl | H | OMe | H | H | tBu | 5-CONH₂ | 0 |
| 599 | Pn | Cl | H | OCH₂CH₂OMe | H | H | tBu | 5-CH₂CONH₂ | 0 |
| 600 | Pn | Cl | H | OCH₂CH₂OEt | H | H | tBu | 5-CONHMe | 0 |
| 601 | iBu | Cl | H | O(CH₂)₃SO₂Pr | H | H | tBu | 5-CONH₂ | 0 |
| 602 | Bu | Cl | H | O(CH₂)₃SO₂Pr | H | H | tBu | 5-CH₂CONHMe | 0 |
| 603 | Bu | Cl | H | OMe | H | H | iPr | 5-CONH₂ | 0 |
| 604 | Pn | Cl | H | OMe | H | H | tBu | 5-CONMe₂ | 1 |
| 605 | Pn | —O(CH₂)₂O— | | H | H | H | tBu | 5-CH₂NPhth | 0 |
| 606 | Pn | —O(CH₂)₂O— | | H | H | H | tBu | 5-CH₂NSucc | 0 |
| 607 | Pn | —O(CH₂)₂O— | | H | H | H | tBu | 5-CH₂NHCOCF₃ | 0 |
| 608 | Pn | —O(CH₂)₂O— | | H | H | H | tBu | 5-CH₂NHCOMe | 0 |

TABLE 1-continued

| Cpd No. | R¹ | R²ᵉ | R²ᶠ | R²ᵍ | R²ʰ | R²ⁱ | R³ | R⁴ | n |
|---|---|---|---|---|---|---|---|---|---|
| 609 | Pn | —O(CH₂)₂O— | H | H | H | H | tBu | 5-CH₂NHCOPh | 0 |
| 610 | Pn | —O(CH₂)₂O— | H | H | H | H | tBu | 5-CH₂NHCO-(3-Pyri) | 0 |
| 611 | Pn | —O(CH₂)₂O— | H | H | H | H | tBu | 5-CH₂NHCO-tBu | 0 |
| 612 | Pn | —O(CH₂)₂O— | H | H | H | H | tBu | 5-CH₂NHCOOCH₂Ph | 0 |
| 613 | Pn | —O(CH₂)₂O— | H | H | H | H | tBu | 5-CH₂OCONH₂ | 0 |
| 614 | Pn | —O(CH₂)₂O— | H | H | H | H | tBu | 5-CH₂NHCONHMe | 0 |
| 615 | Pn | —O(CH₂)₂O— | H | H | H | H | tBu | 5-CH₂NHCONH₂ | 0 |
| 616 | Pn | —O(CH₂)₂O— | H | H | H | H | tBu | 5-CH₂NHSO₂Me | 0 |
| 617 | Pn | —O(CH₂)₂O— | H | H | H | H | tBu | 5-CN | 0 |
| 618 | Pn | —O(CH₂)₂O— | H | H | H | H | tBu | 5-CONHCOMe | 0 |
| 619 | Pn | —O(CH₂)₂O— | H | H | H | H | tBu | 5-CH₂NHSO₂Et | 0 |
| 620 | iBu | —O(CH₂)₂O— | H | H | H | H | tBu | 5-CH₂NHCONHMe | 0 |
| 621 | Bu | —O(CH₂)₂O— | H | H | H | H | tBu | 5-CH₂NHSO₂Ph | 0 |
| 622 | Pr | —O(CH₂)₂O— | H | H | H | H | iPr | 5-CONHCOMe | 0 |
| 623 | iBu | —O(CH₂)₂O— | H | H | H | H | tBu | 5-CO(4-Morp) | 0 |
| 624 | Pn | —O(CH₂)₂O— | H | H | H | H | tBu | 5-CH₂NHCONHPh | 0 |
| 625 | Pn | —O(CH₂)₂O— | H | H | H | H | tBu | 5-CH₂NHCONHiPr | 0 |
| 626 | Pn | —O(CH₂)₂O— | H | H | H | H | tBu | 5-CH₂NHCO(2-Imid) | 0 |
| 627 | Pn | —O(CH₂)₂O— | H | H | H | H | tBu | 5-CONH(2-Thia) | 0 |
| 628 | Pn | —O(CH₂)₂O— | H | H | H | H | tBu | 5-CONH(2-Pyrz) | 0 |
| 629 | Bu | —O(CH₂)₂O— | H | H | H | H | tBu | 5-CO(1-Ppra) | 0 |
| 630 | iBu | —O(CH₂)₂O— | H | H | H | H | tBu | 5-CO(1-Pipe) | 0 |
| 631 | Pr | —O(CH₂)₂O— | H | H | H | H | tBu | 5-CO(1-Pyro) | 0 |
| 632 | iPr | —O(CH₂)₂O— | H | H | H | H | tBu | 5-CH₂NHCO(2-Pyrm) | 0 |
| 633 | Pn | —O(CH₂)₂O— | H | H | H | H | tBu | 5-CONH(2-Imid) | 0 |
| 634 | Pn | —O(CH₂)₂O— | H | H | H | H | tBu | 5-CONHCH₂(1-Tria) | 0 |
| 635 | Pn | —O(CH₂)₂O— | H | H | H | H | tBu | 5-CONH(3-Pyzo) | 0 |
| 636 | Bu | —O(CH₂)₂O— | H | H | H | H | tBu | 5-CONHCOEt | 0 |
| 637 | Bu | —O(CH₂)₂O— | H | H | H | H | tBu | 5-CONHCOiPr | 0 |
| 638 | iBu | —O(CH₂)₂O— | H | H | H | H | tBu | 5-CH₂CH₂CONHMe | 0 |
| 639 | iPr | —O(CH₂)₂O— | H | H | H | H | tBu | 5-CH₂CH₂CONHMe | 0 |
| 640 | Pn | —O(CH₂)₂O— | H | H | H | H | tBu | 5-CH₂NHSO₂Me | 0 |
| 641 | iBu | —O(CH₂)₂O— | H | H | H | H | tBu | 5-CONHCO(2-Pyro) | 0 |
| 642 | Bu | —O(CH₂)₂O— | H | H | H | H | tBu | 5-CONHCO(2-Pipe) | 0 |
| 643 | iBu | —OCH₂O— | H | H | H | H | tBu | 5-CH₂OCONH₂ | 0 |
| 644 | Pn | —OCH₂O— | H | H | H | H | tBu | 5-CH₂NHCONHMe | 0 |
| 645 | Pn | —OCH₂O— | H | H | H | H | tBu | 5-CH₂NHSO₂Me | 0 |
| 646 | Pn | —OCH₂O— | H | H | H | H | tBu | 5-CH₂NHCO(3-Pyri) | 0 |
| 647 | Bu | —OCH₂O— | H | H | H | H | iPr | 5-CH₂CONH₂ | 0 |
| 648 | iBu | —OCH₂O— | H | H | H | H | tBu | 5-CH₂NSucc | 0 |
| 649 | Pn | —OCH₂O— | H | H | H | H | tBu | 5-CONHCOMe | 0 |
| 650 | Pn | —OCH₂O— | H | H | H | H | tBu | 5-CH₂NHCONHiPr | 0 |
| 651 | iBu | —OCH₂O— | H | H | H | H | tBu | 5-CH₂NHCO(3-Pyri) | 0 |
| 652 | iBu | —OCH₂O— | H | H | H | H | tBu | 5-CO(4-Morp) | 0 |
| 653 | Bu | —OCH₂O— | H | H | H | H | tBu | 5-CO(4-Morp) | 0 |
| 654 | iBu | —OCH₂O— | H | H | H | H | tBu | 5-CONHCOEt | 0 |
| 655 | Bu | —OCH₂O— | H | H | H | H | tBu | 5-CONHCOiPr | 0 |
| 656 | Bu | —OCH₂O— | H | H | H | H | tBu | 5-CN | 0 |
| 657 | Pn | —OCH₂O— | H | H | H | H | tBu | 5-CN | 1 |
| 658 | Pn | OMe | H | CH(OH)iPr | H | H | tBu | 5-CONH₂ | 0 |
| 659 | Pn | OMe | H | CH(OH)iBu | H | H | tBu | 5-CONH₂ | 0 |
| 660 | Pn | OMe | H | COiPr | H | H | tBu | 5-CONH₂ | 0 |
| 661 | Pn | OMe | H | COiBu | H | H | tBu | 5-CONH₂ | 0 |
| 662 | iPn | OMe | H | OMe | H | H | tBu | 5-CONH₂ | 0 |
| 663 | Pn | OH | OMe | H | H | H | tBu | 5-CONH₂ | 0 |
| 664 | Pn | OMe | H | OCH₂COCH₃ | H | H | tBu | 5-CONHMe | 0 |
| 665 | Bu | OMe | H | O(CH₂)₃SO₂Pr | H | H | tBu | 5-CONH₂ | 0 |
| 666 | Bu | OMe | H | O(CH₂)₃SO₂Pr | H | Cl | tBu | 5-CONH₂ | 0 |
| 667 | iBu | OMe | H | COEt | H | H | tBu | 5-CONH₂ | 0 |
| 668 | iBu | OMe | H | CH(OH)Et | H | H | tBu | 5-CONH₂ | 0 |
| 669 | Pn | OMe | H | OMe | H | H | iPr | 6-CN | 0 |
| 670 | Pn | OMe | H | SO₂iPr | H | H | tBu | 5-CH₂CN | 0 |
| 671 | Pn | OMe | H | OMe | H | H | tBu | 5-CH₂CN | 1 |
| 672 | Pn | OMe | H | OMe | H | H | tBu | 5-CH₂NHCONHMe | 0 |
| 673 | Pr | OMe | H | COPr | H | H | tBu | 5-CONH₂ | 0 |
| 674 | Pr | OMe | H | CH(OH)Pr | H | H | tBu | 5-CONH₂ | 0 |
| 675 | Pr | OMe | H | COiPr | H | H | tBu | 5-CONH₂ | 0 |
| 676 | Pr | OMe | H | CH(OH)iPr | H | H | tBu | 5-CONH₂ | 0 |
| 677 | Bu | OMe | H | SO₂iPr | H | H | tBu | 5-CH₂CONH₂ | 0 |
| 678 | Pn | OMe | OMe | OMe | H | H | tBu | 5-CONH(3-Pyzo) | 0 |
| 679 | Pn | OMe | OMe | H | H | H | tBu | 5-CONH(3-Pyzo) | 0 |

Of the compounds listed above, preferred compounds are as follows, that is to say Compounds No.: 1, 2, 3, 5, 6, 7, 8, 10, 26, 27, 28, 30, 31, 32, 36, 37, 38, 39, 42, 46, 55, 57, 58, 59, 60, 64, 65, 71, 72, 76, 82, 83, 85, 93, 96, 97, 98, 100, 101, 103, 104, 105, 117, 120, 124, 129, 131, 135, 138, 222, 227, 229, 230, 233, 238, 252, 272, 275, 277, 280, 281, 285, 288, 343, 346, 353, 355, 356, 357, 358, 363, 365, 384, 386, 387, 390, 392, 393, 394, 400, 407, 408, 415, 419, 443, 448, 452, 453, 455, 459, 460, 461, 465, 472, 481, 487, 504, 505, 508, 528, 564, 565, 569, 578, 579, 582, 583, 588, 589, 592, 598, 605, 610, 616, 618, 625, 636, 644, 645, 646, 649, 658, 660, 662, 665, 667, 668, 669, 670, 671, 672 and 677.

More preferred compounds are as follows, that is to say Compounds No.: 1, 5, 10, 26, 27, 28, 30, 31, 36, 38, 39, 42, 46, 57, 58, 59, 60, 64, 71, 82, 83, 93, 96, 97, 98, 101, 103, 124, 129, 131, 135, 138, 222, 227, 229, 252, 272, 281, 288, 343, 355, 356, 358, 363, 384, 386, 387, 390, 392, 393, 394, 407, 408, 415, 419, 443, 448, 452, 455, 460, 465, 508, 579, 585, 605, 618, 625, 644, 658, 660, 662, 669, 672 and 677.

The most preferred compounds are Compounds No.:

5. N-[2-t-butyl-5-(N-methylcarbamoylmethyl)phenyl)-3-(2,3-methylenedioxy-phenyl)octanamide;
28. N-[2-t-butyl-5-(N-methylcarbamoylmethyl)phenyl]-3-(2,3-dimethoxyphenyl)octanamide;
30. N-(2-t-butyl-5-carbamoylphenyl)-3-(2,4-dimethoxyphenyl)octanamide;
31. N-(2-t-butyl-5-N'-methylcarbamoylphenyl)-3-(2,4-dimethoxyphenyl)-octanamide;
38. N-[2-t-butyl-5-(carbamoylmethyl)phenyl]-3-(2,4-dimethoxyphenyl)-octanamide;
39. N-[2-t-butyl-5-(N-methylcarbamoylmethyl)phenyl]-3-(2,4-dimethoxyphenyl)octanamide;
42. N-[2-t-butyl-5-[2-(N-methylcarbamoyl)ethyl]phenyl]-3-(2,4-dimethoxy-phenyl)octanamide;
46. N-[2-t-butyl-5-(carbarnoyloxymethyl)phenyl]-3-(2,4-dimethoxyphenyl)-octanamide;
57. N-(2-t-butyl-5-carbamoylphenyl)-3-(2,4-dimethoxyphenyl)heptanamide;
60. N-[2-t-butyl-5-(N-methylcarbamoylmethyl)phenyl]-3-(2,4-dimethoxyphenyl)heptanamide;
64. N-(2-t-butyl-5-carbamoylphenyl)-3-(2,4-dimethoxyphenyl)nonanamide;
82. N-(2-t-butyl-5-carbamoylphenyl)-N'-[2-(2,4-dimethoxyphenyl)heptyl]urea;
93. N-[2-t-butyl-5-carbamoylphenyl]-3-(2,3,4-trimethoxyphenyl)octanamide;
96. N-[2-t-butyl-5-carbamoylphenyl]-3-(2,4,5-trimethoxyphenyl)octanamide;
222. N-(2-t-butyl-5-carbamoylphenyl)-3-[4-(1-hydroxy-1-methylethyl)-2-methoxyphenyl]octanamide;
227. N-(2-t-butyl-5-carbamoylphenyl)-3-[4-(1-hydroxybutyl)-2-methoxyphenyl]octanarnide;
272. N-(2-t-butyl-5-carbamoylphenyl)-3-(4-butyryl-2-methoxyphenyl)-octanamide;
356. N-(2-t-butyl-5-acetylaminocarbonylphenyl)-3-(2,4-dimethoxyphenyl)-octanamide;
387. N-[2-t-butyl-5-(2-methylpropanoyl)aminocarbonylphenyl]-3-(2,4-dimethoxyphenyl)octanamide;
392. N-(2-t-butyl-5-propanoylaminocarbonylphenyl)-3-(2,4-dimethoxyphenyl)-octanamide;
394. N-(2-t-butyl-5-acetylaminocarbonylphenyl)-3-(2,4-dimethoxyphenyl)-heptanamide;
408. N-(2-t-butyl-5-carbamoylphenyl)-3-(4-ethoxy-2-methoxyphenyl)octanamide;
448. N-[2-t-butyl-5-(2-carbamoylethyl)phenyl]-3-(2,4,5-trimethoxyphenyl)-octanamide;
579. N-(2-t-butyl-5-carbamoylphenyl)-3-(4-isopropylsulfonyl-2-methoxyphenyl)octanamide;
660. N-(2-t-butyl-5-carbamoylphenyl)-3-(4-isobutyryl-2-methoxyphenyl)-octanamide; and
662. N-(2-t-butyl-5-carbamoylphenyl)-3-(2,4-dimethoxyphenyl)-6-methyl-heptanamide.

The compounds of the present invention can be prepared by well known methods conventional for the preparation of compounds of this type, for example, as described below.

Reaction Scheme A:

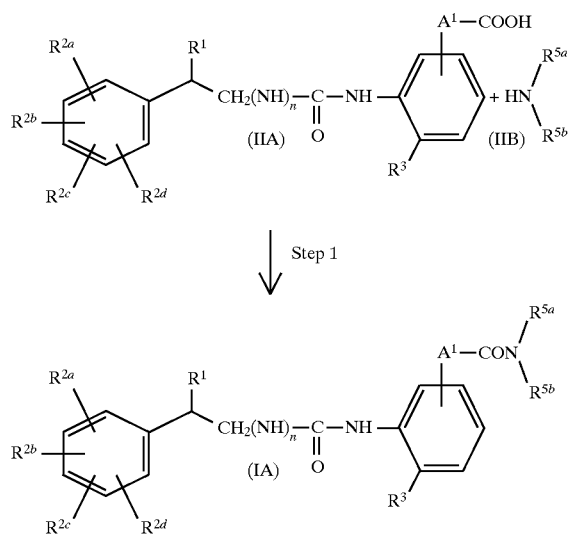

Reaction Scheme B:

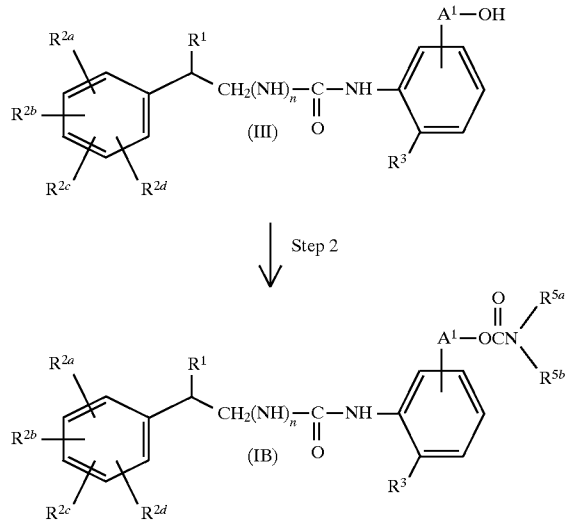

Reaction Scheme C:

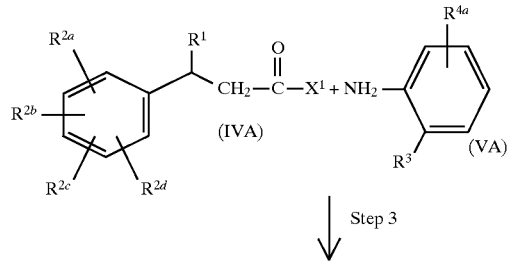

Reaction Scheme C:
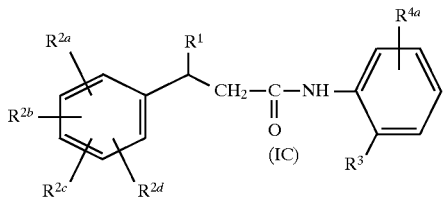
Reaction Scheme D:
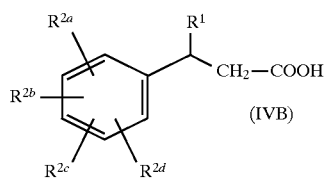
Step 4
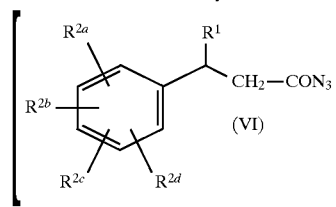
Step 5
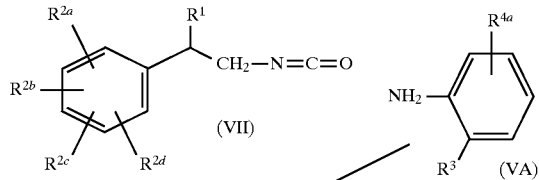
Step 6
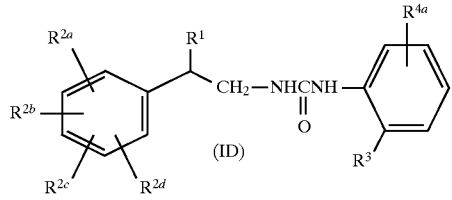
Reaction Scheme E:
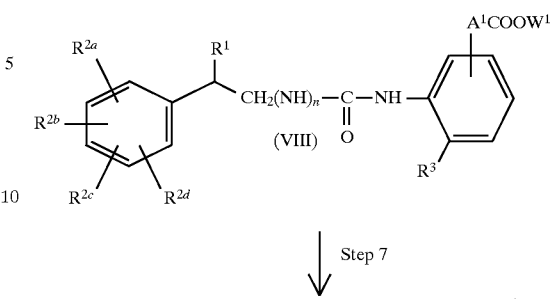
Step 7
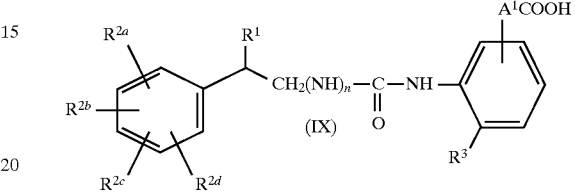
Reaction Scheme F:
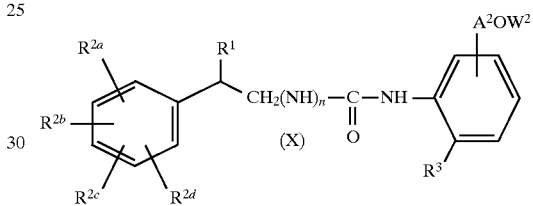
Step 8
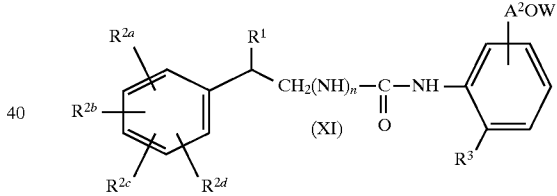
Reaction Scheme G:
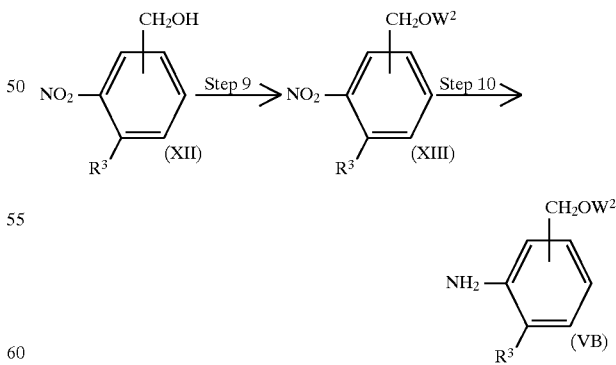

Reaction Scheme H:
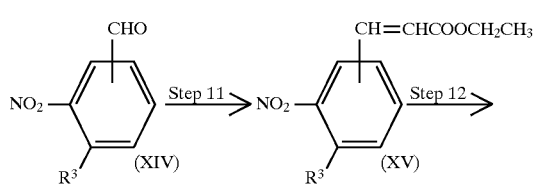
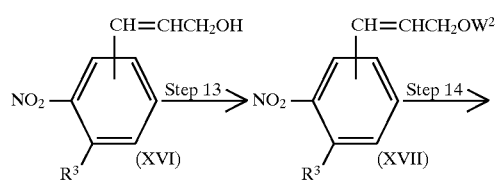
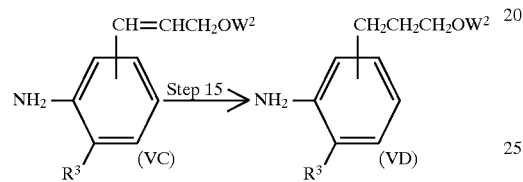
Reaction Scheme I:
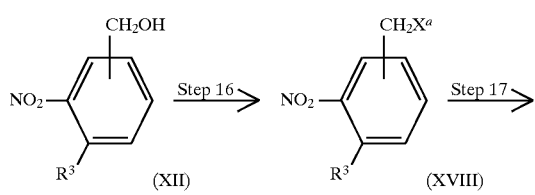
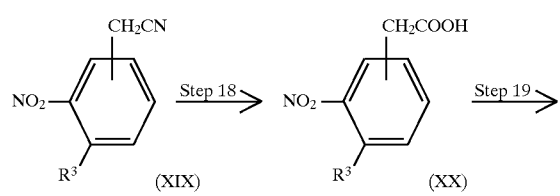
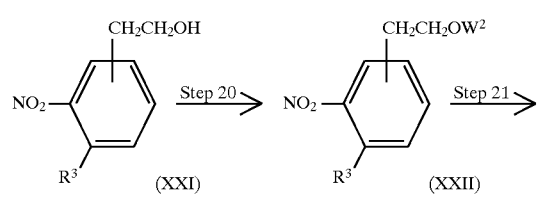
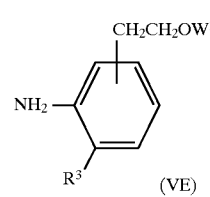
Reaction Scheme J:
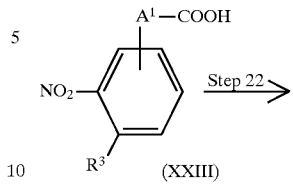
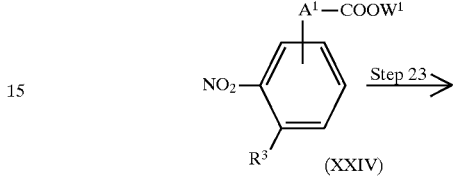
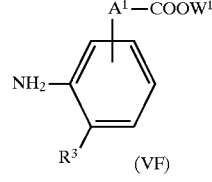
Reaction Scheme K:
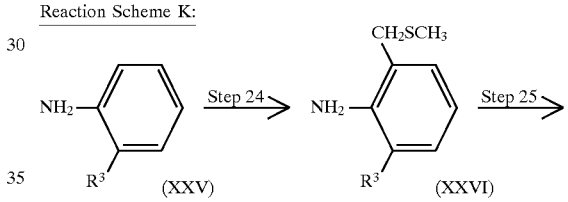
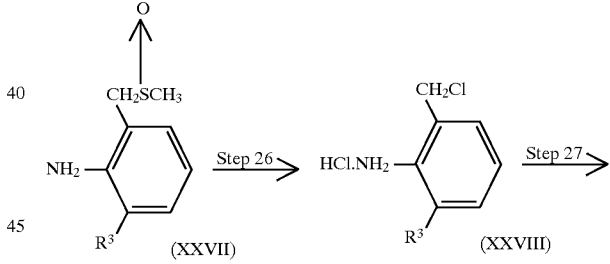
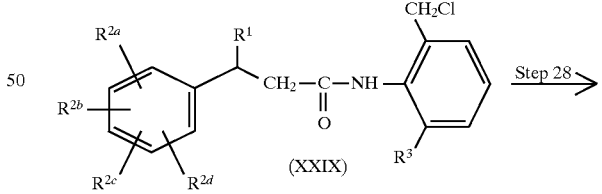
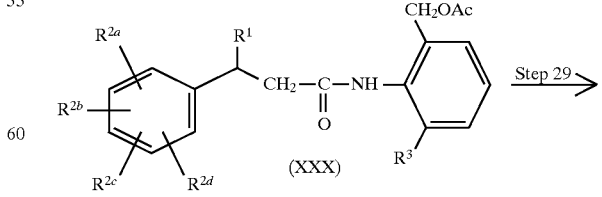

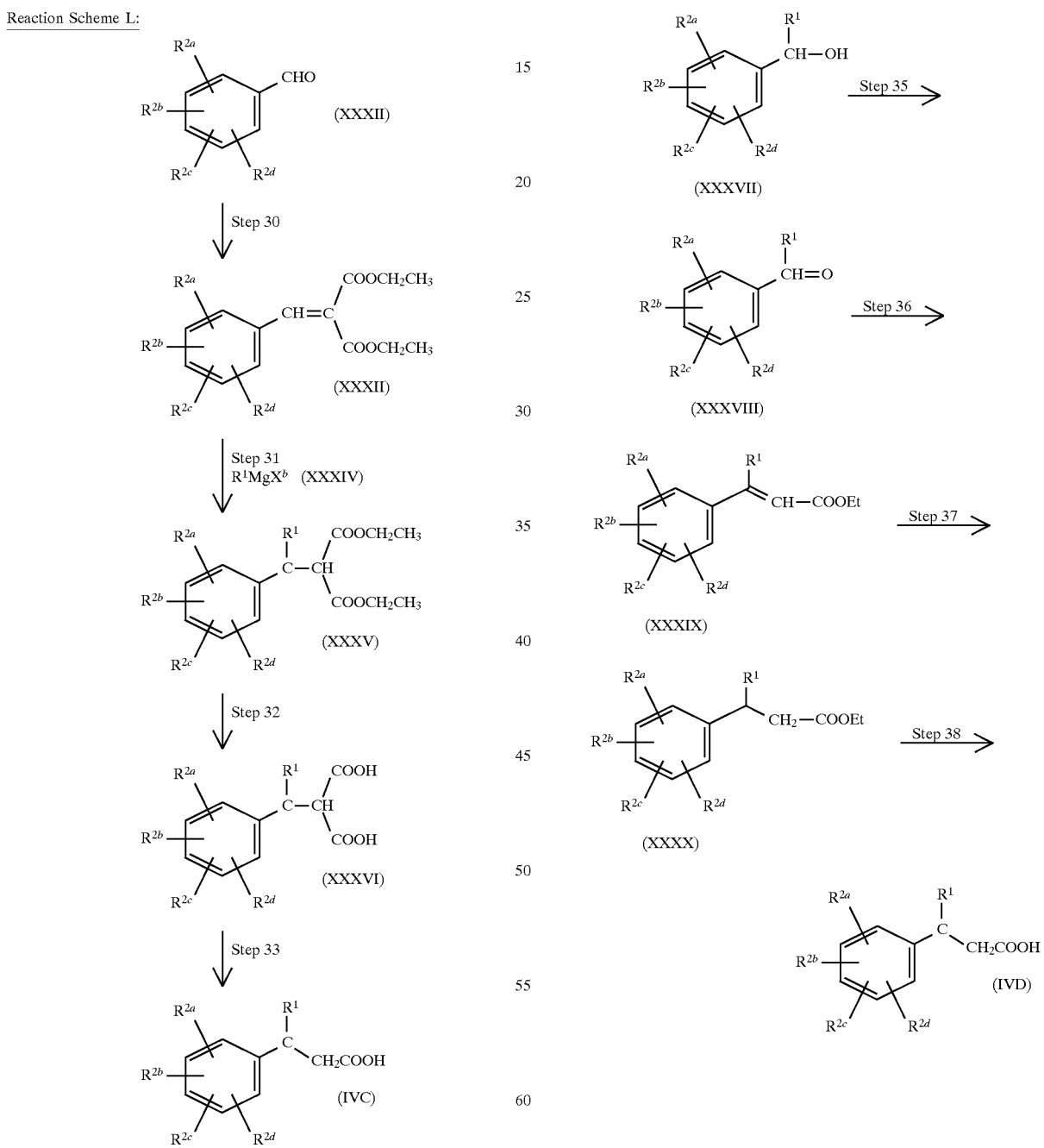

Reaction Scheme N
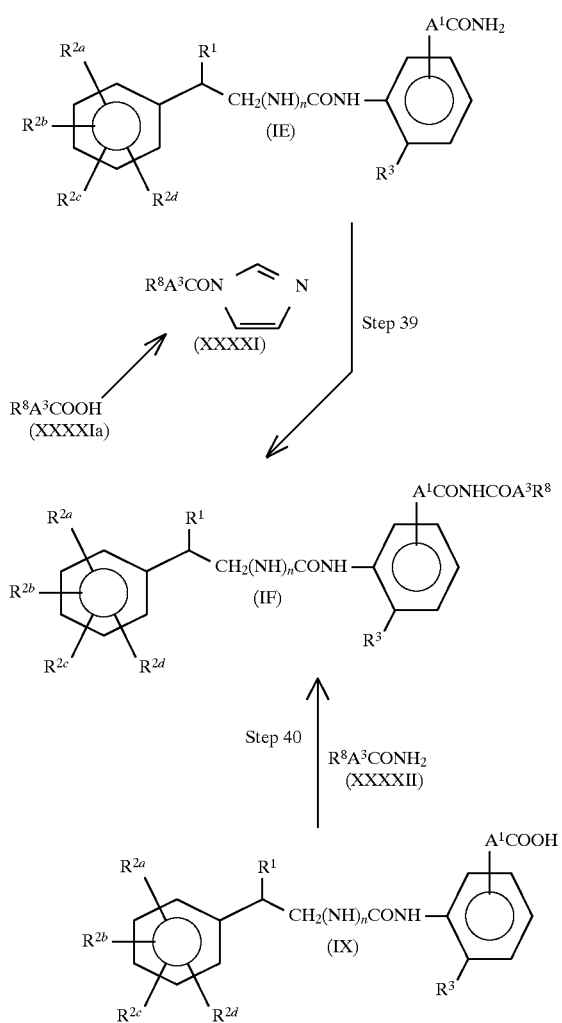
Reaction Scheme O
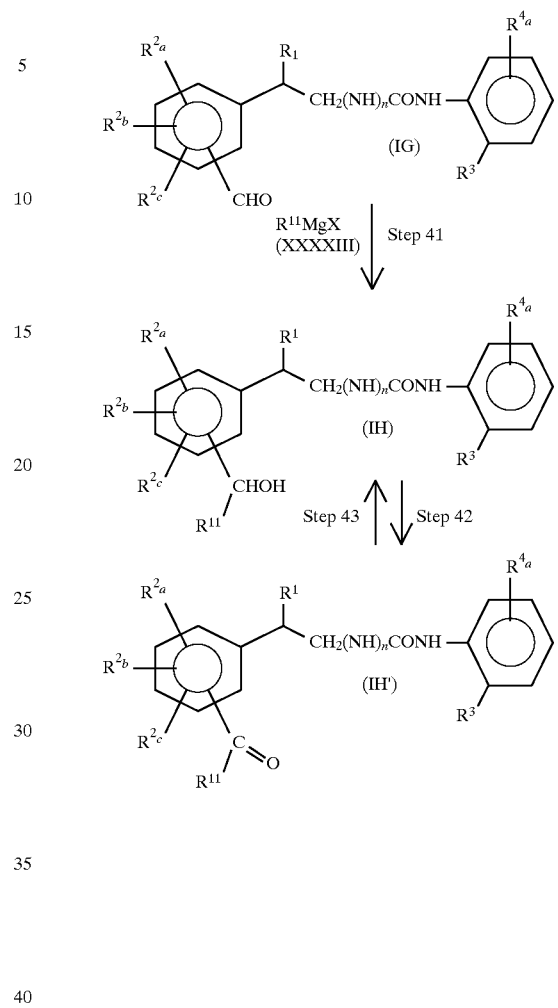
Reaction Scheme P
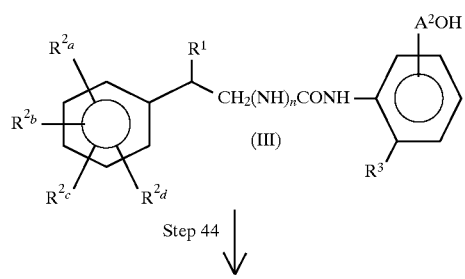

-continued
Reaction Scheme P
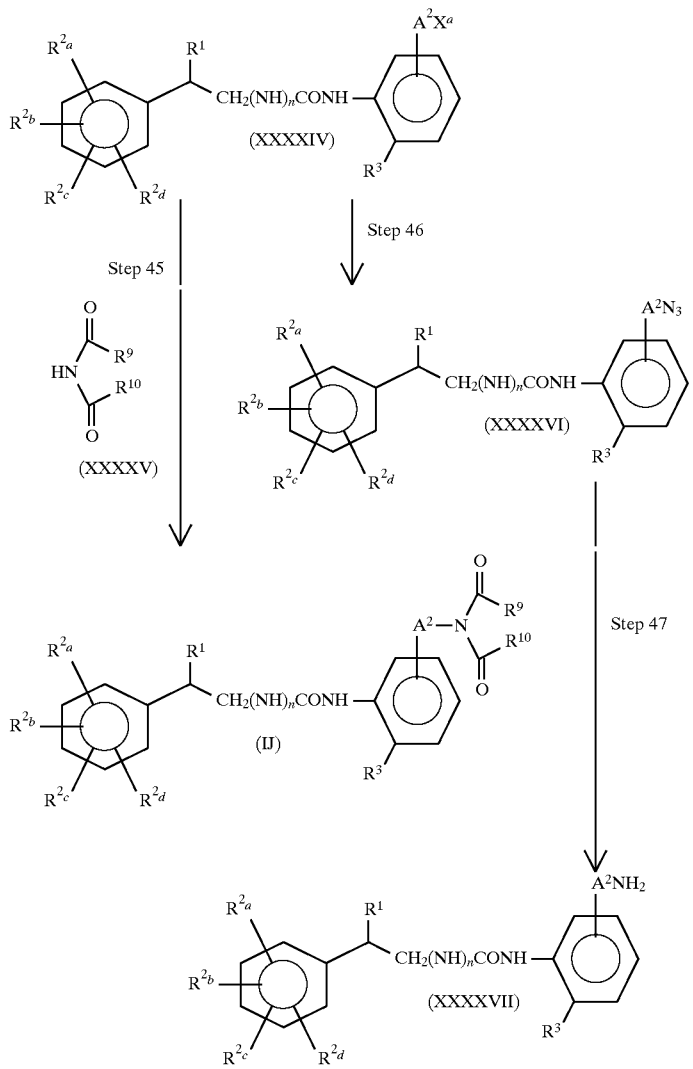
Reaction Scheme Q
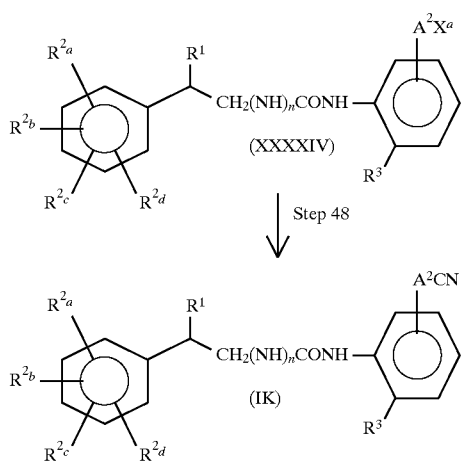
Reaction Scheme R
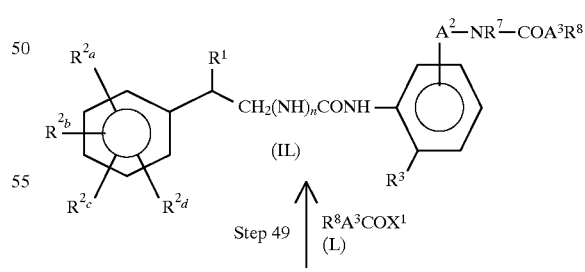

Reaction Scheme R
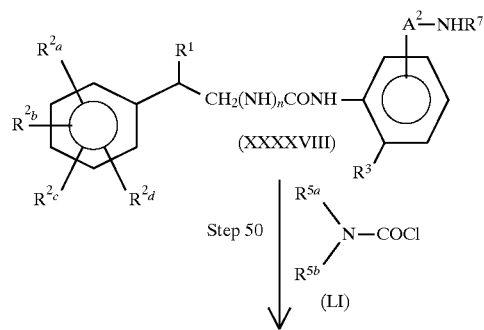
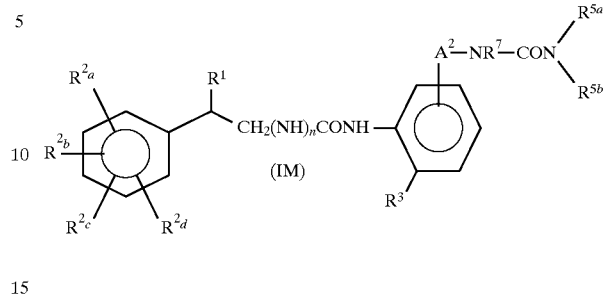
Reaction Scheme S
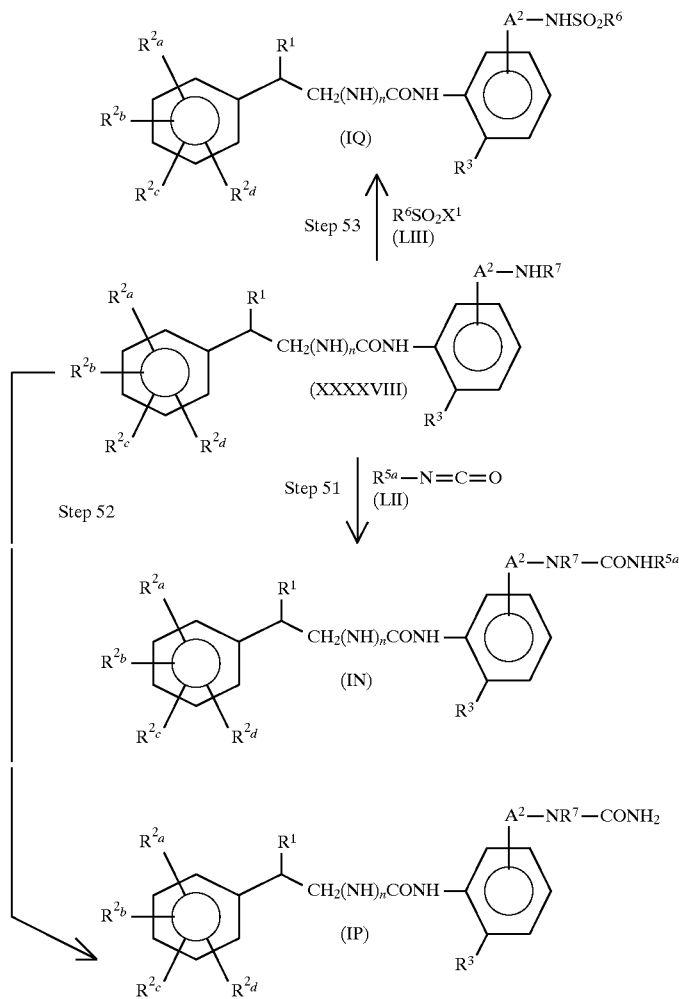

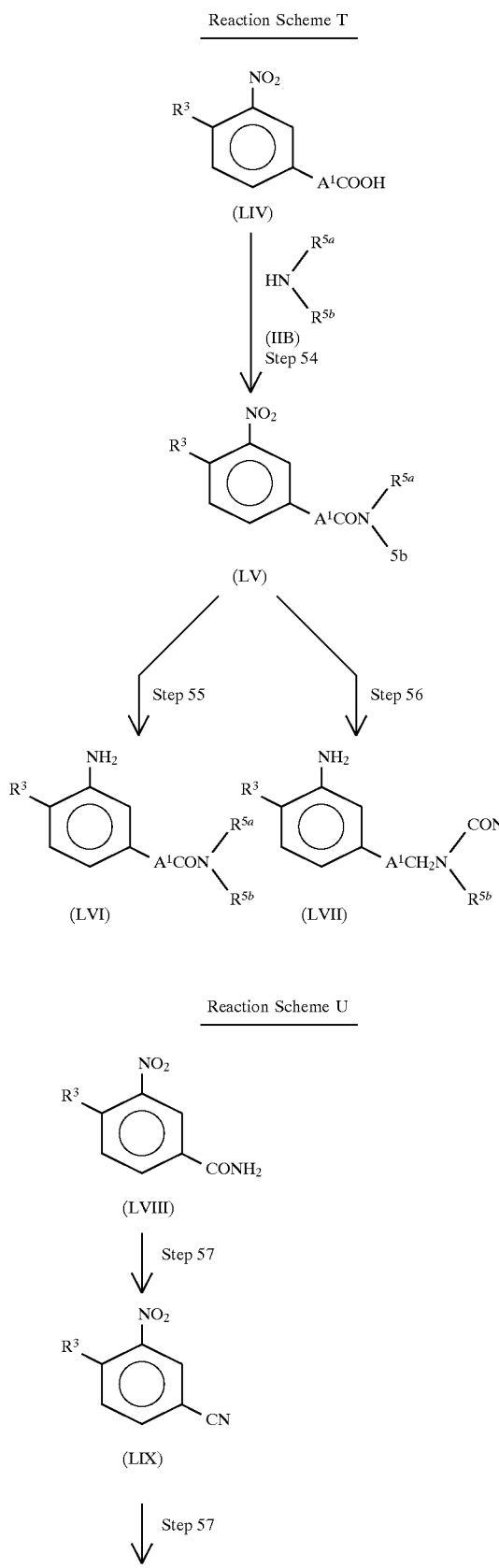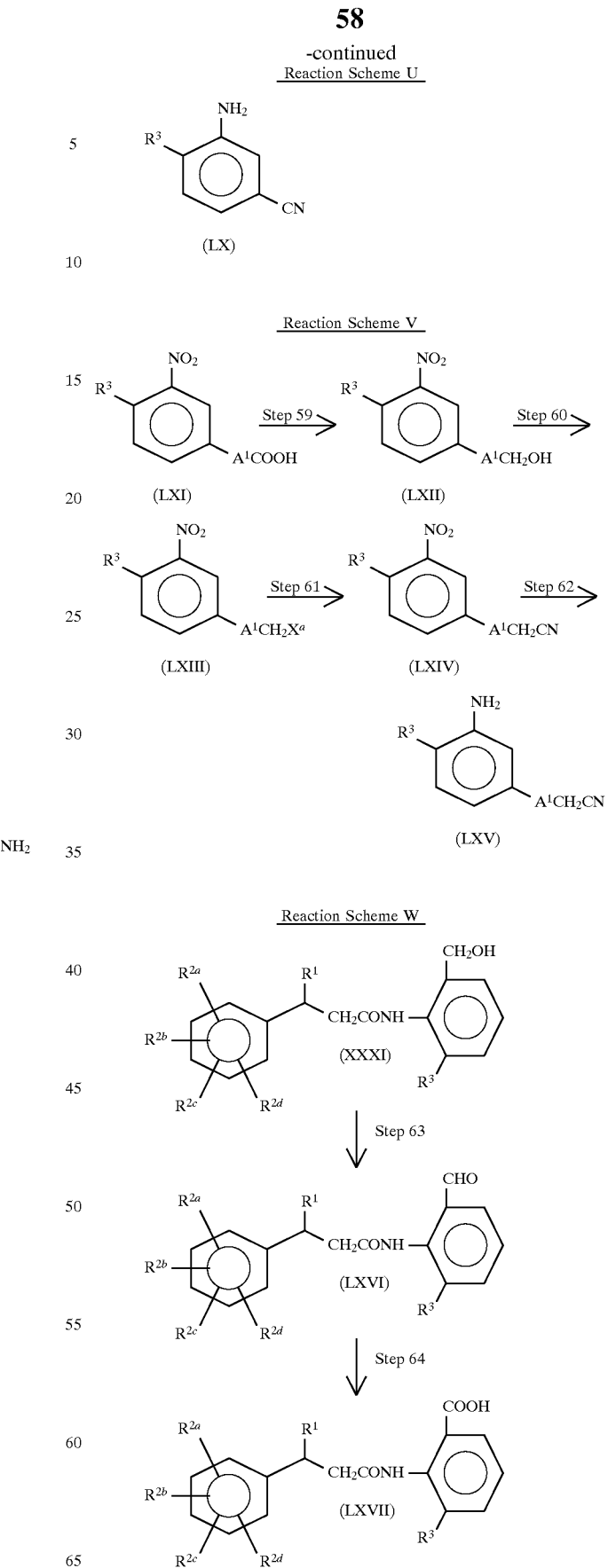

Reaction Scheme X

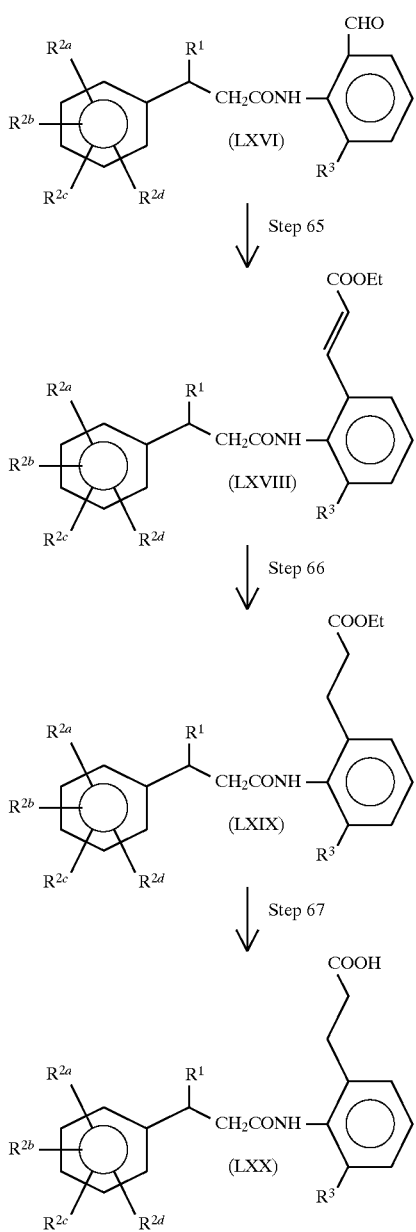

In the formulae of the above reaction schemes:

$R^1$, $R^{2a}$, $R^{2b}$, $R^{2c}$, $R^{2d}$, $R^3$, $R^{5a}$, $R^{5b}$, $R^6$, $R^7$, $R^8$, $A^1$, $A^2$, $A^3$ and n are all as defined above;

$W^1$ represents a carboxy-protecting group, preferably: a lower alkyl group (such as a methyl, ethyl or t-butyl group); a lower alkenyl group (such as an allyl group); or a substituted methyl group (such as a methoxymethyl or benzyl group); more preferably a methyl or ethyl group;

$W^2$ represents a hydroxy-protecting group, preferably a trialkylsilyl group, particularly a t-butyldimethylsilyl group;

$R^{4a}$ represents any of the groups defined above for $R^4$, a group of formula $A^1COOW^1$ (wherein $A^1$ and $W^1$ are as defined above) or a group of formula $A^2OW^2$ (wherein $A^2$ and $W^2$ are as defined abvoe);

$R^{11}$ represents an alkyl group having from 1 to 12 carbon atoms;

$X^a$ represents an alkylsulfonyloxy group (preferably a methanesulfonyloxy group), an arylsulfonyloxy (preferably a R-toluenesulfonyloxy group) or a halogen atom (preferably a chlorine, bromine or iodine atom);

$X^b$ represents a halogen ion (preferably an iodine, chlorine or bromine ion); and $X^1$ represents a hydroxy group or a halogen atom (preferably a chlorine or bromine atom).

Step 1: Condensation

In this reaction scheme, a compound of formula (IA) is prepared by reacting a compound of formula (IIA) with a compound of formula (IIB) in an inert solvent in the presence of a condesning agent and a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform or dichloroethane; esters, such as ethyl acetate or propyl acetate; ethers, such as diethyl ether, tetrahydrofuran, dioxane, dimethoxyethane or diethylene glycol dimethyl ether; ketones, such as acetone or methyl ethyl ketone; nitriles, such as acetonitrile or isobutyronitrile; and amides, such as dimethylformamide, dimethylacetamide or hexamethylphosphoric triamide; more preferably nitriles (particularly acetonitrile), aromatic hydrocarbons (particularly benzene), halogenated hydrocarbons particularly methylene chloride) and ethers particularly tetrahydrofuran).

There is likewise no particular restriction on the nature of the condensing agents, and any such agent commonly used in reactions of this type may equally be used here. Examples of such condensing agents include: di(lower alkyl) azodicarboxylates-triphenylphosphine, such as diethyl azodicarboxylate-triphenylphosphine; $\underline{N},\underline{N}'$-dicycloalkylcarbodiimides, such as $\underline{N},\underline{N}'$-dicyclohexylcarbodiimide (DCC); 2-halo-1-(lower alkyl)pyridiniun halides, such as 2-chloro-1-methylpyridinium iodide; diarylphosphoryl azides, such as diphenylphosphoryl azide (DPPA); lower alkyl chloroformates, such as ethyl chloroformate or isobutyl chloroformate; phosphoryl chlorides, such as diethylphosphoryl chloride; imidazole derivatives, such as $\underline{N},\underline{N}'$-carbodiimidazole (CDI); and carbodiimide derivatives, such as 1-ethyl-3-(3-diethylamino-propyl) carbodiimide hydrochloride (EDAPC); preferably DCC, CDI, 2-chloro-1-methylpyridinium iodide, isobutyl chloroformate and diethylphosphoryl chloride.

There is likewise no particular restriction on the nature of the bases used, and any base commonly used in reactions of this type may equally be used here. Examples of such bases include: organic bases, such as triethylamine, tributylamine, diisopropylethylamine, methylmorpholine, pyridine, 4-($\underline{N},\underline{N}$-dimethyl-amino)pyridine, 4-pyrrolidinopyridine, $\underline{N},\underline{N}$-dimethylaniline, $\underline{N},\underline{N}$-diethylaniline, 1,5-diazabicyclo [4.3.0]non-5-ene, 1,4-diazabicyclo[2.2.2]octane (DABCO) and 1,8-diazabicyclo[5.4.0]undec-7-ene (DBU); preferably triethylamine, diisopropylethylamine, pyridine and 4-pyrrolidinopyridine.

The reaction can take place over a wide range of temperatures, and the precise reaction temperature is not critical to the inyention. The preferred reaction temperature will depend upon such factors as the nature of the solvent, and the starting material or reagent used. However, in general, we find it conyenient to carry out the reaction at a temperature of from 0° to 150° C., more preferably from 250° to 120° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, more preferably from 1 to 24 hours will usually suffice.

After completion of the reaction, the. desired compound of this reaction can be recovered from the reaction mixture by conventional means. An example of one such technique comprises; adding a water-immiscible organic solvent, such as ethyl acetate, to the reaction mixture; washing the organic phase with water; separating the organic phase containing the desired compound; drying it over anhydrous magnesium sulfate or the like; and finally distilling off the organic solvent.

The compound thus obtained may, if necessary, be further purified by standard techniques, e.g. recrystallization, reprecipitation, chromatography or the like.

The reaction in this step can be carried out by using a salt of an inorganic acid (e.g. a hydrochloride) or an organic acid (e.g. p-toluenesulfonic acid) of the amine of formula (IIB) instead of the amine of formula (IIB) itself. In such cases the reaction is carried out in the presence of an organic tertiary amine, such as triethylamine. Where both $R^{5a}$ and $R^{5b}$ in a compound (IIB) represent hydrogen atoms, the reaction may be carried out by using ammonia dissolved in a solvent or aqueous ammonia.

Step 2: Carbamoylation

This step involves the preparation of a compound of formula (IB) of the invention by reacting a compound of formula (III) with a carbamoylating agent in an inert solvent. Where both $R^{5a}$ and $R^{5b}$ represent hydrogen atoms; either $R^{5a}$ or $R^{5b}$ is a hydrogen atom and the other one is a group other than a hydrogen atom; and both $R^{5a}$ and $R^{5b}$ are groups other than hydrogen atoms, the carbamoylating agent used is will be different, as shown below.

Step 2a: Both $R^{5a}$ and $R^{5b}$ are hydrogen atoms

Preferred carbamoylating agents are chlorosulfonyl isocyanate or trichloroacetyl isocyanate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform or dichloroethane; ethers, such as diethyl ether, tetrahydrofuran, dioxane or dimethoxyethane; and nitriles, such as acetonitrile; more preferably aromatic hydrocarbons (particularly benzene), ethers (particularly tetrahydrofuran and dimethoxyethane) and acetonitrile.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −40° to 80° C., more preferably from −20° to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, more preferably from 20 minutes to 12 hours will usually suffice.

After completion of the reaction, the desired compound can be recovered from the reaction mixture by conventional means, for example by pouring it into a buffer solution (pH about 7) or aqueous methanol containing an alkaline metal carbonate, such as potassium carbonate or the like; stirring at room temperature for a period of from 10 minutes to 1 hour; extracting the desired compound with a water-immiscible organic solvent, such as ethyl acetate; washing the organic phase with water; drying the extract; and finally distilling off the organic solvent.

The compound thus obtained may, if necessary, be further purified by standard techniques, e.g. recrystallization, reprecipitation, chromatography or the like.

Step 2b: Either $R^{5a}$ or $R^{5b}$ is a hydrogen atom and the other is a group other than a hydrogen atom:

Suitable carbamoylating agents are alkyl isocyanates.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include the same solvents as those used in Step 2a.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −40° to 120° C., more preferably from room temperature to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, more preferably from 20 minutes to 12 hours, will usually suffice.

After completion of the reaction, the desired compound can be recovered from the reaction mixture by conventional means, for example by pouring it into water; extracting the desired compound with a water-immiscible organic solvent, such as ethyl acetate; washing the organic phase with water; drying it over anhydrous magnesium sulfate or the like; and finally distilling off the solvent.

The compound thus obtained may, if necessary, be further purified by standard techniques, e.g. recrystallization, reprecipitation, chromatography or the like.

Step 2c: Both $R^{5a}$ and $R^{5b}$ are groups other than hydrogen atoms

The reaction may be conducted by using a carbamoyl chloride as a carbamoylating agent in the presence of a base.

There is no particular restriction on the nature of the bases used, and any base commonly used in reactions of this type may equally be used here. Examples of the bases which may be used include: organic bases, such as triethylamine, tributylamine, diisopropylethylamine, methylmorpholine, pyridine, 4-(N,N-dimethylamino)pyridine, 4-pyrrolidin-1'-ylpyridine, N,N-dimethyl-aniline, N,N-diethylaniline, 1,5-diazabicyclo[4.3.0]non-5-ene, 1,4-diazabicyclo-[2.2.2]octane (DABCO) or 1,8-diazabicyclo[5.4.0]undec-7-ene (DBU); preferably triethylamine, diisopropylethylamine, pyridine or 4-pyrrolidin-1'-ylpyridine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include those used in the process of Step 2a.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 150° C., more preferably from 25° to 120° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, more preferably from 1 to 24 hours, will usually suffice.

After completion of the reaction, the desired compound may be recovered from the reaction mixture by conventional means. An example of one such technique comprises: adding a water-immiscible organic solvent, such as ethyl acetate, to the reaction mixture; washing the organic phase with water; drying it over anhydrous magnesium sulfate or the like; and finally distilling off the solvent.

The compound thus obtained may, if necessary, be further purified by standard techniques, e.g. recrystallization, reprecipitation, chromatography or the like.

Step 3: Condensation

This step involves the preparation of a compound of formula (IC) by reacting a compound of formula (IVA) [a compound of formula (IVC) or (IVD) or an acid chloride thereof] with a compound of formula (VA) [a compound of formula (VB), (VC), (VD), (VE), (VF) or the like] in an inert solvent. A condensing agent and/or a base are usually employed. The reaction depends on the nature of the group represented by $X^1$.

Step 3a: $X^1$ is a hydroxyl group

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform or dichloroethane; esters, such as ethyl acetate or propyl acetate; ethers, such as diethyl ether, tetrahydrofuran, dioxane, dimethoxyethane or diethylene glycol dimethyl ether; ketones, such as acetone or methyl ethyl ketone; nitro compounds, such as nitroethane; nitriles, such as acetonitrile or isobutyronitrile; and amides, such as dimethylformamide, dimethylacetamide or hexamethyl-phosphoric triamide; more preferably aromatic hydrocarbons (particularly benzene), halogenated hydrocarbons (particularly methylene chloride) and ethers (particularly tetrahydrofuran).

There is likewise no particular restriction on the nature of the condensing agents, and any such agent commonly used in reactions of this type may equally be used here. Examples of such condensing agents include: di(lower alkyl) azodicarboxylates-triphenylphosphine, such as diethyl azodicarboxylate-triphenylphosphine; N,N'-dicycloalkylcarbodiimides, such as N,N'-dicyclohexylcarbodiimide (DCC); 2-halo-1-(lower alkyl)pyridinium halides, such as 2-chloro-1-methylpyridinium iodide; diarylphosphoryl azides, such as diphenylphosphoryl azide; sulfonyl chlorides, such as 2,4,6-triisopropylbenzenesulfonyl chloride; phosphoryl chlorides, such as diethylphosphoryl chloride; imidazole derivatives, such as N,N'-carbodiimidazole (CDI); and carbodiimide derivatives, such as 1-ethyl-3-(3-dimethylaminopropyl) carbodiimide hyrochloride (EDAPC); preferably DCC, 2-chloro-1-methylpyridinium iodide or diethylphosphoryl chloride.

There is likewise no particular restriction on the nature of the bases used, and any base commonly used in reactions of this type may equally be used here. Examples of such bases include: organic bases, such as triethylamine, tributylamine, diisopropylethylamine, methylmorpholine, pyridine, 4-(N,N-dimethyl-amino)pyridine, 4-pyrrolidin-1'-ylpyridine, N,N-dimethylaniline, N,N-diethyl-aniline, 1,5-diazabicyclo[4.3.0]non-5-ene, 1,4-diazabicyclo[2.2.2] octane (DABCO) or 1,8-diazabicyclo[5.4.0]undec-7-ene (DBU); preferably triethylamine, diisopropylethylamine, pyridine or 4-pyrrolidin-1'-ylpyridine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 150° C., more preferably from 25° to 120° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 hour to 24 hours, will usually suffice.

Step 3b: $X^1$ is a halogen atom

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform or dichloroethane; esters, such as ethyl acetate or propyl acetate; ethers, such as tetrahydrofuran, dioxane or dimethoxyethane; ketones, such as acetone or methyl ethyl ketone; and amides, such as dimethylformamide, dimethylacetamide or hexamethylphosphoric triamide; preferably aromatic hydrocarbons (particularly benzene) and halogenated hydrocarbons (particularly methylene chloride).

There is likewise no particular restriction on the nature of the bases used, and any base commonly used in reactions of this type may equally be used here. Examples of such bases include: organic bases, such as triethylamine, diisopropylethylamine, methylmorpholine, pyridine, 4-(N, N-dimethylamino)-pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo [5.4.0]undec-7-ene (DBU); preferably pyridine or N,N-dimethylaniline.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78° to 50° C., more preferably from −40° to 25° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, more preferably from 10 minutes to 24 hours, will usually suffice.

After completion of the reaction, the desired compound of this reaction can be recovered from the reaction mixture by conventional means. An example of one such technique comprises: adding a water-immiscible organic solvent, such as ethyl acetate, to the reaction mixture; washing the organic phase with water; drying it over anhydrous magnesium sulfate or the like; and finally distilling off the solvent.

The compound thus obtained may, if necessary, be further purified by standard techniques, e.g. recrystallization, reprecipitation, chromatography or the like.

Step 4 and Step 5: Isocyanation

These steps involve the preparation of a compound of formula (VII) by reacting a compound of formula (IVB) [(IVC) or (IVD)] with diphenylphosphoryl azide in an inert solvent and in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as dichloroethane; ethers, such as tetrahydrofuran, dioxane, dimethoxyethane or diethylene glycol dimethyl ether; nitrites, such as acetonitrile or isobutyronitrile; and amides, such as dimethylformamide, dimethylacetamide or hexamethylphosphoric triamide; more preferably aromatic hydrocarbons (particularly benzene) and ethers (particularly tetrahydrofuran).

There is likewise no particular restriction on the nature of the bases used, and any base commonly used in reactions of this type may equally be used here. Examples of such bases include: organic bases, such as triethylamine, diisopropylethylamine, methylmorpholine, pyridine, 4-(N,N-dimethylamino)-pyridine, N,N-dimethylaniline or N,N-diethylaniline; preferably triethylamine and diisopropylethylamine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 50° to 150° C., more preferably from 70° to 120° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 12 hours, will usually suffice.

After completion of the reaction, the desired compound in this step is too labile to exist independently and is employed in the following reaction without separation or purification.

Step 6: Urea formation

This step involves the preparation of a compound of formula (ID) of the invention by reacting a compound of formula (VII) with a compound of formula (VA) in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride or dichloroethane; and ethers, such as tetrahydrofuran, dioxane or dimethoxyethane; more preferably aromatic hydrocarbons (particularly benzene and toluene).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 150° C., more preferably from 25° to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, more preferably from 1 to 24 hours, will usually suffice.

After completion of the reaction, the desired compound in this step can be recovered from the reaction mixture by conventional means. An example of one such technique comprises: adding a water-immiscible organic solvent, such as ethyl acetate, to the reaction mixture; washing the organic phase with water; drying it over anhydrous magnesium sulfate or the like; and finally distilling off the solvent.

The desired compound thus obtained may, if necessary, be purified by conventional menas, e.g. recrystallization, reprecipitation, chromatography or the like.

Step 7: Deprotection

This step involves the preparation of a compound of formula (IX) by removing the carboxy-protecting group ($W^1$) from the compound of formula (VIII).

The reaction employed to remove the protecting group can be carried out in a similar manner to the procedure described in "Protective Group in Organic Synthesis", 2nd edition, T. W. Greene & P. G. M. Wut; John Wiley and Sons Inc., New York (1991), and the nature of the reaction will, as is well known, depend on the nature of the protecting group.

For example, where $W^1$ represents a lower alkyl group, such as a methyl or ethyl group, the protecting group can be removed by hydrolyzing the protected compound in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; and mixtures of water and one or more alcohols.

There is likewise no particular restriction on the nature of the bases used, and any base commonly used in reactions of this type may equally be used here. Examples of such bases include: alkali metal carbonates, such as sodium carbonate, potassium carbonate or lithium carbonate; and alkali metal or alkaline earth metal hydroxides, such as sodium hydroxide, potassium hydroxide, barium hydroxide or lithium hydroxide; preferably sodium hydroxide or potassium hydroxde.

The reaction can take place over a wide range of temperatures, and the precise reaction temperature is not critical to the invention. The preferred reaction temperature will depend upon such factors as the nature of the solvent, and the starting material or reagent used. However, in general, we find it conyenient to carry out the reaction at a temperature of from 0° to 150° C., more preferably from 25° to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 10 hours, will usually suffice.

After completion of the reaction, the desired compound can be recovered from the reaction mixture by conventional means. An example of one such technique comprises: diluting the reaction mixture with water; acidifying the reaction mixture with an acid, such as hydrochloric acid; extracting with a water-immiscible organic solvent, such as diethyl ether; washing the organic phase with water; drying it over anhydrous magnesium sulfate or the like; and finally distilling off the solvent.

Step 8: Deprotection

This step involves the preparation of a compound of formula (XI) by removing a hydroxy-protecting group ($W^2$) from the compound of formula (X).

Elimination of protecting groups can be carried out in a similar manner to the procedure described in "Protective Group in Organic Synthesis", referred to above.

For example, where $W^2$ represents a t-butyldimethyl silyl group, the protecting group may be eliminated by using an inorganic acid, such as hydrochloric acid, or a reagent which is capable of generating a fluorine ion, such as tetrabutylammoniumn fluoride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform or dichloroethane; ethers, such as diethyl ether, tetrahydrofuran, dioxane or dimethoxyethane; alcohols, such as methanol or ethanol; and nitrites, such as acetonitrile or isobutyronitrile; preferably aromatic hydrocarbons (particularly benzene), ethers (particularly tetrahydrofuran) and alcohols (particularly methanol).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from room temperature to 50° C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

After completion of the reaction, the desired compound in this step can be recovered from the reaction mixture by conventional means. An example of one such technique comprises: neutralizing the reaction mixture or filtering off any insoluble materials; adding a water immiscible organic solvent, such as diethyl ether; washing the organic phase with water; drying it over anhydrous magnesium sulfate or the like; and finally distilling off the solvent.

The desired compound thus obtained may, if necessary, be further purified by such conventional techniques as recrystallization, reprecipitation or chromatography.

Step 9: Introduction of a protecting group

This step involves the preparation of a compound of formula (XIII) by reacting a compound of formula (XII) with a hydroxy-protecting agent (preferably a trialkylsilyl halide, particularly t-butyldimethylsilyl chloride) in an inert solvent.

Introduction of a protecting group can be carried out in a similar manner to the procedure described in "Protective Group in Organic Synthesis", referred to above.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, chloroform or dichloroethane; ethers, such as diethyl ether, tetrahydrofuran, dioxane or dimethoxyethane; and amides, such as dimethylformamide or dimethylacetamide; preferably halogenated hydrocarbons (particularly methylene chloride), ethers (particularly tetrahydrofuran) and amides (particularly dimethylformamide).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 100° C., more preferably from 0° to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, more preferably from 30 minutes to 24 hours, will usually suffice.

After completion of the reaction, the desired compound in this step can be recovered from the reaction mixture by conventional means. An example of one such technique comprises: adding a water-immiscible organic solvent, such as ethyl acetate thereto; washing the organic phase with water; drying it over anhydrous magnesium sulfate or the like; and finally distilling off the solvent.

Step 10: Reduction of a nitro group

This step involves the preparation of a compound of formula (VB) by reacting a compound of formula (XIII) with a reducing agent in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; and water; more preferably alcohols.

There is likewise no particular restriction on the nature of the reducing agent used, and any reducing agent commonly used in reactions of this type may equally be used here. Examples of such reducing agents include: zinc/acetic acid, iron/hydrochloric acid, tin/hydrochloric acid, hydrogen in contact with Pd/C as a catalyst (catalytic reduction) and the like agent; preferably zinc/acetic acid or catalytic reduction.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 150° C., more preferably from 0° to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 20 minutes to 12 hours, will usually suffice.

After completion of the reaction, the desired compound in this step can be recovered from the reaction mixture by conventional means. An example of one such technique comprises: in the case of reduction using zinc, making alkaline the reaction mixture or filtering off any insoluble materials; adding a water-immiscible organic solvent, such as ethyl acetate; washing the organic phase with water; drying it over anhydrous magnesium sulfate or the like; and finally distilling off the solvent.

The desired compound thus obtained may, if necessary, be further purified by such conventional techniques as recrystallization, reprecipitation or chromatography.

Step 11: Wittig reaction

This step involves the preparation of a compound of formula (XV) by reacting a compound of formula (XIV) with a Wittig-Honer reagent, such as ethyl 2-diethylphosphonoacetate, in an inert solvent and in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene; ethers, such as diethyl ether, tetrahydrofuran, dioxane or dimethoxyethane; amides, such as dimethylformamide, dimethylacetamide or hexamethylphosphoric triamide; and sulfoxides, such as dimethyl sulfoxide or sulfolane; preferably ethers (particularly tetrahydrofuran) and amides particularly dimethylformamide).

There is likewise no particular restriction on the nature of the bases used, provided that other parts of the compound are not affected, and any base commonly used in reactions of this type may equally be used here. Examples of such bases include: metal hydrides, such as sodium hydride or lithium hydride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 120° C., more preferably from 0° to 80° C. The time required for the reaction may also vary widely, depending on many factors, notably the reaction temperature and the nature of the reagents and solvent employed. However, provided that the reaction is effected under the preferred conditions outlined above, a period of from 10 minutes to 48 hours, more preferably from 1 to 24 hours, will usually suffice.

After completion of the reaction, the desired compound in this step can be recovered from the reaction mixture by conventional means. An example of one such technique comprises; neutralizing the reaction mixture or filtering off any insoluble materials; adding a water-immiscible organic solvent, such as ethyl acetate; washing the organic phase with water; drying it over anhydrous magnesium sulfate or the like; and finally distilling off the solvent.

The desired compound thus obtained may, if necessary, be further purified by such conventional techniques as recrystallization, reprecipitation or chromatography.

Step 12: Reduction of an ester group

This step involves the preparation of a compound of formula (XVI) by reacting a compound of formula (XV) with a reducing agent in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran, dioxane or dimethoxyethane; and alcohols, such as methanol or ethanol; more preferably ethers (particularly tetrahydrofuran) and alcohols (particularly methanol).

There is likewise no particular restriction on the nature of the reducing agent used, and any reducing agent commonly used in reactions of this type may equally be used here. Examples of such reducing agents include: diisobutylaluminum hydride and sodium borohydride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 100° C., more preferably from 0° to 80° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 1 to 10 hours, will usually suffice.

After completion of the reaction, the desired compound in this step can be recovered from the reaction mixture by conventional means. An example of one such technique comprises: neutralizing the reaction mixture or filtering off any insoluble materials; adding a water-immiscible organic solvent, such as ethyl acetate thereto; washing the organic phase with water; drying it over anhydrous magnesium sulfate or the like; and finally distilling off the solvent.

Step 13: Introduction of a protecting group

This step involves the preparation of a compound of formula (XVII) by reacting a compound of formula (XVI) with a hydroxy-protecting agent (preferably a trialkylsilyl halide, particularly t-butyldinethylsilyl chloride) in an inert solvent.

The reaction in this step is essentially the same as that described in Step 9, and may be carried out employing the same reagents and reaction conditions.

Step 14: Reduction of a nitro group

This step involves the preparation of a compound of formula (VC) by reacting a compound of formula (XVII) with a reducing agent in an inert solvent.

The reaction in this step is essentially the same as that described in Step 10, and may be carried out employing the same reagents and reaction conditions.

Step 15: Reduction of a double bond

This step involves the preparation of a compound of formula (VD) by reacting a compound of formula (VC) with a reducing agent in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol (particularly ethanol); and ethers, such as diethyl ether or tetrahydrofuran.

There is likewise no particular restriction on the nature of the reducing agent used, and any reducing agent commonly used in reactions of this type may equally be used here. Examples of such reducing agents include hydrogen (used in contact with Pd as a catalyst).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10° and 80° C. The time required for the reaction may also vary widely, depending on many factors, notably the reaction temperature and the nature of the reagents and solvent employed. However, provided that the reaction is effected under the preferred conditions outlined above, a period of from 1 to 10 hours will usually suffice.

After completion of the reaction, the desired compound can be obtained by filtering off the catalyst and distilling off the solvent.

The product thus obtained may, if desired, be further purified by various types of chromatography or recrystallization.

Step 16: Introduction a leaving group

This step involves the preparation of a compound of formula (XVIII) by reacting a compound of formula (XII) with an alkyl- or aryl-sulfonyl halide (preferably with methanesulfonyl chloride or p-toluenesulfonyl chloride) in an inert solvent and in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene; halogenated hydrocarbons, such as methylene chloride or chloroform; and ethers, such as diethyl ether, tetrahydrofuran, dioxane or dimethoxyethane; more preferably halogenated hydrocarbons (particularly methylene chloride or dichloroethane).

There is likewise no particular restriction on the nature of the bases used, provided that other parts of the compound are not affected, and any base commonly used in reactions of this type may equally be used here. Examples of such bases include: organic bases, such as triethylamine, diisopropylethylamine, methylmorpholine, pyridine, 4-($\underline{N}$,$\underline{N}$-dimethylamino)pyridine, $\underline{N}$,$\underline{N}$-dimethyl-aniline and $\underline{N}$,$\underline{N}$-diethylaniline; preferably triethylamine or diisopropylethylamine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 50° C., more preferably from 0° to 25° C. The time required for the reaction may also vary widely, depending on many factors, notably the reaction temperature and the nature of the reagents and solvent employed. However, provided that the reaction is effected under the preferred conditions outlined above, a period of from 5 minutes to 10 hours, more preferably from 10 minutes to 3 hours, will usually suffice.

After completion of the reaction, the desired compound can be recovered from the reaction mixture by conventional means. An example of one such technique comprises: adding a water-immiscible organic solvent, such as ethyl acetate, to the reaction mixture; washing the organic phase with water; drying it over anhydrous magnesium sulfate or the like; and finally distilling off the solvent.

The desired compound thus obtained may, if necessary, be further purified by such conventional means as recrystallization, reprecipitation or chromatography.

Where $X^a$ of the compound of formula (XVIII) signifies a leaving group, such as chlorine or bromine, the compound of formula (XVIII) can be produced by reacting a compound of formula (XII) with carbon tetrachloride or carbon tetrabromide in the presence of triphenylphosphine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene; halogenated hydrocarbons, such as methylene chloride or chloroform; and ethers, such as diethyl ether or tetrahydrofuran; more preferably tetrahydrofuran or methylene chloride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 100° C., more preferably from 20° to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 10 hours, more preferably from 10 minutes to 5 hours, will usually suffice.

After completion of the reaction, the desired compound can be recovered from the reaction mixture by conventional means.

Step 17: Cyanation

This step involves the preparation of a compound of formula (XIX) by reacting a compound of formula (XVM) with a cyanide (preferably sodium cyanide or potassium cyanide) in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: amides, such as dimethylformamide; and sulfoxides, such as dimethyl sulfoxide; more preferably dimethylformamide or dimethyl sulfoxide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 100° C., more preferably from 0° to 70° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 to 24 hours, will usually suffice.

After completion of the reaction, the desired compound can be recovered from the reaction mixture by conventional means. An example of one such technique comprises: adding a water-immiscible organic solvent, such as ethyl acetate to the reaction mixture; washing the organic phase with water; drying it over anhydrous magnesium sulfate or the like; and finally distilling off the solvent.

Step 18: Hydrolysis of a cyano group

This step involves the preparation of a compound of formula (XX) by hydrolysis of a compound of formula (XIX) in an inert solvent in the presence of an acid catalyst.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; organic carboxylic acids, such as acetic acid; and mixtures of water and organic acids; preferably water.

There is likewise no particular restriction on the nature of the acid catalyst used, and any acid catalyst commonly used in reactions of this type may equally be used here. Examples of such acid catalysts include sulfuric acid, hydrochloric acid, hydrobromic acid and the like acids, preferably sulfuric acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 25° to 200° C., more preferably from 50° to 180° C. The time required for the reaction may also vary widely, depending on many factors, notably the reaction temperature and the nature of the reagents and solvent employed. However, provided that the reaction is effected under the preferred conditions outlined above, a period of from 0.5 to 5 hours, more preferably from 1 to 4 hours, will usually suffice.

After completion of the reaction, the desired compound can be recovered from the reaction mixture by conventional means. An example of one such technique comprises: pouring the reaction mixture into ice-water; extracting with a water-immiscible organic solvent, such as methylene chloride; washing the organic phase with water; and finally drying it.

Step 19: Reduction a carboxyl group

This step involves the preparation of a compound of formula (XXI) by reacting a compound of formula (XX) with a reducing agent in an inert solvent.

There is likewise no particular restriction on the nature of the reducing agent used, and any reducing agent commonly used in reactions of this type may equally be used here. Examples of such reducing agents include borane complexes, such as borane or borane-dimethyl sulfide complex; preferably borane-dimethyl sulfide complex.

After completion of the reaction, the desired compound can be recovered from the reaction mixture by conventional means. An example of one such technique comprises: adding methanol to decompose any excess of the reagent; distilling off the solvent; adding water to the residue; extracting with a water-immiscible solvent, such as ethyl acetate; washing the extract with water; and finally drying it.

The compound thus obtained may, if desired, be further purified by various types of chromatography or recrystallization.

Step 20: Introduction of a protecting group

This step involves the preparation of a compound of formula (XXI) by reacting a compound of formula (XXI) with a hydroxy-protecting agent (preferably a trialkylsilyl halide, particularly t-butyldimethylsilyl chloride) in an inert solvent.

The reaction in this step is essentially the same as that described in Step 9, and may be carried out employing the same reagents and reaction conditions.

Step 21: Reduction of a nitro group

This step involves the preparation of a compound of formula (VE) by reacting a compound of formula (XXI) with a reducing agent in an inert solvent.

The reaction in this step is essentially the same as that described in Step 10, and may be carried out employing the same reagents and reaction conditions.

Step 22: Introduction of a protecting group

This step involves the preparation of a compound of formula (XXIV) by reacting a compound of formula (XXII) with a carboxy-protecting agent (preferably a lower alcohol, such as methanol or ethanol) in an inert solvent.

The step may be accomplished by reacting an acid chloride corresponding to the compound of formula (XXIII), which is produced from the compound of formula (XXII) by conventional means, with a lower alcohol in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene; ethers, such as tetrahydrofuran; and halogenated hydrocarbons, such as methylene chloride; preferably methylene chloride.

There is likewise no particular restriction on the nature of the bases used, provided that other parts of the compound are not affected, and any base commonly used in reactions of this type may equally be used here. Examples of such bases include: organic bases, such as triethylamine, pyridine, N,N-dimethylaniline or the like, preferably pyridine.

After completion of the reaction, the desired compound can be recovered from the reaction mixture by conventional means such as those described in Step 3b.

Step 23: Reduction of a nitro group

This step involves the preparation of a compound of formula (VF) by reacting a compound of formula (XXIV) with a reducing agent in an inert solvent.

The reaction in this step is essentially the same as that described in Step 10, and may be carried out employing the same reagents and reaction conditions.

Step 24: Alkylation

This step involves the preparation of a compound of formula (XXVI) by reacting a compound of formula (XXV) with dimethyl sulfide in an inert solvent in the presence of chlorosuccinimide, and subsequently by treating the product with an organic base, such as triethylamine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include halogenated hydrocarbons, such as methylene chloride or chloroform.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 60° C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

After completion of the reaction, the desired compound can be recovered from the reaction mixture by conventional means. An example of one such technique comprises: filtering insoluble materials, if any, from the reaction mixture; adding a water-immiscible organic solvent, such as methylene chloride, thereto; washing the organic phase, in turn, with a saturated aqueous solution of sodium hydrogencarbonate and water; separating the organic phase containing the desired compound; drying it over anhydrous magnesium sulfate or the like; and finally distilling off the solvent.

Step 25: Oxidation

This step involves the preparation of a compound of formula (XXVII) by reacting a compound of formula (XXVI) with an oxidizing agent in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride or chloroform; and alcohols, such as methanol or ethanol.

There is likewise no particular restriction on the nature of the oxidizing agent used, and any oxidizing agent commonly used in reactions of this type may equally be used here. Examples of such oxidizing agents include m-chloroperbenzoic acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 60° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

After completion of the reaction, the desired compound in this step can be recovered from the reaction mixture by conventional means. An example of one such technique comprises: filtering insoluble materials, if any, from the reaction mixture; adding a water-immiscible organic solvent, such as ethyl acetate thereto; washing the organic phase, in turn, with a saturated aqueous solution of sodium hydrogencarbonate and water; drying it over anhydrous magnesium sulfate or the like; and finally distilling off the solvent.

Step 26: Chlorination

This step involves the preparation of a compound of formula (XXVIII) by reacting a compound of formula (XXVII) with hydrogen chloride in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, chloroform or 1,2-dichloroethane.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 60° C. The time required for the reaction may also vary widely, depending on many factors, notably the reaction temperature and the nature of the reagents and solvent employed. However, provided that the reaction is effected under the preferred conditions outlined above, a period of from 1 to 24 hours will usually suffice.

After completion of the reaction, the desired compound in this step can be recovered from the reaction mixture by conventional means such as collecting the desired compound, which precipitated in the reaction mixture, by filtration.

Step 27: Condensation

This step involves the preparation of a compound of formula (XXIX) by reacting a compound of formula (IVA) with a compound of formula (XXVIII) in an inert solvent.

The reaction in this step is essentially the same as that described in Step 3b, and may be carried out employing the same reagents and reaction conditions.

Step 28: Introduction of an oxygen functional group

This step involves the preparation of a compound of formula (XXX) by reacting a compound of formula (XXIX) with an alkali metal salt of a carboxylic acid, such as acetic acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: amides, such as dimethylformamide; and sulfoxides, such as dimethyl sulfoxide.

There is likewise no particular restriction on the nature of the alkali metal salt of a carboxylic acid used, and any alkali metal salt commonly used in reactions of this type may equally be used here. Examples of such alkali metal salts include sodium acetate and potassium acetate.

In some cases where the reaction is carried out in the presence of an iodide, the reaction may proceed more smoothly.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 150° C., more preferably from 25° to 100° C. The time required for the reaction may also vary widely, depending on many factors, notably the reaction temperature and the nature of the reagents and solvent employed. However, provided that the reaction is effected under the preferred conditions outlined above, a period of from 1 to 5 hours, more preferably from 1 to 3 hours, will usually suffice.

After completion of the reaction, the desired compound can be recovered from the reaction mixture by conventional means. An example of one such technique comprises: diluting the reaction mixture with a water-immiscible solvent, such as ethyl acetate; washing the organic phase with a saturated aqueous solution of sodium hydrogencarbonate and water; drying it over anhydrous magnesium sulfate or the like; and finally distilling off the solvent.

Step 29: Hydrolysis

This step involves the preparation of a compound of formula (XXXI) by hydrolyzing a compound of formula (XXX) in an inert solvent and in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; and mixtures of water and one or more alcohols.

There is likewise no particular restriction on the nature of the bases used, provided that other parts of the compound are not affected, and any base commonly used in reactions of this type may equally be used here. Examples of such bases include: alkali metal carbonates, such as sodium carbonate, potassium carbonate or lithium carbonate; and alkali metal or alkaline earth metal hydroxides, such as sodium hydroxide, potassium hydroxide, barium hydroxide or lithium hydroxide; more preferably sodium hydroxide or potassium hydroxide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 150° C., more preferably from 25° to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 10 hours, will usually suffice.

After completion of the reaction, the desired compound can be recovered from the reaction mixture by conventional means. An example of one such technique comprises: diluting the reaction mixture with a water-immiscible organic solvent, such as diethyl ether; washing the organic phase with water; drying it over anhydrous magnesium sulfate or the like; and finally distilling off the solvent.

Step 30: Knoevenagel reaction

This step involves the preparation of a compound of formula (XXXII) by reacting a compound of formula (XXXII) with a malonate in an inert solvent and in the presence of a base and an acid catalyst.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene (particularly benzene).

There is likewise no particular restriction on the nature of the bases used, provided that other parts of the compound are not affected, and any base commonly used in reactions of this type may equally be used here. Examples of such bases include: secondary amines, such as pyrrolidine or piperidine.

There is likewise no particular restriction on the nature of the acids used and any acid commonly used in reactions of this type may equally be used here. Examples of such acids include: organic carboxylic acids, such as benzoic acid or acetic acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 50° to 150° C., more preferably from 80° to 120° C. The time required for the reaction may also vary widely, depending on many factors, notably the reaction temperature and the nature of the reagents and solvent employed. However, provided that the reaction is effected under the preferred conditions outlined above, a period of from 1 to 72 hours, more preferably from 1 to 40 hours, will usually suffice.

After completion of the reaction, the desired compound can be recovered from the reaction mixture by conventional means. An example of one such technique comprises: adding a water-immiscible solvent, such as ethyl acetate to the reaction mixture; washing the organic phase, in turn, with a saturated aqueous solution of sodium hydrogencarbonate, an acid, such as 1N hydrochloric acid, and water; and finally distilling off the solvent.

The desired compound thus obtained may, if desired, be further purified by various types of chromatography or recrystallization.

Step 31: Grignard reaction

This step involves the preparation of a compound of formula (XXXV) by reacting a compound of formula (XXXIII) with a Grignard reagent (XXXIV) in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran, dioxane, dimethoxyethane and diethylene glycol dimethyl ether particularly tetrahydrofuran or diethyl ether).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −30° to 40° C. The time required for the reaction may also vary widely, depending on many factors, notably the reaction temperature and the nature of the reagents and solvent employed. However, provided that the reaction is effected under the preferred conditions outlined above, a period of from 10 minutes to 2 hours will usually suffice.

After completion of the reaction, the desired compound can be recovered from the reaction mixture by conventional means. For example, an aqueous solution of ammonium chloride may be added to the reaction mixture and the aqueous mixture extracted with a water-immiscible solvent, such as benzene, ether or ethyl acetate. The extract may be washed with water and dried, after which the solvent may be distilled off to give the desired compound.

The product thus obtained may, if desired, be further purified by various types of chromatography or recrystallization.

In some cases where the reaction in this step is carried out in the presence of copper (I) iodide, the yield may be improved.

Step 32: Hydrolysis

This step involves the preparation of a compound of formula (XVI) by hydrolyzing a compound of formula (XXXV) in an inert solvent.

The reaction in this step is essentially the same as that described in Step 7, and may be carried out employing the same reagents and reaction conditions.

Step 33: Decarboxylation

This step involves the preparation of a compound of formula (IVC) by heating a compound of formula (XXXVI) in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene particularly xylene).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 50° to 200° C., more preferably from 70° to 150° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 10 hours, will usually suffice.

After completion of the reaction, the desired compound can be recovered from the reaction mixture by distilling off the solvent.

The desired compound thus obtained may, if necessary, be further purified by such conventional means as recrystallization or chromatography.

Step 34: Grignard reaction

This step involves the preparation of a compound of formula (XXXVI) by reacting a compound of formula (XXXII) with a Grignard reagent of formula (XXXV) in an inert solvent.

The reaction in this step is essentially the same as that described in Step 31, and may be carried out employing the same reagents and reaction conditions.

In some cases where the reaction is carried out in the presence of tetrabutylammonium bromide, the yield may be improved.

Step 35: Oxidation of benzyl alcohol

This step involves the preparation of a compound of formula (XXXVIII) by reacting a compound of formula (XXXVII) with an oxidizing agent in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: include: aromatic hydrocarbons, such as benzene, toluene or xylene; halogenated hydrocarbons, such as methylene chloride, chloroform or dichloroethane; esters, such as ethyl acetate; ethers, such as diethyl ether, tetrahydrofuran, dioxane or dimethoxyethane; ketones, such as acetone or methyl ethyl ketone; and nitriles, such as acetonitrile or isobutyronitrile; more preferably halogenated hydrocarbons (particularly methylene chloride) or ethers (particularly tetrahydrofuran).

There is likewise no particular restriction on the nature of the oxidizing agent used, and any oxidizing agent commonly used in reactions of this type may equally be used here. Examples of such oxidizing agents include: manganese oxides, such as manganese dioxide; chromic acid compounds, such as chromic anhydride-pyridine complex; and the reagents capable of using DMSO oxidation (dimethyl sulfoxide plus dicyclohexylcarbodiimide, oxalyl chloride, acetic anhydride or phosphorus pentaoxide complex, or sulfuric trioxide pyridine complex); or 4-methylmorpholine 4-oxide using tetrapropylammonium perruthenate (VII) as a catalyst.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −60° to 40° C. The time required for the reaction may also vary widely, depending on many factors, notably the reaction temperature and the nature of the reagents and solvent employed. However, provided that the reaction is effected under the preferred conditions outlined above, a period of from 1 to 16 hours will usually suffice.

After completion of the reaction, the desired compound can be recovered from the reaction mixture by conventional means.

Step 36: Wittig reaction

This step involves the preparation of a compound of formula (XXXIX) by reacting a compound of formula (XXXVIII) with a Wittig-Honer reagent, such as ethyl 2-diethylphosphonoacetate, in an inert solvent and in the presence of a base.

The reaction in this step is essentially the same as that described in Step 11, and may be carried out employing the same reagents and reaction conditions.

Step 37: Reduction of a double bond

This step involves the preparation of a compound of formula (XXXX) by reacting a compound of formula (XXXIX) with a reducing agent in an inert solvent.

The reaction in this step is essentially the same as that described in Step 15, and may be carried out employing the same reagents and reaction conditions.

Step 38: Hydrolysis

This step involves the preparation of a compound of formula (IVD) by hydrolyzing a compound of formula (XXXX) in an inert solvent.

The reaction in this step is essentially the same as that described in Step 7, and may be carried out employing the same reagents and reaction conditions.

Step 39: Acylation

This step involves the preparation of a compound of formula (IF) of the present invention by reacting a compound of formula (IE) with a compound of formula (XXXXI) in an inert solvent in the presence of a base.

The compound of formula (XXXXI) used in this step can be prepared by reacting a compound of formula (XXXXIa) with N,N'-carbonyldiimidazole in a solvent, such as an ether (particularly tetrahydrofuran), a nitrile (particularly acetonitrile), an aromatic hydrocarbon particularly benzene) or an amide (particularly dimethylacetamide or dimethylformamide) at room temperature to 60° C. for 10 minutes to 10 hours.

The reaction of the compound of formula (IE) with the compound of formula (XXXXI) is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran; nitrites, such as acetonitrile; aromatic hydrocarbons, such as benzene or toluene; and amides, such as dimethylacetamide or dimethylformamide.

There is likewise no particular restriction on the nature of the bases used, provided that other parts of the compound are not affected, and any base commonly used in reactions of this type may equally be used here. Examples of such bases include: organic bases, such as triethylamine, diisopropylethylamine or 4-N,N-dimethylaminopyridine; alkali metal salts of organic base, such as lithium bistrimethylsilylamide, sodium bistrimethylsilylamide, potassium bistrimethylsilylamide or lithium diisopropylamide; and alkali metal salts of alcohols, such as potassium t-butoxide; preferably 4-N,N-dimethylaminopyridine, potassium bistrimethylsilylamide or potassium t-butoxide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from to –30° to 120° C. The time required for the reaction may also vary widely, depending on many factors, notably the reaction temperature and the nature of the reagents and solvent employed. However, provided that the reaction is effected under the preferred conditions outlined above, a period of from 10 minutes to one week will usually suffice.

It should be noted that, where the compound of formula (XXXXIa) which is a starting material for the compound of formula (XXXI) to be employed in this process contains a secondary amino group in some part of its structure, this step can be achieved by conyerting such a moiety to a 4-nitrobenzyloxycarbonyl derivative or the like using a protecting reagent, such as 4-nitrobenzyloxycarbonyl chloride or the like before the reaction of this step is carried out, and then removing the protecting group.

After completion of the reaction, the desired compound of the present reaction can be recovered from the reaction mixture by conventional means. An example of one such technique comprises: adding a water-immiscible organic solvent, such as ethyl acetate, thereto; washing the resulting mixture with water; separating the organic phase containing the desired compound; drying it over anhydrous magnesium sulfate; and finally distilling off the solvent.

The desired compound thus obtained may, if necessary, be further purified by conventional means, such as recrystallization, reprecipitation or chromatography.

Step 40: Acylation

This step involves the preparation of a compound of formula (IF) of the present invention by reacting a compound of formula (IX) with a carboxy group and an activating reagent articularly N,N'-carbonyldiimidazole) in an inert solvent to synthesize an active ester as an intermediate and then reacting the active ester with a compound of formula (XXXXII) in the presence of a base.

The active ester, which is an intermediate of the present step, can cause the compound of formula (IX) to react with N,N'-carbonyldiimidazole in a solvent, such as an ether (particularly tetrahydrofuran), a nitrile (particularly acetonitrile), an aromatic hydrocarbon (particularly benzene) or an amide (particularly dimethylacetamide or dimethylformamide) at room temperature to 60° C. for 10 minutes to 10 hours.

The reaction of the active ester with the compound of formula (XXXXII) is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran; nitriles, such as acetonitrile; aromatic hydrocarbons, such as benzene or toluene; and amides, such as dimethylacetamide or dimethylformamide.

There is likewise no particular restriction on the nature of the bases used, provided that other parts of the compound are not affected, and any base commonly used in reactions of this type may equally be used here. Examples of such bases include: organic bases, such as triethylamine, diisopropylethylamine or 4-N,N-dimethylaminopyridine; alkali metal salts of organic base, such as lithium bistrimethylsilylamide, sodium bistrimethylsilylamide, potassium bistrimethylsilylamide or lithium diisopropylamide; and alkali metal salts of alcohols, such as potassium t-butoxide; preferably 4-N,N-dimethylaminopyridine, potassium bistrimethylsilylamide or potassium t-butoxide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from –30° to 120° C. The time required for the reaction may also vary widely, depending on many factors, notably the reaction temperature and the nature of the reagents and solvent employed. However, provided that the reaction is effected under the preferred conditions outlined above, a period of from 10 minutes to one week will usually suffice.

After completion of the reaction, the desired compound of the present reaction can be recovered from the reaction mixture according to conventional means. An example of one such technique comprises: adding a water-immiscible organic solvent, such as ethyl acetate, thereto; washing the resulting mixture with water; separating the organic phase containing the desired compound; drying it over anhydrous magnesium sulfate; and finally distilling off the solvent.

The desired compound thus obtained may, if necessary, be further purified by conventional means, such as recrystallization, reprecipitation or chromatography.

Step 41: Grignard reaction

This step involves the preparation of a compound of formula (HI) by reacting a compound of formula (IG) with Grignard reagent of formula (XXXXIII) in an inert solvent.

The reaction in this step is essentially the same as that described in Step 34, and may be carried out employing the same reagents and reaction conditions.

Step 42: Oxidation

This step involves the preparation of a compound of formula (IH') by reacting a compound of formula (IH) with an oxidizing agent in an inert solvent.

The reaction in this step is essentially the same as that described in Step 35, and may be carried out employing the same reagents and reaction conditions.

Step 43: Reduction

This step involves the preparation of a compound of formula (IH) by reacting a compound of formula (IH') with a reducing agent in an inert solvent.

The reaction in this step is essentially the same as that described in Step 12, and may be carried out employing the same reagents and reaction conditions.

Step 44: Introduction of a group to be eliminated

This step involves the preparation of a compound of formula (XXXXIV) by reacting a compound of formula (II) with an alkyl- or aryl-sulfonyl halide (preferably with methanesulfonyl chloride or p-toluenesulfonyl chloride) in an inert solvent and in the presence of a base catalyst.

The reaction in this step is essentially the same as that described in Step 16, and may be carried out employing the same reagents and reaction conditions.

Step 45: Imidation

This step involves the preparation of a compound of formula (IJ) by reacting a compound of formula (XXXXIV) with a compound of formula (XXXXV) in an inert solvent and in the presence of a base catalyst.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene; halogenated hydrocarbons, such as methylene chloride or 1,2-dichloroethane; ethers, such as tetrahydrofuran or 1,2-dimethoxyethane; and amides, such as dimethylformamide or dimethylacetamide; preferably tetrahydrofuran or dimethylformamide.

There is likewise no particular restriction on the nature of the bases used, provided that other parts of the compound are not affected, and any base commonly used in reactions of this type may equally be used here. Examples of such bases include: alkali metal hydroxides, such as sodium hydroxide or potassium hydroxide; alkali metal hydrides, such as sodium hydride or potassium hydride; and alkali metal salts of organic bases, such as lithium diisopropylamide or lithium bistrimethylsilylamide; preferably sodium hydride or lithium diisopropylamide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours will usually suffice.

After completion of the reaction, the desired compound in this step can be recovered from the reaction mixture according to conventional means. An example of one such technique comprises: adding a water-immiscible organic solvent, such as ethyl acetate, thereto; washing the resulting mixture with water; separating the organic phase containing the desired compound; drying it over anhydrous magnesium sulfate; and finally distilling off the solvent.

The desired compound thus obtained may, if necessary, be further purified by conventional means, such as recrystallization, reprecipitation or chromatography.

Step 46: Azidation

This step involves the preparation of a compound of formula (XXXXVI) by reacting a compound of formula (XXXXIV) with an alkali metal azide (particularly sodium azide) in an inert solvent.

The reaction in this step is essentially the same as that described in Step 16, and may be carried out employing the same reagents and reaction conditions, except that sodium cyanide is replaced by sodium azide.

Step 47: Reduction

This step involves the preparation of a compound of formula (XXXXVII) by reacting a compound of formula (XXXXVI) with a reducing agent in an inert solvent.

The reaction in this step is essentially the same as that described in Step 10, and may be carried out employing the same reagents and reaction conditions.

Step 48: Cyanation

This step involves the preparation of a compound of formula (IK) by reacting a compound of formula (XXXXIV) with a cyanide (preferably sodium cyanide or potassium cyanide) in an inert solvent.

The reaction in this step is essentially the same as that described in Step 17, and may be carried out employing the same reagents and reaction conditions.

Step 49: Condensation

This step involves the preparation of a compound of formula (IL) by reacting a compound of formula (XXXXVIII) with a compound of formula (L) in an inert solvent.

The reaction in this step is essentially the same as that described in Step 3, and may be carried out employing the same reagents and reaction conditions.

Step 50: Carbamoylation

This step involves the preparation of a compound of formula (IM) by reacting a compound of formula (XXXXVI) with a compound of formula (LI) (in this formula only, $R^{5a}$ and $R^{5b}$ each represent groups other than a hydrogen atom) in an inert solvent.

The reaction in this step is essentially the same as that described in Step 2c, and may be carried out employing the same reagents and reaction conditions.

Step 51: Carbamoylation

This step involves the preparation of a compound of formula (IN) by reacting a compound of formula (XXXXVII) with a compound of formula (LII) (in this formula only, $R^{5a}$ represents groups other than a hydrogen atom) in an inert solvent.

The reaction in this step is essentially the same as that described in Step 2b, and may be carried out employing the same reagents and reaction conditions.

Step 52: Carbamoylation

This step involves the preparation of a compound of formula (IP) by reacting a compound of formula (XXXXVIII) with an alkali metal salt of cyanic acid (particularly potassium cyanate or sodium cyanate) in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: a mixed solvent of one or more organic acids (particularly acetic acid) and water.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from room temperature to 120° C. The time required for the reaction may also vary widely, depending on many factors, notably the reaction temperature and the nature of the reagents and solvent employed. However, provided that the reaction is effected under the preferred conditions outlined above, a period of from one hour to 10 hours will usually suffice.

After completion of the reaction, the desired compound of the present reaction can be recovered from the reaction mixture by conventional means. An example of one such technique comprises: adding a water-immiscible organic solvent, such as ethyl acetate, thereto; washing the resulting mixture with water; separating the organic phase containing the desired compound; drying it over anhydrous magnesium sulfate; and finally distilling off the solvent.

The desired compound thus obtained may, if necessary, be further purified by conventional means, such as recrystallization, reprecipitation or chromatography.

Step 53: Sulfonylation

This step involves the preparation of a compound of formula (IQ) by reacting a compound of formula (XXXXVIII) with a compound of formula (LIII) in an inert solvent.

The reaction in this step is essentially the same as that described in Step 3b, and may be carried out employing the same reagents and reaction conditions, except that the acid chloride [the compound (IVA), $X^1$=Cl] is replaced by the compound of formula (LIII).

Step 54: Condensation

This step involves the preparation of a compound of formula (LV) by reacting a compound of formula (LIV) with a compound of formula (IIB) in an inert solvent.

The reaction in this step is essentially the same as that described in Step 3, and may be carried out employing the same reagents and reaction conditions.

Step 55: Reduction

This step involves the preparation of a compound of formula (LVI) by reacting a compound of formula (LV) with a reducing agent in an inert solvent.

The reaction in this step is essentially the same as that described in Step 10, and may be carried out employing the same reagents and reaction conditions.

Step 56: Reduction. Carbamoylation and Reduction

This step involves the preparation of a compound of formula (LVII) using a compound of formula (LV) in which $R^{5a}$ represents a hydrogen atom as a starting material.

The reaction in this step is essentially the same as that described in Step 19, 52 and 10, and may be carried out employing the same reagents and reaction conditions.

Step 57: Dehydration reaction

This step involves the preparation of a compound of formula (LIX) by reacting a compound of formula (LVI) with a dehydrating agent in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran, 1,2-dimethoxyethane or dioxane; aromatic hydrocarbons, such as benzene; and halogenated hydrocarbons, such as methylene chloride or 1,2-methylene chloride; preferably tetrahydrofuran or dioxane.

There is likewise no particular restriction on the nature of the dehydrating agents used, and any dehydrating agent commonly used in reactions of this type may equally be used here. Examples of such dehydrating agents include: a mixture of an organic acid anhydride (particularly acetic anhydride or trifluoroacetic anhydride) and an organic base (particularly pyridine or triethylamine).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from room temperature to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 20 hours will usually suffice.

Step 58: Reduction

This step involves the preparation of a compound of formula (LX) by reacting a compound of formula (LIX) with a reducing agent in an inert solvent.

The reaction in this step is essentially the same as that described in Step 10, and may be carried out employing the same reagents and reaction conditions.

Step 59: Reduction

This step involves the preparation of a compound of formula (LXII) by reacting a compound of formula (LXI) with a reducing agent in an inert solvent.

The reaction in this step is essentially the same as that described in Step 19, and may be carried out employing the same reagents and reaction conditions.

Step 60: Introduction of a group to be eliminated

This step involves the preparation of a compound of formula (LXIII) by reacting a compound of formula (LXII) with an alkyl- or aryl-sulfonyl halide (preferably with methanesulfonyl chloride or p-toluenesulfonyl chloride) in an inert solvent in the presence of a base catalyst.

The reaction in this step is essentially the same as that described in Step 16, and may be carried out employing the same reagents and reaction conditions.

Step 61: Cyanation

This step involves the preparation of a compound of formula (LXIV) by reacting a compound of formula (LXIII) with a cyanide (preferably sodium cyanide or potassium cyanide) in an inert solvent.

The reaction in this step is essentially the same as that described in Step 17, and may be carried out employing the same reagents and reaction conditions.

Step 62: Reduction

This step involves the preparation of a compound of formula (LXV) by reacting a compound of formula (LXIV) with a reducing agent in an inert solvent.

The reaction in this step is essentially the same as that described in Step 10, and may be carried out employing the same reagents and reaction conditions.

Step 63: Oxidation

This step involves the preparation of a compound of formula (LXVI) by reacting a compound of formula (XXXI) with an oxidizing agent in an inert solvent.

The reaction in this step is essentially the same as that described in Step 35, and may be carried out employing the same reagents and reaction conditions.

Step 64: Oxidation

This step involves the preparation of a compound of formula (LXVII) by reacting a compound of formula (LXVI) with an oxidizing agent (preferably sodium chlorite) in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include a mixture of dimethyl sulfoxide or t-butanol and water. When t-butanol is used as the solvent, the reaction may be carried out in the presence of sulfamic acid in order to trap any chlorine generated in the reaction.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 50° C. The time required for the reaction may also vary widely, depending on many factors, notably the reaction temperature and the nature of the reagents and solvent employed. However, provided that the reaction is effected under the preferred conditions outlined above, a period of from one hour to 20 hours will usually suffice.

Step 65: Wittig reaction

This step involves the preparation of a compound of formula (LXVIII) by reacting a compound of formula (LXVI) with a Wittig-Honer reagent, such as ethyl diethylphosphonoacetate, in an inert solvent and in the presence of a base.

The reaction in this step is essentially the same as that described in Step 11, and may be carried out employing the same reagents and reaction conditions.

Step 66: Reduction

This step involves the preparation of a compound of formula (LXIX) by reacting a compound of formula (LXVII) with a reducing agent in an inert solvent.

The reaction in this step is essentially the same as that described in Step 15, and may be carried out employing the same reagents and reaction conditions.

Step 67: Hydrolysis

This step involves the preparation of a compound of formula (LXX) by hydrolyzing a compound of formula (LXIX) with a reducing agent in an inert solvent.

The reaction in this step is essentially the same as that described in Step 7, and may be carried out employing the same reagents and reaction conditions.

BIOLOGICAL ACTIVITY

The compounds of the present invention exhibit an excellent inhibitory activity against acyl-CoA: cholesterol acyl transferase, are well absorbed after oral administration and are less toxic than prior compounds. They are, therefore, useful for the therapy and prevention of arteriosclerosis.

The activity of the compounds of the present invention is illustrated by the following test.

Preparation of -very low density lipoprotein (β-VLDL)

Blood was obtained [using the anticoagulant ethylene diamine tetraacetic acid (5 mM)] from Japanese White rabbits which had been fed a 2% w/w cholesterol diet for 2 weeks and then fasted overnight prior to removing the blood. β-VLDL (d<1.006 g/ml) was isolated by ultracentrifugation from the plasma according to the method of Hatch and Lees [Hatch, F T. and Lees, R S.,Adv. Lipid Res., 6 1–68 (1968)] and dialyzed at 4° C. against 10 mM of a sodium phosphate buffer (pH 7.4) containing 150 mM sodium chloride.

Preparation of Mouse Macrophazes (Mφ)

Peritoneal cells were harvested from unstimulated female DDY mice (body weight 20–30 g) in phosphate buffer saline (PBS) as described by Edelson and Cohn [Edelson, P J. and Cohn, Z A.,1976, "In Vitro Methods in Cell-Mediated and Tumor Immunity", editors Bloon, B R and David, J R., (Academic Press, New York), 330–340.]. The fluid from the mice was pooled and the cells were collected by centrifugation at 400×g for 10 minutes at 4° C., and washed once with PBS. The cells were resuspended in Dulbecco's modified Eagle's medium (DMEM) containing 10% (vol/vol) fetal calf serum (FCS), penicillin (100 units/ml), and streptomycin (100 μg/ml) at a final concentration of $3 \times 10^6$ cells per ml. Aliquots (1 ml) of this cell suspension were dispersed onto plastic petri dishes (35×10 mm) and then incubated in a $CO_2$ incubator (5% $CO_2$/95% air) at 37° C. for 2 hours. Each dish was washed twice with PBS without serum to remove nonadherent cells.

Inhibition of ACAT in Mφ

Inhibition of ACAT in Mφ was determined according to the method described by Brown et al. Brown, M S., Goldstein J L., Krieger, M., Ho, Y K. and Anderson, R G W. (1979) J. Cell Biol., 82, 597–613.]. Cholesterol reacylation was initiated by adding β-VLDL (final concentration 50 μg cholesterol/ml), [$^{14}C$]oleate-albumin complex (final concentrations: 0.2 mM oleate and 0.6 mg/ml albumin) and a test compound dissolved in ethanol into the Mφ monolayer, and the preparation was incubated at 37° C. for 3 hours in a $CO_2$ incubator. Cells were washed three times with PBS and cellular lipid was extracted with 1 ml hexane/isopropanol (3:2 vol/vol). A lipid extract was evaporated to dryness in a stream of nitrogen. Cholesterol [$^{14}C$]oleated was seperated by thin layer chromatography through silica gel using an 85:15:1 by volume mixture of hexane, diethyl ether and acetic acid as developing solvents. The ACAT activity in Mφ was determined by measuring the radioactivity and an inhibition rate (%) was calculated by comparing a control activity with those of the test compound at given concentrations. The results are shown in the following Table, in which the compounds of the present invention are identified by the number of the Example given hereafter in which they are prepared.

| Example No. | $IC_{50}$ (ng/ml) |
|---|---|
| 1 | 28 |
| 2 | 19 |
| 3 | 15 |
| 4 | 2.8 |
| 5 | 33 |
| 11 | 5.2 |
| 19 | 13 |
| 23 | 5.4 |
| 35 | 33 |
| 44 | 11 |
| 64 | 17 |
| 131 | 9.1 |
| 136 | 5.4 |
| 142 | 20 |
| 158 | 9.8 |
| 165 | 0.73 |
| 173 | 9.2 |
| 186 | 42 |

The compounds of the present invention may be administered by any desired route and may be formulated as preparations suitable for that route. For example, for oral administration they may be formulated as tablets, capsules, granules, powders or syrups; and for parenteral administration they may be formulated as injections or suppositories. These preparations can be prepared by the conventional methods using various additives. For example, the pharmaceutical composition may include vehicles, which may be: organic vehicles such as sugar derivatives (for example lactose, white sugar, glucose, mannitol or sorbitol), starch derivatives (for example corn starch, potato starch, α-starch, dextrin or carboxymethyl starch), cellulose derivatives (for example crystalline cellulose, low-substituted hydroxypropyl cellulose, hydroxypropylmethyl cellulose, carboxymethyl cellulose, calcium carboxymethyl cellulose and innerbridged sodium carboxymethyl cellulose), gum arabic, dextran and Pluran; and inorganic vehicles such as silicate derivatives (for example light silicic anhydride; synthetic aluminum silicate and magnesium metasilicoaluminate), phosphates (for example calcium phosphate), carbonates (for example calcium carbonate), and sulfates (for example calcium sulfate). They may also include lubricants, such as: stearic acid; metal stearates such as calcium stearate and magnesium stearate; talc; colloidal silica; beegum; waxes, such as whale wax; boric acid; adipic acid; sulfates such as sodium sulfate; glycol; fumaric acid; sodium benzoate; DL-leucine; fatty acid sodium salts; laurylsulfates such as sodium laurylsulfate and magnesium laurylsulfate; silicates such as silicic anhydride and silicic acid hydrate; and the starch derivatives mentioned above). They may include binders, such as polyvinylpyrrolidone, macrogol and the same compounds as mentioned above for the vehicles). They may include disintegrators, which may include the same compounds as mentioned above for the vehicles; and chemically modified starches and celluloses such as sodium crosscarmelose, sodium carboxymethyl starch and bridged polyvinylpyrrolidone. They may include stabilisers, for example: paraoxybenzoate esters such as methylparaben and propylparaben; alcohols such as chlorobutanol, benzyl alcohol and phenylethyl alcohol; benzalkonium chloride; phenols such as phenol and cresol; timerosal; dehydroacetic acid; and sorbitan. They may include corrigents, for example conventional sweetening agents, acidifying agents and flavors. They may also include various diluents.

The dosage may vary depending on the symptoms, body weight and age of the patients and the mode of administration. However, for an adult human patient, a suitable dose is from 10 mg to 1000 mg, preferably from 50 mg to 500 mg, which may be given once a day or in divided doses.

EXAMPLE 1

N-(2-t-Butyl-5-N'-methylcarbamoylphenyl)-3-(2,4-dimethoxphenyl)octanamide (Compound No. 31)

186 mg (1.15 mmol) of N,N'-carbonyldiimidazole were added to a suspension of 392 mg (0.86 mmol) of N-(2-t-butyl-5-carboxyphenyl)-3-(2,4-dimethoxyphenyl) octanamide (prepared as described in Preparation 7) in 8 ml of acetonitrile, and the resulting mixture was stirred at room temperature for 40 minutes, after which 295 mg (4.37 mmol) of monomethylamine hydrochloride and 0.60 ml (4.30 mmol) of triethylamine were added thereto. The mixture was then stirred for 3 hours, after which water was added to the reaction mixture and the aqueous mixture was freed from acetonitrile by distillation under reduced pressure. The residue was extracted with ethyl acetate, and the extract was washed with 2N aqueous hydrochloric acid, with a saturated aqueous solution of sodium hydrogencarbonate, with water and with a saturated aqueous solution of sodium chloride, in that order, after which it was dried. The solvent was removed by distillation under reduced pressure, and the resulting residue was purified by column chromatography through 50 g of silica gel, using ethyl acetate as the eluent, to give 369 mg (yield 91%) of the title compound as crystals, melting at 168.5°–170° C. (from a mixture of hexane and ethyl acetate).

Nuclear Magnetic Resonance Spectrum (270M Hz, CDCl$_3$) δ ppm:
0.84 (3H, triplet, J=7 Hz);
1.10–1.40 (6H, multiplet);
1.29 (9H, singlet);
1.62–1.82 (2H, multiplet);
2.60–2.80 (2H, multiplet);
2.96 (3H, doublet, J=5 Hz);
3.41–3.58 (1H, multiplet);
3.78 (6H, singlet);
6.07–6.19 (1H, multiplet);
6.41–6.52 (2H, multiplet);
7.07–7.66 (5H, multiplet).

Infrared Absorption Spectrum (KBr) $v_{max}$ cm$^{-1}$:
3306,3257, 1637, 1614, 1507, 1290, 1209, 1157, 1037, 835.

EXAMPLE 2

N-(2-t-Butyl-5-carbamoylphenyl)-3-(2,4-dimethoxyphenyl)octanamide (Compound No. 30)

188 mg (1.16 mmol) of N,N'-carbonyldiimidazole were added to a suspension of 381 mg (0.84 mmol) of N-(2-t-butyl-5-carboxyphenyl)-3-(2,4-dimethoxyphenyl) octanamide (prepared as described in Preparation 7) in 8 ml of acetonitrile, and the resulting mixture was stirred at room temperature for 40 minutes, after which 282 mg (4.18 mmol) of ammonium chloride and 0.59 ml (4.23 mmol) of triethylamine were added thereto. The reaction mixture was then stirred for 2 hours, after which water was added, and the aqueous mixture was freed from acetonitrile by distillation under reduced pressure. The resulting residue was extracted with ethyl acetate, and the extract was washed with 2N aqueous hydrochloric acid, with a saturated aqueous solution of sodium hydrogencarbonate, with water and with a saturated aqueous solution of sodium chloride, in that order, after which it was dried. The solvent was removed by distillation under reduced pressure, and the resulting residue was purified by column chromatography through 50 g of silica gel, using ethyl acetate as the eluent, to give 352 mg (yield 93%) of the title compound as crystals, melting at 151°–152° C. (from a mixture of hexane and ethyl acetate).

Nuclear Magnetic Resonance Spectrum (270M Hz, CDCl$_3$) δ ppm:
0.84 (3H, triplet, J=7 Hz);
1.16–1.37 (6H, multiplet);
1.29 (9H, singlet);
1.65–1.80 (2H, multiplet);
2.60–2.82 (2H, multiplet);
3.42–3.58 (1H, multiplet);
3.78 (6H, singlet);
5.54 (1H, broad);
6.14 (1H, broad);
6.39–6.54 (2H, multiplet);
7.07–7.68 (5H, multiplet).

Infrared Absorption Spectrum (KBr) $v_{max}$ cm$^{-1}$:
3332,3234, 1655, 1614, 1507, 1420, 1289, 1209, 1157, 1038, 835.

EXAMPLE 3

N-[2-t-Butyl-5-(N'-methylcarbamoyl)methylphenyl]-3-(2,4-dimethoxphenyl octanamide (Compound No. 39)

Following a procedure similar to that described in Example 1, but using 4-t-butyl-3-[3-(2,4-dimethoxyphenyl)

octanoyl]aminophenylacetic acid (prepared as described in Preparation 15) as a starting material, the title compound was obtained as a foam-like substance.
Nuclear Magnetic Resonance Spectrum (270M Hz, CDCl$_3$)
δ ppm:
0.84 (3H, triplet, J=7 Hz);
1.12–1.34 (6H, multiplet);
1.28 (9H, singlet);
1.62–1.80 (2H, multiplet);
2.58–2.82 (2H, multiplet);
2.75 (3H, doublet, J=5 Hz);
3.41–3.57 (1H, multiplet);
3.46 (2H, singlet);
3.78 (6H, singlet);
5.56 (1H, broad);
6.42–6.52 (2H, multiplet);
6.97–7.16 (4H, multiplet);
7.23–7.34 (1H, multiplet).
Infrared Absorption Spectrum (KBr) $v_{max}$ cm$^{-1}$:
3283, 3084, 1649, 1613, 1507, 1415, 1290, 1209, 1157, 1039, 834.

EXAMPLE 4

N-[2-t-Butyl-5-(carbamoylmethyl)phenyl]-3-(2,4-dimethoxyphenyl)octanamide (Compound No. 38)

Following a procedure similar to that described in Example 2, but using 4-t-butyl-3-[3-(2,4-dimethoxyphenyl) octanoyl]aminophenylacetic acid (prepared as described in Preparation 15) as a starting material, the title compound was obtained as a foam-like substance.
Nuclear Magnetic Resonance Spectrum (270M Hz, CDCl$_3$)
δ ppm:
0.84 (3H, triplet, J=6 Hz);
1.10–1.35 (6H, multiplet);
1.27 (9H, singlet);
1.60–1.80 (2H, multiplet);
2.58–2.82 (2H, multiplet);
3.42–3.55 (1H, multiplet);
3.47 (2H, singlet);
3.79 (6H, singlet);
5.34 (1H, broad);
5.62 (1H, broad);
6.40–6.52 (2H, multiplet);
6.98–7.17 (4H, multiplet);
7.23–7.35 (1H, multiplet).
Infrared Absorption Spectrum (KBr) $v_{max}$ cm$^{-1}$:
3287, 3193, 1660, 1613, 1507, 1465, 1289, 1209, 1157, 1038, 833.

EXAMPLE 5

N-[2-t-Bu=l-5-(carbamoyloxymethyl)phenyl]-3-(2,4-dimethoxyphenyl)octanamide (Compound No. 46)

A solution of 401 mg (0.91 mmol) of N-[2-t-butyl-5-(hydroxy-methyl)phenyl]-3-(2,4-dimethoxyphenyl) octanamide (prepared as described in Preparation 9) in 4 ml of tetrahydrofuran was cooled to −40° C. in a dry ice-acetonitrile bath. 102 μl (1.17 mmol) of chlorosulfonyl isocyanate were added to the cooled solution, and the resulting mixture was stirred for 2.5 hours. At the end of this time, the reaction was quenched by the addition of a phosphate buffer solution (pH 6.9), and the mixture was then extracted with ethyl acetate. The extract was washed with water and then with a saturated aqueous solution of sodium chloride, after which it was dried. The solvent was removed by distillation under reduced pressure, and the resulting residue was purified by column chromatography through 30 g of silica gel, using a gradient elution method, with mixtures ethyl acetate of and hexane ranging from 2:1 to 3:1 by volume as the eluent, to give 260 mg (yield 59%) of the title compound as a foam-like substance.
Nuclear Magnetic Resonance Spectrum (270M Hz, CDCl$_3$)
δ ppm:
0.78–0.89 (3H, multiplet);
1.09–1.38 (6H, multiplet);
1.28 (9H, singlet);
1.63–1.80 (2H, multiplet);
2.60–2.79 (2H, multiplet);
3.40–3.57 (1H, multiplet);
3.77 (3H, singlet);
3.78 (3H, singlet);
4.58–4.80 (2H, broad singlet);
5.00 (2H, singlet);
6.40–6.51 (2H, multiplet);
7.00–7.35 (5H, multiplet).
Infrared Absorption Spectrum (liquid film) $v_{max}$ cm$^{-1}$:
2955, 1729, 1715, 1661, 1651, 1613, 1507, 1464, 1457, 1329, 1208.

EXAMPLE 6

N-[2-t-Butyl-5-(3-carbamoyloxypropyl)phenyl]-3-(2,4-dimethoxyphenl)octanamide (Compound No. 52)

Following a procedure similar to that described in Example 5, but using N-[2-t-butyl-5-(3-hydroxypropyl) phenyl]-3-(2,4-dimethoxyphenyl)octanamide (prepared as described in Preparation 17) as a starting material, the title compound was obtained as foam-like substance.
Nuclear Magnetic Resonance Spectrum (270M Hz, CDCl$_3$)
δ ppm:
0.79–0.91 (3H, multiplet);
1.09–1.36 (6H, multiplet);
1.26 (9H, singlet);
1.60–1.79 (2H, multiplet);
1.84–1.98 (2H, multiplet);
2.61 (2H, triplet, J=7.5 Hz);
2.59–2.80 (2H, multiplet);
3.41–3.56 (1H, multiplet);
3.78 (6H, singlet);
4.07 (2H, triplet, J=6 Hz);
4.47–5.04 (2H, broad);
6.41–6.52 (2H, multiplet);
6.89–7.26 (5H, multiplet).
Infrared Absorption Spectrum (KBr) $v_{max}$ cm$^{-1}$:
1717, 1659, 1612, 1588, 1507, 1465, 1416, 1333, 1208, 1157, 756.

EXAMPLE 7

N-(2-t-Butyl-5-N'-methylcarbamoylphenyl)-3-(2-trifluoromethylphenyl)octanamide (Compound No. 117)

Following a procedure similar to that described in Example 1, but using N-(2-t-butyl-5-carboxyphenyl)-3-(2-trifluoromethylphenyl)octanamide (prepared as described in Preparation 21) as a starting material, the title compound was obtained as crystals, melting at 202°–203° C. (from a mixture of hexane and ethyl acetate).
Infrared Absorption Spectrum (KBr) $v_{max}$ cm$^{-1}$:
3309, 2959, 2932, 2873, 1637, 1560, 1528, 1313, 1157, 1125, 1037, 769.

Nuclear Magnetic Resonance Spectrum (400M Hz, CDCl$_3$) δ ppm:
0.78–0.88 (3H, multiplet);
1.07–1.32 (6H, multiplet);
1.35 (9H, singlet);
1.74–1.94 (2H, multiplet);
2.61 (1H, doublet of doublets, J=8.8 & 14.2 Hz);
2.70 (1H, doublet of doublets, J=5.7 & 14.2 Hz);
2.97 (1.2H, singlet);
2.98 (1.8H, singlet);
3.64–3.71 (1H, multiplet);
6.25 (1H, broad singlet);
7.15 (1H, broad singlet);
7.29–7.30 (1H, multiplet);
7.31 (1H, doublet, J=7.5 Hz);
7.36–7.68 (4H, multiplet);
7.88 (1H, doublet, J=1.0 Hz).

EXAMPLE 8

N-(2-t-Butyl-5-N'-t-butylcarbamoylphenyl)-3-(2-trifluoromethylphenyl)octanamide (Compound No. 118)

204 mg of 2,4,6-triisopropylbenzenesulfonyl chloride were added at room temperature and under a stream of nitrogen, in three separate 68 mg portions every 30 minutes, to a solution of 207 mg (0.45 mmol) of N-(2-t-butyl-5-carboxyphenyl)-3-(2-trifluoromethylphenyl)octanamide (prepared as described in Preparation 21), 187 ml (1.34 mmol) of triethylamine, 70 ml (0.67 mmol) of t-butylamine and 10 mg of N,N-dimethylaminopyridine in 4 ml of dry chloroform, and the resulting mixture was stirred at room temperature for a further 2 hours. At the end of this time, the reaction mixture was diluted with methylene chloride, and the diluted solution was washed with a 10% aqueous solution of hydrochloric acid, with a saturated aqueous solution of sodium hydrogencarbonate and with a saturated aqueous solution of sodium chloride, after which it was dried over anhydrous sodium sulfate and filtered. The solvent was removed by distillation under reduced pressure, and the resulting residue was purified by column chromatography through silica gel, using a 1:2 by volume mixture of ethyl acetate and hexane as the eluent, to give 93 mg (yield 40%) of the title compound as crystals, melting at 196°–197° C. (from a mixture of methylene chloride and hexane).

Infrared Absorption Spectrum (CHCl$_3$) ν$_{max}$ cm$^{-1}$:
3441, 2967, 2933, 2873, 1664, 1527, 1496, 1479, 1455, 1367, 1314, 1160, 1125, 1037

Nuclear Magnetic Resonance Spectrum (400M Hz, CDCl$_3$) δ ppm:
0.82–0.92 (3H, multiplet);
1.03–1.30 (6H, multiplet);
1.33 (9H, singlet);
1.45 (9H, singlet);
1.75–1.91 (2H, multiplet);
2.63–2.70 (2H, multiplet);
3.63–3.70 (1H, multiplet);
5.95–6.00 (1H, multiplet);
7.05 (1H, singlet);
7.32–7.36 (1H, multiplet);
7.41 (1H, doublet, J=8.4 Hz);
7.66 (1H, doublet, J=8.4 Hz).

EXAMPLE 9

N-(2-t-Butyl-5-carbamoylphenyl)-3-(2,3-dimethoxyphenol)octanamide (Compound No. 26)

Following a procedure similar to that described in Example 2, but using N-(2-t-butyl-5-carboxyphenyl)-3-(2,3-dimethoxyphenyl)octanamide (prepared as described in Preparation 25) as a starting material, the title compound was obtained as crystals, melting at 89°–90° C. (from a mixture of methylene chloride and hexane).

Infrared Absorption Spectrum (CHCl$_3$) ν$_{max}$ cm$^{-1}$:
3528, 3475, 3414, 2962, 2934, 2874, 1676, 1587, 1479, 1378, 1271, 1073, 1006.

Nuclear Magnetic Resonance Spectrum (400M Hz, CDCl$_3$) δ ppm:
0.81–0.90 (3H, multiplet);
1.14–1.30 (6H, multiplet);
1.30 (9H, singlet);
1.60–1.81 (2H, multiplet);
2.61–2.75 (2H, multiplet);
3.60–3.66 (1H, multiplet);
3.81 (3H, singlet);
3.85 (3H, singlet);
5.45 (1H, broad singlet);
6.34 (1H, broad singlet);
6.77–6.79 (1H, multiplet);
6.87 (1H, doublet, J=7.4 Hz);
7.00 (1H, singlet);
7.06 (1H, triplet, J=8.0 Hz);
7.41 (1H, doublet, J=8.0 Hz);
7.55 (1H, singlet);
7.66–7.68 (1H, multiplet).

EXAMPLE 10

N-(2-t-Butyl-5-ureidomethylphenyl)-3-(2,4-dimethoxyphenyl)octanamide (Compound No. 355)

A mixture of 450 mg (0.94 mmol) of N-[2-t-butyl-5-(aminomethyl)phenyl]-3-(2,4-dimethoxyphenyl)octanamide-hydrochloride (prepared as described in Preparation 26B), 203 mg (2.50 mmol) of potassium cyanate, 30 ml of water and 1 ml of acetic acid was heated under reflux for 2 hours. At the end of this time, the reaction mixture was neutralized by adding sodium hydrogencarbonate, after which the mixture was extracted with ethyl acetate. The extract was washed several times with water and once with a saturated aqueous solution of sodium chloride, after which it was dried over anhydrous magnesium sulfate. The solvent was removed by distillation under reduced pressure, and the resulting residue was purified by column chromatography through 37 g of silica gel using a 100:5 mixture of ethyl acetate and methanol as the eluent, to give a crystalline product. This product was recrystallized from a mixture of methylene chloride and hexane to give 273 mg of the title compound in a 60% yield, melting at 112°–113° C. (from methylene chloride-methanol). Nuclear Magnetic Resonance Spectrum (270MHz, CDCl$_3$) δ ppm:
0.77–0.90 (3H, multiplet);
1.09–1.30 (6H, multiplet);
1.22 (9H, singlet);
1.60–1.80 (2H, multiplet);
2.59–2.80 (2H, multiplet);
3.40–3.53 (1H, multiplet);
3.76 (3H, singlet);
3.78 (3H, singlet);
3.98 (2H, doublet, J=5 Hz);
4.56–4.74 (2H, multiplet);
5.41–5.53 (1H, singlet);
6.40–6.51 (2H, multiplet);
6.83–7.30 (5H, multiplet).

Infrared Absorption Spectrum (KBr) ν$_{max}$ cm$^{-1}$:
2956, 2930, 1653, 1612, 1507, 1465, 1418, 1290, 1261, 1209, 1156, 1038.

EXAMPLE 11

N-[2-t-Butyl-5-(ethylsulfonylaminomethyl)phenyl]-3-(2,4-dimethoxyphenyl)octanamide (Compound No. 358)

180 μl (1.90 mmol) of ethanesulfonyl chloride and then 213 mg (1.75 mmol) of 4-N,N-dimethylaminopyridine were added to a solution of 700 mg (1.59 mmol) of N-[2-t-butyl-5-(aminomethyl)phenyl]-3-(2,4-dimethoxyphenyl)octanamide (prepared as described in Preparation 26A) in 15 ml of methylene chloride, whilst cooling in an ice-salt bath, and the resulting mixture was stirred at the same temperature for 1 hour. At the end of this time, the reaction mixture was diluted with ethyl acetate, and the diluted solution was washed with water, with a saturated aqueous solution of sodium hydrogencarbonate and with a saturated aqueous solution of sodium chloride, in that order, after which it was dried over anhydrous magnesium sulfate. The solvent was removed by distillation under reduced pressure, and the resulting residue was purified by column chromatography through 38 g of silica gel, using a 3:1 by volume mixture of ethyl acetate and hexane as the eluent, to give 360 mg of the title compound as a foam-like substance.

Nuclear Magnetic Resonance Spectrum (270 MHz, $CDCl_3$) δ ppm:
0.80–0.90 (3H, multiplet);
1.16–1.37 (6H, multiplet);
1.32 (3H, triplet, J=7 Hz);
1.28 (9H, singlet);
1.65–1.80 (2H, multiplet);
2.61–2.80 (2H, multiplet);
2.99 (2H, quartet, J=7 Hz);
3.42–3.53 (1H, multiplet);
3.79 (6H, singlet);
4.20 (2H, doublet, J=6 Hz);
4.42–4.53 (1H, multiplet);
6.41–6.52 (2H, multiplet);
7.04–7.36 (5H, multiplet).

Infrared Absorption Spectrum (film) $v_{max}$ $cm^{-1}$:
2955, 2930, 1657, 1613, 1588, 1507, 1459, 1420, 1320, 1289, 1208.

EXAMPLE 12

N-[2-t-Butyl-5-(methylsulfonylaminomethyl)pheny]-3-(2,4-dimethoxyphenyl)octanamide (Compound No. 357)

Following a similar procedure to that described in Example 11, but using N-[2-t-butyl-5-(aminomethyl)phenyl]-3-(2,4-dimethoxy-phenyl)octanamide (prepared as described in Preparation 26A) and methanesulfonyl chloride in similar relative proportions, the title compound was obtained as a foam-like substance.

Nuclear Magnetic Resonance Spectrum (270 MHz, $CDCl_3$) δ ppm:
0.79–0.90 (3H, multiplet);
1.01–1.37 (6H, multiplet);
1.28 (9H, singlet);
1.61–1.80 (2H, multiplet);
2.59–2.80 (2H, multiplet);
2.88 (3H, singlet);
3.40–3.57 (1H, multiplet);
3.78 (3H, singlet);
3.79 (3H, singlet);
4.22 (2H, doublet, J=6 Hz);
4.71–4.81 (1H, multiplet);
6.41–6.52 (2H, multiplet);
7.03–7.34 (5H, multiplet).

Infrared Absorption Spectrum (film) $v_{max}$ $cm^{-1}$:
2957, 2930, 1657, 1613, 1588, 1508, 1464, 1418, 1320, 1208, 1154.

EXAMPLE 13

N-(2-t-Butyl-5-carbamoylphenyl -3-(2,4-dimethoxy-5-carboxyphenyl octanamide (Compound No. 244)

Following a similar procedure to that described in Preparation 7, but using N-(2-t-butyl-5-carbamoylphenyl)-3-(2,4-dimethoxy-5-methoxycarbonylphenyl)-octanamide (prepared as described in Example 32), the title compound was obtained as a foam-like substance.

Nuclear Magnetic Resonance Spectrum (270 MHz, $CDCl_3$) δ ppm:
0.77–0.91 (3H, multiplet);
1.05–1.36 (6H, multiplet);
1.33 (9H, singlet);
1.54–1.83 (2H, multiplet);
2.57–2.78 (2H, multiplet);
3.62–3.78 (1H, multiplet);
3.92 (3H, singlet);
4.07 (3H, singlet);
5.51–5.81 (1H, broad);
6.26–6.50 (1H, broad);
6.51 (1H, singlet);
7.07–7.19 (1H, broad singlet);
7.37–7.48 (1H, multiplet);
7.57–7.74 (2H, multiplet);
8.03 (1H, singlet).

Infrared Absorption Spectrum (KBr) $v_{max}$ $cm^{-1}$:
1664, 1610, 1578, 1560, 1508, 1466, 1421, 1365, 1275, 1211, 1024.

EXAMPLE 14

N-[2-t-Butyl-5-(3-ureidopropyl)phenyl]-3-(2,4-dimethoxyphenyl)octanamide (Compound No. 361)

Following a similar procedure to that described in Example 10, but using N-[2-t-butyl-5-(3-aminopropyl)phenyl]-5-(2,4-dimethoxyphenyl)octanamide (prepared as described in Preparation 27), the title compound was obtained as crystals, melting at 125° C. (from methylene chloride-hexane).

Nuclear Magnetic Resonance Spectrum (270 MHz, $CDCl_3$) δ ppm:
0.75–0.92 (3H, multiplet);
1.08–1.46 (6H, multiplet);
1.24 (9H, singlet);
1.58–1.90 (4H, multiplet);
2.50–2.82 (4H, multiplet);
3.06–3.20 (2H, multiplet);
3.40–3.53 (1H, multiplet);
3.79 (6H, singlet);
4.50–4.64 (2H, multiplet);
4.95–5.09 (1H, multiplet);
6.40–7.38 (7H, multiplet).

Infrared Absorption Spectrum (KBr) $v_{max}$ $cm^{-1}$:
1649, 1612, 1527, 1506, 1464, 1290, 1261, 1209, 1156, 1038, 832.

EXAMPLE 15

N-[2-t-Butyl-5-(2-N'-methlycarbamoylethyl)phenyl) -3-(2,4-dimethoxyphenyl)octanamide (Compound No. 42)

Following a similar procedure to that described in Example 1, but using N-[2-t-butyl-5-(2-carboxyethyl)

phenyl]-3-(2,4-dimethoxyphenyl)octanamide (prepared as described in Preparation 28), the title compound was obtained as crystals, melting at 141°–142.5° C. (from methylene chloride-hexane).

Nuclear Magnetic Resonance Spectrum (270 MHz, CDCl$_3$) δ ppm:
0.84 (3H, triplet, J=6 Hz);
1.09–1.33 (6H, multiplet);
1.26 (9H, singlet);
1.63–1.79 (2H, multiplet);
2.40 (2H, triplet, J=7 Hz);
2.59–2.80 (2H, multiplet);
2.71 (3H, doublet, J=5 Hz);
2.85 (2H, triplet, J=7 Hz);
3.42–3.55 (1H, multiplet);
3.78 (3H, singlet);
3.79 (3H, singlet);
5.61–5.72 (1H, multiplet);
6.40–6.52 (2H, multiplet);
6.91–7.27 (5H, multiplet).

Infrared Absorption Spectrum (KBr) $v_{max}$ cm$^{-1}$:
3297, 3244, 1646, 1614, 1507, 1465, 1290, 1208, 1157, 1037, 833.

EXAMPLE 16

N-[2-t-Butyl-5-(2-carbamoylethyl)phenyl]-3-(2,4-dimethoxyphenyl)octanamide (Compound No. 41)

Following a similar procedure to that described in Example 20, but using N-[2-t-butyl-5-(2-carboxyethyl)phenyl]-3-(2,4-dimethoxyphenyl)octanamide (prepared as described in Preparation 28), the title compound was obtained as crystals, melting at 113°–114.5° C. (from diethyl ether-hexane).

Nuclear Magnetic Resonance Spectrum (270 MHz, CDCl$_3$) w ppm:
0.84 (3H, triplet, J=6 Hz);
1.12–1.32 (6H, multiplet);
1.27 (9H, singlet);
1.64–1.79 (2H, multiplet);
2.44 (2H, triplet, J=7 Hz);
2.58–2.80 (2H, multiplet);
2.83 (2H, triplet, J=7 Hz);
3.41–3.55 (1H, multiplet);
3.78 (3H, singlet);
3.79 (3H, singlet);
5.13–5.27 (1H, broad);
5.54–5.69 (1H, broad);
6.42–6.52 (2H, multiplet);
6.92–7.29 (5H, multiplet).

Infrared Absorption Spectrum (KBr) $v_{max}$ cm$^{-1}$:
3286, 3194, 1659, 1613, 1507, 1465, 1290, 1209, 1157, 1038, 832.

EXAMPLE 17

N-[2-t-Butyl-5-(2-N',N'-dimethylcarbamoylethyl)phenyl]-3-(2,4-dimethoxyphenyl)octanamide (Compound No. 362)

Following a similar procedure to that described in Example 20, but using N-[2-t-butyl-5-(2-carboxyethyl)phenyl]-3-(2,4-dimethoxyphenyl)octanamide (prepared as described in Preparation 28) and a 2N solution of dimethylamine in tetrahydrofuran, the title compound was obtained as a foam-like substance.

Nuclear Magnetic Resonance Spectrum (270 MHz, CDCl$_3$) δ ppm:
0.83 (3H, triplet, J=6 Hz);
1.11–1.38 (6H, multiplet);
1.27 (9H, singlet);
1.64–1.79 (2H, multiplet);
2.57 (2H, triplet, J=7 Hz);
2.53–2.79 (2H, multiplet);
2.87 (2H, triplet, J=7 Hz);
2.94 (6H, singlet);
3.42–3.56 (1H, multiplet);
3.78 (6H, singlet);
6.40–6.50 (2H, multiplet);
6.94–7.27 (5H, multiplet).

Infrared Absorption Spectrum (melted film) $v_{max}$ cm$^{-1}$:
3270, 1651, 1636, 1507, 1289, 1262, 1208, 1156, 1038, 934, 834.

EXAMPLE 18

N-(2-t-Butyl-5-N',N'-dimethylcarbamoylphenyl)-3-(2,4-dimethoxyphenyl)octanamide (Compound No. 32)

Following a similar procedure to that described in Example 20, but using N-(2-t-butyl-5-carboxyphenyl)-3-(2,4-dimethoxyphenyl)octanamide (prepared as described in Preparation 7) and a 2M solution of diethylamine in tetrahydrofuran, the title compound was obtained as a foam-like substance.

Nuclear Magnetic Resonance Spectrum (270 MHz, CDCl$_3$) δ ppm:
0.77–0.91 (3H, multiplet);
1.12–1.31 (6H, multiplet);
1.27 (9H, singlet);
1.61–1.81 (2H, multiplet);
2.64 (1H, doublet of doublets, J=6.5 Hz & 14.5 Hz);
2.74 (1H, doublet of doublets, J=8.5 Hz & 14.5 Hz);
3.01 (3H, singlet);
3.07 (3H, singlet);
3.45–3.55 (1H, multiplet);
3.78 (6H, singlet);
6.41–6.50 (2H, multiplet);
7.02–7.26 (3H, multiplet);
7.32–7.43 (2H, multiplet).

Infrared Absorption Spectrum (KBr) $v_{max}$ cm$^{-1}$:
1614, 1587, 1558, 1506, 1460, 1398, 1290, 1261, 1207, 1157, 1109, 1036.

EXAMPLE 19

N-(2-t-Butyl-5-cyanomethylphenyl)-3-(2,4-dimethoxyphenyl)octanamide (Compound No. 363)

Following a similar procedure to that described in Preparation 6, but using 2-t-butyl-5-cyanomethylaniline (prepared as described in Preparation 29), the title compound was obtained as a viscous substance.

Nuclear Magnetic Resonance Spectrum (270 MHz, CDCl$_3$) δ ppm:
0.83 (3H, triplet, J=6 Hz);
1.11–1.34 (6H, multiplet);
1.28 (9H, singlet);
1.63–1.80 (2H, multiplet);
2.60–2.80 (2H, multiplet);
3.42–3.55 (1H, multiplet);
3.64 (2H, singlet);
3.78 (6H, singlet);
6.43–6.51 (2H, multiplet);
7.04–7.37 (5H, multiplet).

Infrared Absorption Spectrum (melted film) $v_{max}$ cm$^{-1}$:

99

3270, 2250, 1658, 1507, 1291, 1208, 1158, 1038, 934, 834.

EXAMPLE 20

N-(2-t-Butyl-5-carbamoylphenyl)-3-(2-methoxy-4-methylthiophenyl)octanamide (Compound No. 550)

510 mg (3.15 mmol) of N,N'-carbonyldiimidazole were added to a solution of 1.142 g (2.42 mmol) of N-(2-t-butyl-5-carboxyphenyl)-3-(2-methoxy-4-methylthiophenyl)octanamide (prepared as described in Preparation 31A) in 10 ml of acetonitrile, and the resulting mixture was stirred at room temperature for 1 hour, after which 0.79 ml (12.1 mmol) of 28% w/w aqueous ammonia. The reaction mixture was stirred for 5 hours, after which it was diluted with water, and the diluted aqueous mixture was freed from the organic solvent by distillation under reduced pressure. The aqueous concentrate was extracted with ethyl acetate. The extract was washed with 2N aqueous hydrochloric acid, with a 0.5N aqueous solution of sodium hydroxide, with water and with a saturated aqueous solution of sodium chloride, after which it was dried over magnesium sulfate. The solvent was removed by distillation under reduced pressure, and the resulting residue was recrystallized from ethyl acetate, to give 962 mg (yield 84%) of the title compound as crystals, melting at 171°–172° C. (from ethyl acetate).
Nuclear Magnetic Resonance Spectrum (270 MHz, CDCl₃) δ ppm:
0.77–0.92 (3H, multiplet);
1.09–1.39 (6H, multiplet);
1.30 (9H, singlet);
1.62–1.80 (2H, multiplet);
2.47 (3H, singlet);
2.61–2.81 (2H, multiplet);
3.46–3.61 (1H, multiplet);
3.80 (3H, singlet);
5.35–5.68 (1H, broad);
6.02–6.45 (1H, broad);
6.77 (1H, doublet, J=1.5 Hz);
6.84 (1H, doublet of doublets, J=1.5 Hz & J=8 Hz);
7.03–7.15 (1H, broad);
7.14 (1H, doublet, J=8 Hz);
7.38–7.46 (1H, multiplet);
7.56–7.68 (2H, multiplet).
Infrared Absorption Spectrum (KBr) $\nu_{max}$ cm⁻¹:
1653, 1614, 1560, 1527, 1493, 1462, 1423, 1398, 1379, 1365, 1244, 1132, 1036.

EXAMPLES 21 AND 22

N-(2-t-Butyl-5-carbamoylphenyl)-3-(2-methoxy-4-methylsulfonylphenyl)-octanamide (Example 21, Compound No. 552) and N-(2-t-Butyl-5-carbamoylphenyl)-3-(2-methoxy-4-methylsulfinylphenyl)octanamide (Example 22, Compound No. 551))

3.8 ml of a 1M aqueous solution of sodium hydrogencarbonate and 357.5 mg (1.65 mmol) of m-chloroperoxybenzoic acid (purity 80%) were added, whilst ice-cooling, to a solution of 600 mg (1.27 mmol) of N-(2-t-butyl-5-carbamoylphenyl)-3-(2-methoxy-4-methylthiophenyl)octanamide (prepared as described in Example 20) in 12 ml of methylene chloride, and the resulting mixture was stirred at the same temperature for 1.5 hours. At the end of this time, the reaction mixture was diluted with diethyl ether, and the diluted solution was washed with a saturated aqueous solution of sodium sulfite, with water and with a saturated aqueous solution of sodium chloride, in that order, after which it was dried over anhydrous sodium sulfate. The solvent was removed by distillation under reduced pressure, and the resulting residue was purified by column chromatography through 35 g of silica gel, using a 20:1 by volume mixture of methylene chloride and methanol as the eluent, to give 296.5 mg (yield 46%) of a sulfone derivative (Example 21) as a foam-like substance from the less polar fractions and 323.2 mg (yield 52%) of a sulfoxide derivative (Example 22) as a foam-like substance from more polar fractions.
Sulfone derivative (compound of Example 21):
Nuclear Magnetic Resonance Spectrum (270 MHz, CDCl₃) δ ppm:
0.76–0.93 (3H, multiplet);
1.05–1.41 (6H, multiplet);
1.32 (9H, singlet);
1.66–1.85 (2H, multiplet);
2.61–2.83 (2H, multiplet);
3.06 (3H, singlet);
3.63–3.79 (1H, multiplet);
3.91 (3H, singlet);
5.46–5.75 (1H, broad);
6.04–6.40 (1H, broad);
7.11–7.21 (1H, broad singlet);
7.36–7.74 (6H, multiplet).
Infrared Absorption Spectrum (KBr) $\nu_{max}$ cm⁻¹:
1653, 1614, 1560, 1518, 1495, 1466, 1404, 1302, 1248, 1146, 1093, 1032, 962.
Sulfoxide derivative (compound of Example 22):
Nuclear Magnetic Resonance Spectrum (270 MHz, CDCl₃) δ ppm:
0.77–0.93 (3H, multiplet);
1.05–1.41 (6H, multiplet);
1.31 (9H, singlet);
1.66–1.87 (2H, multiplet);
2.63–2.87 (2H, multiplet);
2.70 (1.5H, singlet);
2.72 (1.5H, singlet);
3.58–3.74 (1H, multiplet);
3.91 (3H, singlet);
5.41–5.73 (1H, broad);
6.08–6.41 (1H, broad);
7.04–7.21 (2H, multiplet);
7.24–7.48 (3H, multiplet);
7.57–7.75 (2H, multiplet).
Infrared Absorption Spectrum (KBr) $\nu_{max}$ cm⁻¹:
1653, 1616, 1558, 1520, 1493, 1464, 1416, 1367, 1246, 1126, 1088, 1038.

EXAMPLE 23

N-[2-t-Butyl-5-(N',N'-dimethylaminocarbonylaminomethyl)phenyl]-3-(2,4-dimethoxyphenyl)octanamide (Compound No. 364)

300 μl (3.26 mmol) of N,N-dimethylcarbamoyl chloride and 740 μl (5.31 mmol) of triethylamine were added, whilst ice-cooling, to a solution of 419 mg (0.88 mmol) of N-[2-t-butyl-5-(aminomethyl)phenyl]-3-(2,4-dimethoxyphenyl)octanamide·hydrochloride (prepared as described in Preparation 26B) in 5 ml of methylene chloride and, after the reaction temperature had been allowed to rise to room temperature, the resulting mixture was stirred for 2.5 hours and then water was added thereto. The reaction mixture was then extracted with ethyl acetate. The extract was washed with a saturated aqueous solution of sodium hydrogencarbonate, with 1N aqueous hydrochloric acid, with water and with a saturated aqueous solution of sodium chloride, in that order, after which it was dried over anhydrous magnesium sulfate. The solvent was removed by distillation under reduced pressure, after which the residue was purified by column chromatography through 25 g of silica gel, using ethyl acetate as the eluent, to give 369 mg (yield 76%) of the title compound, melting at 145.5°–147° C. (from ethyl acetate-hexane).
Nuclear Magnetic Resonance Spectrum (270 MHz, CDCl$_3$) δ ppm:
0.84 (3H, triplet, J=6 Hz);
1.10–1.35 (6H, multiplet);
1.26 (9H, singlet);
1.63–1.79 (2H, multiplet);
2.59–2.80 (2H, multiplet);
2.91 (6H, singlet);
3.40–3.55 (1H, multiplet);
3.78 (6H, singlet);
4.31 (2H, doublet, J=6 Hz);
4.64–4.75 (1H, multiplet);
6.40–6.51 (2H, multiplet);
7.01–7.34 (5H, multiplet).
Infrared Absorption Spectrum (KBr) ν$_{max}$ cm$^{-1}$:
    3331, 3251, 1633, 1529, 1465, 1375, 1291, 1209, 1156, 1036, 834.

EXAMPLE 24

N-(2-t-Butyl-5-carbamoylphenyl)-3-(5-cyano-2,4-dimethoxyphenyl)octanamide (Compound No. 539)

Following a similar procedure to that described in Example 20, but using N-(2-t-butyl-5-carboxyphenyl)-3-(2,4-dimethoxy-5-cyanophenyl)octanamide (prepared as described in Preparation 35), the title compound was obtained as a powdery substance.
Nuclear Magnetic Resonance Spectrum (270 MHz, CDCl$_3$) δ ppm:
0.77–0.94 (3H, multiplet);
1.05–1.41 (6H, multiplet);
1.33 (9H, singlet);
1.53–1.82 (2H, multiplet);
2.54–2.78 (2H, multiplet);
3.53–3.72 (1H, multiplet);
3.89 (3H, singlet);
3.92 (3H, singlet);
5.45–5.76 (1H, broad);
6.17–6.42 (1H, broad);
6.44 (1H, singlet);
7.12–7.86 (5H, multiplet).
Infrared Absorption Spectrum (KBr) ν$_{max}$ cm$^{-1}$:
    3318, 2221, 1631, 1612, 1505, 1468, 1286, 1214, 1026.

EXAMPLE 25

N-(2-t-Butyl-5-N'-methylcarbamoylphenyl)-3-(5-cyano-2,4-dimethoxyphenyl)octanamide (Compound No. 540)

Following a similar procedure to that described in Example 44, but using N-(2-t-butyl-5-carboxyphenyl)-3-(2,4-dimethoxy-5-cyanophenyl)octanamide (prepared as described in Preparation 35) and 2-t-butyl-5-carbamoylaniline (prepared as described in Preparation 38), the title compound was obtained as crystals, melting at 217°–218° C. (from methylene chloride-ethyl acetate).
Nuclear Magnetic Resonance Spectrum (270 MHz, CDCl$_3$) δ ppm:
0.77–0.92 (3H, multiplet);
1.05–1.34 (6H, multiplet);
1.33 (9H, singlet);
1.60–1.79 (2H, multiplet);
2.56–2.75 (2H, multiplet);
2.96 (3H, doublet, J=5 Hz);
3.53–3.69 (1H, multiplet);
3.89 (3H, singlet);
3.92 (3H, singlet);
6.21–6.34 (1H, multiplet);
6.43 (1H, singlet);
7.06–7.18 (1H, broad singlet);
7.32–7.47 (2H, multiplet);
7.55–7.71 (2H, multiplet).
Infrared Absorption Spectrum (KBr) ν$_{max}$ cm$^{-1}$:
    2222, 1635, 1612, 1560, 1522, 1504, 1466, 1412, 1323, 1286, 1255, 1213, 1169, 1030.

EXAMPLE 26

(+)-N-(2-t-Butyl-5-carbamoylphenyl)-3-(2,4-dimethoxyphenyl)octanamide (Compound No. 30)

0.90 ml (10.4 mmol) of oxalyl chloride and a catalytic amount of N,N-dimethylformamide were added at room temperature to a solution of 1.38 g (4.92 mmol) of (+)-3-(2,4-dimethoxyphenyl)octanoic acid (prepared as described in Preparation 89) in 20 ml of methylene chloride, and the resulting mixture was stirred for 1 hour. At the end of this time, the excess reagent and solvent were removed by distillation under reduced pressure, to give the acid chloride. A solution of this acid chloride in 9 ml of methylene chloride was then added to an ice-cooled solution of 1.15 g (5.98 mmol) of 2-t-butyl-5-carbamoylaniline (prepared as described in Preparation 38), in 10 ml of pyridine over a period of 3 minutes. At the end of this time, the reaction temperature was allowed to rise to room temperature, after which the mixture was stirred for 2 hours at room temperature. The reaction mixture was then poured into ice-water and the aqueous mixture was extracted with ethyl acetate. The extract was washed with 2N aqueous hydrochloric acid, with water, with a saturated aqueous solution of sodium hydrogencarbonate and with a saturated aqueous solution of sodium chloride, in that order, after which it was dried over anhydrous magnesium sulfate. The solvent was then removed by distillation under reduced pressure, and the resulting residue was purified by column chromatography through 100 g of silica gel using a gradient elution method, with mixtures of isopropanol and methylene chloride ranging from 1:12 to 1:10 by volume as the eluent, to give 1.93 g (yield 86%) of the title compound as crystals, melting at 151.5°–152.5° C. (from ethyl acetate-hexane).
Nuclear Magnetic Resonance Spectrum (400 MHz, CDCl$_3$) δ ppm:
0.84 (3H, triplet, J=6.5 Hz);
1.13–1.33 (6H, multiplet);
1.29 (9H, singlet);
1.66–1.79 (2H, multiplet);
2.68 (1H, doublet of doublets, J=6.3 Hz & 14.3 Hz);
2.74 (1H, doublet of doublets, J=9.0 Hz & 14.3 Hz);
3.45–3.53 (1H, multiplet);
3.78 (6H, singlet);
5.48–5.65 (1H, broad);
6.12–6.28 (1H, broad);
6.44 (1H, doublet, J=2.3 Hz);
6.47 (1H, doublet of doublets, J=2.3 Hz & 8.2 Hz);
7.11 (1H, singlet);
7.12 (1H, doublet, J=8.2 Hz);
7.41 (1H, doublet, J=8.2 Hz);
7.59 (1H, singlet);

7.63 (1H, doublet of doublets, J=2.0 Hz & J=8.2Hz).
Infrared Absorption Spectrum (KBr) $v_{max}$ cm$^{-1}$:
1653, 1615, 1506, 1419, 1291, 1260, 1210, 1158, 1041, 835.
$[\alpha]_D^{25}$=+51° C. (c=0.69, CHCl$_3$).

EXAMPLE 27

(−)-N-(2-t-Butyl-5-carbamoylphenyl)-3-(2,4-dimethoxyphenyl)octanamide (Compound No. 30)

Following a similar procedure to that described in Example 26, but using (−)-3-(2,4-dimethoxyphenyl) octanoic acid (prepared as described in Preparation 90), the title compound was obtained as crystals, melting at 151°–152° C. (from ethyl acetate-hexane).
$[\alpha]_D^{25}$=−51° C. (c=0.83, CHCl$_3$).

EXAMPLE 28

N-(2-t-Butyl-5-cyanophenyl)-3-(2,4-dimethoxphenyl)octanamide (Compound No. 365)

Following a similar procedure to that described in Preparation 6, but using 2-t-butyl-5-cyanoaniline (prepared as described in Preparation 34), the title compound was obtained as a foam-like substance.
Nuclear Magnetic Resonance Spectrum (270 MH, CDCl$_3$) δ ppm:
0.84 (3H, triplet, J=6 Hz);
1.11–1.35 (6H, multiplet);
1.29 (9H, singlet);
1.62–1.80 (2H, multiplet);
2.58–2.80 (2H, multiplet);
3.39–3.54 (1H, multiplet);
3.78 (6H, singlet);
6.42–6.52 (2H, multiplet);
6.98–7.70 (5H, multiplet).
Infrared Absorption Spectrum (melted film) $v_{max}$ cm$^{-1}$:
3248, 2231, 1653, 1613, 1507, 1466, 1291, 1209, 1157, 1037, 832.

EXAMPLE 29

N-(2-t-Butyl-5-carbamoylphenyl)-3-(2,4-dimethoxy-5-carbamoylphenyl)octanamide (Compound No. 248)

Following a similar procedure to that described in Example 20, but using N-(2-t-butyl-5-carbamoylphenyl)-3-(2,4-dimethoxy-5-carboxyphenyl)octanamide (prepared as described in Example 13), the title compound was obtained as crystals, melting at 160°–163° C. (from methylene chloride-methanol-ethyl acetate).
Nuclear Magnetic Resonance Spectrum (270 MHz, CDCl$_3$) δ ppm:
0.76–0.91 (3H, multiplet);
1.09–1.32 (6H, multiplet);
1.31 (9H, singlet);
1.64–1.79 (2H, multiplet);
2.70 (2H, doublet, J=7.5 Hz);
3.59–3.73 (1H, multiplet);
3.89 (3H, singlet);
3.97 (3H, singlet);
5.45–5.74 (1H, broad);
5.77–5.88 (1H, broad singlet);
6.47 (1H, singlet);
6.58–6.79 (1H, broad);
7.11–7.20 (1H, broad singlet);
7.37–7.46 (1H, multiplet);
7.56–7.72 (3H, multiplet);
8.10 (1H, singlet).
Infrared Absorption Spectrum (KBr) $v_{max}$ cm$^{-1}$:
1655, 1612, 1587, 1560, 1522, 1466, 1460, 1425, 1275, 1209, 1086, 1026.

EXAMPLE 30

N-(2-t-Butyl-5-carbamoylphenyl)-3-(2,4-dimethoxy-5-N',N'-dimethylcarbamoylphenyl)octanamide (Compound No. 247)

Following a similar procedure to that described in Example 20, but using N-(2-t-butyl-5-carbamoylphenyl)-3-(2,4-dimethoxy-5-carboxyphenyl)octanamide (prepared as described in Example 13) and a 2M solution of dimethylamine in tetrahydrofuran, the title compound was obtained as an amorphous substance.
Nuclear Magnetic Resonance Spectrum (270 MHz, CDCl$_3$) δ ppm:
0.77–0.90 (3H, multiplet);
1.10–1.34 (6H, multiplet);
1.34 (9H, singlet);
1.61–1.79 (2H, multiplet);
2.59–2.78 (2H, multiplet);
2.85 (3H, singlet);
3.08 (3H, singlet);
3.39–3.71 (1H, broad);
3.82 (3H, singlet);
3.84 (3H, singlet);
5.31–5.56 (1H, broad singlet);
6.43 (1H, singlet);
6.97–7.22 (1H, broad);
7.13 (1H, singlet);
7.29–7.48 (2H, multiplet);
7.68–7.75 (1H, multiplet).
Infrared Absorption Spectrum (KBr) $v_{max}$ cm$^{-1}$:
1655, 1639, 1605, 1543, 1502, 1466, 1410, 1377, 1315, 1277, 1207, 1028.

EXAMPLE 31

N-(2-t-Butyl-5-carbamoylphenyl)-3-(2,4-dimethoxy-5-N'-methylcarbamoylphenyl)octanamide (Compound No. 249)

Following a similar procedure to that described in Example 1, but using N-(2-t-butyl-5-carbamoylphenyl)-3-(2,4-dimethoxy-5-carboxyphenyl)octanamide (prepared as described in Example 13), the title compound was obtained as crystals, melting at 125°–127° C. (from methylene chloride-diethyl ether).
Nuclear Magnetic Resonance Spectrum (270 MHz, CDCl$_3$) δ ppm:
0.77–0.91 (3H, multiplet);
1.06–1.35 (6H, multiplet);
1.31 (9H, singlet);
1.68–1.73 (2H, multiplet);
2.60–2.77 (2H, multiplet);
2.97 (3H, doublet, J=5 Hz);
3.57–3.72 (1H, multiplet);
3.88 (3H, singlet);
3.96 (3H, singlet);
5.38–5.65 (1H, broad);
6.46 (1H, singlet);
6.64–6.93 (1H, broad);
7.01–7.11 (1H, broad singlet);
7.37–7.45 (1H, multiplet);

7.58–7.82 (3H, multiplet);
8.13 (1H, singlet).
Infrared Absorption Spectrum (KBr) $v_{max}$ cm$^{-1}$:
  1655, 1639, 1605, 1543, 1502, 1466, 1410, 1377, 1315, 1277, 1207, 1028.

EXAMPLE 32

N-(2-t-Butyl-5-carbamoylphenyl)-3-(2,4-dimethoxy-5-methoxycarbonylphenyl)octanamide (Compound No. 250)

Following a similar procedure to that described in Example 44, but using 3-(2,4-dimethoxy-5-methoxycarbonylphenyl)octanoic acid (prepared as described in Preparation 37) and 2-t-butyl-5-carbamoylaniline (prepared as described in Preparation 38), the title compound was obtained as crystals, melting at 101°–103° C. (from methylene chloride-diethyl ether).
Nuclear Magnetic Resonance Spectrum (270 MHz, CDCl$_3$) δ ppm:
0.77–0.92 (3H, multiplet);
1.07–1.35 (6H, multiplet);
1.31 (9H, singlet);
1.62–1.81 (2H, multiplet);
2.60–2.79 (2H, multiplet);
3.52–3.69 (1H, multiplet);
3.86 (3H, singlet);
3.88 (3H, singlet);
3.90 (3H, singlet);
5.35–5.68 (1H, broad);
6.06–6.42 (1H, broad);
6.45 (1H, singlet);
6.98–7.13 (1H, broad singlet);
7.38–7.48 (1H, multiplet);
7.59–7.72 (2H, multiplet);
7.75 (1H, singlet).
Infrared Absorption Spectrum (KBr) $v_{max}$ cm$^{-1}$:
  1713, 1661, 1612, 1574, 1560, 1510, 1437, 1365, 1281, 1252, 1211, 1144, 1026.

EXAMPLE 33

N-[2-t-Butyl-5-(aminocarbonyl-N'-methylamino) phenyl]1-3-(2,4-dimethoxyphenyl)octanamide (Compound No. 366)

Following a similar procedure to that described in Preparation 6, but using 2-t-butyl-5-aminocarbonyl-N-methylaminomethylaniline (prepared as described in Preparation 33), the title compound was obtained as crystals, melting at 159°–163° C. (from ethyl acetate-hexane).
Nuclear Magnetic Resonance Spectrum (270 MHz, CDCl$_3$) δ ppm:
0.84 (3H, triplet, J=6 Hz);
1.10–1.34 (6H, multiplet);
1.27 (9H, singlet);
1.63–1.79 (2H, multiplet);
2.57–2.81 (2H, multiplet);
2.91 (3H, singlet);
3.41–3.57 (1H, multiplet);
3.79 (6H, singlet);
4.43 (1H, broad singlet);
4.46 (1H, broad singlet);
4.39 (2H, singlet);
6.40–6.51 (2H, multiplet);
6.95–7.35 (5H, multiplet).
Infrared Absorption Spectrum (KBr) $v_{max}$ cm$^{-1}$:
  3427,3331,3263, 1647, 1609, 1506, 1414, 1210, 1157, 1038, 832.

EXAMPLE 34

N-(2-t-Butyl-5-N'-methylcarbamoylphenyl)-3-(2,4-dimethoxy-5-carbamoylphenyl)octanamide (Compound No. 251)

Following a similar procedure to that described in Example 20, but using N-(2-t-butyl-5-N'-methylcarbamoylphenyl)-3-(2,4-dimethoxy-5-carboxyphenyl)-octanamide (prepared as described in Example 107), the title compound was obtained as crystals, melting at 205°–206° C. (from methylene chloride-methanol-ethyl acetate).
Nuclear Magnetic Resonance Spectrum (270 MHz, CDCl$_3$) δ ppm:
0.76–0.92 (3H, multiplet);
1.02–1.34 (6H, multiplet);
1.30 (9H, singlet);
1.63–1.81 (2H, multiplet);
2.69 (2H, doublet, J=7.5 Hz);
2.95 (3H, doublet, J=5 Hz);
3.59–3.73 (1H, multiplet);
3.88 (3H, singlet);
3.97 (3H, singlet);
5.66–5.78 (1H, multiplet);
6.46 (1H, singlet);
6.55–6.70 (1H, multiplet);
7.07–7.17 (1H, broad singlet);
7.36–7.43 (1H, multiplet);
7.57–7.72 (3H, multiplet);
8.09 (1H, singlet).
Infrared Absorption Spectrum (KBr) $v_{max}$ cm$^{-1}$:
  1649, 1585, 1560, 1502, 1437, 1363, 1342, 1275, 1209, 1086, 1028.

EXAMPLE 35

N-(2-t-Butyl-5-N'-methylcarbamoylphenyl)-3-(2,4-dimethoxy-5-N"-methylcarbamoylphenyl) octanamide (Compound No. 252)

Following a similar procedure to that described in Example 1, but using N-(2-t-butyl-5-N'-methylcarbamoylphenyl)-3-(2,4-dimethoxy-5-carboxyphenyl)-octanamide (prepared as described in Example 107), the title compound was obtained as crystals, melting at. 153°–155° C. (from methylene chloride-methanol-ethyl acetate).
Nuclear Magnetic Resonance Spectrum (270 MHz, CDCl$_3$) δ ppm:
0.73–0.89 (3H, multiplet);
1.04–1.33 (6H, multiplet);
1.30 (9H, singlet);
1.67–1.81 (2H, multiplet);
2.57–2.78 (2H, multiplet);
2.97 (3H, doublet, J=5 Hz);
2.98 (3H, doublet, J=5 Hz);
3.54–3.71 (1H, multiplet);
3.88 (3H, singlet);
3.96 (3H, singlet);
6.45 (1H, singlet);
6.72–6.86 (1H, multiplet);
6.94–7.03 (1H, broad singlet);
7.33–7.43 (1H, multiplet);
7.55–7.80 (3H, multiplet);
8.12 (1H, singlet).
Infrared Absorption Spectrum (KBr) $v_{max}$ cm$^{-1}$:
  1649, 1637, 1607, 1545, 1502, 1410, 1365, 1319, 1209, 1165, 1082, 1026.

EXAMPLE 36

N-(2-t-Butyl-5-N'-methylcarbamoylphenyl)-3-(2,4-dimethoxyphenyl-5-N'',N''-dimethylcarbamoylphenyl)octanamide (Compound No. 253)

Following a similar procedure to that described in Example 20, but using N-(2-t-butyl-5-N'-methylcarbamoylphenyl)-3-(2,4-dimethoxy-5-carboxyphenyl)-octanamide (prepared as described in Example 107) and a 2M solution of dimethylamine in tetrahydrofuran, the title compound was obtained as a foam-like substance.

Nuclear Magnetic Resonance Spectrum (270 MHz, CDCl$_3$) δ ppm:
0.77–0.92 (3H, multiplet);
1.08–1.34 (6H, multiplet);
1.33 (9H, singlet);
1.57–1.83 (2H, multiplet);
2.56–2.80 (2H, multiplet);
2.85 (3H, singlet);
2.88 (3H, doublet, J=5 Hz);
3.09 (3H, singlet);
3.35–3.75 (1H, broad);
3.18 (3H, singlet);
3.82 (3H, singlet);
6.40 (1H, singlet);
6.95–7.42 (1H, broad);
7.13 (1H, singlet);
7.24 (1H, doublet, J=1.5 Hz);
7.38 (1H, doublet, J=8 Hz);
7.69 (1H, doublet of doublets, J=1.5 Hz & 8Hz).

Infrared Absorption Spectrum (KBr) cm$^{-1}$:
1618, 1499, 1462, 1412, 1365, 1284, 1207, 1144, 1078, 1032.

EXAMPLE 37 AND 38

N-(2-t-Butyl -5-carbamoylphenyl)-3-(4-cyano-2-methoxyphenyl)octanamide (Example 37, Compound No. 535) and N-(2-t-Butyl-5-cyanophenyl)-3-(4-cyano-2-methoxyphenyl) octanamide (Example 38, Compound No. 534)

320 mg (0.965 mmol) of carbon tetrabromide were added to a solution of 405 mg (0.866 mmol) of N-(2-t-butyl-5-carbamoylphenyl)-3-(4-hydroxyimino-2-methoxyphenyl) octanamide (prepared as described in Example 111) and 687 mg (2.62 mmol) of triphenylphosphine in 12 ml of methylene chloride and then, 2 minutes later, 0.37 ml (2.65 mmol) of triethylamine were added, all with ice-cooling, and the resulting mixture was then stirred at the temperature of ice-cooling for 20 minutes. The reaction mixture was then diluted with ethyl acetate, and the diluted solution was washed with water and with a saturated aqueous solution of sodium chloride, in that order, after which it was dried over anhydrous magnesium sulfate. The solvent was removed by distillation under reduced pressure, and the resulting residue was purified by column chromatography through 100 g of silica gel using a gradient elution method, with mixtures of isopropanol and methylene chloride ranging from 1:20 to 1:10 by volume as the eluent, to give the compound of Example 37 as crystals in a 54% yield and a mixture containing a compound of Example 38. The mixture containing the compound of Example 38 was separated by column chromatography through 50 g of silica gel using a gradient elution method, with mixtures of ethyl acetate and hexane ranging from 3:7 to 2:3 by volume as the eluent, to give 144 mg (yield 39%) of the compound of Example 38 as a foam-like substance.

Compound of Example 37:
melting at 185°–186° C. (with decomposition) (from diethyl ether).

Nuclear Magnetic Resonance Spectrum (270 MHz, CDCl$_3$) δ ppm:
0.83 (3H, triplet, J=6 Hz);
1.19–1.31 (6H, multiplet);
1.30 (9H, singlet);
2.70–2.78 (2H, multiplet);
2.65–2.80 (2H, multiplet);
3.63–3.74 (1H, multiplet);
3.87 (3H, singlet);
5.50–5.80 (1H, broad);
6.10–6.40 (1H, broad);
7.09 (1H, singlet);
7.15 (1H, singlet);
7.25 (1H, doublet, J=8 Hz);
7.30 (1H, doublet, J=8 Hz);
7.43 (1H, doublet, J=8 Hz);
7.61 (1H, doublet of doublets, J=2 Hz & 8 Hz);
7.80 (1H, doublet, J=2 Hz).

Infrared Absorption Spectrum (KBr) $v_{max}$ cm$^{-1}$:
2230, 1657, 1615, 1561, 1504, 1464, 1408, 1366, 1263, 1036.

Compound of Example 38:
Nuclear Magnetic Resonance Spectrum (270 MHz, CDCl$_3$) δ ppm:
0.84 (3H, triplet, J=6 Hz);
1.10–1.30 (6H, multiplet);
1.31 (9H, singlet);
1.71–1.79 (2H, multiplet);
2.69–2.73 (2H, multiplet);
3.63–3.72 (1H, multiplet);
3.87 (3H, singlet);
7.05–7.10 (1H, broad singlet);
7.09 (1H, singlet);
7.24–7.31 (2H, multiplet);
7.38–7.47 (2H, multiplet);
7.89–7.92 (1H, broad singlet).

Infrared Absorption Spectrum (KBr) $v_{max}$ cm$^{-1}$:
2230, 1655, 1605, 1505, 1465, 1407, 1367, 1264, 1036, 829.

EXAMPLE 39

N-(2-t-But=1-5-carbamoylpheny)-3-(4-N',N'-dimethylcarbamoyl-2-methoxyphenyl)octanamide (Compound No. 265)

Following a similar procedure to that described in Example 20, but using N-(2-t-butyl-5-carbamoylphenyl)-3-(4-carboxy-2-methoxyphenyl)octanamide (prepared as described in Example 112) and a 2M solution of dimethylamine in tetrahydrofuran, the title compound was obtained as a foam-like substance.

Nuclear Magnetic Resonance Spectrum (270 MHz, CDCl$_3$) δ ppm:
0.84 (3H, triplet, J=6 Hz);
1.14–1.35 (6H, multiplet);
1.32 (9H, singlet);
1.70–1.79 (2H, multiplet);
2.65–2.81 (2H, multiplet);
2.90–3.13 (6H, multiplet);
3.56–3.68 (1H, multiplet);
3.83 (3H, singlet);
5.50–5.80 (1H, broad);

6.25–6.55 (1H, broad);
6.94–6.98 (2H, multiplet);
7.21–7.25 (2H, multiplet);
7.41 (1H, doublet, J=8 Hz);
7.51 (1H, doublet, J=2 Hz);
7.62 (1H, doublet of doublets, J=2 Hz & 8Hz).
Infrared Absorption Spectrum (KBr) $v_{max}$ cm$^{-1}$:
  1661, 1618, 1568, 1515, 1490, 1411, 1252, 1202, 1090, 1036.

EXAMPLE 40

N-(2-t-Butyl-5-carbamoylphenyl)-3-(4-N'-methylcarbamoyl-2-methoxyphenyl)octanamide (Compound No. 266)

Following a similar procedure to that described in Example 1, but using N-(2-t-butyl-5-carbamoylphenyl)-3-(4-carboxy-2-methoxyphenyl)octanamide (prepared as described in Example 112), the title compound was obtained as a foam-like substance.
Nuclear Magnetic Resonance Spectrum (270 MHz, CDCl$_3$-Hexadeuterated dimethyl sulfoxide) δ ppm:
0.83 (3H, triplet, J=6 Hz);
1.18–1.30 (6H, multiplet);
1.29 (9H, singlet);
1.70–1.79 (2H, multiplet);
2.62–2.71 (2H, multiplet);
2.93 (3H, doublet, J=5 Hz);
3.60–3.71 (1H, multiplet);
3.88 (3H, singlet);
6.30–6.40 (1H, broad);
7.18–7.30 (1H, broad);
7.26–7.41 (5H, multiplet);
7.61–7.65 (1H, multiplet);
7.83–7.87 (1H, multiplet);
8.16 (1H, singlet).
Infrared Absorption Spectrum (KBr) $v_{max}$ cm$^{-1}$:
  1659, 1558, 1523, 1501, 1414, 1367, 1306, 1244, 1157, 1043.

EXAMPLE 41

N-(2-t-Butyl-5-N'-methylcarbamoylphenyl)-3-(2,4-dimethoxyphenyl)heptanamide (Compound No. 58)

Following a similar procedure to that described in Example 44, but using 3-(2,4-dimethoxyphenyl)heptanoic acid prepared as described in Preparation 42a) and 2-t-butyl-5-carbamoylaniline (prepared as described in Preparation 38), the title compound was obtained as crystals, melting at 181°–181.5° C. (from ethyl acetate-diethyl ether).
Nuclear Magnetic Resonance Spectrum (270 MHz, CDCl$_3$) δ ppm:
0.86 (3H, triplet, J=7 Hz);
1.03–1.40 (4H, multiplet);
1.31 (9H, singlet);
1.68–1.83 (2H, multiplet);
2.60–2.81 (2H, multiplet);
2.97 (3H, triplet, J=5 Hz);
3.42–3.57 (1H, multiplet);
3.79 (6H, singlet);
6.16–6.30 (1H, broad);
6.44–6.53 (2H, multiplet);
7.08–7.67 (5H, multiplet).
Infrared Absorption Spectrum (KBr) $v_{max}$ cm$^{-1}$:
  3294, 1638, 1614, 1587, 1559, 1507, 1465, 1413, 1318, 1291, 1260, 1209, 1157.

EXAMPLE 42

N-(2-t-Butyl-5-carbamoylphenyl)-3-(2,4-dimethoxyphenyl)heptanamide (Compound No. 57)

Following a similar procedure to that described in Example 44, but using 3-(2,4-dimethoxyphenyl)heptanoic acid (prepared as described in Preparation 42a), the title compound was obtained as crystals, melting at 186.5°–187.5° C. (from methylene chloride-ethyl acetate).
Nuclear Magnetic Resonance Spectrum (270 MHz, CDCl$_3$) δ ppm:
0.85 (3H, triplet, J=7 Hz);
1.05–1.40 (4H, multiplet);
1.30 (9H, singlet);
1.74–1.80 (2H, multiplet);
2.61–2.83 (2H, multiplet);
3.40–3.57 (1H, multiplet);
3.78 (6H, singlet);
5.43–5.63 (1H, broad);
6.08–6.30 (1H, broad);
6.42–6.52 (2H, multiplet);
7.06–7.67 (5H, multiplet).
Infrared Absorption Spectrum (KBr) $v_{max}$ cm$^{-1}$:
  3339, 3182, 1655, 1613, 1507, 1421, 1292, 1209, 1156.

EXAMPLE 43

N-(2-t-Butyl-5-acetylaminocarbonylphenyl)-3-(2,4-dimethoxphenyl)octanamide (Compound No. 356)

Method A:
A solution of 113 mg (0.25 mmol) of N-(2-t-butyl-5-carbamoylphenyl)-3-(2,4-dimethoxyphenyl)octanamide (prepared as described in Example 2), 110 mg (1.0 mmol) of 1-acetylimidazole and 122 mg (1.0 mmol) of 4-N,N-dimethyl-aminopyridine in 2 ml of acetonitrile was heated under reflux for 24 hours. At the end of this time, the reaction temperature was allowed to cool to room temperature. The reaction mixture was then diluted with ethyl acetate, and the diluted solution was washed with 2N aqueous hydrochloric acid and with water, after which it was dried over anhydrous sodium sulfate. The solvent was removed by distillation under reduced pressure, and the resulting residue was purified by column chromatography through 8 g of silica gel using a gradient elution method, with mixtures of methylene chloride and ethyl acetate ranging from 1:1 to 1:1.5 by volume as the eluent, to give 12 mg (yield 9.7%) of the title compound as crystals.
Method B:
Following a similar procedure to that described in Example 139, but using N-(2-t-butyl-5-carboxyphenyl)-3-(2,4-dimethoxyphenyl)octanamide (prepared as described in Preparation 7), the title compound was obtained as crystals, melting at 111°–114° C. (from ethyl acetate-diisopropyl ether).
Nuclear Magnetic Resonance Spectrum (270 MHz, CDCl$_3$) δ ppm:
0.78–0.95 (3H, multiplet);
1.06–1.42 (6H, multiplet);
1.30 (9H, singlet);
1.64–1.85 (2H, multiplet);
2.57 (3H, singlet);
2.58–2.86 (2H, multiplet);
3.40–3.58 (1H, multiplet);
3.78 (3H, singlet);
3.79 (3H, singlet);
6.40–6.56 (2H, multiplet);
7.02–7.68 (5H, multiplet);
8.68 (1H, broad singlet).
Infrared Absorption Spectrum (KBr) $v_{max}$ cm$^{-1}$:
  3263, 1742, 1717, 1697, 1656, 1612, 1507, 1480, 1468, 1373, 1261, 1246, 1209.

EXAMPLE 44

N-(2-t-Butyl-5-carbamoylphenyl)-3-(2,4-dimethoxyphenyl)nonanamide (Compound No. 64)

0.31 ml (3.57 mmol) of oxalyl chloride and a catalyic amount of dimethyl-formamide were added, with ice-cooling, to a solution of 350 mg (1.19 mmol) of 3-(2,4-dimethoxyphenyl)nonanoic acid (prepared as described in Preparation 42B), in 7 ml of methylene chloride and the reaction temperature was raised to room temperature at once. The resulting mixture was then stirred for 50 minutes. The solvent and an excess of the reagent were removed by distillation under reduced pressure, and the resulting residue was dissolved in 7 ml of methylene chloride. 0.48 ml (5.95 mmol) of pyridine were added to the solution, followed by 206 mg (1.07 mmol) of 2-t-butyl-5-carbamoylaniline (prepared as described in Preparation 38), all with ice-cooling, and the resulting mixture was stirred at the same temperature for 30 minutes. At the end of this time, the reaction mixture was diluted with diethyl ether, and the diluted solution was washed with 1N aqueous hydrochloric acid, with a 0.5N aqueous solution of sodium hydroxide, with water and with a saturated aqueous solution of sodium chloride, in that order, after which it was dried over anhydrous magnesium sulfate. The solvent was removed by distillation under reduced pressure, and the resulting residue was purified by column chromatography through 25 g of silica gel using a gradient elution method, with mixtures of methylene chloride and methanol ranging from 100:2 to 100:4 by volume as the eluent, to give 433 mg (yield 86%) of the title compound as crystals, melting at 152°–153° C. (from methylene chloride-diethyl ether).

Nuclear Magnetic Resonance Spectrum (270 MHz, CDCl$_3$) δ ppm:
0.85 (3H, triplet, J=6.5 Hz);
1.07–1.38 (8H, multiplet);
1.30 (9H, singlet);
1.63–1.81 (2H, multiplet);
2.61–2.82 (2H, multiplet);
3.41–3.56 (1H, multiplet);
5.33–5.69 (1H, broad);
6.00–6.31 (1H, broad);
6.44 (1H, doublet, J=2.0 Hz);
6.48 (1H, doublet of doublets, J=2 Hz & 8 Hz);
7.04–7.21 (1H,, broad singlet);
7.12 (1H, doublet, J=8 Hz);
7.38–7.47 (1H, multiplet);
7.55–7.69 (2H, multiplet).
Infrared Absorption Spectrum (KBr) ν$_{max}$ cm$^{-1}$:
1655, 1612, 1587, 1560, 1506, 1466, 1421, 1367, 1290, 1259, 1207, 1157, 1038.

EXAMPLE 45

N-(2-t-Butyl-5-N'-methylcarbamoylphenyl)-3-(2,4-dimethoxyphenyl)nonanamide (Compound No. 65)

Following a similar procedure to that described in Example 44, but using 2-t-butyl-5-N-methylcarbamoylaniline (prepared as described in Preparation 36), the title compound was obtained as crystals, melting at 163°–165° C. (from methylene chloride-ethyl acetate).

Nuclear Magnetic Resonance Spectrum (270 MHz, CDCl$_3$) δ ppm:
0.85 (3H, triplet, J=6.5 Hz);
1.06–1.35 (8H, multiplet);
1.29 (9H, singlet);
1.62–1.81 (2H, multiplet);
2.60–2.81 (2H, multiplet);
2.96 (3H, doublet, J=5 Hz);
3.42–3.56 (1H, multiplet);
3.78 (6H, singlet);
6.11–6.28 (1H, multiplet);
6.42 (1H, doublet, J=2 Hz);
6.43 (1H, doublet of doublets, J=2 Hz & 8 Hz);
7.05–7.18 (1H, broad singlet);
7.11 (1H, doublet, J=8 Hz);
7.35–7.43 (1H, multiplet);
7.49–7.65 (2H, multiplet).
Infrared Absorption Spectrum (KBr) ν$_{max}$ cm$^{-1}$:
1655, 1637, 1614, 1560, 1508, 1460, 1412, 1321, 1290, 1259, 1207, 1157.

EXAMPLE 46A

N-(2-t-Butyl-5-[(3-carboxypropionyl)aminocarbonyl]phenyl)-3-(2,4-dimethoxyphenyl)octanamide (Compound No. 367)

Following a similar procedure to that described in Example 124, but using N-{2-t-butyl-5-[3-(benzyloxycarbonyl)propionylaminocarbonyl]phenyl}-3-(2,4-dimethoxyphenyl)octanamide (prepared as described in Example 118), debenzylation was carried out, to give the title compound as a foam-like substance.

Nuclear Magnetic Resonance Spectrum (270 MHz, CDCl$_3$) δ ppm:
0.74–0.97 (3H, multiplet);
1.03–1.40 (6H, multiplet);
1.27 (9H, singlet);
1.59–1.83 (2H, multiplet);
2.58–2.86 (4H, multiplet);
3.19 (2H, triplet-like, J=6 Hz);
3.39–3.57 (1H, multiplet);
3.77 (3H, singlet);
3.78 (3H, singlet);
6.41–6.56 (2H, multiplet);
7.08–7.73 (5H, multiplet);
9.27 (1H, broad singlet).
Infrared Absorption Spectrum (KBr) ν$_{max}$ cm$^{-1}$:
3275, 1717, 1688, 1612, 1507, 1482, 1468, 1377, 1297, 1260, 1246, 1209, 1157, 1037.

EXAMPLE 46B

Sodium salt of N-(2-t-Butyl-5-[(3-carboxypropionyl)aminocarbonyl]phenyl)-3-(2,4-dimethoxyphenyl)octanamide (Compound No. 36)

A methanolic solution of N-(2-t-butyl-5-[(3-carboxypropionyl)amino-carbonyl]phenyl)-3-(2,4-dimethoxyphenyl)octanamide (prepared as described in Example 46A) was mixed with 0.95 equivalent of a 7% w/v methanolic solution of sodium hydrogencarbonate, and the solvent was distilled off to give the desired sodium salt as an oily substance.

Infrared Absorption Spectrum (KBr) ν$_{max}$ cm$^{-1}$:
3261, 1743, 1684, 1659, 1610, 1587, 1507, 1416, 1209, 1156.

EXAMPLE 47

N-(2-t-Butyl-5-carbamoylphenyl)-3-(2-hydroxy-3-methoxyphenyl)octanamide (Compound No. 663)

Following a similar procedure to that described in Preparation 124, but using N-(2-t-butyl-5-carbamoylphenyl)-3-(2-benzyloxy-3-methoxyphenyl)-octanamide (prepared as described in Example 119), the title compound was obtained as crystals, melting at 118°–121° C. (from diethyl ether).

Nuclear Magnetic Resonance Spectrum (270 MHz, CDCl$_3$) δ ppm:

0.84 (3H, triplet, J=6 Hz);
1.13–1.38 (6H, multiplet);
1.29 (9H, singlet);
1.69–1.86 (2H, multiplet);
2.70–2.87 (2H, multiplet);
3.47–3.60 (1H, multiplet);
3.86 (3H, singlet);
5.36–5.51 (1H, broad);
5.97 (1H, broad singlet);
6.00–6.27 (1H, broad);
6.70–6.89 (3H, multiplet);
7.15–7.70 (4H, multiplet).
Infrared Absorption Spectrum (KBr) $v_{max}$ cm$^{-1}$:
3429, 3306, 3261, 1668, 1614, 1479, 1271, 1074, 841, 771, 733.

EXAMPLE 48

N-(2-t-Butyl-5-N'-methylcarbamoylphenyl)-3-(2-hydroxy-3-methoxyphenyl)octanamide (Compound No. 124)

Following a similar procedure to that described in Preparation 124, but using N-(2-t-butyl-5-N'-methylcarbamoylphenyl)-3-(2-benzyloxy-3-methoxyphenyl)octanamide (prepared as described in Example 120) the title compound was obtained as crystals, melting at 160.5°–162° C. (from methylene chloride-hexane).
Nuclear Magnetic Resonance Spectrum (270 MHz, CDCl$_3$) δ ppm:
0.84 (3H, triplet, J=6 Hz);
1.12–1.38 (6H, multiplet);
1.29 (9H, singlet);
1.70–1.87 (2H, multiplet);
2.69–2.90 (2H, multiplet);
2.97 (3H, doublet, J=5 Hz);
3.46–3.60 (IH, multiplet);
3.85 (3H, singlet);
5.94–6.27 (2H, multiplet);
6.71–6.90 (3H, multiplet);
7.17–7.65 (4H, multiplet).
Infrared Absorption Spectrum (KBr) $v_{max}$ cm$^{-1}$:
3548, 3311, 3230, 1669, 1632, 1478, 1272, 1080, 837, 732.

EXAMPLE 49

N-(2-t-Butyl-5-N'-methylcarbamoylphenyl)-3-(2-methoxy-4-carbamoylphenyl)octanamide (Compound No. 262)

Following a similar procedure to that described in Example 20, but using N-(2-t-butyl-5-N'-methylcarbamoylphenyl)-3-(4-carboxy-2-methoxyphenyl)-octanamide (prepared as described in Example 116) the title compound was obtained as crystals, melting at 250° 250.5° C. (from ethyl acetate-methanol).
Nuclear Magnetic Resonance Spectrum (270 MHz, CDCl$_3$) δ ppm:
0.79–0.82 (3H, multiplet);
1.06–1.18 (6H, multiplet);
1.26 (9H, singlet);
1.60–1.70 (2H, multiplet);
2.60–2.71 (2H, multiplet);
2.76 (3H, doublet, J=4 Hz);
3.57–3.66 (1H, multiplet);
3.83 (3H, singlet);
7.25–7.30 (2H, multiplet);
7.40–7.46 (4H, multiplet);
7.62–7.64 (1H, multiplet);
7.93 (1H, singlet);
7.33°–7.38 (1H, multiplet);
9.21 (1H, singlet).
Infrared Absorption Spectrum (KBr) $v_{max}$ cm$^{-1}$:
1671, 1647, 1617, 1564, 1520, 1414, 1367, 1320, 1250, 1038.

EXAMPLE 50

N-(2-t-Butyl-5-N'-methylcarbamoylphenyl)-3-(2-methoxy-4-N''-methylcarbamoylphenyl)octanamide (Compound No. 263)

Following a similar procedure to that described in Example 1, but using N-(2-t-butyl-5-N'-methylcarbamoylphenyl)-3-(4-carboxy-2-methoxyphenyl)-octanamide (prepared as described in Example 116), the title compound was obtained as crystals, melting at 154°–157° C. (from ethyl acetate-methanol).
Nuclear Magnetic Resonance Spectrum (270 MHz, CDCl$_3$) δ ppm:
0.84 (3H, multiplet);
1.20–1.30 (6H, multiplet);
1.26 (9H, singlet);
1.72–1.88 (2H, multiplet);
2.71–2.74 (2H, multiplet);
2.94 (3H, doublet, J=5 Hz);
2.97 (3H, doublet, J=5 Hz);
3.52–3.63 (1H, multiplet);
3.87 (3H, singlet);
6.20–6.25 (1H, multiplet);
6.94–7.13 (3H, multiplet);
7.22–7.40 (5H, multiplet).
Infrared Absorption Spectrum (KBr) $v_{max}$ cm$^{-1}$:
1636, 1554, 1502, 1466, 1412, 1367, 1321, 1254, 1159, 1042.

EXAMPLE 51

N-(2-t-Butyl-5-N'-methylcarbamoylphenyl)-3-(4-N'', N''-dimethylcarbamoyl-2-methoxyphenyl) octanamide (Compound No. 264)

Following a similar procedure to that described in Example 20, but using N-(2-t-butyl-5-N'-methylcarbamoylphenyl)-3-(4-carboxy-2-methoxyphenyl)-octanamide (prepared as described in Example 116) and a 2M solution of dimethylamine in tetrahydrofuran, the title compound was obtained as crystals, melting at 104°–107° C. (from ethyl acetate).
Nuclear Magnetic Resonance Spectrum (270 MHz, CDCl$_3$) δ ppm:
0.84 (3H, triplet, J=6 Hz);
1.15–1.30 (6H, multiplet);
1.32 (9H, singlet);
1.71–1.80 (2H, multiplet);
2.65–2.81 (2H, multiplet);
2.90–3.14 (6H, multiplet);
2.94 (3H, doublet, J=5 Hz);
3.56–3.67 (1H, multiplet);
3.83 (3H, multiplet);
6.28–6.34 (1H, multiplet);
6.94–6.97 (2H, multiplet);
7.17–7.24 (2H, multiplet);
7.39 (1H, doublet, J=8 Hz);
7.55–7.61 (2H, multiplet).
Infrared Absorption Spectrum (KBr) $v_{max}$ cm$^{-1}$:
1637, 1514, 1410, 1318, 1267, 1252, 1202, 1166, 1087, 1036.

EXAMPLE 52

N-(2-t-Butyl-5-N'-methylcarbamoylphenyl)-3-(4-cyano-2-methoxyphenyl)octanamide (Compound No. 536)

Following a similar procedure to that described in Example 37, but using N-(2-t-butyl-5-N'-methylcarbamoylphenyl)-3-(4-hydroxyimino-2-methoxyphenyl)octanamide (prepared as described in Example 117) the title compound was obtained as crystals, melting at 190°–193° C. (from ethyl acetate).

Nuclear Magnetic Resonance Spectrum (270 MHz, CDCl$_3$) δ ppm:
0.84 (3H, triplet, J=6 Hz);
1.10–1.30 (6H, multiplet);
1.30 (9H, singlet);
1.70–1.79 (2H, multiplet);
2.65–2.79 (2H, multiplet);
2.97 (3H, doublet, J=5 Hz);
3.63–3.75 (1H, multiplet);
3.87 (311, singlet);
6.14–6.21 (1H, multiplet);
7.09–7.42 (5H, multiplet);
7.56–7.60 (1H, multiplet);
7.75 (1H, singlet).

Infrared Absorption Spectrum (KBr) ν$_{max}$ cm$^{-1}$:
2230, 1637, 1561, 1526, 1465, 1409, 1323, 1264, 1162, 1036.

EXAMPLE 53

N-(2-t-Butyl-5-N'-methylcarbamoylphenyl)-3-(2,4-dimethoxy-5-propionylphenyl)octanamide (Compound No. 257)

Following a similar procedure to that described in Example 44, but using 3-(2,4-dimethoxy-5-propionylphenyl)octanoic acid (prepared as described in Preparation 43) and 2-t-butyl-5-N-methylcarbamoylaniline (prepared as described in Preparation 36), the title compound was obtained as crystals, melting at 200°–201.5° C. (from ethyl acetate-hexane).

Nuclear Magnetic Resonance Spectrum (270 MHz, CDCl$_3$) δ ppm:
0.74–0.94 (3H, multiplet),
1.08–1.45 (6H, multiplet);
1.14 (3H, triplet, J=7 Hz);
1.30 (9H, singlet);
1.65–1.84 (2H, multiplet);
2.66 (3H, doublet, J=7 Hz);
2.86–3.10 (SH, multiplet);
3.52–3.70 (1H, multiplet);
3.88 (3H, singlet);
3.90 (3H, singlet);
6.41 (1H, singlet);
6.42–6.56 (1H, multiplet);
7.03 (1H, broad singlet);
7.38 (1H, doublet, J=8 Hz);
7.52–7.80 (3H, multiplet).

Infrared Absorption Spectrum (KBr) ν$_{max}$ cm$^{-1}$:
20 3313, 3197, 1659, 1634, 1602, 1561, 1529, 1502, 1462, 1270, 1212, 1147, 1027.

EXAMPLE 54

N-(2-t-Butyl-5-N'-methylcarbamoylphyl)-3-(5-N"-butylcarbamoyl-2,4-dimethoxyphenyl)octanamide (Compound No. 254)

Following a similar procedure to that described in Example 20, but using N-(2-t-butyl-5-N'-methylcarbamoylphenyl)-3-(2,4-dimethoxy-5-carboxyphenyl)-octanamide (prepared as described in Example 107) and butylamine, the title compound was obtained as crystals, melting at 195°–197° C. (from methylene chloride-ethyl acetate).

Nuclear Magnetic Resonance Spectrum (270 MHz, CDCl$_3$) δ ppm:
0.76–0.90 (3H, multiplet);
0.96 (3H, triplet, J=7 Hz);
1.04–1.38 (6H, multiplet);
1.30 (9H, singlet);
1.40 (2H, sextet, J=7.0 Hz);
1.58 (2H, quintet, J=7 Hz);
1.69–1.81 (2H, multiplet);
2.57–2.75 (2H, multiplet);
2.97 (3H, doublet, J=5 Hz);
3.56–3.71 (1H, multiplet);
3.88 (3H, singlet);
3.95 (3H, singlet);
6.44 (1H, singlet);
6.67–6.84 (1H, multiplet);
6.91–7.02 (1H, broad singlet);
7.34–7.43 (1H, multiplet);
7.60–7.70.(2H, multiplet);
7.71–7.83 (1H, multiplet);
8.12 (1H, singlet).

Infrared Absorption Spectrum (KBr) ν$_{max}$ cm$^{-1}$:
1647, 1607, 1543, 1535, 1502, 1466, 1410, 1365, 1317, 1277, 1027, 1163, 1026.

EXAMPLE 55

N-(2-t-Butyl-5-N'-methylcarbamoylphenyl)-3-[2,4-dimethoxy-5-(1-pyrrolidinyl)carbonylphenyl]octanamide (Compound No. 255)

Following a similar procedure to that described in Example 20, but using N-(2-t-butyl-5-N'-methylcarbamoylphenyl)-3-(2,4-dimethoxy-5-carboxyphenyl)-octanamide (prepared as described in Example 107) and pyrrolidine, the title compound was obtained as a foam-like substance.

Nuclear Magnetic Resonance Spectrum (270 MHz, CDCl$_3$) δ ppm:
0.78–0.93 (3H, multiplet);
1.09–1.34 (6H, multiplet);
1.33 (9H, singlet);
1.61–2.02 (6H, multiplet);
2.60–2.77 (2H, multiplet);
2.91 (3H, doublet, J=5 Hz);
3.13–3.32 (2H, multiplet);
3.44–3.65 (3H, multiplet);
3.80 (3H, singlet);
3.83 (3H, singlet);
6.41 (1H, singlet);
7.03–7.13 (1H, broad singlet);
7.14–7.27 (1H, multiplet);
7.16 (1H, singlet);
7.29 (1H, doublet, J=2 Hz);
7.39 (1H, doublet, J=8 Hz);
7.70 (1H, doublet of doublets, J=2 Hz & 8Hz).

Infrared Absorption Spectrum (KBr) ν$_{max}$ cm$^1$:
1614, 1556, 1508, 1412, 1390, 1365, 1311, 1282, 1254, 1207, 1165, 1124, 1032.

EXAMPLE 56

N-(2-t-Butyl-5-carbamoylphenyl)-3-(4-ethoxy-2-methoxyphenyl)octanamide (Compound No. 408)

Following a similar procedure to that described in Example 44, but using 3-(4-ethoxy-2-methoxyphenyl)

octanoic acid (prepared as described in Preparation 45A), the title compound was obtained as a foam-like substance.
Nuclear Magnetic Resonance Spectrum (270 MHz, CDCl$_3$) δ ppm:
0.79–0.90 (3H, multiplet);
1.14–1.34 (6H, multiplet);
1.30 (9H, singlet);
1.39 (3H, triplet, J=7 Hz);
1.63–1.80 (2H, multiplet);
2.62–2.82 (2H, multiplet);
3.48–3.55 (1H, multiplet);
3.77 (3H, singlet);
3.99 (2H, quartet, J=7 Hz);
5.35–5.60 (1H, broad);
5.96–6.19 (1H, broad);
6.41–6.50 (2H, multiplet);
7.03–7.70 (5H, multiplet).
Infrared Absorption Spectrum (KBr) ν$_{max}$ cm$^{-1}$:
1653, 1613, 1507, 1420, 1289, 1260, 1202, 1163, 1119, 1050.

EXAMPLE 57

N-(2-t-Butyl-5-carbamoylphenyl)-3-(4-isopropoxy-2-methoxyphenyl)octanamide (Compound No. 409)

Following a similar procedure to that described in Example 44, but using 3-(4-isopropoxy-2-methoxyphenyl) octanoic acid (prepared as described in Preparation 45B), the title compound was obtained as a foam-like substance.
Nuclear Magnetic Resonance Spectrum (270 MHz, CDCl$_3$) δ ppm:
0.80–0.89 (3H, multiplet);
1.15–1.39 (12H, multiplet);
1.29 (9H, singlet);
1.65–1.79 (2H, multiplet);
2.62–2.82 (2H, multiplet);
3.41–3.54 (1H, multiplet);
3.76 (3H, singlet);
4.50 (1H, septet, J=6 Hz);
5.32–5.57 (1H, broad);
5.92–6.17 (1H, broad);
6.40–6.50 (2H, multiplet);
7.04–7.68 (5H, multiplet).
Infrared Absorption Spectrum (film) ν$_{max}$ cm$^{-1}$:
1653, 1613, 1505, 1455, 1420, 1381, 1374, 1287, 1260, 1200, 1121.

EXAMPLE 58

N-(2-t-Butyl-5-N'-methylcarbamoylphenyl)-3-(4-ethoxy-2-methoxyphenyl)octanamide (Compound No. 411)

Following a similar procedure to that described in Example 1, but using N-2-t-Butyl-5-carboxyphenyl)-3-(4-ethoxy-2-methoxyphenyl)octanamide(prepared as described in Preparation 31 C), the title compound was obtained as crystals, melting at 178°–179° C. (from ethyl acetate).
Nuclear Magnetic Resonance Spectrum (270 MHz, CDCl$_3$) δ ppm:
0.79–0.90 (3H, multiplet);
1.13–1.34 (6H, multiplet);
1.29 (9H, singlet);
1.39 (3H, triplet, J=7 Hz);
1.64–1.80 (2H, multiplet);
2.61–2.80 (2H, multiplet);
3.96 (3H, doublet, J=5 Hz);
3.42–3.55 (1H, multiplet);
3.77 (3H, singlet);
3.99 (2H, quartet, J=7 Hz);
6.05–6.18 (1H, multiplet);
6.41–6.50 (2H, multiplet);
7.07–7.65 (5H, multiplet).
Infrared Absorption Spectrum (KBr) ν$_{max}$ cm$^{-1}$:
1638, 1614, 1559, 1507, 1413, 1318, 1289, 1260, 1202, 1163, 1118.

EXAMPLE 59

N-(2-t-Butyl-5-N'-methylcarbamoylphenyl)-3-(4-isopropoxy-2-methoxyphenyl)octanamide (Compound No. 410)

Following a similar procedure to that described in Example 44, but using 3-(4-isopropoxy-2-methoxyphenyl) octanoic acid (prepared as described in Preparation 45B) and 2-t-butyl-5-N'-methylcarbamoylaniline (prepared as described in Preparation 36) the title compound was obtained as crystals, melting at 175°–176° C. (from acetonitrile).
Nuclear Magnetic Resonance Spectrum (270 MHz, CDCl$_3$) δ ppm:
0.80–0.90 (3H, multiplet);
1.14–1.38 (12H, multiplet);
1.29 (9H, singlet);
1.65–1.80 (2H, multiplet);
2.62–2.80 (2H, multiplet);
2.96 (3H, doublet, J=5 Hz);
3.41–3.53 (1H, multiplet);
3.76 (3H, singlet);
4.50 (1H, septet, J=6 Hz);
6.07–6.19 (1H, multiplet);
6.40–6.49 (2H, multiplet);
7.05–7.65 (5H, multiplet).
Infrared Absorption Spectrum (KBr) ν$_{max}$ cm$^{-1}$:
1637, 1613, 1560, 1524, 1505, 1413, 1317, 1286, 1261, 1201, 1162, 1123.

EXAMPLE 60

N-[2-t-Butyl-5-N'-(2-methoxyethyl) carbamoylphenyl]-3-(2,4-dimethoxyphenyl) octanamide (Compound No. 353)

Following a similar procedure to that described in Example 20, but using N-(2-t-butyl-5-carboxyphenyl)-3-(2, 4-dimethoxyphenyl)octanamide (prepared as described in Preparation 7) and 2-methoxyethylamine, the title compound was obtained as crystals, melting at 137°–138.5° C.
Nuclear Magnetic Resonance Spectrum (270 MHz, CDCl$_3$) δ ppm:
0.84 (3H, triplet, J=6 Hz);
1.11–1.35 (6H, multiplet);
1.28 (9H, singlet);
1.62–1.80 (2H, multiplet);
2.59–2.80 (2H, multiplet);
3.37 (3H, singlet);
3.43–3.68 (5H, multiplet);
3.77 (3H, singlet);
3.78 (3H, singlet);
6.40–6.53 (3H, multiplet);
7.00–7.65 (5H, multiplet).
Infrared Absorption Spectrum (KBr) ν$_{max}$ cm$^{-1}$:
3232, 1661, 1634, 1507, 1290, 1209, 1157, 1123, 1038, 834.

EXAMPLE 61

N-[2-t-Butyl-5-N'-(2-methoxyethyl)carbamoylphenyl]-3-(2,4-dimethoxyphenyl)nonanamide (Compound No. 354)

Following a similar procedure to that described in Example 20, but using N-[2-t-butyl-5-carboxyphenyl]-3-(2,4-dimethoxyphenyl)nonanamide (prepared as described in Preparation 3 1D) and 2-methoxyethylamine, the title compound was obtained as crystals, melting at 130.5°–133° C. (from hexane-ethyl acetate).
Nuclear Magnetic Resonance Spectrum (270 MHz, CDCl$_3$) δ ppm:
0.85 (3H, triplet, J=6 Hz);
1.09–1.35 (8H, multiplet);
1.28 (9H, singlet);
1.64–1.80 (2H, multiplet);
2.60–2.80 (2H, multiplet);
3.37 (3H, singlet);
3.42–3.67 (5H, multiplet);
3.77 (3H, singlet);
3.78 (3H, singlet);
6.38–6.54 (3H, multiplet);
7.01–7.65 (5H, multiplet).
Infrared Absorption Spectrum (KBr) ν$_{max}$ cm$^{-1}$:
3236, 1657, 1634, 1507, 1465, 1292, 1209, 1157, 1123, 1038, 834.

EXAMPLE 62

N-[2-t-Butyl-5-N'-methvycarbamoylphenyl]-3-(4-N'',N''-diethylcarbamoyl-methoxy-2-methoxyphenyl)octanamide (Compound No. 475)

Following a similar procedure to that described in Example 1, but using N-(2-t-butyl-5-carboxyphenyl)-3-(4-N',N'-diethylcarbamoylmethoxy-2-methoxy-phenyl)octanamide (prepared as described in Preparation 47), the title compound was obtained as a foam-like substance.
Nuclear Magnetic Resonance Spectrum (270 MHz, CDCl$_3$) δ ppm:
0.78–0.90 (3H, multiplet);
1.07–1.36 (6H. multiplet);
1.12 (3H, triplet, J=7 Hz);
1.20 (3H, triplet, J=7 Hz);
1.29 (9H, singlet);
1.60–1.80 (2H, multiplet);
2.60–2.80 (2H, multiplet);
2.96 (3H, doublet, J=5 Hz);
3.37 (2H, quartet, J=7 Hz);
3.39 (2H, quartet, J=7 Hz);
3.42–3.56 (1H, multiplet);
3.77 (3H, singlet);
4.64 (2H, singlet);
6.15–6.29 (1H, broad singlet);
6.41–6.59 (2H, multiplet).
Infrared Absorption Spectrum (film) ν$_{max}$ cm$^{-1}$:
1646, 1613, 1557, 1507, 1414, 1364, 1318, 1260, 1200, 1038.

EXAMPLE 63

N-[2-t-Butyl-5-carbamoylphenyl]-3-(4-N'',N''-diethylcarbamoylmethyloxy-2-methoxyphenyl)octanamide (Compound No. 476)

Following a similar procedure to that described in Example 20, but using 5 N-(2-t-butyl-5-carboxyphenyl)-3-(4-N',N'-diethylcarbamoylmethyloxy-2-methoxy-phenyl)octanamide (prepared as described in Preparation 47), the title compound was obtained as a foam-like substance.
Nuclear Magnetic Resonance Spectrum (270 MHz, CDCl$_3$) δ ppm:
0.79–0.90 (3H, multiplet);
1.07–1.37 (6H. multiplet);
1.13 (3H, triplet, J=7 Hz);
1.21 (3H, triplet, J=7 Hz);
1.31 (9H, singlet);
1.64–1.80 (2H, multiplet);
2.61–2.80 (2H, multiplet);
3.37 (2H, quartet, J=7 Hz);
3.39 (2H, quartet, J=7 Hz);
3.41–3.57 (1H, multiplet);
3.77 (3H, singlet);
4.64 (2H, singlet);
5.41–5.68 (1H, multiplet);
6.02–6.28 (1H, multiplet);
6.42–6.60 (2H, multiplet);
7.07–7.70 (5H, multiplet).
Infrared Absorption Spectrum (KBr) ν$_{max}$ cm$^{-1}$:
1653, 1613, 1506, 1465, 1419, 1379, 1365, 1282, 1260, 1200, 1165.

EXAMPLE 64

N-(2-t-Butyl-5-N'-methylcarbamoylphenyl)-3-(4-N''-butylcarbamoylmethloxy-2-methoxyphenyl)octanamide (Compound No. 477)

Following a similar procedure to that described in Example 1, but using N-(2-t-butyl-5-carboxyphenyl)-3-(4-N'-butylcarbamoylmethyloxy-2-methoxy-phenyl)octanamide (prepared as described in Preparation 48), the title compound was obtained as crystals, melting at 99°–108° C. (from ethyl acetate).
Nuclear Magnetic Resonance Spectrum (270 MHz, CDCl$_3$) δ ppm:
0.80–0.92 (3H, multiplet);
0.91 (3H, triplet, J=7 Hz);
1.10–1.40 (8H. multiplet);
1.31 (9H, singlet);
1.43–1.60 (2H, multiplet);
1.63–1.80 (2H, multiplet);
2.60–2.75 (2H, multiplet);
2.96 (3H, doublet, J=5 Hz);
3.24–3.37 (2H, multiplet);
3.46–3.59 (1H, multiplet);
3.79 (3H, singlet);
4.56 (2H, singlet);
6.01–6.14 (1H, singlet);
6.40–6.65 (3H, multiplet);
7.01–7.65 (5H, multiplet).
Infrared Absorption Spectrum (KBr) ν$_{max}$ cm$^{-1}$:
1656, 1543, 1506, 1465, 1413, 1318, 1284, 1258, 1200, 1162.

EXAMPLE 65

N-(2-t-Butyl-5-N'-methylcarbamoylphenyl)-3-[4-(2-oxopropoxy)-2-methoxyphenyl]octanamide (Compound No. 664)

106 mg (1.15 mmol) of chloroacetone, 166 mg (1.20 mmol) of potassium carbonate and 200 mg (1.20 mmol) of potassium iodide were added, in that order, to a solution of 437 mg (0.96 mmol) of N-(2-t-butyl-5-N'-methylcarbamoyl-phenyl)-3-(4-hydroxy-2-methoxyphenyl)octanamide (prepared as described in Example 122) in 10 ml of dimethylformamide, and the resulting mixture was stirred for 2 hours. At the end of this time, the reaction mixture was diluted with ethyl acetate, and the diluted solution was washed several times with water and once with a saturated aqueous solution of sodium chloride, after which it was dried over anhydrous sodium sulfate. The solvent was removed by distillation under reduced pressure, and the resulting residue was purified by column chromatography through 40 g of silica gel, using a 50:1 by volume mixture of ethyl acetate and methanol as the eluent, to give 450 mg of a crude product containing the title compound. The produce was further purified by preparative liquid chromatography through a YMC PACK ODS-A column (manufactured by YMC Co. Ltd.) using a 90:10:0.02:0.02 mixture of acetonitrile, water, triethylamine and acetic acid as the eluent, to give the title compound as crystals, melting at 84°–85° C. (from methylene chloride-hexane).
Nuclear Magnetic Resonance Spectrum (270 MHz, CDCl$_3$) δ ppm:
0.80–0.90 (3H, multiplet);
1.10–1.41 (6H, multiplet);
1.30 (9H, singlet);
1.65–1.85 (2H, multiplet);
2.26 (3H, singlet);
2.60–2.80 (2H, multiplet);
2.96 (3H, doublet, J=5 Hz);
3.42–3.58 (1H, multiplet);
3.78 (3H, singlet);
4.52 (2H, singlet);
6.09–6.21 (1H, multiplet);
6.32–6.51 (2H, multiplet);
7.07–7.68 (5H, multiplet).
Infrared Absorption Spectrum (KBr) ν$_{max}$ cm$^{-1}$:
1725, 1645, 1613, 1558, 1506, 1466, 1414, 1318, 1291, 1257, 1201, 1160.

EXAMPLE 66

N-(2-t-Butyl-5-N'-methylcarbamoylphenyl-3-(2,4-dimethoxy-5-methylphenyl)octanamide (Compound No. 201)

Following a similar procedure to that described in Example 1, but using N-(2-t-butyl-5-carboxyphenyl)-3-(2,4-dimethoxy-5-methylphenyl)octanamide (prepared as described in Preparation 3 1E), the title compound was obtained as crystals, melting at 191°–192.5° C. (from ethyl acetate).
Nuclear Magnetic Resonance Spectrum (270 MHz, CDCl$_3$) δ ppm:
0.75–0.91 (3H, multiplet);
1.08–1.38 (6H, multiplet);
1.28 (9H, singlet);
1.54–1.80 (2H, multiplet);
2.14 (3H, singlet);
2.70 (2H, doublet, J=7 Hz);
2.96 (3H, doublet, J=5 Hz);
3.40–3.58 (1H, multiplet);
3.77 (3H, singlet);
3.80 (3H, singlet);
6.08–6.21 (1H, multiplet);
6.38 (1H, singlet);
6.95 (1H, singlet);
7.08–7.19 (1H, broad singlet);
7.38–7.64 (3H, multiplet).
Infrared Absorption Spectrum (KBr) ν$_{max}$ cm$^{-1}$:
3302, 3225, 1665, 1633, 1616, 1561, 1512, 1466, 1299, 1205, 1039.

EXAMPLE 67

N-(2-t-Butyl-5-carbamoylphenyl)-3-(2,4-dimethoxy-5-methylphenyl)octanamide (Compound No. 202)

Following a similar procedure to that described in Example 20, but using N-(2-t-butyl-5-carboxyphenyl)-3-(2,4-dimethoxy-5-methylphenyl)octanamide (prepared as described in Preparation 31E), the title compound was obtained as crystals, melting at 179°–180° C. (from ethyl acetate-hexane).
Nuclear Magnetic Resonance Spectrum (270 MHz, CDCl$_3$) δ ppm:
0.77–0.93 (3H, multiplet);
1.06–1.40 (6H, multiplet);
1.29 (9H, singlet);
1.63–1.80 (2H, multiplet);
2.13 (3H, singlet);
2.62–2.80 (2H, multiplet);
3.40–3.58 (1H, multiplet);
3.78 (3H, singlet);
3.80 (3H, singlet);
5.38–5.62 (1H, broad);
6.07–6.24 (1H, broad);
6.29 (1H, singlet);
6.95 (1H, singlet);
7.11 (1H, broad singlet);
7.39–7.70 (3H, multiplet).
Infrared Absorption Spectrum (KBr) ν$_{max}$ cm$^{-1}$:
3328, 3179, 1678, 1655, 1615, 1512, 1422, 1297, 1205, 1041.

EXAMPLE 68

N-(2-t-Butyl-5-N'-methylcarbamoylphenyl)-3-[4-(3-ethoxypropoxy)-2-methoxyphenyl]octanamide (Compound No. 491)

Following a similar procedure to that described in Example 44, but using 3-[4-(3-ethoxypropoxy)-2-methoxyphenyl]octanoic acid (prepared as described in Preparation 50B) and 2-t-butyl-5-N-methylcarbamoylaniline (prepared as described in Preparation 36), the title compound was obtained as crystals, melting at 136°–138° C. (from methylene chloride-hexane).
Nuclear Magnetic Resonance Spectrum (270 MHz, CDCl$_3$) δ ppm:
0.80–0.90 (3H, multiplet);
1.12–1.41 (6H, multiplet);
1.19 (3H, triplet, J=7 Hz);
1.29 (9H, singlet);
1.64–1.80 (2H, multiplet);
2.02 (2H, quintet, J=6 Hz);
2.60–2.80 (2H, multiplet);
2.96 (3H, doublet, J=5 Hz);
3.49 (2H, quintet, J=7 Hz);
3.42–3.56 (1H, multiplet);
3.58 (2H, triplet, J=6 Hz);
3.77 (3H, singlet);
4.02 (2H, triplet, J=6 Hz);
6.06–6.18 (1H, multiplet);
6.40–6.50 (2H, multiplet);
7.06–7.66 (5H, multiplet).
Infrared Absorption Spectrum (KBr) ν$_{max}$ cm$^{-1}$:
1635, 1614, 1560, 1525, 1507, 1321, 1287, 1259, 1201, 1162, 1119.

EXAMPLE 69

N-(2-t-Butyl-5-N'-methylcarbamoylphenyl)-3-[4-(3-methoxypropoxy)-2-methoxyphenyl]octanamide (Compound No. 493)

Following a similar procedure to that described in Example 44, but using 3-[4-(3-methoxypropoxy)-2-methoxyphenyl]octanoic acid (prepared as described in Preparation 50A) and 2-t-butyl-5-N-methylcarbamoylaniline (prepared as described in Preparation 36), the title compound was obtained as crystals, melting at 149°–150° C. (from methylene chloride-hexane).
Nuclear Magnetic Resonance Spectrum (270 MHz, CDCl$_3$) δ ppm:
0.80–0.90 (3H, multiplet);
1.15–1.34 (6H, multiplet);
1.29 (9H, singlet);
1.65–1.80 (2H, multiplet);
2.02 (2H, quintet, J=6 Hz);
2.60–2.81 (2H, multiplet);
2.96 (3H, doublet, J=5 Hz);
3.35 (3H, singlet);
3.42–3.56 (1H, multiplet);
3.54 (2H, triplet, J=6 Hz);
3.77 (3H, singlet);
4.02 (2H, triplet, J=6 Hz);
6.08–6.20 (1H, multiplet);
6.41–6.51 (2H, multiplet);
7.04–7.65 (5H, multiplet).
Infrared Absorption Spectrum (KBr) $v_{max}$ cm$^{-1}$:
1637, 1614, 1559, 1507, 1466, 1413, 1319, 1288, 1259, 1202, 1162.

EXAMPLE 70

N-(2-t-Butyl-5-carbamoylphenyl)-3-[2-methoxy-4-(3-methoxypropoxy)phenyl]octanamide (Compound No. 492)

Following a similar procedure to that described in Example 44, but using a 3-[4-(3-methoxypropoxy)-2-methoxyphenyl]octanoic acid (prepared as described in Preparation 50A), the title compound was obtained as crystals, melting at 65°–67° C. (from ethyl acetate-hexane).
Nuclear Magnetic Resonance Spectrum (270 MHz, CDCl$_3$) δ ppm:
0.79–0.90 (3H, multiplet);
1.13–1.38 (6H, multiplet);
1.30 (9H, singlet);
1.64–1.80 (2H, multiplet);
2.03 (2H, quintet, J=6 Hz);
2.65–2.77 (2H, multiplet);
3.36 (3H, singlet);
3.42–3.56 (1H, multiplet);
3.55 (2H, triplet, J=5 Hz);
3.77 (3H, singlet);
4.01 (2H,t-J=6 Hz);
5.50–5.71 (1H, multiplet);
6.90–7.11 (1H, multiplet);
6.41–6.51 (2H, multiplet);
7.01–7.70 (5H, multiplet).
Infrared Absorption Spectrum (KBr) $v_{max}$ cm$^1$:
1656, 1614, 1507, 1466, 1420, 1288, 1260, 1201, 1162, 1123.

EXAMPLE 71

N-(2-t-Butyl-5-carbamoylphenyl)-3-[4-(3-ethoxypropoxy)-2-methoxyphenyl]octanamide (Compound No. 494)

Following a similar procedure to that described in Example 44, but using 3-[4-(3-ethoxypropoxy)-2-methoxyphenyl]octanoic acid (prepared as described in Preparation 50B) the title compound was obtained as crystals, melting at 135°–136° C. (from ethyl acetate-hexane).
Nuclear Magnetic Resonance Spectrum (270 MHz, CDCl$_3$) δ ppm:
0.80–0.90 (3H, multiplet);
1.12–1.38 (6H, multiplet);
1.21 (3H, triplet, J=7 Hz);
1.30 (9H, singlet);
1.64–1.80 (2H, multiplet);
2.03 (2H, quintet, J=6 Hz);
2.65–2.77 (2H, multiplet);
3.42–3.56 (1H, multiplet);
3.51 (2H, quintet, J=7 Hz);
3.59 (2H, triplet, J=6 Hz);
3.77 (3H, singlet);
4.02 (2H, triplet, J=6 Hz);
5.51–5.74 (1H, broad);
5.91–6.13 (1H, broad);
6.41–6.52 (2H, multiplet);
7.03–7.70 (5H, multiplet).
Infrared Absorption Spectrum (KBr) $v_{max}$ cm$^{-1}$:
1655, 1614, 1507, 1420, 1377, 1287, 1260, 1201, 1162, 1118.

EXAMPLE 72

N-(2-t-Butyl-5-carbamoylphenyl)-3-(2,4-dimethoxy-5-N',N'-dimethylaminosulfonylphenyl)octanamide (Compound No. 586)

Following a similar procedure to that described in Example 44, but using 3-(2,4-dimethoxy-5-N',N'-dimethylaminosulfonylphenyl)octanoic acid (prepared as described in Preparation 30D), the title compound was obtained as crystals, melting at 206°–207° C. (from methylene chloride-ethyl acetate).
Nuclear Magnetic Resonance Spectrum (270 MHz, CDCl$_3$) δ ppm:
0.77–0.91 (3H, multiplet);
1.04–1.33 (6H, multiplet);
1.35 (9H, singlet);
1.64–1.81 (2H, multiplet);
2.58–2.74 (2H, multiplet);
2.77 (6H, singlet);
3.61–3.76 (1H, multiplet);
3.90 (3H, singlet);
3.92 (3H, singlet);
5.33–5.66 (1H, broad);
6.32–6.61 (1H, broad);
6.48 (1H, singlet);
7.10–7.19 (1H, broad singlet);
7.39–7.48 (1H, multiplet);
7.57–7.69 (2H, multiplet);
7.74 (1H, singlet).
Infrared Absorption Spectrum (KBr) $v_{max}$ cm$^{-1}$:
1666, 1607, 1560, 1524, 1508, 1473, 1466, 1439, 1425, 1396, 1323, 1284, 1215, 1142, 1070, 1028.

EXAMPLE 73

N-(2-t-B=1y-5-N'-methylcarbamoylphenyl)-3-(2,4-dimethoxy-5-N'',N''-dimethylaminosulfonylphenyl)octanamide (Compound No. 587)

Following a similar procedure to that described in Example 44, but using 3-(2,4-dimethoxy-5-N',N'-dimethylaminosulfonylphenyl)octanoic acid (prepared as described in Preparation 30D) and 2-t-butyl-5-N-methylcarbamoylaniline (prepared as described in Preparation 36), the title compound was obtained as crystals, melting at 147°–149° C. (from methylene chloride-ethyl acetate).

Nuclear Magnetic Resonance Spectrum (270 MHz, CDCl$_3$) δ ppm:
0.76–0.91 (3H, multiplet);
1.07–1.34 (6H, multiplet);
1.34 (9H, singlet);
1.62–1.81 (2H, multiplet);
2.56–2.73 (2H, multiplet);
2.78 (6H, singlet);
2.95 (3H, doublet, J=5 Hz);
3.59–3.74 (1H, multiplet);
3.89 (3H, singlet);
3.91 (3H, singlet);
6.43–6.56 (1H, multiplet);
6.48 (1H, singlet);
7.06–7.16 (1H, broad singlet);
7.37–7.46 (1H, multiplet);
7.53–7.67 (2H, multiplet);
7.73 (1H, singlet).
Infrared Absorption Spectrum (KBr) ν$_{max}$ cm$^{-1}$:
1655, 1649, 1605, 1560, 1545, 1508, 1466, 1460, 1408, 1363, 1325, 1281, 1213, 1142, 1026.

EXAMPLE 74

N-(2-t-Butyl-5-carbamoylphenyl)-3-[2-methoxy-4-(3-methylsulfonyl-propoxy)phenyl]octanamide (Compound No. 506)

Following a similar procedure to that described in Example 20, but using N-(2-t-butyl-5-carboxyphenyl)-3-[2-methoxy-4-(3-methylsulfonylpropoxy)-phenyl]octanamide (prepared as described in Preparation 31F), the title compound was obtained as a foam-like substance.
Nuclear Magnetic Resonance Spectrum (270 MHz, CDCl$_3$) δ ppm:
0.79–0.90 (3H, multiplet);
1.11–1.36 (6H, multiplet);
1.32 (9H, singlet);
1.64–1.80 (2H, multiplet);
2.26–2.40 (2H, multiplet);
2.62–2.77 (2H, multiplet);
2.98 (3H, singlet);
3.20–3.30 (2H, multiplet);
3.42–3.54 (1H, multiplet);
3.77 (3H, singlet);
4.04–4.15 (2H, multiplet);
5.50–5.72 (1H, broad);
5.90–6.17 (1H, broad);
6.40–6.50 (2H, multiplet);
7.50–7.64 (5H, multiplet).
Infrared Absorption Spectrum (KBr) ν$_{max}$ cm$^{-1}$:
1663, 1613, 1507, 1467, 1419, 1290, 1201, 1162, 1132, 1040.

EXAMPLE 75

N-(2-t-Butyl-5-N'-methylcarbamoylphenyl)-3-[2-methoxy-4-(3-methylsulfonyl-propoxy)phenyl] octanamide (Compound No. 507)

Following a similar procedure to that described in Example 1, but using N-(2-t-butyl-5-carboxyphenyl)-3-[2-methoxy-4-(3-methylsulfonylpropoxy)-phenyl]octanamide (prepared as described in Preparation 31F), the title compound was obtained as crystals, melting at 77°–78° C. (from methylene chloride-hexane).
Nuclear Magnetic Resonance Spectrum (270 MHz, CDCl$_3$) δ ppm:
0.80–0.91 (3H, multiplet);
1.12–1.40 (6H, multiplet);
1.31 (9H, singlet);
1.61–1.80 (2H, multiplet);
2.26–2.40 (2H, multiplet);
2.61–2.80 (2H, multiplet);
2.95 (3H, singlet);
2.96 (3H, doublet, J=5 Hz);
3.25 (2H, triplet, J=8 Hz);
3.43–3.57 (1H, multiplet);
3.78 (3H, singlet);
4.08 (2H, triplet, J=6 Hz);
6.11–6.25 (1H, multiplet);
6.40–6.50 (2H, multiplet);
7.07–7.62 (5H, multiplet).
Infrared Absorption Spectrum (KBr) ν$_{max}$ cm$^{-1}$:
1649, 1613, 1559, 1507, 1414, 1310, 1291, 1201, 1162, 1132.

EXAMPLE 76

N-(2-t-Butyl-5-carbamoylphenyl)-3-(5-fluoro-2,4-dimethoxyphenyl)octanamide (Compound No. 380)

Following a similar procedure to that described in Example 20, but using N-(2-t-butyl-5-carboxyphenyl)-3-(5-fluoro-2,4-dimethoxyphenyl)octanamide (prepared as described in Preparation 31G), the title compound was obtained as crystals, melting at 149.5°–150° C. (from ethyl acetate-diethyl ether).
Nuclear Magnetic Resonance Spectrum (270 MHz, CDCl$_3$) δ ppm:
0.76–0.94 (3H, multiplet);
1.06–1.40 (6H, multiplet);
1.30 (9H, singlet);
1.55–1.80 (2H, multiplet);
2.57–2.73 (2H, multiplet);
3.47–3.65 (1H, multiplet);
3.79 (3H, singlet);
3.87 (3H, singlet);
5.60–5.95 (1H, broad);
6.17–6.47 (1H, broad);
6.52 (1H, doublet, J=7 Hz);
6.94 (1H, doublet, J=12 Hz);
7.20 (1H, broad singlet);
7.40 (1H, doublet, J=8 Hz);
7.57–7.72 (2H, multiplet).
Infrared Absorption Spectrum (KBr) ν$_{max}$ cm$^{-1}$:
3437, 3183, 1656, 1615, 1517, 1422, 1323, 1203, 1037.

EXAMPLE 77

N-(2-t-Butyl-5-carbamoylphenyl)-3-[2-methoxy-4-(3-methylsulfonyl-aminopropoxy)phenyl] octanamide (Compound No. 525)

Following a similar procedure to that described in Example 20, but using N-(2-t-butyl-5-carboxyphenyl)-3-[2-methoxy-4-(3-methylsulfonylamino-propoxy)phenyl] octanamide (prepared as described in Preparation 31H), the title compound was obtained as crystals, melting at 77°–79° C. (from methylene chloride-hexane).
Nuclear Magnetic Resonance Spectrum (270 MHz, CDCl$_3$) δ ppm:
0.80–0.96 (3H, multiplet);
1.15–1.43 (6H, multiplet);
1.34 (9H, singlet);
1.60–1.82 (2H, multiplet);
1.98–2.10 (2H, multiplet);
2.63–2.82 (2H, multiplet);

2.96 (3H, singlet);
3.32–3.49 (3H, multiplet);
3.73 (3H, singlet);
4.01–4.25 (2H, multiplet);
6.08–6.20 (1H, multiplet);
6.45–7.60 (9H, multiplet).
Infrared Absorption Spectrum (KBr) $v_{max}$ cm$^{-1}$:
    1661, 1613, 1507, 1467, 1454, 1420, 1317, 1260, 1201, 1152.

EXAMPLE 78

N-(2-t-Butyl-5-N'-methylcarbamoylphenyl)-3-[2-methoxy-4-(3-methylsulfonyl-aminopropoxy)phenyl]octanamide (Compound No. 526)

Following a similar procedure to that described in Example 1, but using N-(2-t-butyl-5-carboxyphenyl)-3-[2-methoxy-4-(3-methylsulfonylamino-propoxy)phenyl]octanamide (prepared as described in Preparation 31H), the title compound was obtained as crystals, melting at 70°–75° C. (from methylene chloride-hexane).
Nuclear Magnetic Resonance Spectrum (270 MHz, CDCl$_3$) δ ppm:
0.80–0.91 (3H, multiplet);
1.11–1.42 (6H, multiplet);
1.30 (9H, singlet);
1.61–1.80 (2H, multiplet);
1.93–2.08 (2H, multiplet);
2.60–2.80 (2H, multiplet);
2.91 (6H, broad singlet);
3.24–3.47 (2H, multiplet);
3.39–3.54 (1H, multiplet);
3.77 (3H, singlet);
3.95–4.10 (2H. multiplet);
5.38–5.50 (1H, multiplet);
6.36–6.50 (3H, multiplet);
7.01–7.50 (5H, multiplet).
Infrared Absorption Spectrum (KBr) $v_{max}$ cm$^{-1}$:
    1647, 1613, 1558, 1507, 1467, 1414, 1319, 1260, 1201, 1154.

EXAMPLE 79

N-(2-t-Butyl-5-carbamoylphenyl)-3-(2,4-dimethoxyphenyl)-5-methylhexanamide (Compound No. 371)

Following a similar procedure to that described in Example 20, but using N-(2-t-butyl-5-carboxyphenyl)-3-(2,4-dimethoxyphenyl)-5-methylhexanamide (prepared as described in Preparation 31I), the title compound was obtained as crystals, melting at 194.5°–196.5° C. (from methylene chloride-hexane).
Nuclear Magnetic Resonance Spectrum (270 MHz, CDCl$_3$) δ ppm:
0.86 (3H, doublet, J=6 Hz);
0.88 (3H, doublet, J=6 Hz);
1.30 (9H, singlet);
1.33–1.56 (2H, multiplet);
1.66–1.82 (1H, multiplet);
2.59–2.78 (2H, multiplet);
3.53–3.70 (1H, multiplet);
3.77 (6H, singlet);
5.31–5.62 (1H, broad);
6.00–6.30 (1H, broad);
6.40–6.53 (2H, multiplet);
7.02–7.69 (7H, multiplet).
Infrared Absorption Spectrum (KBr) $v_{max}$ cm$^{-1}$:
    3358, 3210, 1651, 1612, 1508, 1422, 1285, 1206, 1034, 822.

EXAMPLE 80

N-(2-t-Butyl-5-N'-methylcarbamoylpheny)-3-(2,4-dimethoxyphenyl-5-methylhexanamide (Compound No. 372)

Following a similar procedure to that described in Example 1, but using N-(2-t-butyl-5-carboxyphenyl)-3-(2,4-dimethoxyphenyl)-5-methylhexanamide (prepared as described in Preparation 31I), the title compound was obtained as crystals, melting at 200.5°–203° C. (from ethyl acetate-hexane).
Nuclear Magnetic Resonance Spectrum (270 MHz, CDCl$_3$) δ ppm:
0.86 (3H, doublet, J=6 Hz);
0.88 (3H, doublet, J=6 Hz);
1.29 (9H, singlet);
1.33–1.63 (2H, multiplet);
1.65–1.80 (1H, multiplet);
2.58–2.74 (2H, multiplet);
2.96 (3H, doublet, J=5 Hz);
3.52–3.68 (1H, multiplet);
3.77 (6H, singlet);
6.06–6.52 (3H, multiplet);
7.02–7.66 (5H, multiplet).
Infrared Absorption Spectrum (KBr) $v_{max}$ cm$^{-1}$:
    3308, 3221, 1664, 1634, 1507, 1288, 1208, 1158, 1039, 835.

EXAMPLE 81

N-(2-t-Butyl-5-carbamoylphenyl -3-(5-chloro-2,4-dimethoxyphenyl)octanamide (Compound No. 377)

181 mg (1.36 mmol) of N-chlorosuccinimide were added to a solution of 504 mg (1.11 mmol) of N-(2-t-butyl-5-carbamoylphenyl)-3-(2,4-dimethoxy-phenyl)octanamide (prepared as described in Example 2) in a mixture of 10 ml of acetonitrile and 4 ml of methylene chloride, and the resulting mixture was stirred at 50° C. for 15 hours. At the end of this time, the reaction mixture was allowed to cool to room temperature, after which a 1M aqueous solution of sodium sulfite was added to decompose any excess of the reagent. The mixture was then extracted with ethyl acetate. The extract was washed with water and then with a saturated aqueous solution of sodium chloride, after which it was dried over magnesium sulfate. The solvent was removed by distillation under reduced pressure, and the resulting residue was purified by column chromatography through 50 g of silica gel using ethyl acetate as the eluent, to give 434 mg (yield 80%) of the title compound as crystals, melting at 161.5°–163.5° C. (from ethyl acetate-isopropyl ether).
Nuclear Magnetic Resonance Spectrum (270 MHz, CDCl$_3$) δ ppm:
0.85 (3H, triplet, J=6 Hz);
1.15–1.30 (6H, multiplet);
1.31 (9H, singlet);
1.64–1.72 (2H, multiplet);
2.60–2.71 (2H, multiplet);
3.51–3.61 (1H, multiplet);
3.82 (3H, singlet);
3.88 (3H, singlet);
5.40–5.70 (1H, broad);
6.00–6.30 (1H, broad);
6.48 (1H, singlet);
7.09 (1H, singlet);

7.18 (1H, singlet);
7.43 (1H, doublet, J=8 Hz);
7.62–7.66 (2H, multiplet).
Infrared Absorption Spectrum (KBr) $\nu_{max}$ cm$^{-1}$:
  1656, 1612, 1531, 1505, 1423, 1299, 1207, 1143, 1073, 1036.

EXAMPLE 82

N-(2-t-Butyl-5-carbamoylphenyl)-3-(5-bromo-2,4-dimethoxyphenyl)octanamide (Compound No. 378)

Following a similar procedure to that described in Example 81, but using N-bromosuccinimide, the title compound was obtained as crystals, melting at 101.5°–103.5° C. (from ethyl acetate-hexane).
Nuclear Magnetic Resonance Spectrum (270 MHz, CDCl$_3$) δ ppm:
0.85 (3H, triplet, J=6 Hz);
1.15–1.30 (6H, multiplet);
1.32 (9H, singlet);
1.61–1.72 (2H, multiplet);
2.60–2.71 (2H, multiplet);
3.50–3.61 (1H, multiplet);
3.82 (3H, singlet);
3.88 (3H, singlet);
5.40–5.70 (1H, broad);
6.00–6.30 (1H, broad);
6.46 (1H, singlet);
7.07 (1H, singlet);
7.33 (1H, singlet);
7.43 (1H, doublet, J=8 Hz);
7.62–7.66 (2H, multiplet).
Infrared Absorption Spectrum (KBr) $\nu_{max}$ cm$^{-1}$:
  1647, 1600, 1561, 1465, 1422, 1376, 1298, 1279, 1145, 1033.

EXAMPLE 83

N-[2-t-Butyl-5-(N'-methycarbamoylmethyl)phenyl]-3-(2,4-dimethoxyphenyl-5-methylhexanamide (Compound No. 374)

Following a similar procedure to that described in Example 1, but using N-(2-t-butyl-5-carboxymethylphenyl)-3-(2,4-dimethoxyphenyl)-5-methylhexanoic acid prepared as described in Preparation 54A), the title compound was obtained as crystals, melting at 192°–195.5° C. (from methylene chloride-hexane).
Nuclear Magnetic Resonance Spectrum (270 MHz, CDCl$_3$) δ ppm:
0.86 (3H, doublet, J=6 Hz);
0.88 (3H, doublet, J=6 Hz);
1.28 (9H, singlet);
1.32–1.65 (2H, multiplet);
1.66–1.81 (1H, multiplet);
2.57–2.81 (2H, multiplet);
2.75 (3H, doublet, J=5 Hz);
3.46 (2H, singlet);
3.53–3.68 (1H, multiplet);
3.78 (6H, singlet);
5.51–5.68 (1H, multiplet);
6.41–6.52 (2H, multiplet);
6.92–7.36 (5H, multiplet).
Infrared Absorption Spectrum (KBr) $\nu_{max}$ cm$^{-1}$:
  3256, 3094, 1645, 1528, 1505, 1260, 1207, 1156, 1128, 1035, 835.

EXAMPLE 84

N-[2-t-Butyl-5-(carbamoylmethyl)phenyl]-3-(2,4-dimethoxyphenyl -5-methylhexanamide (Compound No. 373)

Following a similar procedure to that described in Example 20, but using N-(2-t-butyl-5-carboxymethylphenyl)-3-(2,4-dimethoxyphenyl)-5-methylhexanoic acid (prepared as described in Preparation 54A), the title compound was obtained as a foam-like substance.
Nuclear Magnetic Resonance Spectrum (270 MHz, CDCl$_3$) δ ppm:
0.86 (3H, doublet, J=6 Hz);
0.88 (3H, doublet, J=6 Hz);
1.27 (9H, singlet);
1.33–1.64 (2H, multiplet);
1.65–1.81 (1H, multiplet);
2.57–2.77 (2H, multiplet);
3.48 (2H, singlet);
3.53–3.68 (1H, multiplet);
3.78 (6H, singlet);
5.22–5.40 (1H, broad);
5.60–5.75 (1H, broad);
6.41–6.51 (2H, multiplet);
6.97–7.36 (5H, multiplet).
Infrared Absorption Spectrum (KBr) $\nu_{max}$ cm$^{-1}$:
  3294, 3194, 1663, 1612, 1507, 1466, 1287, 1208, 1156, 1038, 834.

EXAMPLE 85

N-(2-t-Butyl-5-carbamoylphenyl)-3-(5-chloro-2,4-dimethoxphenyl)heptanamide (Compound No. 379)

Following a similar procedure to that described in Example 20, but using N-(2-t-butyl-5-carboxyphenyl)-3-(5-chloro-2,4-dimethoxyphenyl)heptanamide prepared as described in Preparation 31J), the title compound was obtained as crystals, melting at 211.5°–214° C. (from methylene chloride-ethyl acetate-methanol).
Nuclear Magnetic Resonance Spectrum (270 MHz, CDCl$_3$) δ ppm:
0.85 (3H, triplet, J=7 Hz);
1.05–1.38 (4H, multiplet);
1.32 (9H, singlet);
1.55–1.80 (2H, multiplet);
2.67 (2H, doublet-like, J=7 Hz);
3.46–3.63 (1H, multiplet);
3.82 (3H, singlet);
3.88 (3H, singlet);
5.40–5.56 (1H, broad);
6.05–6.25 (1H, broad);
6.48 (1H, singlet);
7.08 (1H, broad singlet);
7.18 (1H, singlet);
7.43 (1H, doublet, J=8 Hz);
7.63–7.75 (2H, multiplet).
Infrared Absorption Spectrum (KBr) $\nu_{max}$ cm$^{-1}$:
  3340, 3181, 1676, 1657, 1612, 1506, 1423, 1303, 1205, 1035.

EXAMPLE 86

N-(2-t-Butyl-5-carbamoylphenyl)-3-(4-t-butyloxycarbonylmethyloxy-2-methoxy)octanamide (Compound No. 489)

266 μl (1.80 mmol) of t-butyl bromoacetate and 586 mg (1.80 mmol) of cesium carbonate were added to a solution of 733 mg (1.66 mmol) of N-(2-t-butyl-5-carbamoylphenyl)-3-(4-hydroxy-2-methoxyphenyl)octanamide (prepared as described in Example 124) in 15 ml of dimethylformamide, and the resulting mixture was stirred for 6.5 hours. At the end of this time, the reaction mixture was diluted with ethyl acetate, and the diluted solution was washed several times with water and once with a saturated aqueous solution of sodium chloride, after which it was dried over anhydrous sodium sulfate. The solvent was removed by distillation under reduced pressure, and the resulting residue was purified by column chromatography through 125 g of silica gel using a 49:1 by volume mixture of ethyl acetate and methanol as the eluent, to give a crude product containing the title compound. The product was again chromatographed through silica gel under the same conditions as above to give 667 mg (yield 70%) of the title compound as crystals, melting at 121.5°–122.5° C. (from methylene chloride-diethyl ether).

Nuclear Magnetic Resonance Spectrum (270 MHz, CDCl$_3$) δ ppm:
0.80–0.90 (3H, multiplet);
1.12–1.39 (6H, multiplet);
1.30 (9H, singlet);
1.48 (9H, singlet);
1.63–1.80 (2H, multiplet);
2.61–2.82 (2H, multiplet);
3.42–3.57 (1H, multiplet);
3.76 (3H, singlet);
4.47 (2H, singlet);
5.40–5.61 (1H, broad);
6.08–6.28 (1H, broad);
6.36–6.52 (2H, multiplet);
7.05–7.70 (5H, multiplet).

Infrared Absorption Spectrum (KBr) ν$_{max}$ cm$^{-1}$:
1755, 1659, 1614, 1506, 1464, 1419, 1395, 1369, 1257, 1201, 1153.

EXAMPLE 87

N-(2-t-Butyl-5-carbamoylphenyl)-3-[2-methoxy-4-(2-methoxyethoxy)-phenyl]octanamide (Compound No. 495)

Following a similar procedure to that described in Example 20, but using N-(2-t-butyl-5-carboxyphenyl)-3-[2-methoxy-4-(2-methoxyethoxy)phenyl]-octanamide (prepared as described in Preparation 31K), the title compound was obtained as a foam-like substance.

Nuclear Magnetic Resonance Spectrum (270 MHz, CDCl$_3$) δ ppm:
0.80–0.91 (3H, multiplet);
1.12–1.41 (6H, multiplet);
1.32 (9H, singlet);
1.61–1.80 (2H, multiplet);
2.61–2.81 (2H, multiplet);
3.41–3.57. (1H, multiplet);
3.45 (3H, singlet);
3.59–3.83 (2H, multiplet);
3.76 (3H, singlet);
4.04–4.16 (2H, multiplet);
5.51–5.73 (1H, broad);
5.95–6.19 (1H, broad);
6.46–6.53 (2H, multiplet);
7.01–7.70 (5H, multiplet).

Infrared Absorption Spectrum (KBr) ν$_{max}$ cm$^{-1}$:
1656, 1614, 1506,1420, 1367,1289, 1260, 1202, 1163, 1125.

EXAMPLE 88

N-(2-t-Butyl-5-carbamoylphenyl)-3-(2,4-dimethoxyphenyl)-4-methylpentanamide (Compound No. 375)

Following a similar procedure to that described in Example 20, but using N-(2-t-butyl-5-carboxyphenyl)-3-(2,4-dimethoxyphenyl)-4-methylpentanamide (prepared as described in Preparation 31M), the title compound was obtained as a foam-like substance.

Nuclear Magnetic Resonance Spectrum (270 MHz, CDCl$_3$) δ ppm:
0.78 (3H, doublet, J=6.5 Hz);
1.02 (3H, doublet, J=6.5 Hz);
1.26 (9H, singlet);
1.90–2.10 (1H, multiplet);
2.74 (1H, doublet of doublets, J=11.5 Hz & 14.5 Hz);
2.87 (1H, doublet of doublets, J=5 Hz & 14.5 Hz);
3.15–3.30 (1H, multiplet);
3.76 (3H, singlet);
3.77 (3H, singlet);
5.34–5.73 (1H, broad);
5.95–6.33 (1H, broad);
6.43 (1H, doublet, J=2.5 Hz);
6.48 (1H, doublet of doublets, J=2.5 Hz & 8 Hz);
6.93–7.10 (1H, broad singlet);
7.11 (1H, doublet, J=8 Hz);
7.28 (1H, doublet, J=2 Hz);
7.39 (1H, doublet, J=8.5 Hz);
7.63 (1H, doublet of doublets, J=2 Hz & 8.5Hz).

Infrared Absorption Spectrum (film) ν$_{max}$ cm$^{-1}$:
1659, 1612, 1587, 1558, 1506, 1466, 1419, 1367, 1292, 1265, 1207, 1157, 1117, 1038.

EXAMPLE 89

N-(2-t-Butyl-5-carbamoylmethylphenyl)-3-(2,4-dimethoxyphenyl)-4-methylpentanamide (Compound No. 376)

Following a similar procedure to that described in Example 20, but using N-(2-t-butyl-5-carboxymethylphenyl)-3-(2,4-dimethoxyphenyl)-4-methylpentanoic acid (prepared as described in Preparation 54B), the title compound was obtained as a foam-like substance.

Nuclear Magnetic Resonance Spectrum (270 MHz, CDCl$_3$) δ ppm:
0.78 (3H, doublet, J=6.5 Hz);
1.01 (3H, doublet, J=6.5 Hz);
1.23 (9H, singlet);
1.90–2.09 (1H, multiplet);
2.74 (1H, doublet of doublets, J=11.5 Hz & 14.5 Hz);
2.85 (1H, doublet of doublets, J=5 Hz & 14.5 Hz);
3.13–3.27 (1H, multiplet);
3.42 (2H, singlet);
3.76 (3H, singlet);
3.78 (3H, singlet);
5.23–5.45 (1H, broad);
5.54–5.76 (1H, broad);
6.42 (1H, doublet, J=2.5 Hz);
6.47 (1H, doublet of doublets, J=2.5 Hz & 8 Hz);
6.78 (1H, doublet, J=2 Hz);
6.94–7.07 (1H, broad singlet);
7.01 (1H, doublet of doublets, J=2 Hz & 8.5 Hz);
7.09 (1H, doublet, J=8 Hz);
7.28 (1H, doublet, J=8.5Hz).

Infrared Absorption Spectrum (film) ν$_{max}$ cm$^{-1}$:
1666, 1612, 1587, 1506, 1466, 1419, 1365, 1294, 1265, 1207, 1157, 1038.

EXAMPLE 90

N-(2-t-Butyl-5-carbamoylphenyl)-3-[5-chloro-2-methoxy-4-(2-methoxyethoxy)-phenyl]octanamide (Compound No. 496)

Following a similar procedure to that described in Example 81, but using N-(2-t-butyl-5-carbamoylphenyl)-3-

[2-methoxy-4-(2-methoxyethoxy)phenyl]-octanamide (prepared as described in Example 87) the title compound was obtained as a foam-like substance.
Nuclear Magnetic Resonance Spectrum (270 MHz, CDCl$_3$) δ ppm:
0.80–0.90 (3H, multiplet);
1.11–1.37 (6H, multiplet);
1.32 (9H, singlet);
1.60–1.80 (2H, multiplet);
2.60–2.73 (2H, multiplet);
3.42–3.60 (1H, multiplet);
3.47 (3H, singlet);
3.74–3.82 (2H, multiplet);
3.79 (3H, singlet);
4.14–4.20 (2H, multiplet);
5.45–5.67 (1H, broad);
6.00–6.20 (1H, broad);
6.56–7.70 (6H, multiplet).
Infrared Absorption Spectrum (film) ν$_{max}$ cm$^{-1}$:
1655, 1605, 1505, 1449, 1366, 1302, 1200, 1129, 1071, 1036.

EXAMPLE 91

N-(2-t-Butyl-5-carbamoylphenyl)-3-[2-methoxy-4-(2-methoxyethoxy)-phenyl]octanamide (Compound No. 497)

Following a similar procedure to that described in Example 20, but using N-(2-t-butyl-5-carboxyphenyl)-3-[2-methoxy-4-(2-methoxyethoxy)-phenyl]octanamide (prepared as described in Example 31L), the title compound was obtained as crystals, melting at 134°–135° C. (from diethyl ether).
Nuclear Magnetic Resonance Spectrum (270 MHz, CDCl$_3$) δ ppm:
0.79–0.90 (3H, multiplet);
1.16–1.47 (6H, multiplet);
1.27 (3H, triplet, J=7 Hz);
1.31 (9H, singlet);
1.63–1.80 (2H, multiplet);
2.67–2.77 (2H, multiplet);
3.51–3.65 (1H, multiplet);
3.60 (2H, quartet, J=7 Hz);
3.73–3.82 (2H, multiplet);
3.76 (3H, singlet);
4.05–4.13 (2H, multiplet);
5.61–5.85 (1H, broad);
5.85–6.11 (1H, broad);
6.46–6.53 (2H, multiplet);
7.00–7.70 (5H, multiplet).
Infrared Absorption Spectrum (KBr) ν$_{max}$ cm$^{-1}$:
1656, 1614, 1507, 1452, 1420, 1373, 1289, 1260, 1202, 1163, 1123.

EXAMPLE 92

N-(2-t-Butyl-5-carbamoylphenyl)-3-[2-methoxy-4-methylphenyl]octanamide (Compound No. 203)

Following a similar procedure to that described in Example 20, but using N-(2-t-butyl-5-carboxyphenyl)-3-(2-methoxy-4-methylphenyl)octanamide prepared as described in Preparation 62), the title compound was obtained as crystals, melting at 175°–177° C. (from ethyl acetate).
Nuclear Magnetic Resonance Spectrum (270 MHz, CDCl$_3$) δ ppm:
0.84 (3H, triplet, J=6 Hz);
1.16–1.32 (6H, multiplet);
1.29 (9H, singlet);
1.65–1.77 (2H, multiplet);
2.31 (3H, singlet);
2.63–2.80 (2H, multiplet);
3.48–3.59 (2H, multiplet);
5.30–5.70 (1H, broad);
6.00–6.30 (1H, broad);
6.67 (1H, singlet);
6.76 (1H, doublet, J=8 Hz);
7.09–7.11 (2H, multiplet);
7.41 (1H, doublet, J=8 Hz);
7.57–7.66 (2H, multiplet).
Infrared Absorption Spectrum (KBr) ν$_{max}$ cm$^{-1}$:
1653, 1614, 1522, 1508, 1466, 1421, 1366, 1260, 1043, 814.

EXAMPLE 93

N-[2-t-Butyl-5-N'-(2-methylpropyl) carbamoylphenyl]-3-[2-methoxy-4-methylphenyl) octanamide (Compound No. 204)

Following a similar procedure to that described in Example 20, but using N-(2-t-butyl-5-carboxyphenyl)-3-(2-methoxy-4-methylphenyl)octanamide (prepared as described in Preparation 62) and 2-methylpropylamine, the title compound was obtained as crystals, melting at 150°–151° C. (from ethyl acetate-hexane).
Nuclear Magnetic Resonance Spectrum (27.0 MHz, CDCl$_3$) δ ppm:
0.84 (3H, triplet, J=6 Hz);
0.96 (6H, doublet, J=7 Hz);
1.17–1.30 (6H, multiplet);
1.28 (9H, singlet);
1.67–1.78 (2H, multiplet);
1.87 (1H, septet, J=7 Hz);
2.30 (3H, singlet);
2.63–2.80 (2H, multiplet);
3.24 (2H, triplet, J=6 Hz);
3.49–3.60 (1H, multiplet);
3.78 (3H, singlet);
6.18–6.22 (1H, multiplet);
6.66 (1H, singlet);
6.75 (1H, doublet, J=7 Hz);
7.08–7.13 (2H, multiplet);
7.40 (1H, doublet, J=9 Hz);
7.57–7.61 (2H, multiplet).
Infrared Absorption Spectrum (KBr) ν$_{max}$ cm$^{-1}$:
1657, 1634, 1548, 1528, 1466, 1366, 1321, 1261, 1158, 1043.

EXAMPLE 94

N-{2-t-Butyl-5-[4-methyl(1-piperazinyl)carbonyl] phenyl}-3-(2-methoxy-4-methylphenyl)octanamide (Compound No. 205)

Following a similar procedure to that described in Example 20, but using N-(2-t-butyl-5-carboxyphenyl)-3-(2-methoxy-4-methylphenyl)octanamide (prepared as described in Preparation 62) and 4-methylpiperazine, the title compound was obtained as a foam-like substance.
Nuclear Magnetic Resonance Spectrum (270 MHz, CDCl$_3$) δ ppm:
0.84 (3H, triplet, J=6 Hz);
1.17–1.32 (6H, multiplet);
1.27 (9H, singlet);
1.65–1.76 (2H, multiplet);
2.30–2.50 (4H, multiplet);

2.30 (3H, singlet);
2.32 (3H, singlet);
2.60–2.79 (2H, multiplet);
3.45–3.60 (3H, multiplet);
3.70–3.81 (2H, multiplet);
3.78 (3H, singlet);
6.66 (1H, singlet);
6.74 (1H, doublet, J=7 Hz);
7.07–7.38 (5H, multiplet).
Infrared Absorption Spectrum (KBr) $v_{max}$ cm$^{-1}$:
1683, 1612, 1508, 1461, 1438, 1300, 1265, 1133, 1040, 1002.

EXAMPLE 95

N-(2-t-Butyl-5-N'-methoxycarbamoylphenyl)-3-(2-methoxy-4-methylphenyl)octanamide (Compound No. 351)

Following a similar procedure to that described in Example 1, but using a 0.5M aqueous solution of sodium hydrogencarbonate instead of triethylamine, and using N-(2-t-butyl-5-carboxyphenyl)-3-(2-methoxy-4-methylphenyl)-octanamide (prepared as described in Preparation 62) and O-methylhydroxylamine hydrochloride, the title compound was obtained as crystals, melting at 162°–163° C. (from ethyl acetate-hexane).
Nuclear Magnetic Resonance Spectrum (270 MHz, CDCl$_3$) δ ppm:
0.84 (3H, triplet, J=6 Hz);
1.17–1.32 (6H, multiplet);
1.28 (9H, singlet);
1.69–1.77 (2H, multiplet);
2.31 (3H, singlet);
2.63–2.80 (2H, multiplet);
3.48–3.59 (1H, multiplet);
3.78 (3H, singlet);
3.86 (3H, singlet);
6.67 (1H, singlet);
6.77 (1H, doublet, J=8 Hz);
7.08–7.11 (2H, multiplet);
7.39–7.43 (2H, multiplet);
7.55–7.59 (1H, multiplet);
9.03 (1H, singlet).
Infrared Absorption Spectrum (KBr) $v_{max}$ cm$^{-1}$:
1641, 1613, 1524, 1466, 1319, 1262, 1158, 1082, 1042, 939.

EXAMPLE 96

N-(2-t-Butyl-5-carbamolphenyl)-3-[5-chloro-4-(2-ethoxyethoxy)-2-methoxyphenyl]octanamide (Compound No. 4981)

Following a similar procedure to that described in Example 20, but using N-(2-t-butyl-5-carboxyphenyl)-3-[5-chloro-4-(2-ethoxyethoxy)-2-methoxy-phenyl]octanamide (prepared as described in Preparation 31 N), the title compound was obtained as a foam-like substance.
Nuclear Magnetic Resonance Spectrum (270 MHz, CDCl$_3$) δ ppm:
0.80–0.90 (3H, multiplet);
1.12–1.32 (6H, multiplet);
1.24 (3H, triplet, J=7 Hz);
1.32 (9H, singlet);
1.60–1.76 (2H, multiplet);
2.60–2.73 (2H, multiplet);
3.48–3.61 (1H, multiplet);
3.62 (2H, quartet, J=7 Hz);
3.79 (3H, singlet);
3.79–3.87 (2H, multiplet);
4.12–4.20 (2H, multiplet);
15.50–5.72 (1H, broad);
6.00–6.24 (1H, broad);
6.55–7.68 (6H, multiplet).
Infrared Absorption Spectrum (KBr) $v_{max}$ cm$^{-1}$:
1656, 1604, 1505, 1461, 1446, 1396, 1366, 1302, 1202, 1122.

EXAMPLE 97

N-(2-t-Butyl-5-carbamoylphenyl)-3-(4-acetyl-2-methoxyphenyl)octanamide (Compound No. 273)

Following a similar procedure to that described in Example 99) but using N-(2-t-butyl-5-carboxyphenyl)-3-(4-acetyl-2-methoxyphenyl)octanamide prepared as described in Example 64A) the title compound was obtained as a foam-like substance.
Nuclear Magnetic Resonance Spectrum (270 MHz, CDCl$_3$) δ ppm:
0.84 (3H, triplet, J=6 Hz);
1.14–1.33 (6H. multiplet);
1.30 (9H, singlet);
1.70–1.85 (2H, multiplet);
2.58 (3H, singlet);
2.67–2.83 (2H, multiplet);
3.61–3.71 (1H,. multiplet);
3.89 (3H, singlet);
5.40–5.80 (1H, broad);
5.90–6.30 (1H, broad);
7.13 (1H, singlet);
7.31 (1H, doublet, J=8 Hz);
7.41 (1H, doublet, J=8 Hz);
7.48–7.63 (3H, multiplet);
7.72 (1H, singlet).
Infrared Absorption Spectrum (KBr) $v_{max}$ cm$^{-1}$:
1660, 1615, 1518, 1463, 1413, 1364, 1270, 1225, 1074, 1036.

EXAMPLE 98

N-(2-t-Butyl-5-carbamoylphenyl)-3-[2,4-dimethoxy-5-(methoxyimino)phenyl]octanamide (Compound No. 544)

Following a similar procedure to that described in Example 20, but using N-(2-t-butyl-5-carboxyphenyl)-3-(2,4-dimethoxy-5-methoxyiminophenyl)octanamide (prepared as described in Preparation 65), the title compound was obtained as a foam-like substance.
Nuclear Magnetic Resonance Spectrum (270 MHz, CDCl$_3$) δ ppm:
0.77–0.93 (3H, multiplet);
1.06–1.45 (6H. multiplet);
1.31 (9H, singlet);
1.64–1.78 (2H, multiplet);
2.64–2.77 (2H, multiplet);
3.50–3.69 (1H, multiplet);
3.82 (3H, singlet);
3.84 (3H, singlet);
3.93 (3H, singlet);
5.45–5.67 (1H, broad);
6.18–6.38 (1H, broad);
6.39 (1H, singlet);
7.11 (1H, broad singlet);
7.41 (1H, doublet, J=8.5 Hz);
7.57–7.70 (3H, multiplet);

8.36 (1H, singlet).
Infrared Absorption Spectrum (KBr) $\nu_{max}$ cm$^{-1}$:
   3295, 1660, 1616, 1561, 1499, 1466, 1419, 1366, 1295, 1207, 1058, 1033.

EXAMPLE 99

N-(2-t-Butyl-5-carbamoylphenyl)-3-[4-(1-oxobutyl)-2-methoxyphenyl]octanamide (Compound No. 272)

210 mg (1.30 mmol) of N,N'-carbonyldiimidazole were added to a suspension of 530 mg (1.07 mmol) of N-(2-t-butyl-5-carboxyphenyl)-3-(4-butyryl-2-methoxyphenyl)octanamide prepared as described in Preparation 64C), in 10 ml of acetonitrile, and the resulting mixture was stirred for 35 minutes, after which 1.0 ml (15 mmol) of concentrated aqueous ammonia were added. The reaction mixture was stirred for 20 minutes, after which it was freed from the organic solvent by distillation under reduced pressure. The concentrate was extracted with ethyl acetate. The extract was washed with 2N aqueous hydrochloric acid, with water, with a saturated aqueous solution of sodium hydrogencarbonate and with a saturated aqueous solution of sodium chloride, in that order, after which it was dried over anhydrous magnesium sulfate. The solvent was removed by distillation under reduced pressure, and the resulting residue was purified by column chromatography through 50 g of silica gel using a gradient elution method, with mixtures of hexane and ethyl acetate ranging from 1:9 to 0:9 by volume as the eluent, to give 511 mg (yield 97%) of the title compound as a foam-like substance.
Nuclear Magnetic Resonance Spectrum (270 MHz, CDCl$_3$) δ ppm:
0.83 (3H, triplet, J=6 Hz);
0.99 (3H, triplet, J=7 Hz);
1.13–1.32 (6H. multiplet);
1.29 (9H, singlet);
1.67–1.82 (4H, multiplet);
2.67–2.84 (2H, multiplet);
2.91 (2H, triplet, J=7 Hz);
3.60–3.71 (1H, multiplet);
3.89 (3H, singlet);
5.30–5.70 (1H, broad);
5.90–6.30 (1H, broad);
7.13 (1H, singlet);
7.30 (1H, doublet, J=8 Hz);
7.41 (1H, doublet, J=8 Hz);
7.48–7.64 (3H, multiplet);
7.72 (1H, singlet).
Infrared Absorption Spectrum (KBr) $\nu_{max}$ cm$^{-1}$:
   1660, 1615, 1561, 1518, 1464, 1413, 1366, 1253, 1200, 1164.

EXAMPLE 100

N-(2-t-Butyl-5-carbamoylphenyl)-3-(2,4-dimethoxyphenyl)hexanamide (Compound No. 381)

Following a similar procedure to that described in Example 20, but using N-(2-t-butyl-5-carboxyphenyl)-3-(2,4-dimethoxyphenyl)hexanamide (prepared as described in Preparation 31P), the title compound was obtained as crystals, melting at 191.5°–192° C. (from ethyl acetate).
Nuclear Magnetic Resonance Spectrum (270 MHz, CDCl$_3$) δ ppm:
0.88 (3H, triplet, J=7 Hz);
1.17–1.38 (2H, multiplet);
1.30 (9H, singlet);
1.60–1.81 (2H, multiplet);
2.61–2.83 (2H, multiplet);
3.43–3.59 (1H, multiplet);
3.78 (6H, singlet);
5.33–5.61 (1H, broad);
6.10–6.36 (1H, broad);
6.40–6.52 (2H, multiplet);
7.07–7.70 (5H, multiplet).
Infrared Absorption Spectrum (KBr) $\nu_{max}$ cm$^{-1}$:
   1653, 1612, 1526, 1508, 1425, 1286, 1264, 1207, 1120, 1034.

EXAMPLE 101

N-(2-t-Butyl-5-carbamoylphenyl)-3-[2-methoxy-4-(1-oxopropyl)phenyl]octanamide (Compound No. 274)

Following a similar procedure to that described in Example 99, but using N-(2-t-butyl-5-carboxyphenyl)-3-(2-methoxy-4-propionylphenyl)octanamide (prepared as described in Preparation 64B), the title compound was obtained as a foam-like substance.
Nuclear Magnetic Resonance Spectrum (270 MHz, CDCl$_3$) δ ppm:
0.83 (3H, triplet, J=6 Hz);
1.13–1.32 (6H, multiplet);
1.21 (3H, triplet, J=7 Hz);
1.29 (9H, singlet);
1.72–1.81 (2H, multiplet);
2.67–2.84 (2H, multiplet);
2.97 (2H, quartet, J=7 Hz);
3.60–3.71 (1H, multiplet);
3.89 (3H, singlet);
5.40–5.80 (1H, broad);
5.90–6.30 (1H, broad);
7.14 (1H, singlet);
7.30 (1H, doublet, J=8 Hz);
7.41 (1H, doublet, J=8 Hz);
7.48–7.63 (3H, multiplet);
7.71 (1H, singlet).
Infrared Absorption Spectrum (KBr) $\nu_{max}$ cm$^{-1}$:
   1660, 1615, 1517, 1463, 1413, 1366, 1257, 1204, 1165, 1042.

EXAMPLE 102

N-(2-t-Butyl-5-carbamoylphenyl)-3-(2-ethoxy-4-methoxyphenyl)heptanamide (Compound No. 412)

Following a similar procedure to that described in Example 20, but using N-(2-t-butyl-5-carboxyphenyl)-3-(2-ethoxy-4-methoxyphenyl)heptanamide (prepared as described in Preparation 31 Q), the title compound was obtained as crystals, melting at 184.5°–185.5° C.
Nuclear Magnetic Resonance Spectrum (270 MHz, CDCl$_3$) δ ppm:
0.85 (3H, triplet, J=7 Hz);
1.09–1.33 (4H. multiplet);
1.29 (9H, singlet);
1.40 (3H, triplet, J=7 Hz);
1.65–1.80 (2H, multiplet);
2.63–2.87 (2H, multiplet);
3.40–3.55 (1H, multiplet);
3.76 (3H, singlet);
3.92–4.06 (2H, multiplet);
5.30–5.55 (1H, broad);
6.03–6.31 (1H, broad);
6.40–6.50 (2H, multiplet);
7.04–7.69 (5H, multiplet).

Infrared Absorption Spectrum (KBr) $v_{max}$ cm$^{-1}$:
1654, 1612, 1558, 1530, 1422, 1292, 1258, 1200, 1165, 1044.

EXAMPLE 103

N-(2-t-Butyl-5-carbamoylphenyl)-3-[5-chloro-2-methoxy-4-(3-methoxy-propoxy)phenyl]heptanamide (Compound No. 500)

Following a similar procedure to that described in Example 20, but using N-(2-t-butyl-5-carboxyphenyl)-3-[5-chloro-2-methoxy-4-(3-methoxypropoxy)-phenyl]heptanamide (prepared as described in Preparation 31 S), the title compound was obtained as crystals, melting at 176°–190° C. (from ethyl acetate).

Nuclear Magnetic Resonance Spectrum (270 MHz, CDCl$_3$) δ ppm:
0.85 (3H, triplet, J=7 Hz);
1.02–1.40 (4H. multiplet);
1.32 (9H, singlet);
1.48–1.82 (2H, multiplet);
2.02–2.16 (2H, multiplet);
2.59–2.77 (2H, multiplet);
3.36 (3H, singlet);
3.46–3.64 (1H, multiplet);
3.60 (2H, triplet, J=6 Hz);
3.79 (3H, singlet);
4.10 (2H, triplet, J=6 Hz);
5.42–5.71 (1H, broad);
6.09–6.35 (1H, broad);
6.50 (1H, singlet);
7.02–7.70 (5H, multiplet).

Infrared Absorption Spectrum (KBr) $v_{max}$ cm$^{-1}$:
3333, 3200, 1655, 1605, 1507, 1422, 1303, 1201, 1124, 773.

EXAMPLE 104

N-(2-t-Butyl-5-carbamoylphenyl)-3-[2-methoxy-4-(3-methoxy-propoxy)phenyl]heptanamide (Compound No. 499)

Following a similar procedure to that described in Example 20, but using N-(2-t-butyl-5-carboxyphenyl)-3-[2-methoxy-4-(3-methoxypropoxy)phenyl]-heptanamide (prepared as described in Preparation 31T), the title compound was obtained as crystals, melting at 157°–162° C. (from diethyl ether).

Nuclear Magnetic Resonance Spectrum (270 MHz, CDCl$_3$) δ ppm:
0.85 (3H, triplet, J=7 Hz);
1.10–1.39 (4H. multiplet);
1.31 (9H, singlet);
1.64–1.81 (2H, multiplet);
1.95–2.08 (2H, multiplet);
2.62–2.78 (2H, multiplet);
3.36 (3H, singlet);
3.40–3.64 (1H, multiplet);
3.56 (2H, triplet, J=6 Hz);
3.77 (3H, singlet);
4.02 (2H, triplet, J=6 Hz);
5.43–6.53 (4H, multiplet);
7.04–7.70 (5H, multiplet).

Infrared Absorption Spectrum (KBr) $v_{max}$ cm$^{-1}$:
3323, 3199, 1653, 1614, 1507, 1421, 1291, 1201, 1124, 1038 837.

EXAMPLE 105

N-(2-t-Butyl-5-carbamoylphenyl)-3-(2-ethoxy-4-methoxyphenyl)-5-methylhexanaamide (Compound No. 413)

Following a similar procedure to that described in Example 20, but using N-(2-t-butyl-5-carboxyphenyl)-3-(2-ethoxy-4-methoxyphenyl)-5-methyl-hexanamide (prepared as described in Preparation 31R), the title compound was obtained as crystals, melting at 216°–217° C. (from methanol-ethyl acetate).

Nuclear Magnetic Resonance Spectrum (270 MHz, CDCl$_3$) δ ppm:
0.87 (3H, doublet, J=9 Hz);
0.89 (3H, doublet, J=9 Hz);
1.29 (9H, singlet);
1.32–1.50 (2H, multiplet);
1.40 (3H, triplet, J=7 Hz);
1.70–1.84 (1H, multiplet);
2.61–2.82 (2H, multiplet);
3.53–3.68 (1H, multiplet);
3.76 (3H, singlet);
3.92–4.07 (2H, multiplet);
5.35–5.60 (1H, broad);
6.11–6.30 (1H, broad);
6.39–6.50 (2H, multiplet);
7.02–7.68 (5H, multiplet).

Infrared Absorption Spectrum (KBr) $v_{max}$ cm$^{-1}$:
1653, 1612, 1531, 1507, 1424, 1286, 1258, 1200, 1166, 1045.

EXAMPLE 106

N-(2-t-Butyl-5-N'-methylcarbamoylphenyl)-3-[2,4-dimethoxyphenyl-5-methoxycarbonylphenyl)octanamide (Compound No. 246)

Following a similar procedure to that described in Example 44, but using 3-(2,4-dimethoxy-5-methoxycarbonylphenyl)octanoic acid (prepared as described in Preparation 37) and 2-t-Butyl-5-N-methylcarbamoylaniline (prepared as described in Preparation 36), the title compound was obtained as crystals, melting at 168°–169° C. (from methylene chloride-ethyl acetate).

Nuclear Magnetic Resonance Spectrum (270 MHz, CDCl$_3$) δ ppm:
0.78–0.91 (3H, multiplet);
1.06–1.37 (6H, multiplet);
1.30 (9H, singlet);
1.60–1.81 (2H, multiplet);
2.69 (2H, doublet, J=7.5 Hz);
2.96 (3H, doublet, J=5 Hz);
3.52–3.67 (1H, multiplet);
3.86 (3H, singlet);
3.87 (3H, singlet);
3.90 (3H, singlet);
6.24–6.41 (1H. multiplet);
6.44 (1H, singlet);
7.01–7.12 (1H, broad singlet);
7.36–7.44 (1H, multiplet);
7.55–7.66 (2H, multiplet);
7.75 (1H, multiplet).

Infrared Absorption Spectrum (KBr) $v_{max}$ cm$^{-1}$:
1718, 1703, 1655, 1647, 1639, 1613, 1560, 1510, 1460, 1437, 1365, 1323, 1281, 1252, 1211, 1153, 1030.

EXAMPLE 107

N-(2-t-Butyl-5-N'-methylcarbamoylphenyl)-3-(2,4-dimethoxy-5-carboxyphenyl)octanamide (Compound No. 245)

Following a similar procedure to that described in Preparation 7, but using N-(2-t-butyl-5-N'-methylcarbamoylphenyl)-3-(2,4-dimethoxyphenyl-5- methoxy-carbonylphenyl)octanamide (prepared as described in Example 106), the title compound was obtained as crystals, melting at 128°–130° C. (from methylene chloride-methanol-ethyl acetate).

Nuclear Magnetic Resonance Spectrum (270 MHz, CDCl$_3$) δ ppm:
0.75–0.90 (3H, multiplet);
1.02–1.33 (6H, multiplet);
1.32 (9H, multiplet);
1.53–1.83 (2H, multiplet);
2.59–2.78 (2H, multiplet);
2.95 (3H, doublet, J=5 Hz);
3.63–3.78 (1H, multiplet);
3.92 (3H, singlet);
4.08 (3H, singlet);
6.33–6.49 (1H, multiplet);
6.50 (1H, singlet);
7.06–7.18 (1H, broad singlet);
7.36–7.45 (1H, multiplet);
7.55–7.69 (2H, multiplet);
8.03 (1H, singlet).

Infrared Absorption Spectrum (KBr) $v_{max}$ cm$^{-1}$:
1718, 1686, 1655, 1639, 1610, 1560, 1508, 1439, 1419, 1365, 1323, 1277, 1211, 1082, 1024.

EXAMPLE 108

N-(2-t-Butyl-5-carbamoylphenyl)-3-(4-acetoxymethyl-2-methoxyphenyl)octanamide (Compound No. 211)

Following a similar procedure to that described in Example 26, but using 3-(4-acetoxymethyl-2-methoxyphenyl)octanoic acid (prepared as described in Preparation 41), the title compound was obtained as a foam-like substance.

Nuclear Magnetic Resonance Spectrum (270 MHz, CDCl$_3$) δ ppm:
0.84 (3H, triplet, J=6 Hz);
1.15–1.32 (6H, multiplet);
1.29 (9H, singlet);
1.70–1.78 (2H, multiplet);
2.09 (3H, singlet);
2.64–2.81 (2H, multiplet);
3.54–3.66 (1H, multiplet);
3.82 (3H, singlet);
5.06 (2H, singlet);
5.40–5.70 (1H, broad);
6.00–6.40 (1H, broad);
6.85 (1H, singlet);
6.94 (1H, doublet, J=8 Hz);
7.12 (1H, singlet);
7.21 (1H, doublet, J=8 Hz);
7.42 (1H, doublet, J=8 Hz);
7.62–7.68 (2H, multiplet).

Infrared Absorption Spectrum (KBr) $v_{max}$ cm$^{-1}$:
1742, 1656, 1615, 1510, 1464, 1420, 1378, 1258, 1229, 1042.

EXAMPLE 109

N-(2-t-Butyl-5-carbamoylphenyl)-3-(4-hydroxymethyl-2-methoxyphenyl)octanamide (Compound No. 218)

3.0 ml of a 2 N aqueous solution of sodium hydroxide were added to a solution of 2.25 g (4.95 mmol) of N-(2-t-Butyl-5-carbamoylphenyl)-3-(4-acetoxymethyl-2-methoxyphenyl)octanamide (prepared as described in Example 108) in 15 ml of methanol, and the resulting mixture was stirred for 40 minutes. At the end of this time, the reaction mixture was freed from the solvent by distillation under reduced pressure, and the resulting residue was mixed with water. The aqueous mixture was extracted with ethyl acetate. The extract was washed with a saturated aqueous solution of ammonium chloride and with a saturated aqueous solution of sodium chloride, in that order, after which it was dried over anhydrous magnesium sulfate. The solvent was removed by distillation under reduced pressure, and the resulting residue was purified by column chromatography through 100 g of silica gel using a gradient elution method, with mixtures of methylene chloride and methanol ranging from 12:1 to 10:1 by volume as the eluent, to give 1.99 g (yield 96%) of the title compound as a foam-like substance.

Nuclear Magnetic Resonance Spectrum (270 MHz, CDCl$_3$) δ ppm:
0.85 (3H, triplet, J=6 Hz);
1.15–1.35 (6H, multiplet);
1.32 (9H, singlet);
1.69–1.80 (2H, multiplet);
2.74 (2H, doublet, J=8 Hz);
3.20–3.31 (1H, broad);
3.49–3.61 (1H, multiplet);
3.80 (3H, singlet);
4.65 (2H, singlet);
5.40–5.60 (1H, broad);
6.20–6.40 (1H, broad);
6.85 (1H, doublet, J=2 Hz);
6.96–6.99 (2H, multiplet);
7.08 (1H, singlet);
7.19 (1H, doublet, J=7 Hz);
7.30 (1H, doublet, J=8 Hz);
7.41 (1H, doublet of doublets, J=2 Hz & 8 Hz).

Infrared Absorption Spectrum (KBr) $v_{max}$ cm$^{-1}$:
1659, 1614, 1509, 1464, 1419, 1366, 1258, 1157, 1125, 1043.

EXAMPLE 110

N-(2-t-Butyl-5-carbamoylphenyl -3-(4-formyl-2-methoxyphenyl)octanamide (Compound No. 299)

7.60 g (87.4 mmol) of manganese dioxide were added to a solution of 1.98 g (4.36 mmol) of N-(2-t-butyl-5-carbamoylphenyl)-3-(4-hydroxymethyl-2-methoxyphenyl)octanamide (prepared as described in Example 109), and the resulting mixture was stirred at room temperature for 6 hours. At the end of this time, the reaction mixture was filtered using a Celite (trade mark) filter aid to remove the oxidizing agent used. The filtrate was then concentrated by evaporation under reduced pressure, to give 1.88 g (yield 95%) of the title compound as a foam-like substance.

Nuclear Magnetic Resonance Spectrum (270 MHz, CDCl$_3$) δ ppm:
0.83 (3H, triplet, J=6 Hz);
1.13–1.32 (6H, multiplet);
1.29 (9H, singlet);
1.73–1.81 (2H, multiplet);
2.68–2.84 (2H, multiplet);
3.64–3.76 (1H, multiplet);
3.91 (3H, singlet);
5.50–5.80 (1H, broad);
6.00–6.40 (1H, broad);
7.16 (1H, singlet);
7.39–7.46 (4H, multiplet);
7.61 (1H,, doublet of doublets, J=2 Hz & 8 Hz);

7.74 (1H, doublet, J=2 Hz);
9.94 (1H, singlet).
Infrared Absorption Spectrum (KBr) $v_{max}$ cm$^{-1}$:
1683, 1659, 1603, 1519, 1463, 1421, 1387, 1259, 1154, 1038.

EXAMPLE 111

N-(2-t-Butyl-5-carbamoylphenyl)-3-(4-hydroxyimino-2-methoxyphenyl)octanamide (Compound No. 542)

137 mg (1.97 mmol) of hydroxylamine hydrochloride were added to a solution of 398 mg (0.879 mmol) of N-(2-t-butyl-5-carbamoylphenyl)-3-(4-formyl-2-methoxyphenyl)octanamide (prepared as described in Example 110) in 5 ml of pyridine, and the resulting mixture was stirred for 20 minutes. At the end of this time, the reaction mixture was diluted with water, and the diluted aqueous mixture was extracted with methylene chloride. The extract was dried over anhydrous magnesium sulfate, and the solvent was removed by distillation under reduced pressure. In order to remove the pyridine remaining in the residue, it was dissolved in toluene and the solvent was azeotropically distilled off. Repetition of this procedure gave 414 mg (a quantitative yield) of the title compound as a foam-like substance.
Nuclear Magnetic Resonance Spectrum (270 MHz, CDCl$_3$) δ ppm:
0.84 (3H, doublet, J=6 Hz);
1.15–1.34 (6H, multiplet);
1.31 (9H, singlet);
1.70–1.79 (2H, multiplet);
2.72 (2H, doublet, J=8 Hz);
3.59–3.70 (1H, multiplet);
3.86 (3H, singlet);
5.90–6.45 (2H, multiplet);
7.06–7.29 (4H, multiplet);
7.42 (1H, doublet, J=8 Hz);
7.51 (1H, doublet, J=2 Hz);
7.63 (1H, doublet of doublets, J=2 Hz & 8 Hz);
8.07 (1H, singlet);
8.30–8.50 (1H, broad).
Infrared Absorption Spectrum (KBr) $v_{max}$ cm$^{-1}$:
1660, 1614, 1560, 1510, 1465, 1301, 1255, 1040, 980.

EXAMPLE 112

N-(2-t-Butyl-5-carbamoylphenyl)-3-(4-carboxy-2-methoxyphenyl)octanamide (Compound No. 302)

A solution of 650 mg (7.19 mmol) of sodium chlorite in 7 ml of water was added dropwise over a period of 15 minutes to a solution of 1.44 g (3.18 mmol) of N-(2-t-butyl-5-carbamoylphenyl)-3-(4-formyl-2-methoxyphenyl)octanamide (prepared as described in Example 110) in a mixture of 15 ml of dimethyl sulfoxide and a 1M aqueous solution of sodium dihydrogenphosphate, and the resulting mixture was stirred for 4.5 hours. At the end of this time, the reaction mixture was acidified with 1N aqueous hydrochloric acid, and methylene chloride was added thereto to separate out crystals, which were collected by filtration. The crystals were washed with water and then with ethyl acetate to give 1.32 g (yield 89%) of the title compound as a powdery substance, melting at 204°–206° C. (from methylene chloride).
Nuclear Magnetic Resonance Spectrum (270 MHz; CDCl$_3$-Hexadeuterated dimethyl sulfoxide) δ ppm:
0.83 (3H, triplet, J=6 Hz);
1.10–1.35 (6H, multiplet);
1.26 (9H, singlet);
1.68–1.76 (2H, multiplet);
2.66–2.82 (2H, multiplet);
3.64–3.76 (1H, multiplet);
3.88 (3H, singlet);
6.50–6.70 (1H. broad);
7.29–7.68 (7H, multiplet);
8.57 (1H, singlet).
Infrared Absorption Spectrum (KBr) $v_{max}$ cm$^{-1}$:
1694, 1656, 1612, 1505, 1454, 1418, 1256, 1105, 1038, 771.

EXAMPLE 113

N-(2-t-Butyl-5-N'-methylcarbamoylphenyl-3-(4-acetoxymethyl-2-methoxyphenyl)octanamide (Compound No. 219)

Following a similar procedure to that described in Example 26, but using 3-(4-acetoxymethyl-2-methoxyphenyl)octanoic acid (prepared as described in Preparation 41) and 2-t-butyl-5-N-methylcarbamoylaniline (prepared as described in Preparation 36), the title compound was obtained as crystals, melting at 174°–176° C. (from ethyl acetate-hexane).
Nuclear Magnetic Resonance Spectrum (270 MHz, CDCl$_3$) δ ppm:
0.84 (3H, triplet, J=6 Hz);
1.15–1.30 (6H, multiplet);
1.28 (9H, singlet);
1.70–1.82 (2H, multiplet),
2.09 (3H, singlet);
2.63–2.80 (2H, multiplet);
2.95 (3H, doublet, J=5 Hz);
3.55–3.66 (1H, multiplet);
3.82 (3H, singlet);
5.05 (2H, singlet);
6.28–6.37 (1H, multiplet);
6.84–6.95 (2H, multiplet);
7.16–7.22 (2H, multiplet);
7.39 (1H, doublet, J=8 Hz);
7.57–7.66 (2H, multiplet).
Infrared Absorption Spectrum (KBr) $v_{max}$ cm$^{-1}$:
1742, 1637, 1559, 1510, 1464, 1418, 1364, 1257, 1227, 1041.

EXAMPLE 114

N-(2-t-Butyl-5-N'-methylcarbamoylphenyl)-3-(4-hydroxymethyl-2-methoxyphenyl)octanamide (Compound No. 220)

Following a similar procedure to that described in Example 109, but using N-(2-t-butyl-5-N'-methylcarbamoylphenyl)-3-(4-acetoxymethyl-2-methoxyphenyl)octanamide (prepared as described in Example 113), the title compound was obtained as crystals, melting at 144°–146° C. (from benzene-ethyl acetate).
Nuclear Magnetic Resonance Spectrum (270 MHz, CDCl$_3$) δ ppm:
0.85 (3H, triplet, J=6 Hz);
1.17–1.32 (6H, multiplet);
1.31 (9H, singlet);
1.71–1.78 (2H, multiplet);
2.73 (2H, doublet, J=8 Hz);
2.92 (3H, doublet, J=5 Hz);
3.48–3.60 (1H, multiplet);
3.79 (3H, singlet);

4.65 (2H, singlet);
6.16–6.23 (1H, multiplet);
6.82 (1H, singlet);
6.95–7.03 (3H, multiplet);
7.19 (1H, doublet, J=8 Hz);
7.29–7.38 (3H, multiplet).
Infrared Absorption Spectrum (KBr) $v_{max}$ cm$^{-1}$:
  1672, 1641, 1560, 1525, 1465, 1418, 1326, 1263, 1168, 1032.

EXAMPLE 115

N-(2-t-Butyl-5-N'-methylcarbamoylphenyl)-3-(4-formyl-2-methoxyphenyl)octanamide (Compound No. 300)

Following a similar procedure to that described in Example 110, but using N-(2-t-Butyl-5-N'-methylcarbamoylphenyl)-3-(4-hydroxymethyl-2-methoxyphenyl)octanamide (prepared as described in Example 114), the title compound was obtained as a powdery substance.
Nuclear Magnetic Resonance Spectrum (270 MHz, CDCl$_3$) δ ppm:
0.84 (3H, triplet, J=6 Hz);
1.15–1.31 (6H, multiplet);
1.29 (9H, singlet);
1.74–1.82 (2H, multiplet);
2.67–2.84 (2H, multiplet);
2.95 (3H, doublet, J=5 Hz);
3.64–3.76 (1H, multiplet);
3.90 (3H, singlet);
6.13–6.19 (1H, multiplet);
7.16 (1H, singlet);
7.38–7.46 (4H, multiplet);
7.57 (1H, doublet of doublets, J=2 Hz & 8 Hz);
7.72 (1H, doublet, J=2 Hz);
9.94 (1H, singlet).
Infrared Absorption Spectrum (KBr) $v_{max}$ cm$^{-1}$:
  1690, 1641, 1559, 1524, 1463, 1420, 1319, 1258, 1155, 1037.

EXAMPLE 116

N-(2-t-Butyl-5-N'-methylcarbamoylphenyl)-3-(4-carboxy-2-methoxyphenyl)octanamide (Compound No. 301)

Following a similar procedure to that described in Example 112, but using N-(2-t-butyl-5-N'-methylcarbamoylphenyl)-3-(4-formyl-2-methoxyphenyl)-octanamide (prepared as described in Example 115), the title compound was obtained as crystals, melting at 227°–229.5° C. (from benzene-ethanol).
Nuclear Magnetic Resonance Spectrum (400 MHz, Hexadeuterated dimethyl sulfoxide) δ ppm:
0.80 (3H, triplet, J=6 Hz);
1.05–1.30 (6H, multiplet);
1.21 (9H, singlet);
1.58–1.73 (2H, multiplet);
2.61–2.72 (2H, multiplet);
2.76 (3H, doublet, J=5 Hz);
3.61–3.68 (1H, multiplet);
3.84 (3H, singlet);
7.33 (1H, doublet, J=8 Hz);
7.39–7.41 (2H, multiplet);
7.46 (1H, doublet, J=1 Hz);
7.53 (1H, doublet of doublets, J=1 Hz & 8 Hz);
7.63 (1H, doublet of doublets, J=2 Hz & 8 Hz);
8.33–8.36 (1H, multiplet);
9.23 (1H, singlet).
Infrared Absorption Spectrum (KBr) $v_{max}$ cm$^{-1}$:
  1701, 1658, 1633, 1556, 1525, 1416, 1324, 1249, 1216, 1037.

EXAMPLE 117

N-(2-t-Butyl-5-N'-methylcarbamoylphenyl)-3-(4-hydroxyimino-2-methoxyphenyl)octanamide (Compound No. 543)

Following a similar procedure to that described in Example 111, but using N-(2-t-butyl-5-N'-methylcarbamoylphenyl)-3-(4-formyl-2-methoxyphenyl)-octanamide (prepared as described in Example 115), the title compound was obtained as crystals.
Nuclear Magnetic Resonance Spectrum (270 MHz, CDCl$_3$) δ ppm:
0.84 (3H, triplet, J=6 Hz);
1.15–1.30 (6H, multiplet);
1.30 (9H, singlet);
1.70–1.79 (2H, multiplet);
2.66–2.82 (2H, multiplet);
2.94 (3H, doublet, J=5 Hz);
3.56–3.67 (1H, multiplet);,
3.83 (3H, singlet);
6.12–6.17 (1H, multiplet);
7.06–7.63 (8H, multiplet);
8.08 (1H, singlet).
Infrared Absorption Spectrum (KBr) $v_{max}$ cm$^{-1}$:
  1645, 1560, 1510, 1465, 1414, 1306, 1254, 1161, 1039, 965.

EXAMPLE 118

N-{12-t-Butyl-5-[3-(benzyloxycarbonyl)propionylaminocarbonyl]phenyl}-3-(2,4-dimethoxyphenyl)octanamide (Compound No. 369)

810 mg (5.0 mmol) of N,N-carbonyldiimidazole were added to a solution of 1.04 g (5.0 mmol) of benzyl hydrogen succinate in 10 ml of acetonitrile, and the resulting mixture was stirred for 15 minutes, after which 565 mg (1.22 mmol) of N-(2-t-butyl-S-carbamoylphenyl)-3-(2,4-dimethoxyphenyl)octanamide (prepared as described in Example 2) and 610 mg (5.0 mmol) of 4-N,N-dimethylaminopyridine were added. The mixture was then heated under reflux for 4 days, after which the reaction mixture was allowed to cool to room temperature. The reaction mixture was then diluted with ethyl acetate, and the diluted solution was washed with 2 N aqueous hydrochloric acid and with 2 a saturated aqueous solution of sodium chloride, in that order, after which it was dried over anhydrous sodium sulfate. The solvent was removed by distillation under reduced pressure, and the resulting residue was purified by column chromatography through 15 g of silica gel using a gradient elution method, with mixtures of hexane and ethyl acetate ranging from 3:1 to 1:1 by volume as the eluent, to give a crude product containing the title compound. The product was: further purified by column chromatography through silica gel under the same conditions as above, to give the title compound as a viscous substance in a 15% yield.
Nuclear Magnetic Resonance Spectrum (270 MHz, CDCl$_3$) δ ppm:
0.77–0.93 (3H, multiplet);
1.10–1.43 (6H, multiplet);
1.29 (9H, singlet);
1.62–1.81 (2H, multiplet);

2.63–2.90 (4H, multiplet);
3.29 (2H, triplet, J=6 Hz);
3.41–3.58 (1H, multiplet);
3.76 (3H, singlet);
3.78 (3H, singlet);
5.15 (2H, singlet);
6.42–6.56 (2H, multiplet);
7.05–7.70 (12H, multiplet);
8.97 (1H, broad singlet).
Infrared Absorption Spectrum (CHCl$_3$) $v_{max}$ cm$^{-1}$:
3401, 1723, 1701, 1612, 1587, 1567, 1506, 1465.

EXAMPLE 119

N-(2-t-Butyl-5-carbamoylphenyl)-3-(2-benzyloxy-3-methoxyphenyl)octanamide (Compound No. 316)

Following a similar procedure to that described in Example 26, but using 3-(2-benzyloxy-3-methoxyphenyl) octanoic acid (prepared as described in Preparation 30B), the title compound was obtained as a foam-like substance.
Nuclear Magnetic Resonance Spectrum (270 MHz, CDCl$_3$) δ ppm:
0.83 (3H, triplet, J=6 Hz);
1.07–1.15 (6H, multiplet);
1.24 (9H, singlet);
1.56–1.82 (2H, multiplet);
2.45–2.79 (2H, multiplet);
3.60–3.75 (1H, multiplet);
3.80 (3H, singlet);
5.00 (1H, doublet, J=11 Hz);
5.05 (1H, doublet, J=11 Hz);
5.20–5.48 (1H, broad);
6.12–6.35 (1H, broad);
6.76–7.71 (12H, multiplet).
Infrared Absorption Spectrum (KBr) $v_{max}$ cm$^{-1}$:
3278, 3190, 1656, 1476, 1273, 1202, 1073, 982, 751, 698.

EXAMPLE 120

N-(2-t-Butyl-5-N'-methylcarbamoylphenyl)-3-(2-benzyloxy-3-methoxyphenyl)octanamide
(Compound No. 317)

Following a similar procedure to that described in Preparation 6, but using 3-(2-benzyloxy-3-methoxyphenyl) octanoic acid (prepared as described in Preparation 30B) and 2-t-butyl-5-N-methylcarbamoylaniline (prepared as described in Preparation 36), the title compound was obtained as crystals, melting at 158.5–160.5° C (from ethyl acetate-hexane).
Nuclear Magnetic Resonance Spectrum (270 MHz, CDCl$_3$) δ ppm:
0.85 (3H, triplet, J=6 Hz);
1.10–1.33 (6H, multiplet);
1.26 (9H, singlet);
1.52–1.85 (2H, multiplet);
2.48–2.79 (2H, multiplet);
2.85 (3H, doublet, J=5 Hz);
3.62–3.77 (1H, multiplet);
3.82 (3H, singlet);
5.03 (1H, doublet, J=11 Hz);
5.10(1H, doublet, J=11 Hz);
6.25–7.74 (13H, multiplet).
Infrared Absorption Spectrum (KBr) $v_{max}$ cm$^{-1}$:
3311, 1638, 1559, 1525, 1476, 1274, 1203, 1077, 982, 751, 698.

EXAMPLE 121

N-(2-t-Butyl-5-N'-methylcarbamoylphenyl -3-(4-benzyloxy-2-methoxyphenyl)octanamide
(Compound No. 318)

Following a similar procedure to that described in Example 44, but using 3-(4-benzyloxy-2-methoxyphenyl) octanoic acid (prepared as described in Preparation 30C) and 2-t-butyl-5-N-methylcarbamoylaniline (prepared as described in Preparation 36), the title compound was obtained as crystals, melting at 138°–140° C. (from methylene chloride-hexane).
Nuclear Magnetic Resonance Spectrum (270 MHz, CDCl$_3$) δ ppm:
0.80–0.91 (3H, multiplet);
1.16–1.38 (6H, multiplet);
1.28 (9H, singlet);
1.65–1.80 (2H, multiplet);
2.60–2.80 (2H, multiplet);
2.95 (3H, doublet, J=5 Hz);
3.41–3.56 (1H, multiplet);
3.76 (3H, singlet);
5.02 (2H, singlet);
6.07–6.18 (1H, multiplet);
6.50–6.60 (2H, multiplet);
7.08–7.67 (10H, multiplet).
Infrared Absorption Spectrum (KBr) $v_{max}$ cm$^{-1}$:
1641, 1613, 1559, 1506, 1465, 1455, 1414, 1318, 1288, 1258, 1201, 1160.

EXAMPLE 122

N-(2-t-Butyl-5-N'-methylcarbamoylphenyl)-3-(4-hydroxy-2-methoxyphenyl)octanamide (Compound
No. 129)

Following a similar procedure to that described in Example 124, but using N-(2-t-butyl-5-N'-methylcarbamoylphenyl)-3-(4-benzyloxy-2-methoxyphenyl)-octanamide (prepared as described in Example 121) the title compound was obtained as crystals.
Nuclear Magnetic Resonance Spectrum (270 MHz, CDCl$_3$) δ ppm:
0.80–0.90 (3H, multiplet);
1.11–1.36 (6H, multiplet);
1.30 (9H, singlet);
1.60–1.80 (2H, multiplet);
2.65–2.76 (2H, multiplet);
2.92 (3H, doublet, J=5 Hz);
3.39–3.51 (1H, multiplet);
3.70 (3H, singlet);
6.22–6.53 (4H, multiplet);
6.96–7.62 (5H, multiplet).
Infrared Absorption Spectrum (KBr) $v_{max}$ cm$^{-1}$:
1648, 1557 1511, 1468, 1435, 1414, 1366, 1322, 1289, 1198, 1160.

EXAMPLE 123

N-(2-t-Butyl-5-carbamoylphenyl)-3-(4-benzyloxy-2-methoxyphenyl octanamide (Compound No. 320)

Following a similar procedure to that described in Example 44, but using 3-(4-benzyloxy-2-methoxyphenyl) octanoic acid (prepared as described in Preparation 30C), the title compound was obtained as a foam-like substance.
Nuclear Magnetic Resonance Spectrum (270 MHz; CDCl$_3$) δ ppm:
0.80–0.90 (3H, multiplet);
1.14–1.47 (6H, multiplet);
1.29 (9H, singlet);
1.62–1.80 (2H, multiplet);
2.61–2.82 (2H, multiplet);
3.42–3.57 (1H, multiplet);
3.77 (3H, singlet);
5.02 (2H, singlet);

5.38–5.60 (1H, broad);
5.98–6.21 (1H, broad);
6.50–6.60 (2H, multiplet);
7.02–7.68 (10H, multiplet).
Infrared Absorption Spectrum (melted film) $\nu_{max}$ cm$^{-1}$:
 1653, 1613, 1505, 1455, 1420, 1377, 1289, 1258, 1200, 1160.

EXAMPLE 124

N-(2-Butyl-5-carbamoylphenyl)-3-(4-hydroxy-2-methoxyphenyl)octanamide (Compound No. 128)

A solution of 2.46 g (4.64 mmol) of N-(2-t-butyl-5-carbamoylphenyl)-3-(4-benzyloxy-2-methoxyphenyl) octanamide (prepared as described in Example 123) in 100 ml of ethanol was vigorously stirred at 40° C. under a stream of hydrogen in the presence of 10% palladium-on-charcoal for 1.5 hours. At the end of this time, the reaction mixture was filtered using a Celite (trade mark) filter aid to remove the catalyst, and the filtrate was concentrated to dryness by evaporation under reduced pressure. The residue was purified by column chromatography through 100 g of silica gel using a 49:1 by volume mixture of ethyl acetate and methanol as the eluent, to give a crude product containing the title compound. This product was further purified by column chromatography through silica gel under the same conditions as above to give 1.62 g (yield 79%) of the title compound as a foam-like substance.
Nuclear Magnetic Resonance Spectrum (270 MHz, CDCl$_3$) δ ppm:
0.70–0.90 (3H, multiplet);
1.11–1.39 (6H, multiplet);
1.33 (9H, singlet);
1.60–1.80 (2H, multiplet);
2.67–2.79 (2H, multiplet);
3.36–3.51 (1H, multiplet);
3.69 (3H, singlet);
5.72–5.93 (1H, broad);
6.26–6.46 (3H, multiplet);
6.95–6.63 (6H, multiplet).
Infrared Absorption Spectrum (KBr) $\nu_{max}$ cm$^{-1}$:
 1660, 1615, 1598, 1509, 1468, 1432, 1366, 1288, 1198, 1159.

EXAMPLE 125

N-[2-(2,4-Dimethoxyphenyl)heptyl]-N'-(2-t-butyl-5-carbamoylphenyl)urea (Compound No. 82)

Following a similar procedure to that described in Example 20, but using N-[2-(2,4-dimethoxyphenyl)heptyl]-N'-(2-t-butyl-5-carboxyphenyl)urea (prepared as described in Preparation 60), the title compound was obtained as crystals, melting at 223°–224° C. (from methylene chloride-methanol-hexane).
Nuclear Magnetic Resonance Spectrum (270 MHz, CDCl$_3$) δ ppm:
0.77–0.88 (3H, multiplet);
1.10–1.30 (6H, multiplet);
1.33 (9H, singlet);
1.50–1.64 (2H, multiplet);
3.04–3.33 (2H, multiplet);
3.44–3.56 (1H, multiplet);
3.57 (3H, singlet);
3.78 (3H, singlet);
4.71 (1H, triplet, J=2.5 Hz);
5.52–5.76 (1H, broad);
5.90–6.20 (1H, broad);
5.96 (1H, singlet);
6.32 (1H, doublet, J=2.5 Hz);
6.41 (1H, doublet of doublets, J=8.5 Hz & 2.5 Hz);
6.95 (1H, doublet, J=8.5 Hz);
7.26 (1H, doublet, J=2 Hz);
7.44 (1H, doublet, J=8.5 Hz);
7.68 (1H, doublet of doublets, J=8.5 Hz & 2Hz).
Infrared Absorption Spectrum (KBr) $\nu_{max}$ cm$^{-1}$:
 1652, 1615, 1586, 1556, 1506, 1465, 1289, 1258, 1209, 1158.

EXAMPLE 126

N-(2-t-Butyl-5-carbamoylphenyl)-3-[5-chloro-2-methoxy-4-(2-methoxy-ethoxy)phenyl]-5-methylhexanamide (Compound No.503)

Following a similar procedure to that described in Example 20, but using N-(2-t-butyl-5-carboxyphenyl)-3-[5-chloro-2-methoxy-4-(2-methoxy-ethoxy)phenyl]-5-methylhexanamide (prepared as described in Preparation 31U), the title compound was obtained as crystals, melting at 178°–179° C. (from methylene chloride-methanol-ethyl acetate).
Nuclear Magnetic Resonance Spectrum (270 MHz, CDCl$_3$) δ ppm:
0.86 (3H, doublet, J=6 Hz);
0.89 (3H, doublet, J=6 Hz);
1.27–1.56 (2H, multiplet);
1.32 (9H, singlet);
1.59–1.77 (1H, multiplet);
2.55–2.70 (2H, multiplet);
3.46 (3H, singlet);
3.58–3.74 (1H, multiplet);
3.78 (2H, triplet, J=5 Hz);
3.79 (3H, singlet);
4.16 (2H, triplet, J=5 Hz);
5.45–5.74 (1H, broad);
6.14–6.40 (1H, broad);
6.54 (1H, singlet);
7.01–7.11 (1H, broad singlet);
7.18 (1H, singlet);
7.37–7.56 (2H, multiplet);
7.62–7.68 (1H, multiplet).
Infrared Absorption Spectrum (KBr) $\nu_{max}$ cm$^{-1}$:
 1657, 1612, 1527,1504, 1462, 1421, 1396, 1365, 1302, 1254, 1281, 1173, 1128, 1072.

EXAMPLE 127

N-(2-t-Butyl-5-carbamoylphenyl)-3-[5-chloro-4-(2-ethoxyethoxy)-2-methoxyphenyl]-5-methylhexanamide (Compound No. 504)

Following a similar procedure to that described in Example 20, but using N-(2-t-butyl-5-carboxyphenyl)-3-[5-chloro-4-(2-ethoxyethoxy)-2-methoxy-phenyl]-5-methylhexanamide (prepared as described in Preparation 31V), the title compound was obtained as crystals, melting at 180°–181 ° C. (from methylene chloride-methanol-diethyl ether).
Nuclear Magnetic Resonance Spectrum (270 MHz, CDCl$_3$) δ ppm:
0.86 (3H, doublet, J=6 Hz);
0.88 (3H, doublet, J=6 Hz);
1.23 (3H, triplet, J=7 Hz);
1.25–1.57 (2H, multiplet);
1.32 (9H, singlet);
1.58–1.77 (1H, multiplet);

2.55–2.73 (2H, multiplet);
3.58–3.73 (1H, multiplet);
3.62 (2H, quartet, J=7 Hz);
3.79 (3H, singlet);
3.81 (2H, triplet, J=5 Hz);
4.16 (2H, triplet, J=5 Hz);
5.47–5.81 (1H, broad);
6.04–6.33 (1H, broad);
6.56 (1H, singlet);
6.99–7.11 (1H, broad singlet);
7.18 (1H, singlet);
7.38–7.57 (2H, multiplet);
7.60–7.72 (1H, multiplet).
Infrared Absorption Spectrum (KBr) $\nu_{max}$ cm$^{-1}$:
 1655, 1610, 1527, 1502, 1460, 1421, 1396, 1365, 1302, 1201, 1173, 1124, 1072, 1049.

EXAMPLE 128

N-(2-t-Butyl-5-carbamoylphenyl)-3-[4-(1-hydroxybutyl)-2-methoxyphenyl]octanamide (Compound No. 227)

70 mg (1.85 mmol) of sodium borohydride were added to a solution of 207 mg (0.418 mmol) of N-(2-t-butyl-5-carbamoylphenyl)-3-[4-(1-oxobutyl)-2 -methoxyphenyl] octanamide (prepared as described in Example 99) in 5 ml of ethanol, and the resulting mixture was stirred for 3.5 hours. At the end of this time, the mixture was ice-cooled, acetone was added to the reaction mixture to decompose any excess of the reagent, and the solvent was removed by distillation under reduced pressure. The resulting residue was mixed with water and then extracted with ethyl acetate. The extract was washed with a saturated aqueous solution of sodium chloride and dried over anhydrous magnesium sulfate. The solvent was then removed by evaporation under reduced pressure. The residue thus obtained was purified by column chromatography through 15 g of silica gel using a gradient elution method, with mixtures of ethyl acetate and methanol ranging from 20:0 to 20:1 by volume as the eluent, to give 203 mg (yield 98%) of the title compound as crystals, melting at 153°–155° C.

Nuclear Magnetic Resonance Spectrum (270 MHz, CDCl$_3$) δ ppm:
0.85 (3H, triplet, J=6 Hz);
0.92 (3H, triplet, J=7 Hz);
1.16–1.87 (12H, multiplet);
1.30 (4.5H, singlet);
1.31 (4.5H, singlet);
2.65–2.80 (2H, multiplet);
3.29 (0.5H, broad singlet);
3.41 (0.5H, broad singlet);
3.46–3.62 (1H, multiplet);
3.78 (1.5H, singlet);
3.81 (1.5H, singlet);
4.63–4.68 (1H, multiplet);
5.35–5.60 (1H, broad);
6.20–6.45 (1H, broad);
6.86–6.96 (3H, multiplet);
7.10–7.18 (2H, multiplet);
7.26–7.41 (2H, multiplet).
Infrared Absorption Spectrum (KBr) $\nu_{max}$ cm$^{-1}$:
 1642, 1613, 1522, 1460, 1422, 1254, 1160, 1109, 1069, 1040.

EXAMPLE 129

N-(2-t-Butyl-5-carbamoylphenyl)-3-[2-methoxy-4-(3-propylsulfonyl-propoxy)phenyl]heptanamide (Compound No. 665)

Following a similar procedure to that described in Example 20, but using N-(2-t-butyl-5-carboxyphenyl)-3-[2-methoxy-4-(3-propylsulfonylpropoxy)-phenyl]heptanamide (prepared as described in Preparation 31W), the title compound was obtained as crystals, melting at 108°–127.5° C. (diethyl ether-ethyl acetate)

Nuclear Magnetic Resonance Spectrum (270 MHz, CDCl$_3$) δ ppm:
0.85 (3H, triplet, J=7 Hz);
1.04–1.38 (4H, multiplet);
1.1 0(3H, triplet, J=7 Hz);
1.32 (9H, singlet);
1.57–1.82 (2H, multiplet);
1.83–2.00 (2H, multiplet);
2.25–2.39 (2H, multiplet);
2.61–2.80 (2H, multiplet);
2.95–3.05 (2H, multiplet);
3.18 (3H, triplet, J=7 Hz);
3.41–3.56 (1H, multiplet);
3.77 (3H, singlet);
4.08 (2H, triplet, J=6 Hz);
5.49–5.70 (1H, broad);
6.15–6.35 (1H, broad);
6.39–6.51 (2H, multiplet);
7.03–7.69 (5H, multiplet).
Infrared Absorption Spectrum (KBr) $\nu_{max}$ cm$^{-1}$:
 3350, 3255, 1659, 1613, 1507, 1287, 1200, 1129, 1038, 970, 835.

EXAMPLE 130

N-(2-t-Butyl-5-butanoylaminocarbonylphenyl)-3-(2,4-dimethoxyphenyl)octanamide (Compound No. 386)

Following a similar procedure to that described in Example 139, but using N-(2-t-butyl-5-carboxyphenyl)-3-(2,4-dimethoxyphenyl)octanamide (prepared as described in Preparation 7) and butanamide, the title compound was obtained as crystals, melting at 79° C. (from diisopropyl ether).

Nuclear Magnetic Resonance Spectrum (270 MHz, CDCl$_3$) δ ppm:
0.84 (3H, triplet, J=6.5 Hz);
1.02 (3H, triplet, J=7.4 Hz);
1.16–1.37 (6H, multiplet);
1.30 (9H, singlet);
1.67–1.81 (4H, multiplet);
2.64–2.78 (2H, multiplet);
2.88 (2H, triplet, J=7.4 Hz);
3.43–3.55 (1H, multiplet);
3.78 (3H, singlet);
3.79 (3H, singlet);
6.44 (1H, singlet);
6.51 (1H, doublet of doublets, J=2.3 Hz & 8.1 Hz);
7.08 (1H, singlet);
7.13 (1H, doublet, J=8.4 Hz);
7.45 (1H, doublet, J=8.9 Hz);
7.60–7.65 (2H, multiplet);
8.57 (1H, broad singlet).
Infrared Absorption Spectrum (KBr) $\nu_{max}$ cm$^{-1}$:
 3268, 1687, 1612, 1507.

EXAMPLE 131

N-[2-t-Butyl-5-(2-methylpropanoyl) aminocarbonylphenyl]-3-(2,4-dimethoxyphenyl] octanamide (Compound No. 387)

Following a similar procedure to that described in Example 139, but using N-(2-t-butyl-5-carboxyphenyl)-3-

(2,4-dimethoxyphenyl)octanamide (prepared as described in Preparation 7) and 2-methylpropanamide, the title compound was obtained as crystals, melting at 157°–159° C. (from acetonitrile).

Nuclear Magnetic Resonance Spectrum (270 MHz, CDCl$_3$) δ ppm:
0.84 (3H, triplet, J=6.4 Hz);
1.10–1.30 (21H, multiplet);
1.64–1.78 (2H, multiplet);
2.64–2.81 (2H, multiplet);
3.43–3.61 (2H, multiplet);
3.77 (3H, singlet);
3.79 (3H, singlet);
6.44 (1H, doublet, J=2.4 Hz);
6.50 (1H, doublet of doublets, J=2.4 Hz & 8.4 Hz);
7.08 (1H, broad);
7.13 (1H, doublet, J=8.4 Hz);
7.45 (1H, doublet, J=8.2 Hz);
7.60–7.64 (2H, multiplet);
8.46 (1H, broad).

Infrared Absorption Spectrum (KBr) ν$_{max}$ cm$^{-1}$:
1732, 1655, 1506.

EXAMPLE 132

N-(2-t-Butyl-5-[(4-pyridyl)carbonylaminocarbonyl] phenyl)-3-(2,4-dimethoxyphenyl)octanamide (Compound No. 388)

Following a similar procedure to that described in Example 139, but using N-(2-t-butyl-5-carboxyphenyl)-3-(2,4-dimethoxyphenyl)octanamide (prepared as described in Preparation 7) and isonicotinamide, the title compound was obtained as crystals, melting at 184°–185° C. (from ethyl acetate).

Nuclear Magnetic Resonance Spectrum (270 MHz, CDCl$_3$) δ ppm:
0.83 (3H, triplet, J=6.4 Hz);
1.10–1.38 (6H. multiplet);
1.31 (9H, singlet);
1.60–1.80 (2H, multiplet);
2.65–2.82 (2H, multiplet);
3.45–3.51 (1H, multiplet);
3.74 (3H, singlet);
3.77 (3H, singlet);
6.42–6.46 (2H, multiplet);
7.10 (1H, doublet, J=8.0 Hz);
7.18 (1H, broad singlet);
7.49 (1H, doublet, J=8.3 Hz);
7.64–7.69 (4H, multiplet);
8.10 (2H, doublet, J=13.1 Hz);
9.43 (1H, broad singlet).

Infrared Absorption Spectrum (KBr) ν$_{max}$ cm$^{-1}$:
1682, 1481.

EXAMPLE 133

N-[2-t-Butyl-5-(2,2-dimethylpropanoyl) aminocarbonylphenyl]-3-(2,4-dimethoxyphenyl) octanamide (Compound No. 389)

Following a similar procedure to that described in Example 139, but using N-(2-t-butyl-5-carboxyphenyl)-3-(2,4-dimethoxyphenyl)octanamide (prepared as described in Preparation 7) and 2,2-dimethylpropanamide, the title compound was obtained as crystals, melting at 170°–172° C. (from ethyl acetate).

Nuclear Magnetic Resonance Spectrum (270 MHz, CDCl$_3$) δ ppm:
0.84 (3H, triplet, J=6.4 Hz);
1.10–1.85 (8H. multiplet);
1.30 (9H, singlet);
1.32 (9H, singlet);
2.63–2.79 (2H, multiplet);
3.43–3.54 (1H, multiplet);
3.77 (3H, singlet);
3.78 (3H, singlet);
6.42–6.48 (2H, multiplet);
7.10 (1H, doublet, J=8.1 Hz);
7.15 (1H, broad);
7.45 (1H, doublet, J=8.4 Hz);
7.57 (1H, doublet of doublets, J=2.0 Hz & 8.4 Hz);
7.84–7.90 (1H, multiplet);
8.64 (1H, broad singlet).

Infrared Absorption Spectrum (KBr) ν$_{max}$ cm$^{-1}$:
3328, 1733, 1656, 1505.

EXAMPLE 134

N-[2-t-Butyl-5-(2-methylpropanoyl) aminocarbonylphenyl]-3-(2,4-dimethoxyphenyl) heptanamide (Compound No. 395)

Following a similar procedure to that described in Example 139, but using 2-methylpropanamide and N-(2-t-butyl-5-carboxyphenyl)-3-(2,4-dimethoxy-phenyl) heptanamide (prepared as described in Preparation 3 1B), the title compound was obtained as crystals, melting at 139°–140° C. (from diisopropyl ether).

Nuclear Magnetic Resonance Spectrum (270 MHz, CDCl$_3$) δ ppm:
0.85 (3H, triplet, J=6.7 Hz);
1.10–1.39 (19H, multiplet);
1.65–1.80 (2H, multiplet);
2.64–2.81 (2H, multiplet);
3.43–3.67 (2H, multiplet);
3.78 (3H, singlet);
3.79 (3H, singlet),
6.44 (1H, doublet, J=2.4 Hz);
6.51 (1H, doublet of doublets, J=2.4 Hz & 8.3 Hz);
7.08 (1H, broad);
7.13 (1H, doublet, J=8.3. Hz);
7.46 (1H, doublet, J=8.2 Hz);
7.60–7.65 (2H, multiplet);
8.46 (1H, broad singlet).

Infrared Absorption Spectrum (KBr) ν$_{max}$ cm$^{-1}$:
1733, 1683, 1655, 1506.

EXAMPLE 135

N-[2-t-Butyl-5-(2,2-dimethylpropanoyl) aminocarbonylphenyl]-3-(2,4-dimethoxyphenyl) heptanamide (Compound No. 396)

Following a similar procedure to that described in Example 139, but using N-(2-t-butyl-5-carboxyphenyl)-3-(2,4-dimethoxyphenyl)heptanamide(prepared as described in Preparation 3 1B) and 2,2-dimethylpropanamide, the title compound was obtained as crystals, melting at 170°–171° C. (from ethyl acetate-diisopropyl ether).

Nuclear Magnetic Resonance Spectrum (270 MHz, CDCl$_3$) δ ppm:
0.85 (3H, triplet, J=6.9 Hz);
1.07–1.35 (4H, multiplet);
1.31 (9H, singlet);
1.32 (9H, singlet);
1.60–1.80 (2H, multiplet);
2.64–2.80 (2H, multiplet);

3.43–3.55 (1H, multiplet);
3.77 (3H, singlet);
3.78 (3H, singlet);
6.43–6.48 (2H, multiplet);
7.10 (1H, doublet, J=8.2 Hz);
7.15 (1H, broad);
7.45 (1H, doublet, J=8.4 Hz);
7.58 (1H, doublet of doublets, J=2.1 Hz & 8.4 Hz);
7.85–7.90 (1H, multiplet);
8.64 (1H, broad).
Infrared Absorption Spectrum (KBr) $v_{max}$ cm$^{-1}$:
3307, 1732, 1656, 1505.

EXAMPLE 136

N-{2-t-Butyl-5-[(3-pyridyl)carbonlaminocarbonyl]phenyl}-3-(2,4-dimethoxyphenyl)octanamide (Compound No. 390)

Following a similar procedure to that described in Example 139, but using N-(2-t-butyl-5-carboxyphenyl)-3-(2,4-dimethoxyphenyl)octanamide (prepared as described in Preparation 7) and nicotinamide, the title compound was obtained as crystals.
Nuclear Magnetic Resonance Spectrum (270 MHz, CDCl$_3$) δ ppm:
0.83 (3H, triplet, J=5.6 Hz);
1.12–1.35 (6H, multiplet);
1.30 (9H, singlet);
1.61–1.81 (2H, multiplet);
2.60–2.80 (2H, multiplet);
3.47 (1H, quintet, J=7.3 Hz);
3.74 (3H, singlet);
3.77 (3H, singlet);
6.42 (1H, singlet);
6.41–6.48 (1H, multiplet);
7.09 (1H, doublet, J=7.9 Hz);
7.18 (1H, broad singlet);
7.40–7.48 (2H, multiplet);
7.66 (1H, doublet of doublets, J=2.0 Hz & 8.6 Hz);
7.73 (1H, singlet);
8.10–8.19 (1H, multiplet);
8.76–8.83 (1H, multiplet);
9.03 (1H, singlet);
9.37 (1H, broad singlet).

EXAMPLE 137

N-(2-t-Butyl-5-decanoylaminocarbonylphenyl)-3-(2,4-dimethoxyphenyl)octanamide (Compound No. 391)

Following a similar procedure to that described in Example 139, but using N-(2-t-butyl-5-carboxyphenyl)-3-(2,4-dimethoxyphenyl)octanamide (prepared as described in Preparation 7) and decanamide, the title compound was obtained as crystals.
Nuclear Magnetic Resonance Spectrum (270 MHz, CDCl$_3$) δ ppm:
0.79–0.93 (6H, multiplet);
1.15–1.45 (18H, multiplet);
1.30 (9H, singlet);
1.62–1.82 (2H, multiplet);
1.63–1.83 (2H, multiplet);
2.94 (2H, triplet, J=7.6 Hz);
3.48 (1H, quintet, J=7.9 Hz);
3.77 (3H, singlet);
3.78 (3H, singlet);
6.43–6.55 (2H, multiplet);
7.07 (1H, broad singlet);
7.13 (1H, doublet, J=8.6 Hz);
7.45 (1H, doublet, J=8.6 Hz);
7.59–7.64 (2H, multiplet);
8.42 (1H, broad singlet).

EXAMPLE 138

N-(2-t-Butyl-5-propanoylaminocarbonylphenyl)-3-(2,4-dimethoxyphenyl)octanamide (Compound No. 392)

Following a similar procedure to that described in Example 139, but using N-(2-t-butyl-5-carboxyphenyl)-3-(2,4-dimethoxyphenyl)octanamide (prepared as described in Preparation 7) and propanamide, the title compound was obtained as crystals.
Nuclear Magnetic Resonance Spectrum (270 MHz, CDCl$_3$) δ ppm:
0.86 (3H, triplet, J=5.9 Hz);
1.19 (3H, triplet, J=7.3 Hz);
1.12–1.32 (6H. multiplet);
1.28 (9H, singlet);
1.62–1.77 (2H, multiplet);
2.60–2.82 (2H, multiplet);
2.95 (2H, quartet, J=7.5 Hz);
3.49 (1H, quintet, J=7.6 Hz);
3.76 (3H, singlet);
3.78 (3H, singlet);
6.44 (1H, singlet);
6.48 (1H, doublet, J=7.9 Hz);
7.10 (1H, doublet, J=7.9 Hz);
7.20 (1H, broad singlet);
7.42 (1H, doublet, J=8.6 Hz);
7.57–7.73 (2H, multiplet);
8.82 (1H, broad singlet).

EXAMPLE 139

N-(2-t-Butyl-5-acetylaminocarbonylphenyl)-3-(2,4-dimethoxyphenyl)nonanamide (Compound No. 393)

0.63 g of N,N'-carbonyldiimidazole was added to a solution of 1.208 g of N-(2-t-butyl-5-carboxyphenyl)-3-(2,4-dimethoxyphenyl)nonanamide (prepared as described in Preparation 31D) in 12 ml of tetrahydrofuran, and the resulting mixture was stirred at 40° C. for 3 hours. At the end of this time, the reaction mixture was poured into a mixture of a saturated aqueous solution of sodium hydrogencarbonate and ethyl acetate and was partitioned between the aqueous and organic phases. The ethyl acetate phase was washed three times with a saturated aqueous solution of sodium chloride and dried over anhydrous sodium sulfate. The solvent was removed by distillation under reduced pressure, and the resulting residue was dissolved in 10 ml of dimethylacetamide to produce a solution containing an active ester compound. Meanwhile, 0.61 g of potassium t-butoxide was added to a solution of 0.304 g of acetamide in 10 ml of dimethylacetamide, and the resulting mixture was stirred for 30 minutes. The solution containing an active ester compound prepared above was added dropwise to the mixture thus obtained, and the resulting mixture was stirred for 1 hour. At the end of this time, the reaction mixture was poured into a saturated aqueous solution of potassium hydrogensulfate and the aqueous mixture was extracted three times with ethyl acetate. The combined extracts were washed three times with a saturated aqueous solution of sodium chloride and dried over anhydrous sodium sulfate, after which the solvent was removed by distillation under reduced pressure. The resulting residue was purified by column chromatography through silica gel using a 1:1 by volume mixture of hexane and ethyl acetate as the eluent. The desired fractions were collected and concentrated by evaporation under reduced pressure. The concentrate was triturated with hexane to cause crystallization, giving 0.985 g of the title compound.
Nuclear Magnetic Resonance Spectrum (270 MHz, CDCl$_3$) δ ppm:
0.85 (3H, triplet, J=6.6 Hz);
1.12–1.32 (8H. multiplet);
1.30 (9H, singlet);
1.65–1.79 (2H, multiplet);
2.57 (3H, singlet);
2.65–2.82 (2H, multiplet);
3.40–3.55 (1H, multiplet);
3.77 (3H, singlet);
3.78 (3H, singlet);
6.44 (1H, doublet, J=2.6 Hz);
6.50 (1H, doublet of doublets, J=2.0 Hz & 8.6 Hz);
7.07–7.15 (2H, multiplet);
7.45 (1H, doublet, J=7.9 Hz);
7.58–7.68 (2H, multiplet);
8.59 (1H, broad singlet).

EXAMPLE 140

N-(2-t-Butyl-5-acetylaminocarbonylphenyl)-3-(2,4-dimethoxyphenyl)heptanamide (Compound No. 394)

Following a similar procedure to that described in Example 139, but using N-(2-t-butyl-5-carboxyphenyl)-3-(2,4-dimethoxyphenyl)heptanamide(prepared as described in Preparation 311B), the title compound was obtained as crystals.
Nuclear Magnetic Resonance Spectrum (270 MHz, CDCl$_3$) δ ppm:
0.85 (3H, triplet, J=7.0 Hz);
1.10–1.37 (4H, multiplet);
1.30 (9H, singlet);
1.67–1.80 (2H, multiplet);
2.58 (3H, singlet);
2.64–2.81 (2H, multiplet);
3.48 (1H, quintet, J=5 Hz);
6.44 (3H, doublet, J=2.4 Hz);
6.51 (1H, doublet of doublets, J=2.4 Hz & 8.4 Hz);
7.08 (1H, broad singlet);
7.13 (1H, doublet, J=8.4 Hz);
7.46 (1H, doublet, J=8.3 Hz);
7.59–7.63 (2H, multiplet);
8.53 (1H, broad singlet).

EXAMPLE 141

N-(2-Butyl-5-carbamoylphenyl)-3-(2,3-ethylenedioxyphenyl)octanamide (Compound No. 10)

165 mg (1.02 mmol) of 1,1'-carbonylbis(1H-imidazole) were added to a solution of 355 mg (0.783 mmol) of N-(2-t-butyl-5-carboxyphenyl)-3-(2,3-ethylenedioxyphenyl)octanamide (prepared as described in Preparation 74C) in 7.0 ml of dry acetonitrile, and the resulting mixture was stirred at room temperature for 30 minutes, after which 0.46 ml of 29% v/v aqueous ammonia was added. The reaction mixture was stirred at room temperature for 1 hour, after which the mixture was freed from the solvent by distillation under reduced pressure. The residue was purified by column chromatography through silica gel using ethyl acetate as the eluent, to give 327 mg (yield 92%) of the title compound as a colorless foam-like substance.
Nuclear Magnetic Resonance Spectrum (400 MHz, CDCl$_3$) δ ppm:
0.83–0.88 (3H, multiplet);
1.14–1.33 (6H, multiplet);
1.30 (9H, singlet);
1.67–1.78 (2H, multiplet);
2.71 (2H, doublet, J=7.5 Hz);
3.55–3.62 (1H, multiplet);
4.10–4.29 (4H, multiplet);
5.48–5.50 (1H, multiplet);
6.24–6.26 (1H, multiplet);
6.72–6.74 (1H, multiplet);
6.76–6.84 (1H, multiplet);
6.81 (1H, singlet);
7.07 (1H, singlet);
7.42 (1H, doublet, J=8.3 Hz);
7.63–7.67 (2H, multiplet).
Infrared Absorption Spectrum (CHCl$_3$) $v_{max}$ cm$^{-1}$:
2926, 2869, 1510, 1499, 1473, 1350, 1158, 1084, 1013, 943.

EXAMPLE 142

N-[2-t-Butyl-5-(phthalimidomethyl)phenyl]-3-(2,3-ethylenedioxyphenyl)octanamide (Compound No. 605)

138 mg (0.745 mmol) of potassium phthalimide were added to a solution of 288 mg (0.573 mmol) of N-[2-t-butyl-5-bromomethyl-phenyl]-3-(2,3-ethylene-dioxyphenyl)octanamide (prepared as described in Preparation 70E) in 5 ml of dimethylformamide, and the resulting mixture was stirred at room temperature for 4 hours. At the end of this time, the reaction mixture was diluted with water and then extracted with ethyl acetate. The extract was washed with a saturated aqueous solution of sodium hydrogencarbonate and with a saturated aqueous solution of sodium chloride, in that order, after which it was dried over anhydrous sodium sulfate. The solvent was removed by distillation under reduced pressure, and the resulting residue was purified by column chromatography through silica gel using a 3:1 by volume mixture of hexane and ethyl acetate as the eluent, to give 295 mg (yield 91%) of the title compound as a colorless foam-like substance.
Nuclear Magnetic Resonance Spectrum (400 MHz, CDCl$_3$) δ ppm:
0.83–0.86 (3H, multiplet);
1.19–1.30 (6H, multiplet);
1.22 (9H, singlet);
1.70–1.73 (2H, multiplet);
2.67–2.69 (2H, multiplet);
3.55–3.62 (1H, multiplet);
4.11–4.25 (4H, multiplet);
4.73–4.81 (2H, multiplet);
6.68–6.71 (1H, multiplet);
6.79–6.82 (2H, multiplet);
6.95 (1H, broad singlet);
7.15 (1H, doublet, J=8 Hz);
7.27 (1H, doublet, J=8 Hz);
7.47 (2H, singlet);
7.68–7.72 (2H, multiplet);
7.81–7.85 (2H, multiplet).
Infrared Absorption Spectrum (CHCl$_3$) $v_{max}$ cm$^{-1}$:
2960, 2932, 2875, 2861, 1772, 1716, 1681, 1601, 1511, 1473, 1456, 1432, 1394, 1367, 1346, 1327, 1309, 1283, 1260, 1102, 1088.

EXAMPLE 143

N-[2-t-Butyl-5-(succinimidomethyl)phenyl]-3-(2,3-ethylenedioxy-phenyl)octanamide (Compound No. 606)

2 ml (2.00 mmol) of a 1M potassium t-butoxide solution in tetrahydrofuran were added to a solution of 200 mg (2.02 mmol) of succinimide in 10 ml of dimethylformamide, and the resulting mixture was stirred at room temperature for 15 minutes. A solution of 680 mg (1.35 mmol) of N-[2-t-butyl-5-bromomethylphenyl]-3-(2,3-ethylenedioxyphenyl)octanamide (prepared as described in Preparation 70E) in 5 ml of dimethylformamide was then added to the mixture. The mixture was stirred at room temperature for 1 hour, after which water was added, and the aqueous mixture was extracted with diethyl ether. The extract was washed with 10% v/v aqueous hydrochloric acid, with a saturated aqueous solution of sodium hydrogencarbonate and a with saturated aqueous solution of sodium chloride, in that order, after which it was dried over anhydrous sodium sulfate. The solvent was removed by distillation under reduced pressure, and the resulting residue was purified by column chromatography through silica gel using a 2:3 by volume mixture of hexane and ethyl acetate as the eluent, to give 565 mg of the title compound as a colorless foam-like substance in a 80% yield.

Nuclear Magnetic Resonance Spectrum (400 MHz, CDCl$_3$) δ ppm:
0.84–0.86 (3H, multiplet);
1.23–1.28 (6H, multiplet);
1.23 (9H, singlet);
1.69–1.73 (2H, multiplet);
2.62–2.70 (6H, multiplet);
3.55–3.62 (1H, multiplet);
4.13–4.28 (4H, multiplet);
4.54–4.63 (2H, multiplet);
6.71–6.73 (1H, multiplet);
6.78–6.83 (2H, multiplet);
6.95 (1H, broad singlet);
7.10 (1H, doublet, J=8 Hz);
7.26 (1H, doublet, J=8 Hz);
7.41 (2H, singlet).
Infrared Absorption Spectrum (CHCl$_3$) $v_{max}$ cm$^{-1}$:
3693, 2960, 2933, 2875, 2862, 1777, 1706, 1682, 1601, 1572, 1521, 1474, 1456, 1432, 1399, 1348, 1336, 1282, 1167, 1087.

EXAMPLE 144

N-[2-t-Butyl-5-(N'-trifluoroacetylaminomethyl)phenyl]-3-(2,3-ethylenedioxyphenyl)octanamide (Compound No. 607)

A solution of 200 mg (0.456 mmol) of N-(2-t-butyl-5-aminomethylphenyl)-3-(2,3-ethylenedioxyphenyl)octanamide (prepared as described in Preparation 71) and 0.5 ml of triethylamine in 4 ml of methylene chloride was cooled to 0° C. and then 67 μl (0.549 mmol) of trifluoroacetic anhydride were added thereto. The resulting mixture was stirred at 0° C. for 15 minutes and then at room temperature for 15 minutes. At the end of this time, the reaction mixture was diluted with ethyl acetate, and the diluted solution was washed with 10% v/v aqueous hydrochloric acid, with a saturated aqueous solution of sodium hydrogencarbonate and with a saturated aqueous solution of sodium chloride. The organic phase was dried over anhydrous sodium sulfate and the solvent was removed by distillation under reduced pressure. The resulting residue was purified by column chromatography through silica gel using a 5:2 by volume mixture of hexane and ethyl acetate as the eluent, to give 206 mg (yield 85%) of the title compound as a colorless foam-like substance.

Nuclear Magnetic Resonance Spectrum (400 MHz, CDCl$_3$) δ ppm:
0.83–0.86 (3H, multiplet);
1.24–1.31 (6H. multiplet);
1.28 (9H, singlet);
1.70–1.75 (2H, multiplet);
2.70–2.75 (2H, multiplet);
3.52–3.60 (1H, multiplet);
4.11–4.26 (4H, multiplet);
4.38–4.44 (2H, multiplet);
6.72–6.84 (3H, multiplet);
6.90 (1H, broad singlet);
7.04–7.06 (2H, multiplet);
7.19 (3H, singlet);
7.33 (1H, doublet, J=8Hz).
Infrared Absorption Spectrum (CHCl$_3$) $v_{max}$ cm$^{-1}$:
3435, 2960, 2933, 2875, 2862, 1725, 1679, 1595, 1571, 1531, 1515, 1474, 1456, 1424, 1367, 1308, 1282, 1169, 1109, 1088, 1052, 1005.

EXAMPLE 145

N-2-t-Butyl-5-(N'-acetylaminomethyl)phenyl]-3-(2,3-ethylenedioxyphenyl)octanamide (Compound No. 607)

Following a similar procedure to that described in Example 144, but using acetic anhydride, the title compound was obtained as a colorless foam-like substance.

Nuclear Magnetic Resonance Spectrum (400 MHz, CDCl$_3$) δ ppm:
0.83–0.86 (3H, multiplet);
1.14–1.34 (6H, multiplet);
1.27 (9H, singlet);
1.70–1.75 (2H, multiplet);
2.00 (3H, singlet);
2.65–2.75 (2H, multiplet);
3.53–3.60 (1H, multiplet);
4.10–4.28 (4H, multiplet);
4.31 (2H, doublet, J=6 Hz);
5.90 (1H, broad);
6.72–6.84 (3H, multiplet);
7.04 (2H, doublet, J=6 Hz);
7.18 (1H, broad singlet);
7.30 (1H, doublet, J=8Hz).
Infrared Absorption Spectrum (CHCl$_3$) $v_{max}$ cm$^{-1}$:
3447, 2960, 2932, 2875, 2862, 1672, 1595, 1571, 1514, 1474, 1456, 1422, 1371, 1354, 1307, 1282, 1161, 1108, 1089, 1052.

EXAMPLE 146

N-[2-t-Butyl-5-(N'-benzoylaminomethyl)phenyl]-3-(2,3-ethylenedioxyphenyl)octanamide (Compound No. 609)

Following a similar procedure to that described in Example 144, but using benzoyl chloride, the title compound was obtained as a colorless foam-like substance.

Nuclear Magnetic Resonance Spectrum (400 MHz, CDCl$_3$) δ ppm:
0.82–0.85 (3H, multiplet);
1.21–1.33 (6H, multiplet);
1.27 (9H, singlet);
1.69–1.72 (2H, multiplet);

2.65–2.75 (2H, multiplet);
3.52–3.60 (1H, multiplet);
4.07–4.25 (4H, multiplet);
4.54 (2H, doublet, J=6 Hz);
6.54 (1H, broad);
6.68–6.76 (1H, multiplet);
6.78 (2H, doublet, J=5 Hz);
7.05 (1H, broad singlet);
7.13 (1H, doublet, J=8 Hz);
7.25–7.26 (1H, multiplet);
7.31 (1H, doublet, J=8 Hz);
7.40–7.50 (3H, multiplet);
7.78–7.81 (2H, multiplet).
Infrared Absorption Spectrum (CHCl$_3$) $\nu_{max}$ cm$^{-1}$:
3451, 2960, 2932, 2875, 2862, 1664, 1603, 1596, 1581, 1572, 1515, 1474, 1456, 1422, 1366, 1282, 1150, 1108, 1088, 1052, 1027, 1003.

EXAMPLE 147

N-[2-t-Butyl-5-(N'-3-pyridylcarbonylaminomethyl) phenyl]-3-(2,3-ethylenedioxyphenyl)octanamide (Compound No. 610)

Following a similar procedure to that described in Example 144, but using nicotinoyl chloride, the title compound was obtained as a colorless foam-like substance.
Nuclear Magnetic Resonance Spectrum (400 MHz, CDCl$_3$) δ ppm:
0.82–0.85 (3H, multiplet);
1.21–1.33 (6H, multiplet);
1.27 (9H, singlet);
1.69–1.74 (2H, multiplet);
2.65–2.75 (2H, multiplet);
3.51–3.59 (1H, multiplet);
4.08–4.25 (4H, multiplet);
4.52 (2H, doublet, J=5 Hz);
6.69–6.81 (3H, multiplet);
6.87 (1H, broad singlet);
7.08–7.14 (2H, multiplet);
7.24 (1H, singlet);
7.32 (1H, doublet, J=8 Hz);
7.36–7.39 (1H, multiplet);
8.13 (1H, triplet of doublets, J=2 Hz & 8 Hz);
8.71 (1H, doublet of doublets, J=2 Hz & 5 Hz);
9.01 (1H, doublet, J=2Hz).
Infrared Absorption Spectrum (CHCl$_3$) $\nu_{max}$ cm$^{-1}$:
3446, 2961, 2933, 2875, 2862, 1668, 1593, 1571, 1518, 1515, 1474, 1456, 1421, 1366, 1300, 1283, 1260, 1155, 1109, 1089, 1052, 1027.

EXAMPLE 148

N-[2-t-Butyl-5-(N'-t-butoxycarbonylaminomethyl) phenpl]-3-(2,3-ethylenedioxyphenyl)octanamide (Compound No. 611)

Following a similar procedure to that described in Example 144, but using di-t-butyl dicarbonate, the title compound was. obtained as a colorless foam-like substance.
Nuclear Magnetic Resonance Spectrum (400 MHz, CDCl$_3$) δ ppm:
0.83–0.86 (3H, multiplet);
1.27–1.42 (6H, multiplet);
1.27 (9H, singlet);
1.46 (9H, singlet);
1.70–1.75 (2H, multiplet);
2.68–2.71 (2H, multiplet);
3.53–3.61 (2H, multiplet);
4.12–4.27 (6H, multiplet);
4.84 (1H, broad);
6.72–6.74 (1H, multiplet);
6.78–6.84 (2H, multiplet);
7.01 (1H, broad singlet);
7.05 (1H, doublet, J=8 Hz);
7.20 (1H, singlet);
7.29 (1H, doublet, J=8Hz).
Infrared Absorption Spectrum (CHCl$_3$) $\nu_{max}$ cm$^{-1}$:
3452, 2961, 2933, 2875, 2862, 1709, 1595, 1571, 1510, 1505, 1474, 1456, 1423, 1394, 1368, 1307, 1282, 1259, 1167, 1109, 1089, 1052, 1030.

EXAMPLE 149

N-[2-t-Butyl-5-(N'-benzyloxycarbonylaminomethyl) phenyl]-3-(2,3-ethylenedioxyphenyl)octanamide (Compound No. 612)

Following a similar procedure to that described in Example 144, but using benzyloxycarbonyl chloride, the title compound was obtained as a colorless foam-like substance.
Nuclear Magnetic Resonance Spectrum (400 MHz, CDCl$_3$) δ ppm:
0.83–0.86 (3H, multiplet);
1.12–1.42 (6H, multiplet);
1.26 (9H, singlet);
1.66–1.73 (2H, multiplet);
2.66–2.74 (2H, multiplet);
3.53–3.60 (1H, multiplet);
4.09–4.26 (4H, multiplet);
4.29 (2H, doublet, J=6 Hz);
5.09 (1H, broad singlet);
5.12 (2H, singlet);
6.71–6.74 (1H, multiplet);
6.79–6.82 (2H, multiplet);
7.00 (1H, singlet);
7.06 (1H, doublet, J=8 Hz);
7.19 (1H, singlet);
7.26–7.37 (6H, multiplet).
Infrared Absorption Spectrum (CHCl$_3$) $\nu_{max}$ cm$^{-1}$:
3448, 2960, 2933, 2875, 2862, 1721, 1679, 1595, 1571, 1511, 1473, 1456, 1423, 1398, 1366, 1354, 1331, 1308, 1282, 1133, 1109, 1088, 1051, 1029.

EXAMPLE 150

N-[2-t-Butyl-5-(N',N'-dimethylcarbamoyl)phenyl]-3-(2-methoxyphenyl)octanamide (Compound No. 325)

Following a similar procedure to that described in Preparation 18, but using 3-(2-methoxyphenyl)octanoic acid (prepared as described in Preparation 66H) and 2-t-butyl-5-(N,N-dimethylcarbamoyl)aniline (prepared as described in Preparation 81), the title compound was obtained as a colorless foam-like substance.
Nuclear Magnetic Resonance Spectrum (270 MHz, CDCl$_3$) δ ppm:
0.82–0.90 (3H, multiplet);
1.10–1.36 (6H, multiplet);
1.27 (9H, singlet);
1.70–1.78 (2H, multiplet);
2.62–2.81 (2H, multiplet);
3.00 (3H, singlet);
3.07 (3H, singlet);
3.54–3.65 (1H, multiplet);
3.80 (3H, singlet);

6.85 (1H, doublet, J=8.0 Hz);
6.93 (1H, triplet, J=7.3 Hz);
7.10 (1H, broad singlet);
7.14–7.21 (3H, multiplet);
7.29–7.37 (2H, multiplet).
Infrared Absorption Spectrum (CHCl$_3$) $v_{max}$ cm$^{-1}$:
2933, 2873, 1680, 1625, 1493, 1401, 1292, 1107, 1031.

EXAMPLE 151

N-(2-t-Butyl-5-carbamoylphenyl)-3-(2-methoxyphenyl)octanamide (Compound No. 326)

Following a similar procedure to that described in Example 141, but using N-(2-t-butyl-5-carboxyphenyl)-3-(2-methoxyphenyl)octanamide (prepared as described in Preparation 74F), the title compound was obtained as a colorless glassy substance.
Nuclear Magnetic Resonance Spectrum (400 MHz, CDCl$_3$) δ ppm:
0.84–0.85 (3H, multiplet);
1.13–1.36 (6H, multiplet);
1.29 (9H, singlet);
1.71–1.78 (2H, multiplet);
2.68–2.80 (2H, multiplet);
3.56–3.64 (1H, multiplet);
3.81 (3H, singlet);
5.52 (1H, multiplet);
6.13 (1H, multiplet);
6.86 (1H, doublet, J=8.1 Hz);
6.95 (1H, triplet, J=7.4 Hz);
7.12 (1H, singlet);
7.17–7.24 (2H, multiplet);
7.41 (1H, doublet, J=8.1 Hz);
7.57 (1H, doublet, J=1.5 Hz);
7.64 (1H, doublet of doublets, J=2.0 Hz & 8.1Hz).
Infrared Absorption Spectrum (CHCl$_3$) $v_{max}$ cm$^{-1}$:
3529, 3414, 2961, 2932, 1678, 1587, 1493, 1375, 1290, 1030.

EXAMPLE 152

N-[2-t-Butyl-5-(4-methyl-1-pierizinecarbonyl)phenyl]-3-(2-methoxyphenyl)octanamide (Compound No. 327)

Following a similar procedure to that described in Example 8, but using N-(2-t-butyl-5-carboxyphenyl)-3-(2-methoxyphenyl)octanamide (prepared as described in Preparation 74F) and 4-methylpiperazine, the title compound was obtained as a colorless foam-like substance.
Nuclear Magnetic Resonance Spectrum (400 MHz, CDCl$_3$) δ ppm:
0.82–0.85 (3H, multiplet);
1.11–1.34 (6H, multiplet);
1.27 (9H, singlet);
1.69–1.76 (2H, multiplet);
2.26–2.46 (4H, multiplet);
2.32 (3H, singlet);
2.64–2.79 (2H, multiplet);
3.49–3.63 (3H, multiplet);
3.76–3.85 (2H, multiplet);
3.80 (3H, singlet);
6.85 (1H, doublet, J=8.1 Hz);
6.93 (1H, triplet, J=7.4 Hz);
7.09 (1H, broad singlet);
7.16–7.22 (3H, multiplet);
7.31 (1H, singlet);
7.36 (1H, doublet, J=8.1Hz).
Infrared Absorption Spectrum (CHCl$_3$) $v_{max}$ cm$^{-1}$:
2459, 2933, 1680, 1623, 1614, 1463, 1440, 1301, 1136.

EXAMPLE 153

N-(2-t-Butyl-5-morpholinocarbonylphelyl)-3-(2-methoxyphenyl)octanamide (Compound No. 328)

Following a similar procedure to that described in Example 8, but using N-(2-t-butyl-5-carboxyphenyl)-3-(2-methoxyphenyl)octanamide (prepared as described in Preparation 74F) and morpholine, the title compound was obtained as a colorless foam-like substance.
Nuclear Magnetic Resonance Spectrum (270 MHz, CDCl$_3$) δ ppm:
0.82–0.90 (3H, multiplet);
1.10–1.33 (6H, multiplet);
1.28 (9H, singlet);
1.70–1.77 (2H, multiplet);
2.63–2.81 (2H, multiplet);
3.34–3.84 (9H, multiplet);
3.81 (3H, singlet);
6.85 (1H, doublet, J=8.2 Hz);
6.94 (1H, triplet, J=7.3 Hz);
7.11 (1H, broad singlet);
7.14–7.24 (3H, multiplet);
7.30 (1H, singlet);
7.38 (1H, doublet, J=8.2Hz).
Infrared Absorption Spectrum (CHCl$_3$) $v_{max}$ cm$^{-1}$:
3459, 2963, 2930, 2862, 1680, 1614, 1493, 1460,1438, 1277, 1114, 1031.

EXAMPLE 154

N-[2-t-Butyl-5-acetylcarbamoyl)phenyl]-3-(2-methoxyphenyl)octanamide (Compound No. 329)

2.39 ml (1.19 mmol) of a 0.5M potassium bis(trimethylsilyl)amide solution in toluene were added dropwise at room temperature over a period of 3 minutes to a solution of 338 mg (0.78 mmol) of N-(2-t-butyl-5-carbamoyl-phenyl)-3-(2-methoxyphenyl)octanamide (prepared as described in Example 151) in 5.0 ml of dry tetrahydrofuran, and the resulting mixture was stirred for 15 minutes, after which 175 mg (1.59 mmol) of 1-acetylimidazole were added. The reaction mixture was stirred for 40 minutes, after which it was diluted with ethyl acetate, and the diluted solution was washed with a saturated aqueous solution of potassium hydrogensulfate and with a saturated aqueous solution of sodium chloride, in that order. It was then dried over anhydrous sodium sulfate. The solvent was removed by distillation under reduced pressure, and the resulting residue was purified by column chromatography through silica gel using a 1:1 by volume mixture of hexane and ethyl acetate as the eluent, to give 363 mg (a quantitative yield) of the title compound as a colorless foam-like substance.
Nuclear Magnetic Resonance Spectrum (270 MHz, CDCl$_3$) δ ppm:
0.83–0.87 (3H, multiplet);
1.13–1.38 (6H, multiplet);
1.30 (9H, singlet);
1.67–1.83 (2H, multiplet);
2.58 (3H, singlet);
2.67–2.83 (2H, multiplet);
3.54–3.65 (1H, multiplet);
3.82 (3H, singlet);
6.88 (1H, doublet, J=8.1 Hz);
6.99 (1H, triplet, J=7.2 Hz);

7.07 (1H, broad singlet);
7.20–7.26 (2H, multiplet);
7.44–7.47 (2H, multiplet);
7.64 (1H, doublet of doublets, J=2.0 Hz & 8.1 Hz);
8.57 (1H, broad singlet).

EXAMPLE 155

N-[2-t-Butyl-5-(3-N-metylamino-3-oxoproyl)
phenyl]-3-(2,3-dimethoxyphenyl)octanamide
(Compound No. 348)

Following a similar procedure to that described in Example 8, but using N-[2-t-butyl-5-(2-carboxyethyl)phenyl]-3-(2,3-dimethoxyphenyl)octanamide (prepared as described in Preparation 77), the title compound was obtained as a colorless foam-like substance.
Nuclear Magnetic Resonance Spectrum (400 MHz, CDCl$_3$) δ ppm:
0.82–0.89 (3H, multiplet);
1.11–1.37 (6H, multiplet);
1.27 (9H, singlet);
1.57–1.80 (2H, multiplet);
2.41 (2H, triplet, J=7.8 Hz);
2.67–2.71 (5H, multiplet);
2.85 (2H, triplet, J=7.8 Hz);
3.58–3.67 (1H, multiplet);
3.84 (3H, singlet);
3.85 (3H, singlet);
5.60 (1H, broad singlet);
6.79 (1H, doublet, J=7.9 Hz);
6.85 (1H, doublet, J=7.9 Hz);
6.93 (1H, doublet, J=8.0 Hz);
6.99 (1H, singlet);
7.05 (1H, triplet, J=8.0 Hz);
7.12 (1H, singlet);
7.22 (1H, doublet, J=8.0Hz).
Infrared Absorption Spectrum (CHCl$_3$) ν$_{max}$ cm$^{-1}$:
3464, 2961, 2934, 1669, 1526, 1479, 1272, 1006.

EXAMPLE 156

N-[2-t-Butyl-5-(N'-2-pyridylcarbonylcarbamoyl)
phenyl]-3-(2,4-dimethoxyphenyl)octanamide
(Compound No. 382)

5.0 ml (2.5 mmol) of a 0.5M solution of potassium bis(trimethylsilyl)-amide in toluene were added to a solution of 760 mg (1.67 mmol) of N-(2-t-butyl-5-carbamoylphenyl)-3-(2,4-dimethoxyphenyl)octanamide (prepared as described in Example 2) in 10 ml of tetrahydrofuran, and the resulting mixture was stirred at room temperature for 1 hour and then cooled to 0° C. To the cold mixture was added a solution, which was prepared by stirring a solution of 230 mg (1.87 mmol) of picolinic acid and 300 mg (1.85 mmol) of N,N'-carbonyl-diimidazole in 10 ml of tetrahydrofuran at room temperature for 55 minutes. The temperature of the reaction mixture was then allowed to rise to room temperature. The reaction mixture was then stirred for 20 minutes, after which a saturated aqueous solution of potassium hydrogensulfate was added thereto, and the mixture was then extracted with ethyl acetate. The extract was washed with a saturated aqueous solution of sodium hydrogencarbonate and with a saturated aqueous solution of sodium chloride, in that order, after which it was dried over anhydrous sodium sulfate. The solvent was removed by distillation under reduced pressure, and the resulting residue was purified by column chromatography through silica gel using a 1:2 by volume mixture of hexane and ethyl acetate as the eluent, to give 854 mg (yield 91%) of the title compound as a colorless foam-like substance.
Nuclear Magnetic Resonance Spectrum (400 MHz, CDCl$_3$) δ ppm:
0.83–0.85 (3H, multiplet);
1.15–1.31 (6H, multiplet);
1.31 (9H, singlet);
1.72–1.74 (2H, multiplet);
2.68–2.79 (2H, multiplet);
3.48–3.56 (1H, multiplet);
3.75 (3H, singlet);
3.80 (3H, singlet);
6.44–6.45 (2H, multiplet);
7.06 (1H, singlet);
7.13 (1H, doublet, J=8 Hz);
7.50 (1H, doublet, J=8 Hz);
7.55–7.58 (1H, multiplet);
7.73 (1H, doublet, J=8 Hz);
7.93–7.97 (2H, multiplet);
8.33 (1H, doublet, J=8 Hz);
8.66 (1H, doublet, J=4 Hz);
11.42 (1H, singlet).
Infrared Absorption Spectrum (CHCl$_3$) ν$_{max}$ cm$^{-1}$:
3344, 2961, 2933, 2873, 2861, 2841, 1753, 1684, 1612, 1588, 1572, 1506, 1476, 1464, 1435, 1411, 1368, 1309, 1290, 1261, 1158, 1125, 1100, 1088, 1039, 1000.

EXAMPLE 157

N-[2-t-Butyl-5-(N'-3-pyridylacetylcarbamoyl)
phenyl]-3-(2,4-dimethoxyphenyl octanamide
(Compound No. 383)

A mixture of 500 mg (1.10 mmol) of N-(2-t-butyl-5-carboxyphenyl)-3-(2,4-dimethoxyphenyl)octanamide (prepared as described in Preparation 7) and 260 mg (1.60 mmol) of N,N-carbonyldiimidazole in 10 ml of tetrahydrofuran was stirred at 40° C. for 45 minutes and then the reaction temperature was allowed to cool to room temperature. A saturated aqueous solution of cerium hydrogensulfate was added to the mixture, and the resulting mixture was extracted with ethyl acetate. The extract was washed with a saturated aqueous solution of sodium chloride and dried over anhydrous sodium sulfate. The solvent was removed by distillation under reduced pressure, which gave an active ester compound. Meanwhile, 1.6 ml (1.6 mmol) of a 1.0M solution of potassium t-butoxide in toluene were added to a solution of 210 mg (1.54 mmol) of 3-pyridylacetamide in 10 ml of dimethylacetamide, and the resulting mixture was stirred at room temperature for 1 hour. A solution of the active ester compound prepared above in 5 ml of dimethylacetamide was then added to the resulting mixture. The mixture thus obtained was stirred at room temperature for a further 1 hour, after which a saturated aqueous solution of potassium hydrogensulfate was added thereto, and the mixture was extracted with diethyl ether. The extract was washed with water and then with a saturated aqueous solution of sodium chloride, after which it was dried over anhydrous sodium sulfate. The solvent was removed by distillation under reduced pressure, and the resulting residue was purified by column chromatography through silica gel using a 1:4 by volume mixture of hexane and ethyl acetate as the eluent, to give 382 mg (yield 61%) of the title compound as a colorless foam-like substance.
Nuclear Magnetic Resonance Spectrum (400 MHz, CDCl$_3$) δ ppm:
0.82–0.85 (3H, multiplet);
1.16–1.27 (6H, multiplet);

1.30 (9H, singlet);
1.70–1.75 (2H, multiplet);
2.69 (1H, doublet of doublets, J=6 Hz & 14 Hz);
2.77 (1H, doublet of doublets, J=9 Hz & 14 Hz);
3.45–3.52 (1H, multiplet);
3.76 (3H, singlet);
3.78 (3H, singlet);
4.32 (2H, singlet);
6.44 (1H, doublet, J=2 Hz);
6.49 (1H, doublet of doublets, J=2 Hz & 8 Hz);
7.12 (1H, doublet, J=8 Hz);
7.22 (1H, singlet);
7.26–7.29 (1H, multiplet);
7.45 (1H, doublet, J=8.5 Hz);
7.62–7.68 (3H, multiplet);
8.53 (1H, doublet of doublets, J=1.5 Hz & 4.5 Hz);
8.57 (1H, doublet, J=2 Hz);
8.88 (1H, singlet).
Infrared Absorption Spectrum (CHCl$_3$) $\nu_{max}$ cm$^{-1}$:
3463, 3397, 2961, 2934, 2873, 2861, 2841, 1699, 1612, 1587, 1567, 1506, 1480, 1465, 1441, 1429, 1410, 1366, 1297, 1291, 1158, 1126, 1073, 1046, 1031.

EXAMPLE 158

N-[2-t-Butyl-5-(N'-3-pyridylcarbonylaminomethyl) phenyl]-3-(2,4-dimethoxyphenyl)octanamide (Compound No. 384)

Following a similar procedure to that described in Example 144, but using N-[2-t-butyl-5-bromomethylphenyl]-3-(2,4-dimethoxyphenyl)octanamide (prepared as described in Preparation 72F), the title compound was obtained as a colorless foam-like substance.
Nuclear Magnetic Resonance Spectrum (400 MHz, CDCl$_3$) δ ppm:
0.83 (3H, triplet, J=6 Hz);
1.23–1.28 (6H, multiplet);
1.27 (9H, singlet);
1.68–1.73 (2H, multiplet);
2.62–2.78 (2H, multiplet);
3.43–3.51 (1H, multiplet);
3.77 (6H, singlet);
4.52 (2H, doublet, J=5 Hz);
6.42–6.46 (2H, multiplet);
6.70 (1H, broad singlet);
7.08–7.13 (3H, multiplet);
7.22 (1H, singlet);
7.31 (1H, doublet, J=8 Hz);
7.34–7.36 (1H, multiplet);
8.10–8.13 (1H, multiplet);
8.71–8.72 (1H, multiplet);
9.00 (1H, doublet, J=2Hz).
Infrared Absorption Spectrum (CHCl$_3$) $\nu_{max}$ cm$^{-1}$:
3446, 2961, 2934, 1669, 1614, 1591, 1505, 1467, 1421, 1290, 1261, 1157, 1037.

EXAMPLE 159

N-[2-t-Butyl-5-(N'-t-butoxycarbonylcarbamoyl) phenyl]-3-(2,4-dimethoxyphenyl)octanamide (Compound No. 385)

Following a similar procedure to that described in Example 154, but using N-(2-t-butyl-5-carbamoylphenyl)-3-(2,4-dimethoxyphenyl)octanamide (prepared as described in Example 2) and di-t-butyl dicarbonate, the title compound was obtained as a colorless foam-like substance.
Nuclear Magnetic Resonance Spectrum (270 MHz, CDCl$_3$) δ ppm:
0.82–0.90 (3H, multiplet);
1.12–1.34 (6H, multiplet);
1.29 (9H, singlet);
1.55 (9H, singlet);
1.65–1.78 (2H, multiplet);
2.64–2.80 (2H, multiplet);
3.44–3.55 (1H, multiplet);
3.77 (3H, singlet);
3.79 (3H, singlet);
6.43 (1H, doublet, J=8.3 Hz);
6.49 (1H, doublet of doublets, J=2.0 Hz & 8.4 Hz);
7.08 (1H, broad singlet);
7.12 (1H, doublet, J=8.3 Hz);
7.43 (1H, doublet, J=8.4 Hz);
7.57 (1H, doublet, J=2.0 Hz);
7.64 (1H, doublet of doublets, J=2.0 Hz & 8.4 Hz);
8.07 (1H, broad singlet).
Infrared Absorption Spectrum (CHCl$_3$) $\nu_{max}$ cm$^{-1}$:
3433, 2961, 2934, 1778, 1687, 1611, 1507, 1471, 1372, 1152, 1123.

EXAMPLE 160

N-[2-t-Butyl-5-(phthalimidomethyl)phenyl-3-(2,6-dimethoxyphenyl)octanamide (Compound No. 414)

Following a similar procedure to that described in Example 142, but using N-[2-t-butyl-5-bromomethylphenyl]-3-(2,63-dimethoxyphenyl)octanamide (prepared as described in Preparation 70G), the title compound was obtained as a colorless foam-like substance.
Nuclear Magnetic Resonance Spectrum (400 MHz, CDCl$_3$) δ ppm:
0.81–0.84 (3H, multiplet);
1.08–1.12 (1H, multiplet);
1.19–1.32 (5H, multiplet);
1.23 (9H, singlet);
1.63–1.70 (1H, multiplet);
1.88–1.91 (1H, multiplet);
2.72 (1H, doublet of doublets, J=6 Hz & 14.5 Hz);
3.01 (1H, doublet of doublets, J=10 Hz & 14.5 Hz);
3.79 (6H, singlet);
3.91–3.98 (1H, multiplet);
4.73 (2H, singlet);
6.53 (2H, doublet, J=8.5 Hz);
7.06–7.14 (3H. multiplet);
7.18 (1H, singlet);
7.25 (1H, doublet, J=8.5 Hz);
7.68–7.23 (2H, multiplet);
7.81–7.85 (2H, multiplet).
Infrared Absorption Spectrum (CHCl$_3$) $\nu_{max}$ cm$^{-1}$:
2960, 2933, 2873, 2861, 2841, 1772, 1716, 1678, 1594, 1573, 1511, 1474, 1434, 1394, 1367, 1346, 1326, 1295, 1275, 1173, 1114, 1101.

EXAMPLE 161

N-[2-t-Butyl-5-(succiniinidomethyl)phenyl]-3-(2,6-dimethoxyphenyl)octanamide (Compound No. 415)

Following a similar procedure to that described in Example 143, but using N-[2-t-butyl-5-bromomethylphenyl]-3-(2,6-dimethoxyphenyl)octanamide (prepared as described in Preparation 70G), the title compound was obtained as a colorless foam-like substance.
Nuclear Magnetic Resonance Spectrum (400 MHz, CDCl$_3$) δ ppm:
0.81–0.84 (3H, multiplet);
1.08–1.11 (1H, multiplet);

1.18–1.29 (5H, multiplet);
1.24 (9H, singlet);
1.64–1.70 (1H, multiplet);
1.88–1.93 (1H, multiplet);
2.69 (4H, singlet);
2.73 (1H, doublet of doublets, J=6 Hz & 14.5 Hz);
3.02 (1H, doublet of doublets, J=10 Hz & 14.5 Hz);
3.80 (6H, singlet);
3.91–3.98 (1H, multiplet);
4.55 (2H, singlet);
6.55 (2H, doublet, J=8.5 Hz);
7.08–7.16 (4H, multiplet);
7.25 (1H, doublet, J=10 Hz).
Infrared Absorption Spectrum (CHCl$_3$) $v_{max}$ cm$^{-1}$:
2960, 2933, 2873, 2861, 2841, 1777, 1706, 1682, 1594, 1573, 1511, 1474, 1433, 1399, 1366, 1347, 1335, 1296, 1276, 1167, 1115, 1098.

EXAMPLE 162

N-[2-t-Butyl-5-(3-methylamino-3-oxopropyl)phenyl]-3-(2,6-dimethoxyphenyl)octanamide (Compound No. 416)

Following a similar procedure to that described in Example 8, but using N-[2-t-butyl-5-(2-carboxyethyl)phenyl]-3-(2,6-dimethoxyphenyl)octanamide (prepared as described in Preparation 87), the title compound was obtained as colorless crystals, melting at 111°–112° C. (from diethyl ether-hexane).
Nuclear Magnetic Resonance Spectrum (400 MHz, CDCl$_3$) δ ppm:
0.83 (3H, triplet, J=6.5 Hz);
1.27 (9H, singlet);
1.15–1.34 (6H, multiplet);
1.62–1.73 (1H, multiplet);
1.84–1.96 (1H, multiplet);
2.93 (2H, triplet, J=7.6 Hz);
2.68 (3H, doublet, J=4.9 Hz);
2.73 (1H, doublet of doublets, J=6.0 Hz & 14.4 Hz);
2.82 (2H, triplet, J=7.6 Hz);
3.03 (1H, doublet of doublets, J=10.0 Hz & 14.4 Hz);
3.79 (6H, broad singlet);
3.89–3.99 (1H, multiplet);
5.56 (1H, broad singlet);
6.54 (2H, doublet, J=8.2 Hz);
6.87 (1H, doublet, J=1.7 Hz);
6.91 (1H, doublet of doublets, J=1.6 Hz & 8.1 Hz);
7.10–7.18 (2H, multiplet);
7.21 (1H, doublet, J=8.1 Hz).
Infrared Absorption Spectrum (CHCl$_3$) $v_{max}$ cm$^{-1}$:
3463, 2960, 2934, 2861, 1668, 1593, 1474, 1417, 1114, 1099.

EXAMPLE 163

N-(2-t-Butyl-5-carbamoylphenyl)-3-(2,6-dimethoxyphenyl octanamide (Compound No. 417)

Following a similar procedure to that described in Example 141, but using N-(2t-butyl-5-carboxyphenyl)-3-(2,6-dimethoxyphenyl)octanamide (prepared as described in Preparation 74E), the title compound was obtained as colorless crystals.
Nuclear Magnetic Resonance Spectrum (270 MHz, CDCl$_3$) δ ppm:
0.82–0.88 (3H, multiplet);
1.08–1.39 (6H, multiplet);
1.31 (9H, singlet);
1.60–1.78 (1H, multiplet);
1.85–1.98 (1H, multiplet);
2.74 (1H, doublet of doublets, J=5.8 Hz & 14.3 Hz);
3.06 (1H, doublet of doublets, J=10.2 Hz & 14.3 Hz);
3.80 (6H, singlet);
3.86–3.98 (1H, multiplet);
5.45 (1H, broad singlet);
6.29 (1H, broad singlet);
6.55 (2H, doublet, J=7.2 Hz);
7.14 (1H, triplet, J=8.4 Hz);
7.20 (1H, broad singlet);
7.37 (1H, doublet, J=2.1 Hz);
7.37 (1H, doublet, J=2.1 Hz);
7.41 (1H, doublet, J=8.4 Hz);
7.64 (1H, doublet of doublets, J=2.1 Hz & 8.4Hz).
Infrared Absorption Spectrum (CHCl$_3$) $v_{max}$ cm$^{-1}$:
3672, 3527, 3413, 2961,2933, 1676, 1591, 1474, 1375, 1114, 1098.

EXAMPLE 164

N-{2-t-Butyl-5-[N-(4-pyridyl)carbamoyl]phenyl}-3-(2,6-dimethoxyphenyl octanamide (Compound No. 418)

Following a similar procedure to that described in Example 8, but using N-(2-t-butyl-5-carboxyphenyl)-3-(2,6-dimethoxyphenyl)octanamide (prepared as described in Preparation 74E) and 4-aminopyridine, the title compound was obtained as colorless crystals, melting at 169°–172° C.
Nuclear Magnetic Resonance Spectrum (400 MHz, CDCl$_3$) δ ppm:
0.82–0.85 (3H, multiplet);
1.10–1.37 (6H, multiplet);
1.33 (9H, singlet);
1.65–1.73 (1H, multiplet);
1.86–1.97 (1H, multiplet);
2.76 (1H, doublet of doublets, J=5.8 Hz & 14.4 Hz);
3.10 (1H, doublet of doublets, J=10.4 Hz & 14.4 Hz);
3.78 (6H, singlet);
3.91–3.99 (1H, multiplet);
6.52 (2H, doublet, J=8.2 Hz);
7.10 (1H, triplet, J=8.5 Hz);
7.29 (1H, singlet);
7.38 (1H, doublet, J=2.0 Hz);
7.45 (1H, doublet, J=8.2 Hz);
7.61 (2H, doublet of doublets, J=1.4 Hz & 4.7 Hz);
7.67 (1H, doublet of doublets, J=2.0 Hz & 8.5 Hz);
8.53 (2H, doublet of doublets, J=1.4 Hz & 4.7 Hz);
8.60 (1H, broad singlet).
Infrared Absorption Spectrum (CHCl$_3$) $v_{max}$ cm$^{-1}$:
3425, 2962, 2934, 1683, 1593, 1506, 1475, 1415, 1332, 1117, 1097.

EXAMPLE 165

N-{2-t-Butyl-5-[N-(2-pyridyl)carbamoyl]phenyl}-3-(2,6-dimethoxyphenyl)octanamide (Compound No. 419)

Following a similar procedure to that described in Example 8, but using N-(2-t-butyl-5-carboxyphenyl)-3-(2,6-dimethoxyphenyl)octanamide (prepared as described in Preparation 74E) and 2-aminopyridine, the title compound was obtained as a colorless foam-like substance.
Nuclear Magnetic Resonance Spectrum (270 MHz, CDCl$_3$) δ ppm:
0.82–0.86 (3H, multiplet);
1.11–1.36 (6H, multiplet);

1.32 (9H, singlet);
1.55–1.78 (1H, multiplet);
1.85–1.97 (1H, multiplet);
2.75 (1H, doublet of doublets, J=5.8 Hz & 14.1 Hz);
3.07 (1H, doublet of doublets, J=10.6 Hz & 14.1 Hz);
3.82 (6H, singlet);
3.92–4.01 (1H, multiplet);
6.59 (2H, doublet, J=8.3 Hz);
7.06 (1H, doublet of doublets, J=5.5 Hz & 7.1 Hz);
7.16 (1H, triplet, J=8.3 Hz);
7.16 (1H, singlet);
7.36 (1H, doublet, J=1.9 Hz);
7.45 (1H, doublet, J=8.3 Hz);
7.70–7.77 (2H, multiplet);
8.32–8.35 (2H, multiplet);
8.55 (1H, broad singlet).
Infrared Absorption Spectrum (CHCl$_3$) $\nu_{max}$ cm$^{-1}$:
 3413, 2961, 2933, 1679, 1599, 1578, 1519, 1474, 1433, 1309, 1115, 1098.

EXAMPLE 166

N-[2-Butyl-5-(N'-acetylaminomethyl)phenyl]-3-(2,6-dimethoxyphenyl)octanamide (Compound No. 420)

Following a similar procedure to that described in Example 144, but using N-(2-t-butyl-5-aminomethylphenyl)-3-(2,6-dimethoxyphenyl)octanamide prepared as described in Preparation 72E) and acetic anhydride, the title compound was obtained as a colorless foam-like substance.
Nuclear Magnetic Resonance Spectrum (400 MHz, CDCl$_3$) δ ppm:
0.82–0.84 (3H, multiplet);
1.08–1.14 (1H, multiplet);
1.18–1.29 (5H, multiplet);
1.28 (9H, singlet);
1.65–1.72 (1H, multiplet);
1.88–1.93 (1H, multiplet);
1.99 (3H, singlet);
2.74 (1H, doublet of doublets, J=6 Hz & 14.5 Hz);
3.04 (1H, doublet of doublets, J=10.6 Hz & 14.1 Hz);
3.79 (6H, broad singlet);
3.84–3.98 (1H, multiplet);
4.28 (2H, doublet, J=5.5 Hz);
5.79 (1H, broad);
6.54 (2H, doublet, J=8.5 Hz);
6.96 (1H, doublet, J=1.5 Hz);
7.02 (1H, doublet of doublets, J=1.5 Hz & 8 Hz);
7.13 (1H, triplet, J=8.5 Hz);
7.17 (1H, broad singlet);
7.28 (1H, doublet, J=8Hz).
Infrared Absorption Spectrum (CHCl$_3$) $\nu_{max}$ cm$^{-1}$:
 3446, 2961, 2933, 2873, 2861, 2841, 1672, 1618, 1593, 1571, 1511, 1474, 1438, 1422, 1397, 1372, 1177, 1152, 1114, 1098, 1038.

EXAMPLE 167

N-[2-t-Butyl-5-(N-benzoylaminomethyl)phenyl]-3-(2,6-dimethoxyphenyl)octanamide (Compound No. 421)

Following a similar procedure to that described in Example 144, but using N-(2-t-butyl-5-aminomethylphenyl)-3-(2,6-dimethoxyphenyl)octanamide (prepared as described in Preparation 72E) and benzoyl chloride, the title compound was obtained as a colorless foam-like substance.
Nuclear Magnetic Resonance Spectrum (400 Mz, CDCl$_3$) δ ppm:
0.81–0.83 (3H, multiplet);
1.08–1.28 (1H, multiplet);
1.20–1.26 (5H, multiplet);
1.29 (9H, singlet);
1.62–1.71 (1H, multiplet);
1.87–1.93 (1H, multiplet);
2.73 (1H, doublet of doublets, J=6 Hz & 14.5 Hz);
3.04 (1H, doublet of doublets, J=10 Hz & 14.5 Hz);
3.75 (1H, broad singlet);
3.89–3.97 (1H, multiplet);
4.50 (1H, doublet, J=5.5 Hz);
6.48 (6H, broad singlet);
6.49 (2H, doublet, J=8 Hz);
6.96 (1H, doublet, J=2 Hz);
7.06–7.16 (3H, multiplet);
7.30 (1H, doublet, J=8 Hz);
7.41–7.52 (3H, multiplet);
7.78 (2H, multiplet).
Infrared Absorption Spectrum (CHCl$_3$) $\nu_{max}$ cm$^{-1}$:
 3449, 2961, 2933, 2873, 2861, 2841, 1661, 1618, 1593, 1582, 1515, 1484, 1474, 1438, 1422, 1397, 1366, 1275, 1178, 1151, 1114, 1098, 1039, 1003.

EXAMPLE 168

N-2-t-Butyl-5-(N'-3-pyridylcarbonylaminomethyl)phenyl]-3-(2,6-dimethoxyphenyl)octanamide (Compound No. 422)

Following a similar procedure to that described in Example 144, but using N-(2-t-butyl-5-aminomethylphenyl)-3-(2,6-dimethoxyphenyl)octanamide prepared as described in Preparation 72E) and nicotinoyl chloride hydrochloride, the title compound was obtained as a colorless foam-like substance.
Nuclear Magnetic Resonance Spectrum (400 MHz, CDCl$_3$) δ ppm:
0.81–0.84 (3H, multiplet);
1.08–1.12 (1H, multiplet);
1.23–1.32 (5H, multiplet);
1.28 (9H, singlet);
1.62–1.71 (1H, multiplet);
1.85–1.93 (1H, multiplet);
2.72 (1H, doublet of doublets, J=6 Hz & 14.5 Hz);
3.04 (1H, doublet of doublets, J=10 Hz & 14.5 Hz);
3.76 (6H, broad singlet);
3.89–3.96 (1H, multiplet);
4.49 (2H, doublet, J=5 Hz);
6.50 (2H, doublet, J=8.5 Hz);
6.48 (6H, broad);
6.98 (1H, doublet, J=1.5 Hz);
7.06–7.11 (2H, multiplet);
7.20 (6H, broad singlet);
7.31 (1H, doublet, J=8 Hz);
7.35–7.38 (1H, multiplet);
8.12 (1H, triplet of doublets, J=2 Hz & 8 Hz);
8.71 (1H, doublet of doublets, J=1.5 Hz & 14.5 Hz);
9.01 (1H, doublet, J=2Hz).
Infrared Absorption Spectrum (CHCl$_3$) $\nu_{max}$ cm$^{-1}$:
 3445, 2961, 2934, 2873, 2861, 2841, 1668, 1593, 1572, 1515, 1474, 1438, 1420, 1392, 1366, 1294, 1275, 1177, 1153, 1114, 1098, 1039, 1027.

EXAMPLE 169

N-[2-t-Butyl-5-(N'-2-pyridylcarbonylaminomethyl)phenyl]-3-(2,6-dimethoxyphenyl)octanamide (Compound No. 423)

Following a similar procedure to that described in Example 144, but using N-(2-t-butyl-5-aminomethylphenyl)

-3-(2,6-dimethoxyphenyl)octanamide (prepared as described in Preparation 72E) and picolinoyl chloride hydrochloride, the title compound was obtained as a light-yellow foam-like substance.
Nuclear Magnetic Resonance Spectrum (400 MHz, CDCl$_3$) δ ppm:
0.81–0.84 (3H, multiplet);
1.08–1.13 (11, multiplet);
1.20–1.31 (5H, multiplet);
1.28 (9H, singlet);
1.64–1.70 (1H, multiplet);
1.88–1.92 (1H, multiplet);
2.73 (1H, doublet of doublets, J=6 Hz & 14.5 Hz);
3.03 (1H, doublet of doublets, J=10 Hz & 14.5 Hz);
3.77 (6H, broad singlet);
3.90–3.98 (1H, multiplet);
4.53 (2H, doublet, J=6 Hz);
6.51 (2H, doublet, J=8.5 Hz);
7.00 (1H, doublet, J=2 Hz);
7.09 (1H, triplet, J=8.5 Hz);
7.12 (1H, broad singlet);
7.29 (1H, doublet, J=8.5 Hz);
7.40–7.44 (1H, multiplet);
7.85 (1H, doublet of triplets, J=2 Hz & 8 Hz);
8.22 (1H, doublet of doublets, J=1.5 Hz & 8 Hz);
8.28 (1H, broad);
8.52 (1H, doublet, J=4.5Hz).
Infrared Absorption Spectrum (CHCl$_3$) ν$_{max}$ cm$^1$:
3391, 2960, 2933, 2873, 2861, 2841, 1675, 1618, 1593, 1571, 1527, 1474, 1467, 1436, 1423, 1396, 1366, 1299, 1290, 1276, 1177, 1152, 1114, 1098, 1041, 1000.

EXAMPLE 170

N-[2-t-Butyl-5-(N-t-butoxycarbonylaminomethyl) phenyl]-3-(2,6-dimethoxyphenyl)octanamide (Compound No. 424)

Following a similar procedure to that described in Example 144, but using N-(2-t-butyl-5-aminomethylphenyl) -3-(2,6-dimethoxyphenyl)octanamide (prepared as described in Preparation 72E) and di-t-butyl dicarbonate, the title compound was obtained as a colorless foam-like substance.
Nuclear Magnetic Resonance Spectrum (400 MHz, CDCl$_3$) δ ppm:
0.81–0.84 (3H, multiplet);
1.09–1.14 (1H, multiplet);
1.21–1.31 (5H, multiplet);
1.28 (9H, singlet);
1.46 (9H, singlet);
1.66–1.71 (1H, multiplet);
1.88–1.91 (1H, multiplet);
2.73 (1H, doublet of doublets, J=6 Hz & 14.5 Hz);
3.03 (1H, doublet of doublets, J=10 Hz & 14.5 Hz);
3.79 (6H, broad singlet);
3.90–3.98 (1H, multiplet);
4.18 (2H, doublet, J=5.5 Hz);
4.77 (1H, broad);
6.54 (2H, doublet, J=8 Hz);
6.91 (1H, singlet);
7.02 (1H, doublet, J=8 Hz);
7.12 (1H, broad singlet);
7.14 (1H, doublet, J=8.5 Hz);
7.27 (1H, doublet, J=10 Hz).
Infrared Absorption Spectrum (CHCl$_3$) ν$_{max}$ cm$^{-1}$:
3451, 2961, 2933, 2873, 2861, 2841, 1709, 1593, 1572, 1505, 1474, 1438, 1423, 1394, 1368, 1167, 1114, 1099, 1049.

EXAMPLE 171

N-[2-t-Butyl -5-(N'-isopropylureidomethyl)phenyl]- 3-(2,6-dimethoxyphenyl)octanamide (Compound No. 425)

0.45 ml (0.46 mmol) of isopropyl isocyanate was added to a solution of 180 mg (0.409 mmol) of N-(2-t-butyl-5-aminomethylphenyl)-3-(2,6-dimethoxyphenyl)octanamide (prepared as described in Preparation 72E) in 4 ml of methylene chloride cooled to OOC, and the reaction temperature was allowed to rise to room temperature. The resulting mixture was then stirred for 5 hours, after which a few drops of water were added. The reaction mixture was then freed from the solvent by distillation under reduced pressure, and the resulting residue was purified by column chromatography through silica gel using a 1:1 by volume mixture of hexane and ethyl acetate as the eluent, to give 126 mg (yield 58%) of the title compound as a colorless foam-like substance.
Nuclear Magnetic Resonance Spectrum (400 MHz, CDCl$_3$) δ ppm:
0.82–0.85 (3H, multiplet);
1.11 (6H, doublet, J=6.5 Hz);
1.16–1.31 (6H, multiplet);
1.25 (9H, singlet);
1.65–1.72 (1H, multiplet);
1.89–1.93 (1H, multiplet);
2.72 (1H, doublet of doublets, J=6 Hz & 14.5 Hz);
3.04 (1H, doublet of doublets, J=10 Hz & 14.5 Hz);
3.78 (6H, singlet);
3.78–3.89 (1H, multiplet);
3.90–3.97 (1H, multiplet);
4.07 (2H, doublet, J=5.5 Hz);
4.61 (1H, doublet, J=7.5 Hz);
4.79 (1H, triplet, J=5.5 Hz);
6.54 (2H, doublet, J=8.5 Hz);
6.82 (1H, doublet, J=1.5 Hz);
6.98 (1H, doublet, J=8 Hz);
7.14 (1H, triplet, J=8.5 Hz);
7.18 (1H, broad singlet);
7.24 (1H, doublet, J=8Hz).
Infrared Absorption Spectrum (CHCl$_3$) ν$_{max}$ cm$^{-1}$:
3438,3379,2967,2933, 2873,2862,2841, 1665, 1593, 1569, 1530, 1519, 1474, 1438, 1421, 1386, 1367, 1319, 1296, 1177, 1153, 1115, 1098, 1039.

EXAMPLE 172

N-[2-t-Butyl-5-(N'-phenylureidomethyl)phepyl]-3- (2,3-ethylenedioxyphenyl)octanamide (Compound No. 624)

Following a similar procedure to that described in Example 171, but using N-(2-t-butyl-5-aminomethylphenyl) -3-(2,3-ethylenedioxyphenyl)octanamide (prepared as described in Preparation 71) and phenyl isocyanate, the title compound was obtained as white solid, melting at 168.8°–170.0° C. (from methanol-methylene chloride-hexane).
Nuclear Magnetic Resonance Spectrum (400 MHz, CDCl$_3$) δ ppm:
0.83–0.86 (3H, multiplet);
1.21–1.27 (6H, multiplet);
1.16 (9H, singlet);
1.65–1.70 (2H, multiplet);
2.62–2.75 (2H, multiplet);
3.58–3.66 (1H, multiplet);
3.69–3.80 (2H, multiplet);

4.04–4.17 (4H, multiplet);
5.93 (1H, triplet, J=6 Hz);
6.70–6.80 (4H, multiplet);
6.87–6.95 (2H, multiplet);
7.17–7.24 (3H, multiplet);
7.33 (1H, singlet);
7.36 (2H, doublet, J=7.5 Hz);
7.87 (1H, singlet).
Infrared Absorption Spectrum (CHCl$_3$) $\nu_{max}$ cm$^{-1}$:
 3355, 2960, 2932, 2875, 2861, 1660, 1599, 1553, 1532, 1500, 1474, 1456, 1442, 1423, 1396, 1379, 1365, 1354, 1312, 1283, 1178, 1109, 1089, 1051.

EXAMPLE 173

N-[2-t-Butyl-5-(N'-isopropylureidomethyl)phenyl]-3-(2,3-ethylenedioxyphenyl)octanamide (Compound No. 625)

Following a similar procedure to that described in Example 171, but using N-(2-t-butyl-5-aminomethylphenyl)-3-(2,3-ethylenedioxyphenyl)octanamide (prepared as described in Preparation 71), the title compound was obtained as white solid, melting at 184°–185° C. (from methylene chloride-diethyl ether).
Nuclear Magnetic Resonance Spectrum (400 MHz, CDCl$_3$) δ ppm:
0.83–0.86 (3H, multiplet);
1.11 (6H, doublet, J=6.5 Hz);
1.18–1.30 (6H, multiplet);
1.24 (9H, singlet);
1.68–1.72 (2H, multiplet);
2.64–2.74 (2H, multiplet);
3.53–3.66 (1H, multiplet);
3.80–3.88 (1H, multiplet);
4.10 (2H, doublet, J=5.5 Hz);
4.11–4.26 (4H, multiplet);
4.60 (1H, doublet, J=7.5 Hz);
4.82 (1H, triplet, J=5.5 Hz);
6.72–6.83 (3H, multiplet);
7.01 (1H, doublet, J=8 Hz);
7.04 (1H, singlet);
7.11 (1H, broad singlet);
7.24 (1H, doublet, J=8Hz).
Infrared Absorption Spectrum (CHCl$_3$) $\nu_{max}$ cm$^{-1}$:
 3437, 3382, 2970, 2933, 2875, 2862, 1668, 1595, 1531, 1519, 1473, 1456, 1421, 1386, 1367, 1308, 1282, 1162, 1123, 1109.

EXAMPLE 174

N-[2-t-Butyl-5-(N'-isopropylureidomethyl)phenyl]-3-(3,4,5-trimethoxyphenyl octanamide (Compound No. 426)

Following a similar procedure to that described in Example 171, but using N-(2-t-butyl-5-aminomethylphenyl)-3-(3,4,5-trimethoxyphenyl)octanamide (prepared as described in Preparation 72D), the title compound was obtained as a colorless foam-like substance.
Nuclear Magnetic Resonance Spectrum (400 MHz, CDCl$_3$) δ ppm:
0.85–0.87 (3H, multiplet);
1.09–1.13 (6H, triplet, J=6.5 Hz);
1.15–1.27 (6H, multiplet);
1.21 (9H, singlet);
1.64–1.70 (2H, multiplet);
2.47 (1H, doublet of doublets, J=10 Hz & 14 Hz);
2.72 (1H, doublet of doublets, J=5 Hz & 14 Hz);
3.12–3.20 (1H, multiplet);
3.78–3.87 (1H, multiplet);
3.82 (3H, singlet);
3.83 (6H, singlet);
4.08 (1H, doublet of doublets, J=5.5 Hz & 15 Hz);
4.27 (1H, doublet of doublets, J=5.5 Hz & 15 Hz);
4.72 (1H, doublet, J=7.5 Hz);
4.89 (1H, triplet, J=5.5 Hz);
6.49 (2H, singlet);
6.80 (1H, singlet);
6.86 (1H, singlet);
7.05 (1H, doublet, J=8 Hz);
7.25 (1H, doublet, J=8Hz).
Infrared Absorption Spectrum (CHCl$_3$) $\nu_{max}$ cm$^{-1}$:
 3432, 3383, 2968, 2934, 2874, 2861, 1668, 1591, 1531, 1511, 1480, 1465, 1423, 1386, 1366, 1323, 1156, 1130, 1079, 1003.

EXAMPLE 175

N-2-t-Butyl-5-(N'-isopropylureidomethyl)phenyl]-3-(2,4,5-trimethoxyphenyl)octanamide (Compound No. 449)

Following a similar procedure to that described in Example 171, but using N-(2-t-butyl-5-aminomethylphenyl)-3-(2,4,5-trimethoxyphenyl)octanamide (prepared as described in Preparation 72B), the title compound was obtained as white solid, melting at 153°–154° C. (from methylene chloride-hexane).
Nuclear Magnetic Resonance Spectrum (400 MHz, CDCl$_3$) δ ppm:
0.83–0.86 (3H, multiplet);
1.12 (6H, doublet, J=6.5 Hz);
1.16–1.28 (6H, multiplet);
1.25 (9H, singlet);
1.69–1.74 (2H, multiplet);
2.66 (1H, doublet of doublets, J=6 Hz & 14.5 Hz);
2.73 (1H, doublet of doublets, J=9 Hz & 14.5 Hz);
3.45–3.52 (1H, multiplet);
3.78 (3H, singlet);
3.81–3.90 (1H, multiplet);
3.83 (3H, multiplet);
3.86 (3H, multiplet);
4.10–4.23 (2H, multiplet);
4.51 (1H, doublet, J=7.5 Hz);
4.67 (1H, triplet, J=5.5 Hz);
6.51 (1H, singlet);
6.76 (1H, singlet);
6.96 (1H, singlet);
7.03 (1H, doublet, J=8 Hz);
7.27 (1H, doublet, J=8 Hz).
Infrared Absorption Spectrum (CHCl$_3$) $\nu_{max}$ cm$^{-1}$:
 3437, 3387, 2999, 2963, 2935, 2873, 2860, 2838, 1732, 1668, 1612, 1530, 1526, 1510, 1480, 1467, 1456, 1440, 1421, 1400, 1367, 1319, 1181, 1133, 1079, 1036.

EXAMPLE 176

N-[2-t-Butyl-5-(N'-isopropylureidomethyl)phenyl]-3-(2.4,6-trimethoxyphenyl)octanamide (Compound No. 439)

Following a similar procedure to that described in Example 171, but using N-(2-t-butyl-5-aminomethylphenyl)-3-(2,4,6-trimethoxyphenyl)octanamide (prepared as described in Preparation 72C), the title compound was obtained as white solid, melting at 178°–179° C. (from methylene chloride-hexane).

Nuclear Magnetic Resonance Spectrum (400 MHz, CDCl$_3$) δ ppm:
0.82–0.85 (3H, multiplet),
1.10 (6H, doublet, J=6.5 Hz);
1.16–1.31 (6H, multiplet);
1.25 (9H, singlet);
1.61–1.68 (1H, multiplet);
1.84–1.89 (1H, multiplet);
2.68 (1H, doublet of doublets, J=6 Hz & 14.5 Hz);
3.00 (1H, doublet of doublets, J=10 Hz & 14.5 Hz);
3.71–3.87 (2H, multiplet);
3.76 (3H, singlet);
3.79 (6H, singlet);
4.07 (2H, doublet, J=6 Hz);
4.69 (1H, doublet, J=8 Hz);
4.79 (1H, triplet, J=6 Hz);
6.12 (2H, singlet);
6.83 (1H, doublet, J=1.5 Hz);
6.98 (1H, doublet of doublets, J=1.5 Hz & 8 Hz);
7.16 (1H, singlet);
7.24 (1H, doublet, J=8Hz)
Infrared Absorption Spectrum (CHCl$_3$) $v_{max}$ cm$^{-1}$:
  3438, 3387, 2999, 2965, 2935, 2873, 2861, 2841, 1731, 1668, 1608, 1592, 1530, 1492, 1481, 1467, 1456, 1439, 1420, 1386, 1368, 1327, 1153, 1124, 1101, 1063, 1041.

EXAMPLE 177

N-[2-t-Butyl-5-(succinimidomethyl)phenyl]-3-(2,4,5-trimethoxyphenyl)octanamide (Compound No. 440)

Following a similar procedure to that described in Example 143, but using N-(2-t-butyl-5-aminomethylphenyl)-3-(2,4,5-trimethoxyphenyl)octanamide prepared as described in Preparation 72B), the title compound was obtained as a colorless foam-like substance.
Nuclear Magnetic Resonance Spectrum (400 MHz, CDCl$_3$) δ ppm:
0.83–0.86 (3H, multiplet);
1.16–1.28 (6H, multiplet);
1.23 (9H, singlet);
1.69–1.73 (2H, multiplet);
2.63–2.75 (2H, multiplet);
2.69 (4H, singlet);
3.48–3.55 (1H, multiplet);
3.80 (3H, singlet);
3.84 (3H, singlet);
3.87 (3H, singlet);
4.57 (2H, singlet);
6.53 (1H, singlet);
6.74 (1H, singlet);
7.10 (1H, doublet, J=8 Hz);
7.26 (1H, doublet, J=8 Hz);
7.31 (1H, singlet).
Infrared Absorption Spectrum (CHCl$_3$) $v_{max}$ cm$^{-1}$:
  2960, 2935, 2873, 2859, 2838, 1777, 1706, 1683, 1612, 1572, 1510, 1467, 1456, 1439, 1432, 1400, 1367, 1347, 1334, 1296, 1167, 1036.

EXAMPLE 178

N-[2-t-Butyl-5-(phthalimidomethyl)phenyl]-3-(2,4,5-trimethoxyphenyl)octanamide (Compound No. 441)

Following a similar procedure to that described in Example 142, but using N(2-t-butyl-5-aminomethylphenyl)-3-(2,4,5-trimethoxyphenyl)octanamide (prepared as described in Preparation 72B), the title compound was obtained as a pale-yellow foam-like substance.
Nuclear Magnetic Resonance Spectrum (400 MHz, CDCl$_3$) δ ppm:
0.83–0.86 (3H, multiplet);
1.06–1.25 (6H, multiplet);
1.22 (9H, singlet);
1.70–1.71 (2H, multiplet);
2.63–2.75 (2H, multiplet);
3.49–3.54 (1H, multiplet);
3.79 (3H, singlet);
3.83 (3H, singlet);
3.87 (3H, singlet);
4.76 (2H, singlet);
6.54 (1H, singlet);
6.74 (1H, singlet);
7.03 (1H, singlet);
7.15 (1H, doublet, J=8 Hz);
7.26 (1H, doublet, J=8 Hz);
7.40 (1H, singlet);
7.67–7.72 (2H, multiplet);
7.80–7.85 (2H, multiplet).
Infrared Absorption Spectrum (CHCl$_3$) $v_{max}$ cm$^{-1}$:
  2960, 2935, 2873, 2859, 2838, 1772, 1716, 1682, 1613, 1572, 1510, 1468, 1456, 1439, 1433, 1395, 1366, 1346, 1325, 1181, 1134, 1102, 1088, 1080, 1036.

EXAMPLE 179

N-[2-t-Butyl-5-(N-acetylaminomethyl)phenyl]-3-(2,4,5-trimethoxyphenyl)octanamide (Compound No. 442)

Following a similar procedure to that described in Example 144, but using N-(2-t-butyl-5-aminomethylphenyl)-3-(2,4,5-trimethoxyphenyl)octanamide prepared as described in Preparation 72B) and acetic anhydride, the title compound was obtained as a colorless foam-like substance.
Nuclear Magnetic Resonance Spectrum (400 MHz, CDCl$_3$) δ ppm:
0.83–0.86 (3H, multiplet);
1.17–1.30 (6H, multiplet);
1.27 (9H, singlet);
1.69–1.74 (2H, multiplet);
1.99 (3H, singlet);
2.66 (1H, doublet of doublets, J=6 Hz & 14.5 Hz);
2.74 (1H, doublet of doublets, J=9 Hz & 14.5 Hz);
3.46–3.53 (1H, multiplet);
3.79 (3H, singlet);
3.83 (3H, singlet);
3.86 (3H, singlet);
4.26–4.36 (2H, multiplet);
5.85 (1H, broad);
6.51 (1H, singlet);
6.75 (1H, singlet);
7.06 (1H, doublet, J=8 Hz);
7.10 (1H, singlet);
7.12 (1H, broad singlet);
7.30 (1H, doublet, J=8Hz).
Infrared Absorption Spectrum (CHCl$_3$) $v_{max}$ cm$^{-1}$:
  3447, 2960, 2935, 2873, 2859, 2838, 1672, 1612, 1571, 1510, 1480, 1466, 1456, 1440, 1423, 1400, 1370, 1317, 1182, 1135, 1107, 1179, 1136.

EXAMPLE 180

N-[2-t-Butyl-5-(N'-3-pyridylcarbonylaminomethyl)phenyl]-3-(2,4,5-trimethoxyphenynl)octanamide (Compound No. 443)

Following a similar procedure to that described in Example 144, but using N-(2-t-butyl-5-aminomethylphenyl)

-3-(2,4,5-trimethoxyphenyl)octanamide (prepared as described in Preparation 72B) and nicotinoyl chloride hydrochloride, the title compound was obtained as a colorless foam-like substance.
Nuclear Magnetic Resonance Spectrum (400 MHz, CDCl$_3$) δ ppm:
0.82–0.85 (3H, multiplet);
1.16–1.27 (6H, multiplet);
1.27 (9H, singlet);
1.68–1.74 (2H, multiplet);
2.66 (1H, doublet of doublets, J=6 Hz & 14 Hz);
2.74 (1H, doublet of doublets, J=9 Hz & 14 Hz);
3.45–3.52 (1H, multiplet);
3.78 (3H, singlet);
3.81 (3H, singlet);
3.84 (3H, singlet);
4.45–4.57 (2H, multiplet);
6.50 (2H, singlet);
6.74 (1H, singlet);
6.81 (1H, broad);
7.11–7.18 (3H, multiplet);
7.32 (1H, doublet, J=8 Hz);
7.37 (1H, doublet of doublets, J=5 Hz & 8 Hz);
8.12 (1H, triplet of doublets, J=2 Hz & 8 Hz);
8.71 (1H, doublet, J=4 Hz);
9.01 (1H, singlet).
Infrared Absorption Spectrum (CHCl$_3$) $v_{max}$ cm$^{-1}$:
3447, 2960, 2935, 2873, 2859, 2838, 1669, 1612, 1592, 1571, 1510, 1467, 1440, 1421, 1400, 1366, 1292, 1273, 1182, 1154, 1134, 1110, 1181, 1036.

EXAMPLE 181

N-[2-t-Butyl-5-(N'-2-pyridylcarbonylaminomethyl) phenyl]-3-(2,4,5-trimethoxyphenyl)octanamide (Compound No. 444)

Following a similar procedure to that described in Example 144, but using N-(2-t-butyl-5-aminomethylphenyl)-3-(2,4,5-trimethoxyphenyl)octanamide (prepared as described in Preparation 72B) and picolinoyl chloride hydrochloride, the title compound was obtained as a light-yellow foam-like substance.
Nuclear Magnetic Resonance Spectrum (400 MHz, CDCl$_3$) δ ppm:
0.82–0.85 (3H, multiplet);
1.16–1.30 (6H, multiplet);
1.26 (9H, singlet);
1.70–1.71 (2H, multiplet);
2.66 (1H, doublet of doublets, J=6 Hz & 14.5 Hz);
2.73 (1H, doublet of doublets, J=8.5 Hz & 14.5 Hz);
3.48–3.55 (1H, multiplet);
3.78 (3H, singlet);
3.82 (3H, singlet);
3.86 (3H, singlet);
4.57 (2H, doublet, J=6 Hz);
6.50 (1H, singlet);
6.74 (1H, singlet);
7.09 (1H, broad singlet);
7.14 (1H, doublet, J=8 Hz);
7.31 (1H, doublet, J=8 Hz);
7.32 (1H, singlet);
7.40–7.43 (1H, multiplet);
7.84 (1H, doublet of triplets, J=2 Hz & 7.5 Hz);
8.21 (1H, doublet, J=7.5 Hz);
8.34 (1H, broad);
8.52 (1H, doublet, J=4.5Hz).
Infrared Absorption Spectrum (CHCl$_3$) $v_{max}$ cm$^{-1}$:
3392, 2960, 2935, 2873, 2859, 2838, 1675, 1612, 1593, 1571, 1527, 1511, 1466, 1438, 1423, 1400, 1366, 1316, 1301, 1290, 1181, 1162, 1135, 1110, 1089, 1081, 1037, 1000.

EXAMPLE 182

N-[2-t-Butyl-5-(N'-4-pyridylcarbonylaminomethyl) phenyl -3-(2,4,5-trimethoxyphenyl)octanamide (Compound No. 445)

Following a similar procedure to that described in Example 144, but using N-(2-t-butyl-5-aminomethylphenyl)-3-(2,4,5-trimethoxyphenyl)octanamide (prepared as described in Preparation 72B) and isonicotinoyl chloride hydrochloride, the title compound was obtained as a colorless foam-like substance.
Nuclear Magnetic Resonance Spectrum (400 MHz, CDCl$_3$) δ ppm:
0.82–0.85 (3H, multiplet);
1.17–1.28 (6H, multiplet);
1.28 (9H, singlet);
1.70–1.72 (2H, multiplet);
2.67 (1H, doublet of doublets, J=6.5 Hz & 14.5 Hz);
2.74 (1H, doublet of doublets, J=9 Hz & 14.5 Hz);
3.45–3.52 (1H, multiplet);
3.78 (3H, singlet);
3.81 (3H, singlet);
3.84 (3H, singlet);
4.45–4.56 (2H, multiplet);
6.49 (1H, singlet);
6.74 (1H, singlet);
6.74 (1H, broad);
7.11–7.14 (2H, multiplet);
7.19 (1H, broad singlet);
7.32 (11, doublet, J=8 Hz);
7.63–7.65 (2H, multiplet);
8.73 (2H, doublet, J=6Hz).
Infrared Absorption Spectrum (CHCl$_3$) $v_{max}$ cm$^{-1}$:
3444, 2961, 2935, 2873, 2859, 2838, 1672, 1611, 1602, 1570, 1557, 1511, 1482, 1466, 1456, 1440, 1423, 1409, 1400, 1366, 1291, 1271, 1182, 1152, 1135, 1109, 1081, 1068, 1036.

EXAMPLE 183

N-[2-t-Butyl-5-(N'-t-butoxycarbonylaminomethyl) phenyl]-3-(2,4,5-trimethoxyphenyl)octanamide (Compound No. 446)

Following a similar procedure to that described in Example 144, but using N-(2-t-butyl-5-aminomethylphenyl)-3-(2,4,5-trimethoxyphenyl)octanamide prepared as described in Preparation 72B) and di-t-butyl dicarbonate, the title compound was obtained as a colorless foam-like substance.
Nuclear Magnetic Resonance Spectrum (400 MHz, CDCl$_3$) δ ppm:
0.83–0.86 (3H, multiplet);
1.21–1.26 (6H, multiplet);
1.26 (9H, singlet);
1.45 (9H, singlet);
1.69–1.74 (2H, multiplet);
2.66 (1H, doublet of doublets, J=6.5 Hz & 14.5 Hz);
2.73 (1H, doublet of doublets, J=8.5 Hz & 14.5 Hz);
3.47–3.54 (1H, multiplet);
3.79 (3H, singlet);
3.83 (3H, singlet);
3.87 (3H, singlet);

4.21 (2H, doublet, J=5.5 Hz);
4.85 (1H, broad);
6.51 (1H, singlet);
6.74 (1H, singlet);
7.06 (1H, doublet, J=8 Hz);
7.07 (1H, broad singlet);
7.16 (1H, singlet);
7.29 (1H, doublet, J=8Hz).
Infrared Absorption Spectrum (CHCl$_3$) $\nu_{max}$ cm$^{-1}$:
3452, 2960, 2935, 2873, 2860, 2838, 1709, 1612, 1571, 1510, 1480, 1467, 1455, 1440, 1368, 1330, 1317, 1168, 1136, 1111, 1079, 1036.

EXAMPLE 184

N-[2-t-B=1-5-(2-N',N'-dimethylcarbamoylethyl)hylphenyl]-3-(2,4,5-trimethoxyphenyl)octanamide (Compound No. 447)

Following a similar procedure to that described in Example 8, but using N-[2-t-butyl-5-(2-carboxyethyl)phenyl]-3-(2,4,5-trimethoxyphenyl)octanamide (prepared as described in Preparation 84) and dimethylamine, the title compound was obtained as a colorless foam-like substance.
Nuclear Magnetic Resonance Spectrum (400 MHz, CDCl$_3$) δ ppm:
0.84 (3H, triplet, J=5.7 Hz);
1.26 (9H, singlet);
1.15–1.33 (6H, multiplet);
1.66 (2H, multiplet);
2.57 (2H, triplet, J=8.0 Hz);
2.61–2.77 (2H, multiplet);
2.87 (2H, triplet, J=8.0 Hz);
2.94 (6H, singlet);
3.47–3.56 (1H, multiplet);
3.79 (3H, singlet);
3.83 (3H, singlet);
3.86 (3H, singlet);
6.50 (1H, singlet);
6.74 (1H, singlet);
6.99 (1H, doublet, J=8.2 Hz);
7.08 (1H, singlet);
7.17 (1H, singlet);
7.24 (1H, doublet, J=8.2Hz).
Infrared Absorption Spectrum (CHCl$_3$) $\nu_{max}$ cm$^{-1}$:
3463, 3404, 2959, 2935, 2860, 1676, 1636, 1510, 1466, 1401, 1037.

EXAMPLE 185

N-[2-t-Butyl-5-(2-carbamoylethyl)phenyl]-3-(2,4,5-trimethoxyphenyl)octanamide (Compound No. 448)

Following a similar procedure to that described in Example 141, but using N-[2-t-butyl-5-(2-carboxyethyl)phenyl]-3-(2,4,5-trimethoxyphenyl)octanamide (prepared as described in Preparation 84), the title compound was obtained as a colorless foam-like substance.
Nuclear Magnetic Resonance Spectrum (400 MHz, CDCl$_3$) δ ppm:
0.85 (3H, triplet, J=5.5 Hz);
1.28 (9H, singlet);
1.13–1.35 (6H, multiplet);
1.65–1.81 (2H, multiplet);
2.38 (2H, triplet, J=8.0 Hz);
2.67 (1H, doublet of doublets, J=6.0,13.8 Hz);
2.74–2.87 (3H, multiplet);
3.36–3.46 (1H, multiplet);
3.80 (3H, singlet);
3.84 (3H, singlet);
3.85 (3H, singlet);
5.28 (1H, broad singlet);
6.02 (1H, broad singlet);
6.51 (1H, singlet);
6.63 (1H, singlet);
6.77 (1H, singlet);
6.95–7.01 (2H, multiplet);
7.23 (1H, doublet, J=8.2Hz).
Infrared Absorption Spectrum (CHCl$_3$) $\nu_{max}$ cm$^{-1}$:
3530, 3492, 3412, 3372, 2960, 2935, 2860, 1679, 1510, 1466, 1399, 1035.

EXAMPLE 186

N-[2-t-Butyl-5-(3-methylamino-3-oxopropyl)phenyl]-3-(2,4,5-trimethoxyphenyl)octanamide (Compound No. 101)

Following a similar procedure to that described in Example 8, but using N-[2-t-butyl-5-(2-carboxyethyl)phenyl]-3-(2,4,5-trimethoxyphenyl)octanamide prepared as described in Preparation 84) and methylamine, the title compound was obtained as a colorless foam-like substance.
Nuclear Magnetic Resonance Spectrum (400 MHz, CDCl$_3$) δ ppm:
0.79–0.91 (3H, multiplet);
1.27 (9H, singlet);
1.13–1.33 (6H, multiplet);
1.65–1.80 (2H, multiplet);
2.32 (2H, triplet, J=8.0 Hz);
2.66 (1H, doublet of doublets, J=6.1,14.0 Hz);
2.70–2.86 (6H, multiplet);
3.37–3.47 (1H, multiplet);
3.80 (3H, singlet);
3.84 (3H, singlet);
3.85 (3H, singlet);
5.97 (1H, broad singlet);
6.51 (1H, singlet);
6.66 (1H, singlet);
6.77 (1H, singlet);
6.95 (1H, doublet of doublets, J=1.2,8.1 Hz);
6.99 (1H, singlet);
7.22 (1H, doublet, J=8.1Hz).
Infrared Absorption Spectrum (CHCl$_3$) $\nu_{max}$ cm$^{-1}$:
3463, 3395, 2960, 2935, 2860, 1668, 1612, 1510, 1466, 1416, 1035.

EXAMPLE 187

N-(2-t-Butyl-5-carbamoylphenyl)-3-(2,4,5-trimethoxyphenyl)octanamide (Compound No. 450)

Following a similar procedure to that described in Example 8, but using N-(2-t-butyl-5-carboxyphenyl)-3-(2,4,5-trimethoxyphenyl)octanamide (prepared as described in Preparation 74B), the title compound was obtained as colorless crystals, melting at 166°–167° C. (from methylene chloride-hexane).
Nuclear Magnetic Resonance Spectrum (400 MHz, CDCl$_3$) δ ppm:
0.81–0.89 (3H, multiplet);
1.30 (9H, singlet);
1.14–1.35 (6H, multiplet);
1.67–1.77 (2H, multiplet);
2.66–2.78 (2H, multiplet);
3.45–3.54 (1H, multiplet);
3.79 (3H, singlet);
3.84 (3H, singlet);

3.86 (3H, singlet);
5.47 (1H, broad);
6.10 (1H, broad);
6.51 (1H, singlet);
6.76 (1H, singlet);
7.12 (1H, singlet);
7.43 (1H, doublet, J=8.4 Hz);
7.50 (1H, doublet, J=1.5 Hz);
7.65 (1H, doublet of doublets, J=2.0 & 8.4 Hz).
Infrared Absorption Spectrum (CHCl$_3$) $v_{max}$ cm$^{-1}$:
3528, 3414, 2961, 2935, 2859, 1678, 1587, 1510, 1466, 1035.

EXAMPLE 188

N-2-t-Butyl -5-(N'-2-pyridylcarbonylaminomethyl) phenyl]-3-(2,4-dimethoxyphenyl octanamide (Compound No. 397)

Following a similar procedure to that described in Example 169, but using N-(2-t-butyl-5-aminomethylphenyl)-3-(2,4-dimethoxyphenyl)octanamide (prepared as described in Preparation 72F), the title compound was obtained as a colorless foam-like substance.
Nuclear Magnetic Resonance Spectrum (400 MHz, CDCl$_3$) δ ppm:
0.83 (3H, triplet, J=6.3 Hz);
1.26 (9H, singlet);
1.10–1.35 (6H, multiplet);
1.64–1.77 (2H, multiplet);
2.64 (1H, doublet of doublets, J=6.3 & 14.3 Hz);
2.74 (1H, doublet of doublets, J=8.7 & 14.3 Hz);
3.48–3.54 (1H, multiplet);
3.77 (6H, singlet);
4.57 (2H, doublet, J=6.1 Hz);
6.40–6.49 (2H, multiplet);
7.03 (1H, broad singlet);
7.06–7.16 (2H, multiplet);
7.27–7.34 (2H, multiplet);
7.38–7.45 (1H, multiplet);
7.82–7.87 (1H, multiplet);
8.22 (1H, doublet, J=8.2 Hz);
8.33 (1H, broad);
8.53 (1H, doublet, J=4.9Hz).
Infrared Absorption Spectrum (CHCl$_3$) $v_{max}$ cm$^{-1}$:
3392, 2960, 2933, 2861, 1675, 1614, 1527, 1507, 1466, 1290, 1158, 1037.

EXAMPLE 189

N-[2-t-Butyl-5-(succinimidomethyl)phenyl-3-(3,4,5-trimethoxyphenyl]octanamide (Compound No. 427)

Following a similar procedure to that described in Example 143, but using N-[2-t-butyl-5-bromomethylphenyl]-3-(3,4,5-trimethoxyphenyl) octanamide (prepared as described in Preparation 70F), the title compound was obtained as a colorless foam-like substance.
Nuclear Magnetic Resonance Spectrum (400 MHz, CDCl$_3$) δ ppm:
0.84–0.87 (3H, multiplet);
1.14–1.33 (6H, multiplet);
1.17 (9H, singlet);
1.64–1.72 (2H, multiplet);
2.56 (1H, doublet of doublets, J=9 Hz & 14.5 Hz);
2.65–2.73 (5H, multiplet);
3.13–3.20 (1H, multiplet);
3.81 (3H, singlet);
3.84 (6H, singlet);
4.59 (2H, singlet);
6.47 (2H, singlet);
6.84 (1H, singlet);
7.11 (1H, doublet, J=8 Hz);
7.25 (1H, doublet, J=8 Hz);
7.49 (1H, singlet).
Infrared Absorption Spectrum (CHCl$_3$) $v_{max}$ cm$^{-1}$:
2961, 2935, 2874, 2860, 2842, 1777, 1706, 1682, 1591, 1574, 1510, 1464, 1432, 1425, 1400, 1348, 1334, 1166, 1130, 1003.

EXAMPLE 190

N-[2-t-Butyl-5-(phthalimidomethyl)phenyl]-3-(3,4,5-trimethoxyphenyl)octanamide (Compound No. 428)

Following a similar procedure to that described in Example 142, but using N-[2-t-butyl-5-bromomethylphenyl]-3-(3,4,5-trimethoxyphenyl) octanamide (prepared as described in Preparation 70F), the title compound was obtained as a colorless foam-like substance.
Nuclear Magnetic Resonance Spectrum (400 MHz, CDCl$_3$) δ ppm:
0.85–0.87 (3H, multiplet);
1.13–1.32 (6H, multiplet);
1.16 (9H, singlet);
1.61–1.74 (2H, multiplet);
2.56 (1H, doublet of doublets, J=9 Hz & 14.5 Hz);
2.71 (1H, doublet of doublets, J=5.5 Hz & 14.5 Hz);
3.14–3.21 (1H, multiplet);
3.80 (3H, singlet);
3.84 (6H, singlet);
4.78 (2H, singlet);
6.47 (2H, singlet);
6.84 (1H, singlet);
7.16 (1H, doublet, J=8.5 Hz);
7.26 (1H, doublet, J=8.5 Hz);
7.57 (1H, singlet);
7.68–7.71 (2H, multiplet);
7.81–7.84 (2H, multiplet).
Infrared Absorption Spectrum (CHCl$_3$) $v_{max}$ cm$^{-1}$:
2961, 2934, 2874, 2860, 2842, 1772, 1716, 1685, 1591, 1574, 1510, 1465, 1425, 1395, 1366, 1346, 1324, 1153, 1130, 1103, 1088, 1080, 1004.

EXAMPLE 191

N-[2-t-Butyl-5-(N-acetylaminomethyl)phenyl]-3-(3,4,5-trimethoxyphenyl)octanamide (Compound No. 429)

Following a similar procedure to that described in Example 144, but using N-(2-t-butyl-5-aminomethylphenyl)-3-(3,4,5-trimethoxyphenyl)octanamide (prepared as described in Preparation 72D) and acetic anhydride, the title compound was obtained as a colorless foam-like substance.
Nuclear Magnetic Resonance Spectrum (400 MHz, CDCl$_3$) δ ppm:
0.85–0.87 (3H, multiplet);
1.17–1.27 (6H, multiplet);
1.21 (9H, singlet);
1.61–1.73 (2H, multiplet);
2.00 (3H, singlet);
2.53 (1H, doublet of doublets, J=9.5 Hz & 14 Hz);
2.73 (1H, doublet of doublets, J=5.5 Hz & 14 Hz);
3.13–3.20 (1H, multiplet);

3.81 (3H, singlet);
3.84 (6H, singlet);
4.28 (1H, doublet of doublets, J=5.5 Hz & 14.5 Hz);
4.36 (1H, doublet of doublets, J=5.5 Hz & 14.5 Hz);
5.90 (1H, broad);
6.48 (2H, singlet);
6.84 (1H, broad singlet);
7.07 (1H, doublet of doublets, J=1 Hz & 8 Hz);
7.18 (1H, doublet, J=1 Hz);
7.28 (1H, doublet, J=8Hz).
Infrared Absorption Spectrum (CHCl$_3$) $v_{max}$ cm$^{-1}$:
3448, 2961, 2934, 2874, 2861, 2842, 1672, 1591, 1572, 1510, 1477, 1465, 1423, 1397, 1369, 1324, 1259, 1154, 1130, 1004.

EXAMPLE 192

N-[2-t-Butyl-5-(N'-3-pridylcarbonylaminomethyl) phenyl]-3-(3,4,5-trimethoxyphenyl)octanamide (Compound No. 430)

Following a similar procedure to that described in Example 147, but using N-(2-t-butyl-5-aminomethylphenyl)-3-(3,4,5-trimethoxyphenyl)octanamide (prepared as described in Preparation 72D) and nicotinoyl chloride hydrochloride, the title compound was obtained as a colorless foam-like substance.

Nuclear Magnetic Resonance Spectrum (400 MHz, CDCl$_3$) δ ppm:
0.84–0.87 (3H, multiplet);
1.13–1.38 (6H, multiplet);
1.22 (9H, singlet);
1.64–1.71 (2H, multiplet);
2.52 (1H, doublet of doublets, J=9.5 Hz & 14 Hz);
2.74 (1H, doublet of doublets, J=5.5 Hz & 14 Hz);
3.12–3.19 (1H, multiplet);
3.81 (3H, singlet);
3.82 (3H, singlet);
3.84 (3H, singlet);
4.44 (1H, doublet of doublets, J=5.5 Hz & 14.5 Hz);
4.57 (1H, doublet of doublets, J=5.5 Hz & 14.5 Hz);
6.48 (2H, singlet);
6.85 (1H, broad singlet);
6.88 (1H, broad);
7.11 (1H, singlet);
7.16 (1H, doublet, J=8 Hz);
7.31 (1H, doublet, J=8 Hz);
7.37 (1H, doublet of doublets, J=4.5 Hz & 8 Hz);
8.15 (1H, doublet, J=8 Hz);
8.71 (1H, doublet of doublets, J=1.5 Hz & 4.5 Hz);
9.04 (1H, doublet, J=1.5Hz).
Infrared Absorption Spectrum (CHCl$_3$) $v_{max}$ cm$^{-1}$:
3447, 2962, 2935, 2874, 2860, 2842, 1672, 1591, 1573, 1511, 1465, 1422, 1363, 1323, 1296, 1154, 1130, 1082, 1027, 1003.

EXAMPLE 193

N-[2-t-Butyl-5-N'-t-butoxycarbonylaminomethyl) phenyl-3-(3,4,5-trimethoxyphenyl)octanamide (Compound No. 431)

Following a similar procedure to that described in Example 144, but using N-(2-t-butyl-5-aminomethylphenyl)-3-(3,4,5-trimethoxyphenyl)octanamide (prepared as described in Preparation 72D) and di-t-butyl dicarbonate, the title compound was obtained as a colorless foam-like substance.

Nuclear Magnetic Resonance Spectrum (400 MHz, CDCl$_3$) δ ppm:
0.85–0.87 (3H, multiplet);
1.17–1.27 (6H, multiplet);
1.21 (9H, singlet);
1.45 (9H, singlet);
1.61–1.73 (2H, multiplet);
2.55 (1H, doublet of doublets, J=9 Hz & 14 Hz);
2.71 (1H, doublet of doublets, J=5.5 Hz & 14 Hz);
3.12–3.20 (1H, multiplet);
3.81 (3H, singlet);
3.84 (6H, singlet);
4.23 (2H, doublet, J=13 Hz);
4.85 (1H, broad);
6.47 (2H, singlet);
6.87 (1H, broad singlet);
7.06 (1H, doublet, J=5.5 Hz);
7.27–7.31 (2H, multiplet).
Infrared Absorption Spectrum (CHCl$_3$) $v_{max}$ cm$^{-1}$:
3452, 2962, 2934, 2874, 2861, 2842, 1769, 1591, 1574, 1510, 1505, 1477, 1464, 1423, 1394, 1379, 1368, 1324, 1165, 1130, 1079, 1050, 1030, 1004.

EXAMPLE 194

N-[2-t-Butyl-5-(succinimidomethyl)phenyl]-3-(2,4,6-trimethoxyphenyl octanamide (Compound No. 432)

Following a similar procedure to that described in Example 143, but using N-(2-t-butyl-5-aminomethylphenyl)-3-(3,4,5-trimethoxyphenyl)octanamide (prepared as described in Preparation 72D), the title compound was obtained as a colorless foam-like substance.

Nuclear Magnetic Resonance Spectrum (400 MHz, CDCl$_3$) δ ppm:
0.81–0.85 (3H, multiplet);
1.09–1.15 (1H, multiplet);
1.18–1.30 (5H, multiplet);
1.25 (9H, multiplet);
1.60–1.66 (1H, multiplet);
1.84–1.88 (1H, multiplet);
2.65–2.72 (5H, multiplet);
2.98 (1H, doublet of doublets, J=10 Hz & 14.5 Hz);
3.75–3.89 (1H, multiplet);
3.79 (9H, singlet);
4.55 (2H, singlet);
6.14 (2H, singlet);
7.06–7.11 (2H, multiplet);
7.18 (1H, singlet);
7.25 (1H, doublet, J=8.5Hz).
Infrared Absorption Spectrum (CHCl$_3$) $v_{max}$ cm$^{-1}$:
2960, 2938, 2873, 2860, 2841, 1777, 1706, 1682, 1608, 1592, 1510, 1492, 1467, 1456, 1432, 1422, 1399, 1366, 1346, 1333, 1296, 1166, 1153, 1124, 1101, 1163, 1041.

EXAMPLE 195

N-[2-t-Butyl-5-(phthalimidomethyl)phenyl]-3-(2,4,6-trimethoxyphenyl)octanamide (Compound No. 433)

Following a similar procedure to that described in Example 142, but using N-(2-t-butyl-5-aminomethylphenyl)-3-(3,4,5-trimethoxyphenyl)octanamide (prepared as described in Preparation 72D), the title compound was obtained as a colorless foam-like substance.

Nuclear Magnetic Resonance Spectrum (400 MHz, CDCl$_3$) δ ppm:
0.82–0.85 (3H, multiplet);
1.08–1.11 (1H, multiplet);

1.17–1.29 (5H, multiplet);
1.23 (9H, singlet);
1.60–1.65 (1H, multiplet);
1.84–1.88 (1H, multiplet);
2.69 (1H, doublet of doublets, J=5.5 Hz & 14.5 Hz);
2.98 (1H, doublet of doublets, J=10 Hz & 14.5 Hz);
3.78 (9H, singlet);
3.80–3.89 (1H, multiplet);
4.74 (2H, singlet);
6.14 (2H, singlet);
7.06 (1H, singlet);
7.13 (1H, doublet, J=8 Hz);
7.25 (1H, doublet, J=8 Hz);
7.26 (1H, singlet);
7.68–7.72 (2H, multiplet);
7.80–7.85 (2H, multiplet).
Infrared Absorption Spectrum (CHCl$_3$) $v_{max}$ cm$^{-1}$:
2960, 2936, 2873, 2860, 2841, 1772, 1716, 1678, 1608, 1592, 1492, 1469, 1456, 1432, 1422, 1394, 1346, 1328, 1153, 1124, 1101, 1089, 1064, 1041.

EXAMPLE 196

N-[2-t-Butyl-5-(N-acetylaminomethyl)phenyl]-3-(2,4,6-trimethoxyphenyl)octanamide (Compound No. 434)

Following a similar procedure to that described in Example 144, but using N-(2-t-butyl-5-aminomethylphenyl)-3-(2,4,6-trimethoxyphenyl)octanamide (prepared as described in Preparation 72C) and acetic anhydride, the title compound was obtained as a colorless foam-like substance.
Nuclear Magnetic Resonance Spectrum (400 MHz, CDCl$_3$) δ ppm:
0.82–0.85 (3H, multiplet);
1.11–1.12 (1H, multiplet);
1.19–1.32 (5H, multiplet);
1.28 (9H, singlet);
1.62–1.65 (1H, multiplet);
1.83–1.88 (1H, multiplet);
1.99 (3H, singlet);
2.79 (1H, doublet of doublets, J=6 Hz & 14.5 Hz);
3.00 (1H, doublet of doublets, J=10 Hz & 14.5 Hz);
3.73–3.84 (1H, multiplet);
3.77 (3H, singlet);
3.79 (6H, singlet);
4.29 (2H, doublet, J=5.5 Hz);
5.81 (1H, broad);
6.12 (2H, singlet);
7.00 (1H, singlet);
7.03 (1H, doublet, J=8 Hz);
7.29 (1H, doublet, J=8Hz).
Infrared Absorption Spectrum (CHCl$_3$) $v_{max}$ cm$^{-1}$:
3446, 2961, 2935, 2873, 2860, 2841, 1672, 1608, 1592, 1514, 1493, 1467, 1456, 1439, 1420, 1372, 1328, 1153, 1124, 1101, 1063, 1040.

EXAMPLE 197

N-[2-t-Butyl-5-(N'-3-pyridylcarbonylaminomethyl)phenyl]-3-?(2,4,6-trimethoxyphenyl)octanamide (Compound No. 435)

Following a similar procedure to that described in Example 144, but using N-(2-t-butyl-5-aminomethylphenyl)-3-(2,4,6-trimethoxyphenyl)octanamide prepared as described in Preparation 72C) and nicotinoyl chloride hydrochloride, the title compound was obtained as a colorless foam-like substance.
Nuclear Magnetic Resonance Spectrum (400 MHz, CDCl$_3$) δ ppm:
0.81–0.84 (3H, multiplet);
1.13–1.30 (6H, multiplet);
1.29 (9H, singlet);
1.61–1.65 (1H, multiplet);
1.83–1.87 (1H, multiplet);
2.79 (1H, doublet of doublets, J=6 Hz & 14.5 Hz);
3.00 (1H, doublet of doublets, J=10 Hz & 14.5 Hz);
3.71–3.85 (1H, multiplet);
3.75 (3H, singlet);
3.77 (6H, singlet);
4.45–4.54 (2H, multiplet);
6.10 (2H, singlet);
6.75 (1H, broad);
7.06 (1H, doublet, J=1.5 Hz);
7.11 (1H, doublet of doublets, J=2 Hz & 8 Hz);
7.17 (1H, singlet);
7.31 (1H, doublet, J=8 Hz);
7.37 (1H, doublet of doublets, J=5 Hz & 8 Hz);
8.12 (1H, triplet of doublets, J=2 Hz & 6 Hz);
8.71 (1H, doublet of doublets, J=1.5 Hz & J=5 Hz);
9.01 (1H, doublet, J=2Hz).
Infrared Absorption Spectrum (CHCl$_3$) $v_{max}$ cm$^{-1}$:
3445, 2961, 2937, 2873, 2861, 2841, 1668, 1608, 1592, 1574, 1515, 1492, 1467, 1456, 1438, 1420, 1397, 1366, 1329, 1294, 1153, 1124, 1101, 1063, 1040, 1027.

EXAMPLE 198

N-[2-t-Butyl-5-(N'-2-pyridylcarbonylaminomethyl)phenyl]-3-(2,4,6-trimethoxyphenyl)octanamide (Compound No. 436)

Following a similar procedure to that described in Example 144, but using N-(2-t-butyl-5-aminomethylphenyl)-3-(2,4,6-trimethoxyphenyl)octanamide prepared as described in Preparation 72C) and picolinoyl chloride hydrochloride, the title compound was obtained as a colorless foam-like substance.
Nuclear Magnetic Resonance Spectrum (400 MHz, CDCl$_3$) δ ppm:
0.81–0.84 (3H, multiplet);
1.10–1.34 (6H, multiplet);
1.28 (9H, singlet);
1.63–1.67 (1H, multiplet);
1.83–1.88 (1H, multiplet);
2.69 (1H, doublet of doublets, J=6 Hz & 14.5 Hz);
2.99 (1H, doublet of doublets, J=10 Hz & 14.5 Hz);
3.71–3.86 (1H, multiplet);
3.77 (9H, singlet);
4.55 (2H, doublet, J=6 Hz);
6.11 (2H, singlet);
7.11–7.14 (3H, multiplet);
7.30 (1H, doublet, J=8 Hz);
7.40–7.43 (1H, multiplet);
7.85 (1H, doublet of triplets, J=1.5 Hz & 7.5 Hz);
8.31 (1H, broad);
8.52 (1H, doublet, J=5Hz).
Infrared Absorption Spectrum (CHCl$_3$) $v_{max}$ cm$^{-1}$:
3391, 2960, 2934, 2873, 2861, 2841, 1675, 1608, 1592, 1572, 1527, 1492, 1466, 1457, 1436, 1421, 1366, 1328, 1291, 1153, 1124, 1101, 1063, 1042, 1000.

EXAMPLE 199

N-[2-t-Butyl-5-(N'-4-pyridylcarbonylaminomethyl)phenyl]-3-(2,4,6-trimethoxyphenyl)octanamide (Compound No. 437)

Following a similar procedure to that described in Example 144, but using N-(2-t-butyl-5-aminomethylphenyl)

-3-(2,4,6-trimethoxyphenyl)octanamide (prepared as described in Preparation 72C) and isonicotinoyl chloride hydrochloride, the title compound was obtained as white solid, melting at 172.5° C. (from ethyl acetate).
Nuclear Magnetic Resonance Spectrum (400 MHz, CDCl$_3$) δ ppm:
0.81–0.84 (3H, multiplet);
1.08–1.33 (6H, multiplet);
1.29 (9H, singlet);
1.60–1.65 (1H, multiplet);
1.83–1.88 (1H, multiplet);
2.69 (1H, doublet of doublets, J=6 Hz & 14.5 Hz);
3.01 (1H, doublet of doublets, J=10 Hz & 14.5 Hz);
3.75 (3H, singlet);
3.77 (6H, singlet);
3.79–3.84 (1H, multiplet);
4.41–4.50 (2H, multiplet);
6.10 (2H, singlet);
6.88 (1H, broad);
7.04 (1H, doublet, J=1.5 Hz);
7.09 (1H, doublet of doublets, J=1.5 Hz & 8 Hz);
7.19 (1H, singlet);
7.31 (1H, doublet, J=8 Hz);
7.63–7.65 (2H, multiplet);
8.71–8.73 (2H, multiplet).
Infrared Absorption Spectrum (CHCl$_3$) $v_{max}$ cm$^{-1}$:
3671, 3443, 2961, 2937, 2873, 2860, 2841, 1730, 1672, 1608, 1592, 1557, 1525, 1514, 1488, 1467, 1456, 1439, 1420, 1366, 1328, 1295, 1270, 1153, 1124, 1101, 1082, 1066, 1041.

EXAMPLE 200

N-[2-t-Butyl-5-(N-t-butoxycarbonylaminomethyl) phenyl]-3-(2,4,6-trimethoxyphenyl octanamide (Compound No. 438)

Following a similar procedure to that described in Example 144, but using N-(2-t-butyl-5-aminomethylphenyl)-3-(2,4,6-trimethoxyphenyl)octanamide prepared as described in Preparation 72C) and di-t-butyl dicarbonate, the title compound was obtained as a colorless foam-like substance.
Nuclear Magnetic Resonance Spectrum (400 MHz, CDCl$_3$) δ ppm:
0.81–0.85 (3H, multiplet);
1.26–1.32 (6H, multiplet);
1.28 (9H, singlet);
1.45 (9H, singlet);
1.61–1.65 (1H, multiplet);
1.84–1.88 (1H, multiplet);
2.69 (1H, doublet of doublets, J=6 Hz & 14.5 Hz);
2.99 (1H, doublet of doublets, J=10 Hz & 14.5 Hz);
3.74–3.85 (1H, multiplet);
3.77 (3H, singlet);
3.78 (6H, singlet);
4.19 (2H, doublet, J=5.5 Hz);
4.80 (1H, broad);
6.12 (2H, singlet);.
7.01 (1H, singlet);
7.04 (1H, doublet, J=8 Hz);
7.10 (1H, singlet);
7.28 (1H, doublet, J=8Hz).
Infrared Absorption Spectrum (CHCl$_3$) $v_{max}$ cm$^{-1}$:
3451, 3406, 2961, 2934, 2873, 2861, 2841, 1709, 1608, 1592, 1504, 1495, 1467, 14 56, 1439, 1420, 1394, 1368, 1329, 1154, 1125, 1101, 1079, 1063, 1042.

EXAMPLE 201

N-[2-t-Butyl-5-(N-methylcarbamoyl)phenyl]-3-(2,3,4-trimethoxyphenyl)octanamide (Compound No. 465)

Following a similar procedure to that described in Example 8, but using N-(2-t-butyl-5-carboxyphenyl)-3-(2, 3,4-trimethoxyphenyl)octanamide (prepared as described in Preparation 74A), the title compound was obtained as colorless crystals.
Nuclear Magnetic Resonance Spectrum (270 MHz, CDCl$_3$) δ ppm:
0.84–0.92 (3H, multiplet);
1.15–1.38 (6H, multiplet);
1.31 (9H, singlet);
1.65–1.78 (2H, multiplet);
2.60–2.72 (2H, multiplet);
2.96 (3H, doublet, J=4.9 Hz);
3.43–3.56 (1H, multiplet);
3.73 (3H, singlet);
3.83 (3H, singlet);
3.91 (3H, singlet);
6.30 (1H, broad singlet);
6.66 (1H, doublet, J=8.6 Hz);
6.91 (1H, doublet, J=8.6 Hz);
7.14 (1H, broad singlet);
7.40 (1H, doublet, J=8.6 Hz);
7.45 (1H, doublet, J=1.9 Hz);
7.62 (1H, doublet of doublets, J=1.9 Hz & 8.6Hz).
Infrared Absorption Spectrum (CHCl$_3$) $v_{max}$ cm$^{-1}$:
3463, 2961, 2934, 1660, 1563, 1537, 1496, 1466, 1418, 1300, 1278, 1097.

EXAMPLE 202

N-[2-t-Butyl-5'-(-2-pyrazinylcarbamoyl)phenyl]-3-(2,3,4-trimethoxyphenyl octanamide (Compound No. 468)

Following a similar procedure to that described in Example 8, but using N-(2-t-butyl-5-carboxyphenyl)-3-(2, 3,4-trimethoxyphenyl)octanamide (prepared as described in Preparation 74A) and 2-aninopyrazine, the title compound was obtained as a colorless foam-like substance.
Nuclear Magnetic Resonance Spectrum (270 MHz, CDCl$_3$) δ ppm:
0.84–0.86 (3H, multiplet);
1.14–1.37 (6H, multiplet);
1.33 (9H, singlet);
1.68–1.80 (2H, multiplet);
2.70–2.73 (2H, multiplet);
3.41–3.51 (1H, multiplet);
3.68 (3H, singlet);
3.78 (3H, singlet);
3.93 (3H, singlet);
6.70 (1H, doublet, J=8.6 Hz);
6.93 (1H, doublet, J=8.6 Hz);
7.18 (1H, broad singlet);
7.48 (1H, doublet, J=8.6 Hz);
7.67–7.75 (2H, multiplet);
8.29–8.30 (1H; multiplet);
8.37–8.38 (1H, doublet, J=2.6 Hz);
8.77 (1H, broad singlet);
9.67 (1H, doublet, J=1.3Hz).
Infrared Absorption Spectrum (CHCl$_3$) $v_{max}$ cm$^{-1}$:
3412, 2962, 2934, 1687, 1536, 1496, 1466, 1413, 1299, 1097, 1012.

EXAMPLE 203

N-[2-t-Butyl-5-(N'-2-pyridylcarbamoyl)phenyl]-3-3-(2,3,4-trimethoxyphenyl)octanamide (Compound No. 467)

Following a similar procedure to that described in Example 8, but using N-(2-t-butyl-5-carboxyphenyl)-3-(2, 3,4-trimethoxyphenyl)octanamide (prepared as described in Preparation 74A) and 2-aminopyridine, the title compound was obtained as a colorless foam-like substance.
Nuclear Magnetic Resonance Spectrum (270 MHz, CDCl$_3$) δ ppm:
0.83–0.87 (3H, multiplet);
1.18–1.41 (6H, multiplet);
1.33 (9H, singlet);
1.69–1.85 (2H, multiplet);
2.72 (2H, doublet, J=7.5 Hz);
3.42–3.53 (1H, multiplet);
3.68 (3H, singlet);
3.77 (3H, singlet);
3.93 (3H, singlet);
6.72 (1H, doublet, J=8.6 Hz);
6.94 (1H, doublet, J=8.6 Hz);
7.04–7.09 (1H, multiplet);
7.20 (1H, broad singlet);
7.45 (1H, doublet, J=8.6 Hz);
7.65 (1H, doublet, J=2.0 Hz);
7.69–7.76 (2H, multiplet);
8.31–8.36 (2H, multiplet);
8.65 (1H, broad singlet).
Infrared Absorption Spectrum (CHCl$_3$) $v_{max}$ cm$^{-1}$:
3419, 2962, 2934, 1682, 1597, 1578, 1496, 1433, 1309, 1097.

EXAMPLE 204

N-{2-t-Butyl-5-[N'-3-(1H)-pyrazolylcarbamoyl]phenyl}-3-(2,3,4-trimethoxyphenyl)octanamide (Compound No. 678)

Following a similar procedure to that described in Example 141, but using N-(2-t-butyl-5-carboxyphenyl)-3-(2,3,4-trimethoxyphenyl)octanamide (prepared as described in Preparation 74A) and 3-aminopyrazole, the title compound was obtained as a colorless foam-like substance.
Nuclear Magnetic Resonance Spectrum (270 MHz, CDCl$_3$) δ ppm:
0.84–0.91 (3H, multiplet);
1.11–1.42 (6H, multiplet);
1.33 (9H, singlet);
1.57–1.78 (2H, multiplet);
2.70 (2H, doublet, J=7.6 Hz);
3.41–3.55 (1H, multiplet);
3.73 (3H, singlet);
3.82 (3H, singlet);
3.90 (3H, singlet);
4.09 (2H, singlet);
5.96 (1H, doublet, J=2.0 Hz);
6.62 (1H, doublet, J=8.6 Hz);
6.88 (1H, doublet, J=8.6 Hz);
7.20 (1H, broad singlet);
7.45 (1H, doublet, J=8.6 Hz);
7.78 (1H, doublet, J=8.6 Hz);
7.83 (1H, doublet, J=1.7 Hz);
8.07 (1H, doublet, J=1.7Hz).
Infrared Absorption Spectrum (CHCl$_3$) $v_{max}$ cm$^{-1}$:
3487, 3403, 2961, 2934, 1687, 1617, 1575, 1496, 1466, 1374, 1277, 1097.

EXAMPLE 205

N-[2-t-Butyl-5-(N'-4-pyridylcarbamoyl)phenyl]-3-(2,3,4-trimethoxyphenyl)octanamide (Compound No. 469)

Following a similar procedure to that described in Example 141, but using N-(2-t-butyl-5-carboxyphenyl)-3-(2,3,4-trimethoxyphenyl)octanamide (prepared as described in Preparation 74A) and 4-aminopyridine, the title compound was obtained as a colorless foam-like substance.
Nuclear Magnetic Resonance Spectrum (270 Mz, CDCl$_3$) δ ppm:
0.78–0.88 (3H, multiplet);
1.10–1.38 (6H, multiplet);
1.34 (9H, singlet);
1.61–1.82 (2H, multiplet);
2.72–2.80 (2H, multiplet);
3.41–3.50 (1H, multiplet);
3.66 (3H, singlet);
3.73 (3H, singlet);
3.91 (3H, singlet);
6.63 (1H, doublet, J=8.6 Hz);
6.91 (1H, doublet, J=8.6 Hz);
7.25 (1H, singlet);
7.40 (1H, doublet, J=1.9 Hz);
7.48 (1H, doublet, J=8.3 Hz);
7.65–7.72 (3H, multiplet);
8.53 (2H, doublet, J=7.3 Hz);
8.98 (1H, broad singlet).
Infrared Absorption Spectrum (CHCl$_3$) $v_{max}$ cm$^{-1}$:
3427, 2962, 2934, 1687, 1597, 1590, 1506, 1495, 1466, 1416, 1332, 1281, 1096.

EXAMPLE 206

N-[2-t-Butyl-5-(2-carbamoylethyl)phenyl]-3-(2,3,4-trimethoxyphenyl)octanamide (Compound No. 470)

Following a similar procedure to that described in Example 141, but using N-[2-t-butyl-5-(2-carboxyethyl)phenyl]-3-(2,3,4-trimethoxyphenyl)octanamide (prepared as described in Preparation 79), the title compound was obtained as a colorless foam-like substance.
Nuclear Magnetic Resonance Spectrum (400 MHz, CDCl$_3$) δ ppm:
0.83–0.86 (3H, multiplet);
1.13–1.49 (6H, multiplet);
1.29 (9H, singlet);
1.56–1.77 (2H, multiplet);
2.41 (2H, triplet, J=7.9 Hz);
2.59–2.74 (2H, multiplet);
2.82 (2H, triplet, J=7.9 Hz);
3.49–3.57 (1H, multiplet);
3.76 (3H, singlet);
3.84 (3H, singlet);
3.91 (3H, singlet);
5.23 (1H, broad singlet);
5.87 (1H, broad singlet);
6.68 (1H, singlet);
6.69 (1H, doublet, J=8.6 Hz);
6.93 (1H, doublet, J=8.6 Hz);
6.96 (1H, doublet of doublets, J=1.9 Hz & 8.1 Hz);
7.02 (1H, singlet);
7.23 (1H, doublet, J=8.1Hz).
Infrared Absorption Spectrum (CHCl$_3$) $v_{max}$ cm$^{-1}$:
3529, 3490, 3412, 2961, 2934, 1679, 1596, 1495, 1466, 1420, 1276, 1097, 1016.

EXAMPLE 207

N-(2-t-Butyl-5-carbamoylphenyl)-3-(2,3,4-trimethoxyphenyl)octanamide (Compound No. 93)

Following a similar procedure to that described in Example 141, but using N-(2-t-butyl-5-carboxyphenyl)-3-(2,3,4-trimethoxyphenyl)octanamide (prepared as described in Preparation 74A), the title compound was obtained as a colorless foam-like substance.
Nuclear Magnetic Resonance Spectrum (400 MHz, CDCl$_3$) δ ppm:
0.87–0.89 (3H, multiplet);
1.16–1.38 (6H, multiplet);
1.32 (9H, singlet);
1.65–1.77 (2H, multiplet);
2.63–2.75 (2H, multiplet);
3.44–3.53 (1H, multiplet);
3.71 (3H, singlet);
3.83 (3H, singlet);
3.91 (3H, singlet);
5.50 (1H, broad singlet);
6.68 (1H, broad singlet);
6.67 (1H, doublet, J=8.6 Hz);
6.91 (1H, doublet, J=8.6 Hz);
7.17 (1H, singlet);
7.42 (1H, doublet, J=8.6 Hz);
7.49 (1H, doublet, J=1.2 Hz);
7.64 (1H, doublet of doublets, J=1.8 Hz & 8.6Hz).
Infrared Absorption Spectrum (CHCl$_3$) $\nu_{max}$ cm$^{-1}$:
3528, 3475, 3414, 2961, 2934, 2874, 2860, 1676, 1588, 1495, 1466, 1419, 1377, 1278, 1097.

EXAMPLE 208

N-[2-t-Butyl-5-(N'-2-thiazolylcarbamoyl)phenyl]-3-(2,3,4-trimethoxyphenyl)octanamide (Compound No. 471)

Following a similar procedure to that described in Example 8, but using N-20 (2-t-butyl-5-carboxyphenyl)-3-(2,3,4-trimethoxyphenyl)octanamide (prepared as described in Preparation 74A) and 2-aminothiazole, the title compound was obtained as a colorless foam-like substance.
Nuclear Magnetic Resonance Spectrum (270 MHz, CDCl$_3$) δ ppm:
0.84–0.88 (3H, multiplet);
1.14–1.33 (6H, multiplet);
1.33 (9H, singlet);
1.44–1.96 (3H, multiplet);
2.72 (2H, doublet, J=8.0 Hz);
3.40–3.50 (1H, multiplet);
3.65 (3H, singlet);
3.76 (3H, singlet);
3.93 (3H, singlet);
6.72 (1H, doublet, J=8.6 Hz);
6.94 (1H, doublet, J=8.6 Hz);
7.00 (1H, doublet, J=3.3 Hz);
7.21 (1H, broad singlet);
7.47–7.50 (2H, multiplet);
7.56 (1H, doublet, J=2.0 Hz);
7.75 (1H, doublet of doublets, J=2.0 Hz & 8.5Hz).
Infrared Absorption Spectrum (CHCl$_3$) $\nu_{max}$ cm$^{-1}$:
3414, 2962, 2934, 1676, 1601, 1537, 1495, 1466, 1320, 1282, 1096.

EXAMPLE 209

N-[2-t-Butyl-5-(N'-3-pyridylcarbamoyl)phenyl]-3-(2,3,4-trimethoxyphenyl)octanamide (Compound No. 472)

Following a similar procedure to that described in Example 8, but using N-(2-t-butyl-5-carboxyphenyl)-3-(2,3,4-trimethoxyphenyl)octanamide (prepared as described in Preparation 74A) and 3-aminopyridine, the title compound was obtained as an orange foam-like substance.
Nuclear Magnetic Resonance Spectrum (270 MHz, CDCl$_3$) δ ppm:
0.84–0.88 (3H, multiplet);
1.17–1.31 (6H, multiplet);
1.33 (9H, singlet);
1.62–1.80 (2H, multiplet);
2.62–2.80 (2H, multiplet);
3.44–3.53 (1H, multiplet);
3.68 (3H, singlet);
3.74 (3H, singlet);
3.91 (3H, singlet);
6.64 (1H, doublet, J=8.6 Hz);
6.92 (1H, doublet, J=8.6 Hz);
7.24 (1H, broad singlet);
7.31 (1H, doublet of doublets, J=4.8 Hz & 8.4 Hz);
7.45–7.48 (2H, multiplet);
7.70 (1H, doublet of doublets, J=2.0 Hz & 8.4 Hz);
8.25–8.30 (1H, multiplet);
8.38 (1H, doublet of doublets, J=1.3 Hz & 4.6 Hz);
8.73–8.76 (2H, multiplet).
Infrared Absorption Spectrum (CHCl$_3$) $\nu_{max}$ cm$^{-1}$:
3666, 3428, 2962, 2934, 1731, 1679, 1530, 1496, 1466, 1421, 1297, 1096.

EXAMPLE 210

N-{2-t-Butyl-5-[2-N'-(2-pyridyl)carbamoylethyl]phenyl}-3-(2,3,4-trimethoxyphenyl)octanamide (Compound No. 473)

Following a similar procedure to that described in Example 8, but using N-[2-t-butyl-5-(2-carboxyethyl)phenyl]-3-(2,3,4-trimethoxyphenyl)octanamide (prepared as described in Preparation 79) and 2-aminopyridine, the title compound was obtained as a colorless foam-like substance.
Nuclear Magnetic Resonance Spectrum (270 MHz, CDCl$_3$) δ ppm:
0.85–0.87 (3H, multiplet);
1.15–1.38 (6H, multiplet);
1.29 (9H, singlet);
1.64–1.80 (2H, multiplet);
2.53–2.77 (4H, multiplet);
2.91 (2H, triplet, J=7.9 Hz);
3.51–3.61 (1H, multiplet);
3.81 (3H, singlet);
3.85 (3H, singlet);
3.91 (3H, singlet);
6.65 (1H, singlet);
6.70 (1H, doublet, J=8.6 Hz);
6.90–7.05 (4H, multiplet);
7.23 (1H, doublet, J=8.2 Hz);
7.65–7.72 (1H, multiplet);
8.21–8.31 (2H, multiplet);
8.41 (1H, broad singlet).
Infrared Absorption Spectrum (CHCl$_3$) $\nu_{max}$ cm$^{-1}$:
3417, 2961, 2933, 1687, 1597, 1578, 1514, 1495, 1465, 1434, 1301, 1097.

EXAMPLE 211

N-[2-t-Butyl-5-(2-N'-methylcarbamoylethyl)phenyl]-3-(2,3,4-trimethoxyphenyl)octanamide (Compound No. 474)

Following a similar procedure to that described in Example 8, but using N-[2-t-butyl-5-(2-carboxyethyl)phenyl]-3-(2,3,4-trimethoxyphenyl)octanamide (prepared as described in Preparation 79) and methylamine, the title compound was obtained as a colorless foam-like substance.

Nuclear Magnetic Resonance Spectrum (270 MHz, CDCl$_3$)
δ ppm:
0.83–0.87 (3H, multiplet);
1.13–1.37 (6H, multiplet);
1.28 (9H, singlet);
1.55–1.78 (2H, multiplet);
2.34 (2H, triplet, J=8.2 Hz);
2.58–2.83 (4H, multiplet);
2.74 (3H, doublet, J=4.9 Hz);
3.44–3.58 (1H, multiplet);
3.76 (3H, singlet);
3.84 (3H, singlet);
3.91 (3H, singlet);
5.91 (1H, broad singlet);
6.64–6.72 (2H, multiplet);
6.91–7.00 (2H, multiplet);
7.03 (1H, broad singlet);
7.21 (1H, doublet, J=8.1Hz).
Infrared Absorption Spectrum (CHCl$_3$) $v_{max}$ cm$^{-1}$:
3463, 3394, 2961, 2934, 1668, 1495, 1466, 1419, 1296, 1276, 1260, 1097.

EXAMPLE 212

N-{2-t-Butyl-5-[N'-3-(1H)-pyrazolylcarbamoyl]phenyl}-3-(2,3-dimethoxyphenyl)octanamide (Compound No. 679)

Following a similar procedure to that described in Example 141, but using N-(2-t-butyl-5-carboxyphenyl)-3-(2,3-dimethoxyphenyl)octanamide )prepared as described in Preparation 25) and 3-aminopyrazole, the title compound was obtained as a colorless foam-like substance.
Nuclear Magnetic Resonance Spectrum (270 MHz, CDCl$_3$)
δ ppm:
0.73–0.89 (3H, multiplet);
1.10–1.39 (6H, multiplet);
1.31 (9H, singlet);
1.52–1.80 (2H, multiplet);
2.70 (2H, doublet, J=7.7 Hz);
3.55–3.69 (1H, multiplet);
3.82 (3H, singlet);
3.84 (3H, singlet);
4.08 (2H, broad singlet);
5.95 (1H, doublet, J=3.0 Hz);
6.76 (1H, doublet, J=8.1 Hz);
6.83 (1H, doublet, J=7.2 Hz);
7.01 (1H, triplet, J=8.1 Hz);
7.17 (1H, broad singlet);
7.45 (1H, doublet, J=8.6 Hz);
7.78 (1H, doublet, J=8.6 Hz);
7.87 (1H, doublet, J=1.2 Hz);
8.07 (1H, doublet, J=2.7Hz).
Infrared Absorption Spectrum (CHCl$_3$) $v_{max}$ cm$^{-1}$:
3486, 3403, 2961, 2933, 1687, 1618, 1575, 1479, 1375, 1277.

EXAMPLE 213

N-{2-t-Butyl-5-[2-N'-(2-thiazolyl) carbamoylethyl]phenyl}-3-(2,3-dimethoxyphenyl)octanamide (Compound No. 340

Following a similar procedure to that described in Example 8, but using N-[2-t-butyl-5-(2-carboxyethyl)phenyl]-3-(2,3-dimethoxyphenyl)octanamide (prepared as described in Preparation 77), the title compound was obtained as colorless crystals.
Nuclear Magnetic Resonance Spectrum (400 MHz, CDCl$_3$)
δ ppm:
0.82–0.85 (3H, multiplet);
1.1–1.31 (6H, multiplet);
1.28 (9H, singlet);
1.64–1.81 (2H, multiplet);
2.69 (2H, doublet, J=7.5 Hz);
2.78 (2H, triplet, J=7.3 Hz);
2.98 (2H, triplet, J=73 Hz);
3.62–3.67 (1H, multiplet);
3.84 (3H, singlet);
3.85 (3H, singlet);
6.79 (1H, doublet, J=8.0 Hz);
6.84 (1H, doublet, J=7.6 Hz);
6.95–6.97 (2H, multiplet);
7.04 (1H, triplet, J=8.0 Hz);
7.10 (2H, singlet);
7.23 (1H, doublet, J=8.0 Hz);
7.41 (1H, doublet, J=3.6 Hz);
11.3 (1H, broad singlet).
Infrared Absorption Spectrum (CHCl$_3$) $v_{max}$ cm$^{-1}$:
3412, 3173, 2961, 2934, 1731, 1687, 1563, 1536, 1480, 1274, 1167.

EXAMPLE 214

N-(2-t-Butyl-5-carbamoylphenyl-3-[5-chloro-2-methoxy-4-(3-propylsulfonylpropoxy)phenyl]heptanamide (Compound No. 666)

Following a similar procedure to that described in Example 20, but using N-(2-t-butyl-5-carboxyphenyl)-3-[5-chloro-2-methoxy-4-(3-propylsulfonyl-propoxy)phenyl]heptanamide (prepared as described in Preparation 31X), the title compound was obtained as crystals, melting at 144°–150° C. (ethyl acetate-hexane)
Nuclear Magnetic Resonance Spectrum (270 MHz, CDCl$_3$)
δ ppm:
0.85 (3H, triplet, J=7 Hz);
1.05–1.40 (4H, multiplet);
1.10 (3H, triplet, J=7 Hz);
1.33 (9H, singlet);
1.53–1.82 (2H, multiplet);
1.82–2.02 (2H, multiplet);
2.30–2.44 (2H, multiplet);
2.67 (2H, doublet, J=7 Hz);
2.94–3.04 (2H, multiplet);
3.25 (2H, triplet, J=7 Hz);
3.45–3.61 (1H, multiplet);
3.80 (3H, singlet);
4.17 (2H, triplet, J=7 Hz);
5.40–5.61 (1H, broad);
6.12–6.38 (1H, broad);
6.48 (1H, singlet);
7.04–7.68 (5H, multiplet).
Infrared Absorption Spectrum (KBr) $v_{max}$ cm$^{-1}$:
3346, 3183, 1656, 1612, 1506, 1306, 1201, 1127, 1073, 1033.

EXAMPLE 215

N-(2-t-Butyl-5-carbamoylphenyl)-3-(4-butyryl-2-methoxyphenyl)-5-methylhexanamide(Compound No. 277)

Following a similar procedure to that described in Example 99, but using N-(2-t-butyl-5-carboxyphenyl)-3-(4-butyryl-2-methoxyphenyl)-5-methylhexanamide (prepared as described in Preparation 64D), title compound was obtained as crystals, melting at 189°–190° C. (ethyl acetate)
Nuclear Magnetic Resonance Spectrum (270 MHz, CDCl$_3$)
δ ppm:

0.87 (3H, doublet, J=7 Hz);
0.89 (3H, doublet, J=7 Hz);
0.99 (3H, doublet, J=7 Hz);
1.29 (9H, singlet);
1.47–1.69 (2H, multiplet);
1.70–1.86 (1H, multiplet);
1.75 (2H, sextet, J=7 Hz);
2.62–2.80 (2H, multiplet);
2.91 (2H, triplet, J=7 Hz);
3.70–3.83 (1H, multiplet);
3.89 (3H, singlet);
5.27–5.61 (1H, broad);
6.05–6.40 (1H, broad);
7.08–7.71 (7H, multiplet).
Infrared Absorption Spectrum (KBr) $v_{max}$ cm$^{-1}$:
 1684, 1657, 1611, 1532, 1462, 1414, 1302, 1250, 1194, 1163, 1123.

EXAMPLE 216

N-(2-t-Butyl-5-carbamoylphenyl)-3-[4-(1-hydroxybutyl)-2-methoxyphenyl]-5-methylhexanamide (Compound No. 233)

Following a similar procedure to that described in Example 128, but using N-(2-t-butyl-5-carbamoylphenyl)-3-(4-butyryl-2-methoxyphenyl)-5-methylhexanamide (prepared as described in Example 215), the title compound was obtained as a foam-like substance.
Nuclear Magnetic Resonance Spectrum (270 MHz, CDCl$_3$) δ ppm:
0.87 (3H, doublet, J=7 Hz);
0.91 (3H, doublet, J=7 Hz);
0.92 (3H, triplet, J=7 Hz);
1.31 (4.5H, singlet);
1.32 (4.5H, singlet);
1.35–1.70 (5H, multiplet);
1.68–1.84 (2H, multiplet);
2.60–2.80 (2H, multiplet);
2.94–3.02 (0.5H, broad);
3.11–3.20 (0.5H, broad);
3.58–3.75 (1H, multiplet);
3.78 (1.5H, singlet);
3.82 (1.5H, singlet);
4.59–4.69 (1H, multiplet);
5.32–5.57 (1H, broad);
6.18–6.46 (1H, broad);
6.90–7.50 (7H, multiplet).
Infrared Absorption Spectrum (KBr) $v_{max}$ cm$^{-1}$:
 1660, 1614, 1560, 1515, 1465, 1419, 1366, 1254, 1159, 1119, 1039.

EXAMPLE 217

N-(2-t-Butyl-5-carbamoylphenyl)-3-(4-propionyl-2-methoxyphenyl)-5-methylhexanamide (Compound No. 667)

Following a similar procedure to that described in Example 99, but using N-(2-t-Butyl-5-carboxyphenyl)-3-(4-propionyl-2-methoxyphenyl)-5-methyl-hexanamide (prepared as described in Preparation 64E), the title compound was obtained as crystals, melting at 186.5°–187° C. (methylene chloride-hexane).
Nuclear Magnetic Resonance Spectrum (270 MHz, CDCl$_3$) δ ppm:
0.86 (3H, doublet, J=7 Hz);
0.89 (3H, doublet, J=7 Hz);
1.21 (3H, triplet, J=7 Hz);
1.29 (9H, singlet);
1.48–1.61 (2H, multiplet);
1.72–1.87 (1H, multiplet);
2.62–2.83 (2H, multiplet);
2.97 (2H, quartet, J=7 Hz);
3.70–3.85 (1H, multiplet);
3.89 (3H, singlet);
5.34–5.75 (1H, broad);
6.01–6.40 (1H, broad);
7.08–7.81 (7H, multiplet).
Infrared Absorption Spectrum (KBr) $v_{max}$ cm$^{-1}$:
 1680, 1655, 1612, 1533, 1500, 1465, 1450, 1412, 1383, 1366, 1254.

EXAMPLE 218

N-(2-t-Butyl-5-carbamoylphenyl)-3-[4-(1-hydroxypropyl)-2-methoxyphenyl]-5-methylhexanamide (Compound No. 668)

Following a similar procedure to that described in Example 128, but using N-(2-t-butyl-5-carbamoylphenyl)-3-(4-propionyl-2-methoxyphenyl)-5-methylhexanamide (prepared as described in Example 217) the title compound was obtained as a foam-like substance.
Nuclear Magnetic Resonance Spectrum (270 MHz, CDCl$_3$) δ ppm:
0.87 (3H, doublet, J=7 Hz);
0.91 (3H, doublet, J=7 Hz);
0.92 (3H, triplet, J=7 Hz);
1.31 (4.5H, singlet);
1.32 (4.5H, singlet);
1.26–1.76 (3H, multiplet);
1.64–1.90 (2H, multiplet);
2.61–2.78 (2H, multiplet);
2.90–2.99 (0.5H, broad);
3.10–3.19 (0.5H, broad);
3.59–3.78 (1H, multiplet);
3.78 (1.5H, singlet);
3.81 (1.5H, singlet);
4.50–4.62 (1H, multiplet);
5.30–5.64 (1H, broad);
6.10–6.40 (1H, broad);
6.89–7.51 (7H, multiplet).
Infrared Absorption Spectrum (KBr) $v_{max}$ cm$^{-1}$:
 1659, 1613, 1557, 1514, 1464, 1420, 1366, 1254, 1160, 1119, 1040.

EXAMPLE 219

N-(2-t-Butyl-5-carbamoylphenyl)-3-(4-isopropylsulfonyl-2-methoxylphenyl)heptanamide (Compound No. 585)

Following a procedure similar to that described in Example 20, but using N-(2-t-butyl-5-carboxyphenyl)-3-(4-isopropylsulfonyl-2-methoxyphenyl)-heptanamide (prepared as described in Preparation 96), the title compound was obtained as a foam-like substance.
Nuclear Magnetic Resonance Spectrum (270 MHz, CDCl$_3$) δ ppm:
0.85 (3H, triplet, J=7 Hz);
1.05–1.40 (4H, multiplet);
1.27 (3H, doublet, J=7 Hz);
1.28 (3H, doublet, J=7 Hz);
1.33 (9H, singlet);
1.69–1.84 (2H, multiplet);
2.66–2.83 (2H, multiplet);
3.19(1H, septet, J=7Hz)

3.62–3.80 (1H, multiplet);
3.72 (3H, singlet);
5.40–5.72 (1H, broad);
5.90–6.26 (1H, broad);
7.05–7.79 (7H, multiplet).
Infrared Absorption Spectrum (KBr) $\nu_{max}$ cm$^{-1}$:
  3350, 1661, 1615, 1493, 1404, 1302, 1248, 1138, 1032, 837.

EXAMPLE 220

N-(2-t-Butyl-5-carbamoylmethylphenyl)-3-(4-isopropylsulfonyl-2-methoxphenyl)heptanamide (Compound No. 677)

Following a procedure similar to that described in Example 20, but using N-(2-t-butyl-5-carboxymethylphenyl)-3-(4-isopropylsulfonyl-2-methoxyphenyl)-heptanamide (prepared as described in Preparation 97), the title compound was obtained as a foam-like substance.
Nuclear Magnetic Resonance Spectrum (270 MHz, CDCl$_3$) δ ppm:
0.85 (3H, triplet, J=7 Hz);
1.03–1.37 (10H, multiplet);
1.30 (9H, singlet);
1.70–1.85 (2H, multiplet);
2.64–2.81 (2H, multiplet);
3.20 (1H, septet, J=7 Hz);
3.46 (2H, singlet);
3.62–3.78 (1H, multiplet);
3.90 (3H, singlet);
5.32–5.45 (1H, broad);
5.62–5.77 (1H, broad);
6.98–7.12 (3H, multiplet);
7.28–7.51 (4H, multiplet).
Infrared Absorption Spectrum (KBr) $\nu_{max}$ cm$^{-1}$:
  3339, 3212, 1665, 1516, 1493, 1403, 1302, 1247, 1139, 1032.

EXAMPLE 221

N-(2-t-Butyl-5-carbamoylphenyl)-3-(2-methoxy-4-isobutyrylphenyl)octanamide (Compound No. 660)

Following a procedure similar to that described in Example 20, but using N-(2-t-butyl-5-carboxyphenyl)-3-(2-methoxy-4-isobutyrylphenyl)octanamide (prepared as described in Preparation 98), the title compound was obtained as a foam-like substance.
Nuclear Magnetic Resonance Spectrum (270 MHz, CDCl$_3$) δ ppm:
0.77–0.92 (3H, multiplet);
1.10–1.36 (6H, multiplet);
1.19 (3H, doublet, J=7 Hz);
1.20 (3H, doublet, J=7 Hz);
1.29 (9H, singlet);
1.70–1.86 (2H, multiplet);
2.65–2.87 (2H, multiplet);
3.52 (1H, septet, J=7 Hz);
3.59–3.72 (1H, multiplet);
3.89 (3H, singlet);
5.20–5.70 (1H, broad);
5.94–6.45 (1H, broad);
7.08–7.77 (7H, multiplet).
Infrared Absorption Spectrum (film) $\nu_{max}$ cm$^{-1}$:
  1657, 1615, 1603, 1466, 1414, 1379, 1368, 1256, 1206, 1156.

EXAMPLE 222

N-(2-Butyl-5-carbamoylphenyl)-3-[4-(1-hydroxy-2-methylpropyl)-2-methoxylphenyl]octanamide (Compound No. 658)

Following a procedure similar to that described in Example 128, but using N-(2-t-butyl-5-carbamoylphenyl)-3-(2-methoxy-4-isobutyrylphenyl)octanamide (prepared as described in Example 221), the title compound was obtained as crystals, melting at 162°–163° C.
Nuclear Magnetic Resonance Spectrum (270 MHz, CDCl$_3$) δ ppm:
0.76 (1.5H, doublet, J=7 Hz);
0.77 (1.5H, doublet, J=7 Hz);
0.78–0.91 (3H, multiplet);
1.01 (1.5H, doublet, J=7 Hz);
1.02 (1.5H, doublet, J=7 Hz);
1.12–1.40 (6H, multiplet);
1.32 (4.5H, singlet);
1.33 (4.5H, singlet);
1.68–1.81 (2H, multiplet);
1.83–2.02 (1H, multiplet);
2.68–2.83 (2H, multiplet);
2.97–3.09 (1H, broad);
3.41–3.63 (1H, multiplet);
3.78 (1.5H, singlet);
3.81 (1.5H, singlet);
4.29 (0.5H, doublet J=7 Hz);
4.32 (0.5H, doublet, J=7 Hz);
5.21–5.67 (1H, broad);
5.95–6.40 (1H, broad);
6.84–7.52 (7H, multiplet).
Infrared Absorption Spectrum (KBr) $\nu_{max}$ cm$^{-1}$:
  1660, 1614, 1515, 1466, 1419, 1396, 1379, 1366, 1253, 1041.

EXAMPLE 223

N-(2-t-Butyl-5-carbamoylphenyl)-3-(4-isopropylsulfonyl-2-methoxyphenyl)octanamide (Compound No. 579)

Following a procedure similar to that described in Example 20, but using N-(2t-butyl-5-carboxyphenyl)-3-(4-isopropylsulfonyl-2-methoxyphenyl)-octanamide (prepared as described in Preparation 99), the title compound was obtained as a foam-like substance.
Nuclear Magnetic Resonance Spectrum (270 MHz, CDCl$_3$) δ ppm:
0.74–0.93 (3H, multiplet);
1.05–1.38 (6H, multiplet);
1.27 (3H, doublet, J=7 Hz);
1.28 (3H, doublet, J=7 Hz);
1.33 (9H, singlet);
1.66–1.85 (2H, multiplet);
2.63–2.85 (2H, multiplet);
3.19 (1H, septet, J=7 Hz);
3.65–3.78 (1H, multiplet);
3.91 (3H, singlet);
5.32–5.81 (1H, broad);
6.07–6.48 (1H, broad);
7.08–7.22 (1H, broad);
7.29–7.50 (4H, multiplet);
7.57–7.79 (2H, multiplet).
Infrared Absorption Spectrum (film) $\nu_{max}$ cm$^{-1}$:
  1661, 1614, 155 8, 1518, 1493, 1466,1404, 1367, 1302, 1265, 1250, 1138, 1092, 1032.

EXAMPLE 224

N-(2-t-Butyl-5-carbamoylphenyl -3-(2-methoxy-4-butyrylphenyl)hexanamide (Compound No. 673)

Following a procedure similar to that described in Example 20, but using N-(2-t-butyl-5-carboxyphenyl)-3-(2-methoxy-4butyrylphenyl)hexanamide (prepared as described in Preparation 100), the title compound was obtained as crystals, melting at 193°–194° C. (from methylene chloride-hexane).
Nuclear Magnetic Resonance Spectrum (270 MHz, CDCl$_3$) δ ppm:
0.88 (3H, triplet, J=7 Hz);
1.00 (3H, triplet, J=7 Hz);
1.12–1.34 (2H, multiplet);
1.29 (9H, singlet);
1.68–1.88 (2H, multiplet);
1.76 (2H, sextet, J=7 Hz);
2.68–2.85 (2H, multiplet);
2.91 (2H, triplet, J=7 Hz);
3.61–3.77 (1H, multiplet);
3.89 (3H, singlet);
5.40–5.66 (1H, broad);
6.03–6.30 (1H, broad);
7.08–7.78 (7H, multiplet).
Infrared Absorption Spectrum (KBr) ν$_{max}$ cm$^{-1}$:
1682, 1522, 1464, 1414, 1366, 1304, 1254, 1198, 1167, 1136, 1102.

EXAMPLE 225

N-(2-t-Butyl-5-carbamoylphenyl)-3-[4-(1-hydroxybutyl)-2-methoxyphenyl]hexanamide
(Compound No. 674)

Following, a procedure similar to that described in Example 128, but using N-(2-t-butyl-5-carbamoylphenyl)-3-(2-methoxy-4-butyrylphenyl)hexanamide (prepared as described in Example 224), the title compound was obtained as a foam-like substance.
Nuclear Magnetic Resonance Spectrum.(270 MHz, CDCl$_3$) δ ppm:
0.89 (3H, triplet, J=7 Hz);
0.93 (3H, triplet, J=7 Hz);
1.12–1.40 (2H, multiplet);
1.31 (4.5H, singlet);
1.32 (4.5H, singlet);
1.50–1.80 (2H, multiplet);
1.64–1.88 (4H, multiplet);
2.65–2.80 (2H, multiple t);
2.78–2.99 (0.5H, broad);
3.00–3.17 (0.5H, broad);
3.48–3.68 (1H, multiplet);
3.78 (1.5H, singlet);
3.82 (1.5H, singlet);
4.60–4,70 (1H, multiplet);
5.30–5.59 (1H, broad);
6.04–6.30 (1H, broad);
6.90–7.52 (7H, multiplet).
Infrared Absorption Spectrum (film) ν$_{max}$ cm$^{-1}$:
1657, 1615, 1559, 1520, 1462, 1418, 1254, 1159, 1109, 1073, 1038.

PREPARATION 1

Ethyl 3-(2,4-dimethoxyphenyl)-2-ethoxycarbonyl-2-propenoate

A solution of 10.0 g (60.2 mmol) of 2,4-dimethoxybenzaldehyde, 10.6 g (66.3 mmol) of diethyl malonate, 0.19 g (1.6 mmol) of benzoic acid and 0.20 ml (2.0 mmol) of piperidine in 43 ml of benzene was heated under reflux for 16 hours, whilst removing the water formed. At the end of this time, it was allowed to cool to room temperature, and then the reaction mixture was diluted with a 2:1 by volume mixture of ethyl acetate and hexane, and the diluted solution was washed with a saturated aqueous solution of sodium hydrogencarbonate, with 1N aqueous hydrochloric acid, with water and with a saturated aqueous solution of sodium chloride, in that order, after which it was dried. The solvent was removed by distillation under reduced pressure, and the resulting residue was recrystallized from a mixture of diisopropyl ether and hexane, to give 17.1 g (yield 92%) of the title compound as crystals, melting at 40°–41° C. (from a mixture of diisopropyl ether and hexane).
Nuclear Magnetic Resonance Spectrum (270M Hz, CDCl$_3$) δ ppm:
1.28 (3H, triplet, J=7 Hz);
1.32 (3H, triplet, J=7 Hz);
3.83 (3H, singlet);
3.84 (3H, singlet);
4.23–4.36 (4H, multiplet);
6.44 (1H, singlet);
6.45 (1H, doublet, J=8.5 Hz);
7.36 (1H, doublet, J=8.5 Hz);
8.06 (1H, singlet).
Infrared Absorption Spectrum (KBr) ν$_{max}$ cm$^{-1}$:
1719, 1605, 1576, 1503, 1468, 1451, 1377, 1362, 1318, 1298, 1246, 1213.

PREPARATION 2

Diethyl 2-[1-(2,4-dimethoxyphenyl)hexyl]malonate

A solution of 9.15 g (29.7 mmol) of ethyl 3-(2,4-dimethoxyphenyl)-2-ethoxycarbonyl-2-propenoate (prepared as described in Preparation 1) in 9 ml of diethyl ether was added to 72 ml (36 mmol) of a 0.5M ice-cooled solution of pentylmagnesium bromide in diethyl ether, and the resulting mixture was stirred at the same temperature for 1.5 hours. At the end of this title, the reaction mixture was poured into a 10% aqueous solution of hydrochloric acid in ice, and then extracted with ethyl acetate. The extract was washed with water and dried over anhydrous sodium sulfate. The solvent was removed by distillation under reduced pressure, and the resulting residue was purified by column chromatography through 200 g of silica gel, using a 10:1 by volume mixture of hexane and ethyl acetate as the eluent, to give 8.65 g (yield 77%) of the title compound as an oily substance.
Nuclear Magnetic Resonance Spectrum (270M Hz, CDCl$_3$) δ ppm:
0.73–0.85 (3H, multiplet);
0.97 (3H, triplet, J=7 Hz);
1.00–1.32 (6H, multiplet);
1.28 (3H, triplet, J=7 Hz);
1.47–1.62 (1H, multiplet);
1.66–1.85 (1H, multiplet);
3.46–3.66 (1H, multiplet);
3.78 (3H, singlet);
3.80 (3H, singlet);
3.82–3.96 (3H, multiplet);
4.21 (2H, quartet, J=7 Hz);
6.39 (1H, doublet, J=8 Hz);
6.40 (1H, singlet);
7.00 (1H, doublet, J=8 Hz).
Infrared Absorption Spectrum (liquid film) ν$_{max}$ cm$^{-1}$:
1754, 1733, 1613, 1587, 1508, 1466, 1421, 1369, 1292, 1263, 1209, 1158, 1136, 1037.

PREPARATION 3

3-(2,4-Dimethoxyphenyl)octanoic acid
3(i) 2-[1-(2,4-Dimethoxyphenyl)hexyl]malonic acid A solution of 4.40 g (110 mmol) of sodium hydroxide in 14 ml of water was added to a solution of 8.37 g (22.0 mmol) of diethyl 2-[1-(2,4-dimethoxy-phenyl)hexyl]malonate (prepared as described in Preparation 2) in 50ml of ethanol, and the resulting mixture was heated under reflux for 2.5 hours. At the end of this time, the reaction mixture was allowed to cool to room temperature, after which it was freed from ethanol by evaporation under reduced pressure. The resulting residue was acidified with concentrated hydrochloric acid and then extracted with ethyl acetate. The extract was washed with water and then with a. saturated aqueous solution of sodium chloride, after which it was dried over anhydrous sodium sulfate. The solvent was removed by distillation under reduced pressure, to give 6.57 g of the title compound as a foam-like substance.

3(ii) 3-(2,4-Dimethoxyphenyl octanoic acid

A solution of 6.57 g of 2-[1-(2,4-dimethoxyphenyl)hexyl] malonic acid [prepared as described in step (i) above] in 60 ml of xylene was heated under reflux for 3 hours. At the end of this time, the solvent was removed by distillation under reduced pressure, and the resulting residue was purified by column chromatography through 100 g of silica gel, using a gradient elution method, with mixtures of methylene chloride and methanol ranging from 1:0 to 10:1 by volume as the eluent, to give 4.55 g (a total yield of 74% over the two steps) of the title compound as crystals, melting at 52°–53° C. (from hexane). Nuclear Magnetic Resonance Spectrum (270M Hz, CDCl$_3$) δ ppm:
0.78–0.91 (3H, multiplet);
1.06–1.32 (6H, multiplet);
1.50–1.76 (2H, multiplet);
2.58–2.69 (2H, multiplet);
3.39 (1H, quintet, J=7.5 Hz);
3.77 (3H, singlet);
3.79 (3H, singlet);
6.42–6.49 (2H, multiplet);
7.01 (1H, doublet, J=8.5 Hz).
Infrared Absorption Spectrum (KBr) ν$_{max}$ cm$^{-1}$:
1701, 1612, 1587, 1504, 1466, 1437, 1421, 1319, 1294, 1265, 1209, 1155, 1124, 1045.

PREPARATION 4

Methyl 4-t-butyl-3-nitrobenzoate 13 ml (0.15 mol) of oxalyl chloride were added, with ice-cooling, to a solution of 20.9 g (0.094 mol) of 4-t-butyl-3-nitrobenzoic acid in 200 ml of methylene chloride, and then 0.3 ml of dimethylformamide was added to the resulting mixture. After this addition, the temperature of the reaction mixture was allowed to rise to room temperature, and the mixture was then stirred at room temperature for 4 hours. At the end of this time, any excess of the reagent and the solvent were removed by distillation under reduced pressure, and the residue was again dissolved in 150 ml of methylene chloride. 19 ml (0.25 mol) of pyridine and 6.0 ml (0.15 mol) of methanol were then added, with ice-cooling, to the solution, and the resulting mixture was stirred for 30 minutes with ice-cooling and then at room temperature for 30 minutes. At the end of this time, the reaction was quenched by adding water, the solvent was removed by distillation under reduced pressure, and the residue was extracted with ethyl acetate. The extract was washed with 2N aqueous hydrochloric acid, with water, with a saturated aqueous solution of sodium hydrogencarbonate and with water, in that order, and the solvent was removed by distillation under reduced pressure, to give 22.7 g of the title compound as an oily substance.

Infrared Absorption Spectrum (liquid film) ν$_{max}$ cm$^{-1}$:
1731, 1618, 1536, 1437, 1371, 1298, 1266, 1248, 1124.

PREPARATION 5

2-t-Butyl-5-methoxycarbonylaniline 40 g of zinc powder and 8 ml of acetic acid were added to a solution of 22.7 g of methyl 4-t-butyl-3-nitrobenzoate (prepared as described in Preparation 4) in 400 ml of methanol, and the resulting mixture was stirred for 40 minutes. At the end of this time, a further 26.6 g of zinc powder were added (making a total amount of 66.6 g or 1.02 mmol). 20 ml of acetic acid were then added dropwise over a period of 1.5 hours to the mixture, and the resulting mixture was stirred for 2 hours. At the end of this time, the reaction mixture was diluted with a 10:1 by volume mixture of ethyl acetate and hexane, and the diluted mixture was filtered, using a Celite (trade mark) filter aid. The filtrate was concentrated by evaporation under reduced pressure, and the concentrate was dissolved in ethyl acetate. The resulting solution was washed twice with a saturated aqueous solution of ammonium chloride, once with a saturated aqueous solution of sodium hydrogencarbonate and once with water. The solvent was removed by distillation under reduced pressure, and the resulting residue was purified by column chromatography through 150 g of silica gel, using a gradient elution method, with mixtures of hexane and ethyl acetate ranging from 30:1 to 4:1 as the eluent, to give 16.5 g of the title compound as an oily substance, that is an 85% yield based on the starting material used in Preparation 4.
Nuclear Magnetic Resonance Spectrum (270M Hz, CDCl$_3$) δ ppm:
1.43 (9H, singlet);
3.88 (3H, singlet);
3.93 (2H, broad singlet);
7.26–7.41 (3H, multiplet).
Infrared Absorption Spectrum (liquid film) ν$_{max}$ cm$^{-1}$:
3499, 3387, 3237, 1715, 1626, 1568, 1437, 1418, 1308, 1239, 1123.

PREPARATION 6

N-(2-t-Butyl-5-methoxycarbonylphenyl)-3-(2.4-dimethoxphenyl)octanamide 0.64 ml (7.4 mmol) of oxalyl chloride was added to a solution of 1.03 g (3.7 mmol) of 3-(2,4-dimethoxyphenyl) octanoic acid (prepared as described in Preparation 3) and a catalytic amount of dimethylformamide in 10 ml of methylene chloride, and the resulting mixture was stirred for 1 hour. The solvent and an excess of the reagent were removed by distillation under reduced pressure, to give 3-(2,4-dimethoxyphenyl)octanoyl chloride. A solution of this acid chloride in 9 ml of methylene chloride was then added dropwise to an ice-cooled solution of 772 mg (3.7 mmol) of 2-t-butyl-5-methoxycarbonylaniline (prepared as described in Preparation 5) and 2 ml of pyridine in 5 ml of methylene chloride over a period of 2 minutes. The temperature of the mixture was allowed to rise to room temperature, and then the mixture was stirred for 20 minutes. At the end of this time, the reaction was quenched by adding water, the reaction mixture was diluted with a 1:1 by volume mixture of ethyl acetate and hexane and the diluted solution was washed with water, with a saturated aqueous solution of sodium hydrogencarbonate and with a saturated aqueous solution of sodium chloride, in that order, after which it was dried over anhydrous magnesium sulfate. The solvent was removed by distillation under reduced pressure, and the resulting residue was purified by column chromatography through 100 g of silica gel, using a 2:3 by volume mixture of ethyl acetate and hexane as the eluent, to give 1.66 g (yield 96%) of the title compound as an oily substance.
Nuclear Magnetic Resonance Spectrum (270M Hz, CDCl$_3$) δ ppm:
0.81–0.87 (3H, multiplet);
1.18–1.31 (6H, multiplet);
1.28 (9H, singlet);
1.68–1.76 (2H, multiplet);
2.62–2.79 (2H, multiplet);
3.47–3.58 (1H, multiplet);
3.78 (6H, singlet);
3.87 (3H, singlet);
6.43–6.50 (2H, multiplet);
7.01 (1H, broad singlet);
7.12 (1H, doublet, J=8 Hz);
7.40 (1H, doublet, J=8 Hz);
7.75–7.79 (1H, multiplet);
7.93 (1H, broad singlet).
Infrared Absorption Spectrum (film) $v_{max}$ cm$^{-1}$:
  1725, 1651, 1613, 1507, 1464, 1300, 1264, 1210, 1123, 1038.

PREPARATION 7

N-(2-t-Butyl-5-carboxyphenyl-3-(2,4-dimethoxyphenyl)octanamide 3.5 ml (7.0 mmol) of a 2N aqueous solution of sodium hydroxide were added to a solution of 1.64 g (3.48 mmol) of N-(2-t-butyl-5-methoxycarbonyl-phenyl)-3-(2,4-dimethoxyphenyl)octanamide (prepared as described in Preparation 6) in 30 ml of methanol, and the resulting mixture was heated under reflux for 2 hours, after which the solvent was removed by distillation under reduced pressure. The residue was acidified with 2N aqueous hydrochloric acid and extracted with ethyl acetate. The extract was washed with a saturated aqueous solution of sodium chloride, after which it was dried over anhydrous sodium sulfate. The solvent was removed by distillation under reduced pressure, and the resulting residue was recrystallized from a mixture of ethyl acetate and hexane to give 1.13 g (yield 71%) of the title compound, melting at 153°–154° C.
Nuclear Magnetic Resonance Spectrum (270M Hz, CDCl$_3$) δ ppm:
0.82–0.88 (3H, multiplet);
1.20–1.35 (6H, multiplet);
1.29 (9H; singlet);
1.69–1.77 (2H, multiplet);
2.66–2.80 (2H, multiplet);
3.47–3.59 (1H, multiplet);
3.78 (6H, singlet);
6.44–6.52 (2H, multiplet);
7.01 (1H, broad singlet);
7.13 (1H, doublet, J=8 Hz);
7.42 (1H, doublet, J=8 Hz);
7.82 (1H, doublet, J=8 Hz);
7.89 (1H, broad singlet).
Infrared Absorption Spectrum (KBr) $v_{max}$ cm$^{-1}$:
  1694, 1652, 1612, 1507, 1465, 1291, 1209, 1157, 1126, 1038.

PREPARATION 8

N-[2-t-Butyl-5-(t-butyldimethylsilyloxymethyl) phenyl]-3-(2,4-dimethoxyphenyl)octanamide 1.24 ml (14.3 mmol) of oxalyl chloride and 2 drops of dimethyl-formamide were added to a solution of 2.67 g (9.54 mmol) of 3-(2,4-Dimethoxyphenyl)octanoic acid (prepared as described in Preparation 3) in 30 ml of methylene chloride, and the resulting mixture was stirred at room temperature for 2.5 hours. At the end of this time, the solvent and any excess of the reagent were removed by distillation under reduced pressure. The acid chloride thus obtained was dissolved in 20 ml of methylene chloride, and 2 ml of pyridine were added to the resulting mixture, with ice-cooling. A solution of 2.80 g (9.56 mmol) of a 2-t-butyl-5-(t-butyldimethylsilyloxymethyl)aniline (prepared as described in Preparation 12) in 10 ml of methylene chloride was added dropwise to the mixture over a period of 3 minutes, and the resulting mixture was stirred at the same temperature for 30 minutes. At the end of this time, the reaction was quenched by adding water, the solvent was removed by distillation under reduced pressure, and the residue was extracted with ethyl acetate. The extract was washed with dilute aqueous hydrochloric acid, with a saturated aqueous solution of sodium hydrogencarbonate and with water, in that order, after which it was dried over anhydrous sodium sulfate. The solvent was removed by distillation under reduced pressure, and the resulting residue was recrystallized from a mixture of ethyl acetate and hexane to give the title compound, melting at 117°–118° C.
Infrared Absorption Spectrum (KBr) $v_{max}$ cm$^{-1}$:
  3272, 1652, 1612, 1586, 1506, 1464, 1418, 1290, 1258, 1208, 1157, 1110.

PREPARATION 9

N-[2-t-Butyl-5-(hydroxymethyl)phenyl]-3-(2,4-dimethoxyphenyl)octanamide 0.1 ml of concentrated aqueous hydrochloric acid was added, with stirring and ice-cooling, to a solution of 460 mg (0.828 mmol) of N-[2-t-butyl-5-(t-butyldimethylsilyloxymethyl)phenyl]-3-(2,4-dimethoxyphenyl)octanamide (prepared as described in Preparation 8) in a mixture of 9 ml of methanol and 1 ml of methylene chloride, and the resulting mixture was allowed to stand at the same temperature for 40 minutes, after which it was diluted with diethyl ether. The diluted solution was washed twice with water and once with a saturated aqueous solution of sodium chloride, after which it was dried over anhydrous sodium sulfate. The solvent was removed by distillation under reduced pressure, and the resulting residue was recrystallized from a mixture of hexane and ethyl acetate to give 353 mg (yield 96%) of the title compound as crystals, melting at 125°–126° C.
Nuclear Magnetic Resonance Spectrum (270M Hz, CDCl$_3$) δ ppm:
0.76–0.92 (3H, multiplet);
1.09–1.35 (6H, multiplet);
1.27 (9H, singlet);
1.59–1.79 (2H, multiplet);
2.57–2.81 (2H, multiplet);
3.49 (1H, quintet, J=7.5 Hz);
3.78 (6H, singlet);
4.58 (2H, singlet);
6.41–6.51 (2H, multiplet);
7.01–7.38 (5H, multiplet).
Infrared Absorption Spectrum (KBr) $v_{max}$ cm$^{-1}$:
  3248, 1672, 1614, 1587, 1527, 1508, 1460, 1419, 1363, 1296, 1261, 1209, 1157, 1047.

PREPARATION 10

2-t-Butyl-5-hydroxymethyl-1-nitrobenzene

A solution of 3.12 g (28.8 mmol) of ethyl chloroformate in 10 ml of tetrahydrofuran was added dropwise to a solution of 6.0 g (26.9 mmol) of 4-t-butyl-3-nitrobenzoic acid and 3.12 g (30.9 mmol) of triethylamine in 60 ml of tetrahydrofuran over a period of 10 minutes, whilst ice-cooling, and the resulting mixture was then stirred at the same temperature for 45 minutes. At the end of this time, the reaction mixture was filtered using a Celite (trade mark) filter aid, and the precipitates were washed with tetrahydrofuran. A combined solution of the filtrate and the washings was added dropwise to a solution of 3.76 g. (99.5 mmol) of sodium borohydride in a mixture of 40 ml of tetrahydrofuran and 40 ml of water, whilst ice-cooling, over a period of 25 minutes, and the mixture was stirred at the same temperature for 2 hours. At the end of this time, the reaction mixture was freed from the tetrahydrofuran by evaporation under reduced pressure . The resulting residue was partitioned between diethyl ether and water, and the aqueous layer was extracted with diethyl ether. The combined organic layers were washed twice with water and once with a saturated aqueous solution of sodium chloride. The solvent was then removed by distillation under reduced pressure, and the resulting residue was purified by column chromatography through 100 g of silica gel, using a gradient elution method, with mixtures of ethyl acetate and hexane ranging from 20:80 to 30:70 by volume as the eluent, to give 5.24 g (yield 93%) of the title compound as an oily substance.

Nuclear Magnetic Resonance Spectrum (270M Hz, CDCl$_3$) δ ppm:
1.40 (9H, singlet);
4.69 (2H, doublet, J=5 Hz);
7.33 (1H, singlet);
7.41 (2H, doublet, J=9.5 Hz);
7.53 (1H, doublet, J=9.5 Hz).

PREPARATION 11

2-t-Butyl-5-(t-butyldimethylsilyloxymethyl)-1-nitrobenzene 4.15 g (27.5 mmol) of t-butyldimethylsilyl chloride, 3.85 ml (27.6 mmol) of triethylamine and 815 mg (0.503 mmol) of 4-N,N-dimethyl-aminopyridine were added, with ice-cooling, to a solution of 5.24 g (25.0 mmol) of 2-t-butyl-5-hydroxymethyl-1-nitrobenzene (prepared as described in Preparation 10) in 50 ml of methylene chloride, and the resulting mixture was stirred at room temperature for 40 minutes. The reaction mixture was then diluted with a 1:1 by volume mixture of hexane and diethyl ether, and the diluted solution was washed with water, with dilute aqueous hydrochloric acid, with water, with an aqueous solution of sodium hydrogencarbonate and with a saturated aqueous solution of sodium chloride, in that order. The solvent was removed by distillation under reduced pressure, and the resulting residue was purified by column chromatography through 100 g of silica gel, using a 1:1 by volume mixture of methylene chloride and hexane as the eluent, to give 8.04 g (yield 99%) of the title compound as an oily substance.

Infrared Absorption Spectrum (liquid film) ν$_{max}$ cm$^{-1}$:
1533, 1472, 1464, 1367, 1255, 1215, 1157, 1195, 1007, 939.

PREPARATION 12

2-t-Butyl-5-(t-butyldimethylsilyloxymethyl)aniline 81 g (1.24 mol) of zinc powder were added to a solution of 25.19 g (77.9 mmol) of 2-t-butyl-5-(t-butyldimethylsilyloxymethyl)-1-nitrobenzene (prepared as described in Preparation 11) in 270 ml of methanol, and then 10.8 ml of acetic acid were added to the resulting mixture, with ice-cooling. After the exothermic reaction had subsided, the reaction mixture was heated under reflux for 3 hours and then allowed to cool to room temperature, after which it was filtered using a Celite (trade mark) filter aid, and the zinc used was washed with methanol. The filtrate was combined with the washings and the combined mixture was concentrated by evaporation under reduced pressure. The concentrate was dissolved in ethyl acetate, and the resulting solution was washed with a saturated aqueous solution of sodium hydrogencarbonate and with a saturated aqueous solution of sodium chloride, in that order, after which it was dried over anhydrous sodium sulfate. The solvent was removed by distillation under reduced pressure, to give 22.9 g (a quantitative yield) of the title compound as an oily substance. The compound could be used without purification.

Infrared Absorption Spectrum (liquid film) ν$_{max}$ cm$^{-1}$:
3493, 3385, 1622, 1572, 1508, 1470, 1464, 1423, 1367, 1304, 1255, 1095.

PREPARATION 13

2-t-Butyl-5-cyanomethyl-1-nitrobenzene 629 mg (5.49 mmol) of mesyl chloride, followed by 566 mg (5.60 mmol) of triethylamine, were added, with ice-cooling, to a solution of 1.12 g (5.35 mmol) of 2-t-butyl-5-hydroxymethyl-1-nitrobenzene (prepared as described in Preparation 10) in 20 ml of methylene chloride, and the resulting mixture was stirred at the same temperature for 1 hour. At the end of this time, the reaction was quenched by adding water, and the reaction mixture was freed from methylene chloride by distillation under reduced pressure. The resulting residue was dissolved in ethyl acetate, and the solution was washed three times with water, after which it was dried over anhydrous sodium sulfate and the solvent was removed by distillation under reduced pressure, to give the mesyl derivative. The mesyl derivative thus obtained was dissolved in 10 ml of dimethylformamide, and 313 mg (6.39 mmol) of sodium cyanide and then 1.20 g (8.00 mmol) of sodium iodide were added to the solution. The resulting mixture was then stirred overnight at room temperature. At the end of this time, the reaction mixture was diluted with ethyl acetate, and the diluted solution was washed several times with water and once with a saturated aqueous solution of sodium chloride, after which it was dried over anhydrous sodium sulfate. The solvent was removed by distillation under reduced pressure, and then the residue was purified by column chromatography through 20 g of silica gel, using a gradient elution method, with mixtures of hexane and acetone ranging from 8:1 to 5:1 by volume as the eluent, to give 1.10 g (yield 95%) of the title compound as an oily substance.

Nuclear Magnetic Resonance Spectrum (270M Hz, CDCl$_3$) δ ppm:
1.40 (9H, singlet);
3.77 (2H, singlet),
7.28–7.62 (3H, multiplet).

PREPARATION 14

Methyl 2-(4-t-butyl-3-aminophenyl)acetate
14(i) Methyl 2-(4-t-butyl-3-nitrophenyl)acetate 1.50 g (6.87 mmol) of 2-t-butyl-5-cyanomethyl-1-nitrobenzene (prepared as described in Preparation 13) were added to a mixture of 4.1 ml of water and 4.1 ml of concentrated aqueous sulfuric acid, and the mixture was heated under reflux at 160° C. for 30 minutes. At the end of this time, the reaction mixture was poured into ice-water and the aqueous mixture was extracted with methylene chloride. The extract was washed with water and then with a saturated aqueous solution of sodium chloride, after which it was dried over anhydrous sodium sulfate and the solvent was removed by distillation under reduced pressure. The residue was dissolved in a mixture of 18 ml of benzene and 2 ml of methanol, and 4.50 ml (9.0 mmol) of a 10% w/w solution of trimethylsilyl-diazomethane in hexane were added to the resulting solution. The resulting mixture was then stirred for 40 minutes. At the end of this time, the reaction mixture was concentrated by evaporation under reduced pressure, and the concentrate was purified by column chromatography through 100 g of silica gel, using a 10:1 by volume mixture of hexane and ethyl acetate as the eluent, to give 1.46 g (yield 85% based on the compound of Preparation 13) of the title compound as crystals, melting at 92°–95° C. (from a mixture of hexane and ethyl acetate)

Nuclear Magnetic Resonance Spectrum (270M Hz, CDCl$_3$) δ ppm:
1.39 (9H, singlet);
3.63 (2H, singlet);
3.72 (3H, singlet);
7.23–7.27 (1H, multiplet);
7.33–7.39 (1H, multiplet);
7.47–7.54 (1H, multiplet).

Infrared Absorption Spectrum (KBr) $v_{max}$ cm$^{-1}$:
3440, 1738, 1731, 1531, 1373, 1346, 1192, 1174, 998, 814.

14(ii) Methyl 2-(4-t-butyl-3-aminophenyl)acetate 5.52 g (84.4 mmol) of zinc powder were added to a suspension of 1.06 g (4.21 mmol) of methyl 2-(4-t-butyl-3-nitrophenyl)acetate [prepared as described in step (i) above] in 30 ml of methanol, and subsequently acetic acid was added to the mixture in four 0.8 ml portions over a period of 1 hour. The reaction mixture was stirred for 2 hours, after which it was diluted with ethyl acetate. It was then filtered using a Celite (trade mark) filter aid. The filtrate was concentrated by evaporation under reduced pressure, and the concentrate was again dissolved in ethyl acetate. The resulting solution was washed with a saturated aqueous solution of ammonium chloride, with a saturated aqueous solution of sodium hydrogencarbonate, with water and with a saturated aqueous solution of sodium chloride, in that order, after which it was dried. The solvent was removed by distillation under reduced pressure, and the resulting residue was purified by column chromatography through 50 g of silica gel, using a 4:1 by volume mixture of hexane and ethyl acetate as the eluent, to give 870 mg (yield 94%) of the title compound as an oily substance.

Nuclear Magnetic Resonance Spectrum (270M Hz, CDCl$_3$) δ ppm:
1.40 (9H, singlet);
3.50 (2H, singlet);
3.68 (3H, singlet);
3.68 (2H, broad singlet);
6.55–6.68 (2H, multiplet);
7.15–7.21 (1H, multiplet).

Infrared Absorption Spectrum (liquid film) $v_{max}$ cm$^{-1}$:
3490, 3380, 1736, 1624, 1570, 1511, 1426, 1302, 1258, 1156, 1017.

PREPARATION 15

4-t-Butyl-3-[3-(2,4-dimethoxyphenyl)octanoyl] aminophenylacetic acid 15(i) Methyl 4-t-butyl-3-[3-(2,4-dimethoxyphenyl)octanoyl]aminophenylacetate Following a procedure similar to that described in Preparation 8, but using the compounds prepared in Preparations 3 and 14 as starting materials, the title compound was obtained as an oily substance.

Nuclear Magnetic Resonance Spectrum (270M Hz, CDCl$_3$) δ ppm:
0.84 (3H, triplet, J=6 Hz);
1.13–1.34 (6H, multiplet);
1.26 (9H, singlet);
1.62–1.79 (2H, multiplet);
2.55–2.80 (2H, multiplet);
3.42–3.58 (1H, multiplet);
3.54 (2H, singlet);
3.68 (3H, singlet);
3.78 (6H, singlet);
6.39–6.51 (2H, multiplet);
6.95–7.15 (3H, multiplet);
7.20–7.33 (2H, multiplet).

Infrared Absorption Spectrum (liquid film) $v_{max}$ cm$^{-1}$:
3231, 1740, 1655, 1613, 1507, 1291, 1260, 1208, 1158, 1038, 834.

15(ii) 4-t-Butyl-3-[3-(2,4-dimethoxphenyl)octanoyl] aminophenylacetic acid

Following a procedure similar to that described in Preparation 7, but using methyl 4-t-butyl-3-[3-(2,4-dimethoxyphenyl)octanoyl]aminophenylacetate [prepared as described in step (i) above] as a starting material, the title compound was obtained as a viscous substance.

Nuclear Magnetic Resonance Spectrum (270M Hz, CDCl$_3$) δ ppm:
0.84 (3H, triplet, J=6 Hz);
1.15–1.35 (6H, multiplet);
1.27 (9H, singlet);
1.65–1.79 (2H, multiplet);
2.58–2.80 (2H, multiplet);
3.42–3.58 (1H, multiplet);
3.56 (2H, singlet);
3.77 (3H, singlet);
3.78 (3H, singlet);
6.41–6.51 (2H, multiplet);
7.00–7.20 (4H, multiplet);
7.26–7.34 (1H, multiplet).

Infrared Absorption Spectrum (film) $v_{max}$ cm$^{-1}$:
3240, 1715, 1613, 1507, 1289, 1260, 1210, 1158, 1044, 835.

PREPARATION 16

2-t-Butyl-5-(3-t-butyldimethylsilyloxypropyl)aniline
16(i) 2-t-Butyl-5-formyl-1-nitrobenzene 240 g of manganese dioxide were added to a solution of 30 g (0.14 mol) of 2-t-butyl-5-hydroxymethyl-1-nitrobenzene (prepared as described in Preparation 10) in 450 ml of chloroform, and the resulting mixture was stirred at room temperature for 1 hour. At the end of this time, the reaction mixture was filtered to remove manganese dioxide, and the filtrate was freed from the solvent by distillation under reduced pressure. The resulting residue was purified by column chromatography through silica gel, using a 1:5 by volume mixture of ethyl acetate and hexane as the eluent, to give 27.4 g of the title compound.

Infrared Absorption Spectrum (CHCl$_3$) $v_{max}$ cm$^{-1}$:
2975, 1706, 1612, 1537, 1369, 1061.

16(ii) 2-t-Butyl-5-[(E)-2-ethoxycarbonylethenyl]-1-nitrobenzene 15 8.0 g (0.18 mol) of sodium hydride (as a 55% w/w dispersion in mineral oil) was washed twice with hexane and suspended in 250 ml of dimethyl-formamide. A solution of 31 ml (0.16 mol) of ethyl diethyl-phosphonoacetate in 50 ml of dimethylformamide was then added, with ice-cooling, to the suspension, and the resulting mixture was stirred at room temperature for 40 minutes. At the end of this time, the mixture was ice-cooled and a solution of 27 g (0.13 mol) of 2-t-butyl-5-formyl-1-nitrobenzene [prepared as described in step (i) above] in 50 ml of dimethylformamide was added thereto over a period of 30 minutes, after which the mixture was stirred for 1 hour. The reaction mixture was then diluted with diethyl ether, and the diluted solution was washed with a 10% w/w aqueous solution of hydrochloric acid and with water, in that order, after which it was dried over anhydrous sodium sulfate. The solvent was removed by distillation under reduced pressure, and the resulting residue was purified by column chromatography through silica gel, using a 1:6 by volume mixture of ethyl acetate and hexane as the eluent, to give 20.6 g of the title compound as crystals, melting at 77°–78° C. (from ethyl acetate-hexane).

Infrared Absorption Spectrum (KBr) $\nu_{max}$ cm$^{-1}$:
2973, 1708, 1645, 1535, 1372, 1317, 1188, 1036, 833.

16(iii) 2-t-Butyl-5-[(1E)-3-hydroxy-1-propenyl]-1-nitrobenzene

A solution of 9.24 g (33.4 mmol) of 2-t-butyl-5-[(E)-2-ethoxycarbonyl-ethenyl]-1-nitrobenzene [prepared as described in step (ii) above] in 200 ml of tetrahydrofuran was cooled to −70° C. in a dry ice-acetone bath, and 100 ml (100 mmol) of a 1M solution of diisobutylaluminum hydride in tetrahydrofuran were added dropwise thereto over a period of 45 minutes. The resulting mixture was then stirred for a further 30 minutes. At the end of this time, the reaction temperature was allowed to rise to 0° C., and the reaction was quenched by adding dropwise a mixture of 4 ml of methanol and 20 ml of tetrahydrofuran. The reaction mixture was then poured into 2N aqueous hydrochloric acid-ice, after which it was extracted with ethyl acetate. The extract was washed with water and with a saturated aqueous solution of sodium chloride, in that order, after which it was dried over anhydrous sodium sulfate. The solvent was removed by distillation under reduced pressure, and the resulting residue was purified by column chromatography through 300 g of silica gel, using a 2:1 by volume mixture of hexane and ethyl acetate as the eluent, to give 7.06 g (yield 90%) of the title compound as an oily substance.

Infrared Absorption Spectrum (CHCl$_3$) $\nu_{max}$ cm$^{-1}$:
3614, 1531, 1497, 1323, 1088, 1009, 970.

16(iv) 2-t-Butyl-5-[(1E)-3-(t-butyldimethylsilyloxy)propenyl]-1-nitrobenzene 11.6 g (77 mmol) of t-butyldimethylsilane, 7.8 g (77 mmol) of triethylamine and 0.76 g (6.2 mmol) of 4-dimethylaminopyridine were added, in turn, and with ice-cooling, to a solution of 14.5 g (62 mmol) of 2-t-butyl-5-[(1E)-3-hydroxy-1-propenyl]-1-nitrobenzene [prepared as described in step (iii) above] in 140 ml of dimethylformamide, and the resulting mixture was stirred for 1 hour. At the end of this time, the reaction mixture was poured into ice-water and then extracted with diethyl ether. The extract was washed with a 10% w/w aqueous solution of hydrochloric acid, with a saturated aqueous solution of sodium hydrogencarbonate and with a saturated aqueous solution of sodium chloride, in that order, after which it was dried. The solvent was then removed by distillation under reduced pressure, and the resulting residue was purified by column chromatography through silica gel, using a 1:15 by volume mixture of ethyl acetate and hexane, to give 21 g of the title compound as crystals, melting at 33°–34° C. (from ethyl acetate-hexane).

Infrared Absorption Spectrum (KBr) $\nu_{max}$ cm$^{-1}$:
2956, 2929, 2858, 1531, 1373, 1257, 1071, 837, 775.

16(v) 2-t-Butyl-5-(3-t-butyldimethylsilyloxypropyl)aniline

A solution of 16.0 g of 2-t-butyl-5-[(1E)-3-(t-butyldimethylsilyloxy)-propenyl]-1-nitrobenzene [prepared as described in step (iv) above] in 800 ml of diethyl ether was stirred at room temperature for 3 hours in the presence of 8.0 g of 10% palladium-on-charcoal under a stream of hydrogen. At the end of this time, the reaction mixture was filtered and the filtrate was freed from the solvent by distillation under reduced pressure. The residue was purified by column chromatography through silica gel, using a 1:10 by volume mixture of ethyl acetate and hexane as the eluent, to give 12.5 g of the title compound as an oily substance.

Nuclear Magnetic Resonance Spectrum (400M Hz, CDCl$_3$) δ ppm:
0.05 (6H, singlet);
0.91 (9H, singlet);
1.41 (9H, singlet);
1.78–1.85 (2H, multiplet);
2.53–2.57 (2H, multiplet);
3.64 (2H, triplet, J=6 Hz);
3.77 (2H, broad singlet);
6.49 (1H, doublet, J=2 Hz);
6.58 (1H, doublet of doublets, J=2 Hz, 8 Hz);
7.13 (1H, doublet, J=8 Hz).

Infrared Absorption Spectrum (CHCl$_3$) $\delta_{max}$ cm$^{-1}$:
2957, 2931, 2859, 1621, 1101, 837.

PREPARATION 17

N-[2-t-Butyl-5-(3-hydroxypropyl)phenyl]-3-(2,4-dimethoxyphenyl)octanamide

17(i) N-[2-t-Butyl-5-(3-t-butyldimethylsilyloxypropyl)phenyl]-3-(2,4-dimethoxyphenyl)octanamide Following a procedure similar to that described in Preparation 8, but using the compounds prepared in Preparations 3 and 16 as starting materials, acylation was carried out to give the title compound as an oily substance.

Nuclear Magnetic Resonance Spectrum (270M Hz, CDCl$_3$) δ ppm:
0.05 (3H, singlet);
0.10 (3H, singlet);
0.74–0.88 (3H, multiplet);
0.90 (9H, singlet);
1.10–1.34 (6H, multiplet);
1.26 (9H, singlet);
1.65–1.85 (4H, multiplet);
2.50–2.62 (2H, multiplet);
2.56–2.80 (2H, multiplet);
3.42–3.57 (1H, multiplet);
3.63 (2H, triplet, J=6.5 Hz);
3.78 (6H, singlet);
6.40–6.50 (2H, multiplet);
6.90–7.26 (5H, multiplet).

Infrared Absorption Spectrum (film) $\nu_{max}$ cm$^{-1}$:
1651, 1613, 1588, 1505, 1464, 1418, 1289, 1256, 1208, 1157, 1103.

17(ii) N-[2-t-Butyl-5-(3-hydroxypropyl)phenyl]-3-(2,4-dimethoxyphenyl)-octanamide Following a procedure similar to that described in Preparation 9, but using N-[2-t-butyl-5-(3-t-butyldimethylsilyloxypropyl)phenyl]-3-(2,4-dimethoxyphenyl)octanamide [prepared as described in step (i) above] as a starting material, desilylation was carried out to give the title compound as a viscous substance.

Nuclear Magnetic Resonance Spectrum (270M Hz, CDCl$_3$) δ ppm:
0.76–0.90 (3H, multiplet);

1.04–1.37 (6H, multiplet);
1.27 (9H, singlet);
1.58–1.78 (2H, multiplet);
1.76–1.90 (2H, multiplet);
2.55–2.66 (2H, multiplet);
2.59–2.80 (2H, multiplet);
3.48–3.56 (1H, multiplet);
3.63 (2H, triplet, J=6.5 Hz);
3.77 (3H, singlet);
3.79 (3H, singlet);
6.40–6.52 (2H, multiplet);
6.90–7.26 (5H, multiplet).
Infrared Absorption Spectrum (film) $v_{max}$ cm$^{-1}$:
  1655, 1613, 1588, 1507, 1464, 1418, 1364, 1289, 1260, 1208, 1157.

PREPARATION 18

N-[2-t-Butyl-5-(t-butyldimethylsilyloxymethyl) phenyl]-3-(2-trifluoromethylphenyl)octanamide Following a procedure similar to that described in Preparation 8, but using 3-(2-trifluoromethylphenyl)octanoic acid as a starting material, the title compound was obtained as a foam-like substance.

Infrared Absorption Spectrum (CHCl$_3$) $v_{max}$ cm$^{-1}$:
  2959, 2932, 2860, 1683, 1515, 1472, 1422, 1314, 1161, 1124, 1037, 839.

PREPARATION 19

N-[2-t-Butyl-5-(hydroxymethyl)phenyl]-3-(2-trifluoromethylphenyl)octanamide

Following a procedure similar to that described in Preparation 9, but using N-[2-t-butyl-5-(t-butyldimethylsilyloxymethyl)phenyl]-3-(2-trifluoromethyl-phenyl)octanamide (prepared as described in Preparation 18) as a starting material, the title compound was obtained as crystals, melting at 147°–147.5° C. (from ethyl acetate-hexane).

Infrared Absorption Spectrum (CHCl$_3$) $v_{max}$ cm$^{-1}$:
  3608, 3461, 2961, 2933, 1683, 1518, 1314, 1161, 1125, 1037.

PREPARATION 20

N-(2-t-Butyl-5-formylphenyl)-3-(2-trifluoromethylphenyl)octanamide 5.6 g of manganese dioxide were added to a solution of 560 mg (1.3 mmol) of N-[2-t-butyl-5-(hydroxymethyl)phenyl]-3-(2-trifluoromethyl-phenyl)octanamide (prepared as described in Preparation 19) in 20 ml of methylene chloride, and the resulting mixture was stirred at room temperature for 30 minutes. The reaction mixture was then filtered using a Celite (trade mark) filter aid, and the manganese dioxide used was washed several times with methylene chloride. The filtrate was combined with the washings and the solvent was removed by distillation under reduced pressure. The residue was purified by column chromatography through silica gel, using a 1:2 by volume mixture of ethyl acetate and hexane as the eluent, to give 511 mg (yield 91%) of the title compound.

Infrared Absorption Spectrum (CHCl$_3$) $v_{max}$ cm$^{-1}$:
  3469, 2962, 2933, 1699, 1609, 1571, 1424, 1378, 1314, 1161, 1125, 1037.

PREPARATION 21

N-(2-t-Butyl-5-carboxyphenol)-3-(2-trifluoromethylphenyl)octanamide 1.2 ml of 1.6M Jones' reagent were added to a solution of 426 mg (1.0 mmol) of N-(2-t-butyl-5-formylphenyl)-3-(2-trifluoromethylphenyl)-octanamide (prepared as described in Preparation 20) in 8 ml of acetone, whilst ice-cooling, and the resulting mixture was stirred at room temperature for 1 hour. At the end of this time, the reaction mixture was washed three times with water and then once with a saturated aqueous solution of sodium chloride, after which it was dried over anhydrous sodium sulfate. The solvent was removed by distillation under reduced pressure, to give 396 mg (yield 90%) of the title compound as crystals, melting at 199°–200° C. (from ethyl acetate-hexane).

Infrared Absorption Spectrum (KBr) $v_{max}$ cm$^{-1}$:
  3249, 2960, 2932, 2872, 1696, 1650, 1610, 1523, 1425, 1313, 1157, 1124, 1037, 770.

PREPARATION 22

N-[2-t-Butyl-5-(t-butyldimethlsilyloxymethyl) phenyl]-3-(2,3-dimethoxyphenyl)octanamide Following a procedure similar to that described in Preparation 8, but using 3-(2,3-dimethylphenyl)octanoic acid as a starting material, the title compound was obtained as an oily substance.

Infrared Absorption Spectrum (CHCl$_3$) $v_{max}$ cm$^{-1}$:
  2959, 2932, 2859, 1679, 1514, 1479, 1260, 1088, 1006.

PREPARATION 23

N-[2-t-Butyl-5-(hydroxymethylphenyl]-3-(2,3-dimethoxyphenyl)octanamide

Following a procedure similar to that described in Preparation 9, but using N-[2-t-butyl-5-(t-butyldimethylsilyloxymethyl)phenyl]-3-(2,3-dimethoxyphenyl)-octanamide (prepared as described in Preparation 22) as a starting material, the title compound was obtained as an oily substance.

Infrared Absorption Spectrum (CDCl$_3$) $v_{max}$ cm$^{-1}$:
  3427, 3259, 2961, 2934, 1678, 1514, 1479, 1274, 1080, 1006.

PREPARATION 24

N-2-t-Butyl-5-formylphenyl)-3-(2,3-dimethoxyphenyl)octanamide

Following a procedure similar to that described in Preparation 20, but using N-[2-t-butyl-5-(hydroxymethyl)phenyl]-3-(2,3-dimethoxyphenyl)-octanamide (prepared as described in Preparation 23) as a starting material, the title compound was obtained as a foam-like substance.

Infrared Absorption Spectrum (CHCl$_3$) $v_{max}$ cm$^{-1}$:
  2961, 2934, 1699, 1609, 1584, 1571, 1479, 1378, 1298, 1274, 1168, 1076, 1006.

PREPARATION 25

N-(2-t-Butyl-5-carboxyphenyl)-3-(2,3-dimethoxyphenyl)octanamide

Following a procedure similar to that described in Preparation 21, but using N-(2-t-butyl-5-formylphenyl)-3-(2,3-dimethoxyphenyl)octanamide (prepared as described in Preparation 24) as a starting material, the title compound was obtained as crystals, melting at 146°–147° C. (from diethyl ether-hexane).

Infrared Absorption Spectrum (CDCl$_3$) $v_{max}$ cm$^{-1}$:
  2961, 2934, 2874, 1723, 1695, 1479, 1431, 1300, 1273, 1168, 1074, 1006.

PREPARATION 26A

N-[2-t-Butyl-5-(aminomethyl)phenyl]-3-(2,4-dimethoxyphenyl)octanamide

26A(i) N-(2-t-Butyl-5-azidomethylphenyl)-3-(2,4-dimethoxyphenyl)octanamide

100 μl (1.29 mmol) of methanesulfonyl chloride and 168 μl (1.32 mmol) of triethylamine were added to a solution of 450 mg (1.02 mmol) of N-[2-t-butyl-5-(hydroxymethyl)phenyl]-3-(2,4-dimethoxyphenyl)octanamide (prepared as described in Preparation 9) in 15 ml of methylene chloride cooled in an ice-salt bath, and the resulting mixture was stirred for 5 minutes. The reaction mixture was then diluted with ethyl acetate, and the diluted solution was washed with dilute hydrochloric acid, with water and with a saturated aqueous solution of sodium chloride, in that order, after which it was dried over anhydrous magnesium sulfate. The solvent was removed by distillation under reduced pressure, and the mesyl derivative thus obtained was dissolved in 15 ml of dimethylformamide. 650 mg (10.0 mmol) of sodium azide were added to the resulting solution, and the mixture thus obtained was stirred for 2 hours. At the end of this time, the reaction mixture was diluted with ethyl acetate, and the diluted solution was washed with water and then with a saturated aqueous solution of sodium chloride, after which it was dried over anhydrous magnesium sulfate. The solvent was removed by distillation under reduced pressure, and the resulting residue was purified by column chromatography through 20 g of silica gel, using a gradient elution method, with mixtures of hexane and ethyl acetate ranging from 5:1 to 3:1 by volume as the eluent, to give 460 mg (yield 97%) of the title compound, the azide derivative, as a colorless foam-like substance.

26A(ii) N-[2-t-Butyl-5-(aminomethyl)phenyl]-3-(2,4-dimethoxyphenyl)-octanamide 301 mg (4.60 mmol) of zinc dust and then 5 ml of 2N aqueous hydrochloric acid were added to a solution of 430 mg (0.92 mmol) of N-(2-t-butyl-5-azidomethylphenyl)-3-(2,4-dimethoxyphenyl)octanamide [prepared as described in step (i) above] in 10 ml of acetone, and the resulting mixture was stirred for 1 hour. At the end of this time, the reaction mixture was filtered to remove zinc dust, and the filtrate was made alkaline by adding a saturated aqueous solution of sodium hydrogencarbonate. The mixture was then extracted with ethyl acetate. The extract was washed with water and then with a saturated aqueous solution of sodium chloride, after which it was dried over anhydrous magnesium sulfate. The solvent was removed by distillation under reduced pressure, and the resulting residue was purified by column chromatography through 50 g of silica gel using a 10:1 by volume mixture of ethyl acetate and methanol as the eluent, to give 354 mg (yield 86%) of the title compound as a foam-like substance.

Nuclear Magnetic Resonance Spectrum (270 MHz, CDCl$_3$) δ ppm:
0.78–0.90 (3H, multiplet);
1.10–1.36 (6H, multiplet);
1.27 (9H, singlet);
1.64–1.78 (2H, multiplet);
2.58–2.82 (2H, multiplet);
3.40–3.56 (1H, multiplet);
3.75 (2H, broad singlet);
3.78 (6H, singlet);
6.40–6.51 (2H, multiplet);
6.99–7.32 (5H, multiplet).

Infrared Absorption Spectrum (KBr) $v_{max}$ cm$^{-1}$:
2955, 2930, 1652, 1613, 1587, 1507, 1465, 1290, 1261, 1209, 1157, 1039.

PREPARATION 26B

N-[2-t-Butyl-5-(aminomethyl)phenyl]-3-(2,4-dimethoxyphenyl)-octanamide-hydrochloride A 4N solution of hydrogen chloride in dioxane was added to a solution of N-[2-t-butyl-5-(aminomethyl)phenyl]-3-(2,4-dimethoxyphenyl)octanamide (prepared as described in Preparation 26A) in diethyl ether, and the precipitate which separated out was collected by filtration and washed with hexane to give the desired hydrochloride, melting at 102°–106° C.

Infrared Absorption Spectrum (KBr) $v_{max}$ cm$^{-1}$:
1652, 1613, 1587, 1507, 1466, 1289, 1261, 1209, 1157, 1039.

PREPARATION 27

N-[2-t-Butyl-5-(3-aminopropyl)phenyl]-5-(2,4-dimethoxyphenyl)octanamide

Following a similar procedure to that described in Preparation 26A(i), but using N-[2-t-butyl-5-(3-hydroxypropyl)phenyl]-3-(2,4-dimethoxyphenyl)-octanamide (prepared as described in Preparation 17), there was obtained an azide derivative, which was catalytically reduced in a similar manner to that described in Preparation 16(v), to give the title compound as a foam-like substance.

Infrared Absorption Spectrum (film) $v_{max}$ cm$^{-1}$:
1657, 1651, 1613, 1588, 1505, 1464, 1457, 1418, 1364, 1289, 1260.

PREPARATION 28

N-[2-t-Butyl-5-(2-carboxyethyl)phenyl]-3-(2,4-dimethoxyphenyl)octanamide 2-t-Butyl-5-[(E)-2-ethoxycarbonylethenyl]-1-nitrobenzene [prepared as described in Preparation 16(ii)] was subjected to catalytic reduction and subsequent treatment of the reaction mixture in a similar manner to that described in Preparation 16(v), to give 2-t-butyl-5-(2-ethoxycarbonylethyl)aniline as an oily substance.

Infrared Absorption Spectrum (liquid film) $v_{max}$ cm$^{-1}$:
3493, 3385, 1732, 1623, 1570, 1509, 1424, 1370, 1258, 1183, 1041.

This product was acylated in a similar manner to that described in Preparation 8 to give N-[2-t-butyl-5-(2-ethoxycarbonylethyl)phenyl]-3-(2,4-dimethoxyphenyl) octanamide, which was hydrolyzed in a similar manner to that described in Preparation 7 to give the title compound as a foam-like substance.

Nuclear Magnetic Resonance Spectrum (270 MHz, CDCl$_3$) δ ppm:
0.84 (3H, triplet, J=7 Hz);
1.08–1.33 (6H, multiplet);
1.26 (9H, singlet);
1.62–1.80 (2H, multiplet);
2.52–2.91 (6H, multiplet);
3.39–3.58 (1H, multiplet);
3.77 (3H, singlet);
3.79 (3H, singlet);
6.40–6.53 (2H, multiplet);
6.90–7.32 (5H, multiplet).

Infrared Absorption Spectrum (KBr) $v_{max}$ cm$^{-1}$:
3253, 1710, 1651, 1613, 1507, 1290, 1209, 1157, 1038, 833.

PREPARATION 29

2-t-Butyl-5-cyanomethylaniline 2-t-Butyl-5-cyanomethyl-1-nitrobenzene (prepared as described in Preparation 13).was subjected to reduction and subsequent treatment of the reaction mixture in a similar manner to that described in Preparation 5 to give the title compound as an oily substance.

Infrared Absorption Spectrum (neat) $v_{max}$ cm$^{-1}$:
3497, 3387, 2251, 1626, 1509, 1426, 1308, 1258, 1098, 859, 803.

PREPARATION 30

Following a similar procedure to that described in Preparation 1, but using different kinds of aromatic aldehydes instead of 2,4-dimethoxybenzaldehyde, 2-propenoic acid derivatives were obtained. These derivatives were reacted with various kinds of Grignard reagents in a similar manner to that described in Preparation 2 to give malonic acid derivatives. Hydrolysis and subsequent decarboxylation of the malonic acid derivatives thus obtained were conducted in a similar manner to that described in Preparation 3 to give the carboxylic acid derivatives of Preparations 30A to 30J having the following formula and in which the substituent groups are as given in the Table below. Under the heading "Form & IR Spectrum" is given the physical form of each compound as prepared and the Infrared Absorption Spectrum (liquid film) $v_{max}$ cm$^{-1}$. The abbreviations used in this and subsequent Tables for certain groups are as previously defined.

| Prep. No. | $R^A$ | $R^B$ | $R^C$ | $R^D$ | Form & IR Spectrum |
|---|---|---|---|---|---|
| 30A | 2-OMe | 4-SMe | H | (CH$_2$)$_4$CH$_3$ | oil, 2679, 1707, 1595, 1493, 1401, 1244, 1134, 1036, 955, 880, 808 |
| 30B | 2-OCH$_2$Ph | 3-OMe | H | (CH$_2$)$_4$CH$_3$ | oil, 2956, 2930, 2859, 1708, 1584, 1476, 1275, 1204, 1178, 1087 |
| 30C | 2-OMe | 4-OCH$_2$Ph | H | (CH$_2$)$_4$CH$_3$ | oil, 1705, 1613, 1588, 1505, 1464, 1457, 1420, 1379, 1260, 1200, 1161 |
| 30D | 2-OMe | 4-OMe | 5-SO$_2$NMe$_2$ | (CH$_2$)$_4$CH$_3$ | oil, 1734, 1707, 1605, 1572, 1497, 1464, 1441, 1394, 1329, 1282, 1213, 1142, 1070, 1026 |
| 30E | 2-OEt | 4-OMe | H | (CH$_2$)$_3$CH$_3$ | oil, 1707, 1613, 1586, 1507, 1466, 1395, 1293, 1260, 1200, 1167, 1131, 1044 |
| 30F | 2-OEt | 4-OMe | H | CH$_2$CH(CH$_3$)$_2$ | Oil, 1707, 1613, 1588, 1507, 1466, 1395, 1366, 1260, 1200, 1167, 1121, 1044 |
| 30G | 2-OMe | 4-OCH$_2$Ph | H | (CH$_2$)$_3$CH$_3$ | oil, 2670, 2361, 1707, 1613, 1588, 1505, 1455, 1291, 1200, 1038, 835 |
| 30H | 2-OMe | 4-OCH$_2$Ph | H | CH$_2$CH(CH$_3$)$_2$ | oil, 2670, 2361, 1707, 1613, 1505, 1287, 1200, 1161, 1038, 835 |
| 30I | 2-OMe | 4-SO$_2$iPr | H | Bu | oil, 3520, 3240, 1709, 1595, 1493, 1466, 1404, 1304, 1248, 1138, 1032. |
| 30J | 2-OMe | 4-SO$_2$iPr | H | Pn | oil, 1734, 1709, 1595, 1576, |

-continued

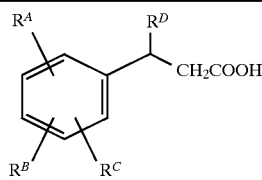

| Prep. No. | $R^A$ | $R^B$ | $R^C$ | $R^D$ | Form & IR Spectrum |
|---|---|---|---|---|---|
| | | | | | 1493, 1466, 1404, 1304, 1248, 1169, 1140, 1053, 1032. |

PREPARATION 31

Using various kinds of carboxylic acid derivatives instead of 3-(2,4-dimethoxyphenyl)octanoic acid, acylation and subsequent treatment of the reaction mixture were conducted in a similar manner to that described in Preparation 6 to give amide derivatives. These derivatives were hydrolyzed in a similar manner to that described in Preparation 7 to give the benzoic acid derivatives of Preparations 31A to 31X having the following formula and in which the substituent groups are as given in the Table below. Under the heading "IR Spectrum, form or melting point (°C)" is given the Infrared Absorption Spectrum (KBr) $\nu_{max}$ cm$^{-1}$ and either the physical form or the melting point of the compound, together with the solvent from which the compound was recrystallised.

| Prep. No. | $R^A$ | $R^B$ | $R^C$ | $R^D$ | IR Spectrum, form or melting point (°C.) |
|---|---|---|---|---|---|
| 31A (30A)** | 2-OMe | 4-SMe | H | $(CH_2)_4CH_3$ | 1653, 1614, 1560, 1527, 1493, 1462, 1423, 1365, 1244, 1132, 1095, 1074, 1036, 196–197 ($CH_2Cl_2$-diethyl ether)* |
| 31B (42A)** | 2-OMe | 4-OMe | H | $(CH_2)_3CH_3$ | 3249, 1692, 1649, 1612, 1507, 1438, 1420, 1293, 1262, 1210, 1157 185.5–186.5 (ethyl acetate)* |
| 31C (45A)** | 2-OMe | 4-OEt | H | $(CH_2)_4CH_3$ | 1692, 1653, 1613, 1586, 1567, 1420, 1296, 1262, 1202, 1123 144–145 ($CH_2Cl_2$-hexane)* |
| 31D (42B)** | 2-OMe | 4-OMe | H | $(CH_2)_5CH_3$ | 3244, 2361, 1694, 1653, 1613, 1507, 1208, 1038, 918, 835, 733 foam |
| 31E (49)* | 2-OMe | 4-OMe | 5-CH$_3$ | $(CH_2)_4CH_3$ | 3248, 1694, 1655, 1614, 1513, 1466, 1300, 1206, 1127, 1039 foam |
| 31F (51)** | 2-OMe | 4-O(CH$_2$)$_3$—SO$_2$CH$_3$ | H | $(CH_2)_4CH_3$ | 1717, 1694, 1611, 1508, 1466, 1131, 1044, 974, 835, 774*** foam |

-continued

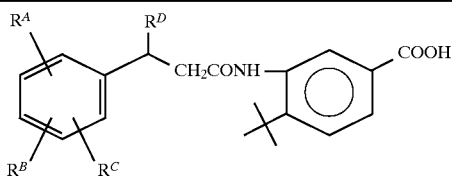

| Prep. No. | $R^A$ | $R^B$ | $R^C$ | $R^D$ | IR Spectrum, form or melting point (°C.) |
|---|---|---|---|---|---|
| 31G (52) ** | 2-OMe | 4-OMe | 5-F | $(CH_2)_4CH_3$ | 3251, 1694, 1653, 1622, 1612, 1517, 1466, 1455, 1408, 1325, 1248, 1203 amorphous |
| 31H (53) ** | 2-OMe | 4-O(CH$_2$)$_3$—NHSO$_2$CH$_3$ | H | $(CH_2)_4CH_3$ | 1694, 1611, 1507, 1466, 1420, 1316, 1200, 1154, 1074, 1038*** foam |
| 31I (42C) ** | 2-OMe | 4-OMe | H | $CH_2CH(CH_3)_2$ | 3249, 1694, 1656, 1612, 1507, 1209, 1157, 1122, 1037, 835, 774 foam |
| 31J (55) ** | 2-OMe | 4-OMe | 5-Cl | $(CH_2)_3CH_3$ | 3251, 1719, 1694, 1656, 1605, 1506, 1438, 1297, 1206, foam |
| 31K (45C) ** | 2-OMe | 4-O(CH$_2$)$_2$—OMe | H | $(CH_2)_4CH_3$ | 1720, 1690, 1651, 1611, 1507, 1465, 1452, 1421, 1297, 1261, 1249 133–134 (CH$_2$Cl$_2$-hexane)* |
| 31L (45D) ** | 2-OMe | 4-O(CH$_2$)$_2$—OEt | H | $(CH_2)_4CH_3$ | 1719, 1694, 1653, 1613, 1588, 1507, 1454, 1420, 1202, 1123*** foam |
| 31M (42D) ** | 2-OMe | 4-OMe | H | $CH(CH_3)_2$ | 1693, 1653, 1612, 1566, 1512, 1468, 1419, 1365, 1296, 1263, 1209, 1155, 1126, 1041 191–192 (CH$_2$Cl$_2$—MeOH—AcOEt)* |
| 31N (57A) ** | 2-OMe | 4-O(CH$_2$)$_2$—OEt | 5-Cl | $(CH_2)_4CH_3$ | 1715, 1694, 1653, 1605, 1568, 1505, 1447, 1366, 1302, 1246*** foam |
| 31P (42E) ** | 2-OMe | 4-OMe | H | $(CH_2)_2CH_3$ | 1690, 1645, 1612, 1525, 1507, 1421, 1312, 1210, 1158, 1119, 1042 230 (AcOEt)* |
| 31Q (30E) ** | 2-OEt | 4-OMe | H | $(CH_2)_3CH_3$ | 1692, 1655, 1611, 1588, 1567, 1507, 1426, 1366, 1293, 1200, 1167*** foam |
| 31R (30F) ** | 2-OEt | 4-OMe | H | $CH_2CH(CH_3)_2$ | 1694, 1611, 1588, 1506, 1426, 1366, 1258, 1200, 1167, 1121, 1044 foam |
| 31S (57B) ** | 2-OMe | 4-O(CH$_2$)$_3$—OMe | 5-Cl | $(CH_2)_3CH_3$ | 3250, 1720, 1694, 1655, 1604, 1506, 1400, 1302, 1202, 1123, 774 foam |
| 31T (59)* * | 2-OMe | 4-O(CH$_2$)$_3$—OMe | H | $(CH_2)_3CH_3$ | 3247, 1721, 1693, 1652, 1612, 1507, 1292, 1201, 1124, |

-continued

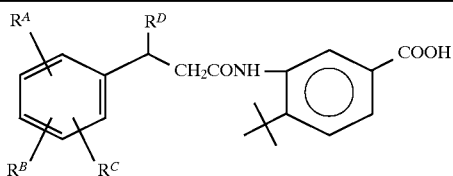

| Prep. No. | $R^A$ | $R^B$ | $R^C$ | $R^D$ | IR Spectrum, form or melting point (°C.) |
|---|---|---|---|---|---|
| 31U (57C)** | 2-OMe | 4-O(CH$_2$)$_2$—OMe | 5-Cl | CH$_2$CH(CH$_3$)$_2$ | 834, 774 foam 1688, 1647, 1607, 1566, 1506, 1464, 1419, 1365, 1300, 1265, 1205, 1147, 1128, 1049*** foam |
| 31V (57D)** | 2-OMe | 4-O(CH$_2$)$_3$—OEt | 5-Cl | CH$_2$CH(CH$_3$)$_2$ | 1693, 1605, 1570, 1504, 1446, 1421, 1365, 1300, 1265, 1203, 1169, 1124, 1070*** foam |
| 31W (92A) | 2-OMe | 4-O(CH$_2$)$_3$—SO$_2$—(CH$_2$)$_2$CH$_3$ | H | (CH$_2$)$_3$CH$_3$ | 3249, 1719, 1693, 1612, 1507, 1419, 1289, 1201, 1128, 1038 foam |
| 31X (92B) | 2-OMe | 4-O(CH$_2$)$_3$—SO$_2$—(CH$_2$)$_2$CH$_3$ | 5-Cl | (CH$_2$)$_3$CH$_3$ | 3260, 1719, 1693, 1604, 1506, 1403, 1305, 1292, 1202, 1128, 1031 foam |

*The solvent used for recrystallization.
**Preparation No. of the starting material.
***IR spectra were measured in a film.

PREPARATION 32

3-(2,4-Dimethoxy-5-formylphenyl)octanoic acid

32(i) Methyl 3-(2,4-dimethoxyphenyl)octanoate 3.3 ml (38 mmol) of oxalyl chloride and 2 drops of dimethylformamide were added to a solution of 6.78 g (24.2 mmol) of 3-(2,4-dimethoxyphenyl)-octanoic acid (prepared as described in Preparation 3) in 70 ml of methylene chloride, and the resulting mixture was stirred for 1 hour. At the end of this time, the reaction mixture was freed from excess reagents and the solvent by distillation under reduced pressure, to give an acid chloride compound, which was dissolved in 100 ml of methylene chloride. 5.1 ml of pyridine and 1.5 ml of methanol were added to the solution, whilst ice-cooling, and the resulting mixture was stirred at the same temperature for 20 minutes. In order to terminate the reaction, water was added to the reaction mixture, and then the organic solvent was removed by distillation under reduced pressure. The resulting residue was extracted with a mixture of ethyl acetate and hexane. The extract was washed with 2N aqueous hydrochloric acid, with water and with a saturated aqueous solution of sodium chloride, in that order, after which the solvent was removed by distillation under reduced pressure. The residue was purified by column chromatography through 50 g of silica gel, using a gradient elution method, with mixtures of hexane and ethyl acetate ranging from 20:1 to 5:1 by volume as the eluent, to give 7.10 g (a quantitative yield) of the title compound as an oily substance.

Infrared Absorption Spectrum (liquid film) $v_{max}$ cm$^{-1}$:

1739, 1614, 1588, 1507, 1466, 1438, 1291, 1261, 1210, 1158, 1037.

32(ii) Methyl 3-(2,4-dimethoxy-5-formylphenyl)octanoate

A solution of 11.56 g (39.3 mmol) of 3-(2,4-dimethoxyphenyl)octanoic acid [prepared as described in step (i) above] and 13.54 g (117.8 mmol) of dichloromethyl methyl ether in 200 ml of methylene chloride was cooled in an ice-salt bath, and then 12.9 ml (118 mmol) of titanium (IV) chloride were added dropwise to the cooled mixture over a period of 10 minutes. The mixture was then stirred at the same temperature for 40 minutes. At the end of this time, the reaction was terminated by adding ice-water, and the aqueous mixture was extracted with diethyl ether. The extract was washed with a saturated aqueous solution of sodium hydrogencarbonate and with a saturated aqueous solution of sodium chloride, in that order, after which it was dried over anhydrous magnesium sulfate. The solvent was removed by distillation under reduced pressure, and the resulting residue was purified by column chromatography through 250 g of silica gel, using a gradient elution method, with mixtures of hexane and ethyl acetate ranging from 3:0 to 3:2 by volume as the eluent, to give 11.70 g (yield 92%) of the desired formyl derivative as crystals, melting at 70°–71° C. (from diethyl ether-hexane).

Infrared Absorption Spectrum (KBr) $v_{max}$ cm$^{-1}$:

1738, 1666, 1605, 1578, 1500, 1470, 1437, 1418, 1356, 1325, 1273, 1217, 1161, 1134, 1103, 1026.

32(iii) 3-(2,4-Dimethoxy-5-formylphenyl)octanoic acid

Methyl 3-(2,4-dimethoxy-5-formylphenyl)octanoate [prepared as described in step (ii) above] was hydrolyzed in a similar manner to that described in Preparation 7 to give the title compound as crystals, melting at 110°–111.5° C. (from ethyl acetate-hexane).

Infrared Absorption Spectrum (KBr) $v_{max}$ cm$^{-1}$:
1709, 1672, 1609, 1471, 1440, 1417, 1277, 1215, 1134, 1106, 1030.

PREPARATION 33

2-t-Butyl-5-aminocarbonyl-N-methylaminomethylaniline 10.5 ml (111 mmol) of diborane dimethyl sulfide complex were added to a solution of 2.18 g (9.22 mmol) of 2-t-butyl-5-N'-methylcarbamoyl-1-mitrobenzene [prepared as described in Preparation 36(i)] in 20 ml of tetrahydrofuran, and the resulting mixture was heated under reflux for 12 hours. At the end of this time, the reaction was terminated by adding methanol. 6 ml of concentrated aqueous hydrochloric acid were added to the reaction mixture, which was then heated under reflux for 1 hour. The reaction mixture was freed from the organic solvent by distillation under reduced pressure, and the aqueous residue was adjusted to pH 11 by the addition of a 2N aqueous solution of sodium hydroxide. The mixture was then extracted with ethyl acetate. The extract was washed with water and with a saturated aqueous solution of sodium chloride, after which it was dried over anhydrous sodium sulfate. The solvent was removed by distillation under reduced pressure, to give crude 2-t-butyl-5-N-methylaminomethyl-1-nitrobenzene.

The whole of the crude 2-t-butyl-5-N-methylaminomethyl-1-nitrobenzene thus obtained was derivatised to 2-t-butyl-5-aminocarbonyl-N-methylaminomethyl-1-nitrobenzene in a similar manner to that described in Example 10. Reduction of the product and subsequent treatment of the reaction mixture were conducted in a similar manner to that described in Preparation 5 to give the title compound as crystals, melting at 143°–144° C. (from ethyl acetate-hexane).

Infrared Absorption Spectrum (KBr)$v_{max}$ cm$^{-1}$:
3433, 3420, 3361, 3189, 1656, 1616, 1507, 1414, 1109, 1101.

PREPARATION 34

2-t-Butyl-5-cyanoaniline

34(i) 2-t-Butyl-5-cyano-1-nitrobenzene 3.3 ml of pyridine and then 4.3 ml of trifluoroacetic anhydride were added to a solution of 2.25 g (10.1 mmol) of 2-t-butyl-5-carbamoyl-1-nitrobenzene [prepared as described in Preparation 38(i)] in 20 ml of tetrahydrofuran, and the resulting mixture was stirred for 20 minutes. The reaction mixture was then mixed with water, and the aqueous mixture was extracted with a mixture of ethyl acetate and hexane. The extract was washed with water and with a saturated aqueous solution of sodium chloride, after which it was dried over anhydrous sodium sulfate and the solvent was removed by distillation under reduced pressure. The residue was purified by column chromatography through 50 g of silica gel to give 1.99 g (yield 96%) of the title compound as crystals, melting at 70.5°–71.5° C. (from hexane).

Infrared Absorption Spectrum (film) $v_{max}$ cm$^{-1}$:
2361, 2238, 1538, 1493, 1476, 1370, 1065, 907, 845, 793.

34(ii) 2-t-Butyl-5-cyanoaniline 2-t-Butyl-5-cyano-1-nitrobenzene [prepared as described in step (i) above] was reduced in a similar manner to that described in Preparation 5 to give the title compound as crystals, melting at 94.5°–95° C. (from hexane-ethyl acetate).

Infrared Absorption Spectrum (KBr) $v_{max}$ cm$^{-1}$:
3509, 3385, 3237, 2229, 1628, 1557, 1414, 1096, 870, 814.

PREPARATION 35

N-(2-t-Butyl-5-carboxyphenyl)-3-(2.4-dimethoxy-5-cyanophenyl)octanamide

Following a similar procedure to that described in Example 111, N-(2-t-butyl-5-methoxycarbonylphenyl)-3-(2,4-dimethoxy-5-formylphenyl)octanamide [prepared as described in Preparation 65(i)] was derivatised to an oxime derivative. The product was then reacted in a similar manner to that described in Example 37 to give a cyano derivative, which was hydrolyzed in a similar manner to that described in Preparation 7 to give the title compound as an amorphous substance.

Infrared Absorption Spectrum (CHCl$_3$) $v_{max}$ cm$^{-1}$:
2223, 1695, 1612, 1577, 1504, 1468, 1438, 1288, 1031.

PREPARATION 36

2-t-Butyl-5-N'-methylcarbamoylaniline

36(i) 2-t-Butyl-5-N'-methylcarbamoyl-1-nitrobenzene 6.61 g (40.8 mmol) of N,N'-carbonyldiimidazole were added to a solution of 7.00 g (31.4 mmol) of 4-t-butyl-3-nitrobenzoic acid in 60 ml of acetonitrile, and the resulting mixture was stirred for 40 minutes. 4.23 g (62.7 mmol) of monomethylamine hydrochloride and 15.86 g (156.8 mmol) of triethylamine were then added to the mixture. The reaction mixture was then stirred for a further 40 minutes, after which it was diluted with diethyl ether. The diluted solution was then washed with 0.5N aqueous hydrochloric acid, with a 0.5N aqueous solution of sodium hydroxide, with water and with a saturated aqueous solution of sodium carbonate, after which the organic phase was dried over anhydrous magnesium sulfate. The solvent was then removed by distillation under reduced pressure, and the resulting residue was crystallized from a mixture of methylene chloride, methanol and ethyl acetate to give 6.75 g (yield 91%) of the title compound as crystals, melting at 165°–166° C.

Infrared Absorption Spectrum (KBr) $v_{max}$ cm$^{-1}$:
1637, 1568, 1551, 1535, 1412,1363, 1327, 1279, 1252, 1153, 1061.

36(ii) 2-t-Butyl-5-N-methylcarbamoylaniline

Following a similar procedure to that described in Preparation 38(ii), 2-t-butyl-5-N'-methylcarbamoyl-1-nitrobenzene [prepared as described in step (i) above] was reduced and the reaction mixture was subsequently treated, to give the title compound as crystals, melting at 149°–150° C. (from ethyl acetate).

Nuclear Magnetic Resonance Spectrum (270 MHz, CDCl$_3$) δ ppm:
1.42 (9H, singlet);
2.98 (3H, doublet, J=5 Hz);
3.77–4.11 (2H, broad);
5.96–6.22 (IH, multiplet);
6.99 (1H, doublet of doublets, J=2 Hz & 8 Hz);
7.11 (1H, doublet, J=2 Hz);
7.25 (1H, doublet, J=8Hz).

Infrared Absorption Spectrum (KBr) $v_{max}$ cm$^{-1}$:
1641, 1614, 1560, 1416, 1394, 1367, 1313, 1257, 1163, 1149, 1103, 1028, 1016.

PREPARATION 37

3-(2,4-Dimethoxy-5-methoxycarbonylphenyl) octanoic acid 2.66 g (54.3 mmol) of sodium cyanide, 37.78 g (434.4 mmol) of manganese dioxide and 979 mg (16.3 mmol) of acetic acid were added to a solution of 3.35 g (10.9 mmol) of 3-(2,4-dimethoxy-5-formylphenyl)octanoic acid (prepared as described in Preparation 32) in 70 ml of methanol, and the resulting mixture was stirred for 4 hours. At the end of this time, the reaction mixture was acidified with 1N aqueous hydrochloric acid and filtered using a Celite (trade mark) filter aid. The filtrate was then concentrated by evaporation under reduced pressure, and the concentrate was mixed with a small amount of water, after which it was extracted with ethyl acetate. The extract was washed with water and with a saturated aqueous solution of sodium chloride, in that order, after which it was dried over anhydrous magnesium sulfate. The solvent was removed by distillation under reduced pressure, and the resulting residue was purified by column chromatography through 100 g of silica gel, using a gradient elution method, with mixtures of ethyl acetate and methanol ranging from 50:0 to 50:3 by volume as the eluent, to give 3.25 g (yield 88%) of the title compound, melting at 106°–107° C. (from ethyl acetate-hexane).

Infrared Absorption Spectrum (KBr) $\nu_{max}$ cm$^{-1}$:
    1716, 1701, 1612, 1574, 1508, 1470, 1458, 1435, 1329, 1282, 1244, 1221, 1186, 1140, 1086, 1028.

PREPARATION 38

2-t-Butyl-5-carbamoylaniline

38(i) 2-t-Butyl-5-carbamoyl-1-nitrobenzene 12.0 g (74.0 mmol) of N,N'-carbonyldiimidazole were added to a suspension of 15.03 g (67.3 mmol) of 4-t-butyl-3-nitrobenzoic acid in 150 ml of acetonitrile, and the resulting mixture was stirred for 1 hour, after which 20 ml (0.31 mol) of aqueous ammonia were added. The reaction mixture was stirred for 30 minutes, after which it was concentrated by evaporation under reduced pressure, and the concentrate was dissolved in ethyl acetate. The organic phase was washed with water, with 2N aqueous hydrochloric acid, with water, with a saturated aqueous solution of sodium hydrogencarbonate and with a saturated aqueous solution of sodium chloride, in that order, after which it was dried over anhydrous magnesium sulfate. The solvent was removed by distillation under reduced pressure, and the resulting residue was purified by column chromatography through 150 g of silica gel, using a gradient elution method, with mixtures of ethyl acetate and hexane ranging from 1:1 to 2:1 by volume as the eluent, to give 12.68 g (yield 85%) of the title compound as crystals, melting at 114°–115° C. (from ethyl acetate-hexane).

Infrared Absorption Spectrum (KBr) $\nu_{max}$ cm$^{-1}$:
    1678, 1648, 1620, 1536, 1420, 1399, 1368, 1251, 1095, 1060.

38(ii) 2-t-Butyl-5-carbamoylaniline 38.98 g (596 mmol) of zinc dust were added to a solution of 13.24 g (59.6 mmol) of 2-t-butyl-5-carbamoyl-1-nitrobenzene [prepared as described in step (i) above] in 150 ml of methanol, and then 13 ml of acetic acid were added dropwise over a period of 10 minutes, whilst ice-cooling. The resulting mixture was then stirred at room temperature for 2 hours and then at 50° C. for 30 minutes. At the end of this time, the reaction mixture was diluted with ethyl acetate and filtered using a Celite (trade mark) filter aid. The filtrate was concentrated by evaporation under reduced pressure and the concentrate was dissolved in ethyl acetate. The resulting solution was washed with a saturated aqueous solution of ammonium chloride, with water and with a saturated aqueous solution of sodium chloride, in that order, after which it was dried over anhydrous magnesium sulfate. The solvent was removed by distillation under reduced pressure, and the resulting residue was crystallized from a mixture of ethyl acetate and hexane, to give 8.94 g (yield 78%) of the title compound, melting at 140.5°–142° C. (from ethyl acetate-hexane).

Nuclear Magnetic Resonance Spectrum (270 MHz, CDCl$_3$) δ ppm:
    1.42 (9H, singlet);
    3.85–4.10 (2H, broad singlet);
    5.80–6.30 (2H, broad);
    7.08 (1H, doublet of doublets, J=2 Hz & 8 Hz);
    7.16 (1H, doublet, J=2 Hz);
    7.27 (1H, doublet, J=8Hz).

Infrared Absorption Spectrum (KBr) $\nu_{max}$ cm$^{-1}$:
    3463, 3349, 1654, 1601, 1562, 1433, 1391, 1098, 896, 776.

PREPARATION 39

Methyl 4-(t-butyldimethylsilyloxymethyl)-2-methoxybenzoate

39(i) Methyl 4-hydroxymethyl-2-methoxybenzoate 9.07 g (51.0 mmol) of N-bromosuccinimide and 120 mg of azobis(isobutyronitrile) were added to a solution of 7.64 g (42.4 mmol) of methyl 4-methyl-2-methoxybenzoate in 140 ml of carbon tetrachloride under a stream of nitrogen, and the resulting mixture was stirred at 70° C. for 1 hour. A further 200 mg of azobis(isobutyronitrile) were then added, making a total addition of 320 mg (1.95 mmol). The reaction mixture was then stirred for 1 hour, after which an aqueous solution of sodium sulfite was added to the mixture to decompose any excess of the reagent. The organic phase was concentrated by evaporation under reduced pressure to one-fourth of its original volume. The concentrate was diluted with ethyl acetate, and the diluted solution was washed with a saturated aqueous solution of sodium hydrogencarbonate, with water and with a saturated aqueous solution of sodium chloride, in that order, after which it was dried over anhydrous magnesium sulfate. The solvent was removed by distillation under reduced pressure, giving 11.26 of crude methyl 4-bromomethyl-2-methoxybenzoate as a residue.

The whole of this crude product was dissolved in 100 ml of dimethylformamide, and 13.48 g (164 mmol) of sodium acetate were added to the solution. The resulting mixture was then stirred at 60° C. for 2.5 hours. At the end of this time, the reaction mixture was freed from the solvent by distillation under reduced pressure and the concentrate was mixed with water. It was then extracted with a mixture of ethyl acetate and hexane. The extract was washed with 2N aqueous hydrochloric acid, with a saturated aqueous solution of sodium hydrogencarbonate and with water, in that order, after which it was dried over anhydrous sodium sulfate. The solvent was then removed by distillation under reduced pressure, to obtain 10.49 g of crude methyl 4-acetoxymethyl-2-methoxybenzoate.

The whole of the crude methyl 4-acetoxymethyl-2-methoxybenzoate thus obtained was dissolved in 100 ml of methanol, and 9.6 ml (4.9 mmol) of a 0.51M sodium methoxide solution in methanol were added to the solution. The resulting mixture was then stirred for 1 hour. At the end of this time, 0.6 ml of acetic acid were added, to terminate the reaction, and then the reaction mixture was freed from the solvent by distillation under reduced pressure . The resulting residue was mixed with water, and the resulting aqueous solution was extracted with a mixture of ethyl acetate and hexane. The extract was washed with a saturated aqueous solution of sodium hydrogencarbonate, with water and with a saturated aqueous solution of sodium chloride, in that order, after which it was dried over anhydrous sodium sulfate. The solvent was removed by distillation under reduced pressure, and the resulting residue was purified by column chromatography through 250 g of silica gel, using a 2:1 by volume mixture of hexane and ethyl acetate as the eluent, to give 4.39 g of the title compound as an Is oily substance in a 53% yield (total yield of three steps).

Infrared Absorption Spectrum (liquid film) $v_{max}$ cm$^{-1}$:
3430, 1713, 1614, 1576, 1503, 1463, 1436, 1415, 1292, 1255, 1090.

39(ii) Methyl-4-(t-butyldimethylsilyloxymethyl-2-methoxybenzoate 15.5 ml (0.110 mol) of triethylamine and 616 mg (5.04 mmol) of 4-N,N-dimethylaminopyridine were added to a solution of 19.8 g (0.101 mol) of methyl 4-hydroxymethyl-2-methoxybenzoate [prepared as described in step (i) above] and 16.91 g (0.112 mol) of t-butyldimethylsilyl chloride in 150 ml of methylene chloride, and the resulting mixture was stirred for 2 hours. At the end of this time, the reaction mixture was diluted with a mixture of ethyl acetate and hexane, and the diluted mixture was washed with ice-cooled 1N aqueous hydrochloric acid, with water, with a saturated aqueous solution of sodium hydrogencarbonate and with a saturated aqueous solution of sodium chloride, in that order, after which it was dried over anhydrous sodium sulfate. The solvent was then removed by distillation under reduced pressure, giving 32.20 g (a quantitative yield) of the title compound as an oily substance.

Nuclear Magnetic Resonance Spectrum (270 MHz, CDCl$_3$) δ ppm:
0.11 (6H, singlet);
0.95 (9H, singlet);
3.88 (3H, singlet);
3.91 (3H, singlet);
4.76 (2H, singlet);
6.89 (1H, doublet, J=8 Hz);
7.03 (1H, singlet);
7.77 (1H, doublet, J=8Hz).

Infrared Absorption Spectrum (liquid film) $v_{max}$ cm$^{-1}$:
1732, 1615, 1462, 1416, 1370, 1293, 1256, 1088, 1036, 839.

PREPARATION 40

4-t-Butyldimethylsilyloxymethyl-2-methoxybenzaldehyde

40(i) (4-t-Butyldimethylsilyloxymethyl-2-methoxyphenyl) methanol

A solution of 32.19 g (0.101 mol) of methyl 4-(t-butyldimethylsilyl-oxymethyl)-2-methoxybenzoate (prepared as described in Preparation 39) in 50 ml of tetrahydrofuran was added dropwise to an ice-cooled suspension of 3.51 g (92.5 mmol) of lithium aluminum hydride in 250 ml of tetrahydrofuran over a period of 30 minutes. The resulting mixture was then stirred at the same temperature for 1 hour and then at room temperature for 40 minutes. At the end of this time, the reaction mixture was again cooled with ice, and 3.5 ml of water were added to the mixture to terminate the reaction. 3.5 ml of a 15% w/v aqueous solution of sodium hydroxide and 10.5 ml of water were then added, with stirring, to the mixture. Anhydrous magnesium sulfate was added, and the reaction mixture was filtered. The filtrate was freed from the solvent by distillation under reduced pressure, to give 29.30 g (a quantitative yield) of the title compound.

Infrared Absorption Spectrum (liquid film) $v_{max}$ cm$^{-1}$:
1615, 1588, 1464, 1420, 1256, 1156, 1096, 1044, 839, 778.

40(ii) 4-t-Butyldimethylsilyloxymethyl-2-methoxybenzaldehyde 87.65 g (1.01 mol) of manganese dioxide were added to a solution of 29.30 g of (4-t-butyldimethylsilyloxymethyl-2-methoxyphenyl)methanol [prepared as described in step (i) above] in 150 ml of methylene chloride, and the resulting mixture was stirred at room temperature for 2 hours. At the end of this time, 41.2 g (0.474 mol) of manganese dioxide were added, with stirring, to the mixture. The reaction mixture was then stirred at 30° C. for 1.5 hours and heated under reflux for 1 hour with stirring, after which it was filtered. The filtrate was freed from the solvent by distillation under reduced pressure, to give 27.29 g (a quantitative yield) of the title compound as an oily substance.

Nuclear Magnetic Resonance Spectrum (270 MHz, CDCl$_3$) δ ppm:
0.12 (6H, singlet);
0.96 (9H, singlet);
3.93 (3H, singlet);
4.78 (2H, singlet);
6.93 (1H, doublet, J=8 Hz);
7.05 (1H, singlet);
7.78 (1H, doublet, J=8 Hz);
10.43 (1H, singlet).

Infrared Absorption Spectrum (liquid film) $v_{max}$ cm$^{-1}$:
1686, 1611, 1462, 1422, 1395, 1258, 1160, 1100, 1034, 841.

PREPARATION 41

3-(4-Acetoxymethyl-2-methoxyphenyl)octanoic acid

41(i) 1-4-t-Butyldimethylsilyloxymethyl-2-methoxphenyl) hexyl alcohol

A solution of 27.91 g (99.5 mmol) of 4-t-butyldimethylsilyloxymethyl-2-methoxybenzaldehyde (prepared as described in Preparation 40) in 100 ml of tetrahydrofuran was added dropwise to 100 ml of an ice-cooled 1.62M solution of pentylmagnesium bromide in tetrahydrofuran over a period of 30 minutes, and then the resulting mixture was stirred at room temperature for 1 hour. The reaction mixture was then mixed with a saturated aqueous solution of ammonium chloride, and the resulting mixture was extracted with a mixture of ethyl acetate and hexane. The extract was washed with a saturated aqueous solution of sodium chloride, after which it was dried over anhydrous magnesium sulfate. The solvent was removed by distillation under reduced pressure, and the resulting residue was purified by column chromatography through 250 g of silica gel using a 1:5 by volume mixture of ethyl acetate and hexane as the eluent, to give 30.67 g (yield 87%) of the title compound as an oily substance.

Infrared Absorption Spectrum (liquid film) $v_{max}$ cm$^1$:
1615, 1584, 1464, 1420, 1372, 1254, 1158, 1096, 839, 778.

41 (ii) 1-(4-t-Butyldimethylsilyloxymethyl-2-methoxyphenyl)-1-oxohexane

A solution of 14.0 ml (0.20 mol) of dimethyl sulfoxide in 50 ml of methylene chloride was added dropwise over a period of 35 minutes to a solution of 9.0 ml (0.10 mol) of oxalyl chloride in 100 ml of methylene chloride cooled to −78° C., whilst the internal temperature of the mixture was kept below −60° C. The resulting mixture was then stirred at −78° C. for 30 minutes, after which a solution of 30.65 g (86.9 mmol) of 1-(4-t-butyldimethylsilyloxymethyl-2 -methoxy-phenyl)hexyl alcohol [prepared as described in step (i) above] in 60 ml of methylene chloride was added dropwise at the same temperature over a period of 35 minutes. The mixture was then stirred for 30 minutes. 60 ml (0.43 mol) of triethylamine were added dropwise to the mixture at the same temperature over a period of 17 minutes, and then the reaction mixture was stirred for 10 minutes, after which the dry ice-acetone bath was removed and the mixture was stirred for a further 50 minutes. At the end of this time, the reaction was terminated by adding water. The reaction mixture was then diluted with methylene chloride, and the organic phase was separated and then washed with 2N aqueous hydrochloric acid, with water and with a saturated aqueous solution of sodium hydrogencarbonate, in that order, after which it was dried over anhydrous magnesium sulfate. The solvent was then removed by distillation under reduced pressure, and the resulting residue was purified by column chromatography through 250 g of silica gel, using a 1:9 by volume mixture of ethyl acetate and hexane as the eluent, to give 27.84 g (yield 91%) of the title compound as an oily substance.

Infrared Absorption Spectrum (liquid film) $v_{max}$ cm$^{-1}$:
  1675, 1611, 1464, 1416, 1370, 1254, 1165, 1100, 1036, 839.

41(iii) Ethyl 3-(4-butyldimethylsilyloxymethyl-2-methoxyphenyl-2-octenoate 5.25 g (0.120 mol) of sodium hydride (as a 55% w/w dispersion in mineral oil) was washed with hexane and then suspended in 70 ml of tetrahydrofuran. A solution of 26.0 ml (0.131 mol) of ethyl diethylphosphonoacetate in 30 ml of tetrahydrofuran was added dropwise over a period of 40 minutes to the suspension, whilst ice-cooling, and the resulting mixture was stirred at room temperature for 10 minutes. A solution of 27.83 g (79.4 mmol) of 1-(4-t-butyldimethylsilyloxymethyl-2-methoxyphenyl)-2-oxohexane [prepared as described in step (ii) above] in 50 ml of tetrahydrofuran was then added to the mixture, which was then heated under reflux for 2.5 hours. At the end of this time, the reaction temperature was allowed to reduce to room temperature, and then a saturated aqueous solution of ammonium chloride was added to the reaction mixture. The resulting aqueous mixture was then extracted with diethyl ether. The extract was washed with water and with a saturated aqueous solution of sodium chloride, in that order, after it was dried over anhydrous magnesium sulfate, and the solvent was removed by distillation under reduced pressure. The resulting residue was purified by column chromatography through 250 g of silica gel, using a 1:9 by volume mixture of ethyl acetate and hexane as the eluent, to give 32.95 g (yield 98.7%) of the title compound as an oily substance.

Infrared Absorption Spectrum (liquid film) $v_{max}$ cm$^{-1}$:
  1728, 1717, 1642, 1464, 1414, 1256, 1221, 1152, 1098, 839.

41(iv) Ethyl 3-(4-t-butyldimethylsilyloxymethyl-2-methoxyphenyl)octanoate

A solution of 27.92 g (66.4 mmol) of ethyl 3-(4-t-butyldimethylsilyl-oxymethyl-2-methoxyphenyl)-2-octenoate [prepared as described in step (iii) above] in 200 ml of ethyl acetate was vigorously stirred for 8 hours in the presence of 1.58 g of 10% palladium-on-charcoal in a stream of hydrogen. At the end of this time, the catalyst was filtered off, and the filtrate was concentrated by evaporation under reduced pressure, to give 28.25 g (a quantitative yield) of the title compound as an oily substance.

Infrared Absorption Spectrum (liquid film) $v_{max}$ cm$^{-1}$:
  1736, 1507, 1464, 1420, 1372, 1256, 1160, 1096, 1040, 839.

41(v) 3-(4-Hydroxymethyl-2-methoxyphenyl)octanoic acid 80 ml of a 2N aqueous solution of sodium hydroxide were added to a solution of 32.64 g (77.2 mmol) of ethyl 3-(4-t-butyldimethylsilyloxymethyl-2-methoxyphenyl)octanoate [prepared as described in step (iv) above] in 80 ml of ethanol, and the resulting mixture was heated under reflux for 1 hour and 40 minutes. At the end of this time, the reaction mixture was freed from the solvent by distillation under reduced pressure, and the resulting residue was acidified with 2N aqueous hydrochloric acid and then extracted with ethyl acetate. The extract was washed with a saturated aqueous solution of sodium chloride, and then the solvent was removed by distillation under reduced pressure, to give 22.09 g (a quantitative yield) of the title compound as an oily substance.

Infrared Absorption Spectrum (liquid film) $v_{max}$ cm$^{-1}$:
  1709, 1613, 1582, 1507, 1464, 1420, 1260, 1160, 1044, 820.

41 (vi) 2-(4-Acetoxymethyl-2-methoxyphenyl)octanoic acid 12.0 ml (127 mmol) of acetic anhydride and 106 mg (0.868 mmol) of 4-N,N-dimethylaminopyridine were added to a solution of 11.53 g (41.1 mmol) of 3-(4-hydroxymethyl-2-methoxyphenyl)octanoic acid [prepared as described in step (v) above] and 12 ml (148 mmol) of pyridine in 100 ml of toluene, and the resulting mixture was stirred at room temperature for 30 minutes. Ice-water and acetone were then added to the reaction mixture, and the resulting mixture was stirred for 2 hours. At the end of this time, the solvent was removed by distillation under reduced pressure. The resulting residue was dissolved in ethyl acetate, and the solution was washed with 2N aqueous hydrochloric acid and with a saturated aqueous solution of sodium chloride, in that order, after which it was dried over anhydrous magnesium sulfate. The solvent was then removed by distillation under reduced pressure, and the resulting residue was purified by column chromatography through 250 g of silica gel, using a gradient elution method, with mixtures of ethyl acetate and hexane ranging from 1:2 to 2:1 by volume as the eluent, to give 12.11 g (yield 91%) of the title compound as an oily substance.

Nuclear Magnetic Resonance Spectrum (270 MHz, CDCl$_3$) δ ppm:
  0.83 (3H, triplet, J=6 Hz);
  1.10–1.29 (6H, multiplet);
  1.59–1.71 (2H, multiplet);
  2.11 (3H, singlet);
  2.57–2.71 (2H, multiplet);
  3.43–3.53 (1H, multiplet);
  3.81 (3H, singlet);
  5.06 (2H, singlet);
  6.83 (1H, doublet, J=1 Hz);
  6.89 (1H, doublet of doublets, J=1 Hz & 8 Hz);
  7.11 (1H, doublet, J=8Hz).

Infrared Absorption Spectrum (liquid film) $v_{max}$ cm$^{-1}$:
  1742, 1709, 1509, 1464, 1422, 1379, 1260, 1227, 1161, 1042.

PREPARATION 42A 3-(2,4-Dimethoxyphenyl)heptanoic acid 686 mg (3.60 mmol) of copper (I) iodide were added to 24.2 ml (36.3 mmol) of a 1.5M butylmagnesium bromide solution in tetrahydrofuran, whilst cooling in an ice-salt bath, and the resulting mixture was stirred for 15 minutes to form a suspension. A solution of 7.47 g (24.3 mmol) of ethyl 3-(2,4-dimethoxyphenyl)-2-ethoxycarbonyl-2-propenoate (prepared as described in Preparation 1) in 25 ml of tetrahydrofuran was then added dropwise to this suspension at the same temperature over a period of 20 minutes, and the resulting mixture was stirred for 30 minutes. The reaction mixture was then neutralized with concentrated aqueous hydrochloric acid and the resulting mixture was filtered using a Celite (trade mark) filter aid. The filtrate was concentrated by evaporation under reduced pressure, and the concentrate was dissolved in ethyl acetate. The resulting solution was washed three times with a saturated aqueous solution of ammonium chloride and once with a saturated aqueous solution of sodium chloride, after which it was dried over anhydrous sodium sulfate. The solvent was then removed by distillation under reduced pressure, and the resulting residue was purified by column chromatography through 100 g of silica gel, using a gradient elution method, with mixtures of hexane and ethyl acetate ranging from 10:1 to 5:1 by volume as the eluent, to give 9.15 g (a quantitative yield) of diethyl 2-[1-(2,4-dimethoxyphenyl)pentyl] malonate as an oily substance.

Following a similar procedure to that described in Preparation 3, but using the diethyl 2-[1-(2,4-dimethoxyphenyl) pentyl]malonate prepared as described above, the title compound was obtained as an oily substance.

Infrared Absorption Spectrum (liquid film) $v_{max}$ cm$^{-1}$:
2675, 1707, 1614, 1588, 1507, 1466, 1292, 1210, 1158, 1038.

PREPARATION 42B 3-(2,4-Dimethoxyphenyl)nonanoic acid

Following a similar procedure to that described in Preparation 42a, but using hexylmagnesium bromide instead of butylmagnesium bromide, the title compound was obtained as an oily substance.

Infrared Absorption Spectrum (liquid film) $v_{max}$ cm$^{-1}$:
1707, 1612, 1587, 1506, 1464, 1439, 1418, 1292, 1261, 1209, 1157, 1132, 1038.

PREPARATION 42C 3-(2,4-Dimethoxyphenyl)-5-methylhexanoic acid

Following a similar procedure to that described in Preparation 42a, but using isobutylmagnesium bromide instead of butylmagnesium bromide, the title compound was obtained as an oily substance.

Infrared Absorption Spectrum (liquid film) $v_{max}$ cm$^{-1}$:
2680, 2361, 1707, 1613, 1507, 1289, 1210, 1158, 1038, 835.

PREPARATION 42D 3-(2,4-Dimethoxyphenyl)-4-methylpentanoic acid

Following a similar procedure to that described in Preparation 42a, but using isopropylmagnesium bromide instead of butylmagnesium bromide, the title compound was obtained as an oily substance.

Infrared Absorption Spectrum (liquid film) $v_{max}$ cm$^{-1}$:
1707, 1612, 1587, 1506, 1466, 1439, 1418, 1385, 1367, 1294, 1261, 1209, 1157, 1134, 1038.

PREPARATION 42E 3-(2,4-Dimethoxyphenyl)hexanoic acid

Following a similar procedure to that described in Preparation 42a, but using propylmagnesium bromide instead of butylmagnesium bromide, the title compound was obtained as an oily substance.

Infrared Absorption Spectrum (liquid film) $v_{max}$ cm$^{-1}$:
1709, 1613, 1588, 1507, 1464, 1439, 1418, 1262, 1210, 1158, 1129, 1040.

PREPARATION 43

3-(2,4-Dimethoxy-5-propionylphenyl)octanoic acid
43(i) Methyl 3-(2,4-dimethoxy-5-propionylphenyl) octanoate A solution of 644 mg (2.0 mmol) of methyl 3-(2,4-dimethoxy-5-formylphenyl)octanoate [prepared as described in Preparation 32(ii)] in 10 ml of tetrahydrofuran was added dropwise over a period of 5 minutes to a solution of 1.2 ml (2.2 mmol) of a 1.8M solution of ethylmagnesium iodide in diethyl ether diluted with 20 ml of tetrahydrofuran, whilst ice-cooling, and the resulting mixture was stirred at the same temperature for 40 minutes. The reaction was then terminated by the addition of a saturated aqueous solution of ammonium chloride, and the resulting mixture was extracted with a mixture of ethyl acetate and hexane. The extract was washed several times with water and once with a saturated aqueous solution of sodium chloride, after which it was dried over anhydrous sodium sulfate. The solvent was then removed by distillation under reduced pressure, giving the title compound as a crude product. This product was dissolved in 40 ml of methylene chloride, and 3.48 g of manganese dioxide were added to the resulting solution. The resulting mixture was stirred for 1 hour, after which a further 3.48 g of manganese dioxide were added. The mixture was then stirred for 12 hours, and then a further 1.72 g of manganese dioxide [8.68 g (99.8 mmol) in total] were added to the mixture, which was then stirred for 8 hours. At the end of this time, the reaction mixture was filtered using a Celite (trade mark) filter aid, and the filtrate was concentrated by evaporation under reduced pressure. The concentrate was triturated with hexane to give approximately pure crystals of the title compound. The compound was further purified by column chromatography through 10 g of silica gel, using a gradient elution method, with mixtures of hexane and ethyl acetate ranging from 5:1 to 3:1 by volume as the eluent, to give 416 mg (yield 59%) of the desired propionyl derivative, melting at 75.5°–77.5° C. (from hexane).

Infrared Absorption Spectrum (liquid film) $v_{max}$ cm$^{-1}$:
1739, 1666, 1601, 1569, 1500, 1471, 1457, 1435, 1345, 1265, 1212, 1150

43(ii) 3-(2,4-Dimethoxy-5-propionylphenyl)octanoic acid

The methyl 3-(2,4-dimethoxy-5-propionylphenyl) octanoate prepared as described in step (i) above was hydrolyzed in a similar manner to that described in Preparation 7 to give the title compound as crystals, melting at 92.5°–94° C. (from ethyl acetate-hexane).

Infrared Absorption Spectrum (KBr) $v_{max}$ cm$^{-1}$:
1702, 1658, 1603, 1571, 1501, 1458, 1409, 1319, 1273, 1214, 1026.

PREPARATION 44

Methyl 3-(4-hydroxy-2-methoxyphenyl)octanoate
44(i) 3-(4-Methylbenzyloxy-2-methoxyphenyl)octanoate 6.26 ml of a 2M solution of trimethylsilyl diazomethane in hexane were added to a solution of 3.72 g (10.4 mmol) of 3-(4-benzyloxy-2-methoxyphenyl)-octanoic acid (prepared as described in Preparation 30C) in a mixture of 30 ml of benzene and 10 ml of methanol, and the resulting mixture was allowed to stand at room temperature for 30 minutes. At the end of this time, the solvent was removed by distillation under reduced pressure, and the resulting residue was purified by column chromatography through 150 g of silica gel, using a 1:4 by volume mixture of ethyl acetate and hexane as the eluent, to give 4.09 g of the title compound as an oily substance.

Infrared Absorption Spectrum (liquid film) $v_{max}$ cm$^{-1}$:
1734, 1613, 1588, 1507, 1457, 1420, 1377, 1036, 957, 940

44ii) Methyl 3-(4-hydroxy-2-methoxyphenyl)octanoate

Reduction for debenzylation and subsequent treatment of the reaction mixture were conducted in a similar manner to that described in Example 124 to give the title compound as an oily substance.
Infrared Absorption Spectrum (liquid film) $v_{max}$ cm$^{-1}$:
1738, 1713, 1615, 1597, 1509, 1468, 1435, 1289, 1196, 1160, 1125.

PREPARATION 45A 3-(4-Ethoxy-2-methoxyphenyl)octanoic acid

45A(i) Methyl 3-(4-ethoxy-2-methoxyphenyl)octanoate 489 p$\mu$(6.12 mmol) of ethyl iodide and 1.99 g of cesium carbonate were added to a solution of 1.43 g (5.10 mmol) of methyl 3-(4-hydroxy-2-methoxy-phenyl)octanoate (prepared as described in Preparation 44) in 50 ml of dimethylformamide, and the resulting mixture was stirred overnight. The reaction mixture was then diluted with ethyl acetate and the diluted solution was washed several times with water and once with a saturated aqueous solution of sodium chloride, after which it was dried over anhydrous magnesium sulfate. The solvent was then removed by distillation under reduced pressure, and the resulting residue was purified by column chromatography through 100 g of silica gel, using a 1:2 by volume mixture of ethyl acetate and hexane as the eluent, to give 1.39 g (yield 88%) of the desired ethyl ether derivative as an oily substance.
Infrared Absorption Spectrum (liquid film) $v_{max}$ cm$^{-1}$:
1738, 1613, 1586, 1507, 1464, 1457, 1291, 1262, 1202, 1163.

45A(ii) 3-(4-Ethoxy-2-methoxyphenyl)octanoic acid

Methyl 3-(4-ethoxy-2-methoxyphenyl)octanoate [prepared as described in step (i) above] was treated in a similar manner to that described in Preparation 7 to give the title compound as an oily substance.
Infrared Absorption Spectrum (liquid film) $v_{max}$ cm$^{-1}$:
1709, 1615, 1286, 1507, 1464, 1455, 1420, 1291, 1262, 1202, 1163.

PREPARATIONS 45B TO 45D

Following a similar procedure to that described in Preparation 45A, but using various kinds of alkyl halides, there were obtained corresponding ether derivatives. These derivatives were hydrolyzed to give the compounds of Preparations 45b to 45d, having the following formula and in which the substituent groups are as shown in the following Table. In the Table, the column headed "IR spectrum" shows the Infrared Absorption Spectrum (liquid film) $v_{max}$ cm$^{-1}$ of the compound.

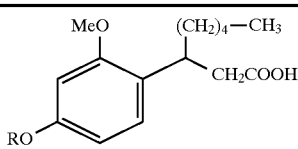

| Preparation No. | R | Form | IR spectrum |
| --- | --- | --- | --- |
| 45B | iPr | oil | 1707, 1612, 1584, 1505, 1456, 1418, 1383, 1289, 1200, 1163 |
| 45C | (CH$_2$)$_2$OMe | oil | 1732, 1707, 1613, 1588, 1505, 1464, 1455, 1291, 1262, 1202, 1127 |
| 45D | (CH$_2$)$_2$OEt | oil | 1732, 1709, 1613, 1588, 1507, 1462, 1455, 1420, 1291, 1262, 1202, 1123 |

PREPARATION 46

N-(2-t-Butyl-5-methoxycarbonylphenyl)-3-(4-hydroxy-2-methoxyphenyl)octaniamide

46(i) N-(2-t-Butyl-5-methoxycarbonylphenyl)-3-(4-benzyloxy-2-methoxy-phenyl)octanamide Following a similar procedure to that described in Preparation 6, but using 3-(4-benzyloxy-2-methoxyphenyl) octanoic acid (prepared as described in Preparation 30C), the title compound was obtained as a foam-like substance.
Nuclear Magnetic Resonance Spectrum (270 MHz, CDCl$_3$), $\delta$ ppm:
0.77–0.90 (3H, multiplet);
1.10–1.36 (6H, multiplet);
1.27 (9H, singlet);
1.63–1.80 (2H, multiplet);
2.61–2.81 (2H, multiplet);
3.42–3.60 (1H, multiplet);
3.77 (3H, singlet);
3.87 (3H, singlet);
5.03 (2H, singlet);
6.47–6.60 (2H, multiplet);
6.95–7.99 (11H, multiplet)

46(ii) N-(2-t-Butyl-5-methoxycarbonylphenyl)-3-(4-hydroxy-2-methoxyphenyl-octanamide Debenzylation of N-(2-t-butyl-5-methoxycarbonylphenyl)-3-(4-benzyloxy-2-methoxyphenyl)octanamide [prepared as described in step (i) above] and subsequent treatment of the reaction mixture were conducted in a similar manner to that described in Example 124 to give the title compound as a foam-like substance.
Infrared Absorption Spectrum (liquid film) $v_{max}$ cm$^{-1}$:
1725, 1707, 1655, 1613, 1599, 1511, 1466, 1437, 1302, 1269, 1248.

PREPARATION 47

N-(2-t-Butyl-5-carboxyphenyl)-3-(4-N',N'-diethylcarbamoylmethoxy-2-methoxyphenyl octanamide 47(i) N-(2-t-Butyl-5-methoxycarbonylphenyl)-3-(4-t-butoxycarbonylmethoxy-2-methoxyphenyl)octanamide Following a similar procedure to that described in Preparation 45A(i), but using N-(2-t-butyl-5-methoxycarbonylphenyl)-3-(4-hydroxy-2-methoxyphenyl)-octanamide (prepared as described in Preparation 46) and t-butyl bromoacetate, the title compound was obtained as a foam-like substance.
Infrared Absorption Spectrum (KBr) $v_{max}$ cm$^{-1}$:
1756, 1725, 1651, 1612, 1507, 1455, 1437, 1369, 1301, 1249, 1153.

47(ii) N-(2-t-Butyl-5-methoxycarbonylphenyl)-3-(4-carboxymethoxy-2-methoxy phenyl)octanamide 1.0 ml (15.0 mmol) of trifluoroacetic acid was added to a solution of 575 mg (1.01 mmol) of N-(2-t-butyl-5-methoxycarbonylphenyl)-3-(4-t-butoxycarbonylmethoxy-2-methoxyphenyl)octanamide [prepared as described in step (i) above] and 241 $\mu$l (2.22 mmol) of anisole in 15 ml of methylene chloride, and the resulting mixture was stirred overnight at 30° C. At the end of this time, the reaction mixture was freed from the solvent and excess reagents by distillation under reduced pressure, and the resulting residue was purified by column chromatography through 50 g of silica gel using ethyl acetate as the eluent, to give 506 mg (yield 98%) of the title carboxylic acid derivative as a foam-like substance.
Infrared Absorption Spectrum (film) $v_{max}$ cm$^{-1}$:
1725, 1651, 1611, 1505, 1439, 1412, 1368, 1302, 1248, 1200, 1163.

47(iii) N-(2-t-Butyl-5-methoxycarbonylphenyl)-3-(4-N',N'-diethylcarbamoylmethoxy-2-methoxyphenyl)octanamide Following a similar procedure to that described in Example 20, but using N-(2-t-butyl-5- methoxycarbonylphenyl)-3-(4-carboxymethoxyphenyl)-octanamide [prepared as described in step (ii) above] and diethylamine, the title carbamoyl derivative was obtained as a foam-like substance.

Infrared Absorption Spectrum (film) $v_{max}$ cm$^{-1}$:
1723, 1651, 1611, 1507, 1464, 1437, 1300, 1264, 1248, 1200, 1123.

47(iv) N-(2-t-Butyl-5-carboxyphenyl)-3-(4-N',N'-diethylcarbamoylmethoxy-2-methoxyphenyl)octanamide Hydrolysis of N-(2-t-butyl-5-methoxycarbonylphenyl)-3-(4-N',N'-diethylcarbamoylmethoxy-2-methoxyphenyl)octanamide [prepared as described in step (iii) above] and subsequent treatment of the reaction mixture were conducted in a similar manner to that described in Preparation 7 to give the title compound as crystals, melting at 85°–86° C. (from methylene chloride-hexane).

Infrared Absorption Spectrum (film) $v_{max}$ cm$^{-1}$:
1717, 1693, 1648, 1612, 1506, 1465, 1285, 1261, 1244, 1200, 1165.

PREPARATION 48

N-(2-t-Butyl-5-carboxyphenyl)-3-(4-N'-butylcarbamoylmethoxy-2-methoxyphenyl)octanamide Following a similar procedure to that described in Example 20, but using N-(2-t-butyl-5-methoxycarbonylphenyl)-3-(4-carboxymethoxy-2-methoxyphenyl)octanamide [prepared as described in Preparation 47(ii)] and butylamine; N-(2-t-butyl-5-methoxycarbonylphenyl)-3-(4-N'-butylcarbamoylmethoxy-2-methoxyphenyl)octanamide was obtained. Hydrolysis of this derivative and subsequent treatment of the reaction mixture were conducted in a similar manner to that described in Preparation 7 to give the title compound as a foam-like substance.

Infrared Absorption Spectrum (KBr) $v_{max}$ cm$^{-1}$:
1715, 1691, 1656, 1612, 1506, 1465, 1419, 1288, 1260, 1245, 1200.

PREPARATION 49

3-(2,4-Dimethoxy-5-methylphenyl)octanoic Acid

49(i) Methyl 3-[2,4-dimethoxy-5-(1,3-dithian-2-yl)phenyl]octanoate 150 mg (1.39 mmol) of 1,3-propanedithiol, 1.0 g of magnesium sulfate and a catalytic amount of boron trifluoride etherate were added, with ice-cooling, to a solution of 447 mg (1.39 mmol) of methyl 3-(2,4-dimethoxy-5-formylphenyl)-octanoate [prepared as described in Preparation 32(ii)] in 12 ml of methylene chloride, and the resulting mixture was stirred at the same temperature for 2 hours. At the end of this time, the reaction mixture was neutralized with a saturated aqueous solution of sodium hydrogencarbonate, and then the dehydrating agent was removed by filtration using a Celite (trade mark) filter aid. The filtrate was concentrated by evaporation under reduced pressure, and the concentrate was extracted with ethyl acetate. The extract was washed with water and with a saturated aqueous solution of sodium chloride, in that order, after is which it was dried over anhydrous sodium sulfate. The solvent was removed by distillation under reduced pressure, and the resulting residue was purified by column chromatography through 10 g of silica gel, using a 5:1 by volume mixture of hexane and ethyl acetate as the eluent, to give 589 mg (a quantitative yield) of the 1,3-dithiane derivative as an oily substance.

Infrared Absorption Spectrum (liquid film) $v_{max}$ cm$^{-1}$:
1737, 1613, 1585, 1508, 1465, 1438, 1299, 1207, 1035.

49(ii) 3-(2,4-Dimethoxy-5-methylphenyl)octanoic acid

A solution of 558 mg (1.35 mmol) of methyl 3-[2,4-dimethoxy-5-(1,3-dithian-2-yl)phenyl]octanoate [prepared as described in step (i) above], 1.576 g (5.42 mmol) of tributyltin hydride and 15 mg of azobis(isobutyronitrile) in 20 ml of toluene was stirred whilst heating at 100° C. for 6.5 hours. At the end of this time, the reaction temperature was allowed to reduce to room temperature, and the reaction mixture was purified by column chromatography through 15 g of silica gel, using a gradient elution method, with mixtures of hexane and ethyl acetate ranging from 6:0 to 6:1 by volume as the eluent, to give a mixture containing the reduced product. The mixture was further purified by column chromatography through 30 g of alumina, using a gradient elution method, with mixtures of hexane and ethyl acetate ranging from 20:0 to 20:1 by volume as the eluent, to give 385 mg (yield 92%) of methyl 3-(2,4-dimethoxy-5-methylphenyl)octanoate as an oily substance.

Infrared Absorption Spectrum (liquid film) $v_{max}$ cm$^{-1}$:
1739, 1615, 1591, 1513, 1466, 1438, 1301, 1207, 1159, 1040.

Hydrolysis of the compound thus obtained and subsequent treatment of the reaction mixture were conducted in a similar manner to that described in Preparation 7 to give the title compound as an oily substance.

Infrared Absorption Spectrum (liquid film) $v_{max}$ cm$^{-1}$:
1707, 1615, 1591, 1513, 1466, 1439, 1301, 1207, 1041.

PREPARATION 50A

3-[4-(3-Methoxypropoxy)-2-methoxyphenyl]octanoic Acid

50A(i) Methyl 3-[4-(3-bromopropoxy)-2-methoxyphenyl]octanoate

Following a similar procedure to that described in Preparation 45A(i), but using methyl 3-(4-hydroxy-2-methoxyphenyl)octanoate (prepared as described in Preparation 44) and 1,3-dibromopropane, the title compound was obtained as an oily substance.

Infrared Absorption Spectrum (liquid film) $v_{max}$ cm$^{-1}$:
1738, 1613, 1587, 1506, 1466, 1290, 1260, 1202, 1162, 1131, 1038.

50A(ii) 3-[4-(3-Methoxypropoxy-2-methoxyphenyl]octanoic acid 1.65 g (8.58 mmol) of a 28% w/w methanolic solution of sodium methoxide were added to a solution of 689 mg (1.72 mmol) of methyl 3-[4-(3-bromopropoxy)-2-methoxyphenyl]octanoate [prepared as described in step (i) above] in 6 ml of methanol, and the resulting mixture was stirred overnight at room temperature. At the end of this time, 1 ml of water was added to the reaction mixture, after which it was stirred whilst heating at 40° C. for 2 hours. The reaction mixture was then freed from the organic solvent by distillation under reduced pressure, and the residue was acidified with 2N aqueous hydrochloric acid and then extracted with ethyl acetate. The extract was washed with a saturated aqueous solution of sodium chloride and dried over anhydrous magnesium sulfate, after which the solvent was removed by distillation under reduced pressure. The residue was purified by column chromatography through 60 g of silica gel, using a gradient elution method, with mixtures of ethyl acetate and hexane ranging from 1:3 to 1:1 by volume, to give 466 mg (yield 78%) of the title compound as an oily substance.

Infrared Absorption Spectrum (liquid film) $v_{max}$ cm$^{-1}$:
1707, 1613, 1586, 1507, 1466, 1457, 1420, 1289, 1262, 1202.

PREPARATION 50B

3-[4-(3-Ethoxypropoxy)-2-methoxyphenyl]octanoic Acid

Following a similar procedure to that described in Preparation 50A, but using an ethanolic sodium ethoxide solution instead of a methanolic sodium methoxide solution, the title compound was obtained as an oily substance.

Infrared Absorption Spectrum (liquid film) $v_{max}$ cm$^{-1}$:
1707, 1613, 1586, 1507, 1466, 1457, 1289, 1262, 1202, 1163.

PREPARATION 51

3-[4-(3-Methylsulfonylpropoxy)-2-methoxyphenyl] octanoic Acid 200 mg (2.85 mmol) of sodium thiomethoxide were added to a solution of 278 mg (0.69 mmol) of methyl 3-[4-(3-bromopropoxy)-2-methoxyphenyl]-octanoate, which was a synthetic intermediate of the compound of Preparation 50A, in 6 ml of methanol, and the resulting mixture was stirred for 1 hour. The reaction mixture was then diluted with ethyl acetate, and the diluted solution was washed several times with water and once with a saturated aqueous solution of sodium chloride, after which it was dried over anhydrous magnesium sulfate. The solvent was then removed by distillation under reduced pressure, and the resulting residue was purified by column chromatography through 50 g of silica gel, using a 1:3 by volume mixture of ethyl acetate and hexane as the eluent, to give methyl 3-[4-(3-methylthiopropoxy)-2-methoxyphenyl]octanoate containing a small amount of impurities. Oxidation of the product and subsequent treatment of the reaction mixture were conducted in a similar manner to that described in Example 21 to give 230 mg of the sulfone derivative as an oily substance in a 83% yield over the two steps. This product was hydrolyzed in a similar manner to that described in Preparation 7 to give the title compound as an oily substance.

Infrared Absorption Spectrum (liquid film) $v_{max}$ cm$^{-1}$:
1705, 1613, 1588, 1507, 1466, 1418, 1290, 1202, 1163, 1131.

PREPARATION 52

3-(2,4-Dimethoxy-5-fluorophenyl)octanoic Acid

52(i) Methyl 3-(2,4-dimethoxy-5-fluorophenyl)octanoate

A solution of 943 mg (3.20 mmol) of methyl 3-(2,4-dimethoxyphenyl)-octanoate [prepared as described in Preparation 32(i)] in 5 ml of 1,2-dichloroethane was added to a suspension of 864 mg (3.53 mmol) of 1-fluoro-5-trifluoromethylpyridinium-2-sulfonate in 10 ml of 1,2-dichloroethane, and the resulting mixture was stirred at 90° C. for 2.5 hours. The reaction mixture was then poured into a saturated aqueous solution of sodium sulfite, and the aqueous mixture was freed from the solvent by evaporation under reduced pressure, after which it was extracted with ethyl acetate. The extract was washed with water and with a saturated aqueous solution of sodium chloride, in that order, after which it was dried over anhydrous sodium sulfate. The solvent was then removed by distillation under reduced pressure, and the resulting residue was purified by column chromatography through 20 g of silica gel, using an 8:1 by volume mixture of hexane and ethyl acetate as the eluent, to give a mixture containing the title compound. This mixture was further purified by column chromatography through 40 g of silica gel, using a 7:1 by volume mixture of hexane and acetone as the eluent, to give the desired fluoride compound as an oily substance in a 18% yield.

Infrared Absorption Spectrum (liquid film) $v_{max}$ cm$^{-1}$:
1739, 1622, 1518, 1466, 1456, 1439, 1326, 1205, 1035.

52(ii) 3-(2.4-Dimethoxy-5-fluorophenyl)octanoic acid

Hydrolysis of the methyl 3-(2,4-dimethoxy-5-fluorophenyl)octanoate prepared as described in step (i) above and subsequent treatment of the reaction mixture were conducted in a similar manner to that described in Preparation 7 to give the title compound as an oily substance.

Infrared Absorption Spectrum (liquid film) $v_{max}$ cm$^{-1}$:
1708, 1622, 1518, 1466, 1456, 1440, 1326, 1205, 1036.

PREPARATION 53

3-[4-(3-Methylsulfonylaminopropoxy)-2-methoxyphenyl]octanoic Acid

Methyl 3-[4-(3-bromopropoxy)-2-methoxyphenyl] octanoate, which was a synthetic intermediate of the compound of Preparation 50A, was reacted with sodium azide in a similar manner to that described in Preparation 26A to give the desired azide derivative, which was catalytically reduced in a similar manner to that described in Preparation 16(v) to give methyl 3-[4-(3-aminopropoxy)-2-methoxyphenyl] octanoate. Following a similar procedure to that described in Example 11, but using the compound thus obtained and methanesulfonyl chloride, there was obtained the desired sulfonamide derivative. Hydrolysis of this derivative and subsequent treatment of the reaction mixture were conducted in a similar manner to that described in Preparation 7 to give the title compound as an oily substance.

Infrared Absorption Spectrum (liquid film) $v_{max}$ cm$^{-1}$:
1732, 1705, 1670, 1613, 1588, 1507, 1470, 1318, 1200, 1154.

PREPARATION 54A

N-(2-t-Butyl -5-carboxymethylphenyl)-3-(2,4-dimethoxyphenyl)-5-methylhexanoic Acid Following a similar procedure to that described in Example 44, but using 3-(2,4-dimethoxyphenyl)-5-methylhexanoic acid (prepared as described in Preparation 42C) and methyl 2-(4-t-butyl-3-aminophenyl)acetate (prepared as described in Preparation 14), the corresponding amide derivative was obtained. Hydrolysis of this derivative and subsequent treatment of the reaction mixture were conducted in a similar manner to that described in Preparation 7 to give the title compound as a foam-like substance.

Infrared Absorption Spectrum (liquid film) $v_{max}$ cm$^{-1}$:
3251, 2624, 1713, 1613, 1507, 1287, 1209, 1157, 1037, 934, 834.

PREPARATION 54B

N-(2-t-Butyl-5-carboxymethylphenyl)-3-(2,4-dimethoxyphenyl)-4-methylpentanoic Acid Following a similar procedure to that described in Example 44, but using 3-(2,4dimethoxyphenyl)-4-methylpentanoic acid (prepared as described in Preparation 42D) and methyl 2-(4-t-butyl-3-aminophenyl)acetate (prepared as described in Preparation 14), the corresponding amide derivative was obtained. Hydrolysis of this derivative and subsequent treatment of the reaction mixture were conducted in a similar manner to that described in Preparation 7 to give the title compound as a foam-like substance.

Infrared Absorption Spectrum (liquid film) $v_{max}$ cm$^{-1}$:

1715, 1657, 1612, 1585, 1506, 1466, 1419, 1365, 1294, 1265, 1207, 1157, 1082, 1036.

PREPARATION 55

3-(5-Chloro-2,4-dimethoxyphenyl)heptanoic Acid

Following a similar procedure to that described in Preparation 32(i), but using 3-(2,4-dimethoxyphenyl)heptanoic acid (prepared as described in Preparation 42A), the corresponding methyl ester derivative was obtained. This was chlorinated in a similar manner to that described in Example 81. Hydrolysis of the product and subsequent treatment of the reaction mixture were conducted in a similar manner to that described in Preparation 7 to give the title compound as crystals, melting at 91°–92° C. (from hexane-ethyl acetate).
Infrared Absorption Spectrum (KBr) $v_{max}$ cm$^{-1}$:
 1704, 1604, 1506, 1465, 1439,1303, 1292, 1206, 1160, 1033.

PREPARATION 56A

Methyl 3-(5-chloro-4-hydroxy-2-methoxyphenyl) octanoate 604 mg (4.48 mmol) of sulfuryl chloride were added to a solution of 1.26 g (4.48 mmol) of methyl 3-(4-hydroxy-2-methoxyphenyl)octanoate (prepared as described in Preparation 44) in 10 ml of benzene, and the resulting mixture was stirred at 70° C. for 3.5 hours. At the end of this time, the reaction mixture was diluted with ethyl acetate, and the diluted solution was washed with an aqueous solution of sodium carbonate, with water and with a saturated aqueous solution of sodium chloride, after which it was dried over anhydrous magnesium sulfate. The solvent was then removed by distillation under reduced pressure, and the resulting residue was purified by column chromatography through 100 g of silica gel, using a 1:2 by volume mixture of ethyl acetate and hexane as the eluent, to give the title compound as an oily substance in a 88% yield.
Infrared Absorption Spectrum (liquid film) $v_{max}$ cm$^{-1}$:
 1736, 1611, 1586, 1496, 1465, 1419, 1319, 1294, 1283, 1208, 1163.

PREPARATION 56B

Methyl 3-(5-chloro-4-hydroxy-2-methoxyphenyl) heptanoate

Following a similar procedure to that described in Preparation 56a, but using methyl 3-(4-hydroxy-2-methoxyphenyl)heptanoate (prepared as described in Preparation 58A), the title compound was obtained as an oily substance.
Infrared Absorption Spectrum (neat) $v_{max}$ cm$^{-1}$:
 3230, 2361, 1732, 1611, 1497, 1206, 1165, 996, 884, 832.

PREPARATION 57A

3-[5-Chloro-4-(2-ethoxyethoxy)-2-methoxyphenyl] octanoic Acid

Following a similar procedure to that described in Preparation 45a-(i), but using methyl 3-(5-chloro-4-hydroxy-2-methoxyphenyl)octanoate (prepared as described in Preparation 56A) and 2-ethoxyethyl bromide, the corresponding. ether derivative was obtained. Hydrolysis of this derivative and subsequent treatment of the reaction mixture were conducted in a similar manner to that described in Preparation 7 to give the title compound as an oily substance.

Infrared Absorption Spectrum (liquid film) $v_{max}$ cm$^{-1}$:
 1732, 1705, 1603, 1578, 1505, 1459, 1449, 1397, 1071, 999.

PREPARATION 57B

3-[5-Chloro-4-(3-methoxypropoxy)-2-methoxyphenyl]heptanoic Acid

Following a similar procedure to that described in Preparation 45A(i), but using methyl 3-(5-chloro-4-hydroxy-2-methoxyphenyl)heptanoate (prepared as described in Preparation 56B) and 3-methoxy-1-tosyloxypropane, the corresponding ether derivative was obtained. Hydrolysis of this derivative and subsequent treatment of the reaction mixture were conducted in a similar manner to that described in Preparation 7 to give the title compound as a viscous substance.
Infrared Absorption Spectrum (neat) $v_{max}$ cm$^{-1}$:
 3100, 1709, 1603, 1505, 1466, 1401, 1302, 1202, 886, 818.

PREPARATIONS 57C AND 57D

Methyl 3-[2-methoxy-4-(2-methoxyethoxy)phenyl]-5-methylhexanoate (prepared as described in Preparation 91A) was chlorinated in a similar manner to that described in Preparation 56 and the product was then hydrolyzed in a similar manner to that described in Preparation 7 to give the compound of Preparation 57c.

In the same way as described in Preparation 57c, the compound of Preparation 57d was prepared from methyl 3-[2-methoxy-4-(2-ethoxyethoxy)-phenyl]-5-methylhexanoate (prepared as described in Preparation 91B).

The compounds have the following formula in which the substituent groups and properties are shown in the following Table, in which the values given under the heading " " are the Infrared Absorption Spectrum (liquid film) $v_{max}$ cm$^{-1}$.

| Prep. No. | R$^A$ | R$^B$ | R$^C$ | form | IR spectrum |
|---|---|---|---|---|---|
| 57C | 2-OMe | 4-O(CH$_2$)$_2$OMe | 5-Cl | oil | 1707, 1603, 1578, 1502, 1464, 1448, 1396, 1302, 1203, 1169, 1151, 1128, 1070, 1036 |
| 57D | 2-OMe | 4-O(CH$_2$)$_2$OEt | 5-Cl | oil | 1707, 1603, 1578, 1504, 1464, 1448, 1396, 1302, 1203, 1178, 1151, 1126, 1070, 1051, |

PREPARATION 58A

Methyl 3-(4-hydroxy-2-methoxyphenyl)heptanoate

Following a similar procedure to that described in Preparation 32(i), but using 3-(4-benzyloxy-2-methoxyphenyl) heptanoic acid prepared as described in Preparation 30G), the corresponding methyl ester derivative was obtained.

Hydrogenolysis of this derivative and subsequent treatment of the reaction mixture were conducted in a similar manner to that described in Example 124 to give the title compound as an oily substance.

Infrared Absorption Spectrum (liquid film) $v_{max}$ cm$^{-1}$:
  1738, 1613, 1586, 1507, 1291, 1260, 1200, 1163, 1123, 1038, 835.

PREPARATION 58B

Methyl 3-(4-hydroxy-2-methoxyphenyl -5-methylhexanoate

Following a similar procedure to that described in Preparation 58A, but using 3-(2-benzyloxy-3-methoxyphenyl)-5-methylhexanoic acid (prepared as described in Preparation 30H), the title compound was obtained as an oily substance.

Infrared Absorption Spectrum (liquid film) $v_{max}$ cm$^{-1}$:
  1736, 1713, 1614, 1597, 1510, 1468, 1437, 1365, 1335, 1286, 1240, 1198, 1161, 1119, 1038.

PREPARATION 59

3-[4-(3-Methoxypropoxy)-2-methoxyphenyl] heptanoic Acid

Following a similar procedure to that described in Preparation 45A(i), but using methyl 3-(4-hydroxy-2-methoxyphenyl)heptanoate (prepared as described in Preparation 58A), and 3-methoxy-1-tosyloxypropane, the corresponding ether derivative was obtained. Hydrolysis of this derivative and subsequent treatment of the reaction mixture were conducted in a similar manner to that described in Preparation 7 to give the title compound as an oily substance.

Infrared Absorption Spectrum (neat) $v_{max}$ cm$^{-1}$:
  1729, 1709, 1613, 1586, 1507, 1291, 1200, 1123, 1038, 835.

PREPARATION 60

N-[2-(2,4-Dimethoxyphenyl)heptyl]-N'-(2-t-butyl-5-carboxyphenyl)urea

A solution of 1.00 g (3.57 mmol) of 3-(2,4-dimethoxyphenyl)octanoic acid (prepared as described in Preparation 3), 982 mg (3.57 mmol) of diphenylphosphoryl azide and 361 mg (3.57 mmol) of triethylamine in 15 ml of benzene was heated under reflux for 2.5 hours. At the end of this time, the reaction temperature was allowed to reduce to room temperature, after which a solution of 739 mg (3.57 mmol) of 2-t-butyl-5-methoxycarbonylaniline (prepared as described in Preparation 5) in 10 ml of benzene was added to the mixture, and the resulting mixture was heated under reflux for 2 hours and 45 minutes. The reaction mixture was cooled to room temperature, and then the mixture was diluted with ethyl acetate. The diluted solution was washed with 2N aqueous hydrochloric acid, with water, with a saturated aqueous solution of sodium hydrogencarbonate and with a saturated aqueous solution of sodium chloride, in that order, after which it was dried over anhydrous magnesium sulfate. The solvent was then removed by distillation under reduced pressure, and the resulting residue was purified by column chromatography through 100 g of silica gel, using a 2:1 by volume mixture of ethyl acetate and hexane as the eluent, to give 728 mg of the desired urea derivative as a foam-like substance in a 42% yield. The derivative thus obtained was hydrolyzed in a similar manner to that described in Preparation 7 to give the title compound as a foam-like substance.

Infrared Absorption Spectrum (film) $v_{max}$ cm$^{-1}$:
  1692, 1634, 1613, 1553, 1507, 1464, 1422, 1366, 1291, 1258, 1208.

PREPARATION 61

N-(2-t-Butyl-5-methoxycarbonylphenyl)-3-(4-hydroxymethyl-2-methoxyphenyl)octanamide One drop of dimethylformamide and then 3.0 ml (34.5 mmol) of oxalyl chloride were added to a solution of 6.06 g (18.8 mmol) of 3-(4-acetoxymethyl-2-methoxyphenyl) octanoic acid (prepared as described in Preparation 41) in 40 ml of methylene chloride, and the resulting mixture was stirred at room temperature for 50 minutes. At the end of this time, the reaction mixture was freed from excess reagents and the solvent by distillation under reduced pressure. The resulting residue was dissolved in 20 ml of methylene chloride, and this solution was added to a solution of 4.12 g (19.9 mmol) of 2-t-butyl-5-methoxycarbonylaniline (prepared as described in Preparation 5) and 5 ml of pyridine in 20 ml of methylene chloride, whilst ice-cooling. The resulting mixture was then stirred at the same temperature for 20 minutes. At the end of this time, the reaction mixture was mixed with water, and the aqueous mixture was extracted with ethyl acetate. The extract was washed with 2N aqueous hydrochloric acid, with water, with a saturated aqueous solution of sodium hydrogencarbonate and with a saturated aqueous solution of sodium chloride, in that order, after which it was dried over anhydrous magnesium sulfate. The solvent was then removed by distillation under reduced pressure, and the resulting residue was dissolved in 200 ml of absolute methanol. 2.0 ml (2.0 mmol) of a 1.0M methanolic sodium methoxide solution were then added to the resulting solution. The resulting mixture was then stirred at room temperature for 2.5 hours. In order to terminate the reaction, a saturated aqueous solution of ammonium chloride was added to the reaction mixture, after which it was freed from methanol by distillation under reduced pressure. It was then extracted with ethyl acetate. The extract was washed with water and with a saturated aqueous solution of sodium chloride, in that order, after which it was dried over anhydrous magnesium sulfate. The solvent was then removed by distillation under reduced pressure, and the resulting residue was purified by column chromatography through 250 g of silica gel using a 1:1 by volume mixture of ethyl acetate and hexane as the eluent, to give 7.80 g (yield 88%, based on the compound of Preparation 41)of the title compound as a foam-like substance.

Nuclear Magnetic Resonance Spectrum (270 MHz, CDCl$_3$) δ ppm:
  0.84 (3H, triplet, J=6 Hz);
  1.12–1.35 (6H, multiplet);
  1.31 (9H, singlet);
  1.71–1.83 (2H, multiplet);
  2.25–2.40 (1H, broad singlet);
  2.73 (2H, doublet, J=8 Hz);
  3.53–3.65 (1H, multiplet);
  3.81 (3H, singlet);
  3.86 (3H, singlet);
  4.66 (2H, broad singlet);
  6.94–6.99 (3H, multiplet);
  7.21 (1H, doublet, J=8 Hz);
  7.37–7.41 (2H, multiplet);
  7.73–7.76 (1H, multiplet).

Infrared Absorption Spectrum (KBr) $v_{max}$ cm$^{-1}$:
  1725, 1653, 1518, 1436, 1418, 1302, 1264, 1250, 1123, 1043.

PREPARATION 62

N-(2-t-Butyl-5-carboxyphenyl)-3-(2-methoxy-4-methylphenyl)octanamide

62(i) N-(2-t-Butyl-5-methoxycarboxyphenyl-3-(4-acetoxymethyl-2-methoxyphenyl)octanamide 2.0 ml of pyridine, 1.0 ml (10.6 mmol) of acetic anhydride and 10 mg (0.082 mmol) of 4-N,N-dimethylaminopyridine were added to a solution of 1.10 g (2.34 mmol) of N-(2-t-butyl-5-methoxycarbonylphenyl)-3-(4-hydroxymethyl-2-methoxyphenyl)octanamide (prepared as described in Preparation 61) in 10 ml of toluene, and the resulting mixture was stirred at room temperature for 30 minutes. At the end of this time, the reaction mixture was freed from excess reagents and the solvent by distillation under reduced pressure, and the resulting residue was dissolved in ethyl acetate. The solution thus obtained was washed with 2N aqueous hydrochloric acid, with water, with a saturated aqueous solution of sodium hydrogencarbonate and with a saturated aqueous solution of sodium chloride, in that order, after which it was dried over anhydrous magnesium sulfate. The solvent was then removed by distillation under reduced pressure, giving 1.21 g (a quantitative yield) of the title acetic acid ester derivative as a viscous oily substance.

Infrared Absorption Spectrum (film) $v_{max}$ cm$^{-1}$:
1725, 1651, 1613, 1514, 1462, 1377, 1300, 1229, 1123, 1042.

62(ii) N-(2-t-Butyl-5-methoxycarbonylphenyl)-3-(2-methoxy-4-methylphenyl)-octanamide A solution of the whole of the N-(2-t-butyl-5-methoxycarboxyphenyl)-3-(4-acetoxymethyl-2-methoxyphenyl)octanamide prepared as described in step (i) above in 10 ml of methanol was vigorously stirred at room temperature for 2 hours and was then heated at 40° C. for 2 hours in the presence of 115 mg of 10% w/w palladium-on-charcoal under one atmospheres pressure of hydrogen. The reaction mixture was filtered to remove the catalyst, and the filtrate was concentrated by evaporation under reduced pressure, to give 1.11 g (a quantitative yield) of the title deacetoxy derivative as a viscous oily substance.

Infrared Absorption Spectrum (film) $v_{max}$ cm$^{-1}$:
1725, 1651, 1613, 1511, 1464, 1410, 1302, 1264, 1123, 1042.

62(iii) N-(2-t-Butyl-5-carboxyphenyl)-3-(2-methoxy-4-methylphenyl)-octanamide 3.0 ml (6.0 mmol) of a 2N aqueous aqueous solution of sodium hydroxide were added to a solution of 1.11 g (2.34 mmol) of N-(2-t-butyl-5-methoxycarbonylphenyl)-3-(2-methoxy-4-methylphenyl)octanamide [prepared as described in step (ii) above] in 30 ml of methanol, and the resulting mixture was heated under reflux for 1 hour, after which the solvent was removed by distillation under reduced pressure. The resulting residue was acidified with 1N aqueous hydrochloric acid, and the aqueous mixture was extracted with ethyl acetate. The extract was washed with a saturated aqueous solution of sodium chloride, afterwhich it was dried over anhydrous magnesium sulfate. The solvent was then removed by distillation under reduced pressure, giving 1.02 g (a quantitative yield) of the title compound as crystals, melting at 163.5°–165° C.

Nuclear Magnetic Resonance Spectrum (270 MHz, CDCl$_3$) δ ppm:
0.84 (3H, triplet, J=6 Hz);
1.15–1.37 (6H, multiplet);
1.28 (9H, singlet);
1.70–1.88 (2H, multiplet);
2.31 (3H, singlet);
2.66–2.80 (2H, multiplet);
3.52–3.63 (1H, multiplet);
3.80 (3H, singlet);
6.68 (1H, singlet);
6.78 (1H, doublet, J=8 Hz);
7.02 (1H, singlet);
7.11 (1H, doublet, J=8 Hz);
7.43 (1H, doublet, J=8 Hz);
7.80–7.90 (2H, multiplet).

Infrared Absorption Spectrum (KBr) $v_{max}$ cm$^{-1}$:
1692, 1652, 1611, 1508, 1425, 1366, 1307, 1252, 1134, 1043.

PREPARATION 63A

N-(2-t-Butyl-5-methoxycarbonylphenyl)-3-(4-formyl-2-methoxyphenyl)octanamide 12.67 g (14.6. mmol) of manganese dioxide were added to a solution of 3.45 g (7.35 mmol) of N-(2-t-butyl-5-methoxycarbonylphenyl)-3-(4-hydroxymethyl-2-methoxyphenyl)octanamide (prepared as described in Preparation 61) in 40 ml of methylene chloride, and the resulting mixture was vigorously stirred at room temperature for 10 hours. At the end of this time, the reaction mixture was filtered using a Celite (trade mark) filter aid, and the filtrate was concentrated by evaporation under reduced pressure to give the title compound as a foam-like substance in a 86% yield.

Nuclear Magnetic Resonance Spectrum (270 MHz, CDCl$_3$) δ ppm:
0.84 (3H, triplet, J=6 Hz);
1.10–1.34 (6H, multiplet);
1.29 (9H, singlet);
1.75–1.86 (2H, multiplet);
2.68–2.83 (2H, multiplet);
3.66–3.77 (1H, multiplet);
3.86 (3H, singlet);
3.91 (3H, singlet);
7.03 (1H, broad singlet);
7.39–7.47 (4H, multiplet);
7.76–7.90 (2H, multiplet);
9.94 (1H, singlet).

Infrared Absorption Spectrum (KBr) $v_{max}$ cm$^{-1}$:
1725, 1692, 1651, 1603, 1519, 1463, 1301, 1262, 1123, 1038.

PREPARATION 63B

N-(2-t-Butyl-5-methoxycarbonylphenyl-3-(4-formyl-2-methoxyphenyl)-5-methylhexanamide Using N-(2-t-butyl-5-methoxycarbonylphenyl)-3-(4-hydroxymethyl-2-methoxyphenyl)-5-methylhexanamide (prepared as described in Preparation 95A), the procedure described in Preparation 63A was repeated to give the title compound as a foam-like substance.

Infrared Absorption Spectrum (film) $v_{max}$ cm$^{-1}$:
1723, 1692, 1651, 1603, 1580, 1518, 1505, 1464, 1387, 1366, 1302, 1254.

PREPARATION 63C

N-(2-t-Butyl-5-methoxycarbonylphenyl)-3-(4-formyl-2-methoxyphenyl)hexanamide

Following a procedure similar to that described in Preparation 63A, but using N-(2-t-butyl-5-methoxycarbonylphenyl)-3-[4-hydroxymethyl-2-methoxyphenyl]hexanamide (prepared as described in Preparation 95B), the title compound was obtained as a foam-like substance.

Infrared Absorption Spectrum (film) $v_{max}$ cm$^{-1}$:
1723, 1692, 1651, 1605, 1578, 1520, 1462, 1420, 1302, 1261, 1123.

PREPARATION 64A

N-(2-t-Butyl-5-carboxyphenyl)-3-(4-acetyl-2-methoxyphenyl)octanamide

64A(i) N-(2-t-Butyl-5-methoxycarbonylphenyl-3-[4-(1-hydroxyethyl)-2-methoxyphenyl)octanamide A solution of 537 mg (1.15 mmol) of N-(2-t-butyl-5-methoxycarbonylphenyl)-3-(4-formyl-2-methoxyphenyl)octanamide (prepared as described in Preparation 63A) in 10 ml of tetrahydrofuran was cooled to −78° C., and 4.1 ml (3.9 mmol) of a 0.95M solution of methylmagnesium bromide in tetrahydrofuran were added dropwise thereto over a period of 5 minutes. The reaction mixture was stirred at the same temperature for 1 hour and then at 0° C. for 90 minutes, after which a saturated aqueous solution of ammonium chloride was added to the mixture to terminate the reaction. The mixture was then extracting with ethyl acetate. The extract was washed with water and with a saturated aqueous solution of sodium chloride, after which it was dried over anhydrous magnesium sulfate. The solvent was then removed by distillation under reduced pressure, and the resulting residue was purified by column chromatography through 25 g of silica gel, using a gradient elution method, with mixtures of ethyl acetate and hexane ranging from 1:1 to 3:2 by volume, to give 479 mg (yield 86%) of the title compound as a foam-like substance.

Infrared Absorption Spectrum (KBr) $v_{max}$ cm$^{-1}$:
1725, 1653, 1612, 1517, 1463, 1412, 1302, 1250, 1123, 1042.

64A(ii) N-(2-t-Butyl-5-methoxycarbonylphenyl)-3-(4-acetyl-2-methoxphenyl)-octanamide 500 mg of 4A molecular sieves and 185 mg (1.58 mmol) of 4-methylmorpholin-4-oxide were added to a solution of 466 mg (0.964 mmol) of N-(2-t-butyl-5-methoxycarbonylphenyl)-3-[4-(1-hydroxyethyl)-2-methoxyphenyl)-octanamide [prepared as described in step (i) above] in 10 ml of methylene chloride, and the resulting mixture was stirred at room temperature for 10 minutes. At the end of this time, 34 mg (0.097 mmol) of tetrapropylammonium perruthenate were added to the mixture. The reaction mixture was stirred at room temperature for 1 hour, after which it was diluted with hexane and the diluted solution was subjected to column chromatography through 25 g of silica gel, using a 1:1 by volume mixture of ethyl acetate and hexane as the eluent, to give 456 mg (yield 98%) of the title ketone derivative as a foam-like substance.

Infrared Absorption Spectrum (KBr) $v_{max}$ cm$^{-1}$:
1725, 1683, 1651, 1519, 1412, 1364, 1300, 1268, 1122, 1036.

64A(iii) N-(2-t-Butyl-5-carboxyphenyl)-3-(4-acetyl-2-methoxyphenyl)-octanamide

Following a similar procedure to that described in Preparation 62(iii), but using N-(2-t-butyl-5-methoxycarbonylphenyl)-3-(4-acetyl-2-methoxyphenyl)-octanamide [prepared as described in step (ii) above], the title compound was obtained as a foam-like substance.

Nuclear Magnetic Resonance Spectrum (270 MHz, CDCl$_3$) δ ppm:
0.84 (3H, triplet, J=6 Hz);
1.13–1.35 (6H, multiplet);
1.30 (9H, singlet);
1.72–1.82 (2H, multiplet);
2.59 (3H, singlet);
2.70–2.84 (2H, multiplet);
3.62–3.73 (1H, multiplet);
3.89 (3H, singlet);
7.01 (1H, broad singlet);
7.31–7.56 (4H, multiplet);
7.80–7.87 (2H, multiplet).

Infrared Absorption Spectrum (KBr) $v_{max}$ cm$^{-1}$:
1722, 1686, 1663, 1608, 1518, 1413, 1270, 1226, 1127, 1036.

PREPARATION 64B

N-(2-t-Butyl-5-carboxyphenyl)-3-(2-methoxy-4-propionylphenyl)octanamide

64B(i) N-(2-t-Butyl-5-methoxycarbonylphenyl)-3-[4-(1-hydroxypropyl)-2-methoxyphenyl]octanamide Following a similar procedure to that described in Preparation 64A(i), but using N-(2-t-butyl-5-methoxycarbonylphenyl)-3-(4-formyl-2-methoxyphenyl)-octanamide (prepared as described in Preparation 63A) and ethylmagnesium bromide, the title compound was obtained as a foam-like substance.

Infrared Absorption Spectrum (KBr) $v_{max}$ cm$^{-1}$:
1725, 1653, 1612, 1517, 1463, 1411, 1302, 1249, 1123, 1041.

64B(ii) N-(2-t-Butyl-5-methoxycarbonylphenyl)-3-(2-methoxy-4-propionylphenyl)octanamide Following a similar procedure to that described in Preparation 64A(ii), but using N-(2-t-butyl-5-methoxycarbonylphenyl)-3-[4-(1-hydroxypropyl)-2-methoxyphenyl]octanamide [prepared as described in step (i) above], the title ketone derivative was obtained as a glassy substance.

Infrared Absorption Spectrum (KBr) $v_{max}$ cm$^{-1}$:
1725, 1684, 1651, 1605, 1519, 1411, 1301, 1250, 1210, 1123.

64B(iii) N-(2-t-Butyl-5-carboxyphenyl-3-(2-methoxy-4-propionylphenyl)-octanamide Following a similar procedure to that described in Preparation 62(iii), but using N-(2-t-butyl-5-methoxycarbonylphenyl)-3-(2-methoxy-4-propionylphenyl)octanamide [prepared as described in step (ii) above], the title compound was obtained as crystals, melting at 197°–199° C.

Nuclear Magnetic Resonance Spectrum (270 MHz, CDCl$_3$) δ ppm:
0.84 (3H, triplet, J=6 Hz);
1.10–1.35 (6H, multiplet);
1.21 (3H, triplet, J=7 Hz);
1.29 (9H, singlet);
1.75–1.83 (2H, multiplet);
2.70–2.84 (2H, multiplet);
2.99 (2H, quartet, J=7 Hz);
3.61–3.72 (1H, multiplet);
3.89 (3H, singlet);
7.02 (1H, broad singlet);
7.30–7.57 (4H, multiplet);
7.80–7.89 (2H, multiplet).

Infrared Absorption Spectrum (KBr) $v_{max}$ cm$^{-1}$:
1693, 1642, 1611, 1567, 1519, 1463, 1412, 1251, 1203, 1129.

PREPARATION 64C

N-(2-t-Butyl-5-carboxyphenyl)-3-(4-butyryl-2-methoxyphenyl)octanamide

64C(i) N-(2-t-Butyl-5-methoxycarbonylphenyl)-3-[4-(1-hydroxybutyl)-2-methoxyphenyl]octanamide Following a similar procedure to that described in Preparation 64A(i), but using N-(2-t-butyl-5-methoxycarbonylphenyl)-3-(4-formyl-2-methoxyphenyl)-octanamide (prepared as described in Preparation 63A) and propylmagnesium bromide, the title compound was obtained as a foam-like substance.

Infrared Absorption Spectrum (KBr) $v_{max}$ cm$^{-1}$:
1725, 1653, 1612, 1518, 1464, 1412, 1302, 1250, 1123, 1041.

64C(ii) N-(2-t-Butyl-5-methoxycarbonylphenyl)-3-(4-butyryl-2-methoxyphenyl)octanamide Following a similar procedure to that described in Preparation 64A(ii), but using N-(2-t-butyl-5-methoxycarbonylphenyl)-3-[4-(1-hydroxybutyl)-2-methoxyphenyl]octanamide [prepared as described in step (i) above], the title ketone derivative was obtained as a foam-like substance.

Infrared Absorption Spectrum (KBr) $v_{max}$ cm$^{-1}$:
1725, 1683, 1651, 1519, 1464, 1411, 1301, 1249, 1199, 1122.

64C(iii) N-(2-t-Butyl-5-carboxyphenyl)-3-(4-butyryl-2-methoxyphenyl)-octanamide

Following a similar procedure to that described in Preparation 62(iii), but using N-(2-t-butyl-5-methoxycarbonylphenyl)-3-(4-butyryl-2-methoxyphenyl)-octanamide [prepared as described in step (ii) above], the title compound was obtained as crystals, melting at 135.5°–137.5° C.

Nuclear Magnetic Resonance Spectrum (270 MHz, CDCl$_3$) δ ppm:
0.84 (3H, triplet, J=6 Hz);
0.99 (3H, triplet, J=7 Hz);
1.13–1.35 (6H, multiplet);
1.29 (9H, singlet);
1.69–1.82 (4H, multiplet);
2.69–2.83 (2H, multiplet);
2.92 (2H, triplet, J=7 Hz);
3.61–3.72 (1H, multiplet);
3.89 (3H, singlet);
7.01 (1H, broad singlet);
7.30–7.56 (4H, multiplet);
7.80–7.92 (2H, multiplet).

Infrared Absorption Spectrum (KBr) $v_{max}$ cm$^{-1}$:
1688, 1652, 1609, 1518, 1464, 1413, 1302, 1250, 1199, 1129.

PREPARATION 64D

N-(2-t-Butyl-5-carboxyphenyl)-3-(4-butyryl-2-methoxyphenyl)-5-methylhexanamide

Using N-(2-t-butyl-5-methoxycarbonylphenyl)-3-(4-formyl-2-methoxyphenyl)-5-methylhexanamide (prepared as described in Preparation 63B), the procedure described in Example 64C was repeated to give the title compound as a foam-like substance.

Infrared Absorption Spectrum (film) $v_{max}$ cm$^{-1}$:
1684, 1661, 1607, 1570, 1520, 1464, 1412, 1366, 1302, 1252, 1200.

PREPARATION 64E

N-(2-t-Butyl-5-carboxyphenyl)-3-(4-propionyl-2-methoxyphenyl)-5-methylhexanamide Using N-(2-t-butyl-5-methoxycarbonylphenyl)-3-(4-formyl-2-methoxyphenyl)-5-methylhexanamide (prepared as described in Preparation 63B), the procedure described in Preparation 64B was repeated to give the title compound as a foam-like substance.

Infrared Absorption Spectrum (film) $v_{max}$ cm$^{-1}$:
1682, 1661, 1607, 1570, 1520, 1464, 1412, 1366, 1254, 1204, 1167.

PREPARATION 65

N-(2-t-Butyl-5-carboxyphenyl-3-(2,4-dimethoxy-5-methoxyiminophenyl)octanamide

65(i) N-(2-t-Butyl-5-methoxycarbonylphenyl)-3-(2,4-dimethoxy-5-formylphenyl)octanamide Following a similar procedure to that described in Preparation 6, but using 3-(2,4-dimethoxy-5-formylphenyl)octanoic acid (prepared as described in Preparation 32), the title amide derivative was obtained as a foam-like substance.

Infrared Absorption Spectrum (KBr) $v_{max}$ cm$^{-1}$:
3271, 1724, 1672, 1607, 1510, 1498, 1468, 1437, 1301, 1275, 1249, 1211, 1125, 1028.

65(ii) N-(2-t-Butyl-5-carboxyphenyl)-3-(2,4-dimethoxy-5-methoxyiminophenyl)octanamide Following a similar procedure to that described in Example 111, but using N-(2-t-butyl-5-methoxycarbonylphenyl)-3-(2,4-dimethoxy-5-formylphenyl)-octanamide [prepared as described in step (i) above] and O-methylhydroxylamine hydrochloride, there was obtained the desired methoxyimino derivative. This was hydrolyzed by a similar procedure to that described in Preparation 7 to give the title compound as a powdery substance.

Infrared Absorption Spectrum (KBr) $v_{max}$ cm$^{-1}$:
3267, 1698, 1648, 1614, 1516, 1499, 1466, 1297, 1208, 1128, 1056, 1034.

PREPARATION 66

Following a similar procedure to that described in Preparation 3, there were obtained the carboxylic acid derivatives of Preparations 66A to 66H having the following formula in which the substituent groups are as shown in the following Table. In the column headed "form" is given the physical form or the melting point range and the solvent from which the product was crystallised. In the column headed "IR spectrum" is given the Infrared Absorption Spectrum (CHCl$_3$) $v_{max}$ cm$^{-1}$.

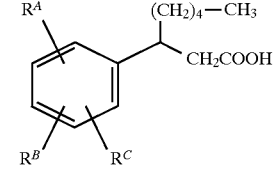

| Prep. No. | R$^A$ | R$^B$ | R$^C$ | form | IR spectrum |
| --- | --- | --- | --- | --- | --- |
| 66A | 2-OMe | 3-OMe | 4-OMe | oil | 2960, 2933, 1741, 1709, 1601, 1496, 1466, 1276, 1097 |
| 66B | 2-OMe | 4-OMe | 5-OMe | 39–41 (diethyl ether-hexane)* | 2959, 2934, 1708, 1612, 1511, 1466, 1400, 1134, 860 |
| 66C | 2-OMe | 3-OMe | H | oil | 3088, 2959, 2933, 2860, 1709, 1585, 1479, 1432, 1074, 1006 |
| 66D | 2-OMe | 4-OMe | 6-OMe | oil | 3097, 2959, 2933, 1705, 1608, 1593, 1493, 1419, 1153, 1128, 1063, 950 |

-continued

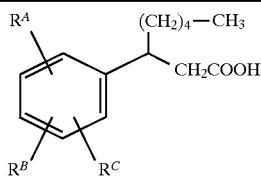

| Prep. No. | R^A | R^B | R^C | form | IR spectrum |
|---|---|---|---|---|---|
| 66E | 2,3-OCH$_2$CH$_2$O | | H | oil | 2959, 2931, 1741, 1709, 1474, 1456, 1283, 1090 |
| 66F | 3-OMe | 4-OMe | 5-OMe | 93.5–94.5 (AcOEt-hexane)* | 2961, 2934, 1742, 1709, 1592, 1511, 1464, 1131, 1004 |
| 66G | 2-OMe | H | 6-OMe | 74.5–75 (AcOEt-hexane)* | 3518, 2959, 2933, 2860, 2841, 1706, 1593, 1474, 1437, 1117 |
| 66H | 2-OMe | H | H | 41–43(hexane)* | 3516, 3107, 2959, 2931, 1741, 1708, 1494, 1465, 1290, 1032 |

*The solvent used for recrystallization.

PREPARATION 67

Following a similar procedure to that described in Preparation 8, but using the substituted phenyloctanoic acid derivatives of Preparations 66A to 66H instead of 3-(2,4-dimethoxyphenyl)octanoic acid, the compounds of Preparations 67A to 67H having the following formula were obtained. The substituent groups and properties are as shown in the following Table. In the column headed "form" is given the physical form or the melting point range and the solvent from which the product was crystallised. In the column headed "IR spectrum" is given the Infrared Absorption Spectrum (CHCl$_3$) $v_{max}$ cm$^{-1}$.

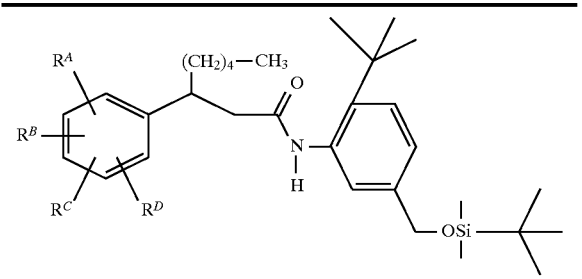

| Prep. No. | R^A | R^B | R^C | R^D | form | IR spectrum |
|---|---|---|---|---|---|---|
| 67A | 2-OMe | 3-OMe | 4-OMe | H | oil | 2958, 2932, 2859, 1676, 1495, 1465, 1420, 1260, 1097, 1016, 839 |
| 67B | 2-OMe | 4-OMe | 5-OMe | H | 130–131 (AcOEt-hexane)* | 2959, 2932, 2859, 1676, 1510, 1466, 1106, 839 |
| 67C | 2-OMe | 3-OMe | H | H | oil | 2959, 2932, 2859, 1679, 1514, 1479, 1260, 1088, 1006 |
| 67D | 2-OMe | 4-OMe | 6-OMe | H | oil | 2959, 2931, 2859, 1675, 1608, 1593, 1466, 1420, 1153, 1124, 951, 839 |
| 67E | 2,3-OCH$_2$CH$_2$O | | H | H | viscous liquid | 2958, 2931, 2859, 1678, 1473, 1282, 1259, 1090, 839 |
| 67F | 3-OMe | 4-OMe | 5-OMe | H | foam | 3255, 2956, 2929, 1651, 1591, 1511, 1463, 1421, 1129, 1012, 838, 777 |
| 67G | 2-OMe | 6-OMe | H | H | oil | 2959, 2931, 2859, 1732, 1675, 1593, 1474, 1114, 839 |
| 67H | 2-OMe | H | H | H | viscous | 3470, 2958, 2931, 2859, 1678, 1493, 1472, 1422, 1365, 1107 |

*The solvent used for recrystallization.

PREPARATION 68

Following a similar procedure to that described in Preparation 9, but using the compounds 67A to 67H, the compounds of Preparations 68A to 68H having the following formula were obtained. The substituent groups and properties are as shown in the following Table. In the column headed "form" is given the physical form or the melting point range and the solvent from which the product was crystallised. In the column headed "IR spectrum" is given the Infrared Absorption Spectrum $v_{max}$ cm$^{-1}$; where appropriate, the medium employed for the Infrared Absorption Spectrum is also given.

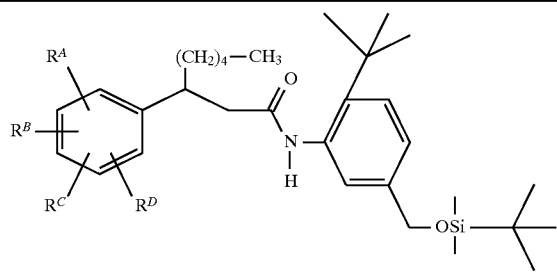

| Prep. No. | R^A | R^B | R^C | R^D | form | IR spectrum |
|---|---|---|---|---|---|---|
| 68A | 2-OMe | 3-OMe | 4-OMe | H | oil | 3607, 2960, 2934, 1676, 1600, 1495, 1466, 1097, 1016, 884, 829 (CHCl$_3$) |
| 68B | 2-OMe | 4-OMe | 5-OMe | H | oil | 3607, 3419, 2960, 2935, 1676, 1611, 1571, 1510, 1479, 1466, 1180, (CHCl$_3$) |
| 68C | 2-OMe | 3-OMe | H | H | oil | 3427, 2961, 2934, 1678, 1514, 1479, 1274, 1080, 1006, (CHCl$_3$) |

-continued

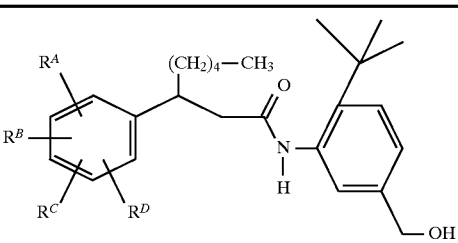

| Prep. No. | R^A | R^B | R^C | R^D | form | IR spectrum |
|---|---|---|---|---|---|---|
| 68D | 2-OMe | 4-OMe | 6-OMe | H | 118–120 (AcOEt-hexane)* | 3606, 3403, 2960, 2935, 1732, 1675, 1608, 1592, 1153, 1124, 950 (CHCl$_3$) |
| 68E | 2,3-OCH$_2$CH$_2$O | | H | H | powder | 3607, 3427, 2960, 2932, 1678, 1514, 1474, 1283, 1089, 1051 (CHCl$_3$) |
| 68F | 3-OMe | 4-OMe | 5-OMe | H | oil | 3607, 3419, 2960, 2935, 1676, 1612, 1510, 1466, 1180, 1080, 889, 861 (CHCl$_3$) |
| 68G | 2-OMe | 6-OMe | H | H | 100–101 (CH$_2$Cl$_2$-hexane)* | 3607, 3409, 2960, 2933, 2873, 2861, 1675, 1593, 1474, 1367, 1114, 1098, 1039 (CHCl$_3$) |
| 68H | 2-OMe | H | H | H | 91–93 (AcOEt-hexane)* | 3422, 3277, 1661, 1520, 1495, 1466, 1439, 1414, 1363, 1292, 1279, 1242, 1124, 1082, 1049 (KBr) |

*: The solvent used for recrystallization.

PREPARATION 69

N-[2-t-Butyl-5-bromomethylphenyl]-3-(2,3-methylenedioxyphenyl)octanamide 11.09 g (42.3 mmol) of triphenylphosphine were added, with ice-cooling, to a solution of 15.00 g (35.2 mmol) of diethyl 2-[1-(2,4-dimethoxyphenyl)-hexyl]malonate (prepared as described in Preparation 2) and 14.03 g (42.3 mmol) of carbon tetrabromide in 40 ml of methylene chloride, and the resulting mixture was stirred at room temperature for 30 minutes. At the end of this time, the reaction mixture was diluted with methylene chloride, and the diluted solution was washed with a saturated aqueous solution of sodium hydrogencarbonate and with a saturated aqueous solution of sodium chloride, in that order, after which it was dried over anhydrous magnesium sulfate, and the solvent was removed by distillation under reduced pressure. The resulting residue was purified by column chromatography through silica gel using a gradient elution method, with mixtures of ethyl acetate and hexane ranging from 1:6 to 1:5 by volume as the eluent, to give 17.19 g (a quantitative yield) of the title compound as crystals,. melting at 119°–120° C. (from hexane-diethyl ether).
Nuclear Magnetic Resonance Spectrum (270 MHz, CDCl$_3$) δ ppm:
0.84–0.90 (3H, multiplet);
1.20–1.32 (6H, multiplet);
1.26 (9H, singlet);
1.63–1.82 (2H, multiplet);
2.73 (2H, doublet, J=7.5 Hz);
3.31–3.37 (1H, multiplet);
4.40 (2H, singlet);
5.90 (1H, singlet);
5.94 (1H, singlet);
6.69–6.79 (3H, multiplet);
6.99 (1H, broad singlet);
7.12–7.15 (1H, multiplet);
7.29–7.31 (1H, multiplet);
7.41 (1H, broad singlet).
Infrared Absorption Spectrum (CHCl$_3$) $v_{max}$ cm$^{-1}$:
3464, 1680, 1479, 1458, 1257, 1053, 939, 877, 831.

PREPARATION 70

Following a similar procedure to that described in Preparations 69, but using the compounds of Preparations 68A to 68H and Preparation 9, the compounds of Preparations 70A to 70I having the following formula were obtained. The substituent groups and properties are as shown in the following Table. In the column headed "form" is given the physical form or the melting point range and the solvent from which the product was crystallised. In the column headed "IR spectrum" is given the Infrared Absorption Spectrum $v_{max}$ cm$^{-1}$; where appropriate, the medium employed for the Infrared Absorption Spectrum is also given.

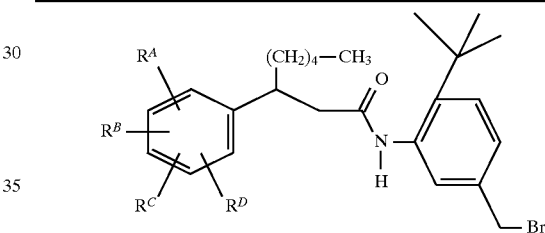

| Prep No. | R^A | R^B | R^C | R^D | form | IR spectrum |
|---|---|---|---|---|---|---|
| 70A | 2-OMe | 3-OMe | 4-OMe | H | foam | 3607, 2960, 2934, 1676, 1600, 1495, 1466, 1420, 1297, 1277, 1260, 1097, 1016 (CHCl$_3$) |
| 70B | 2-OMe | 4-OMe | 5-OMe | H | foam | 2960, 2935, 2859, 1678, 1612, 1570, 1510, 1466, 1400, 1300, 1182, 861, 827 (CHCl$_3$) |
| 70C | 2-OMe | 3-OMe | H | H | 119–120 (AcOEt-hexane)* | 3473, 3418, 2961, 2934, 1679, 1584, 1515, 1479, 1421, 1300, 1274, 1080, 1006 (CHCl$_3$) |
| 70D | 2-OMe | 4-OMe | 6-OMe | H | foam | 2957, 2859, 1672, 1608, 1591, 1514, 1466, 1418, 1205, 1152, 1123, 1063, 950, 815, 756, 637 (CHCl$_3$) |
| 70E | 2,3-OCH$_2$CH$_2$O | | H | H | foam | 2960, 2932, 1679, 1474, 1282, 1088 (CHCl$_3$) |
| 70F | 3-OMe | 4-OMe | 5-OMe | H | foam | 2961, 2934, 2874, 2860, 2842, 1683, 1591, 1572, 1510, 1464, 1423, 1366, 1324, 1300, 1154, 1130, 1080, 1004 (CHCl$_3$) |
| 70G | 2-OMe | 6-OMe | H | H | 101 (CH$_2$Cl$_2$- | 3408, 2961, 2933, 2873, 2861, 2841, |

-continued

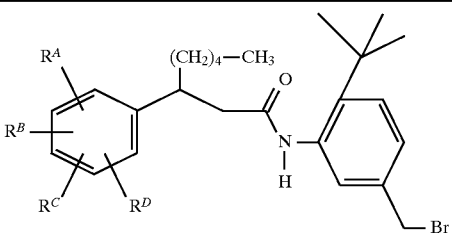

| Prep No. | $R^A$ | $R^B$ | $R^C$ | $R^D$ | form | IR spectrum |
|---|---|---|---|---|---|---|
| | | | | | hexane)* | 1677, 1593, 1571, 1514, 1474, 1438, 1420, 1397, 1367, 1299, 1277, 1274, 1252, 1114, 1098, 1039, 891 (CHCl$_3$) |
| 70H | 2-OMe | H | H | H | 102–104 (diethyl ether-hexane)* | 3475, 3421, 2960 2932, 1679, 1493, 1466, 1299, 1031 |
| 70I | 2-OMe | 4-OMe | H | H | foam | 2960, 2933, 1732, 1678, 1613, 1587, 1506, 1367, 1290, 1261, 1157, 1037 |

*: The solvent used for recrystallization.

PREPARATION 71

N-(2-t-Butyl-5-aminomethylphenyl-3-(2,3-ethylenedioxyphenyl)octanamide

A catalytic amount of sodium iodide was added to a solution of 1.33 g (2.27 mmol) of N-[2-t-butyl-5-bromomethylphenyl]-3-(2,3-ethylenedioxyphenyl) octanamide (prepared as described in Preparation 70E) and 295 mg (4.54 mmol) of sodium azide in a mixture of 20 ml of dimethylformamide and 5 ml of water, and the resulting mixture was stirred at room temperature for 30 minutes. The reaction mixture was then diluted with water, and the aqueous mixture was extracted with ethyl acetate. The extract was washed with a 10% w/v aqueous solution of sodium thiosulfate and with a saturated aqueous solution of sodium chloride, in that order, after which it was dried over anhydrous sodium sulfate, and the solvent was removed by distillation under reduced pressure. The resulting residue was purified by column chromatography through silica gel using, a 3:1 by volume mixture of hexane and ethyl acetate as the eluent, to give 1.12 g (a quantitative yield) of the corresponding azide compound as a colorless foam-like substance.

A solution of 1.22 g (2.27 mmol) of this azide compound in 25 ml of ethanol was vigorously stirred for 6 hours in an atmosphere of hydrogen and in the presence of 112 mg of 10% w/w palladium-on-charcoal. The reaction mixture was then filtered using a Celite (trade mark) filter aid to remove the catalyst, and the catalyst was washed with ethanol. The filtrate and the washings were combined and concentrated by evaporation under reduced pressure. The residue was purified by column chromatography through silica gel, using a 8:1 by volume mixture of methylene chloride and methanol as the eluent, to give 913 mg (yield 92%) of the title compound as a light-yellow foam-like substance.
Infrared Absorption Spectrum (CHCl$_3$) $v_{max}$ cm$^-$:
3421, 2960, 2933, 2875, 2862, 1677, 1596, 1570, 1512, 1474, 1456, 1422, 1397, 1379, 1368, 1367, 1.052, 945, 907, 885.

PREPARATION 72

Following a similar procedure to that described in Preparation 71, the compounds of Preparations 72A to 72F were obtained using the compounds of Preparations 70A, 70B, 70D, 70F, 70G and 70I, respectively. These compounds have the following formula. The substituent groups and properties are as shown in the following Table. In the column headed "form" is given the physical form of the product. In the column headed "IR spectrum" is given the Infrared Absorption Spectrum $v_{max}$ cm$^{-1}$; where appropriate, the medium employed for the Infrared Absorption Spectrum is also given.

| Prep No. | $R^A$ | $R^B$ | $R^C$ | $R^D$ | form | IR spectrum |
|---|---|---|---|---|---|---|
| 72A | 2-OMe | 3-OMe | 4-OMe | H | foam | 2960, 2934, 1676, 1601, 1495, 1466, 1420, 1277, 1097, 1017 |
| 72B | 2-OMe | 4-OMe | 5-OMe | H | foam | 3393, 2960, 2935, 2873, 1675, 1611, 1571, 1510, 1480, 1466, 1456, 1440, 1423, 1400, 1378, 1366, 1317, 1300, 1182, 1134, 1109, 1080, 1036, 861 (CHCl$_3$) |
| 72C | 2-OMe | 4-OMe | 6-OMe | H | foam | 3393, 2960, 1675, 1608, 1592, 1467, 1456, 1153, 1124 |
| 72D | 3-OMe | 4-OMe | 5-OMe | H | foam | 2961, 2934, 2874, 2861, 2842, 1679, 1591, 1510, 1476, 1464, 1423, 1365, 1324, 1153, 1130, 1081, 1004 (CHCl$_3$) |
| 72E | 2-OMe | 6-OMe | H | H | foam | 3394, 2960, 2934, 2872, 2861, 2841, 1675, 1593, 1571, 1511, 1474, 1438, 1422, 1396, 1367, 1296, 1274, 1177, 1152, 1115, 1098, 1039, 890, 829 (CHCl$_3$) |
| 72F | 2-OMe | 4-OMe | H | H | foam | 2960, 2933, 1676, 1613, 1587, 1506, 1467, 1422, 1290, 1261, 1157, 1037 (CHCl$_3$) |

PREPARATION 73

Following a similar procedure to that described in Preparation 6, the compounds of Preparations 73A to 73F were obtained using the substituted phenyloctanoic acid derivatives obtained as described in Preparations 66A, 66B, 66C, 66E, 66G and 66H, respectively. These compounds have the following formula. The substituent groups and properties are as shown in the following Table. In the column headed "form" is given the physical form or the melting point range and the solvent from which the product was crystallised. In the column headed "IR spectrum" is given the Infrared Absorption Spectrum $v_{max}$ cm$^{-1}$.

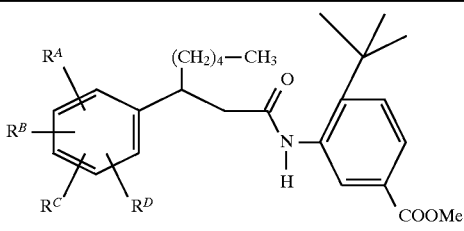

| Prep. No. | $R^A$ | $R^B$ | $R^C$ | $R^D$ | form | IR spectrum |
|---|---|---|---|---|---|---|
| 73A | 2-OMe | 3-OMe | 4-OMe | H | foam | 3420, 2958, 2934, 1721, 1681, 1496, 1466, 1438, 1302, 1273, 1125, 1097, 1016 |
| 73B | 2-OMe | 4-OMe | 5-OMe | H | 59.5–60.5 (diethyl ether-hexane)* | 3252, 2955, 2931, 2857, 1724, 1651, 1511, 1302, 1207, 1123, 1036, 771 |
| 73C | 2-OMe | 3-OMe | H | H | foam | 3472, 3427, 2958, 2934, 1721, 1685, 1476, 1438, 1302, 1270, 1125 |
| 73D | 2-OCH$_2$CH$_2$O-3 | | H | H | foam | 2957, 2932, 1721, 1686, 1470, 1439, 1302, 1270, 1126, 1068 |
| 73E | 2-OMe | 6-OMe | H | H | foam | 3401, 2958, 2933, 1720, 1679, 1594, 1474, 1438, 1303, 1268, 1118 |

-continued

| Prep. No. | $R^A$ | $R^B$ | $R^C$ | $R^D$ | form | IR spectrum |
|---|---|---|---|---|---|---|
| 73F | 2-OMe | H | H | H | foam | 3425, 2958, 1721, 1682, 1493, 1466, 1438, 1302, 1269, 1125, 1030 |

*: The solvent used for recrystallization.

PREPARATION 74

Following a similar procedure to that described in Preparation 7, the compounds 74A, 74B, 74C, 74E and 74F were obtained using the compounds of Preparations 73A, 73B, 73D, 73E and 73F, respectively. These compounds have the following formula. The substituent groups and properties are as shown in the following Table. In the column headed "melting point" is given the melting point range and the solvent from which the product was crystallised. In the column headed "IR spectrum" is given the Infrared Absorption Spectrum $v_{max}$ cm$^{-1}$; where appropriate, the medium employed for the Infrared Absorption Spectrum is also given.

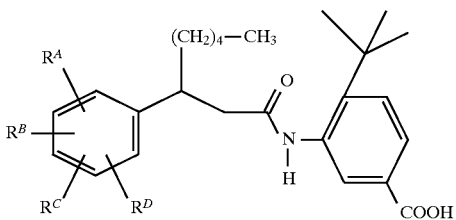

| Prep. No | $R^A$ | $R^B$ | $R^C$ | $R^D$ | melting point | IR spectrum |
|---|---|---|---|---|---|---|
| 74A | 2-OMe | 3-OMe | 4-OMe | H | 150–151 (diethyl ether-hexane)* | 2961, 2934, 1730, 1695, 1496, 1466, 1420, 1298, 1275, 1097 (CHCl$_3$) |
| 74B | 2-OMe | 4-OMe | 5-OMe | H | 112.5–113.5 (diethyl ether-hexane)* | 2960, 2934, 2873, 2859, 1695, 1612, 1568, 1510, 1466, 1300, 1036 (CHCl$_3$) |
| 74C | | 2,3-OCH$_2$CH$_2$O | H | H | 174.5–175.2 (AcOEt-hexane)* | 2961, 2932, 2876, 2862, 1727, 1695, 1613, 1596, 1569, 1510, 1474, 1456, 1426, 1367, 1306, 1283, 1166, 1109, 1088, 1052 (CHCl$_3$) |
| 74E | 2-OMe | 6-OMe | H | H | oil | 2961, 2933, 1731, 1694, 1594, 1474, 1437, 1424, 1271, 1150, 1098 (CHCl$_3$) |

-continued

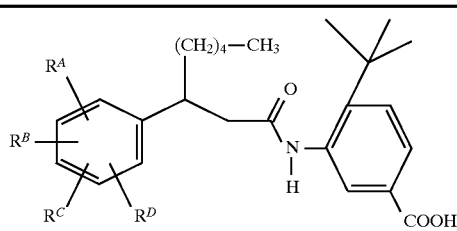

| Prep. No | $R^A$ | $R^B$ | $R^C$ | $R^D$ | melting point | IR spectrum |
|---|---|---|---|---|---|---|
| 74F | 2-OMe | H | H | H | 151–153 (diethyl ether-hexane)* | 2961, 2932, 1730, 1695, 1493, 1467, 1299, 1272, (CHCl$_3$) |

*The solvent used for recrystallization.

PREPARATION 75

N-(2-t-Butyl-5-formylphenyl)-3-(2,3,4-trimethoxyphenyl)octanamide 31.0 g of mangenese dioxide were added to a solution of 3.10 g (6.57 mmol) of N-[2-t-butyl-5-(hydroxymethyl)phenyl]-3-(2,3,4-trimethoxyphenyl)octanamide (prepared as described in Preparation 68A) in 60 ml of chloroform, and the resulting mixture was stirred for 1.5 hours. At the end of this time, the reaction mixture was filtered using a Celite (trade mark) filter aid, and the manganese dioxide used was thoroughly washed with methylene chloride. The filtrate and the washings were combined and concentrated by evaporation under reduced pressure. The resulting residue was purified by column chromatography through silica gel, using a 1:1 by volume mixture of ethyl acetate and hexane as the eluent, to give 2.68 g (yield 87%) of the title compound as a foam-like substance.

Infrared Absorption Spectrum (CHCl$_3$) $v_{max}$ cm$^{-1}$:
2961, 2934, 1699, 1608, 1570, 1496, 1466, 1421, 1298, 1277, 1097, 1016.

PREPARATION 76

N-(2-t-Butyl-5-(2-ethoxycarbonylethyl)phenyl]-3-(2,3-dimethoxyphenyl)octanamide 1.23 ml (6.22 mmol) of ethyl diethylphosphonoacetate were added dropwise, whilst ice-cooling, over a period of 3 minutes to a suspension of 271 mg (6.22 mmol) of sodium hydride (as a 55% w/w dispersion in mineral oil) in 7 ml of dimethylformamide, and the resulting mixture was then stirred at room temperature for 30 minutes. A solution of 1.37 g (3.11 mmol) of N-(2-t-butyl-5-formylphenyl)-3-(2,3-dimethoxyphenyl)octanamide (prepared as described in Preparation 24), in 6 ml of dimethylformamide was ice-cooled and then added dropwise to the mixture over a period of 3 minutes. The resulting mixture was stirred at room temperature for 1.5 hours. At the end of this time, the reaction mixture was diluted with ethyl acetate, and the diluted solution was washed with water and with a saturated aqueous solution of sodium chloride, in that order, after which it was dried over anhydrous magnesium sulfate, and the solvent was removed by distillation under reduced pressure. A solution of the residue in 20 ml of ethanol was stirred at room temperature for 8 hours in an atmosphere of hydrogen and in the presence of 400 mg of 10% palladiun-on-charcoal. At the end of this time, the reaction mixture was filtered using a Celite (trade mark) filter aid to remove the catalyst, and the filtrate was freed from the solvent by distillation under reduced pressure. The resulting residue was purified by column chromatography through silica gel, using a 2:1 by volume mixture of hexane and ethyl acetate as the eluent, to give 1.56 g (yield 98%) of the title compound as an oily substance.

Infrared Absorption Spectrum (CHCl$_3$) $v_{max}$ cm$^{-1}$:
2961, 2934, 1727, 1678, 1513, 1479, 1266, 1074, 1007.

PREPARATION 77

N-[2-t-Butyl-5-(2-carboxyethyl)phenyl]-3-(2,3-dimethoxyphenyl)octanamide 5 ml of an aqueous solution containing 490 mg (12.2 mmol) of sodium hydroxide were added to a solution of 1.56 g (3.05 mmol) of N-[2-t-butyl-5-(2-ethoxycarbonylethyl)phenyl]-3-(2,3-dimethoxyphenyl)octanamide (prepared as described in Preparation 76) in 15 ml of ethanol, and the resulting mixture was stirred at room temperature for 13 hours. At the end of this time, the solvent was removed by distillation under reduced pressure, and the resulting residue was dissolved in water. The aqueous mixture was then washed with diethyl ether. The aqueous phase was acidified with hydrochloric acid and then extracted with ethyl acetate. The extract was washed with a saturated aqueous solution of sodium chloride and dried over anhydrous magnesium sulfate, after which the solvent was removed by distillation under reduced pressure. The residue was purified by column chromatography through silica gel, using a 10:1 by volume mixture of methylene chloride and methanol as the eluent, to give 1.45 g (yield 98%) of the title compound as a foam-like substance.

Infrared Absorption Spectrum (CHCl$_3$) $v_{max}$ cm$^{-1}$:
2933, 2873, 1711, 1678, 1479, 1431, 1421, 1273, 1074, 1006.

PREPARATION 78

N-[2-t-Butyl-5-(2-ethoxycarbonylethylphenyl-3-(2,3,4-trimethoxyphenyl)octanamide Following a similar procedure to that described in Preparation 76, but using N-(2-t-butyl-5-formylphenyl)-3-(2,3,4-trimethoxyphenyl)octanamide (prepared as described in Preparation 75), the title compound was obtained as a colorless foam-like substance.

Infrared Absorption Spectrum (CHCl$_3$) $v_{max}$ cm$^{-1}$:

2961, 2933, 1703, 1640, 1496, 1466, 1419, 1297, 1276, 1181, 1097.

PREPARATION 79

N-[2-t-Butyl-5-(2-carboxyethyl)phenyl]-3-(2,3,4-trimethoxyphenyl)octanamide

Following a similar procedure to that described in Preparation 77, but using N-[2-t-butyl-5-(2-ethoxycarbonylethyl)phenyl]-3-(2,3,4-trimethoxyphenyl)-octanamide (prepared as described in Preparation 78), the title compound was obtained as a colorless foam-like substance.

Infrared Absorption Spectrum (CHCl$_3$) $v_{max}$ cm$^{-1}$:
3089, 2960, 2934, 1711, 1676, 1495, 1466, 1277, 1097, 1016.

PREPARATION 80

2-t-Butyl-5-(N,N-dimethylcarbamoyl)-1-nitrobenzene

Following a similar procedure to that described in Preparation 4, but using 4-t-butyl-3-nitrobenzoic acid and dimethylamine hydrochloride instead of methanol, the title compound was obtained as an oily substance.

Infrared Absorption Spectrum (CHCl$_3$) $v_{max}$ cm$^{-1}$:
2938, 1634, 1536, 1401, 1371, 1097, 841.

PREPARATION 81

2-t-Butyl-5-(N,N-dimethylcarbamoyl)aniline

Following a similar procedure to that described in Preparation 5, but using the compound obtained in Preparation 80, the title compound was obtained as crystals, melting at 186°–188° C.

Infrared Absorption Spectrum (CHCl$_3$) $v_{max}$ cm$^{-1}$:
3505, 3411, 2972, 1621, 1562, 1491, 1416, 1398, 1107.

PREPARATION 82

N-(2-t-Butyl-5-formylphenyl)-3-(2,4,5-trimethoxyphenyl)octanamide

Following a similar procedure to that described in Preparation 75, but using N-[2-t-butyl-5-(hydroxymethyl)phenyl]-3-(2,4,5-trimethoxyphenyl)octanamide prepared as described in Preparation 68B) the title compound was obtained as a foam-like substance.

Infrared Absorption Spectrum (CHCl$_3$) $v_{max}$ cm$^{-1}$:
2963, 2935, 1700, 1610, 1568, 1499, 1468, 1423, 1300, 1280, 1093, 1014

PREPARATION 83

N-2-t-Butyl-5-(2-carboethoxyethyl)phenyl]-3-(2,4,5-trimethoxyphenyl)octanamide

Following a similar procedure to that described in Preparation 76, but using N-(2-t-butyl-5-formylphenyl)-3-(2,4,5-trimethoxyphenyl)octanamide (prepared as described in Preparation 82), the title compound was obtained as a colorless foam-like substance.

Infrared Absorption Spectrum (CHCl$_3$) $v_{max}$ cm$^{-1}$:
2963, 2929, 1705, 1638, 1642, 1495, 1468, 1421, 1296, 1278, 1179, 1098.

PREPARATION 84

N-[2-t-Butyl-5-(2-carboxyethyl)phenyl]-3-(2,4,5-trimethoxyphenyl)octanamide

Following a similar procedure to that described in Preparation 77, but using N-[2-t-butyl-5-(2-carboethoxyethyl)phenyl]-3-(2,4,5-trimethoxyphenyl)-octanamide (prepared as described in Preparation 83), the title compound was obtained as a colorless foam-like substance.

Infrared Absorption Spectrum (CHCl$_3$) $v_{max}$ cm$^{-1}$:
2960, 2935, 2860, 1711, 1678, 1612, 1568, 1510, 1466, 1421, 1132, 1036.

PREPARATION 85

N-(2-t-Butyl-5-formylphenyl)-3-(2,6-dimethoxyphenyl)octanamide

Following a similar procedure to that described in Preparation 75, but using N-[2-t-butyl-5-(hydroxymethyl)phenyl]-3-(2,6-dimethoxyphenyl)octanamide prepared as described in Preparation 68G), the title compound was obtained as a foam-like substance.

Infrared Absorption Spectrum (CHCl$_3$) $v_{max}$ cm$^{-1}$:
2934, 2870, 1710, 1675, 1478, 1432, 1420, 1275, 1074, 1003.

PREPARATION 86

N-2-t-Butyl-5-(2-carboethoxyethyl)phenyl]-3-(2,6-dimethoxyphenyl)octanamide

Following a similar procedure to that described in Preparation 76, but using N-(2-t-butyl-5-formylphenyl)-3-(2,6-dimethoxyphenyl)octanamide (prepared as described in Preparation 85), the title compound was obtained as a colorless oily substance.

Infrared Absorption Spectrum (CHCl$_3$) $v_{max}$ cm$^1$:
3408, 2960, 2933, 2861, 1728, 1676, 1593, 1474, 1374, 1114, 1041.

PREPARATION 87

N-[2-t-Butyl-5-(2-carboxyethyl)phenyl]-3-(2,6-dimethoxyphenyl)octanamide

Following a similar procedure to that described in Preparation 77, but using N-[2-t-butyl-5-(2-carboethoxyethyl)phenyl]-3-(2,6-dimethoxyphenyl)octanamide (prepared as described in Preparation 86), the title compound was obtained as colorless crystals, melting at 52°–53° C. (from methylene chloride-hexane).

Infrared Absorption Spectrum (CHCl$_3$) $v_{max}$ cm$^1$:
3402, 3096, 2960, 2932, 2861, 1711, 1675, 1593, 1514, 1474, 1420, 1115, 1098, 1039.

PREPARATIONS 88A AND 88B (−)-3-[2-(2,4-Dimethoxyphenyl)heptanoyl]-4S-benzyl-2-oxazolidinone (Preparation 88a) and (+)-3-[2-(2,4-Dimethoxyphenol)heptanoyl]-4S-benzyl-2-oxazolidinone (Preparation 88b)

88(i) Diethyl 2-(2,4-dimethoxyphenyl)-2-pentylmalonate A solution of 1.29 g (4.34 mmol) of diethyl 2-(2,4-dimethoxyphenyl)-malonate [J. Heterocyclic Chem., 21, 737 (1984)] in 9 ml of dimethylformamide was added dropwise to an ice-cooled suspension of 195 mg (4.50 mmol) of sodium hydride (as a 55% w/w dispersion in mineral oil) in 5 ml of dimethylformamide over a period of 2 minutes, and the resulting mixture was stirred at the same temperature for 20 minutes. At the end of this time, 1.1 ml (8.9 mmol) of pentyl bromide were added. The reaction mixture was then stirred at room temperature for 15 minutes and then at 80° C. for 3 hours, after which the mixture was ice-cooled, and a saturated aqueous solution of ammonium chloride was added to terminate the reaction. The resulting mixture was extracted with a 1:1 by volume mixture of ethyl acetate and hexane. The extract was washed with water and with a saturated aqueous solution of sodium chloride, in that order, after which it was dried over anhydrous magnesium sulfate, and the solvent was removed by distillation under reduced pressure. The resulting residue was purified by column chromatography through 100 g of silica gel, using a 1:3 by volume mixture of ethyl acetate and hexane as the eluent, to give 1.32 g (yield 83%) of the title diester derivative as an oily substance.

Infrared Absorption Spectrum (liquid film) $v_{max}$ cm$^{-1}$:
1738, 1613, 1586, 1507, 1464, 1366, 1241, 1210, 1142, 1038.

88(ii) 2-(2,4-Dimethoxphenyl)heptanoic acid 10.0 ml (20.0 mmol) of a 2N aqueous aqueous solution of sodium hydroxide were added to a solution of 1.30 g (3.55 mmol) of diethyl 2-(2,4-dimethoxyphenyl)-2-pentyhnalonate [prepared as described in step (i) above] in 20 ml of ethanol, and the resulting mixture was heated under reflux for 3 hours. At the end of this time, the reaction mixture was freed from ethanol by distillation under reduced pressure, and the resulting residue was acidified with 1N aqueous hydrochloric acid and then extracted with ethyl acetate. The extract was washed with a saturated aqueous solution of sodium chloride and dried over anhydrous magnesium sulfate, after which the solvent was removed by distillation under reduced pressure. The resulting residue was disssolved in 20 ml of xylene, and the solution was heated under reflux for 80 minutes. At the end of this time, the reaction mixture was cooled to room temperature, after which it was purified by column chromatography through 50 g of silica gel using a gradient elution method, with mixtures of ethyl acetate and hexane ranging from 1:3 to 1:1 by volume as the eluent, to give 805 mg (yield 85%) of the title carboxylic acid derivative as an oily substance.

Infrared Absorption Spectrum (liquid film) $v_{max}$ cm$^{-1}$:
1703, 1613, 1590, 1509, 1464, 1293, 1266, 1210, 1160, 1040.

88(iii) (−)-3-[2-(2,4-Dimethoxyphenyl)heptanoyl]-4S-benzyl-2-oxazolidinone (Preparation 88A) and (+)-3-[2-(2,4-Dimethoxyphenyl)heptanol]-4S-benzyl-2-oxazolidinone (Preparation 88B)

Two drops of dimethylformamide followed by 3.0 ml (34.5 mmol) of oxalyl chloride were added to a solution of 4.67 g (17.5 mmol) of 2-(2,4-dimethoxyphenyl)heptanoic acid [prepared as described in step (ii) above] in 30 ml of methylene chloride, and the resulting mixture was stirred at room temperature for 1 hour. At the end of this time, the reaction mixture was freed from excess reagents and the solvent by distillation under reduced pressure, and the resulting residue was dissolved in 15 ml of methylene chloride to give an acid chloride solution.

Meanwhile, a solution of 3.13 g (17.7 mmol) of (S)-4-benzyl-2-oxazolidinone in 30 ml of tetrahydroftran was cooled to −78° C. and 11.1 ml (17.8 mmol) of a 1.6M solution of butyllithium in hexane were added dropwise to the solution over a period of 10 minutes, and the solution was stirred for 25 minutes. The whole of the acid chloride solution prepared above was added dropwise to the solution thus obtained over a period of 10 minutes, and the resulting mixture was stirred at the same temperature for 30 minutes and then at room temperature for 30 minutes. At the end of this time, a saturated aqueous solution of ammonium chloride was added to the reaction mixture to terminate the reaction, and the resulting mixture was extracted with a 1:1 by volume mixture of ethyl acetate and hexane. The extract was washed with water and with a saturated aqueous solution of sodium chloride, in that order, after which it was dried over anhydrous magnesium sulfate. The solvent was then removed by distillation under reduced pressure. The resulting residue was purified by column chromatography through 250 g of silica gel using a gradient elution method, with mixtures of ethyl acetate and hexane ranging from 3:7 to 1:2 by volume as the eluent, to give the compound of Preparation 88A from the less polar fractions and the compound of Preparation 88B from the more polar fractions. Other fractions, from which neither compound could be separated, were twice subjected to column chromatography under the same conditions as above. There were obtained, in total, 4.14 g and 4.23 g of the respective title compounds as oily substances, representing yields of 48% and 49%, respectively.

Compound of Preparation 88A:

$[\alpha]_D^{25}$=−39.1° (CHCl$_3$, c=1.50).

Nuclear Magnetic Resonance Spectrum (270 MHz, CDCl$_3$) δ ppm:
0.86 (3H, triplet, J=6 Hz);
1.23–1.38 (6H, multiplet);
1.69–1.81 (1H, multiplet);
1.92–2.04 (1H, multiplet);
2.57 (1H, doublet of doublets, J=10 Hz & 13 Hz);
3.30 (1H, doublet of doublets, J=3 Hz & 13 Hz);
3.80 (3H, singlet);
3.82 (3H, singlet);
4.05–4.19 (2H, multiplet);
4.67–4.76 (1H, multiplet);
5.18 (1H, triplet, J=7 Hz);
6.46–6.50 (2H, multiplet);
7.14–7.33 (6H, multiplet).

Infrared Absorption Spectrum (liquid film) $v_{max}$ cm$^{-1}$:
1784, 1698, 1613, 1507, 1457, 1383, 1295, 1210, 1079, 1038.

Compound of Preparation 88B:

$[\alpha]_D^{25}$=80.7° (CHCl$_3$, c=1.06).

Nuclear Magnetic Resonance Spectrum (270 MHz, CDCl$_3$) δ ppm:
0.87 (3H, triplet, J=6 Hz);
1.23–1.41 (6H, multiplet);
1.71–1.83 (1H, multiplet);
1.99–2.11 (1H, multiplet);
2.78 (1H, doublet of doublets, J=10 Hz & 13 Hz);
3.35 (1H, doublet of doublets, J=3 Hz & 13 Hz);
3.79 (6H, singlet);
4.04–4.16 (2H, multiplet);
4.58–4.67 (1H, multiplet);
5.26 (1H, triplet, J=7 Hz);
6.43–6.49 (2H, multiplet);
7.18–7.36 (6H, multiplet).

Infrared Absorption Spectrum (liquid film) $v_{max}$ cm$^{-1}$:
1784, 1698, 1613, 1507, 1457, 1381, 1293, 1210, 1098, 1038.

PREPARATION 89

(+-3-(2,4-Dimethoxyphenyl)octanoic Acid

89(i) (−)-2-(2,4-Dimethoxyphenyl)heptanol

A suspension of 412 mg of lithium aluminum hydride in 20 ml of tetrahydrofuran was added dropwise to an ice-cooled solution of 4.12 g (9.68 mmol) of (−)-3-[2-(2,4-dimethoxyphenyl)heptanoyl]-4S-benzyl-2-oxazolidinone (prepared as described in Preparation 88A) in 50 ml of tetrahydrofuran over a period of 1 hour, and the resulting mixture was stirred at the same temperature for 1 hour. At the end of this time, 0.4 ml of water, 0.4 ml of a 15% aqueous solution of sodium hydroxide and finally 0.8 ml of water were added to the reaction mixture, in that order, and the resulting mixture was stirred at room temperature for 10 minutes. The reaction mixture was then filtered using a Celite (trade mark) filter aid, and the filtrate was concentrated by evaporation under reduced pressure. The concentrate was purified by column chromatography through 150 g of silica gel, using a 1:2 by volume mixture of ethyl acetate and hexane as the eluent, to give 2.18 g (yield 89%) of the title compound as an oily substance.

$[\alpha]_D^{24}$=12.80 (CHCl$_3$, c=1.01).

Infrared Absorption Spectrum (liquid film) $\nu_{max}$ cm$^{-1}$:
1613, 1588, 1505, 1464, 1289, 1260, 1208, 1158, 1136, 1038.

89(ii) (−)-2-(2,4-Dimethoxyphenyl)heptyl Cyanide 0.68 ml (8.79 mmol) of methanesulfonyl chloride was added to a solution of 2.01 g (7.97 mmol) of (−)-2-(2,4-dimethoxyphenyl)heptanol [prepared as described in step (i) above] in 20 ml of methylene chloride, and then 1.3 ml (9.33 mmol) of triethylamine were added dropwise to the resulting mixture over a period of 2 minutes, whilst ice-cooling. The resulting mixture was then stirred at the same temperature for 15 minutes, after which it was mixed with water and then extracted with diethyl ether. The extract was washed with 2N aqueous hydrochloric acid, with water, with a saturated aqueous solution of sodium hydrogencarbonate and with a saturated aqueous solution of sodium chloride, in that order, after which it was dried over anhydrous magnesium sulfate, and the solvent was removed by distillation under reduced pressure. The residue was dissolved in 10 ml of dimethylformamide, and to the resulting solution were added 611 mg (12.4 mmol) of sodium cyanide and 0.80 ml (4.0 mmol) of 15-crown-5. The resulting mixture was then stirred at 50° C. for 1 hour and then at 100° C. for 1 hour. At the end of this time, the reaction mixture was cooled to room temperature, after which it was mixed with water and then extracted with diethyl ether. The extract was washed with a saturated aqueous solution of sodium chloride and dried over anhydrous magnesium sulfate, after which the solvent was removed by distillation under reduced pressure. The resulting residue was purified by column chromatography through 150 g of silica gel using a gradient elution method, with mixtures of ethyl acetate and hexane ranging from 1:10 to 1:5 by volume as the eluent, to give fractions containing a pure compound. Fractions containing impure products were repeatedly subjected to column chromatography under the same conditions as above. A total of 1.58 g (yield 75%) of the title nitrile derivative was obtained as an oily substance.

$[\alpha]_D^{24}$=−39.8° (CHCl$_3$, c=1.02).

Infrared Absorption Spectrum (liquid film) $\nu_{max}$ cm$^{-1}$:
2245, 1613, 1588, 1509, 1464, 1291, 1208, 1160, 1134, 1036.

89(iii) (+)-3-(2,4-Dimethoxyphenyl)octanoic acid 1.00 g (17.8 mmol) of potassium hydroxide was added to a solution of 1.27 g (4.86 mmol) of (−)-2-(2,4-dimethoxyphenyl)heptyl cyanide [prepared as described in step (ii) above] in 6 ml of ethylene glycol, and the resulting mixture was heated under reflux for 2.5 hours in an atmosphere of nitrogen. At the end of this time, the reaction mixture was cooled to room temperature, after which it was acidified with 1N aqueous hydrochloric acid and then extracted with diethyl ether. The extract was washed with a saturated aqueous solution of sodium chloride and dried over anhydrous magnesium sulfate, after which the solvent was removed by distillation under reduced pressure. The resulting residue was purified by column chromatography through I 00 g of silica gel, using a 1:2 by volume mixture of ethyl acetate and hexane as the eluent, to give 1.19 g (yield 87%) of the title compound as crystals, melting at 51°–52° C. (from pentane).

$[\alpha]_D^{29}$=6.4° (CHCl$_3$, c=1.08).

PREPARATION 90

(−)-3-(2,4-Dimethoxyphenyl)octanoic Acid

90(i) (+)-2-(2,4-Dimethoxyphenyl)heptanol

Following a similar procedure to that described in Preparation 89(i), but using (+)-3-[2-(2,4-Dimethoxyphenyl)heptanoyl]-4S-benzyl-2-oxazolidinone (prepared as described in Preparation 88B), the title compound was obtained as an oily substance.

$[\alpha]_D^{26}$=13.2° (CHCl$_3$, c=1.01).

90(ii) (+)-2-(2,4-Dimethoxyphenyl)heptyl Cyanide

Following a similar procedure to that described in Preparation 89(ii), but using (+)-2-(2,4-dimethoxyphenyl)heptanol [prepared as described in step (i) above], the title nitrile derivative was obtained as an oily substance.

$[\alpha]_D^{26}$=38.5° (CHCl$_3$, c=1.01).

90(iii) (−)-3-(2,4-Dimethoxyphenyl)octanoic acid

Following a similar procedure to that described in Preparation 89(iii), but using (+)-2-(2,4-dimethoxyphenyl)heptyl cyanide [prepared as described in step (ii) above], the title compound was obtained as an oily substance.

$[\alpha]_D^{25}$=−6.5° (CHCl$_3$, c=1.00).

PREPARATION 91A

Methyl 3-[2-methoxy-4-(2-methoxyethoxy)phenyl]-5-methylhexanoate

Following a similar procedure to that described in Preparation 45A(i), but using methyl 3-(4-hydroxy-2-methoxyphenyl)-5-methylhexanoate (prepared as described in Preparation 58B) and 2-methoxyethyl bromide, the title compound was obtained as an oily substance.

Infrared Absorption Spectrum (liquid film) $\nu_{max}$ cm$^{-1}$:
1738, 1612, 1585, 1506, 1466, 1452, 1421, 1367, 1288, 1261, 1201, 1163, 1126, 1066, 1036.

PREPARATION 91B

Methyl 3-[2-methoxy-4-(2-ethoxyethoxy)phenyl]-5-methylhexanoate

Following a similar procedure to that described in Preparation 45A(i), but using methyl 3-(4-hydroxy-2-methoxyphenyl)-5-methylhexanoate (prepared as described in Preparation 58B) and 2-ethoxyethyl bromide, the title compound was obtained as an oily substance.

Infrared Absorption Spectrum (liquid film) $\nu_{max}$ cm$^{-1}$:
1738, 1612, 1585, 1506, 1464, 1452, 1421, 1367, 1288, 1261, 1201, 1163, 1122, 1066, 1038.

PREPARATION 92A

3-[2-Methoxy-4-(3-propylsulfonylpropoxy)phenyl] heptanoic Acid

Following a similar procedure to that described in Preparation 45A(i), but using methyl 3-(4-hydroxy-2-methoxyphenyl)heptanoate (prepared as described in Preparation 58A) and 1,3-dibromopropane, methyl 3-[4-(3-bromopropoxy)-2-methoxyphenyl]heptanoate was obtained as an oily substance.

The whole of the methyl 3-[4-(3-bromopropoxy)-2-methoxyphenyl]-heptanoate thus obtained and propyl mercaptan were then reacted following the procedure described in Preparation 51, to give the title compound as an oily substance.
Infrared Absorption Spectrum (liquid film) $v_{max}$ cm$^{-1}$:
  3490, 3260, 1732, 1709, 1603, 1505, 1304, 1204, 1129, 1034.

PREPARATION 92B

3-[5-Chloro-2-methoxy-4-(3-propylsulfonylpropoxy)phenyl]heptoic Acid

Following a similar procedure to that described in Preparation 45A(i), but using methyl 3-(5-chloro-4-hydroxy-2-methoxyphenyl)heptanoate (prepared as described in Preparation 56B) and 1,3-dibromopropane, methyl 3-[5-chloro-2-methoxy-4-(3-bromopropoxy)phenyl]heptanoate was obtained as an oily substance.

The whole of the methyl 3-[5-chloro-2-methoxy-4-(3-bromopropoxy)-phenyl]heptanoate thus obtained and propyl mercaptan were then reacted following the procedure described in Preparation 51, to give the title compound as an oily substance.
Infrared Absorption Spectrum (liquid film) $v_{max}$ cm$^{-1}$:
  3500, 3240, 1709, 1613, 1507, 1289, 1200, 1129, 1038, 970

PREPARATION 93A 1-(4-t-Butyldimethylsilyloxymethyl-2-methoxyphenyl)-3-methylbutyl Alcohol 55 ml (55 mmol) of a 1.0M solution of isobutyl magnesium bromide in tetrahydrofuran were added to a solution of 23.6 g (73.1 mmol) of tetrabutyl ammonium bromide in 50 ml of tetrahydrofuran, and the resulting mixture was immediately cooled in a dry ice-acetone bath, after which a solution of 10.25 g (36.5 mmol) of 4-t-butyldimethylsilyloxymethyl-2-methoxybenzaldehyde (prepared as described in Preparation 40) in 60 ml of tetrahydrofuran were added dropwise over 30 minutes. After the dropwise addition, the reaction temperature was gradually allowed to return to room temperature, and then the reaction was terminated by adding a saturated aqueous solution of ammonium chloride. The reaction mixture was then extracted with diethyl ether, and the extract was washed with water and with a saturated aqueous solution of sodium chloride, in that order, after which it was dried over anhydrous magnesium sulfate. The solvent was then removed by distillation under reduced pressure, and the resulting residue was purified by column chromatography through 250 g of silica gel using a gradient elution method, with mixtures of hexane and ethyl acetate ranging from 3:1 to 2:1 by volume as the eluent, to give 6.81 g (yield 57%) of the title compound as an oily substance.
Infrared Absorption Spectrum (liquid film) $v_{max}$ cm$^{-1}$:
  1615, 1586, 1505, 1464, 1420, 1368, 1254, 1190, 1158, 1096, 1042.

PREPARATION 93B 1-(4-t-Butyldimethylsilyloxymethyl-2-methoxyphenyl) Butyl Alcohol Following a similar procedure to that described in Preparation 93A, but using propylmagnesium bromide, the title compound was obtained as an oily substance.
Infrared Absorption Spectrum (liquid film) $v_{max}$ cm$^{-1}$:
  1615, 1584, 1505, 1464, 1418, 1372, 1256, 1190, 1158, 1098, 1040.

PREPARATION 93C 1-(4-t-Butyldimethylsilyloxymethyl-2-methoxphenyl)-2-methylpropyl Alcohol Following a similar procedure to that described in Preparation 93A, but using isopropylmagnesium bromide, the title compound was obtained as an oily substance.
Infrared Absorption Spectrum (liquid film) $v_{max}$ cm$^{-1}$:
  1615, 1584, 1505, 1464, 1420, 1368, 1256, 1190, 1158, 1094, 1040.

PREPARATION 94A 3-(4-Acetoxymethyl-2-methoxyphenyl)-5-methylhexanoic Acid

Following a similar procedure to that described in Preparations 41(ii) to (vi), but using 1-(4-t-butyldimethylsilyloxymethyl-2-methoxyphenyl)-3-methylbutyl alcohol (prepared as described in Preparation 93A), the title compound was obtained as an oily substance.
Infrared Absorption Spectrum (liquid film) $v_{max}$ cm$^{-1}$:
  1740, 1709, 1615, 1582, 1509, 1464, 1422, 1381, 1366, 1260.

PREPARATION 94B 3-(4-Acetoxymethyl-2-methoxyphenyl)hexanoic Acid

Following a procedure similar to that described in Preparation 41(ii)-(vi), but using 1-(4-t-butyldimethylsilyloxymethyl-2-methoxyphenyl)butanol (prepared as described in Preparation 93B), the title compound was obtained as an oily substance.
Infrared Absorption Spectrum (liquid film) $v_{max}$ cm$^{-1}$:
  1740, 1707, 1615, 1582, 1509, 1464, 1422, 1379, 1364, 1262, 1231.

PREPARATION 95A

N-(2-t-Butyl-5-methoxycarbonylphenyl)-3-(4-hydroxymethyl-2-methoxyphenyl)-5-methylhexanamide Following a similar procedure to that described in Preparation 61, but using 3-(4-acetoxymethyl-2-methoxyphenyl)-5-methylhexanoic acid (prepared as described in Preparation 94A), the title compound was obtained as a foam-like substance.
Infrared Absorption Spectrum (liquid film) $v_{max}$ cm$^{-1}$:
  1723, 1653, 1613, 1518, 1509, 1464, 1437, 1418, 1366, 1302, 1252

PREPARATION 95B

N-(2-t-Butyl-5-methoxycarbonylphenyl)-3-(4-hydroxymethyl-2-methoxyphenyl)hexanamide Following a procedure similar to that described in Preparation 61, but using 3-(4-acetoxymethyl-2-methoxyphenyl)hexanoic acid (prepared as described in Preparation 94B), the title compound was obtained as a foam-like substance.
Infrared Absorption Spectrum (film) $v_{max}$ cm$^{-1}$:
  1723, 1657, 1653, 1613, 1514, 1437, 1416, 1366, 1302, 1252, 1123.

PREPARATION 96

N-(2-t-Butyl-5-carboxyphenyl)-3-(4-isopropylsulfonyl-2-methoxyphenyl)heptanamide Following a procedure similar to that described in Preparation 31, but using 3-(4-isopropylsulfonyl-2-methoxyphenyl)heptanoic acid (prepared as described in Preparation 301), the title compound was obtained as a foam-like substance.

Infrared Absorption Spectrum (KBr) $v_{max}$ cm$^{-1}$:
3260, 1722, 1694, 1656, 1493, 1404, 1303, 1247, 1139, 1032.

PREPARATION 97

N-(2-t-Butyl-5-carboxymethylphenyl)-3-(4-isopropylsulfonyl-2-methoxyphenyl)hetanamide Following a procedure similar to that described in Preparation 15, but using 3-(4-isopropylsulfonyl-2-methoxyphenyl)heptanoic acid (prepared as described in Preparation 301), the title compound was obtained as a foam-like substance Infrared Absorption Spectrum (KBr) $v_{max}$ cm$^{-1}$:
3318, 3263, 1732, 1655, 1519, 1494, 1403, 1303, 1248, 1139, 1032.

PREPARATION 98

N-(2-t-Butyl-5-carboxyphenyl)-3-(2-methoxy-4-isobutyrylphenyl)octanamide

Following a procedure similar to that described in Preparation 93a, but using N-(2-t-butyl-5-methoxycarbonylphenyl)-3-(4-formyl-2-methoxyphenyl)-octanamide (prepared as described in Preparation 63a) and isopropylmagnesium chloride, N-(2-t-butyl-5-methoxycarbonylphenyl)-3-[4-(1-hydroxy-2-methylpropyl-2-methoxyphenyl]octanamide was obtained. This was then converted to the titl compound, as crystals melting at 132°–134° C. (methylene chloride-hexane) by a procedure similar to that described in Preparation 64-(ii) and (iii).

Infrared Absorption Spectrum (KBr) $v_{max}$ cm$^{-1}$:
1722, 1684, 1663, 1609, 1570, 1517, 1504, 1466, 1413, 1256, 1207.

PREPARATION 99

N-(2-t-Butyl-5-carboxyphenyl)-3-(4-isopropylsulfonyl-2-methoxyphenyl)octanamide

Following a procedure similar to that described in Preparation 31, but using 3-(4-isopropylsulfonyl-2-methoxyphenyl)octanoic acid (prepared as described in Preparation 30J), the title compound was obtained as a foam-like substance.

Infrared Absorption Spectrum (film) $v_{max}$ cm$^{-1}$:
1693, 1612, 1568, 1512, 1493, 1466, 1421, 1404, 1367, 1302, 1265, 1138, 1032.

PREPARATION 100

N-(2-t-Butyl-5-carboxyphenyl)-3-(2-methoxy-4-butyry)phenyl)hexanamide

Following a procedure similar to that described in Preparation 64A, but using N-(2-t-butyl-5-methoxycarbonylphenyl)-3-(4-formyl-2-methoxyphenyl)-hexanamide (prepared as described in Preparation 63C) and propylmagnesium bromide, the title compound was obtained as a foam-like substance.

Infrared Absorption Spectrum (film) $v_{max}$ cm$^{-1}$:
1723, 1682, 1651, 1609, 1570, 1520, 1410, 1366, 1302, 1250, 1123.

FORMULATION

Hard capsule Preparation

A mixture of 100 mg of powdery N-(2-t-butyl-5-N'-methylcarbamoylphenyl)-3-(2,4-dimethoxyphenyl) octanamide (Compound No. 31, prepared as described in Example 1), 150 mg of lactose, 50 mg of cellulose and 6 mg of magnesium stearate was packed into a standard double-separated hard gelatin capsule to prepare a unit capsule. After washing, each capsule was dried.

We claim:

1. A compound of formula (I):

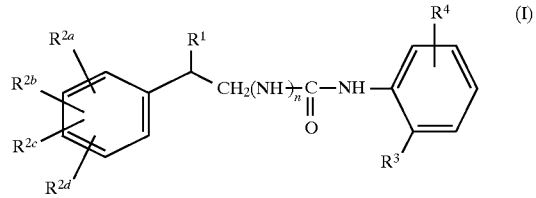

wherein:

$R^1$ represents an alkyl group having from 1 to 12 carbon atoms;

$R^{2a}$, $R^{2b}$, $R^{2c}$ and $R^{2d}$ are the same or different and each represents:
  a hydrogen atom;
  an alkyl group having from 1 to 12 carbon atoms;
  an alkyl group which has from 1 to 4 carbon atoms and which is substituted by from 1 to 5 fluorine atoms;
  an alkyl group which has from 1 to 12 carbon atoms and which is substituted by an unprotected or protected hydroxy group;
  a group of formula —(C=O)—B$^1$
    wherein B$^1$ represents a hydrogen atom, or an alkyl group having from 1 to 12 carbon atoms,
  a nitro group;
  a group of formula —NR$^c$R$^d$
    wherein R$^c$ represents a hydrogen atom or an alkyl group having from 1 to 4 carbon atoms and R$^d$ represents an alkyl group having from 1 to 4 carbon atoms;
  a hydroxy group or a protected hydroxy group;
  an alkoxy group having from 1 to 10 carbon atoms;
  a cyano group;
  an alkylthio group having from 1 to 6 carbon atoms;
  an alkylsulfinyl group having from 1 to 6 carbon atoms;
  an alkylsulfonyl group having from 1 to 6 carbon atoms;
  or a halogen atom; or $R^{2a}$ and $R^{2b}$ are adjacent to each other and together represent a group of formula —O—(CH$_2$)$_m$—O— wherein m is an integer of from 1 to 3;

$R^3$ represents an alkyl group having from 1 to 6 carbon atoms;

271

$R^4$ represents a group of formula (II):

wherein:
- $A^1$ represents a single bond, an alkylene group having from 1 to 6 carbon atoms or an alkenylene group having from 2 to 6 carbon atoms;
- $R^{5a}$ and $R^{5b}$ are the same or different and each represents a hydrogen atom, an alkyl group having from 1 to 4 carbon atoms or a group of formula —$A^4R^{5c}$
  - wherein $A^4$ represents a single bond, an alkylene group having from 1 to 6 carbon atoms or an alkenylene group having from 2 to 6 carbon atoms;
    - $R^{5c}$ represents an alkoxy group having from 1 to 4 carbon atoms and
- n represents 0, and pharmaceutically acceptable salts thereof.

2. The compound of claim 1, wherein $R^1$ represents a propyl, isopropyl, butyl, isobutyl, pentyl, isopentyl, hexyl or heptyl group.

3. The compound of claim 1, wherein two adjacent groups among $R^{2a}$, $R^{2b}$, $R^{2c}$ and $R^{2d}$ together represent a methylenedioxy or ethylenedioxy group and the remaining two groups each represents a hydrogen atom.

4. The compound of claim 1, wherein two or three groups among $R^{2a}$, $R^{2b}$, $R^{2c}$ and $R^{2d}$ each represents a methoxy group and the remaining two or one groups each represents a hydrogen atom.

5. The compound of claim 1, wherein one of $R^{2a}$, $R^{2b}$, $R^{2c}$ and $R^{2d}$ represents a methoxy group, another one group represents a hydroxy group, and the remaining two groups each represents a hydrogen atom.

6. The compound of claim 1, wherein one of $R^{2a}$, $R^{2b}$, $R^{2c}$ and $R^{2d}$ represents a methoxy group, another one group represents a ethoxy group and the remaining two groups each represents a hydrogen atom.

7. The compound of claim 1, wherein one of $R^{2a}$, $R^{2b}$, $R^{2c}$ and $R^{2d}$ represents a methoxy group, another one group represents a 1-hydroxy-1-methylethyl, 1-hydroxypropyl, 1-hydroxy-2-methylpropyl, 1-hydroxybutyl or 1-hydroxy-3-methylbutyl group and the remaining two groups each represents a hydrogen atom.

8. The compound of claim 1, wherein one of $R^{2a}$, $R^{2b}$, $R^{2c}$ and $R^{2d}$ represents a methoxy group, another one group represents a propionyl, isobutyryl, butyryl or isovaleryl group and the remaining two groups each represents a hydrogen atom.

9. The compound of claim 1, wherein one of $R^{2a}$, $R^{2b}$, $R^{2c}$ and $R^{2d}$ represents a methoxy group, another one group represents an isopropylsulfonyl, isobutylsulfonyl or butylsulfonyl group and the remaining two groups each represents a hydrogen atom.

10. The compound of claim 1, wherein $R^3$ represents an isopropyl or t-butyl group.

11. The compound of claim 1, wherein $R^4$ represents a carbamoyl, methylcarbamoyl, carbamoylmethyl, 2-carbamoylethyl, methylcarbamoylmethyl or 2-N methylcarbamoyl)ethyl.

12. The compound of claim 1, wherein $R^4$ represents a carbamoyl, methylcarbamoyl carbamoylmethyl, 2-carbamoylethyl, methylcarbamoylmethyl or 2-N-methylcarbamoylethyl group.

13. The compound of claim 1, wherein:
- $R^1$ represents a propyl, isopropyl, butyl, isobutyl, pentyl, isopentyl, hexyl or heptyl group;

272

- two adjacent groups among $R^{2a}$, $R^{2b}$, $R^{2c}$ and $R^{2d}$ together represent a methylenedioxy or ethylenedioxy group and the remaining two groups each represents a hydrogen atom;
- $R^3$ represents an isopropyl or t-butyl group; and
- $R^4$ represents a carbamoyl, methylcarbamoyl, carbamoylmethyl, 2-carbamoylethyl, methylcarbamoylmethyl or 2-(N-methylcarbamoyl)ethyl.

14. The compound of claim 1, wherein:
- $R^1$ represents a propyl, isopropyl, butyl, isobutyl, pentyl, isopentyl, hexyl or heptyl group;
- two or three groups among $R^{2a}$, $R^{2b}$, $R^{2c}$ and $R^{2d}$ each represents a methoxy group and the remaining two or one groups each represents a hydrogen atom;
- $R^3$ represents an isopropyl or t-butyl group; and
- $R^4$ represents a carbamoyl, methylcarbamoyl, carbamoylmethyl, 2-carbamoylethyl, methylcarbamoylmethyl or 2-(N-methylcarbamoyl)ethyl.

15. The compound of claim 1, wherein:
- $R^1$ represents a propyl, isopropyl, butyl, isobutyl, pentyl, isopentyl, hexyl or heptyl group;
- one of $R^{2a}$, $R^{2b}$, $R^{2c}$ and $R^{2d}$ represents a methoxy group, another one group represents a hydroxy group, and the remaining two, groups each represents a hydrogen atom;
- $R^3$ represents an isopropyl or t-butyl group; and
- $R^4$ represents a carbamoyl, methylcarbamoyl, carbamoylmethyl, 2-carbamoylethyl, methylcarbamoylmethyl or 2-(N-methylcarbamoyl)ethyl.

16. The compound of claim 1, wherein:
- $R^1$ represents a propyl, isopropyl, butyl, isobutyl, pentyl, isopentyl, hexyl or heptyl group;
- one of $R^{2a}$, $R^{2b}$, $R^{2c}$ and $R^{2d}$ represents a methoxy group, another one group represents a ethoxy group and the remaining two groups each represents a hydrogen atom;
- $R^3$ represents an isopropyl or t-butyl group; and
- $R^4$ represents a carbamoyl, methylcarbamoyl, carbamoylmethyl, 2-carbamoylethyl, methylcarbamoylmethyl or 2-(N-methylcarbamoyl)ethyl.

17. The compound of claim 1, wherein:
- $R^1$ represents a propyl, isopropyl, butyl, isobutyl, pentyl, isopentyl, hexyl or heptyl group;
- one of $R^{2a}$, $R^{2b}$, $R^{2c}$ and $R^{2d}$ represents a methoxy group, another one group represents a 1-hydroxy-1-methylethyl, 1-hydroxypropyl, 1-hydroxy-2-methylpropyl, 1-hydroxybutyl or 1-hydroxy-3-methylbutyl group and the remaining two groups each represents a hydrogen atom;
- $R^3$ represents an isopropyl or t-butyl group; and
- $R^4$ represents a carbamoyl, methylcarbamoyl, carbamoylmethyl, 2-carbamoylethyl, methylcarbamoylmethyl or 2-(N-methylcarbamoyl)ethyl.

18. The compound of claim 1, wherein:
- $R^1$ represents a propyl, isopropyl, butyl, isobutyl, pentyl, isopentyl, hexyl or heptyl group;
- one of $R^{2a}$, $R^{2b}$, $R^{2c}$ and $R^{2d}$ represents a methoxy group, another one group represents a propionyl, isobutyryl, butyryl or isovaleryl group and the remaining two groups each represents a hydrogen atom;
- $R^3$ represents an isopropyl or t-butyl group; and
- $R^4$ represents a carbamoyl, methylcarbamoyl, carbamoylmethyl, 2-carbamoylethyl, methylcarbamoylmethyl or 2-(N-methylcarbamoyl)ethyl.

19. The compound of claim 1, wherein:
$R^1$ represents a propyl, isopropyl, butyl, isobutyl, pentyl, isopentyl, hexyl or heptyl group;
one of $R^{2a}$, $R^{2b}$, $R^{2c}$ and $R^{2d}$ represents a methoxy group, another one group represents an isopropylsulfonyl, isobutylsulfonyl or butylsulfonyl group and the remaining two groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylmethyl or 2-(N-methylcarbamoyl)ethyl.

20. The compound of claim 1 selected from the group consisting of N-[2-t-butyl-5-(N-methylcarbamoylmethyl)phenyl)-3-(2,3-methylenedioxyphenyl)-octanamide and pharmaceutically acceptable salts thereof.

21. The compound of claim 1 selected from the group consisting of N-[2-t-butyl-5-(N-methylcarbamoylmethyl)phenyl]-3-(2,3-dimethoxyphenyl)octanamide and pharmaceutically acceptable salts thereof.

22. The compound of claim 1 selected from the group consisting of N-(2-t-butyl-5-carbamoylphenyl)-3-(2,4-dimethoxyphenyl)octanamide and pharmaceutically acceptable salts thereof.

23. The compound of claim 1 selected from the group consisting of N-(2-t-butyl-5-N'-methylcarbamoylphenyl)-3-(2,4-dimethoxyphenyl)octanamide and pharmaceutically acceptable salts thereof.

24. The compound of claim 1 selected from the group consisting of N-[2-t-butyl-5-(carbamoylhethyl)phenyl]-3-(2,4-dimethoxyphenyl)octanamide and pharmaceutically acceptable salts thereof.

25. The compound of claim 1 selected from the group consisting of N-[2-t-butyl-5-(N-methylcarbamoylmethyl)phenyl]-3-(2,4-dimethoxyphenyl)octanamide and pharmaceutically acceptable salts thereof.

26. The compound of claim 1 selected from the group consisting of N-[2-t-butyl-5-[2-(N-methylcarbamoyl)ethyl]phenyl]-3-(2,4-dimethoxyphenyl)-octanamide and pharmaceutically acceptable salts thereof.

27. The compound of claim 1 selected from the group consisting of N-(2-t-butyl-5-carbamoylphenyl)-3-(2,4-dimethoxyphenyl)heptanamide and pharmaceutically acceptable salts thereof.

28. The compound of claim 1 selected from the group consisting of N-[2-t-butyl-5-(N-methylcarbamoylmethyl)phenyl]-3-(2,4-dimethoxyphenyl)-heptanamide and pharmaceutically acceptable salts thereof.

29. The compound of claim 1 selected from the group consisting of N-(2-t-butyl-5-carbamoylphenyl)-3-(2,4-dimethoxyphenyl)nonanamide and pharmaceutically acceptable salts thereof.

30. The compound of claim 1 selected from the group consisting of N-[2-t-butyl-5-carbamoylphenyl]-3-(2,3,4-trimethoxyphenyl)octanamide and pharmaceutically acceptable salts thereof.

31. The compound of claim 1 selected from the group consisting of N-[2-t-butyl-5-carbamoylphenyl]-3-(2,4,5-trimethoxyphenyl)octanamide and pharmaceutically acceptable salts thereof.

32. The compound of claim 1 selected from the group consisting of N-(2-t-butyl-5-carbamoylphenyl)-3-[4-(1-hydroxy-1-methylethyl)-2-methoxyphenyl]-octanamide and pharmaceutically acceptable salts thereof.

33. The compound of claim 1 selected from the group consisting of N-(2-t-butyl-5-carbamoylphenyl)-3-[4-(1-hydroxybutyl)-2-methoxyphenyl]octanamide and pharmaceutically acceptable salts thereof.

34. The compound of claim 1 selected from the group consisting of N-(2-t-butyl-5-carbamoylphenyl)-3-(4-butyryl-2-methoxyphenyl)octanamide and pharmaceutically acceptable salts thereof.

35. The compound of claim 1 selected from the group consisting of N-(2-t-butyl-5-carbamoylphenyl)-3-(4-ethoxy-2-methoxyphenyl)octanamide and pharmaceutically acceptable salts thereof.

36. The compound of claim 1 selected from the group consisting of N-[2-t-butyl-5-(2-carbamoylethyl)phenyl]-3-(2,4,5-trimethoxyphenyl)octanamide and pharmaceutically acceptable salts thereof.

37. The compound of claim 1 selected from the group consisting of N-(2-t-butyl-5-carbamoylphenyl)-3-(4-isopropylsulfonyl-2-methoxyphenyl)octanamide and pharmaceutically acceptable salts thereof.

38. The compound of claim 1 selected from the group consisting of N-(2-t-butyl-5-carbamoylphenyl)-3-(4-isobutyryl-2-methoxyphenyl)octanamide and pharmaceutically acceptable salts thereof.

39. The compound of claim 1 selected from the group consisting of N-(2-t-butyl-5-carbamoylphenyl)-3-(2,4-dimethoxyphenyl)-6-methylheptanamide and pharmaceutically acceptable salts thereof.

40. A composition for the treatment and prophylaxis of hypercholesteremia or arteriosclerosis, which comprises an effective amount of an active compound of formula (I), as defined in claim 1, or a pharmaceutically acceptable salt thereof in admixture with a pharmaceutically acceptable carrier or diluent.

41. The composition of claim 40, wherein $R^1$ represents a propyl, isopropyl, butyl, isobutyl, pentyl, isopentyl, hexyl or heptyl group.

42. The composition of claim 40, wherein two adjacent groups among $R^{2a}$, $R^{2b}$, $R^{2c}$ and $R^{2d}$ together represent a methylenedioxy or ethylenedioxy group and the remaining two groups each represents a hydrogen atom.

43. The composition of claim 40, wherein two or three groups among $R^{2a}$, $R^{2b}$, $R^{2c}$ and $R^{2d}$ each represents a methoxy group and the remaining two or one groups each represents a hydrogen atom.

44. The composition of claim 40, wherein one of $R^{2a}$, $R^{2b}$, $R^{2c}$ and $R^{2d}$ represents a methoxy group, another one group represents a hydroxy group, and the remaining two groups each represents a hydrogen atom.

45. The composition of claim 40, wherein one of $R^{2a}$, $R^{2b}$, $R^{2c}$ and $R^{2d}$ represents a methoxy group, another one group represents a ethoxy group and the remaining two groups each represents a hydrogen atom.

46. The composition of claim 40, wherein one of $R^{2a}$, $R^{2b}$, $R^{2c}$ and $R^{2d}$ represents a methoxy group, another one group represents a 1-hydroxy-1-methylethyl, 1-hydroxypropyl, 1-hydroxy-2-methylpropyl, 1-hydroxybutyl or 1-hydroxy-3-methylbutyl group and the remaining two groups each represents a hydrogen atom.

47. The composition of claim 40, wherein one of $R^{2a}$, $R^{2b}$, $R^{2c}$ and $R^{2d}$ represents a methoxy group, another one group represents a propionyl, isobutyryl, butyryl or isovaleryl group and the remaining two groups each represents a hydrogen atom.

48. The composition of claim 40, wherein one of $R^{2a}$, $R^{2b}$, $R^{2c}$ and $R^{2d}$ represents a methoxy group, another one group represents an isopropylsulfonyl, isobutylsulfonyl or butylsulfonyl group and the remaining two groups each represents a hydrogen atom.

49. The composition of claim 40, wherein $R^3$ represents an isopropyl or t-butyl group.

50. The composition of claim 40, wherein $R^4$ represents a carbamoyl, methyl-carbamoyl, carbamoylmethyl, 2-carbamoylethyl, methylcarbamoylmethyl or 2-(N-methylcarbamoyl)ethyl.

51. The composition of claim 40, wherein $R^4$ represents a carbamoyl, methylcarbamoyl, carbamoylmethyl, 2-carbamoylethyl, methylcarbamoylmethyl or 2-N-methylcarbamoylethyl group.

52. The composition of claim 40, wherein:
$R^1$ represents a propyl, isopropyl, butyl, isobutyl, pentyl, isopentyl, hexyl or heptyl group;
two adjacent groups among $R^{2a}$, $R^{2b}$, $R^{2c}$ and $R^{2d}$ together represent a methylenedioxy or ethylenedioxy group and the remaining two groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylmethyl or 2-(N-methylcarbamoyl)ethyl.

53. The composition of claim 40, wherein:
$R^1$ represents a propyl, isopropyl, butyl, isobutyl, pentyl, isopentyl, hexyl or heptyl group;
two or three groups among $R^{2a}$, $R^{2b}$, $R^{2c}$ and $R^{2d}$ each represents a methoxy group and the remaining two or one groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylmethyl or 2-(N-methylcarbamoyl)ethyl.

54. The composition of claim 40, wherein:
$R^1$ represents a propyl, isopropyl, butyl, isobutyl, pentyl, isopentyl, hexyl or heptyl group;
one of $R^{2a}$, $R^{2b}$, $R^{2c}$ and $R^{2d}$ represents a methoxy group, another one group represents a hydroxy group, and the remaining two groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylmethyl or 2-(N-methylcarbamoyl)ethyl.

55. The composition of claim 40, wherein:
$R^1$ represents a propyl, isopropyl, butyl, isobutyl, pentyl, isopentyl, hexyl or heptyl group;
one of $R^{2a}$, $R^{2b}$, $R^{2c}$ and $R^{2d}$ represents a methoxy group, another one group represents a ethoxy group and the remaining two groups each represents a hydrogen atom;
$R^3$ represents an isopropyl or t-butyl group; and
$R^4$ represents a carbamoyl, methylcarbamoyl, carbamoylmethyl 2-carbamoylethyl, methylcarbamoylmethyl or 2-(N-methylcarbamoyl)ethyl.

56. The composition of claim 40, wherein:
$R^1$ represents a propyl, isopropyl, butyl, isobutyl, pentyl, isopentyl, hexyl or heptyl group;
one of $R^{2a}$, $R^{2b}$, $R^{2c}$ and $R^{2d}$ represents a methoxy group, another one group represents a 1-hydroxy-1-methylethyl, 1-hydroxypropyl, 1-hydroxy-2-methylpropyl, 1-hydroxybutyl or 1-hydroxy-3-methylbutyl group and the remaining two groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylmethyl or 2-(N-methylcarbamoyl)ethyl.

57. The composition of claim 40, wherein:
$R^1$ represents a propyl, isopropyl, butyl, isobutyl, pentyl, isopentyl, hexyl or heptyl group;
one of $R^{2a}$, $R^{2b}$, $R^{2c}$ and $R^{2d}$ represents a methoxy group, another one group represents a propionyl, isobutyryl, butyryl or isovaleryl group and the remaining two groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylmethyl or 2-N-methylcarbamoyl)ethyl.

58. The composition of claim 40, wherein:
$R^1$ represents a propyl, isopropyl, butyl isobutyl, pentyl, isopentyl, hexyl or heptyl group;
one of $R^{2a}$, $R^{2b}$, $R^{2c}$ and $R^{2d}$ represents a methoxy group, another one group represents an isopropylsulfonyl, isobutylsulfonyl or butylsulfonyl group and the remaining two groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylmethyl or 2-(N-methylcarbamoyl)ethyl.

59. The composition of claim 40, wherein said active compound is selected from the group consisting of:

N-[2-t-butyl-5-(N-methylcarbamoylmethyl)phenyl)-3-(2,3-methylenedioxyphenyl)octanamide;

N-[2-t-butyl-5-(N-methylcarbamoylmethyl)phenyl]-3-(2,3-dimethoxyphenyl)-octanamide;

N-(2-t-butyl-5-carbamoylphenyl)-3-(2,4-dimethoxyphenyl)octanamide;

N-(2-t-butyl-5-N'-methylcarbamoylphenyl)-3-(2,4-dimethoxyphenyl)octanamide;

N-[2-t-butyl-5-(carbamoylmethyl)phenyl]-3-(2,4-dimethoxyphenyl)octanamide;

N-[2-t-butyl-5-(methylcarbamoylmethyl)phenyl]-3-(2,4-dimethoxyphenyl)-octanamide;

N-[2-t-butyl-5-[2-(methylcarbamoyl)ethyl]phenyl]-3-(2,4-dimethoxyphenyl)-octanamide;

N-(2-t-butyl-5-carbamoylphenyl)-3-(2,4-dimethoxyphenyl)heptanamide;

N-[2-t-butyl-5-(N-methylcarbamoylmethyl)phenyl]-3-(2,4-dimethoxyphenyl)-heptanamide;

N-(2-t-butyl-5-carbamoylphenyl)-3-(2,4-dimethoxyphenyl)nonanamide;

N-[2-t-butyl-5-carbamoylphenyl]-3-(2,3,4-trimethoxyphenyl)octanamide;

N-[2-t-butyl-5-carbamoylphenyl]-3-(2,4,5-trimethoxyphenyl)octanamide;

N-(2-t-butyl-5-carbamoylphenyl)-3-[4-(1-hydroxy-1-methylethyl)-2-methoxyphenyl]octanamide;

N-(2-t-butyl-5-carbamoylphenyl)-3-[4-(1-hydroxybutyl)-2-methoxyphenyl]-octanamide;

N-(2-t-butyl-5-carbamoylphenyl)-3-(4-butyryl-2-methoxyphenyl)octanamide;

N-(2-t-butyl-5-carbamoylphenyl)-3-(4-ethoxy-2-methoxyphenyl)octanamide;

N-[2-t-butyl-5-(2-carbamoylethyl)phenyl]-3-(2,4,5-trimethoxyphenyl)-octanamide;

N-(2-t-butyl-5-carbamoylphenyl)-3-(4-isopropylsulfonyl-2-methoxyphenyl)-octanamide;

N-(2-t-butyl-5-carbamoylphenyl)-3-(4-isobutyryl-2-methoxyphenyl)octanamide; and

N-(2-t-butyl-5-carbamoylphenyl)-3-(2,4-dimethoxyphenyl)-6-methylheptanamide.

60. A method for the treatment and prophylaxis of hypercholesteremia or arteriosclerosis in a mammal which comprises administering to said mammal an effective amount of an active compound of formula (I), as defined in claim 1, or a pharmaceutically acceptable salt thereof.

61. The method of claim 60, wherein $R^1$ represents a propyl, isopropyl, butyl, isobutyl, pentyl, isopentyl, hexyl or heptyl group.

62. The method of claim 60, wherein two adjacent groups among $R^{2a}$, $R^{2b}$, $R^{2c}$ and $R^{2d}$ together represent a methylenedioxy or ethylenedioxy group and the remaining two groups each represents a hydrogen atom.

63. The method of claim 60, wherein two or three groups among $R^{2a}$, $R^{2b}$, $R^{2c}$ and $R^{2d}$ each represents a methoxy group and the remaining two or one groups each represents a hydrogen atom.

64. The method of claim 60, wherein one of $R^{2a}$, $R^{2b}$, $R^{2c}$ and $R^{2d}$ represents a methoxy group, another one group represents a hydroxy group, and the remaining two groups each represents a hydrogen atom.

65. The method of claim 60, wherein one of $R^{2a}$, $R^{2b}$, $R^{2c}$ and $R^{2d}$ represents a methoxy group, another one group represents a ethoxy group and the remaining two groups each represents a hydrogen atom.

66. The method of claim 60, wherein one of $R^{2a}$, $R^{2b}$, $R^{2c}$ and $R^{2d}$ represents a methoxy group, another one group represents a 1-hydroxy-1-methylethyl, 1-hydroxypropyl, 1-hydroxy-2-methylpropyl, 1-hydroxybutyl or 1-hydroxy-3-methylbutyl group and the remaining two groups each represents a hydrogen atom.

67. The method of claim 60, wherein one of $R^{2a}$, $R^{2b}$, $R^{2c}$ and $R^{2d}$ represents a methoxy group, another one group represents a propionyl, isobutyryl, butyryl or isovaleryl group and the remaining two groups each represents a hydrogen atom.

68. The method of claim 60, wherein one of $R^{2a}$, $R^{2b}$, $R^{2c}$ and $R^{2d}$ represents a methoxy group, another one group represents an isopropylsulfonyl, isobutylsulfonyl or butylsulfonyl group and the remaining two groups each represents a hydrogen atom.

69. The method of claim 60, wherein $R^3$ represents an isopropyl or t-butyl group.

70. The method of claim 60, wherein $R^4$ represents a carbamoyl, methylcarbamoyl, carbamoylmethyl, 2-carbamoylethyl, methylcarbamoylmethyl or 2-(N-methylcarbamoyl)ethyl.

71. The method of claim 60, wherein $R^4$ represents a carbamoyl, methylcarbamoyl, carbamoylmethyl, 2-carbamoylethyl, methylcarbamoylmethyl or 2-N-methylcarbamoylethyl group.

72. The method of claim 60, wherein:
$R^1$ represents a propyl, isopropyl, butyl, isobutyl, pentyl, isopentyl, hexyl or heptyl group;
two adjacent groups among $R^{2a}$, $R^{2b}$, $R^{2c}$ and $R^{2d}$ together represent a methylenedioxy or ethylenedioxy group and the remaining two groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylmethyl or 2-(N-methylcarbamoyl)ethyl.

73. The method of claim 60, wherein:
$R^1$ represents a propyl, isopropyl, butyl, isobutyl, pentyl, isopentyl, hexyl or heptyl group;
two or three groups among $R^{2a}$, $R^{2b}$, $R^{2c}$ and $R^{2d}$ each represents a methoxy group and the remaining two or one groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylmethyl or 2-(N-methylcarbamoyl)ethyl.

74. The method of claim 60, wherein:
$R^1$ represents a propyl, isopropyl, butyl, isobutyl, pentyl, isopentyl, hexyl or heptyl group;
one of $R^{2a}$, $R^{2b}$, $R^{2c}$ and $R^{2d}$ represents a methoxy group, another one group represents a hydroxy group, and the remaining two groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylmethyl or 2-(N-methylcarbamoyl)ethyl.

75. The method of claim 60, wherein:
$R^1$ represents a propyl, isopropyl, butyl, isobutyl, pentyl, isopentyl, hexyl or heptyl group;
one of $R^{2a}$, $R^{2b}$, $R^{2c}$ and $R^{2d}$ represents a methoxy group, another one group represents a ethoxy group and the remaining two groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylrnethyl or 2-(N-methylcarbamoyl)ethyl.

76. The method of claim 60, wherein:
$R^1$ represents a propyl, isopropyl, butyl, isobutyl, pentyl, isopentyl, hexyl or heptyl group;
one of $R^{2a}$, $R^{2b}$, $R^{2c}$ and $R^{2d}$ represents a methoxy group, another one group represents a 1-hydroxy-1-methylethyl, 1-hydroxypropyl, 1-hydroxy-2-methylpropyl, 1-hydroxybutyl or 1-hydroxy-3-methylbutyl group and the remaining two groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylmethyl or 2-(N-methylcarbamoyl)ethyl.

77. The method of claim 60, wherein:
$R^1$ represents a propyl, isopropyl, butyl, isobutyl, pentyl, isopentyl, hexyl or heptyl group;
one of $R^{2a}$, $R^{2b}$, $R^{2c}$ and $R^{2d}$ represents a methoxy group, another one group represents a propionyl, isobutyryl, butyryl or isovaleryl group and the remaining two groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylmethyl or 2-(N-methylcarbamoyl)ethyl.

78. The method of claim 60, wherein:
$R^1$ represents a propyl, isopropyl, butyl, isobutyl, pentyl, isopentyl, hexyl or heptyl group;
one of $R^{2a}$, $R^{2b}$, $R^{2c}$ and $R^{2d}$ represents a methoxy group, another one group represents an isopropylsulfonyl, isobutylsulfonyl or butylsulfonyl group and the remaining two groups each represents a hydrogen atom;
$R^3$ represents an isopropyl or t-butyl group; and
$R^4$ represents a carbamoyl, methylcarbamoyl, carbamoylmethyl, 2-carbamoylethyl, methylcarbamoylmethyl or 2-(N-methylcarbamoyl)ethyl.

79. The method of claim 60, wherein said active compound is selected from the group consisting of:

N̲-[2-t-butyl-5-(N̲-methylcarbamoylmethyl)phenyl]-3-(2,3-methylenedioxyphenyl)octanamide;

N̲-[2-t-butyl-5-(N̲-methylcarbamoylmethyl)phenyl]-3-(2,3-dimethoxyphenyl)-octanamide;

N̲-(2-t-butyl-5-carbamoylphenyl)-3-(2,4-dimethoxyphenyl)octanamide;

N̲-(2-t-butyl-5-(N̲'-methylcarbamoylphenyl) -3-(2,4-dimethoxyphenyl)octanamide;

N̲-[2-t-butyl-5-(carbamoylmethyl)phenyl]-3-(2,4-dimethoxyphenyl)octanamide;

N̲-[2-t-butyl-5-(N̲-methylcarbamoylmethyl)phenyl]-3-(2,4-dimethoxyphenyl)-octanamide;

N̲-[2-t-butyl-5-[2-(N̲-methylcarbamoyl)ethyl]phenyl]-3-(2,4-dimethoxyphenyl)-octanamide;

N̲-(2-t-butyl-5-carbamoylphenyl)-3-(2,4-dimethoxyphenyl)heptanamide;

N̲-[2-t-butyl-5-(N̲-methylcarbamoylmethyl)phenyl]-3-(2,4-dimethoxyphenyl)-heptanamide;

N̲-(2-t-butyl-5-carbamoylphenyl)-3-(2,4-dimethoxyphenyl)nonanamide;

N̲-[2-t-butyl-5-carbamoylphenyl]-3-(2,3,4-trimethoxyphenyl)octanamide;

N̲-[2-t-butyl-5-carbamoylphenyl]-3-(2,4,5-trimethoxyphenyl)octanamide;

N̲-(2-t-butyl-5-carbamoylphenyl)-3-[4-(1-hydroxy-1-methylethyl)-2-methoxyphenyl]octanamide;

N̲-(2-t-butyl-5-carbamoylphenyl)-3-[4-(1-hydroxybutyl)-2-methoxyphenyl]-octanamide;

N̲-(2-t-butyl-5-carbamoylphenyl)-3-(4-butyryl-2-methoxyphenyl)octanamide;

N̲-(2-t-butyl-5-carbamoylphenyl)-3-(4-ethoxy-2-methoxyphenyl)octanamide;

N̲-[2-t-butyl-5-(2-carbamoylethyl)phenyl]-3-(2,4,5-trimethoxyphenyl)-octanamide;

N̲-(2-t-butyl-5-carbamoylphenyl)-3-(4-isopropylsulfonyl-2-methoxyphenyl)-octanamide;

N̲-(2-t-butyl-5-carbamoylphenyl)-3-(4-isobutyryl-2-methoxyphenyl)octanamide; and N̲-(2-t-butyl-5-carbamoylphenyl)-3-(2,4-dimethoxyphenyl)-6-methylheptanamide.

80. The method of claim 60, wherein the mammal is a human.

* * * * *

UNITED STATES PATENT AND TRADEMARK OFFICE
CERTIFICATE OF CORRECTION

PATENT NO. : 5,880,147
DATED : March 9, 1999
INVENTOR(S) : YOSHIDA et al

It is certified that error appears in the above-identified patent and that said Letters Patent is hereby corrected as shown below:

Title Page, left column, item [54]: delete "AMIDE" and insert -- AMIDO --.
Column 61, last line: delete "conyentional" and insert --conventional--.
Column 72, line 42: delete "(XVM)" and insert --(XVIII)--.
Column 74, line 3: delete "(XXI)" (first occurrence) and insert --(XXII)--.
Column 74, line 12: delete "(XXI)" and insert --(XXII)--.
Column 74, line 19: delete "(XXII)" and insert --(XXIII)--.
Column 74, line 24: delete "(XXII)" and insert --(XXIII)--.
Column 77, line 51: delete "(XXXII)" and insert --(XXXIII)--.
Column 79, line 6: delete "(XVI)" and insert --(XXXVI)--.
Column 79, line 45: delete "(XXXVI)" and insert --(XXXVII)--.
Column 79, line 46: delete "(XXXV)" and insert --(XXXIV)--.

UNITED STATES PATENT AND TRADEMARK OFFICE
CERTIFICATE OF CORRECTION

PATENT NO. : 5,880,147
DATED      : March 9, 1999
INVENTOR(S): YOSHIDA et al

It is certified that error appears in the above-identified patent and that said Letters Patent is hereby corrected as shown below:

```
Column 81, line 39:  delete "(XXXI)" and insert
--(XXXXI)--.
Column 83, line 6:   delete (II) and insert --(III)--.
Column 84, line 31:  delete "(XXXXVI)" and insert
--(XXXXVIII)--.
Column 84, line 40:  delete (XXXXVII)" and insert
--(XXXXVIII)--.
Column 85, line 49:  delete "(LVI)" and insert
--(LVIII)--.
Column 87, line 32:  delete "(LXVII)" and insert
--(LXVIII)--.
Column 87, line 52:  before "-very" insert --ß--.
```

Signed and Sealed this

Twenty-sixth Day of September, 2000

Attest:

Q. TODD DICKINSON

*Attesting Officer*    *Director of Patents and Trademarks*